US009574193B2

(12) United States Patent
Crooke et al.

(10) Patent No.: US 9,574,193 B2
(45) Date of Patent: Feb. 21, 2017

(54) METHODS AND COMPOSITIONS FOR MODULATING APOLIPOPROTEIN (A) EXPRESSION

(71) Applicant: Ionis Pharmaceuticals, Inc., Carlsbad, CA (US)

(72) Inventors: Rosanne M. Crooke, Carlsbad, CA (US); Mark J. Graham, San Clemente, CA (US); Susan M. Freier, San Diego, CA (US); Marc Lim, Oceanside, CA (US); Andrew Dibble, Vista, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 14/552,436

(22) Filed: Nov. 24, 2014

(65) Prior Publication Data

US 2015/0337303 A1    Nov. 26, 2015

Related U.S. Application Data

(63) Continuation of application No. PCT/US2013/042532, filed on May 23, 2013, and a continuation-in-part of application No. 14/401,761, filed as application No. PCT/US2013/041701 on May 17, 2013.

(60) Provisional application No. 61/651,539, filed on May 24, 2012, provisional application No. 61/648,556, filed on May 17, 2012.

(51) Int. Cl.
*C12N 15/113* (2010.01)

(52) U.S. Cl.
CPC ......... *C12N 15/113* (2013.01); *C12N 2310/11* (2013.01); *C12N 2310/315* (2013.01); *C12N 2310/321* (2013.01); *C12N 2310/323* (2013.01); *C12N 2310/3341* (2013.01); *C12N 2310/3525* (2013.01)

(58) Field of Classification Search
None
See application file for complete search history.

(56) References Cited

U.S. PATENT DOCUMENTS

| 3,687,808 A | 8/1972 | Merigan et al. |
| 4,845,205 A | 7/1989 | Huynh Dinh et al. |
| 5,034,506 A | 7/1991 | Summerton et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,185,444 A | 2/1993 | Summerton et al. |
| 5,367,066 A | 11/1994 | Urdea et al. |
| 5,374,527 A | 12/1994 | Grossman |
| 5,432,272 A | 7/1995 | Benner |
| 5,457,187 A | 10/1995 | Gmelner et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,645,985 A | 7/1997 | Froehler et al. |
| 5,681,941 A | 10/1997 | Cook et al. |
| 5,698,685 A | 12/1997 | Summerton et al. |
| 5,721,138 A | 2/1998 | Lawn |
| 5,750,692 A | 5/1998 | Cook et al. |
| 5,763,588 A | 6/1998 | Matteucci et al. |
| 5,801,154 A | 9/1998 | Baracchini et al. |
| 5,830,653 A | 11/1998 | Froehler et al. |
| 5,866,551 A | 2/1999 | Benoit et al. |
| 5,877,022 A | 3/1999 | Stinchcomb et al. |
| 6,005,096 A | 12/1999 | Matteucci et al. |
| 6,008,344 A | 12/1999 | Bennett et al. |
| 6,080,580 A | 6/2000 | Baker et al. |
| 6,268,490 B1 | 7/2001 | Imanishi et al. |
| 6,512,161 B1 | 1/2003 | Rouy et al. |
| 6,515,191 B2 | 2/2003 | Lal et al. |
| 6,525,191 B1 | 2/2003 | Ramasamy |
| 6,573,050 B1 | 6/2003 | Ben-David et al. |
| 6,582,908 B2 | 6/2003 | Fodor et al. |
| 6,613,567 B1 | 9/2003 | Bennett et al. |
| 6,670,461 B1 | 12/2003 | Wengel et al. |

(Continued)

FOREIGN PATENT DOCUMENTS

| WO | WO 96/09392 | 3/1996 |
| WO | WO 97/17371 | 5/1997 |

(Continued)

OTHER PUBLICATIONS

Agrawal et al., "Antisense oligonucleotides: towards clinical trials" TIBTECH (1996) 14:376-387.
Anderson et al., "A comparison of selected mRNA and protein abundances in human liver" Electrophoresis (1997) 18:533-537.
Berg et al. "Spontaneous Atherosclerosis in the Proximal Aorta of LPA Transgenic Mice on a Normal Diet," Atherosclerosis (2002) vol. 163:99-104.

(Continued)

*Primary Examiner* — Tracy Vivlemore

(74) *Attorney, Agent, or Firm* — Ionis Pharmaceuticals, Inc. Patent Dept.

(57) ABSTRACT

Disclosed herein are antisense compounds and methods for decreasing apo(a) to treat, prevent, or ameliorate diseases, disorders or conditions related to apo(a) or Lp(a). Certain diseases, disorders or conditions related to apo(a) or Lp(a) include inflammatory, cardiovascular and/or metabolic diseases, disorders or conditions. The antisense compounds disclosed herein can be used to treat such diseases, disorders or conditions in an individual in need thereof.

25 Claims, No Drawings

(56) References Cited

U.S. PATENT DOCUMENTS

| | | | |
|---|---|---|---|
| 6,764,822 | B1 | 7/2004 | Butler et al. |
| 6,770,748 | B2 | 8/2004 | Imanishi et al. |
| 6,794,499 | B2 | 9/2004 | Wengel et al. |
| 6,809,193 | B2 | 10/2004 | McKay et al. |
| 7,034,133 | B2 | 4/2006 | Wengel et al. |
| 7,053,207 | B2 | 5/2006 | Wengel |
| 7,227,014 | B2 | 6/2007 | Crooke et al. |
| 7,259,150 | B2 | 8/2007 | Crooke et al. |
| 7,399,845 | B2 | 7/2008 | Seth et al. |
| 7,427,672 | B2 | 9/2008 | Imanishi et al. |
| 7,547,684 | B2 | 6/2009 | Seth et al. |
| 7,696,345 | B2 | 4/2010 | Allerson et al. |
| 7,723,508 | B2 | 5/2010 | Crooke et al. |
| 7,741,305 | B2 | 6/2010 | Crooke et al. |
| 7,741,457 | B2 | 6/2010 | Seth et al. |
| 8,138,328 | B2 | 3/2012 | Crooke et al. |
| 8,673,632 | B2 | 3/2014 | Crooke et al. |
| 2001/0053519 | A1 | 12/2001 | Fodor et al. |
| 2003/0104410 | A1 | 6/2003 | Mittmann |
| 2003/0165948 | A1 | 9/2003 | Alsmadi et al. |
| 2003/0228597 | A1 | 12/2003 | Cowsert et al. |
| 2004/0171570 | A1 | 9/2004 | Allerson et al. |
| 2004/0242516 | A1 | 12/2004 | Crooke |
| 2005/0130923 | A1 | 6/2005 | Bhat et al. |
| 2006/0281698 | A1 | 12/2006 | Crooke et al. |
| 2007/0031844 | A1 | 2/2007 | Khvorova et al. |
| 2007/0110757 | A1 | 5/2007 | Wei et al. |
| 2007/0287831 | A1 | 12/2007 | Seth et al. |
| 2008/0039618 | A1 | 2/2008 | Allerson et al. |
| 2009/0012281 | A1 | 1/2009 | Swayze et al. |
| 2011/0039910 | A1 | 2/2011 | Crooke et al. |
| 2011/0044977 | A1 | 2/2011 | Adler et al. |
| 2011/0098343 | A1 | 4/2011 | Hayes et al. |
| 2011/0294868 | A1 | 12/2011 | Monia et al. |
| 2012/0316219 | A1 | 12/2012 | Crooke et al. |
| 2014/0206750 | A1 | 7/2014 | Crooke et al. |
| 2015/0184156 | A1 | 7/2015 | Crooke et al. |

FOREIGN PATENT DOCUMENTS

| | | |
|---|---|---|
| WO | WO 98/39352 | 9/1998 |
| WO | WO 99/14226 | 3/1999 |
| WO | WO 99/34016 | 7/1999 |
| WO | WO 99/35241 | 7/1999 |
| WO | WO 03/004602 | 1/2003 |
| WO | WO 03/014307 | 2/2003 |
| WO | WO 03/014397 | 2/2003 |
| WO | WO 2004/031237 | 4/2004 |
| WO | WO 2004/106356 | 12/2004 |
| WO | WO 2004/108916 | 12/2004 |
| WO | WO 2005/000201 | 1/2005 |
| WO | WO 2005/021570 | 3/2005 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/100320 | 8/2009 |
| WO | WO 2010/006215 | 1/2010 |
| WO | WO 2010/036698 | 4/2010 |
| WO | WO 2011/017521 | 2/2011 |
| WO | WO 2013/173789 | 11/2013 |
| WO | WO 2014/179625 | 11/2014 |

OTHER PUBLICATIONS

Braasch et al., "Novel antisense and peptide nucleic acid strategies for controlling gene expression" Biochemistry (2002) 41(14):4503-4510.

Callow et al., "Expression of human apolipoprotein B and assembly of lipoprotein (a) in transgenic mice" PNAS (1994) 91:2130-2134.

Chiesa et al., "Reconstitution of Lipoprotein (a) by Infusion of Human Low Density Lipoprotein into Transgenic Mice Expressing Human Apolipoprotein (a)" J. of Biological Chem. (1992) 267:24369-24374.

Crooke et al., "Pharmacokinetic Properties of Several Novel Oligonucleotide Analogs in mice" J. Pharmacol. Exp. Ther. (1996) 277(2):923-937.

Deverre et al., "A competitive enzyme hybridization assay for plasma determination of phosphodiester and phosphorothioate antisense oligonucleotides" Nucleic Acids Res. (1997) 25:3584-3589.

Dias et al., "Potential roles of antisense oligonucleotides in cancer therapy. The example of bcl-2 antisense oligonucleotides." European J. of Pharmaceutics and Biopharmaceutics (2002) 54:263-269.

Elbashir et al., "Functional anatomy of siRNAs for mediating efficient RNAi in Drosophila melanogaster embryo lysate" The EMBO Journal (2001) 20(23):6877-6888.

Englisch et al., "Chemically Modified Oligonucleotides as Probes and Inhibitors" Agnew Chem. Int. Ed. Engl. (1991) 30:613-629.

Frank et al., "Adenovirus-mediated apo(a)-antisense-RNA expression efficiently inhibits apo(a) synthesis in vitro and in vivo" Gene Therapy (2001) 8:425-430.

Frank et al., "The apolipoprotein (a) gene resides on human chromosome 6q26-27, in close proximity to the homologous gene for plasminogen" Hum. Genet. (1988) 79:352-356.

Fritz et al., "Cationic Polystyrene Nonoparticles: Preparation and Characterization of a Model Drug Carrier System for Antisense Oligonucleotides" Journal of Colloid and Interface Science (1997) 195:272-288.

Gewirtz et al., "Facilitating oligonucleotide delivery: Helping antisense deliver on its promise" PNAS (1996) 93:3161-3163.

Grainger et al., "Activation of transforming growth factor-beta is inhibited in transgenic apolipoprotein (a) mice" Nature (1994) 370:460-462.

Green et al., "Antisense Oligonucleotides: An Evolving Technology for the Modulation of Gene Expression in Human Disease" J. Am. Coll. Surg. (2000) 191:93-105.

Hajjar et al., "The role of lipoprotein (a) in atherogenesis and thrombosis" Annu. Rev. Med. (1996) 47:423-442.

Holen et al., "Positional effects of short interfering RNAs targeting the human coagulation trigger Tissue Factor" Nucleic Acids Research (2002) 30(8):1757-1766.

Jen, "Suppression of Gene Expression by Targeted Disruption of Messenger RNA: Available Options and Current Strategies" Stem Cells (2000) 18:307-319.

Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327-330.

Katan et al., "Characteristics of human hypo- and hyperresponders to dietary cholesterol" Am. J. Epidemiol. (1987) 125:387-399.

Koschinsky, Marlys L., "Lipoprotein(A): On the Cutting Edge of Occam's Razor, website." 8 pages, Jun. 2004.

Kostner et al., "Lipoprotein (a) Still an Enigma?" Current Opinion in Lipidolo (2002) 13:391-396.

Lawn et al., "Atherogenesis in transgenic mice expressing human apolipoprotein (a)" Nature (1992) 360:670-672.

Letsinger et al., "Cholesteryl-conjugated oligonucleotides: Synthesis, properties, and activity as inhibitors of replication of human immunodeficiency virus in cell culture" PNAS (1989) 86:6553-6556.

Manoharan et al., "Cholic Acid-Oligonucleotide Conjugates for Antisense Applications" Bioorg. Med. Chem. Lett. (1994) 4:1053-1060.

Manoharan et al., "Introduction of a Lipophilic Thioether Tether in the Minor Groove of Nucleic Acids for Antisense Applications" Bioorg. Med. Chem. Lett. (1993) 3(12):2765-2770.

Manoharan et al., "Lipidic Nucleic Acids" Tetrahedron Lett. (1995) 36(21):3651-3654.

Manoharan et al., "Oligonucleotide Conjugates: Alteration of the Pharmacokinetic Properties of Antisense Agents" Nucleosides & Nucleotides (1995) 14(3-5):969-973.

McLean et al., "cDNA sequence of human apolipoprotein (a) is homologous to plasminogen" Nature (1987) 330:132-137.

(56) References Cited

OTHER PUBLICATIONS

Milligan et al., "Current Concepts in Antisense Drug Design" J. Medicinal Chemistry (1993) 36: 1923-1927.
Mishra et al., "Improved leishmanicidal effect of phosphorotioate antisense oligonucleotides by LDL-mediated delivery" Biochim. Biophys. Acta (1995) 1264:229-237.
Morishita et al., "Novel therapeutic strategy for atherosclerosis: ribozyme oligonucleotides against apolipoprotein (a) selectively inhibit apolipoprotein (a) but not plasminogen gene expression" Circulation (1998) 98:1898-1904.
Nowak-Gottl et al., "Lipoprotein (a): its role in childhood thromboembolism" Pediatrics (1997) 99:E11.
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Ohmichi et al., "The virtues of self-binding: high sequence specificity for RNA cleavage by self-processed hammerhead ribozymes" Nucleic Acids Res. (2000) 28:776-783.
Olie et al., "Analysis of ribosyl-modified, mixed backbone analogs of a bcl-2/bcl-xL antisense oligonucleotide" Biochimica et Biophysica Acta (2002) 1576:101-109.
Opalinski et al., "Nucleic-Acid Therapeutics: Basic Principles and Recent Applications" Nature Reviews (2002) 1:503-514.
Prosnyak et al., "Substitution of 2-aminoadenine and 5-methylcytosine for adenine and cytosine in hybridization probes increases the sensitivity of DNA fingerprinting" Genomics (1994) 21:490-494.
Rainwater et al., "Lipoprotein Lp (a): effects of allelic variation at the LPA locus" J. Exp. Zool. (1998) 282:54-61.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sandkamp et al., "Lipoprotein (a) is an independent risk factor for myocardial infarction at a young age" Clin. Chem. (1990) 36:20-23.
Seed et al., "Relation of serum lipoprotein (a) concentration and apolipoprotein (a) phenotype to coronary heart disease in patients with familial hypercholesterolemia" N. Engl. J. Med. (1990) 322:1494-1499.
Shea et al., "Synthesis, hybridization properties and antiviral activity of lipid-oligodeoxynucleotide conjugates" Nucl. Acids Res. (1990) 18(13):3777-3783.
Skerra, "Phosphorothioate primers improve the amplification of DNA sequences by DNA polymerase with proofreading activity" Nucleic Acids Res. (1992) 20:3551-3554.
Sohail et al., "Selecting optimal antisense reagents" Advanced Drug Delivery Review (2000) 44(1):23-34.
Svinarchuk et al., "Inhibition of HIV proliferation in MT-4 cells by antisense oligonucleotide conjugated to lipophilic groups" Biochimie (1993) 75:49-54.
Tamm et al., "Antisense therapy in oncology: new hope for an old idea?" The Lancet (2001) 358:489-497.
Tuschl et al., 2004, "Selection of siRNA Duplexes from the Target mRNA Sequence," The siRNA user guide, (Rev. 5/04), retrieved Apr. 7, 2009, Max Planck Institute for Biophysical Chemistry, (available at) http://www.rockefeller.edu/labheads/tuschl/sirna.html.
U.S.P.T.O. Office Action from U.S. Appl. No. 12/726,286 dated Sep. 19, 2011.
U.S.P.T.O. Office Action from U.S. Appl. No. 12/726,286 dated Apr. 16, 2012.
U.S.P.T.O. Office Action from U.S. Appl. No. 12/726,286 dated Jun. 6, 2013.
Vessby et al., "Diverging Effects of Cholestyramine on Apolipoprotein B and Lipoprotein Lp (a)" Atherosclerosis (1982) 44:61-71.
Weintraub et al., "Antisense RNA and DNA" Scientific American (1990) 40-46.

Yang et al., "Transforming Growth Factor-B1 Inhibits Human Keratinocyte Proliferation by Upregulation of a Receptor-Type Tyrosine Phosphatase R-PTP-K Gene Expression" Biochem. Biophys. Res. Commun. (1996) 228:807-812.
Zhang et al., "Antisense Inhibition" Methods in Molecular Medicine (2005) 106: 11-34.
Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.
Altmann et al., "Second Generation Antisense Oligonucleotides—Inhibition of PKC-α and c-raf Kinase Expression by Chimeric Oligonucleotides Incorporating 6"-Substituted Carbocyclic Nucleosides and 2'-O-Ethylene Glycol Substituted Ribonucleosides" Nuclewsodies Nucleotides. (1997) 16:917-926.
Altmann et al., "Second Generation of Antisense Oligonucleotides: From Nuclease Resistance to Biological Efficacy in Animals" Chimia. (1996) 50(4):168-176.
Altmann et al., "Second-generation antisense oligonucleotides: structure-activity relationships and the design of improved signal-transduction inhibitors" Biochem. Soc. Trans. (1996) 24:630-637.
Altschul et al., "Basic Local Alignment Search Tool" J. Mol. Biol. (1990) 215:403-410.
Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.
Bergmark et al., "A novel function of lipoprotein [a] as a preferential carrier of oxidized phospholipids in human plasma" J. Lipid Res. (2008) 49(10)2230-2239.
Braasch et al., "Locked nucleic acid (LNA): fine-tuning the recognition of DNA and RNA" Chem. Biol. (2001) 8:1-7.
Branch et al., "A good antisense molecule is hard to find," TIBS (1998) 23:45-50.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Clarke et al., "Genetic variants associated with Lp(a) lipoprotein level and coronary disease" N. Engl. J. Med. (2009) 361(26):2518-2528.
Crooke et al., "Basic Principles of Antisense Therapeutics" Antisense Research and Application (1998) Chapter 1:1-50.
Elayadi et al., "Application of PNA and LNA oligomers to chemotherapy" Curr. Opinion Invens. Drugs (2001) 2:558-561.
Erqou et al., "Lipoprotein(a) concentration and the risk of coronary heart disease, stroke, and nonvascular mortality" JAMA. (2009) 302(4):412-423.
Expert Panel on Detection, Evaluation, and Treatment of High Blood Cholesterol in Adults, "Executive Summary of the Third Report of the National Cholesterol Education Program (NCEP) Expert Panel on Detection, Evaluation, and Treatment of High Blood Cholesterol in Adults (Adult Treatment Panel III)" JAMA (2001) 285(19):2486-2497.
Frazer et al., "The apolipoprotein(a) gene is regulated by sex hormones and acute-phase inducers in YAC transgenic mice" Nat. Genet. (1995) 9(4):424-431.
Fredrickson et al., "A system for phenotyping hyperlipoproteinemia" Circulation (1965) 31:321-327.
Fredrickson et al., "Fat transport in lipoproteins—an integrated approach to mechanisms and disorders" N. Engl. J. Med. (1967) 276(1):34-42.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Gautschi et al. "Activity of a Novel bcl-2/bcl-xL-Bispecific Antisense Oligonucleotide Against Tumors of Diverse Histologic Origins" J. Natl. Cancer Inst. (2001) 93:463-471.

(56) References Cited

OTHER PUBLICATIONS

Geary et al., "A nonradioisotope biomedical assay for intact oligonucleotide and its chain-shortened metabolites used for determination of exposure and elimination half-life of antisense drugs in tissue" Anal. Biochem. (1999) 274(2):241-248.

International Search Report for application PCT/US2013/042532 dated Dec. 6, 2013.

Jones et al., "RNA quantitation by fluorescence-based solution assay: RiboGreen reagent characterization" Anal. Biochem. (1998) 265(2):368-374.

Kamstrup et al., "Extreme lipoprotein(a) levels and risk of myocardial infarction in the general population: the Copenhagen City Heart Study" Circulation (2008) 117(2):176-184.

Koornneef et al., "Apolipoprotein B knockdown by AAV-delivered shRNA lowers plasma cholesterol in mice" Mol. Ther. (2011) 19(4):731-740.

Koschinsky et al., "Structure-function relationships in apolipoprotein(a): insights into lipoprotein(a) assembly and pathogenicity" Curr. Opin. Lipidol. (2004) 15(2):167-174.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Kraft et al., "Frequency distributions of apolipoprotein(a) kringle IV repeat alleles and their effects on lipoprotein(a) levels in Caucasian, Asian, and African populations: the distribution of null alleles is non-random" Eur. J. Hum. Genet. (1996) 4(2):74-87.

Kumar et al., "The first analogues of LNA (locked nucleic acids): phosphorothioate-LNA and 2'-thio-LNA" Bioorg Med Chem Lett. (1998) 8:2219-2222.

Leeds et al., "Quantitation of phosphorothioate oligonucleotides in human plasma" Anal. Biochem. (1996) 235(1):36-43.

Leumann et al., "DNA Analogues: From Supramolecular Principles to Biological Properties" Bioorganic & Medicinal Chemistry (2002) 10:841-854.

Lippi et al., "Screening and therapeutic management of lipoprotein(a) excess: review of the epidemiological evidence, guidelines and recommendations" Clin. Chim. Acta. (2011) 412(11-12):797-801.

Maher et al., "Comparative hybrid arrest by tandem antisense oligodeoxyribonucleotides or oligodeoxyribonucleoside methylphosphonates in a cell-free system" Nuc. Acid. Res. (1988) 16(8):3341-3358.

Martin, "New acces to 2'-O-alkylated ribonucleosides and properties of 2'-O-alkylated oligoribonucleotides" Helv. Chim. Acta. (1995) 78:486-504.

Merki et al., "Antisense oligonucleotide lowers plasma levels of apolipoprotein (a) and lipoprotein (a) in transgenic mice" J. Am. Coll. Cardiol. (2011) 57(15):1611-1621.

New England Biolabs 1998/99 Catalog (cover page and pp. 121 and 284).

Orum et al., "Locked nucleic acids: A promising molecular family for gene-function analysis and antisense drug development" Curr. Opinion Mol. Ther. (2001) 3:239-243.

Reynolds et al., "Rational siRNA design for RNA interference" Nature Biotechnology (2004) 22(3):326-330.

Rifai et al., "Apolipoprotein(a) size and lipoprotein(a) concentration and future risk of angina pectoris with evidence of severe coronary atherosclerosis in men: The Physicians' Health Study" Clin. Chem. (2004) 50(8):1364-1371.

Sanghvi et al., "Heterocyclic Base Modifications in Nucleic Acids and Their Applications in Antisense Oligonucleotides" Antisense Research and Applications (1993) pp. 273-288.

Schultz et al., "Effects of inhibition of interleukin-6 signalling on insulin sensitivity and lipoprotein (a) levels in human subjects with rheumatoid diseases" PLoS One (2010) 5(12):e14328.

Singh et al., "LNA (locked nucleic acids): synthesis and high-affinity nucleic acid recognition" Chem. Commun. (1998) 455-456.

Singh et al., "Synthesis of 2'-amino-LNA: A novel conformationally restricted high-affinity oligonucleotide analogue with a handle" J. Org. Chem. (1998) 63: 10035-10039.

Smith et al., "Comparison of biosequences" Adv. Appl. Math. (1981) 2(4):482-489.

Solfrizzi et al., "Lipoprotein(a), apolipoprotein E genotype, and risk of Alzheimer's disease" J. Neurol. Neurosurg. Psychiatry (2002) 72(6):732-736.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.

Tsimikas et al., "Relationship of oxidized phospholipids on apolipoprotein B-100 particles to race/ethnicity, apolipoprotein(a) isoform size, and cardiovascular risk factors: results from the Dallas Heart Study" Circulation (2009) 119(13):1711-1719.

Wahlestedt et al., "Potent and nontoxic antisense oligonucleotide containing locked nucleic acids" Proc. Natl. Acad. Sci. USA (2000) 97: 5633-5638.

Woolf et al. "Specificity of antisense oligonucleotides in vivo" PNAS (1992) 89:7305-7309.

Yuan et al., "Hypertriglyceridemia: its etiology, effects and treatment" CMAJ. (2007) 176(8):1113-1120.

Zhang et al., "PowerBLAST: A New Network Blast Application for Interactive or Automated Sequence Analysis and Annotation" Genome Res. (1997) 7:649-656.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

International Search Report for application PCT/US2013/041701 dated Nov. 12, 2013.

Graham et al., "Antisense inhibition of apolipoprotein(a) in cynomolgus monkeys significantly reduces plasma apolipoprotein(a) levels without affecting plasminogen or other major lipid classes" Circulation (2012) 126(21): abstract A11050.

Graham et al., "Antisense inhibition of apolipoprotein(a) in cynomolgus monkeys significantly reduces plasma apolipoprotein(a) levels without affecting plasminogen or other major lipid classes" Poster from American Heart Association (AHA) 2012 Scientific Sessions, presented Nov. 5, 2012.

Graham et al., "Antisense inhibition of apolipoprotein(a) in cynomolgus monkeys significantly reduces plasma apolipoprotein(a) levels without affecting plasminogen or other major lipid classes" Powerpoint presentation from American Heart Association (AHA) 2012 Scientific Sessions, presented Nov. 5, 2012.

Lippi et al., "Antisense therapy, in the treatment of hypercholesterolemia" European Journal of Internal Medicine (2011) 22(6): 541-546.

Graham et al., "Antisense inhibition of apolipoprotein(a) in cynomolgus monkeys significantly reduces plasma apolipoprotein(a) levels without affecting plasminogen or other major lipid classes" Powerpoint presentation from American Hearth Association(AHA) 2012 Scientific Sessions, presented Nov. 5, 2012.

SEQUENCE LISTING

<160> NUMBER OF SEQ ID NOS: 134

<210> SEQ ID NO 1
<211> LENGTH: 6489
<212> TYPE: DNA
<213> ORGANISM: Homo sapiens

<400> SEQUENCE: 1

| | | | | | |
|---|---|---|---|---|---:|
| aggtaccttt | ggggctggct | ttctcaagga | agcccagctc | cctgtgattg | agaatgaagt | 60 |
| gtgcaatcgc | tatgactggg | attgggacac | actttctggg | cactgctggc | cagtcccaaa | 120 |
| atggaacata | aggaagtggt | tcttctactt | cttttatttc | tgaaatcagc | agcacctgag | 180 |
| caaagccatg | tggtccagga | ttgctaccat | ggtgatggac | agagttatcg | aggcacgtac | 240 |
| tccaccactg | tcacaggaag | gacctgccaa | gcttggtcat | ctatgacacc | acatcaacat | 300 |
| aataggacca | cagaaaacta | cccaaatgct | ggcttgatca | tgaactactg | caggaatcca | 360 |
| gatgctgtgg | cagctcctta | ttgttatacg | agggatcccg | gtgtcaggtg | ggagtactgc | 420 |
| aacctgacgc | aatgctcaga | cgcagaaggg | actgccgtcg | cgcctccgac | tgttaccccg | 480 |
| gttccaagcc | tagaggctcc | ttccgaacaa | gcaccgactg | agcaaaggcc | tggggtgcag | 540 |
| gagtgctacc | atggtaatgg | acagagttat | cgaggcacat | actccaccac | tgtcacagga | 600 |
| agaacctgcc | aagcttggtc | atctatgaca | ccacactcgc | atagtcggac | cccagaatac | 660 |
| tacccaaatg | ctggcttgat | catgaactac | tgcaggaatc | cagatgctgt | ggcagctcct | 720 |
| tattgttata | cgagggatcc | cggtgtcagg | tgggagtact | gcaacctgac | gcaatgctca | 780 |
| gacgcagaag | ggactgccgt | cgcgcctccg | actgttaccc | cggttccaag | cctagaggct | 840 |
| ccttccgaac | aagcaccgac | tgagcaaagg | cctggggtgc | aggagtgcta | ccatggtaat | 900 |
| ggacagagtt | atcgaggcac | atactccacc | actgtcacag | gaagaacctg | ccaagcttgg | 960 |
| tcatctatga | caccacactc | gcatagtcgg | accccagaat | actacccaaa | tgctggcttg | 1020 |
| atcatgaact | actgcaggaa | tccagatgct | gtggcagctc | cttattgtta | tacgagggat | 1080 |
| cccggtgtca | ggtgggagta | ctgcaacctg | acgcaatgct | cagacgcaga | agggactgcc | 1140 |
| gtcgcgcctc | cgactgttac | cccggttcca | agcctagagg | ctccttccga | acaagcaccg | 1200 |
| actgagcaga | ggcctggggt | gcaggagtgc | taccacggta | atggacagag | ttatcgaggc | 1260 |
| acatactcca | ccactgtcac | tggaagaacc | tgccaagctt | ggtcatctat | gacaccacac | 1320 |
| tcgcatagtc | ggaccccaga | atactaccca | aatgctggct | tgatcatgaa | ctactgcagg | 1380 |
| aatccagatg | ctgtggcagc | tccttattgt | tatacgaggg | atcccggtgt | caggtgggag | 1440 |
| tactgcaacc | tgacgcaatg | ctcagacgca | gaagggactg | ccgtcgcgcc | tccgactgtt | 1500 |
| accccggttc | caagcctaga | ggctccttcc | gaacaagcac | cgactgagca | aaggcctggg | 1560 |
| gtgcaggagt | gctaccatgg | taatggacag | agttatcgag | gcacatactc | caccactgtc | 1620 |
| acaggaagaa | cctgccaagc | ttggtcatct | atgacaccac | actcgcatag | tcggacccca | 1680 |
| gaatactacc | caaatgctgg | cttgatcatg | aactactgca | ggaatccaga | tgctgtggca | 1740 |
| gctccttatt | gttatacgag | ggatcccggt | gtcaggtggg | agtactgcaa | cctgacgcaa | 1800 |
| tgctcagacg | cagaagggac | tgccgtcgcg | cctccgactg | ttaccccggt | tccaagccta | 1860 |
| gaggctcctt | ccgaacaagc | accgactgag | caaaggcctg | gggtgcagga | gtgctaccat | 1920 |
| ggtaatggac | agagttatcg | aggcacatac | tccaccactg | tcacaggaag | aacctgccaa | 1980 |
| gcttggtcat | ctatgacacc | acactcgcat | agtcggaccc | cagaatacta | cccaaatgct | 2040 |
| ggcttgatca | tgaactactg | caggaatcca | gatgctgtgg | cagctcctta | ttgttatacg | 2100 |

```
agggatcccg gtgtcaggtg ggagtactgc aacctgacgc aatgctcaga cgcagaaggg   2160
actgccgtcg cgcctccgac tgttaccccg gttccaagcc tagaggctcc ttccgaacaa   2220
gcaccgactg agcaaaggcc tggggtgcag gagtgctacc atggtaatgg acagagttat   2280
cgaggcacat actccaccac tgtcacagga agaacctgcc aagcttggtc atctatgaca   2340
ccacactcgc atagtcggac cccagaatac tacccaaatg ctggcttgat catgaactac   2400
tgcaggaatc cagatgctgt ggcagctcct tattgttata cgagggatcc cggtgtcagg   2460
tgggagtact gcaacctgac gcaatgctca gacgcagaag ggactgccgt cgcgcctccg   2520
actgttaccc cggttccaag cctagaggct ccttccgaac aagcaccgac tgagcagagg   2580
cctggggtgc aggagtgcta ccacggtaat ggacagagtt atcgaggcac atactccacc   2640
actgtcactg gaagaacctg ccaagcttgg tcatctatga caccacactc gcatagtcgg   2700
accccagaat actacccaaa tgctggcttg atcatgaact actgcaggaa tccagatcct   2760
gtggcagccc ttattgttta tacgagggat cccagtgtca ggtgggagta ctgcaacctg   2820
acacaatgct cagacgcaga agggactgcc gtcgcgcctc caactattac cccgattcca   2880
agcctagagc tccttctga acaagcacca actgagcaaa ggcctggggt gcaggagtgc   2940
taccacggaa atggacagag ttatcaaggc acatacttca ttactgtcac aggaagaacc   3000
tgccaagctt ggtcatctat gacaccacac tcgcatagtc ggaccccagc atactaccca   3060
aatgctggct tgatcaagaa ctactgccga atccagatc ctgtggcagc cccttggtgt   3120
tatacaacag atcccagtgt caggtgggag tactgcaacc tgacacgatg ctcagatgca   3180
gaatggactg ccttcgtccc tccgaatgtt attctggctc aagcctaga ggcttttttt   3240
gaacaagcac tgactgagga acccccggg gtacaggact gctactacca ttatggacag   3300
agttaccgag gcacatactc caccactgtc acaggaagaa cttgccaagc ttggtcatct   3360
atgacaccac accagcatag tcggacccca gaaaactacc caaatgctgg cctgaccagg   3420
aactactgca ggaatccaga tgctgagatt cgcccttggt gttacaccat ggatcccagt   3480
gtcaggtggg agtactgcaa cctgacacaa tgcctggtga cagaatcaag tgtccttgca   3540
actctcacgg tggtcccaga tccaagcaca gaggcttctt ctgaagaagc accaacggag   3600
caaagccccg gggtccagga ttgctaccat ggtgatggac agagttatcg aggctcattc   3660
tctaccactg tcacaggaag gacatgtcag tcttggtcct ctatgacacc acactggcat   3720
cagaggacaa cagaatatta tccaaatggt ggcctgacca ggaactactg caggaatcca   3780
gatgctgaga ttagtccttg tgttatacc atggatccca atgtcagatg ggagtactgc   3840
aacctgacac aatgtccagt gacagaatca agtgtccttg cgacgtccac ggctgtttct   3900
gaacaagcac caacggagca aagccccaca gtccaggact gctaccatgg tgatggacag   3960
agttatcgag gctcattctc caccactgtt acaggaagga catgtcagtc ttggtcctct   4020
atgacaccac actggcatca gagaaccaca gaatactacc caaatggtgg cctgaccagg   4080
aactactgca ggaatccaga tgctgagatt cgcccttggt gttataccat ggatcccagt   4140
gtcagatggg agtactgcaa cctgacgcaa tgtccagtga tggaatcaac tctcctcaca   4200
actcccacgg tggtcccagt tccaagcaca gagcttcctt ctgaagaagc accaactgaa   4260
aacagcactg ggtccagga ctgctaccga ggtgatggac agagttatcg aggcacactc   4320
tccaccacta tcacaggaag aacatgtcag tcttggtcgt ctatgacacc acattggcat   4380
cggaggatcc cattatacta tccaaatgct ggcctgacca ggaactactg caggaatcca   4440
```

| | |
|---|---|
| gatgctgaga ttcgcccttg gtgttacacc atggatccca gtgtcaggtg ggagtactgc | 4500 |
| aacctgacac gatgtccagt gacagaatcg agtgtcctca caactcccac agtggccccg | 4560 |
| gttccaagca cagaggctcc ttctgaacaa gcaccacctg agaaaagccc tgtggtccag | 4620 |
| gattgctacc atggtgatgg acggagttat cgaggcatat cctccaccac tgtcacagga | 4680 |
| aggacctgtc aatcttggtc atctatgata ccacactggc atcagaggac cccagaaaac | 4740 |
| tacccaaatg ctggcctgac cgagaactac tgcaggaatc cagattctgg gaaacaaccc | 4800 |
| tggtgttaca caaccgatcc gtgtgtgagg tgggagtact gcaatctgac acaatgctca | 4860 |
| gaaacagaat caggtgtcct agagactccc actgttgttc cagttccaag catggaggct | 4920 |
| cattctgaag cagcaccaac tgagcaaacc cctgtggtcc ggcagtgcta ccatggtaat | 4980 |
| ggccagagtt atcgaggcac attctccacc actgtcacag gaaggacatg tcaatcttgg | 5040 |
| tcatccatga caccacaccg gcatcagagg accccagaaa actacccaaa tgatggcctg | 5100 |
| acaatgaact actgcaggaa tccagatgcc gatacaggcc cttggtgttt taccatggac | 5160 |
| cccagcatca ggtgggagta ctgcaacctg acgcgatgct cagacacaga agggactgtg | 5220 |
| gtcgctcctc cgactgtcat ccaggttcca agcctagggc ctccttctga caagactgt | 5280 |
| atgtttggga atgggaaagg ataccggggc aagaaggcaa ccactgttac tgggacgcca | 5340 |
| tgccaggaat gggctgccca ggagccccat agacacagca cgttcattcc agggacaaat | 5400 |
| aaatgggcag gtctggaaaa aaattactgc cgtaaccctg atggtgacat caatggtccc | 5460 |
| tggtgctaca caatgaatcc aagaaaactt tttgactact gtgatatccc tctctgtgca | 5520 |
| tcctcttcat ttgattgtgg gaagcctcaa gtggagccga gaaatgtcc tggaagcatt | 5580 |
| gtaggggggt gtgtggccca cccacattcc tggccctggc aagtcagtct cagaacaagg | 5640 |
| tttgaaagc acttctgtgg aggcaccta atatccccag agtgggtgct gactgctgct | 5700 |
| cactgcttga agaagtcctc aaggccttca tcctacaagg tcatcctggg tgcacaccaa | 5760 |
| gaagtgaacc tcgaatctca tgttcaggaa atagaagtgt ctaggctgtt cttggagccc | 5820 |
| acacaagcag atattgcctt gctaaagcta agcaggcctg ccgtcatcac tgacaaagta | 5880 |
| atgccagctt gtctgccatc cccagactac atggtcaccg ccaggactga atgttacatc | 5940 |
| actggctggg gagaaaccca aggtaccttt gggactggcc ttctcaagga agcccagctc | 6000 |
| cttgttattg agaatgaagt gtgcaatcac tataagtata tttgtgctga gcatttggcc | 6060 |
| agaggcactg acagttgcca gggtgacagt ggagggcctc tggtttgctt cgagaaggac | 6120 |
| aaatacattt tacaaggagt cacttcttgg ggtcttggct gtgcacgccc caataagcct | 6180 |
| ggtgtctatg ctcgtgtttc aaggtttgtt acttggattg agggaatgat gagaaataat | 6240 |
| taattggacg ggagacagag tgaagcatca acctacttag aagctgaaac gtgggtaagg | 6300 |
| atttagcatg ctggaaataa tagacagcaa tcaaacgaag acactgttcc cagctaccag | 6360 |
| ctatgccaaa ccttggcatt tttggtattt ttgtgtataa gcttttaagg tctgactgac | 6420 |
| aaattctgta ttaaggtgtc atagctatga catttgttaa aaataaactc tgcacttatt | 6480 |
| ttgatttga | 6489 |

<210> SEQ ID NO 2
<211> LENGTH: 150001
<212> TYPE: DNA
<213> ORGANISM: Homo sapiens

<400> SEQUENCE: 2

| | |
|---|---|
| atctttcagc ctctatatta tttttattgtg atttttaatt tccttgaatt ggattttgcc | 60 |

```
attgtgctaa atcttgatga tcttcatttg tatccgtagt ctgaattata tttctgtcat    120
ttgagttagc tcagtcttgt taagaaccct tgttggaaaa ctggtgcagt tgtttggagg    180
acatatgacc ttctggccat ttgatttatt ggagttctta cgttggttct ttctcatgtc    240
tctgtgtggg tgtttcttta actgcagtgt agattgagta cagccaatag acttcttctt    300
tggaggtttt cacagggcca aggccttgta cagggtcttt atttgtagct gacttcttgt    360 cttggtttc atagtgggc atgttagcaa atagttttg ctgttgaagt tttggggtgt        420
gatccatttt ttattttaat gattgtgtat ttcctttata cctaaaacaa gcagaaaacc    480
agtaaaggtc tttgagtctc tgaattcata actccagcat tcatattgct tcctcaggta    540
agtggggttt tcacccagcc cttaaggggtg ttagattatt ttttatgtga aattagccag   600
attgtatttc taaacatgat gtaaaacaat aatgacaaaa gttataataa actagccttc    660
ttaccaaatc cacatgtcta atgtgtgtgg gagggtgtta ggcaggggac ctgcagctaa    720
gggagaggca gacaggcccc atggcccaa atctaggata gtatttggta ttggttgatg     780
ggtgagagaa agagagggaa catctgtgca ggatgtggta tcagcacctg gactacatct    840
tagggattcc ttcttcattt ttcagtatgc cctgacaata attatatcta tcagacttac    900
ccccttgacc actggaacac taagactgtt ttgggatctc tgcctgactt tctcagaggt    960
gctggtgagg acattatgag tctggaacct agaaaagcgt tctgactctg ctgactttct   1020
cagaggtgct ggtgaggaca ttatgagtct ggagccctag aaaagcgttc tgactctgcc   1080
actagccaga cagacctgga ctaggcacgt taactctttg tatgacttga ctccaacccc   1140
tcatttgtaa aaccagcatt ttcaagtggt gttttccaca tcagcctttt gcataagctg   1200
tcatttgaag aaaggttttt gtttgtttgt tttttgttta acaaaaaggt taaaaaccac   1260
tggtctagat aattgcaaag tttgctttcc tttttctgtg cttttttctac tattttaaa   1320 atgtcatcct ccttggtttc ttgatccccc tttctgcact cctgagtctg gaacactga    1380 ggccaactaa aaggaaactt ggcaaaagag gaacaccttt gggtgtgcca ggctgctccc   1440
agtgttttgc acttataaaa atttaaatgc tgcaaacctc taagacttag atattattgt   1500
tcctatttta caagtgagga acctgaggct cagagaaggt gcaggatggc acagggagac   1560
ctgaattgga accctggttc ccacttactg gctgtcggga cttagaaaag tcatgaactc   1620
tcattgattg ttttcttata tgaaatgggg gctgcagggt tgtcggggga gaaacaataa   1680
gaatgtgcat caagtgtcga gcacgtgcta cgcactccat catggcagct cctactaata   1740
tacagaatag agttgtatct aacatgactc tttcttgcaa gtgacagaaa tccaactta    1800 agatggatta agcaaaaaag gggaattctt gttgagctga aaagtcttta ggctcacatg   1860
atggccccag ggcccaggcc ctgtccagcc atgcagtagg catcatcctt gggcacaaag   1920
gtgagattct tgtggtggca gatgctgtgg cagctcttgc tttgccagga aagactgagg   1980
aaggccactg tccccattaa gtgaacaata gttggccagg tctgagaggt tgaacttggg   2040
tcacaggcct gtccctgaac ccatcactga ttggctccaa cctgcatcag ctattacatg   2100
ctagaggtgg aggcaggacc ccactcatac ccagaagggc aaagggtgga tccctcaaca   2160
ggattatggg atgtaggggtg atagactgct ggcagccaaa agcaaaca gatcctctcc    2220 aatacctcaa ctgatgaaag caccaagcta aaatcataag gatctgggtg tgaattctgg   2280
ctctaccatc ttccatgtga cattgggcag ttatttaatc tcttttagcc ttggctttct   2340
tacctgtact aacatataag gtgattgtga tgagcatcat catcgtcaac atcatcatca   2400
```

```
ccatccacat tgccaccacc actcccatta tcatcttcat caacatcatc accaccgcca    2460
ccatcaccat tatcattacc accaccgcta tcactattat catcaccctc aacatcatca    2520
ccatcatcac tatcatcacc accaccatca tcgttactac cactaccacc accatcatca    2580
ccacagccac caccaccatc accatcatta ctactcagca ccaccatcat cattccacca    2640
ccatcaccat cattccacca tcaccattat cattaccacc accactgtca ctattatcat    2700
caccctcaac atcatcacca ccaccatcat cattactacc accaccacca ccatcaccat    2760
catcatcatt ctaccaccat caccattatc atcaccatca ccatcaccac cgctatcatc    2820
atgataatca ttatcattac caccaccatt agcattatca ttaccaccac catcactatc    2880
actatcacca tcaccacgac cactaccacc atcaccaaca ccatcattac tacccaccac    2940
caccatcatc atcattccac caccatcaca attattacca ccaccaccat caccaccacc    3000
accaccatca ctatcatcat cagtagacat catataacca gtttgtagct ggcccagagc    3060
ctacttgctg tttcttctgc cccacaacca tccacacatt tctaaccacc atcccccact    3120
aggcttctgc ctcgcctggt ctcacctgca ggtccactga gaaaatgatt ctcagaacac    3180
taactagacc atgaggtgcc acaaaacata actcaggcct gttcatcaat tttctacatg    3240
tcaataatga catcaggtca attggcgttc tcagcctctg agaggaggt caaagttttc    3300 ctgctctccc cttcatgttt ccaggtgttc cctgacttgg atcaaatgca gagtttggag    3360
gtgttgaggc caaggggatt ttccaggtca gtcgtcatcc acaatcaatg gactgatcct    3420
gccgctggac ttaccctgct gccctctccc caaggcccca tcagggaggg cttcaatcct    3480
cttgtcacct gtggcctacc tgccctcaga gatgacatct ctatgtcggc cactggatgg    3540
cagcacctac tcgcagacca catcaacttt cctggcaact gcggtaggt tttcaccatt    3600 atcaggatgt ttgccttgct caaatagcag attctagaga acgtgctcc ctcacacaac    3660 tatgtagtcc aggtgatgca ccctctgccc gatgcttggt agtcagaaac ttccatcatg    3720
cagctctgcc cagattgagc tgagctggcc tctggagtga ggtgctggga caaacatctt    3780
ccatgctgct catgtcaact ccagatgcag tcaggtttct gaaccaaagt caatgatcta    3840
agtgcagtca aaggctctgg gggaagaaag agagagtgcc tcatctcttg cctgtgccat    3900
gctcgcaaag caaggatttt tgcaaaattc taatgaaagc tgggcttgca aaattagaaa    3960
actggattat ttgtgagaac actgaaacat ccctgggtgt gtccatctgg aaaaacagca    4020
tttcctctgg caattttgca accgttctat ttgaatttgg caaagaaaat aaagcagttt    4080
ttcacaaaag aataaacaca accaggagaa tcttcactct cccaaattgt caaagaagta    4140
taaattagaa aatgaatcag gacaatttca acctgttaga ttagctaata tttaaaaatt    4200
gaacactcat acaagtgtgg tgaagtgatt gttttctagt gacattttac actgtcataa    4260
ccttctagaa aataaattgg cagtgttatt gggagacaga aatatgtcta tataatttat    4320
gggaacttag gctcagaaaa tattaaggaa taagaatgaa ctttatgaac aaagatgtgg    4380
agggttggaa gcaagagggg ggccaacgcg cacggggagg aagcatttgg gcagtgactc    4440
cgcagaccca ggctcaggtt gaactagaca acctccttac acctcagttt ccttaactgt    4500
agagcaggag tgatggaact gcctgtttca taggactgtt gtgaggatga agtgagatac    4560
accacattat aagcttgtgc ctggaaagga taatgcttag taaatgatga ctattctttt    4620
ttattgcaat aaaatgtaca cagcgtaaga gttactattt taaccatttt tgcagggtac    4680
caccaagtgg catttagtac attcacagtg gtgtgcaacc atcatcatat ttccagaata    4740
ttttcctcat ccccaaagga aacctcatgc tcattaatca gtagctctcc tttaaaatat    4800
```

```
tagttatgaa gatcatagca ctatacaaaa ctcattatgt aatgttgagt gaaaaaatca   4860
gggtgtgaaa ttttgtgata tgatgtaatt agtgaaagaa gcatacaaaa agtctgaaaa   4920
tataaaaaca atagcaattg catttctcag actctacatt taaacattat tctttatggt   4980
tttaaaagca aagaaaaagg taagaaaaca acaaccaacc gcaaagcacc atgacaaagc   5040
tcagattgtt aaatccaggt ttttggaaca tagactctta tatgacgttt acactctcca   5100
gggttcagag agtctggcag cattgggagc tgccttgtgt tctacagcct cacggacaga   5160
caggaggtcc atcaccactg ctctgttctt ctggagtttc cttgtgaaca tgttgtggac   5220
gtagttacca tttctttcat cttttttaaac acaggtacct tgggggctgg ctttctcaag   5280
gaagcccagc tccctgtgat tgagaatgaa gtgtgcaatc gctatgagtt tctgaatgga   5340
agagtcaaat ccactgagct ctgtgctggg catttggctg gaggcattga cagttgcaag   5400
gtaagaaaag atcaagagac caaagttagt cttgtgctct cctgtctcag tctcagtccc   5460
ttagacttga gtcccaaagt agcgaattca agtaggattt aatcaatgga agaccccagt   5520
ctaagtgttg ctcagaaact ccctagatct gtcccaaatg tatattcaga tcatccaagg   5580
ggacttcttg gggcttgagt tccagatcag cagcaaggga gccataagtg ccataactac   5640
ctcagaccac tcaccctcct ggggtgtccc ggtggccagg gactaaagtg gtgattttc    5700 tggtagggaa ggaggtagag ggtacaggac agagactaac tgcacacaat atctgagact   5760
ggagctcaga tattgctgat gatcagagtt ggcgtgtctc cccaattgat ttacaactgg   5820
ggcttggata ctgttttaaa cgggaggagc ctcctaacca tcttgacaca accactgacg   5880
tgactacact agagatagac tctttccact taattctacc actcttgctt tacttcatga   5940
gaacgaaaat gtaagattgc accatgaatt catttgcgga aagattgata ctatgctttt   6000
attttatttt attttatttt attttatttt attttatttt attgagactc tcaccccggt   6060
tgaagtgcac tgacgtgatt ttggctcact gcaacttcca cctcctgggt tcaagtgaat   6120
actccagcct cccagtagc tgggattaca ggtgcccacc accacgcctg gctaatttt    6180 gtatttttag tagagatggg gtttcaccac attggcctgg ctggtctcaa actcctgacc   6240
ttgtgatcca cctgtcttgg cctcccaaag tgctgggatt acagagttga gccaccgcac   6300
tcgaccctat gttttatttt taaaaatatt tatttattta tttaagccac aactactaga   6360
ataggaagga ttgatatttt attaattta tttggtattt attattttt tttctttcct     6420 gagacattct tgctctgtca cccaggctgg agtgcagtgg cacattcttg gctcactgca   6480
acctccatct cctgtgttca agcaattcta gtgcctcagc ctacttagta gctgggatga   6540
ctggcatgtg cctccacacc cagctaattt ttgtattttt tgtagagaca gggttttggc   6600
atgttgccca ggcttgtctc aaactcctgg cctcaggtga tccatctgcc gtggcctccc   6660
aaaatgctgg gattataggc atgagccacc accccctcct ggaaggattg atatcttata   6720
acataattta taattacaga aaacatgtga gttcactagg aataaataaa ttttgaagat   6780
aataaaagat tttcacttat gttgtcattt cggcacagtt tggtatagga tgtggagatg   6840
ttaacattta tacctagctt gctcgtaaac taagacctga aagggttgtg tctatcagct   6900 gcaccctgg gtagcgacac aacctcggga aggcctcagc ccctcctcg tacagcactg     6960 cctgttggaa agcttgaggg aggctatgga tgtgcagcac ttggcagagg gtctggtcat   7020
ggaagttacc agcaaatatg agctactttt atgattttat tttatccaaa agaaagagaa   7080
tgaaagaaga ggggaggaaa caagactaat caggaaagat gaaggtctag gggtgaggga   7140
```

```
aggagtaagg agacataaag gcaatgtgga gcagctgagg ggggaaatgg ctttcaccac   7200
ttcccagcat ctattgacat tgcactctca aatattttat aagactctat attcaaggta   7260
atgtttgaac cctgctgagc cagtggcatg ggtctctgag agaatcatta acttaatttg   7320
actatctggt ttgtgggtgc gtttactctc atgtaagtca acaatgtcct gggattggga   7380
cacactttct gggcactgct ggccagtccc aaaatggaac ataaggaagt ggttcttcta   7440
cttcttttat ttctgaaatc aggtaagaca tagttttttt aaattataag aattattttt   7500
tctcccacaa tgtagtaaaa atacatatgc catggcttta tgtgcaattc atttaatttt   7560
tgattcatga aattcccagt tcaaaatctt gtatatgatt gaaaattct taaaaaata    7620 agtttaattt ccccgtgaag actgtcacgg tgctggaatg aatgggcaga aaaataatg    7680 gttgattttt ctaatctaaa agagtgtgcc tacatgatgg ccagtctggc tgaaaaataa   7740
atagccattg tagctaacta tgcaaaggat ggctaagctc ttcgcttggt tctcagtttc   7800
attaatttat atcatctctg ttcaggtgcc atgctcccct cactagcaag ttgaaacaat   7860
gaaataactc tttgaatatg tttggttcct tgacctgttc atggagtggg actcagcatt   7920
tctctctttg ttatggcctg agtaaggctt ccatcggta tacatttgct tcttatccct    7980
ggagaaatta tacacatcca tttgccagat gatatacgca tataatgatt caacaaatac   8040
tcagggtatt tgttgagtgg gttaggtccc cacatttta tacatacata cacacataca    8100
caccgtgtgt gattgtgaat gtaagtgtgt gtcctttaca aatactagct tatttagctc   8160
atggtatagg tagggtagca tagtcatccc cattttataa acaaagaaat ctagacttag   8220
gaaaatcatg ttatttgtct cgtgaccaaa ttcccaaatc aaggaaataa agaaacctgg   8280
atttaagcca gatttccaag aaaaaatcta gggctcttct cacttttta tctttgttcc    8340 aacatttgaa aaaataaatc taaacacatt ccaatgtaac tgaagagcag gttaattgtt   8400
tgccacttgc agaatccaat taagaagaga gaagtctggt ataagaaag tgatttgctt    8460 ccaaagctag cttaggggaa gaaatgcagc agtcctgccg tactacttca ctttaggagc   8520
agaaagtggc acttttaaaa ggcaacagag gaggcgagca aggattcagg ggtccatgct   8580
agcttgggca ccttatccac caggtagttg agcagttgcc tgctggtgcc tttgtgagca   8640
gggtgttgtc ccttgaggca aatctctgga gggtgagagt tttgtagtgg gcatgctttg   8700
gtttataaat cacctgtgaa ctcaggagtt ccatcttgaa gcacatacat agttagatga   8760
acttgccctg cagggagagt ctgatgaaag ggaggtagat gcttgcaatt taatctataa   8820
attaccagat aaaattttac aagttgactt taaagtcaaa cacatttgaa tttagtggaa   8880
gccattcaag aaaatatcaa agaaaataca gagcaggaga agattaagca aagagttttt   8940
tggggaaatt ggtgtctatg tctgtgtgtg taggagtgc aggggatatg aatattctat    9000
ttcagcccat ggaaactagg atgtagatca ctgtgaactt attcagcagg ctacacccaa   9060
aggctagaac aaacttctct gccacaggat taacatatgt tttaatcgac ctgggggca    9120 cattctctga taagctcttt tggaaagcca ggctttctgt ggacgtgtta tctttccaat   9180
gtgtgctgga atgcccgggg agaggaaaaa gtttctttta cagccatgct cagtgagaag   9240
cggagaaaca tcttctattc acaaattgct aagtctttta cacatgcaaa tatgcataca   9300
cattcacaca ccacagtgag gaagaaattc tcacaccatt aataaaatac atttacttca   9360
gtagcaatat acatctacat tttgcctata atataaagt attttcccta ttaaaagatt    9420
tgtttaatgt ttcttcacca acaaataaac cctattaaat ccccattgcc atatgagccc   9480
tggaggtgaa tcagagaaac aaaaggattg tggaaaaatc atcaggttaa aaaagaaaa    9540
```

```
attgattctg ttttgggata tttcctagca acatgagctg gggaggggat ctcagcagtg    9600
atgctctatg aagcataata aaatgacaca gttacaggta acttagttaa aggggggaaat   9660 aaatggaagt ttcctctttt tgaatatcaa ttgtagcctg ctctgctaca tttcaaaaac    9720
actcttcaaa atgtttaact gaactcactg taggaagcac cttattaatt tattgtgtgt    9780
tttgaagtca cactgtgagc tatagaattt acccaagcac aactcttcct ggaaaagaga    9840
gttcaaatga gaaacagtgc ggggtgaaga catggatatg gcctaaaat atctatttct     9900 caatgatatt ttgatatatc tatcaagtgc ttttttagtgg attaggttca gaatgcatca   9960
gccaatgcct gttcaataat ccagttttcc agcatagagc atattaaatt gaggaaggac   10020
aaagtcacag aggtggggag caggtggact gtggccaagg actttgcatg aaacagtgag   10080
cgtgcatcct cctccttgcc ctgccctcat ggtctgtgta ctctcaggag gtcaggacag   10140
gcctttctga gaatgagaat ctgttcatct gcctttctac tggatacttg tcatcggcat   10200
acaaacacat gttctctgca gtgtgtcatc tttcagaacc tcccctgacc ctgtattccc   10260
tagaagtctc gctgctttca gagccaggct tctctcctgc tgccacccccc actgctcttc   10320 tagtcactct ttaacccact ccatctgcat gtggccccca ccacacccct caaagtggtc   10380
aaggttgtcc tgttgcttaa ttccatggaa gcttggctat cttcatttta ttagcctctt   10440
ttggcctctc accctgtgaa aatcactaca ttttgtgcca gagatggagc tggcatctcc   10500
aggcttggaa gagggctgct gaagctcagc caggtgtcct aaggagcctc aggacagggg   10560
atgctcagta gccttgcaat gggaacacag ctgagcccca cttggccacc ctttgccaca   10620
accaggcaga aagcagcttt tgaacagatt tgttgcctca gatttgatct caaagaaaaa   10680
tcgtgggcag tattggtccc aggttctgct ttttacaat ttcctctgaa atctggatgc    10740
ctatcaacac cttggaaaaa ctgaattctc cccaactaat agtggtgtgt cactgtagta   10800
agcctagtac aaaaatggcc ttctttgtgg aggagcttca tatcctccat ttttttttg    10860 cttaattttt gcccaagatg agaacataat ttagttcact ttttatttat tcccaacatc   10920
atccatgcac caacatttttt gtaactaaag gagggaccat tcagaagatg cttatcaact   10980
gtcaaagtga cagtgttaca accaatgcac atattgtaag aaatcaaaca atggcctcca   11040
aggttcattt ctacacaggg attagcagat caacatcaat cttggcaaca cagttgccac   11100
tgatggtgtc ttattttttt tatcatgaca tggcaatcaa gagcaaacat gatttattct   11160
tatttaagat tttatggtta gactaggcag atagctagat atgagcagga ggtggaagcc   11220
cctgagagaa tggaggtctg gagaatctga accccagag attacccaag tcctgcatgc    11280
tagacatgag tggaggaggg ggaataccta ggtagaaaag aatgccccctt aagatgccca   11340 gcagtcgctc actgtgcagt taactttca gaatgctgct agatacatgc tgataggag     11400 ggaagagggc aaaggagaaa ttcctaagag atacacggtt gcagttagta tacatctgag   11460
tgctatacaa ccttctttgg gtggtggcaa gaagcaatgc agccattacg tagaattcat   11520
atcaaacacc tgtatcacag gtgttaaaga aacaagaaac attgtacttc ttgtattctt   11580
aataatgatt tgcaatattg tctttagtat cactgcaaac ctctataaat atgattttta   11640
aaaagtattt ctttaggttg gaattacttc tacgcattga cttatcttcc tgggtttcat   11700
tagccgtacc cgttgtactt tcttccttac cactgtttat ctcaaactct tgagattaaa   11760
gtatgggctc aggagggagc gaggagcttc aggactctca cggacctcca gcacagtgta   11820
gctgccttat ggaaaagtgg ccacactgtt ttctgcactg gtccctgccc ctactattcc   11880
```

```
tcactgggca gagcacagcc accctggccc tgcctgaaca ttttagtcag tgttggctct   11940
gtgcttctct ggggaggaaa tccaagagac aacccacagc ccctctgcca tttcagctgc   12000
agcagtacca ccgttaatgc ccttgggctt gagaagaag ggacctggcc acttccctga    12060
cacctccagc acacagcagg gaaagaattc cagtttctct ttcttgtgag ctttcacctg   12120
ctactcttca ccaggcaagg ctcctggctt gggcccacag tgcaggcacc tcgaactcag   12180
ttgaacattt ccactggctg cactctgtgt ttttgtgggg tgaagctccc agaggtgact   12240
gaaagtcctt ctgccactaa cactgcagtc atactgccct tgctgtactt ggactaggga   12300
aggaaaaaag atcctgagtg ctttactcac accccagtgt gccccagcca ccctatggaa   12360
aagaggccag tgtgtcatcc ctgcaagcac cctgaggccc ctgcccctgc tgcccccaag   12420
ctgtagagcc agaatataaa gctggcagaa aaatgtaaaa aggctagact ggcttagcct   12480
cccagcctac atctttctcc tgtgctggat ccttcctgct cttgaacatc ggactccaag   12540
ttcttcagct gtgggacttg gactgtcttc cttgctcctc agattgcagg tggcctatta   12600
tgggaccttg taatcttgtg agttaatacc acttaataag ctccccttg tgtgagtata    12660 tctatatcta tagatagata taggtatact cactatatat acacatatat acatatactc   12720
tctctctctc tctctcatat atatatatat ataatctcct attagttctg tccctctaga   12780
gaaccccgac taatacagat tttcatacca gaagtggttc ttgaggaaca gaatattaag   12840
gatggaattc tttcattggt tttgggactt ctggtgttgg ctgattaata tgattagacc   12900
aaaaaatgct aaggactcta cttctaatag tatggagaac actgatagta cttggcctga   12960
attgtttaga gagttatgca aaataaatgc atttgacact actgattcat cacttatgag   13020
aggcaaggag tttagtgact ctatacataa tacctttgac tatatgtgga gaaccaagga   13080
acataatgaa gttggttgat tgctcctaag ttctctggag aaagagatga agaaaatga    13140 tgatctcagg ggatctgtct cccaccttca gaagcagata ctgagccaca aatctgctaa   13200
gattgccctg aatgagagtt ttaactcctg tagagaaaga gttgaaattg tgaaaaaaca   13260
gagacaagct gttatcatgc gagtagctga tctgcaacaa gaggtgcatg cacagccttg   13320
ccaggtgttt actgttaaag tgagggcatt gactggaaaa aaatgggacc ctggaacttg   13380
gagtggggat gtgtgggaga accctgatga agctgaggac actgagtttg tgaactctga   13440
tgaaactttt ttgccagaag aaacagtttc cccatcccca gtagtggtaa catcccctcc   13500
ctgacccgtg ctgccattag cctttccacc tttgtctgag gatgtaaacc ctgcactgct   13560
tgaggcaaca gtgatggcct tccctgaggc agctgccagg caagataatg ttgattctcc   13620
tcaagaggca ccctaatgc ccctgaatgc ttctagacct ataactaggc taaattcctt    13680
gcgggcccca gaggtgaggt tcagagtgtg acccatgagg aggtgcatta tactctaaaa   13740
gaactgctta agctttctaa tttatattgg cagaaatctg gagaacaggc atgggaatgg   13800
atattaaggg taagggataa tggtggaagg gacatagagt tggatcaagc tgaatttatt   13860
ggtttggccc tactaagtag ggattctgca tttaatgttg cagctcgggg acttagaaaa   13920
ggttctgata gggccgggag cagtggctca cgcctgtaat cccagcacct gggaggcgg    13980 gggcgggcag atcacgagat caggagattg agacaattct ggctaaaatg gtgaaacccc   14040
atctctgcta aaaatacaaa aattagctgg gcatggtgat gcgtaactgt aatctcatct   14100
acttgggagg ctgaggcaag agaactgctt gaacctgtga ggcagagatt gcagtgagcc   14160
aagatcgccc cactgcattc cagcctggta acagagcaag actccatttc caaaaaaaaa   14220
aaaaaaaaag ttataatagt ttatttgctt ggttagctga aatatggatt aaaagatggt   14280
```

```
ccaatgttag tgagctggaa atgccttggt ttaatgtaga ggaagtgatc caaaggctta   14340
gggagattag gatggtggag tggattagtc actttagacc tactcatccc agctgggagg   14400
gtccagaaga tacacccttg gccgaagctt tgtgaaatag atttgtgaga gcagcacctg   14460 tattttgaa gagcccgtaa ttgctcttct ctgtatgtca gatctaacag taggaaccac   14520
agtcactcaa ctacaaaatt taaatacaat gggaataatt ggatcctgag gtggcagggg   14580
ccaagtgttg gcactgaacc atcaaaggca aggtgggcat aactaccata atagacagca   14640
gaggcaaagc agccatcaga atagtctgac tcatgtagag ctctggcatt ggctaattaa   14700
tcatggtgtt cctagaagtg aaattgatgg gaaacctact gtattcctac ttgatttata   14760
taaacaaaaa actgccaggt agaatggact aaagactaat ctgaattata aaaacagaga   14820
atcatgggcc ctcaatcaat ttccagactc gaacctgtta cagttccaga acccactgaa   14880
tgaaggggag gctggatccc cttgaggaag acaccacta ggctactgac aacttatgct   14940
gttactcttt ctcccatcct tccctaagga gacctctggc cttttaccag ggtaactgtg   15000
tgtactggag aaagggaagt aatgagacat ttcagaaagt actggacact ggctctgagc   15060
tgacgttgat tccagggtac ccaaaacgtt attgtggttc cccagttaaa gtagggcctt   15120
atggaggtta ggtaattaat ggagttttag ctcatttctg acttacagtg gttccagtgg   15180
gtccctggac ttatcctctg gtcattttcc cagtgccaaa atgcataatt tgtatagaca   15240
tacttattag ctggcagaaa tgccacattg gctccctgac tggtaggatg agggctatta   15300
tggtgggaaa ggccaaacag aagccattag agctgtctct acctagaaaa ataaaaaaat   15360
caaaaacaat atcccatccc tggagggact gaagtgatta gtgtcaccat caaggacttg   15420
aaagacgcag gggtggtgat tcccaccaca tccctgttca actctcccat ttgacctgtg   15480
cagaggacag atggatcttg gaaaatgatg gtggattatt ttaagcttaa ccaagtggtg   15540
actccaattg cagctgctct accagttgtg gttttgttgc ttgagcaaat taacacatct   15600
cctggtgcct ggtatgcagc cattggcttg gcaagtggct ttttctccat tcctgtccat   15660
aagacccacc agaagcaatt tgccttcagc tgacaaggcc agcattatac ctttaccacc   15720
ctacctcagg ggtgtatcaa ctctccagct ttgtgtcata atcttatttg gagagaccct   15780
gctcgctttt cacttccacg agatataaca ctggtccatt acattcatga cattatgatg   15840
attggataca gtgagcaaga agtagcaaac acactgaact tattggtgag acatttgtat   15900
gccagaggat gggaaataaa tccagctaaa atttagggac tttctacctc ggtaaaattt   15960
ctagggttcc agtggcatga gacctatgga gatattcctt ctaaggtgaa gcataacttg   16020
ctgcgtttgg cccctcttac aaccaagaaa gaggcacaat gcctggtggg cctatttgga   16080
ttttggaggc aacacattcc tcgtttgggt gtgttactct ggcccattta tcgagtgacc   16140
tgaaaggctg ccagatttaa gtgcagtcta gaacaaaaga aggctctgaa acaggtccag   16200
gctgctgtga aagctgctct gccatttggg ccacatgacc ccgcagatcc aatggtgctt   16260
gaggtgtcag tggcagatag ggatgctgtt tggagccttt ggcaggcccc cataggtgaa   16320
tcacagtgga gacctctagg attttggagc aaggccctgc cacttctgca gataactact   16380
ctccttttga gagacagcta ttggtctgtt attgggcttt ggtggtaact gaacgtttga   16440
ctgtgggtca taaagtcacc atgctacctg aacctgccta tcatgaactg gttgcttttct   16500 gacccatcta gccatgaagt gggtcagcac agcggcattt catcatcaaa ttgaagtggt   16560
gtgtatgtga tcgggcttga gcaggtcctg aaggcacaag taagttacat aaggaagtgg   16620
```

```
ctcaaatgcc catgttctcc actcatgcca ccctgccttc cctcccccag cctgcaccaa    16680
tggcctcatg gggagttccc tatgatcagt tgacagagga agggaagact aaggactggt    16740
tcatagatgg ttctgcacga tatgcaggca ccacccgaaa gtggacagct gcagcactat    16800
atccactttc taaatgcatg tgtacacttg tgctaagaaa atatctttat tttatttcct    16860 ttattttcc tttatcatgt gaccttagat ttatggactt cacatcagca tttaagcatt    16920
taagtgttgt tcatatcagc atttaaatat tgttaacctt atgtaataac ttttggtttg    16980
gggattggtg cgtttctggt tgtatgagga tagttgtatt atattaggca taattatgac    17040
cttattattg tctttatttg aagattatgt atgatttcag gatgtgtgta tgggttcaag    17100
ttgacaagga gttggacttg tgatggttaa tactgtcaac ttgattggat tgaaagatgc    17160
aaagtattaa tctcggttat gtctgtgagg gtgtggcaaa aggagattaa catttgagtc    17220
agtgggctgg gaaggcagac ccacccttaa tctgggtaca caccatctaa tcaagttcca    17280
gtgtggccag attgtaaagc agggagaaaa atgtgaaaag actagactga attagcttcc    17340
cagcctacat ctttctcctg tgccaaatgc ttcctgctct tgaacatcgg actccaagtt    17400
cttcagcgtt gggagttgga ctggcttcct tgctcctcag cttgcagagg gcctgttgtg    17460
gaaccttgtg atccgctgag ttaatactac ttaataagat ccctttata tacatataat    17520 atattatatt atatataata tatataaat attattata taatatatat aatatattat    17580
atattatata taatatatat tatatattat atataatata tattatatat aatatatatt    17640
atatattata tattatatat aatatatatt atatataata tatataaaat atatatatat    17700
cctattagtt ctgtccctct agagaaccct gactaataca atttatgtca ttaatctcat    17760
ttattgattt gtatacattg aaccaacctt atcccagg aataaaacct acttgattgt    17820
ggtggattag cttttgatg tactcttgga ttcaattgct ggtatttat tgagaatttt    17880 tgcatctgtg ttcatcaagg atattggctt gaagttttct tttttgttg ttccatatca    17940 gaatgatgac gacctcatag aatgagttag tctgtcctct tttatctttt ggaattgttt    18000
caggaggctt gatatcagct cttctttata tgactggtat actttggcta ggaatctctc    18060
tggtccaggg gttttctgg tgtaggtttt taattactga ttcaacttca gaactcatta    18120
ctcattattg agttctaaaa ctcactttca tgtactcttc aaaagactgt cttcttctgt    18180
tgttgagcgg ggtgttctct caaggtcgtt taggtgaagg tggttgctgg tgttcttctg    18240
tatccttact gcttgtcttt ctcttttttt attgactact gaggattaat ggtgatgtgt    18300
ccaactttaa ctctagatta gtctatttct cttttagatt gtaactctgt tttatatatt    18360
ttgaagctct gttgttaggc atgtgtattt ggattgttag gtcttcttga tgatgacctt    18420
tatcattatg taatgtttct tcttatctct ggaagtattc gttgttctga agtctatttg    18480
tgctgatatg aatacagcct tcacagctct attttcacta gtatttgtat atcttttct    18540 cagcttttaa attgagatgt tcagaccatt tgcattaaag tagttgttaa taggattaaa    18600
tttaaatcta ccattaagtt ggttatttct ctttgtccca tttaaacttt gttccttttt    18660
tcatattttt ctgccttcat ttatattgag tttatctcca cgacttactt attaaattaa    18720
tttttaatgg tttagtatt ttccacaatg tttataatat atactttgat ttttcacat    18780 tccaccttca aatgacagaa ttatactgga tatatagaaa tcttacatca ttgcacttct    18840
ccttcctccc tctcaaaatg ttgtgctatt gctctttgta atagaggctt acttctatta    18900
tgttatagct ctcataatac attgacacta ttttacccct gaataatcag ttgtttttta    18960
aagtgattat gactacaaat attttgaata atttctttat tttaccatttt ctggtgctcc    19020
```

```
ttatctttta cagtagatcc caatttccat ctggagtcac attctttctg tgaaaaacaa   19080
cctttagcat ttcttatagc acgggactgc tgttgctgtt gtcttccagc ttttctttgt   19140
ctgaagaagt ctttattttg ccttcagttt ttaaaagtga ttttgctgag tatagatact   19200
ggggttgagag tttcattcct tgtatcattt taacaatgat gttccattat attccgtttt   19260
gaatagtttc tgactagaaa tctgatcttt gtttctttgt attcaatagt tccttttttct  19320
ctgactgcct ttaagatatt ctcatctttg tttttcaaca gtttgactat aatttgttta   19380
ttattaactt tttgtattta ttctgcttga ggtttcctga gctccttgga tttgcagatt   19440
gttgattttt attgttttttg taaaattcat agccattatc tattctactg ttttgttttt   19500
tttttcactt ctctctctct gtattcttct ttttggactg taagtattca aatgttagat   19560
cattcatatt gcttcataaa ccttatatgc ttccttctgct tttttttttt tgtcaggaac   19620
tcttttttttg tatctgtgtt ggtttggata agttctagta gactatgttc aagtttatgg   19680
attattttgt tagttgtgtc taattgactc ctcagtgcat tcagagaatt cttcatctct   19740
gatattataa atctcttcct agcattttca tgttactctt ttctatagtt tccatctctt   19800
tgctgaaatt ctcccccctat ccatggatat tgtccacctt taccacaaga ttctttaaca   19860
tattaacata ggtatcatac aaacccaaac tgatagtttc cagatggtgt cttttctgag   19920
tctgtctgtc ttgattgctt tattatttaa cagtgactta tcttccctct tcagcttttg   19980
gtgtgtcttg taattgtttta atcaaacact gggtatcata aatggaggaa cagtagagat   20040
tgcagtaaat attatttatg ctttgaaatg ggcacccatc ttctgttgaa aatatgttt    20100
gtggtcaatt gagtcaacct agtaactggt tgaactgaat ttggcatttg tgcttgttgc   20160
ttttatctta aatgcaccac aggttttaaat tcctccagtg atgggttgct gctatctttt   20220
gcttagagtg gggcctgggg tgtggaagaa ttttctcagt gttcctatct attattagat   20280
tttagcagtc actgcatgcc tgcactacag aggggatatc ttcatacaca taatctaacc   20340
ccattgaaac tgctgtttct tcttaatgaa tgctcaatct ttggtggaaa taaacaaatg   20400
ctgtatctcc tggagccact tcagtcttag tcaggttctg cagggctttg aagggaatgc   20460
attctcagta ttccttgtgcc ttatttggat ggaacttgaa cctgtggtgg gtttggagag   20520
aaagagtagc agacgtctgc tatgttgcaa tgcaggatgc tgggcacaag aaaatttcca   20580
gtctctcctc caaggaaata agatttgatc atctacctat ccctgagaag tgaagggctt   20640
tgcctgcggt gctagatgca aaaccatttt tctccccccca ttgcccagaa acttaaggct   20700
ttggcttttc tgagcagtgg tctagggaat tgtgcaaggt tttcatattt gaccctgaca   20760
gcccatcacc acctacagct tgcagtgcca aatgtatctc cctctgatct ctcctgtcct   20820
gtggtcctca tgaacattaa gaagagattt ctaaaaaaga gcttgcacat gagcatagtt   20880
tctggtgaga agaattctga tatgttaact tcctctaaac ttttaaataa aatatttcta   20940
agaattaaat aaagttctag aatgatatga atctattcct ttggttttttt gcacgtctgt   21000
ctgcctgcta atcaagagaa gagaatggtc gtaattctca gagactttttt cctgtttgtg   21060
tcataaatga cttcacattt ttttctgttc taagaactat tcagcttgat ttcttctgtt   21120
ttaattttag cagcacctga gcaaagccat gtggtccagg attgctacca tggtgatgga   21180
cagagttatc gaggcacgta ctccaccact gtcacaggaa ggacctgcca agcttggtca   21240
tctatgacac cacatcaaca taataggacc acagaaaact acccaaatgc gtatgtcatt   21300
aatcttacag taagcaaaac aaggtccaag taaaatttgt cttagaaaag gtgtgcgtca   21360
```

```
agctaacttc ttatgattaa attttttctca cacatagaat gcatggcaaa atgtctgaga  21420
aacattactt tgagcaaaga gtatgataga agagaaatgt taagctggct ctctttcctg  21480
agagtttgat aaaatcagga gaatatctgg cggtggtgag gccacaataa tggaaaatca  21540
gaatgtttag acagagtcag cttcaacaac actcactaaa ggtcaatgtg atctttaccc  21600
cttgaaattc tataattcta atctccaatt cctgaagtga aggttgtgtt ggccttttct  21660
gtcttggctc acaagtaaat gatatgtgca tatctatgga aaggcgaatc tatctttttc  21720
tatatctatg tctattccaa cgggtagaaa caccctgggt cctgagcacc agtggtctga  21780
aggaatacgg gttgccagga agagagaagc aaaggcagga aggcagatga aagtaagaaa  21840
tgagacagat gctaaacaat aaaaagtgcg ggaagataga cagaagctgg ggtctgacca  21900
caccatggcc agtctttcac acataagtga ctaccaaaga caagaaaaaa tgatttccgc  21960
ttgttggaca atagatggta gaggaccaag ggaattgcga gagagagaac aatgagatca  22020
actcaacaga tgcactggtt ttcttcctgg agacccttcc tgcactgaag ggcaggagat  22080
ggagcccaaa aaaaactgta gccatcttgc tgaacagagg agggacattg gagtttggga  22140
ttattcaggt ggctaggatt ttctaggcct gctaacaatg agaacagatt tgtggaggaa  22200
aggagttcta gaaatatgca tagaaatctc ctcgagtcat tggctaaaca tgaagctgca  22260
tgtacacaga aaatagatcc acaagaaagt agggcaaaga acatctacgg aagagcagca  22320 actcaatgg aacagtgagc tcaataaaca tgacagagct caaatagcac taaggatat  22380 tggagtttgg accacacaga ggagagagac ttcactgaac atcttgggca ttcagtagag  22440
acccaggaaa agccatactt taggagtaga attagtatat tcttagaata aaggcagctc  22500
cacacaaaca atagcaaaac tgaaaaggaa gtctccaagc atcagaatga tgtccaagtc  22560
aatgaactgc ctctgagagg aaaactcaac catctttaga ggtaaacatc aaagtcaagt  22620
ggctcagcta tgcagtatcc acagtgtgag gcctaaatat aaaacttgac tacacataga  22680
aaccttttag tgtgacccac aagcaggagg aaaatcagcc aatacaaaca gacccagaag  22740
agacagaaat gattagaatg gcataaaaat ttgacatatc actatataat aattgagttc  22800
taggatttaa gaaaacatga atatagaatg caacagacac cttatccaga gacagtaaga  22860
gtataaagag ccaaatcgaa gaactactaa gagatatgtc ttaaatgaaa aaattactag  22920
atggcctccc catctagtta gacatttcag aagaaaatac caaatgaaaa ataattgcat  22980
agaacctaca gaaccagata cacacataca aaacacacgc atgcatacac acacactcaa  23040
acatgtataa gcttacaaac acacacacac atccacaaat gctgaaaaat gaaatcaacc  23100
gagccacaca gacataaagg aaaacataaa aagatttcct acatgtggga agcaagtcac  23160 agaaagggg aaggagattg gaacagaaat atatactgaa agcaaggatg gctgaaaatt  23220
ttccaaatat aaagaagatt aaaaaatcac ggactcaaga agctcaatgg atcagaaaaa  23280
taatttctaa aatgacaatt ataggatgcc actgggtaca tagcagttca actgtcagag  23340
ggcaaagaca taatacacag aaaaatctcg taaggaacgg gaaaaacaaa aagctgtgtc  23400
ttgctagagg aacagtgata caagtgacta atgtgttccc atcagaaaca ctgcaacctg  23460
gacacaaaag aataacatta aagtaataaa cgtaagaaag aagagctcaa ctgagaaggc  23520
tacatccagc aataaaatgc cttgaagttc atccatgttg gaggaatgca cattgtgcac  23580 tccccctaaac aaagaaaccg gaaactgtaa gactttggaa tcagcaggct tatgtaacaa  23640
aagaggtgac cctaaggaat taaggagaag aagaatagaa caagagggga actttctgca  23700
gcctatataa tgaagaacct agcaattggc aaatgtagat gaaaatgcta catgtttttct  23760
```

```
tgatcaaacg tttatatctt tttaaatgag agttgacgag ttgaagcaaa atgataccaa   23820
tatatttaac tttaccatat gtagaagtaa aaatttgaac atgtagcata aatcatgtag   23880
ggattaattg gaagtgtacc actgtaagtt tcttacctca tgcacgatag tatgtaatac   23940
taataaaagg ttaatgtgtg ggttcaaagg gatattgcaa atcctagagc aatcacaaag   24000
tttttaactc tgaggtttgt tgtataataa caatatttta tgtattcaaa agagggaagc   24060
caaggaagaa aaaaaagtct ttaaagagct ctggctctta gtacatccag ttgctcattg   24120
aatgagcttc ctggaatgga gggtctggga ctgagactag gccacatgtg tagagccact   24180
agagacacaa tgttggatcc ccatggccca taatacattt cccatttcct caggcagcca   24240
caggtcatga atgtgaggat actgagaggt tggagcaacg ttcttgggag gcataaggaa   24300
gagcgaatgc ttcaagatcc ccgcagccca aactcctcag ctgctttgcc tcctaattca   24360
ttgttttttg ctcctccata gctgtccgac ctcttcagat ctcttagtct tcctgccatc   24420
ttcctttatg ccatgggacc cactgttctt tcaactcatc ccccagttct ggagtggctg   24480
tggacagcag aggatagact gagagcagga gagaaggtcc tgcccaggaa cccattctag   24540
agatactgca ttctgcctgg gagcaagttt tccagggcag cttttgagaag tcttgcagaa   24600 acaaacctac ttgaccgaca tgatatggga atgacagaca gtaatactat ttgcacaatg   24660
cttttccatg ggaaaggtag agccttttca ctaggttttg agtacatgga gtgtgagagt   24720
tgacctggaa aggttatcct ccttgatgcc atgttttctc tgaagaacta catgttcgtt   24780
gcaactccca cattagaata tgaagtccta ccgagagaga tacggagact agacagatac   24840
agatgcattt gcatgtgaat acacaatccc acaatacaga cgtcaaaacc cataccagtt   24900
attccagaga gatggattgg gcagaaggca gaaggagaat actctgatcg ttttttcggcc   24960 acgtgtgtgt gttatctcag tgtttctaag aagcgtttgc tactttagat ttttttattta   25020 aaaaaaatag taataatcta ttaagtatga gagatgtgca gagaggatta gtgatcgaga   25080
gccatttttg ctggtggcaa tcatatggta cttttaatgg gaatattaga aaggcaccgg   25140 taatgaccctt gttgcagcac aaaggagaga gtgtggggtg cccctgcatg ttgtcccacc   25200
tcttgtgacg tgtatcgttt tggaatttcc agtggcttga tcatgaacta ctgcaggaat   25260
ccagatgctg tggcagctcc ttattgttat acgagggatc ccggtgtcag gtgggagtac   25320
tgcaacctga cgcaatgctc agacgcagaa gggactgccg tcgcgcctcc gactgttacc   25380
ccggttccaa gcctagaggc tccttccgaa caaggtaagg agtctgtggc cagacatcta   25440
cacgcttcga tgctgggatg aaaagccatg gaaattccca ctgatgcagc cgccttcaat   25500
ggtaaacgga tgctcgagtg ttgcctgagt tctaccatgt aggaggaagc ctccgtgcac   25560
tctctggggg agccagcgga gtgatttctg tgcaacgtg gttgggcttt gtctttagga   25620
tgggcacaaa ccctccaggg ggatcgactt caaaattcac cttgttgtaa aacgggctac   25680
ctcagtgtcc cagccaaaat ttttattgta acatgctgtc aggtgtgtca ctcttttccaa   25740 gccagtaagc tttccgggg atttcttcaa gtagccagca ttcagagcaa tcttcagcat   25800
tgcagattct gagaaatgtg gctctggagc ctgtcaccct cgagaaacct aagagggctg   25860
cattgattcc atgtggccct gggtctatgg agcagtacat gagctcccag tgctctaagg   25920
ctcttcagcc ctaggctttg aagggagtga tttctcagta ttcttaaacc tctttctgat   25980
gacacttgta cctgtgaggg gtctagagag aaagagtagt agactcctac tttactacaa   26040
ttcaggatgc agggcatgag aggattccct ctctcctcca agggaagaag cttttggcgt   26100
```

```
gcacacatcc ctgagaagca aagtgtcttt gtcttcagtc agatacatag gaccgttttc   26160
tgccccatgg cccggaagcc aaaggccttg gctttcatga tcaacggtct agggaaacat   26220
gcaaaatttc catgtctgtc ccaaactctg cccccgacag ccaattacca cctgcagccc   26280
gcattgccaa atgcggtgcc gtttgcatga agattcagta gagtttccta gaaaggtgct   26340
acctcgtgag ctcactttcc aatgaggaat ctgatctgtt gtgtttctct aaggtgtcag   26400
gtgaaatatt tccaagaact tactacagtt ctagaatggg aggaatctgt tgctttggtg   26460
tttgtttgtt ggtcggtttt ctcacatcca tctgcctatg gataaggaaa agagaacggt   26520
cgtaattctc atagactcct ttctggttgt gtcacaaatg gcttcacatg tttctctatg   26580
ctcagagata ctcagcttga tttcccgtgt tttcatttca gcaccgactg agcaaaggcc   26640
tggggtgcag gagtgctacc atggtaatgg acagagttat cgaggcacat actccaccac   26700
tgtcacagga agaacctgcc aagcttggtc atctatgaca ccacactcgc atagtcggac   26760
cccagaatac tacccaaatg cgtatgtctt tgttctttac cataagagaa gaaagggcca   26820
agtgaagttt ctgttacaag agatgtgtct caagctgagt tctccgaact caacttgtga   26880
cagatgcaga tggcgtagca aaatgtctca ggatgattgc cttggagcta agggtctgag   26940
agaagggaaa tgttaagctc cctctccttc ctcctagttc tattgagcag aagggaaatc   27000
tggaggtgag gagatcacat tatgaagaaa gtcagaatga caaaggacca gacacttaga   27060
ttacccttcc acaacaccaa ctaaacgtca atggagactt tccagttgga attccgttat   27120
tctggcttcc acttcctgaa gggaaggttg cgtttgcctt ttctctctgg gttcaagagg   27180
aaagaatagg tgcttattta tggacaggtg aattgatctg tttctatatc tacgtatatt   27240
ccgattgtca gaaaaacact cgttcctaag taccagtggc ctgaagggat acaggttccc   27300
agcaagagaa gatccaagga aggaaggcag atgagagtca gcacagagag ggatgctgaa   27360
aagtaaaagg gatgggtgga tggagagaag cccgggtctg accacccaat ggccaatatt   27420
ttggccacaa gcgactacca gagacatgga aaaatggttt ctacatgtgg gacaacagat   27480
ggtagaggac ctagagaatt gagagagggg caatgatggg ctccactccg cagatgcctt   27540
ggctttcttc ctggatacccc ttcctgcact gaatagcaag gagatggagc ccaagcagac   27600
tgtagccatc ttgctgaatg gaggagaggg attggagttt gggatgactg tggtagctga   27660
aatttttcta ggtctgctag aaataagaac tggtttgtgt ggaggaaaag agctctacaa   27720
atacgcatag aagtctcctc cagtcgttgg cctgacatga cgctgcctgt gcacaggaaa   27780
tggttccacg agaaagtgtg gcaaagaaca tttactgaga aacagcaagt acaagagcac   27840
aggaagctca ataaagaaga gagagatcac atagcactct gggatactgg agttcttccc   27900
agctagacca gagagtcctc acggagcaca ttgccaattc agtggagacc ccagaacagc   27960
cgtaatttaa aggtacactt agtatattac tagaataaag tcagctgcag acaacccctt   28020
gcacagctgg aaagcaagtg tccaagcatc aaatcggttt ccaatcaatg aagtgcctgt   28080
gagaggaaat ctcaactctc tttagaagta acaacaaag tcgattgcct cagctatgcg   28140
gtatccgcag agtgagtcct aaatttaaaa tctgactaca tgtagaaaag cgtttcgtgt   28200
gacccatgac caggaaataa atcgggtaat acaaacaggc tcaggaatga gagaaatgat   28260
tagaattgcg tgaaaatttg acatatcagt atgataactg atttcaaata tttaaaaaaa   28320
caacatgcaa gaaagcagat atcatatcaa gagaaattaa cagtacagaa tagccaaatt   28380
aaattaaaga ggtagtataa aaaaagtatg tcttaattga aaaaaattac tgtatggccg   28440
gctgatcaat ttagacgttt cagaggaaaa cattacccaa cacacaattc tagagaacct   28500
```

```
acagaatgag ctacacacac acacacacac acacacacac acactgaaaa cacacccata   28560
ctcacacaca cgcagaaact cacaagttct aacacacaca gacacgcgca cccctgaaga   28620
aacagtgaaa tataaaatta agcgagcctc acagacatgt aggaaaatat gaaaagattt   28680
cctgcatgtg ggaagcaagt cacagtaaag agcaaggggc tttataatag aaacaaatac   28740
cagaatcaag gatggctgat aacttttcaa ttacgaagaa cattaaaaaa aatcacagaa   28800
tcgtgaaact caagggatca tagggaat ttcggaaaaa aaacccaacc tgtatgatgt     28860
acttttgtac atcacagttc gaaggtaaca aggcaaagat gtaataagaa gaaacctgtc   28920
acgaaaact ggaggaaaaa gagctgtgtc ttcctacaag tacactgata caaattgcca     28980
atgtgttcac ctcagaaaca ctggaagcca gataccaggg aatattgtta aaatgataat   29040
caggaacaaa aagagatcaa ccgggaatgc tgaatccagc aataaaatgc cttgaaggtc   29100
atccatgtcg gataaatgca tattgtgcac tgccccaaag aaagaaaccg gaaactgtaa   29160
gaattggaaa tcagcaggct tatgtaacaa gagaggtgac ccgaaggaat taggtagaag   29220
aagaattgaa caagaaagga actttctgca gcccacgtaa tgaagaatcc agcaattggc   29280
aaatgtagat agatgtaaat gcaaaatatt ttcttgatca aatttctata tctttgtaaa   29340
tgagagttga ctacttgaaa caaaatgata gcaagatatt taacttcagc atatgtagag   29400
gtaagaattt gaaatggtag cataaatcac gaagggatta attcgaagtg taccgttgta   29460
agtttcttta cctcatgcac gatggtgtgt catattaata aaagggtact gtgcgggttc   29520
gaagggatat tgcaaatcct agagcaatca caaaggtttg aactctgagg tttttggtat   29580
aataagaata gtccatgcat tcaaaagagg gaagccaagg aagaactaga agtctttcaa  29640
gagctcaggc tcttatacat ccagttgctc attgaaccag cttcctggaa tggagggtct   29700
ggggttgaga ctaggccaca agtctagagt ctctagagag acagtgttgg aacccccatgg  29760
cccataatac atttcccatt ttctcaggca gccagaggtc atgaatgtga ggatactggg   29820
aggttggagc aacgttcttg ggaggcataa ggaagagcga atgcttcaag atccccgcag   29880
cccaaactac tcgcctgctt tgcccccctaa tgcattttc tctgctgctc cgtagctgtc   29940
cgacctcttc agatctctta gtccaccctg ccgtcttcct ttatgccatg ggtcccactg   30000
ttctttcaac tcatcccccct ttccctcagt cccggagtag ctgcggccag cagagggtag  30060
actgagagca ggagagaagg acctgcctag gaaccccttc tagagatact gcatcctgcc   30120
tgggagcaag ttttccaggg cagctttgag aagtcttgga gaaacaaacc tactaaacct   30180
gacagacagt aatactattt gcacaatgct tttctgtggg aaaggtagag ccttttcact   30240
acgtattgag tacatagagt gtgagggttg acctggaacg gctatcctcc tggatgacgt   30300
gtgttttctg aagaactaca tgttcgttgc aactcccaca ttagaatatg aagtcctacc   30360
gagagagata cggagactag acagatacag atgcatttgc atgtgaatac acaatcccac   30420
aatacagacg tcaaaaccca taccagttat tccagagaga tggattgggc agaaggcaga   30480
aggagaatac tctgatcgtt tttcggccac gtgtgtgtgt tatctcagtg tttctaagaa   30540
gcgtttgcta ctttagattt tttattaaaa aaaatagtaa taatctatta agtatgagag   30600
atgtgcagag aggattagtg atcgagagcc atttttgctg gtggcaatca tatggtactt   30660
ttaatgggaa tattagaaag gcaccggtaa tgaccttgtt gcagcacaaa ggagagagtg   30720
tggggtgccc ctgcatgttg tcccacctct tgtgacgtgt atcgtttttgg aatttccagt  30780
ggcttgatca tgaactactg caggaatcca gatgctgtgg cagctcctta ttgttatacg   30840
```

```
agggatcccg gtgtcaggtg ggagtactgc aacctgacgc aatgctcaga cgcagaaggg    30900
actgccgtcg cgcctccgac tgttaccccg gttccaagcc tagaggctcc ttccgaacaa    30960
ggtaaggagt ctgtggccag acatctacac gcttcgatgc tgggatgaaa agccatggaa    31020
attcccactg atgcagccgc cttcaatggt aaacggatgc tcgagtgttg cctgagttct    31080
accatgtagg aggaagcctc cgtgcactct ctggggagc cagcggagtg atttctggtg     31140
caacgtggtt gggctttgtc tttaggatgg cacaaaccc tccaggggga tcgacttcaa     31200
aattcacctt gttgtaaaac gggctacctc agtgtcccag ccaaaatttt tattgtaaca    31260
tgctgtcagg tgtgtcactc tttccaagcc agtaagcttt tccggggatt tcttcaagta    31320
gccagcattc agagcaatct tcagcattgc agattctgag aaatgtggct ctggagcctg    31380
tcaccctcga gaaacctaag agggctgcat tgattccatg tggccctggg tctatggagc    31440
agtacatgag ctcccagtgc tctaaggctc ttcagcccta ggctttgaag ggagtgattt    31500
ctcagtattc ttaaacctct ttctgatgac acttgtacct gtgaggggtc tagagagaaa    31560
gagtagtaga ctcctacttt actacaattc aggatgcagg gcatgagagg attccctctc    31620
tcctccaagg gaagaagctt ttggcgtgca cacatccctg agaagcaaag tgtctttgtc    31680
ttcagtcaga tacataggac cgttttctgc cccatggccc ggaagccaaa ggccttggct    31740
ttcatgatca acggtctagg gaaacatgca aaatttccat gtctgtccca aactctgccc    31800
ccgacagcca attccacct gcagcccgca ttgccaaatg cggtgccgtt tgcatgaaga    31860
ttcagtagag tttcctagaa aggtgctacc tcgtgagctc actttccaat gaggaatctg    31920
atctgttgtg tttctctaag gtgtcaggtg aaatatttcc aagaacttac tacagttcta    31980
gaatgggagg aatctgttgc tttggtgttt gtttgttggt cggttttctc acatccatct    32040
gcctatggat aaggaaaaga gaacggtcgt aattctcata gactcctttc tggttgtgtc    32100
acaaatggct tcacatgttt ctctatgctc agagatactc agcttgattt cccgtgtttt    32160
catttcagca ccgactgagc aaaggcctgg ggtgcaggag tgctaccatg gtaatggaca    32220
gagttatcga ggcacatact ccaccactgt cacaggaaga acctgccaag cttggtcatc    32280
tatgacacca cactcgcata gtcggacccc agaatactac ccaaatgcgt atgtctttgt    32340
tctttaccat aagagaagaa agggccaagt gaagtttctg ttacaagaga tgtgtctcaa    32400
gctgagttct ccgaactcaa cttgtgacag atgcagatgg cgtagcaaaa tgtctcagga    32460
tgattgcctt ggagctaagg gtctgagaga agggaaatgt taagctccct ctccttcctc    32520
ctagttctat tgagcagaag ggaaatctgg aggtgaggag atcacattat gaagaaagtc    32580
agaatgacaa aggaccagac acttagatta cccttccaca acaccaacta aacgtcaatg    32640
gagactttcc agttggaatt ccgttattct ggcttccact tcctgaaggg aaggttgcgt    32700
ttgccttttc tctctgggtt caagaggaaa gaataggtgc ttatttatgg acaggtgaat    32760
tgatctgttt ctatatctac gtatattccg attgtcagaa aaacactcgt tcctaagtac    32820
cagtggcctg aagggataca ggttcccagc aagagaagat ccaaggaagg aaggcagatg    32880
agagtcagca cagagaggga tgctgaaaag taaaagggat gggtggatgg agagaagccc    32940
gggtctgacc acccaatggc caatattttg gccacaagcg actaccagag acatggaaaa    33000
atggtttcta catgtgggac aacagatggt agaggaccta gagaattgag agaggggcaa    33060
tgatgggctc cactccgcag atgccttggc tttcttcctg atacccttc ctgcactgaa    33120
tagcaaggag atggagccca agcagactgt agccatcttg ctgaatggag gagagggatt    33180
ggagtttggg atgactgtgg tagctgaaat ttttctaggt ctgctagaaa taagaactgg    33240
```

```
tttgtggagg aaaagagctc tacaaatacg catagaagtc tcctccagtc gttggcctga   33300
catgacgctg cctgtgcaca ggaaatggtt ccacgagaaa gtgtggcaaa gaacatttac   33360
tgagaaacag caagtacaag agcacaggaa gctcaataaa gaagagagag atcacatagc   33420
actctgggat actggagttc ttcccagcta gaccagagag tcctcacgga gcacattgcc   33480
aattcagtgg agaccccaga acagccgtaa tttaaaggta cacttagtat attactagaa   33540
taaagtcagc tgcagacaac cccttgcaca gctggaaagc aagtgtccaa gcatcaaatc   33600
ggtttccaat caatgaagtg cctgtgagag gaaatctcaa ctctctttag aagtaaacaa   33660
caaagtcgat tgcctcagct atgcggtatc cgcagagtga gtcctaaatt taaaatctga   33720
ctacatgtag aaaagcgttt cgtgtgaccc atgaccagga aataaatcgg gtaatacaaa   33780
caggctcagg aatgagagaa atgattagaa ttgcgtgaaa atttgacata tcagtatgat   33840
aactgatttc aaatatttaa aaaaacaaca tgcaagaaag cagatatcat atcaagagaa   33900
attaacagta cagaatagcc aaattaaatt aaagagctag tataaaaaaa gtatgtctta   33960
attgaaaaaa attactgtat ggccggctga tcaatttaga cgtttcagag gaaaacatta   34020
cccaacacac aattctagag aacctacaga atgagctaca cacacacaca cacacacaca   34080
cacaaactga aaacacaccc atactcacac acacgcagaa actcacaagt tctaacacac   34140
acagacacgc gcacccctga agaaacagtg aaatataaaa ttaagcgagc ctcacagaca   34200
tgtaggaaaa tatgaaaaga tttcctgcat gtgggaagca agtcacagta aagagcaagg   34260
gagtttggaa tagaaacaaa taccggaatc aaggatggct gataacttttt caattacgaa   34320 gaacattaaa aaaaatcaca gaatcgtgaa actcaaggga tcacataggg aatttcggaa   34380
aaaaaaccca acctgtatga tgtacttttg tacatcacag ttcgaaggta acaaggcaaa   34440
gatataataa gaagaaacct gtcacgagaa actggaggaa aaagagctgt gtcttcctac   34500
aagtacactg atacaaattg ccaatgtgtt caccctcagaa acactggaag ccagatacca   34560
gggaatattg ttaaaatgat aatcaggaac aaaaagagat caaccgggaa tgctgaatcc   34620
agcaataaaa tgccttgaag atcatccatg tcggataaat gcatattgtg cactgcccca   34680
aagaaagaaa ccggaaactg taagaattgg aaatcagcag gcttatgtaa caagagaggt   34740
gacccgaagg aattaggtag aagaagaatt gaacaagaaa ggaactttct gcagcccacg   34800
taatgaagaa tccagcaatt ggcaaatgta gatagatgta aatgcaaaat attttcttga   34860
tcaaatttct atatctttgt aaatgagagt tgactacttg aaacaaaatg atagcaagat   34920
atttaacttc agcatatgta gaggtaagaa tttgaaatgg tagcataaat cacgaaggga   34980
ttaattcgaa gtgtaccgtt gtaagtttct ttacctcatg cacgatggtg tgtcatatta   35040
ataaagggat actgtgcggg ttcgaaggga tattgcaaat cctagagcaa tcacaaaggt   35100
ttgaactctg aggtttttgg tataataaga atagtccatg cattcaaaag agggaagcca   35160
aggaagaact agaagtcttt caagagctca ggctcttata catccagttg ctcattgaac   35220
cagcttcctg gaatggaggg tctggggttg agactaggcc acaagtctag agtctctaga   35280
gagacagtgt tggaaccccca tggcccataa tacatttccc atttttctcag gcagccagag   35340 gtcatgaatg tgaggatact gggaggttgg agcaacgttc ttgggaggca taaggaagag   35400
cgaatgcttc aagatccccg cagcccaaac tactcgcctg ctttgccccc taatgcattt   35460
ttctctgctg ctccgtagct gtccgacctc ttcagatctc ttagtccacc ctgccgtctt   35520
cctttatgcc atgggtccca ctgttctttc aactcatccc cctttccctc agtcccggag   35580
```

```
tagctgcggc cagcagaggg tagactgaga gcaggagaga aggacctgcc taggaaccccc   35640 ttctagagat actgcatcct gcctgggagc aagttttcca gggcagcttt gagaagtctt   35700
ggagaaacaa acctactaaa cctgacagac agtaatacta tttgcacaat gcttttctgt   35760
gggaaaggta gagccttttc actacgtatt gagtacatag agtgtgaggg ttgacctgga   35820
acggctatcc tcctggatga cgtgtgtttt ctgaagaact acatgttcgt tgcaactccc   35880
acattagaat atgaagtcct accgagagag atacggagac tagacagata cagatgcatt   35940
tgcatgtgaa tacacaatcc cacaatacag acgtcaaaac ccataccagt tattccagag   36000
agatggattg gtaggaggc agaaggagaa tactctgatc gttttcggc cacgtgtgtg     36060 tgttatctca gtgtttctaa gaagcgtttg ctactttaga ttttttattt aaaaaaaata   36120
gtaataatct attaagtatg agagatgtgc agagaggatt agtgatcgag agccattttt   36180
gctggtggca atcatatggt acttttaatg ggaatattag aaaggcaccg gtaatgacct   36240
tgttgcagca caaggagag agtgtgggg gcccctgcat gttgtcccac ctcttgtgac      36300
gtgtatcgtt ttggaatttc cagtggcttg atcatgaact actgcaggaa tccagatgct   36360
gtggcagctc cttattgtta tacgagggat cccggtgtca gtgggagta ctgcaacctg     36420 acgcaatgct cagacgcaga agggactgcc gtcgcgcctc cgactgttac cccggttcca   36480
agcctagagg ctccttccga acaaggtaag gagtctgtgg ccagacatct acacgcttcg   36540
atgctgggat gaaaagccat ggaaattccc actgatgcag ccgccttcaa tggtaaacgg   36600
atgctcgagt gttgccggag ttctgccatg ttggggaag cctccgtgta ctctctgggg     36660 gagccagcg agtgatttct ggtgcaactt gggtgggctt tgtctttaga atgggcacaa     36720
accttccagg gtgatgggct tcacaactca cctccttcta aaatgggcta tctcagtgtc   36780
ttagccaaaa ttttttattgt aacgtgctgt caggtgtgtg attctttctg tcgcagtaag   36840
cttttctggg gatttcttca agtagccagc agtcagtgca atcttcagca ttgcagattt    36900
caaaaaatgt ggctctggag cctgtcatcc tcgagaaacc taacagggct gcattaattc   36960
catatggtcc tgggtctatg gagcagtata tgagctccca atgctctaag gctcttcagt   37020
cctaggcttt gaagggagtg atttctcagt gttcttaaac ctcttctga tggcacttgt     37080 acctgtgagg ggtctagaga gaaaggttag tagacttctc ctttactgca attcaggatg    37140
cagggcatga gaagattccc tccctcctcc aagggaagaa ggttttggcg tgcacacatc    37200
cttgagaagc aaagtgtctt tgccttcagt cagatatata ggatcgtttt ctgccccatg    37260
gcctggaagc cagaggcctt ggctttcatg atcaacgatc tagggaaaca tgcaaaattt   37320
ccatgtcttt cccctcctct gccctcgaca gccaattacc acctgcatcc tgcattgcca   37380
aatgcagtgc cctttgtatg aacattcagt agagtttcat agaaaggtgc tacttcgtga   37440
gcgcactttg cagtgagaag gagtctgttc tgttctgttt ttctaaggat ttcaggtgaa   37500
atatttccta gaacttacta cagttctaga ttggtaggaa tctgtaggtt tgctgtatgt   37560
tttttggttg gttttctccc atccatctgc ctacaggtaa gggaaagata acgttcgtaa   37620
ttctcataga ctccttttctg gttgtgtcat aaatggcttc acatatttcg ttattctcag   37680
agatactcag tttatttctt gtgttttcat ttcagcaccg actgagcaga ggcctggggt   37740
gcaggagtgc taccacggta atggacagag ttatcgaggc acatactcca ccactgtcac   37800
tggaagaacc tgccaagctt ggtcatctat gacaccacac tcgcatagtc ggaccccaga   37860
atactaccca aatgcgtatg tctttgttct ttaccataag agaagaaagg gccaagtgaa   37920
gtttctgtta caagagatgt gtctcaagct gagttctccg aactcaactt gtgacagatg   37980
```

```
cagatggcgt agcaaaatgt ctcaggatga ttgccttgga gctaagggtc tgagagaagg    38040
gaaatgttaa gctccctctc cttcctccta gttctattga gcagaaggga aatctggagg    38100
tgaggagatc acattatgaa gaaagtcaga atgacaaagg accagacact tagattaccc    38160
ttccacaaca ccaactaaac gtcaatggag actttccagt tggaattccg ttattctggc    38220
ttccacttcc tgaagggaag gttgcgtttg ccttttctct ctgggttcaa gaggaaagaa    38280
taggtgctta tttatggaca ggtgaattga tctgtttcta tatctacgta tattccgatt    38340
gtcagaaaaa cactcgttcc taagtaccag tggcctgaag ggatacaggt tcccagcaag    38400
agaagatcca aggaaggaag gcagatgaga gccagcacag agagggatgc tgaaaagtaa    38460
aagggatggg tggatggaga gaagcccggg tctgaccacc caatggccaa tattttggcc    38520
acaagcgact accagagaca tggaaaaatg gtttctacat gtgggacaac agatggtaga    38580
ggacctagag aattgagaga ggggcaatga tgggctccac tccgcagatg ccttggcttt    38640
cttcctggat acccttcctg cactgaatag caaggagatg gagcccaagc agactgtagc    38700
catcttgctg aatggaggag agggattgga gtttgggatg actgtggtag ctgaaatttt    38760
tctaggtctg ctagaaataa gaactggttt gtggaggaaa agagctctac aaatacgcat    38820
agaagtctcc tccagtcgtt ggcctgacat gacgctgcct gtgcacagga aatggttcca    38880
cgagaaagtg tggcaaagaa catttactga gaaacagcaa gtacaagagc acaggaagct    38940
caataaagaa gagagagatc acatagcact ctgggatact ggagttcttc ccagctagac    39000
cagagagtcc tcacggagca cattgccaat tcagtggaga ccccagaaca gccgtaattt    39060
aaaggtacac ttagtatatt actagaataa agtcagctgc agacaacccc ttgcacagct    39120
ggaaagcaag tgtccaagca tcaaatcggt ttccaatcaa tgaagtgcct gtgggaggaa    39180
atctcaactc tctttagaag taaacaacaa agtcgattgc ctcagctatg cggtatccgc    39240
agagtgagtc ctaaatttaa aatctgacta catgtagaaa agcgtttcgt gtgacccatg    39300
accaggaaat aaatcgggta atacaaacag gctcaggaat gagagaaatg attagaattg    39360
cgtgaaaatt tgacatatca gtatgataac tgatttcaaa tatttaaaaa acaacatgc    39420 aagaaagcag atatcatatc aagagaaatt aacagtacag aatagccaaa ttaaattaaa    39480
gagctagtat aaaaaaagta tgtcttaatt gaaaaaaatt actgtatggc cggctgatca    39540
aattagacgt ttcagaggaa acattaccc aacacacaat tctagagaac ctacagaatg    39600
agctacacac acacacacac acacacacac acacactgaa aacacaccca tactcacaca    39660
cacgcagaaa ctcacaagtt ctaacacaca cagacacgcg caccccctgaa gaaacagtga    39720 aatataaaat taagcgagcc tcacagacat gtaggaaaat atgaaaagat ttcctgcatg    39780
tgggaagcaa gtcacagtaa agagcaaggg agtttggaat agaaacaaat accggaatca    39840
aggatggctg ataactttc aattacgaag aacattaaaa aaaatcacag aatcgtgaaa    39900
ctcaagggat catatagga atttcggaaa aaaacccaa cctgtatgat gtacttttgt    39960
acatcacagt tcgaaggtaa caaggcaaag atataataag aagaaacctg tcacgagaaa    40020
ctggaggaaa aagagctgtg tcttcctaca agtacactga tacaaattgc caatgtgttc    40080
acctcagaaa cactggaagc cagataccag ggaatattgt taaatgata atcaggaaca    40140 aaaagagatc aaccgggaat gctgaatcca gcaataaaat gccttgaaga tcatccatgt    40200
cggataaatg catattgtgc actgccccaa agaaagaaac cggaaactgt cagaattgga    40260
aatcagcagg cttatgtaac aagagaggtg acccgaagga attaggtaga agaagaattg    40320
```

```
aacaagaaag gaactttctg cagcccacgt aatgaagaat ccagcaattg gcaaatgtag    40380
atagatgtaa atgcaaaata ttttcttgat caaatttcta tatctttgta aatgagagtt    40440
gactacttga aacaaaatga tagcaagata tttaacttca gcatatgtag aggtaagaat    40500
ttgaaatggt agcataaatc acgaagggat taattcgaag tgtaccgttg taagtttctt    40560
tacctcatgc acgatggtgt gtcatattaa taaaagggta ctgtgcgggt tcgaagggat    40620
attgcaaatc ctagagcaat cacaaaggtt tgaactctga ggttttggt ataataagaa     40680 tagtccatgc attcaaaaga gggaagccaa ggaagaacta gaagtctttc aagagctcag    40740
gctcttatac atccagttgc tcattgaacc agcttcctgg aatggagggt ctggggttga    40800
gactaggcca caagtctaga gtctctagag agacagtgtt ggaaccccat ggcccataat    40860
acatttccca ttttctcagg cagccagagg tcatgaatgt gaggatactg ggaggttgga    40920
gcaacgttct tgggaggcat aaggaagagc gaatgcttca agatcccgc agcccaaact     40980 actcgcctgc tttgcccct aatgcatttt tctctgctgc tccgtagctg tccgacctct     41040
tcagatctct tagtccaccc tgccgtcttc ctttatgcca tgggtcccat tgttctttca    41100
actcatcccc ctttccctca gtcccggagt agctgcggcc agcagagggt agactgagag    41160
caggagagaa ggacctgcct aggaacccct tctagagata ctgcatcctg cctgggagca    41220
agttttccag ggcagctttg agaagtcttg gagaaacaaa cctactaaac ctgacagaca    41280
gtaatactat ttgcacaatg cttttctgtg ggaaggtag agccttttca ctacgtattg     41340
agtacataga gtgtgagggt tgacctggaa cggctatcct cctggatgac gtgcgttttc    41400
tgaagaacta catgttcgtt gcaactccca cattagaata tgaagtccta ccgagagaga   41460
tacggagact agacagatac agatgcattt gcatgtgaat acacaatccc acaatacaga    41520
cgtcaaaacc cataccagtt attccagaga gatggattgg gcagaaggca gaaggagaat    41580
actctgatcg ttttccggcc acgtgtgtgt gttatctcag tgtttctaag aagcgtttgc    41640
tactttagat tttttattta aaaaaaatag taataatcta ttaagtatga gagatgtgca    41700
gagaggatta gtgatcgaga gccattttg ctggtggcaa tcatatggta ctttaatgg      41760 gaatattaga aaggcaccgg taatgacctt gttgcagcac aaaggagaga gtgtggggtg    41820
cccctgcatg ttgtcccacc tcttgtgacg tgtatcgttt tggaatttcc agtggcttga    41880
tcatgaacta ctgcaggaat ccagatgctg tggcagctcc ttattgttat acgagggatc    41940
ccggtgtcag gtgggagtac tgcaacctga cgcaatgctc agacgcagaa gggactgccg    42000
tcgcgcctcc gactgttacc ccggttccaa gcctagaggc tccttccgaa caaggtaagg    42060
agtctgtggc cagacatcta cacgcttcga tgctgggatg aaaagccatg gaaattccca    42120
ctgatgcagc cgccttcaat ggtaaacgga tgctcgagtg ttgcctgagt tctaccatgt    42180
aggaggaagc ctccgtgcac tctctggggg agccagcgga gtgatttctg gtgcaacgtg    42240
gttgggcttt gtctttagga tgggcacaaa ccctccaggg ggatcgactt caaaattcac    42300
cttgttgtaa aacgggctac ctcagtgtcc cagccaaaat ttttattgta acatgctgtc    42360
aggtgtgtca ctctttccaa gccagtaagc ttttccgggg atttcttcaa gtagccagca    42420
ttcagagcaa tcttcagcat tgcagattct gagaaatgtg gctctggagc ctgtcaccct    42480
cgagaaacct aagagggctg cattgattcc atgtggccct gggtctatgg agcagtacat    42540
gagctcccag tgctctaagg ctcttcagcc ctaggctttg aagggagtga tttctcagta    42600
ttcttaaacc tcttttctgat gacacttgta acctgtgaggg gtctagagag aaagagtagt    42660
agactcctac tttactacaa ttcaggatgc agggcatgag aggattccct ctctcctcca    42720
```

```
agggaagaag cttttggcgt gcacacatcc ctgagaagca aagtgtcttt gtcttcagtc   42780
agatacatag gaccgttttc tgccccatgg cccggaagcc aaaggccttg gctttcatga   42840
tcaacggtct agggaaacat gcaaaatttc catgtctgtc ccaaactctg cccccgacag   42900
ccaattacca cctgcagccc gcattgccaa atgcggtgcc gtttgcatga agattcagta   42960
gagtttccta gaaaggtgct acctcgtgag ctcactttcc aatgaggaat ctgatctgtt   43020
gtgtttctct aaggtgtcag gtgaaatatt tccaagaact tactacagtt ctagaatggg   43080
aggaatctgt tgctttggtg tttgtttgtt ggtcggtttt ctcacatcca tctgcctatg   43140
gataaggaaa agagaacggt cgtaattctc atagactcct ttctggttgt gtcacaaatg   43200
gcttcacatg tttctctatg ctcagagata ctcagcttga tttcccgtgt tttcatttca   43260
gcaccgactg agcaaaggcc tggggtgcag gagtgctacc atggtaatgg acagagttat   43320
cgaggcacat actccaccac tgtcacagga agaacctgcc aagcttggtc atctatgaca   43380
ccacactcgc atagtcggac cccagaatac tacccaaatg cgtatgtctt tgttctttac   43440
cataagagaa gaaagggcca agtgaagttt ctgttacaag agatgtgtct caagctgagt   43500
tctccgaact caacttgtga cagatgcaga tggcgtagca aaatgtctca ggatgattgc   43560
cttggagcta agggtctgag agaagggaaa tgttaagctc cctctccttc ctcctagttc   43620
tattgagcag aagggaaatc tggaggtgag gagatcacat tatgaagaaa gtcagaatga   43680
caaaggacca gacacttaga ttaccccttcc acaacaccaa ctaaacgtca atggagactt   43740
tccagttgga attccgttat tctggcttcc acttcctgaa gggaaggttg cgtttgcctt   43800
ttctctctgg gttcaagagg aaagaatagg tgcttattta tggacaggtg aattgatctg   43860
tttctatatc tacgtatatt ccgattgtca gaaaaacact cgttcctaag taccagtggc   43920
ctgaagggat acaggttccc agcaagagaa gatccaagga aggaaggcag atgagagtca   43980
gcacagagag ggatgctgaa aagtaaaagg gatgggtgga tggagagaag cccgggtctg   44040
accacccaat ggccaatatt ttggccacaa gcgactacca gagacatgga aaaatggttt   44100
ctacatgtgg gacaacagat ggtagaggac ctagagaatt gagagagggg caatgatggg   44160
ctccactccg cagatgcctt ggcttttctt ctggataccc ttcctgcact gaatagcaag   44220
gagatggagc ccaagcagac tgtagccatc ttgctgaatg gaggagaggg attggagttt   44280
gggatgactg tggtagctga aatttttcta ggtctgctag aaataagaac tggtttgtgg   44340
aggaaaagag ctctacaaat acgcatagaa gtctcctcca gtcgttggcc tgacatgacg   44400
ctgcctgtgc acaggaaatg gttccacgag aaagtgtggc aaagaacatt tactgagaaa   44460
cagcaagtac aagagcacag gaagctcaat aaagaagaga gagatcacat agcactctgg   44520
gatactggag ttcttcccag ctagaccaga gagtcctcac ggagcacatt gccaattcag   44580
tggagacccc agaacagccg taatttaaag gtacacttag tatattacta gaataaagtc   44640
agctgcagac aacccttgc acagctgaa agcaagtgtc caagcatcaa atcggtttcc   44700
aatcaatgaa gtgcctgtga gaggaaatct caactctctt tagaagtaaa caacaaagtc   44760
gattgcctca gctatgcggt atccgcagag tgagtcctaa atttaaaatc tgactacatg   44820
tagaaaagcg tttcgtgtga cccatgacca ggaaataaat cgggtaatac aaacaggctc   44880
aggaatgaga gaaatgatta gaattgcgtg aaaatttgaa atatcagtat gataactgat   44940
ttcaaatatt taaaaaaaca acatgcaaga aagcagatat catatcaaga gaaattaaca   45000
gtacagaata gccaaattaa attaaagagc tagtataaaa aaagtatgtc ttaattgaaa   45060
```

```
aaaattactg tatggccggc tgatcaattt agacgtttca gaggaaaaca ttacccaaca    45120
cacaattcta gagaacctac agaatgagct acacacacac acacacacac acacacaaac    45180
tgaaaacaca cccatactca cacacacgca gaaactcaca agttctaaca cacacagaca    45240
cgcgcacccc tgaagaaaca gtgaaatata aaattaagcg agcctacag  acatgtagga    45300 aaatatgaaa agatttcctg catgtgggaa gcaagtcaca gtaaagagca agggagtttg    45360
gaatagaaac aaataccaga atcaaggatg gctgataact tttcaattac gaagaacatt    45420
aaaaaaaatc acagaatcgt gaaactcaag ggatcacata gggaatttcg gaaaaaaaac    45480
ccaacctgta tgatgtactt ttgtacatca cagttcgaag gtaacaaggc aaagatataa    45540
taagaagaaa cctgtcacga gaaactggag gaaaagagc  tgtgtcttcc tacaagtaca    45600
ctgatacaaa ttgccaatgt gttcacctca gaaacactgg aagccagata ccagggaata    45660
ttgttaaaat gataatcagg aacaaaaaga gatcaaccgg gaatgctgaa tccagcaata    45720
aaatgccttg aagatcatcc atgtcggata aatgcatatt gtgcactgcc ccaaagaaag    45780
aaaccggaaa ctgtaagaat tggaaatcag caggcttatg taacaagaga ggtgacccga    45840
aggaattagg tagaagaaga attgaacaag aaaggaactt tctgcagccc acgtaatgaa    45900
gaatccagca attggcaaat gtagatagat gtaaatgcaa aatatttct  tgatcaaatt    45960 tctatatctt tgtaaatgag agttgactac ttgaaacaaa atgatagcaa gatatttaac    46020
ttcagcatat gtagaggtaa gaatttgaaa tggtagcata aatcacgaag ggattaattc    46080
gaagtgtacc gttgtaagtt tctttacctc atgcacgatg gtgtgtcata ttaataaaag    46140
ggtactgtgc gggttcgaag ggatattgca aatcctagag caatcacaaa ggtttgaact    46200
ctgaggtttt tggtataata agaatagtcc atgcattcaa agagggaag  ccaaggaaga    46260 actagaagtc tttcaagagc tcaggctctt atacatccag ttgctcattg aaccagcttc    46320
ctggaatgga gggtctgggg ttgagactag gccacaagtc tagagtctct agagagacag    46380
tgttggaacc ccatggccca taatacattt cccatttcct caggcagcca gaggtcatga    46440
atgtgaggat actgggaggt tggagcaacg ttcttgggag gcataaggaa gagcgaatgc    46500
ttcaagatcc ccgcagccca aactactcgc ctgctttgcc ccctaatgca ttttctctg    46560 ctgctccgta gctgtccgac ctcttcagat ctcttagtcc accctgccgt cttcctttat    46620
gccatgggtc ccactgttct ttcaactcat ccccctttcc ctcagtcccg gagtagctgc    46680
ggccagcaga gggtagactg agagcaggag agaaggacct gcctaggaac cccttctaga    46740
gatactgcat cctgcctggg agcaagtttt ccagggcagc tttgagaagt cttgagagaaa   46800 caaacctact aaacctgaca gacagtaata ctatttgcac aatgcttttc tgtgggaaag    46860
gtagagcctt tcactacgt  attgagtaca tagagtgtga gggttgacct ggaacggcta    46920
tcctcctgga tgacgtgtgt tttctgaaga actacatgtt cgttgcaact cccacattag    46980
aatatgaagt cctaccgaga gagatacgga gactagacag atacagatgc atttgcatgt    47040
gaatacacaa tcccacaata cagacgtcaa aacccatacc agttattcca gagagatgga    47100
ttgggcagaa ggcagaagga gaatactctg atcgttttc  ggccacgtgt gtgtgttatc    47160
tcagtgtttc taagaagcgt ttgctacttt agattttta  tttaaaaaa  atagtaataa    47220 tctattaagt atgagagatg tgcagagagg attagtgatc gagagccatt tttgctggtg    47280
gcaatcatat ggtactttta atgggaatat tagaaaggca ccggtaatga ccttgttgca    47340
gcacaaagga gagagtgtgg ggtgcccctg catgttgtcc cacctcttgt gacgtgtatc    47400
gttttggaat ttccagtggc ttgatcatga actactgcag gaatccagat gctgtggcag    47460
```

```
ctccttattg ttatacgagg gatcccggtg tcaggtggga gtactgcaac ctgacgcaat    47520
gctcagacgc agaagggact gccgtcgcgc ctccgactgt taccccggtt ccaagcctag    47580
aggctccttc cgaacaaggt aaggagtctg tggccagaca tctacacgct tcgatgctgg    47640
gatgaaaagc catggaaatt cccactgatg cagccgcctt caatggtaaa cggatgctcg    47700
agtgttgcct gagttctacc atgtaggagg aagcctccgt gcactctctg ggggagccag    47760
cggagtgatt tctggtgcaa cgtggttggg ctttgtcttt aggatgggca caaaccctcc    47820
agggggatcg acttcaaaat tcaccttgtt gtaaaacggg ctacctcagt gtcccagcca    47880 aaattttat tgtaacatgc tgtcaggtgt gtcactcttt ccaagccagt aagcttttcc     47940
ggggatttct tcaagtagcc agcattcaga gcaatcttca gcattgcaga ttctgagaaa    48000
tgtggctctg gagcctgtca ccctcgagaa acctaagagg gctgcattga ttccatgtgg    48060
ccctgggtct atggagcagt acatgagctc ccagtgctct aaggctcttc agccctaggc    48120
tttgaaggga gtgatttctc agtattctta aacctctttc tgatgacact tgtacctgtg    48180
aggggtctag agagaaagag tagtagactc ctactttact acaattcagg atgcagggca    48240
tgagaggatt ccctctctcc tccaagggaa gaagcttttg gcgtgcacac atccctgaga    48300
agcaaagtgt ctttgtcttc agtcagatac ataggaccgt tttctgcccc atggcccgga    48360
agccaaaggc cttggctttc atgatcaacg gtctagggaa acatgcaaaa tttccatgtc    48420
tgtcccaaac tcttcccccg acagccaatt accacctgca gcccgcattg ccaaatgcgg    48480
tgccgtttgc atgaagattc agtagagttt cctagaaagg tgctacctcg tgagctcact    48540
ttccaatgag gaatctgatc tgttgtgttt ctctaaggtg tcaggtgaaa tatttccaag    48600
aacttactac agttctagaa tgggaggaat ctgttgcttt ggtgtttgtt tgttggtcgg    48660
ttttctcaca tccatctgcc tatggataag gaaaagagaa cggtcgtaat tctcatagac    48720
tcctttctgg ttgtgtcaca aatggcttca catgtttctc tatgctcaga gatactcagc    48780
ttgatttccc gtgttttcat ttcagcaccg actgagcaaa ggcctggggt gcaggagtgc    48840
taccatggta atggacagag ttatcgaggc acatactcca ccactgtcac aggaagaacc    48900
tgccaagctt ggtcatctat gacaccacac tcgcatagtc ggaccccaga atactaccca    48960
aatgcgtatg tctttgttct ttaccataag agaagaaagg gccaagtgaa gtttctgtta    49020
caagagatgt gtctcaagct gagttctccg aactcaactt gtgacagatg cagatggcgt    49080
agcaaaatgt ctcaggatga ttgccttgga gctaagggtc tgagagaagg gaaatgttaa    49140
gctccctctc cttcctccta gttctattga gcagaaggga aatctggagg tgagaagatc    49200
acattatgaa gaaagtcaga atgacaaagg accagacact tagattaccc ttccacaaca    49260
ccaactaaac gtcaatggag actttccagt tggaattccg ttattctggc ttccacttcc    49320
tgaagggaag gttgcgtttg ccttttctct ctgggttcaa gaggaaagaa taggtgctta    49380
tttatggaca ggtgaattga tctgtttcta tatctacgta tattccgatt gtcagaaaaa    49440
cactcgttcc taagtaccag tggcctgaag ggatacaggt tcccagcaag agaagatcca    49500
aggaaggaag gcagatgaga gtcagcacag agagggatgc tgaaaagtaa aagggatggg    49560
tggatggaga gaagcccggg tctgaccacc caatggccaa tattttggcc acaagcgact    49620
accagagaca tggaaaaatg gtttctacat gtgggacaac agatggtaga ggacctagag    49680
aattgagaga ggggcaatga tgggctccac tccgcagatg ccttggcttt cttcctggat    49740
acccttcctg cactgaatag caaggagatg gagcccaagc agactgtagc catcttgctg    49800
```

```
aatggaggag  agggattgga  gtttgggatg  actgtggtag  ctgaaatttt  tctaggtctg   49860
ctagaaataa  gaactggttt  gtgtggagga  aaagagctct  acaaatacgc  ataagagtct   49920
cctccagtcg  ttggcctgac  atgacgctgc  ctgtgcacag  gaaatggttc  cacgagaaag   49980
tgtggcaaag  aacatttact  gagaaacagc  aagtacaaga  gcacaggaag  ctcaataaag   50040
aagagagaga  tcacatagca  ctctgggata  ctggagttct  tcccagctag  accagagagt   50100
cctcacggag  cacattgcca  attcagtgga  gaccccagaa  cagccgtaat  ttaaaggtac   50160
acttagtata  ttactagaat  aaagtcagct  gcagacaacc  ccttgcacag  ctggaaagca   50220
agtgtccaag  catcaaatcg  gtttccaatc  aatgaagtgc  ctgtgagagg  aaatctcaac   50280
tctctttaga  agtaaacaac  aaagtcgatt  gcctcagcta  tgcggtatcc  gcagagtgag   50340
tcctaaattt  aaaatctgac  tacatgtaga  aaagcgtttc  gtgtgaccca  tgaccaggaa   50400
ataaatcggg  taatacaaac  aggctcagga  atgagagaaa  tgattagaat  tgcgtgaaaa   50460
tttgacatat  cagtatgata  actgatttca  aatatttaaa  aaaacaacat  gcaagaaagc   50520
agatatcata  tcaagagaaa  ttaacagtac  agaatagcca  aattaaatta  aagaggtagt   50580
ataaaaaaag  tatgtcttaa  ttgaaaaaaa  ttactgtatg  gccggctgat  caatttagac   50640
gtttcagagg  aaaacattac  ccaacacaca  attctagaga  acctacagaa  tgagctacac   50700
acacacacac  acacacacac  acaaactgaa  aacacaccca  tactcacaca  cacgcagaaa   50760
ctcacaagtt  ctaacacaca  cagacacgcg  caccectgaa  gaaacagtga  aatataaaat   50820
taagcgagcc  tcacagacat  gtaggaaaat  atgaaaagat  ttcctgcatg  tgggaagcaa   50880
gtcacagtaa  agagcaaggg  agtttggaat  agaaacaaat  accggaatca  aggatggctg   50940
ataactttc  aattacgaag  aacattaaaa  aaaatcacag  aatcgtgaaa  ctcaagggat   51000
cacataggga  atttcggaaa  aaaaacccaa  cctgtatgat  gtacttttgt  acatcacagt   51060
tcgaaggtaa  caaggcaaag  atataataag  aagaaacctg  tcacgagaaa  ctggaggaaa   51120
aagagctgtg  tcttcctaca  agtacactga  tacaaattgc  caatgtgttc  acctcagaaa   51180
cactggaagc  cagataccag  ggaatatgt  taaaatgata  atcaggaaca  aaaagagatc   51240
aaccgggaat  gctgaatcca  gcaataaaat  gccttgaagg  tcatccatgt  cggataaatg   51300
catattgtgc  actgccccaa  agaaagaaac  cggaaactgt  aagaattgga  aatcagcagg   51360
cttatgtaac  aagagaggtg  acccgaagga  attaggtaga  agaagaattg  aacaagaaag   51420
gaactttctg  cagcccacgt  aatgaagaat  ccagcaattg  gcaaatgtag  atagatgtaa   51480
atgcaaaata  ttttcttgat  caaatttcta  tatctttgta  aatgagagtt  gactacttga   51540
aacaaaatga  tagcaagata  tttaacttca  gcatatgtag  aggtaagaat  ttgaaatggt   51600
agcataaatc  acgaagggat  taattcgaag  tgtaccgttg  taagtttctt  tacctcatgc   51660
acgatggtgt  gtcatattaa  taaaagggta  ctgtgcgggt  tcgaagggat  attgcaaatc   51720
ctagagcaat  cacaaaggtt  tgaactctga  ggttttggt  ataataagaa  tagtccatgc   51780
attcaaaaga  gggaagccaa  ggaagaacta  gaagtctttc  aagagctcag  gctcttatac   51840
atccagttgc  tcattgaacc  agcttcctgg  aatggagggt  ctggggttga  gactaggcca   51900
caagtctaga  gtctctagag  agacagtgtt  ggaaccccat  ggcccataat  acatttccca   51960
ttttctcagg  cagccagagg  tcatgaatgt  gaggatactg  ggaggttgga  gcaacgttct   52020
tgggaggcat  aaggaagagc  gaatgcttca  agatccccgc  agcccaaact  actcgcctgc   52080
tttgccccct  aatgcatttt  tctctgctgc  tccgtagctg  tccgacctct  tcagatctct   52140
tagtccaccc  tgccgtcttc  ctttatgcca  tgggtcccac  tgttcttca  actcatcccc   52200
```

```
ctttccctca gtcccggagt agctgcggcc agcagagggt agactgagag caggagagaa    52260
ggacctgcct aggaacccct tctagagata ctgcatcctg cctgggagca agttttccag    52320
ggcagctttg agaagtcttg gagaaacaaa cctactaaac ctgacagaca gtaatactat    52380
ttgcacaatg cttttctgtg ggaaggtag agccttttca ctacgtattg agtacataga    52440
gtgtgagggt tgacctggaa cggctatcct cctggatgac gtgcgttttc tgaagaacta    52500
catgttcgtt gcaactccca cattagaata tgaagtccta ccgagagaga tacgagact    52560
agacagatac agatgcattt gcatgtgaat acacaatccc acaatacaga cgtcaaaacc    52620
cataccagtt attccagaga gatggattgg gcagaaggca gaaggagaat actctgatcg    52680
ttttcggcc acgtgtgtgt gttatctcag tgtttctaag aagcgtttgc tactttagat    52740
tttttattta aaaaaaatag taataatcta ttaagtatga gagatgtgca gagaggatta    52800
gtgatcgaga gccattttg ctggtggcaa tcatatggta cttttaatgg gaatattaga    52860
aaggcaccgg taatgacctt gttgcagcac aaaggagaga gtgtggggtg cccctgcatg    52920
ttgtcccacc tcttgtgacg tgtatcgttt tggaatttcc agtggcttga tcatgaacta    52980
ctgcaggaat ccagatgctg tggcagctcc ttattgttat acgagggatc ccggtgtcag    53040
gtgggagtac tgcaacctga cgcaatgctc agacgcagaa gggactgccg tcgcgcctcc    53100
gactgttacc ccggttccaa gcctagaggc tccttccgaa caaggtaagg agtctgtggc    53160
cagacatcta cacgcttcga tgctgggatg aaaagccatg gaaattccca ctgatgcagc    53220
cgccttcaat ggtaaacgga tgctcgagtg ttgcctgagt tctaccatgt aggaggaagc    53280
ctccgtgcac tctctggggg agccagcgga gtgatttctg gtgcaacgtg gttgggcttt    53340
gtctttagga tgggcacaaa ccctccaggg ggatcgactt caaaattcac cttgttgtaa    53400
aacgggctac ctcagtgtcc cagccaaaat ttttattgta acatgctgtc aggtgtgtca    53460
ctctttccaa gccagtaagc ttttccgggg atttcttcaa gtagccagca ttcagagcaa    53520
tcttcagcat tgcagattct gagaaatgtg gctctggagc ctgtcaccct cgagaaacct    53580
aagagggctg cattgattcc atgtggcct gggtctatgg agcagtacat gagctcccag    53640
tgctctaagg ctcttcagcc ctaggctttg aagggagtga tttctcagta ttcttaaacc    53700
tctttctgat gacacttgta cctgtgaggg gtctagagag aaagagtagt agactcctac    53760
tttactacaa ttcaggatgc agggcatgag aggattccct ctctcctcca agggaagaag    53820
cttttggcgt gcacacatcc ctgagaagca aagtgtcttt gtcttcagtc agatacatag    53880
gaccgtttc tgccccatgg cccggaagcc aaaggccttg gctttcatga tcaacggtct    53940
agggaaacat gcaaaatttc catgtctgtc ccaaactctg cccccgacag ccaattacca    54000
cctgcagccc gcattgccaa atgcggtgcc gtttgcatga agattcagta gagtttccta    54060
gaaaggtgct acctcgtgag ctcactttcc aatgaggaat ctgatctgtt gtgtttctct    54120
aaggtgtcag gtgaaatatt ccaagaact tactacagtt ctagaatggg aggaatctgt    54180
tgctttggtg tttgtttgtt ggtcggtttt ctcacatcca tctgcctatg gataaggaaa    54240
agaaacggt cgtaattctc atagactcct ttctggttgt gtcacaaatg gcttcacatg    54300
tttctctatg ctcagagata ctcagcttga tttcccgtgt tttcatttca gcaccgactg    54360
agcaaaggcc tggggtgcag gagtgctacc atggtaatgg acagagttat cgaggcacat    54420
actccaccac tgtcacagga agaacctgcc aagcttggtc atctatgaca ccacactcgc    54480
atagtcggac cccagaatac tacccaaatg cgtatgtctt tgttctttac cataagagaa    54540
```

```
gaaagggcca agtgaagttt ctgttacaag agatgtgtct caagctgagt tctccgaact    54600
caacttgtga cagatgcaga tggcgtagca aaatgtctca ggatgattgc cttggagcta    54660
agggtctgag agaagggaaa tgttaagctc cctctccttc ctcctagttc tattgagcag    54720
aagggaaatc tggaggtgag gagatcacat tatgaagaaa gtcagaatga caaaggacca    54780
gacacttaga ttacccttcc acaacaccaa ctaaacgtca atggagactt ccagttgga     54840 attccgttat tctggcttcc acttcctgaa gggaaggttg cgtttgcctt ttctctctgg    54900
gttcaagagg aaagaatagg tgcttattta tggacaggtg aattgatctg tttctatatc    54960
tacgtatatt ccgattgtca gaaaaacact cgttcctaag taccagtggc ctgaagggat    55020
acaggttccc agcaagagaa gatccaagga aggaaggcag atgagagtca gcacagagag    55080
ggatgctgaa aagtaaaagg gatgggtgga tggagagaag cccgggtctg accacccaat    55140
ggccaatatt ttggccacaa gcgactacca gagacatgga aaaatggttt ctacatgtgg    55200
gacaacagat ggtagaggac ctagagaatt gagagagggg caatgatggg ctccactccg    55260
cagatgcctt ggctttcttc ctggataccc ttcctgcact gaatagcaag gagatggagc    55320
ccaagcagac tgtagccatc ttgctgaatg gaggagaggg attggagttt gggatgactg    55380
tggtagctga aattttccta ggtctgctag aaataagaac tggtttgtgt ggaggaaaag    55440
agctctacaa atacgcatag aagtctcctc cagtcgttgg cctgacatga cgctgcctgt    55500
gcacaggaaa tggttccacg agaaagtgtg gcaaagaaca tttactgaga aacagcaagt    55560
acaagagcac aggaagctca ataaagaaga gagagatcac atagcactct gggatactgg    55620
agttcttccc agctagacca gagagtcctc acggagcaca ttgccaattc agtggagacc    55680
ccagaacagc cgtaatttaa aggtacactt agaatattac tagaataaag tcagctgcag    55740 acaaccccctt gcacagctgg aaagcaagtg tccaagcatc aaatcggttt ccaatcaatg    55800
aagtgcctgt gagaggaaat ctcaactctc tttagaagta acaacaaag tcgattgcct     55860 cagctatgcg gtatccgcag agtgagtcct aaatttaaaa tctgactaca tgtagaaaag    55920
cgtttcgtgt gacccatgac caggaaataa atcgggtaat acaaacaggc tcaggaatga    55980
gagaaatgat tagaattgcg tgaaaatttg acatatcagt atgataactg atttcaaata    56040
tttaaaaaaa caacatgcaa gaaagcagat atcatatcaa gagaaattaa cagtacagaa    56100
tagccaaatt aaattaaaga gctagtataa aaaaagtatg tcttaattga aaaaaattac    56160
tgtatggccg gctgatcaaa ttagacgttt cagaggaaaa cattacccaa cacacaattt    56220
tagagaacct acagaatgag ctacacacac acacacacac acacacacac acacaaactg    56280
aaaacacacc catactcaca cacacgcaga aactcacaag ttctaacaca cacagacacg    56340
cgcacccctg aagaaacagt gaaatataaa attaagcgag cctcacagac atgtaggaaa    56400
atatgaaaag atttcctgca tgtgggaagc aagtcacagt aaagagcaag ggagtttata    56460
atagaaacaa ataccagaat caaggatggc tgataacttt tcaattacga agaacattaa    56520
aaaaaatcac agaatcgtga aactcaaggg atcatatagg gaatttcgga aaaaaaaccc    56580
aacctgtatg atgtactttt gtacatcaca gttcgaaggt aacaaggcaa agatgtaata    56640
agaagaaacc tgtcacgaga aactggagga aaaagagctg tgtcttccta caagtacact    56700
gatacaaatt gccaatgtgt tcacctcaga aacactggaa gccagatacc agggaatatt    56760
gttaaaatga taatcaggaa caaaagagaa tcaaccggga atgctgaatc cagcaataaa    56820
atgccttgaa ggtcatccat gtcggataaa tgcatattgt gcactgcccc aaagaaagaa    56880
accggaaact gtaagaattg gaaatcagca ggcttatgta acaagagagg tgacccgaag    56940
```

```
gaattaggta gaagaagaat tgaacaagaa aggaactttc tgcagcccac gtaatgaaga    57000
atccagcaat tggcaaatgt agatagatgt aaatgcaaaa tattttcttg atcaaatttc    57060
tatatctttg taaatgagag ttgactactt gaaacaaaat gatagcaaga tatttaactt    57120
cagcatatgt agaggtaaga atttgaaatg gtagcataaa tcacgaaggg attaattcga    57180
agtgtaccgt tgtaagtttc tttacctcat gcacgatggt gtgtcatatt aataaaaggg    57240
tactgtgcgg gttcgaaggg atattgcaaa tcctagagca atcacaaagg tttgaactct    57300 gaggttttg gtataataag aatagtccat gcattcaaaa gagggaagcc aaggaagaac    57360
tagaagtctt tcaagagctc aggctcttat acatccagtt gctcattgaa ccagcttcct    57420
ggaatggagg gtctggggtt gagactaggc cacaagtcta gagtctctag agagacagtg    57480
ttggaacccc atggcccata atacatttcc cattttctca ggcagccaga ggtcatgaat    57540
gtgaggatac tgggaggttg gagcaacgtt cttgggaggc ataaggaaga gcgaatgctt    57600
caagatcccc gcagcccaaa ctactcgcct gctttgcccc ctaatgcatt tttctctgct    57660
gctccgtagc tgtccgacct cttcagatct cttagtccac cctgccgtct tcctttatgc    57720
catgggtccc actgttcttt caactcatcc ccctttccct cagtcccgga gtagctgcgg    57780
ccagcagagg gtagactgag agcaggagag aaggacctgc ctaggaaccc cttctagaga    57840
tactgcatcc tgcctgggag caagttttcc agggcagctt tgagaagtct tggagaaaca    57900
aacctactaa acctgacaga cagtaatact atttgcacaa tgcttttctg tgggaaaggt    57960
agagcctttt cactacgtat tgagtacata gagtgtgagg gttgacctgg aacggctatc    58020
ctcctggatg acgtgcgttt tctgaagaac tacatgttcg ttgcaactcc cacattagaa    58080
tatgaagtcc taccgagaga gatacggaga ctagacagat acagatgcat ttgcatgtga    58140
atacacaatc ccacaataca gacgtcaaaa cccataccag ttattccaga gagatggatt    58200
gggcagaagg cagaaggaga atactctgat cgttttttcgg ccacgtgtgt gtgttatctc    58260
agtgtttcta agaagcgttt gctactttag atttttttatt taaaaaaaat agtaataatc    58320
tattaagtat gagagatgtg cagagacgat tagtgatcga gagccatttt tgctggtggc    58380
aatcatatgg tacttttaat gggaatatta gaaaggcacc ggtaatgacc ttgttgcagc    58440
acaaaggaga gagtgtgggg tgcccctgca tgttgtccca cctcttgtga cgtgtatcgt    58500
tttgaatttt ccagtggctt gatcatgaac tactgcagga atccagatgc tgtggcagct    58560
ccttattgtt atacgaggga tcccggtgtc aggtgggagt actgcaacct gacgcaatgc    58620
tcagacgcag aagggactgc cgtcgcgcct ccgactgtta ccccggttcc aagcctagag    58680
gctccttccg aacaaggtaa ggagtctgtg gccagacatc tacacgcttc gatgctggga    58740
tgaaaagcca tggaaattcc cactgatgca gccgccttca atggtaaacg gatgctcgag    58800
tgttgcctga gttctaccat gtaggaggaa gcctccgtgc actctctggg ggagccagcg    58860
gagtgatttc tggtgcaacg tggttgggct ttgtctttag gatgggcaca aaccctccag    58920
ggggatcgac ttcaaaattc accttgttgt aaaacgggct acctcagtgt cccagccaaa    58980 attttattg taacatgctg tcaggtgtgt cactctttcc aagccagtaa gcttttccgg    59040
ggatttcttc aagtagccag cattcagagc aatcttcagc attgcagatt ctgagaaatg    59100
tggctctgga gcctgtcatc ctcgagaaac ctaacagggc tgcattaatt ccatatggtc    59160
ctgggtctat ggagcagtat atgagctccc aatgctctaa ggctcttcag tcctaggctt    59220
tgaagggagt gatttctcag tgttcttaaa cctctttctg atggcacttg tacctgtgag    59280
```

```
gggtctagag agaaaggtta gtagacttct cctttactgc aattcaggat gcagggcatg   59340
agaagattcc ctccctcctc caagggaaga aggttttggc gtgcacacat ccttgagaag   59400
caaagtgtct ttgccttcag tcagatatat aggatcgttt tctgcccat ggcctggaag    59460 ccagaggcct tggctttcat gatcaacgat ctagggaaac atgcaaaatt tccatgtctt   59520
tcccctcctc tgccctcgac agccaattac cacctgcatc ctgcattgcc aaatgcagtg   59580
ccctttgtat gaacattcag tagagtttca tagaaaggtg ctacttcgtg agcgcacttt   59640
gcagtgagaa ggagtctgtt ctgttctgtt tttctaagga tttcaggtga aatatttcct   59700
agaacttact acagttctag attggtagga atctgtaggt ttgctgtatg ttttttggtt   59760
ggttttctcc catccatctg cctacaggta agggaaagat aacgttcata attctcatag   59820
actcctttct ggttgtgtca taaatggctt cacatatttc gttattctca gagatactca   59880
gtttatttct tgtgttttca tttcagcacc gactgagcag aggcctgggg tgcaggagtg   59940
ctaccacggt aatggacaga gttatcgagg cacatactcc accactgtca ctggaagaac   60000
ctgccaagct tggtcatcta tgacaccaca ctcgcatagt cggaccccag aatactaccc   60060
aaatgcgtat gtctttgttc tttaccataa gagaataaag gccaactga agtttctgtg    60120 acaagagaca tgcttcaagc tgagttctcc gaactcaact tgtgtcagat tcagatggtg   60180
tagcaaaatg tctcaggatg atttccttgg agctaagggt ctgagagaag agaaatgtta   60240
agctgcctca ccttcctcct agttttgtgg agcagaaggg aaatgaggag gcgaggagat   60300
caccttatga agaaagtcag aatgacgaac caccaaacac ttagattacc cttgcccaac   60360
acccactaag cgtcaatgaa gactttccag ttggaattcc gttattctga cttccaattc   60420
ctgaagggaa gattgtgttt gccttttctg tctgggctca tgaggaaagt ttatgtgctt   60480
acttatggac aggtgaattg atctgtttct atttctacct gtattccaat agggagaaaa   60540
tctcttggtc ctaagtacca gtggcctgaa aggatagagg ttcccagcaa gagaagatcc   60600
aaggaaggaa ggcagatgag agtcagcaca gagagggatg ctgaaaagta aagggatgg    60660 gtagatggat agaagccctg gtctgaccac cccatggcca atcatttggc cataatcaac   60720
aaccaaagac atggaaaaat ggtttctaca tgtgggacaa cagatggtag aggacctaga   60780
gaattgagag agggccaatg atgagctcaa ctccatagat gccttggctt tcttcctgga   60840
tacccttcct gcactgaata gcaaggagat ggagctcaag cagcctgtag ccatctagct   60900
gagcagagga gagggattgg agtttgggat gactctggta ttttctaggt ccgctacaaa   60960
taagaactgg tttgtggagg aaaggagctc tacaaatacg catagaagtc tcctccagta   61020
gttggcctca catgacactg catgtgcaca gaaaatggtt ctacagaaag tgtggcaaag   61080
aacatttact gagaaacagc aactacaaga gaacagcaag ctcaattaag aagatagaga   61140
tcacatagca ctctgtgtta ttggagttct taccagctag atgagagagt gctcacggaa   61200
cacattgcca attcagtgga gaccccagaa cagccataat ttcaaagtac aattagtata   61260
ttactagaat aaaggcagct gcagacaacc ccttgcacag ctgaaaagca agtgtccaag   61320
catcaaatgg gtttccaatc aatgaagtgc ctgtgagagg aaatctcaac tctcttcaga   61380
agtaaacaac aaagtcaatt gcctcagcta tgcggtatcc ccagagtgag tcctaaatta   61440
aaaatttgac tacgtgtaga aaagaatttc gtgtgatcca tgaccagaaa ataaatcagg   61500
caatacaaac aggctcagaa atgacatcga taattagaat tgcatgaaaa tttgacatat   61560
cagtatgata actgatttca gatatttaaa aaaagtgcaa caaagcaggt atcatatcaa   61620
gacaaattaa tagtatagaa tagccaaatc aaattaaaga actattatac aaaaagtatg   61680
```

```
tcttaaatga agaaattact gtatgtccgc ctgaaaaatt tagatgtttc agaagaaaaa   61740
attaaccaaa aacaattctg cagaacctac agaatgagcc acacacacac acattcaaaa   61800
cacacccata cacacacaca tgcaaaaact cacaagttct aacacacaca caaacacaca   61860
cacacatgca catccctaaa gaaataggga aatataaaat taaccgaccc tcagagacat   61920
gcaggaaaat ataagaagat ttcctgcatg tgggaagcaa gtcacagtaa agagcaaggg   61980
agtttggagt agatacaaat accggaatca cggatggctg ataacttttc aattatgaag   62040
aacgttagaa aaatcacaga ttcatgaaac taaagggatc aaataggaaa tttcgagaaa   62100
aaaaactaca tgatgcactt ctctacatca cagttcaaag gtaacaaggc aaggatataa   62160
gaagaagaaa catctcacga gaaactggag aaaaagagc tgtgtcttcc tagagtacag    62220
tgatacaaat tgctaatgcg ttcacctcag aaacactgga agccagatac cagggaatat   62280
tattaaaatg ataatgagga acaagaagag atcaaccgag aatgctgaat ccagcaataa   62340
aatgccttga agatcatcca tgttggataa atgcatattg tgcactgccc aaaacaaaga   62400
aactggaaag tgtaagactt tggaatcagc aggcttatgt agcaacagag gtgacccgaa   62460
agaattaggt ataagaagaa tagaagaatt gcatgaaaat ttgacatatg actaagataa   62520
ctatttcaaa tatttaaaaa aagatgaata tgtaataaaa cagataaaat atcaaaagaa   62580
agtaacagta ttgactagcc aaatcaaatt aaagacttag tgtaaaaagc tatgtcttaa   62640
aagaaaaaat tactggatgg ctgcctgatc aatttagaca tttctgaata ggaaactaac   62700
caaaaatcaa ttctcagaa ccaactacac acatatatac acatacaaca cacccataca    62760
cacccacgca aaaactcaca agttcacaca cacacacaca cacacacaac cctcaagaaa   62820
tagtgaaata gaaaaccaac cgaacctcac agacatgttg caaaatagga aaagatttcc   62880
tgcatatggg aagcaagtca cagaaaagag aacgggagat tggaaacaga aacaaatacc   62940
ggaatcaagg atggccgaaa acttttcatt gatcaagaat attaacaaaa tcgcaaaaac   63000
acgaaattca atgcatcaaa taggcgtttc gaaaaaaaga aaaaatctgg tatgatgcac   63060
ttttgtactt cacattttca cggtaagaag acaaagatat aataacaaga aacttcttat   63120
gagaaactgg ggaaaaacaa gctgtttctt gctagaagaa cagtgataca aattgctaat   63180
gcattctcgt caaaaacact ggaagccaga taccgggaat gttattaatg tggtaaacag   63240
gaacaagaag agatcaacca agaatgctaa atccagcaat aaaatgcctt gaagatcatc   63300
catgctgcat aaatgtatgt tgtgcactgc cccaaacaaa gaaaccggaa actgtaagaa   63360
tttggaatca gcaggctgat gtaacaagag aggtgaccca aaggaattag gtagaagaag   63420
aatagtacaa gaagggaact ttctgcagcc catgtaatga agaacccagc aattggcaaa   63480
tgtagatgta aatgcaaaat attttcttga ccaaatttct atatatttt aaatgagcgt    63540 tgactactgg aaacaaaatg atagcaatat atttaatttt agcatatgta gaggtaagaa   63600
tttgaacaag tagcgtaaat catgtaggga ataattagaa gtgtaccatt gtaagtttct   63660
tacctcatgc acaatggtat gtaatattaa taaaatgtta ctgtgtgggt tcaaggagat   63720
attgcaaatc ctagagcaat cacaaagttt tgaactctga ggtatattgt ataataagaa   63780
tattccatgt attcaaaaga gagaagccaa ggaagaaaga aatttgtcac gagtttgggc   63840
tcttagtaca tcctgtagct cattgaacca gcttcctgga atggagggtc tgggattgac   63900
actaggccac atgtatagag tctctagaga gacagtgttt catccccatg gcccgtaata   63960
catttcccat tttctcaggc agccacaggt catgaatgtg aggatagaga gaggttggag   64020
```

```
caacgttctt gggaggcata aggaagagca aatgcttcaa gatccccgca gcccaaactc    64080
ctacctgctt tgcccCctaa tgcagtgttc ctccgtagct gtccgacctc ttcagatctc    64140
ttagtctacc ctgccatctt cctttatgcc atgggtccca ctgttctttc aactcatccc    64200
cctttccctc agtgcagagt agctgcggcc agcagagggt agactgagag caggagagaa    64260
ggtcctgccc aggaacccat tctagagatg ctgcattctg cctgggagca agttttccag    64320
ggcagctttg agaagtcttg cagaaacaaa cctatttgac ccacatgata tgggaatgac    64380
agaaagtaat acaatttgca cagtgctttt ccatgggaaa agtagagcct tttcgcgagg    64440
ttttgagtac atagagagtg aaggttgacc tggaaaggtt atcctcctgg atcccatgtt    64500
ttttctgaag aactacctgt tagttgcaac ttgcacatta gaatatgaag tcctaccgag    64560
agagatacgg agaactagat aaatacagat acttttgtat gtgaataaac gattccacaa    64620
tacacacatc aaaatccata ccagttattc cagagagatg gattgggcag aaggcagaag    64680
gagaatactc tgatcgtttt ttgcccacgt gtatgtatta tctcagtgtt tctaagaagc    64740
gtttgctact ttagattttt ttttataata ataatctttt aagtatgaga aatgtgcaga    64800
caggattagt gattgagagc catttgtgct tgtggcaatc atatggtact tttatgggaa    64860
tattagaaag gcactggtaa tgaccttgtt gcagcacaaa ggagagggtg tggggtgccc    64920
ctgcatattg tcccacctct tgtgacgtgt atcgttttgg aatttccagt ggcttgatca    64980
tgaactactg caggaatcca gatcctgtgg cagccccttg ttgttatacg agggatccca    65040
gtgtcaggtg ggagtactgc aacctgacac aatgctcaga cgcagaaggg actgccgtcg    65100
cgcctccaac tattacccCg attccaagcc tagaggctcc ttctgaacaa ggtaaggagc    65160
ctgtggccag aaacctacac gtttcgatgc tgggatgaaa agccatggaa attcccactg    65220
atgcagcagc ctccaatggt aaacggatgc tcgagtgttg actgagttct gtcatgtagg    65280
aggaagcctc cgtgcactct ctgggggagc cagcggattg atttctggta caacgttggg    65340
tgggctgtgt ctttagaatt ggcacaaacc ctccagggtg atcgacttca caactcacct    65400
cgttgaaaaa tgggctatct cagtgtctta gccaaaattt ttattgtaac atgctgtcag    65460
atgtgtgact ctttccaagc cagtaagctt tcctgggac ttcttcaatt agccagcatt    65520
cagtgcaatc ttcagcattg cagattcaga gaaatgtggc tctggagcct gtcacccttg    65580
agaaacaggg ctaacagggt tgcattaatt ccaaatcacc ctggttctat ggagcagtac    65640
atgaactccc aatgatctat gtttcaggac ttcctcagtc ataggtgggc tctgcagccc    65700
taggttttta agtgagtgac tgccccgtgt tctggtggca gttgtacctg tgagcggtct    65760
ggatagaaag agtcggagac ttctgtatta ttgcaactca ggatgtgggt catgagagga    65820
tttcatctct cctgcagggg agtaagctgt tcgcctccac ccatccctga taactgaagt    65880
gtctttgtct gcagtcctag acgaaggact gttgtctctc ccatggccca gaagctgaag    65940
accttgcctt ttgttatgaa acgttcattg ttttcatgtc tgtccgtttc tctgccccta    66000
acacccaatc accatgtatg gcctgtaccc ccaaatgcat cgtgctttgc tgtttgctgc    66060
cccatagtcc tcatgaacat tcagtagaaa ttcccataaa tgtgcttgca cgtgagcaca    66120
gtttccattg agaagccctc tcatttgtcc ttttttttcta agcttttatg tgaaatattt    66180
ctaagaactt actacagttc taaagtgtta ggaatttgtt tctttggtgt ttttgtttgt    66240
tggttggttg ttgctttttct caagtccatc tgcctacaaa taaagaaaca agaatgttac    66300
ttgtcatatt ctcctgaggt cataattctc agagactttt ttctggtttg tgccataagt    66360
ggcttcacat gtttgtctct tcttggaaac actcagtttg atttcttttc ttttcatttc    66420
```

```
agcaccaact gagcaaaggc ctggggtgca ggagtgctac cacgaaaatg gacagagtta   66480
tcaaggcaca tacttcatta ctgtcacagg aagaacctgc caagcttggt catctatgac   66540
accacactcg catagtcgga ccccagcata ctacccaaat gcgtatgtct attttcttta   66600
ccataagtga aggaagggtc agtggaaatt tctgttagta gagtcatgct tcaagctgag   66660
tgttcaggac tcaagttgtc tcagatgaac agtgcatagc aaaatgtctc aggaacattg   66720
tctttgagca aagagtctaa gagaagacaa atgttaatct ggctctcctt cctcctagtt   66780
taatggagca gaaaggtatc tggaggcaag gatatcacat taagaaacaa gtcaagatga   66840
caaatgatga aactcttaga gtacccttcc acaacaccca ctaaggttca atgcagcctt   66900
ttctccttgg aattctatta aactaaactc caattcctga agtgaaggtt ctgttggggt   66960
tttctgtttt ggcttacaag gaaagtatat atgtatatct atggagaggc aaatctatct   67020
ctttctatat ctacgtctat tccaatatgt agaaacacag tcggttctga ccaccagtgg   67080
tctgaaggga tactggttgt tagagaataa aaatggcagg aaggcagatg agagtcagca   67140
aagagagaga tcctgtaaag taaaagggtg gatagatgga cagaagccca ggtctgacca   67200
gcccatggcc aggctttagg ccataagtga caccaaagac atggaaaaat ggtttctaca   67260
tgttggacaa cagacagtag tggaccaaaa gaatagtgac agggggaaca atgagatcaa   67320
ctccatagat accttggctt tcttcctgga ggcccttctt gcactgaaga gcaaggtgat   67380
ggagcccaga tggactgtag ccatcttcct gaatgcagga gagagattgg aatttgggac   67440
tactgtggta gctaggattt tataggcctg ctgagaatga gaatggattt gtggatgaaa   67500
ggagctccag gggcacgcat agtagtctcc tcgaatcttt ggctaaacat gacgttgcat   67560
gtgcccagaa aaaggttcca caagaaagta gagaaaagaa tatatcctga ggaatagcaa   67620
ctgcgattga acagtgagct caataaagag gacagagccc tcatagcatt ctgggatact   67680
ggagttctga ccagctggag gagagacctc actgaacctc ttgggaatac agtagagact   67740
ccagaaaagt catactttag gagtagaatt agtaaatttc tagaaaaaaa ggcagctcta   67800
gacaaaccct ggcaaaactg aaaagcaagt ctccaagcat taaaatcatt tccaagtcaa   67860
ttaactgcct gggagaggaa aaccctctt agaggtaaac aacaaagtca agtggctcag   67920
ctatgtggtg ttcacagtgt gagttctaaa tttaaaactt gactacacat agagaagctt   67980
ttagtatgaa ccatgaccag gtgaaaaatc agtcaataca aatagaccta gaaatgcacg   68040
aaatgattag aatggcaaaa aatttgacat atcaatatgt caactgagtt ttaggtttta   68100
agaaaacatg aatacggaat gaagcagata ccatatcaag agacagtaac agtatagaag   68160
agccaaatta aattaaagaa ctagtataag aaggtatgtc ttaaatgaaa aaattactgg   68220
atgtattccc aatggagtga gatgtttcag aagtaaaaac taactgaaaa acaatttat    68280 accacctaca gaaccagcta cacatacaca aatgacacac acatatacac acatactcac   68340
acatgcacag gcttagaaac atgcacgcac acacacacac acacacacac acacctccac   68400
aaatactaaa aaatgaaatc cactgatcct cacagacagg cgggaaaata taaaaagatt   68460
tcctgcatgt gggtaggaag tcacagaagg agaggaagga gagattgcta caggaacaaa   68520
tactggaagc aaggatagct aaaaactttt caaataagaa gaatattaaa aaccacagat   68580
tcaagaagct gaatgaatca gacagggaat ttccaaaaaa aaaaaaaaa aaactgtatg    68640 attcactttt gtcatcacc gttcaacagt cagaaggcaa agatataata acaagaaaca    68700
tctcatgaga aactggagga aaaagagctg tgtcttgcta aagaacagt gatacaaatt    68760
```

```
gctaatgcat tctcatcaga aacactggaa cccagttaac aggggatatc attaaaatga   68820
taaactagaa aaaaaagaga tcaaatgaga atgctacatc cagcaataaa atgccttgaa   68880
gatcatccat gttggataaa tgcatattgt gcactgcccc aaataaataa accaaaaact   68940
aataatttgg aatcagcagg cttgtgtaac aagagatgtt gcccaaagaa aattagctag   69000
aagaagaata gttcaagagg agaactttct gcagcccacg taatgaagaa cccagcaaat   69060
ggcaaatgta gatgtaaatg caaaatattt tcttgatcaa atttctatat ctttttaaat   69120
gagagttgac tacttgaagc aaaatgatag caatatattt aactttagca tatgtagagg   69180
taaaaatttg aacatataga ctaaatcatg tggggaataa ttggaagtgt accattgtaa   69240
gtttcttacc ttatccacga tggtatgtaa tattaatgaa aggttgaatt tgtgggtcca   69300
aagggatatt gtaaatccta aagcaatcat aaaattttga attctgaggg atattatata   69360
ataagaattt tccatgtatc caaagagggg aagccaagga agaaaaagaa gtctttcaag   69420
tactcaagct ctgagcacat ccagttgctc attgaaccag cttcctggaa tggagggtct   69480
gggcttgaga ctaggtcaca tgtgtagagt ctctagagag acagtgttgg atccccatgg   69540
cccataatac atttcccgtt ttcccaggca gccacaggtc acgaatggga ggattctgag   69600
aggttggagc aatgttctta ggaggcataa ggaggagtga atgctctgag atttccccag   69660
cctgaggtcc tccatagctg cccgacctct tcagacctca tagtctgccc agctgtctcc   69720
ctttatgcca tgagtgccac tgttctttca actcatcccc cattccctca gtcccggaat   69780
tgctgtggcc agcagaggat ggactgagag caggagagga agtcctgacc aggaacccat   69840
cctagagata ctgcatcctg cctgaaagct aggtttccag ggcagctttg agaagtcttg   69900
cagaaagaaa cccacttgac ccacctgata cggtatcgac agacaggaat acttttgtg   69960 caatggtttt acatgctgaa catagagcct tttggctaca ttttgagtac attgaatgag   70020
actgctggcc tgggaaggat atcatgctgg atgccatttt tttctctgga gaactatgtg   70080
ttagttccaa ctcgcacatt actatatgaa gtcctacaca gagagatacg gagagctaga   70140
cagatagaga tacttttgta tgtgcataac caattccaca atacacacgt caaaatccat   70200
accagttatt ccagagagat ggattgggca gaaggcagaa ggaggatatt ctgatccctt   70260
tttggccaca tgtatgtata atctcagtgt ttctaggaag tgtgtgctgc attagatttt   70320 ttttcttttaa aaaagtgat aatatattaa gtatgagaaa tgtgcagaga ggattagaga   70380
ttgagagcca tttgtcattg tggcaattgt atggtatctc ttttgggaat atttcaaagg   70440
caccagtaat gaccttgttg tagcaaaata tacagtgttc ctgcatatgt acccattttt   70500
tgtgatgtgt attcttttgg aatttccagt ggcttgatca agaactactg ccgaaatcca   70560
gatcctgtgg cagcccttg tgttataca acagatccca gtgtcaggtg ggagtactgc   70620
aacctgacac gatgctcaga tgcagaatgg actgccttcg tccctccgaa tgttattctg   70680
gctccaagcc tagaggcttt ttttgaacaa ggtaagaagt tgtgccagac atttacctgc   70740
ttggatgctg ggatgaaaag ccatggatac ccccactgac gcacaaccct tcagtgctac   70800
actggttctc gtgtgttggt tctgggtctg ccatgtggga ggaagcctta gcgcactctc   70860
tgggggagcc agaggtgtga ttttggtgc aacctgtgcg agctgtgtct ttaggatggg   70920
cggaaaccat tctgggtgct cgacttcacc actcccctca ttgtaaaagg ggctatctca   70980
ttgtcctaga caaaattctt attgtaatat gctgtcagat gtgtgtgtct ttccaagcca   71040
gtaaactttt ccagggattt cttcaagtag acagcattca gtgcaatctt cagcattgca   71100
gattccgaga aatgtggctc tagatcctgt tatccttgag aaacctaact gggttgcatt   71160
```

```
aattccatat ctccctgggt ctgtggagta gtacatgagc tcccgaagct ctatctctca   71220 ggtcttttc agtccgaggc aggttgtgca gttcttagct ttgaagggag tgattttttc   71280
gtgtgctttt gcctctttct gatggaactt gtacctgcgg ggggtctgga gaaaaagagt   71340
agtagacttt tgctttattg caatgcatta tgctgggcac gagaggattc cctatcttat   71400
tgtaggtgat aagcttttgg cctccactca tccctgagaa gtgaagtgtt gttgcctaca   71460
gttttagctg caggactgtt gtctgcccca tcaccaggag tttaatgctt tctttttga   71520 gcaatcatct agggacacat gcaaggtttt tatatgtcct tgcctcctcc ccaaaaaacc   71580 atttaatgc ttggagactt gcttttcagc tttgccaaat gcatcaccct ttcttctatg   71640
ctgttccatg tcgtcatgaa cactctgtag agattcctag aaatgagctt ccatgttagt   71700
ggagtttccg atgagaagca atctgatatt tcttttccac taagttttac atgaaatatt   71760
tctaagaact tactacagtt ctagaatggt aggcatctct tactttcgtg tttgtttgtg   71820
tgttttctca tgtccatttg cctattaata aagaatagag aatggttgta aatctcagtg   71880 actcttttt ggtttatgtc ataaatggct tcctgtattt ttctgttcta ggaaataata   71940
agcttgatgt cttctgtttt aatttcagca ctgactgagg aaaccccgg ggtacaggac   72000 tgctactacc attatggaca gagttaccga ggcacatact ccaccactgt cacaggaaga   72060
acttgccaag cttggtcatc tatgacacca caccagcata gtcggacccc agaaaactac   72120
ccaaatgcgt acgtctttgt tctttaccat aagcgaagga agggccaatg aagtttctg   72180 ttagaagagt catgcttcaa ggtgactgct caggactcaa cttggctcag atgcagagga   72240
acatttcctg tgagcaaaag ttcttagaga agactttgtt ttttgagac agagtcttgc   72300 tttgttgccc aggctggagt gcagtggcat gatctcggct cactgcaagc tccgcctccc   72360
gggttcacac cattctcctg cttcagcctc tctagcagct gggactacag gcacccacca   72420 ccacaccccgg ctaattttt gtattttag tagagacagg gtttcactgt tctagccagg   72480
atggtcttgg tctcctgacc tcgtgatccg cctgcctcag cctcccaaag tgctgggatt   72540
acaggcgtga gccaccgtgc ctggctgaga agacattttt taagctggct ctccttcctc   72600
ctagttttat ggaagcagaa ggatatatgg agttgagaag atcttattaa taaaacagcc   72660
gggatgacaa atgaccaaag agttagagta tccttctaca acatcggctg agggttaata   72720 caacctttc accttggaat tctatcattc taagctctag tccctgaagt gaatgttgtg   72780
ttggcctttt gcatcttggg tcacagggaa ttgatacttg cacatctatg gagaggcaaa   72840
tcttttccta tctacttctt tttcaatggg tacaaacaca cttggtcctg agcaccagtg   72900
gtctgaagag atacggtctg cccagaggag aagaacaaag gcaggaaagc agatgagagt   72960
cagcaaaggg gcgatgctga aaagtaaaag gggcgggtag atggacagaa gccatgatct   73020
ggccattcta tggccagtct ttcggccata agtgactacc aaagacacgg caaaacggtt   73080
tccacatgtt gaacaacaga tgctagagga ccaagagtat tgcaagaggg agaaaatgag   73140
atcaacccat caatgccttg gctttcttca aggagaccct tcctgcactg aagagcaagg   73200
agatggagcc caagctgact gtagccatgt tgctgaacag aggagagtga ttggactttg   73260
ggattactca ggtagttagg attttctagc catgctaaga gtaagaatgg acttgtggag   73320
gataggagct ccaggcatag aagtctcctc aagtgttagt ctaaacataa agcagcactt   73380
gcatagaaga ttttccacaa gaaaatatgg caaaaaaaca ccatatattg aggaacaaca   73440
actacaaggg aacagtgagc ttaataaagg tgacagagct cacatagtgc tctggaatat   73500
```

```
tggagttttg accagctaga gagaagagac ctcattgaaa atcttgggca ttcagtagag    73560
acctcagaaa agtcagactt tatgagtaga ctttgtatat tcctagaata aaggcagctc    73620
cagaaaaaac ctagcaaagc tgaaaagcaa atctccaagc attaaaatgg tgtcctagtc    73680
aattaactgc cttctagaag aaaactcaac actctttaca ggtgaacaac aaagttaagt    73740
tgctgagcta tgcaatatcc acagtgtgag tcctaaattt ataactttac tacacataaa    73800
aaagcattta gtgtgaacca taaccaggaa aataatcagt caataaaaat agaaccagga    73860
atgatagaaa tgatttaaat ggcatgagaa tttgacatat tagtatcata actgcattgc    73920
tggatttaag aaaacataaa catggaacgt aacagatatc atatcaaggg aaagtaaaag    73980
gataaaagag tcaaatcaaa ttaaaggact attaaaaggt atatcttaaa tgaaaaattc    74040
actggatggt ctcccaatca ggttagttgt ttccagggaa aaaattaact gaaaaataat    74100
tcaatagaat ctacagaaat agctgcacat atatacacac aatggcacac gtgcacacac    74160
ccacacccac acaggtgtga atcctagagc cacacgagca ttgaaacata gagaagtaaa    74220
aattgttcat tgaggaatat gtagcaatgc tcaatgtgtt ttaccctaat aagagctttt    74280
gtgatgtatg attgaaaaac tgacacaact gaagagagaa atagataagc ccacactctg    74340
agttagagat ttccttgatt ctctcactat ggttataaat ctttcccaaa cacaacaggc    74400
tagaacaaat atgcagaaaa ttagacatag tatctttgtt ctcaataaaa acgtcgacct    74460
atttaacatt ataccgaact accgagtaca cattaaagtg tgcatggagc attcactgag    74520
gtgtactcta cacatgacct tccagcaagt ctccatagat ttaaaagaat taaagtcata    74580
cagagtgtgt cactttattc tcccagaata aagtgagata tgaataatga gaagtttgcc    74640
agcttctcaa atatttggga gtcatacggt gcatttcaaa atactctttg ggacaaagaa    74700
aacatcacta aggaatttag aaaagttttg aactgagtaa gaatataaca caatttatcc    74760
aaacttagga gatgcagtga atgtctttag gcttttacat aattttagat gctcttaggg    74820
aaaaacagaa gcatgtaata atcaagattt caaactgcaa ttctcaaagt gtagtctaga    74880
gaaacctgag gacctttgag taccttcaga gacagtccat gaggttaaag gactttgcta    74940
cgtgaaaagt aagatgctat tggccctttt tactttcatt ttccaacaag agaagagggg    75000
agttttccag cagttacata atatgtaatg gcatcatgtc tctgatggct aagaaaatgg    75060
gcaattgttg actttgtgtg ttaaaaaaat tctcagtgtt ggtttcttat actataaata    75120
ttcatcttgt gttttgaaaa agaaaagctc tttggaatcc cctatgaaca aagactttga    75180
cagttgttga tctaagacca cagcttaaat atctacacaa gaaaaaaaaa aaaagcaaat    75240
aagagccaag gaaagcagat ggaaggaagt agtccaaacc agtgacattc agtgaacaag    75300
aaaagagacc aacaagggag taaactcttg aaacagaaag ttgattcttt gaaaagatcc    75360
atatgattga acacagtctg gctaaacaaa tgacagacca atgagggtgc acaaccatca    75420
ccatctggag taacagagga gaggtgccat tactatagca tcttccagtt ctgaaagctg    75480
aaaagaagat tttgagaaca attgtatgtg aataaattca ggaatgttaa tcatgtgggc    75540
caattcctga ggaagacaac aaatcagcaa accagatgct gaatagttag tgtagtcctg    75600
tagagagaca tacagagagg ctgacagaga atatttgta tgtgcataaa acaatctaca    75660
agacacactt caaaatcaat ctcagttaat ctggaggaac atatttcaca gaaggtggaa    75720
ggagggtatt ctgatcctct tgtacattgt acaacattgt acaatgtaca gagtataatt    75780
gtacaagtac aattgaagtt gtacaagtac aagtgcaact tgcacaatgt acagagtaaa    75840
cattgatgtt tactctcaat tttcttatgg agcacagatg actttggatg tgttacaata    75900
```

```
tgaatgataa tttgtctttg agatgttcgc agttgtttag aagttgagga ccatttgtgc   75960
atattatggg acctttagtg aaaatatttc aaagtctctt tttacacttt gttacagcaa   76020
aatgtagagg gcgctaagtg cccttgaatc ttctcccatc tctggtgacc tgtgttgttt   76080
tgaaatttgc agtggcctga ccaggaacta ctgcaggaat ccagatgctg agattcgccc   76140
ttggtgttac accatggatc ccagtgtcag gtgggagtac tgcaacctga cacaatgcct   76200
ggtgacagaa tcaagtgtcc ttgcaactct cacggtggtc ccagatccaa gcacagaggc   76260
ttcttctgaa gaaggtagga agtctatggc cagacaacca caccctagga cgttgggatg   76320
aaaagagttg caaaatctta gtgatataga agccttccat gctcacacaa ttccaagtag   76380
aatgtggact cagggtcagc cactgggaag gaacactcag cgccttctct gggagaacca   76440
gagctgtgat gtttggtacc ctgtgaaagg gtggtatcta taggaagggt gcagaccctc   76500
tagggcactg gacttaccac tcccctggtt attcaaagga tcattttagt gtcttagcca   76560
gaagaatatt ctaacatttt gccaaatttg tgaagattta ccaagctcat gataagcctt   76620
tcatggtatt tcttcaagta gtcagtgttc attgcatctt tggctttgcg gtttcggagg   76680
aatgcggttt ttgagtctgt catccttgag aaacctaata tgacttttct tagttccata   76740
tacttctggg tccaggtagc agtacatagc caacaaatgc tccatcgttc tggcctatct   76800
ccatcttaag ccagtcctgc acaactaggc tttgatggga gggatctctc agtgttcttg   76860
cccctccttc tcatggaaca tatatctgtg ttggtctctg agaagaagag tagtggatat   76920
ctactttgtt gcaatgcaga atcctgggcc aaagatacca gccatccctc caagggaata   76980
aaattttggc cagtagccct ctctgagaga caatttgtct ttgcctacga gtcctagatg   77040
caggaccgct tcctgcccca tcttcaagaa gctgaaggct ttggctttgg aggatcagca   77100
gtctagggaa atgtgtgacg gtttcatgtc tgtccccact gacagtcaat caccacctac   77160
aacctgcaca gcctgatgca tagcagtcta gtttcctgcc ttattctcag gaacacccag   77220
aagatgtcta tattaaagag catgcacatg agtgcaattt tgactgatag gcactctgat   77280 cttcctttg gtgcctgtgt tttaaaggaa atctttctaa gaactcgtta aagttctaga   77340
atgctatgaa tctttgggtt ttattattgg tatgtccatc tgcctgctag tacagaacag   77400
agcatggtag tctttctcag agacaatgat cctgtttcag tcacagattt cttctgatgc   77460
ttctgtgttc tagaaattac tcagcttgat ttctcctctt tgaatttcag caccaacgga   77520
gcaaagcccc ggggtccagg attgctacca tggtgatgga cagagttatc gaggctcatt   77580
ctctaccact gtcacaggaa ggacatgtca gtcttggtcc tctatgacac cacactggca   77640
tcagaggaca acagaatatt atccaaatgg gtacaacctt gagttttctt caaagacaga   77700
cagcagcccc cttacatttc tcttggaagg gccatgcttc caactaactt cttatgacaa   77760
atttatctca gatctggaat gttgggtaga atgtctcagg cttctttctt caggcacagt   77820
gtctgaaagg agagaaatgt caggccagct ctcttttctc atagttgaca gaagcaggag   77880
gatatttgaa ggtggtgagt tctcatgaat agaaagctca ggacacatgg ccacgtgctt   77940
agaaatagca ccattccaca atgcccacta aagaccaatg caatagttca accagggatt   78000
tctgtcattc taatctccaa gtcctgaagt gaaggttgta ttagccatgt tcatcttggg   78060
caacaaataa aggatatcta tgttgacatc cagatcttcc aatcactttc tcctctaacc   78120
tgtacctggg ttctgagaac aaggtatctg aagagctatg tgttgccagc acatgagggg   78180
caaaagtagg aaggcagctg agagtcagga agtataaaga ttctgaagag ttacacatgc   78240
```

```
aggaagatgg acagaaaccc agttcagacc acgtcagcgt ttctgccatg aaggactatc    78300
aaatacatag gaaaagtgtt ttcataggtt ggacaacaga catgacaggc ctgagaaaat    78360
tcagaaaggg aatcaaagga gatcaacctt atcatgtccc tggcatcctt ccttgagacc    78420
cttgaagggc aagcagatgg agcccagctg accacagcag tcttgcttaa ctgaggagag    78480
agactggagt ttgtgatgcc tcaggcatct gacgtattct aggctggcta agaatgagag    78540
gggatttgtg gaggaaagga gctccaagaa tacacaccga agtcttctca aggctttggc    78600
taaatacaaa gctgcgtatg cacaaggaga gttttcacaa agaaagaaca ataaagaaaa    78660
gctactgggg aaagaacaac tgcaagggaa cagtgagctc aatggagatg ctagagctca    78720
catagcactg ggggatattt gagttctgac cactcagagg agagacacct cactgaacat    78780
cttgggcatt cagtagaggt caaagaaagc cataatttgg gagtaggatc ttcggattcc    78840
tagaaataag gtgactccag aaacactcca gcaacccttc ttccaagcca gtctaaaagg    78900
atccaaatga tttccaagta aattaactgc cttccagaaa aaagtaaaact caaccctcct    78960 tagaggtaag gaacgaatac aagtttctca gttatatgac atccccagag tgcaacttgc    79020
atttaaaaat ttactagaca caaaagaagt tttcactgtg atccataact gggagaaaaa    79080
tcactcaaca caaataggcc cagaaataat agaaattatg gcattggcaa gaacatttaa    79140
aatgcacctc tgagaactgt gtttcaggaa aatgtcagca aaagctgacc atgagagaaa    79200
tgaatgcata atatcagaaa agaaaagaat tgaagagcca aatggaaatt taaaaactga    79260
gaaaagttat atctgtaatg aggaattcac tggatggcct tataaccagt ttagatatta    79320
tggtaggaaa aggtgaacga gaaatgattt caattaaagc tagacaaacc acaagacaga    79380
cagacagaca caaatacaca tacacacaat gactgaacca attaatcaac agagcctcaa    79440
ggacatctag gaaaacatcc acacatttaa tatatgtgtt aggcaagtca cagaaagaga    79500
ggaaaaagat aatgtgacag aagttatact tgaagccatg acggctgaca aatttccaaa    79560
catacagaaa atgagaaatt catagtcatg aagctcaatg actcaggtat agatttttaa    79620
agagcaaaac tctgatttac tggggtacat catagttaaa ttgtctgatt tcaaagctaa    79680
gaagaaaaaa agggggttcc tatgaacaaa cattttgaca gttgatctaa gaccacagct    79740
taaatatcta ggcaaggaaa agcaaataag acacaaggaa agggatggga tggaaatagt    79800
ccaaaccaat gacattcagt gaacaagaaa atagaccaac aaaggagtaa atccatgaaa    79860
cagaaagttg gttctttgaa aagattcatg tgattgacca cagtctggct gaacagatga    79920
cagaccaagg agggagtaca accatcacca tttgaagtaa caggggagag gagccattgc    79980
tataccatac tccaggtctg aaagctgaca agaagatatc aagaaaaact gtatgtgaat    80040
aaattcatga atgtagatca tgtggatcaa ttccttaggt aaacaacaaa tcagcaaacc    80100
agatactgaa tagattgggt actcctatag aaagacatac agatagccag acagagaaac    80160
atttgtacgt gcataaaaca atctacaaga ctcacttcaa aatctctcag ttaatccaaa    80220
gtaacatatt tggcagaagg tggaaggagg gtattctgat cctttcttgt acacattgat    80280
gttttctctc ggttttctta tggagtatag acgagtttgg atgtgttaca ataagaatga    80340
taatctgtct ttgaaatgtt cacagttgtt tagaagttga ggacgatttg tgattgttac    80400 aggacccttta gtgagaatat ttcaaagtca cttttttacca ctttgttaca acaaaatgta    80460
gaggatgtct ggtgcccttg tatcttctcc catctctggt gaactgtatt gttttgtaat    80520
ttgcagtggc ctgaccagga actactgcag gaatccagat gctgagatta gtccttggtg    80580
ttataccatg gatcccaatg tcagatggga gtactgcaac ctgacacaat gtccagtgac    80640
```

```
agaatcaagt gtccttgcga cgtccacggc tgtttctgaa caaggtaaga agtctctggc    80700
cagacaacca caccccttgga cgttgggata aaaagagttg caaaatctta gtgatacaga   80760
agccttccat gctgcacggg aatctgaatg tggactcagg gtcagccaat gggaaggaag    80820
cctcagcgcc ttctctgggg gaaccagggc tgagattttt ggcaccccgt gacagggtgg    80880
tgtctttagg aagcgtgcag accttctagg gcactggatt taccactccc ctggttattc    80940
aatagattat ttcagtgtcc tagtgaaaat ggatattcta acatcctgcc aaatttgtga    81000
tgatttacca agctcatcat gagccttttcc tggtatttct tcaagtagac agtactcatt   81060
gcaaacttca gctttacagt ttcagaggaa tgtggttttt gagtctgtca tccttgagaa    81120
acctgatatg actttactta gttccatatc ctcctgggtc taggtaacag tacatagcca    81180
gcaaatgctc tatctccctg tctaccttaa tcttaggcag gtgctgcaca cctaggcttt    81240
gatggaaggg atttcttagt gttcttgccc ctccttctca tggaacacgt atctgtgttg    81300
ctgtttgtga agaagagtag tggatgtcta cttttgttgca atgcaggatc ctgggcccaa   81360
gatttcccgc cgtccctcca agggaataaa attttggcca gtacccctct ctgagagaca    81420
atgtgtcttt gcctggaagt cctagatgga ggaccacttc ctgccccatc ttccagaaac    81480
ttaaggcttt ggctttggag gatcagtgct ctggagaaat gtgtgacggt ttcatgtctg    81540
ccccccactga caaccaccac ctacagcctg caccgcctga tgcatggcac tctggtctcc    81600
tgccttgttc tcaggaacac ccaaaagaga tctttgccaa agaacaggca catgagtgca    81660
attttgactg ataggcactc tgatctgtcc tttggtgccc aggttttaaa gaaaatctttt   81720
ctaaaaactc attgaagttc cagaatgcta tgaatctttg agctttgtta ttggcatgtc    81780
catctgccta ctaatgtaga acagagcatg gtcgtcattt tcagagatga tgtcctgttt    81840
ctatcatgga tttttttttct catgcttctg tgttctggaa attactcagt ttgttttctc   81900
ctcttttgaat ttcagcacca acggagcaaa gccccacagt ccaggactgc taccatggtg   81960
atggacagag ttatcgaggc tcattctcca ccactgttac aggaaggaca tgtcagtctt    82020
ggtcctctat gacaccacac tggcatcaga gaaccacaga atactaccca aatgggtatg    82080
tctttgagtt ttctcccaag agaaacagcc acccacttaa atttctcctg gaagagccat    82140
gcttccagct aacttcttat gacccaattt ctctcagacc cagaatgttg gacagaatgt    82200
ctcaggcttc ttgctttggg cacagggtct gagaggagag aaatgtcagg ccagctctct    82260
tttctcatag ttgatagaag taggaggata cttggaggtg gtgaggtctc atgaatagaa    82320
agctcagaag aacatatgac catgtgctta gaaatagcac cattccacaa tgcccactaa    82380
agaccagtga aatagttcaa ccagggaatt ctgtcattct aatctccaag ccctggagtg    82440
aaggttgtgt ttgccatgtt tgtcttgggt aacaagtgaa ggatatctat attgacttcg    82500
agatcttccg atcactttct cctctaacct gtataaacac attgggttct gagaacaagg    82560
tgtctgaaaa gctatgtgtt gccagcccat gaggggcaaa aggaggaagg cagctgagag    82620
tcaggaagta tagagatgct gaagagttac acattcagga agatggacag aaacccatgt    82680
ctggctatgc cagcctttct gccatgaagg actatcaaat acatgagaaa acagttttca    82740
caggttggac aacagatatg gtaggcttga gagaactgag aaagggaatc aaaggagatc    82800
aacttcatca ttaacctgtc ttccttcctg gacacagtgt tggattgaag gacaagcaga    82860
tggagcccag ctgaccacag cagtcttgct taactgagga gagagactgg agtctgcgat    82920
gcctcaggca gctgatgtgt tctaggctgg ctaagaatga gaagggattt gtggaagaaa    82980
```

```
ggagctccag gaatacacac agaagtctcc tcaaggcttt ggctaaatac aaagctgcgt   83040
atgcacaggg agagttttca taaagaaaga acaacaaaga aaagctactt gggaaagaac   83100
aactgcaggg gaacagtaag ctcaatggag atgccagagc tcacatagca ctgggggata   83160
tttgaattct gaccactcag aggagaaaca cctcactaca ttttgggcat tcagtagaga   83220
ccaaagaaag ctgtattttg ggattgggat catcttattc ctagaatcaa ggtgactcca   83280
gaaaaactcc aacaacccct cttccaagcc agtctaaaag gatccaaatg atctccaagt   83340
aaattaactg cattccacaa gaaaaaaaaa actcaacccc ccttagaggc aagggacaaa   83400
tacaagttgc tcagttatat ggcattccta ttgcgttact tctatttaaa aatttaatag   83460
agacacaaga agctttcact gtgatacata actgggagaa aaaatcactc aacacaaaca   83520
ggcccagaaa ttatagaatt gatgacattg gtgagaacat ttaaaatgca cctctgagaa   83580
ctgtgtttca ggaaaatgtc agcaaaagct gaccatgaga gaaacaaaag cagaatagca   83640
agagaaaaga aaagaaccgg agagccaaat gaaaattaaa gaactgagaa aaggtacatc   83700
tctaatgaag aactcactgg atggccttat catcacttta gacattacgg taggaaaggt   83760
gacctagaaa ataattcaat aggagctaca caaatcacag gacagacaga cagaccaaca   83820
gacagaaaca cacacacaca cacacacaca cacacacaca cacacacaca cacacaaaga   83880
ctgaacctat taatcaacag agcctcaagg gcatctagga aaaatccaca catttaatat   83940
atgtgttagg caagtcacag aaggagaaga aaaagatatc atgacagaca ttatacttga   84000
agcgatgatg gctcgcaaca cgccaaatat acagaaaaca agaaactcat agtcaagaag   84060
ctaaatgact caggtataga attttaaaga gcaaaactct atgatttact gggatatatc   84120
atagttaagt tgcctcaatt caaagctaaa agaaaaaaaa gggggttcct atgaacaaca   84180
gctttgacag ctgttgatct aagaccacag cttaaatatc taggcaagga aaagcaaata   84240
aggcacaagg aaagaggatg gaaggaaata gtccaaacca atgacattca gtggaaaaga   84300
aaatagacca acaaaggagt aaatccatga aacagaaagt taggttcttt gaaaagtcta   84360
tatgattggc caaagtctgg ctaaacagat gacagaccaa ggagggagca tatccatcac   84420
catcatgagt aacaggagag agatgccatt gctatagcat cctccaggtg tgaaagctga   84480
gaagtagata ttgagatcaa ctgtatgtaa ataaattcat gaatgtagat catgtggatg   84540
gattgcttag gtaaataaca aatcagcaaa tcaaacactg aatagatcat gcagttttat   84600
agagacttac agacagcctg acagataaac atttgtatgt acgtgaaaca atctccaaga   84660
cacacttcaa aatccctctc ggttaatcca aaggaatgta tttggcagaa ggtagaagga   84720
gggtattctg atcctttctg gtacacattg atgttttctc tcagtttttct tataaagcat   84780 agattacttt gaatgtgtta caataagaat cataagctgt cttttgaaatg ttgacagttg   84840 tttagaagtt gaggaccatt tgtgagtgtt atgggacttt agtgagaata tttcaaattt   84900
gcttgtttac actttgttac aagaaaacat agagggtgcc aggtggtgct gtatcttctc   84960
caatctctgg tgacctgtat tgtttttggaa tttgcagtgg cctgaccagg aactactgca   85020
ggaatccaga tgctgagatt cgcccttggt gttataccat ggatcccagt gtcagatggg   85080
agtactgcaa cctgacgcaa tgtccagtga tggaatcaac tctcctcaca actcccacgg   85140
tggtcccagt tccaagcaca gagcttcctt ctgaagaagg taagaagcct gcagtcagac   85200
aaccataccc tcggacattg ggataaaaag atttgcaaaa tctttgtgat gcagaaaact   85260
tccatgctgc acaggaagtc gaaggtgaag tcatggacag ccaatgggaa ggaagcttca   85320
gtgccttctc tgggggggacc agagctggga tgttgagtgc cttgtgaggg atggtgtctt   85380
```

```
taaaagggc acagaccctc taggacactg gatttatcac ttccctgtta tcaaacgaat    85440
catattagtg tcctagccaa gatggatatt ctaacatcct gccaaacttg tgaagatata    85500
ccaagctcct aagcctgtcc agcccttct tcaagtaggc agtgtttatt gcagtcttca     85560
gctttaccat tttgaaggaa tgccattttt gaggctgttg ttcttgagaa acctaacatg    85620
tcttcattag atccgtattg tcctgagact ttgaagcagt acatagccac caaattgttt    85680
atctccccag cctaccttca tcttgggcat gccttccaca cctaggattt gagggaaggg    85740
atttctcagt gttctcatcc ctgcttctca tggaacattt atctccgttg ttttttgaga    85800
agaagagtag tggatgtcag ctttcttgta atgagggatc ctgggcccaa gattccctgt    85860
ctcccctcct aggctataaa attttggcct gtactccttc tccctgagag gcaatgtgtc    85920
tttacctaca agtcctagat gcaagatcct tttctgcccc acaccccaga atctgaaggc    85980
ttttgctttg gaggagcagt ggtctagtgt gcaagggttt catgtatacc ccccactaac    86040
agccaatcac cacctatagc ctgaacagct tgatgcatgg caccctggtc tcctgccttg    86100
ttctcatgaa cacccagaag aggtgtaagc aaaagaccat tcacatgagt gtaattttga    86160
agtataggca ctctgatctg ttttttgttt gtttctttgt ttgtttgttt tccagggttg    86220
aattaaaata tttatgacta cttattaaat ttctagaatc ctataagtct atttgtattt    86280
ttattctaca tttcaatttg catgctaata tagaagagtg taaattgtta atcctcagat    86340
tattccactt tgtgtgtcat aatttttttc acatttccct tttctaggca atactgagct    86400
tgattttctc ttttaattc agcaccaact gaaaacagca ctggggtcca ggactgctac     86460
cgaggtgatg gacagagtta tcgaggcaca ctctccacca ctatcacagg aagaacatgt    86520
cagtcttggt cgtctatgac accacattgg catcggagga tcccattata ctatccaaat    86580
gcgtatgtct atcatgttag ccataaaagg aacaatagtc aactaaaatt tctcttagct    86640
ggcccatgct acaagctcac ttcctaggtc caaatttctc atagactcag agtttgtagc    86700
aaaatgtctc aggaaactta cttttgagca aaaggtctga atgaagagaa gttttaggat    86760
tgctatcttt cataacaatt tgatggaagc agcaggatat atggaggtgg tgaagtctca    86820
ttaatgtaaa gctaaggaga tcaaatgacc aaatgctgag acaaagtatc attccacaat    86880
gcccactaaa ggtccatgca gtcttcaac catgcaattc tatcattcta tcctccattc     86940
cctgaagtga aatttgtgtt tgccattttt gacacgaatc agaagtaaca aattcaggct    87000
gggtgcagtg gctcaggcct gtgatcccaa cactttggga ggacaagacg ggcagatcac    87060
cagaggtcag gagttcaaga ccagcctggc taacatggca aaacccccatc tctacgaaaa    87120 attaaaaaat tagccggtca tggtggtggg tacctgtaat tccaactact gggaggctg     87180 aggcaggaga aacacttgag cctgggattc agagtttgct gtgagccgag aacatgccac    87240
tgcactccag cctgggtgac agagcaagac tcaatctcaa aaaaaaaaa aagaagaag      87300 aagaagaaaa gaagaagagg aagaagaaga agaagaagaa gaagaagaag aagaaggga    87360 agaggaagag gaggaggagg aggaggagga agaagaagaa gaagaagaag aagaagaaga    87420
agaagaagaa gaagaagaag aagaagaaga agaagaaaat agaaatgagt gcatatattt    87480
atatatgagt actagcctgt atgaacacac tgggttctaa gcaccagttt tctgaaggga    87540
tatgggttgt caggcagagt aaaagcagga atgcagatga gagtcaggaa gtaaacagat    87600
gtggtgatta aaatgggcag gtacatggac aaaaaaatgc atgtctgaca aaactggcc     87660 tcttgccata agtgagtatg aataatatgg aaaaactgtt tgcacatgtt gaacagcaga    87720
```

```
cagtacaacc tgagatagtt tagaaaggga acaaataag atcaacccca taattaccct    87780
tcctagactt aagggcaaag agttttaacc aaagcattcc acagcagtct tgctaaactg    87840
gggagagaga ctggagtttt gtttactaat aaaaccgaga ttttctaggt taggtaataa    87900
tgagaaagta tttgtggaga aaaggagctc caggaataca cacagaagtc tcttcaagtc    87960
tctggctgaa cagaaagctg tgtatgcaca gaaagagttt ccagagagaa aggagaacaa    88020
agaacagcta ctggggaaag aacaactgct ggggaacagt gagctcaatg aagatgccag    88080
agctcacata gcactgggag gtatttgagc tctgaccagc ctgaggagag acacttcatt    88140
gaacatcttg ggcattcagc aaagacccca aaaaaccata cttcaggagt agaattaatg    88200
cattcctaga ataaagtcta ctccagaaac accctagaaa agcttagaaa ccaagtctaa    88260
aaagatccaa atgatctcca agtaaattaa ttgcctgtca gaagaaaaca acctcttcag    88320
aggtaaacaa caaaattaaa ttgctcaatt atatagtatg cacaatgtgt ggcatacatt    88380
taaaaatttg ctaaacatac aaaaagcatt tagtgtgacc cataaccagg agaaaaatca    88440
gtcaatacaa atagacccaa aaatgataaa aataacagaa ttggcaagga gatttaaaat    88500
gtatgtatca taattgtgtt caaggattta agaaagcgt ggacaagaaa taaataaatg    88560
gataatatca acagaaagaa aaattgtaaa aggaccaaat ggagagtcaa gaactgaaaa    88620
aaaagacatc tctttaatga gaaaatcact acatggcctt ataatcatat tagatagtac    88680
agatgataaa gctaactaga aaatattagg gtggtgcaaa ccatagcacg cttatacaaa    88740
gcctgagaag ataaacagag cctcaaggac atctatgaaa atatcaaaat atttaatatt    88800
tgtttaaagc aagtcacaga ggaagggaaa gagatattgg aacagaaaaa atacttgaag    88860
cagtgatggc tgatgacttt ctaaatatgg aaaaaatgat aaactcacat agtcaagaag    88920
ctcaatggat cagatatagg attttaaaaa gtaaagctgt atgatttatt tggacacatc    88980
ataattaaat tgtccataat caaagataga aagtaaaatc ttatttgaag cccaagggaa    89040
aaaacatacc tttacataga gtaacagtga cacaaatgac tgatgccttc tcatcagaaa    89100
caacacaaat cagaaacaat agaataacac ctttagagtg gtaagaagaa aaaaagatca    89160
aatcagaaac aacaaaataa cacgtttaga gtggtaagga ggaaaacaag atcaaatcag    89220
aaacaatgga ataacacctt tagagtgtaa gaaagaaaaa aagatcaaat caggaacaac    89280
agaataacgc cttcagagtg gtaagaagga aacaagata aatcagaaa caatgaaata    89340 acacctttag agtagtaaga agaagaaaag atcaggtcag aaaaaatgga ataatatgct    89400
aagaagaaaa aaaagatca agtcagaaac aatggaataa caccttttaga gtgaaaagaa    89460 ggaaaaaaac ccagcaagct taaacgctat gcacagcaaa caattccact gaaaatgaat    89520
gttacgtaag tacatattct gtcctcctaa aacaaagaa caaataaaag aatgtttcat    89580
cagcaggatt atgtaataaa agatgtgaaa gaatgctatg taagtagaag aaaaataata    89640
ccatatggga attggcatca aaaccacaaa atactatcaa aacaaaaaaa ctttattgat    89700
aaatttaaca caatatgcaa aagaactata ccatgtatac tacataacat tggtgagaag    89760
aaaattagaa gatctaaata aagacacatc atgcttatag attaaaaaat ccaatgtcac    89820
ttttcacaaa actgatcttt agtttcaacc cacacccaag cagaattcct gcagtctttt    89880
cttgaaaacc taacagaatg tatatgctag aatcaccaag acaatcttta aaagaataa    89940 aaaacttgga ataaaatcac aagtttgtgg gatagatgca tatggtaata tggaaattct    90000
cataaagaca cagtaatcaa gacatgtggt attggctggg acgcttggct gtaatcctaa    90060
cactttggga ggccaagatg agaggattgc ctgagatgag gagttgcaga caagcctggg    90120
```

```
caacatagca agaccctcat ctctacaaat atttaaaaaa attagccagg tttggtgcca   90180
tgtgcctgta gtcccagcta ttcaggaagc tgaggtggga ggatcactgg agcccatgag   90240
gtggaggctg aaatgagcca tgattgtgct actgaacttt agcctgggag acagattaaa   90300
accttccctc tctctctcaa acaaacaaac aaaaaataca tagtattggg caaaacatat   90360
gcaaacaaaa acagaaaagg gtcagcataa atttacatat atggtcaatt tattttcaat   90420
acaggtagca aagcaattta atgaggaaat ttttttccaa aattggtctg aaacaactgg   90480
atagccatag aaaaaaacta taacaaatgt gacgcttgaa tcctactgta tgactcaaat   90540
taaattaatt tgagatagct cttagacctc aatgtaacag ctaattctga ggctgaaata   90600
taagactgct atgaaaaagt atagtatctt ataaccttgg agaaggaaaa attttttgag   90660
ggaagaacca gaaacactaa actgtaaaag aaaacaaatg ataatgtgga cattcattga   90720
ataaaaactt atgctcacca aatatgactg ttaagaaaat aaataagtaa gtaacacact   90780
ggaagaaaaa cactctcatc catatatctg acaaatggcc tgtatccaga gtatagaaac   90840
atttctccca ctcactaatc agaggacaaa caacctaatc aaaatgggca acaggcttga   90900
atagtcattt cttaggagaa gatgcacaca gagccaacaa tcacctgaaa aagtgcacaa   90960
catcttagcc atcaaaaatc aagagttata accctcataa gatgacactg aacatccagt   91020
gtacatggat atcattaaga agacacaata ataagtggtg tcaccgattt ggagctagaa   91080
tgtgccactc tctcatatgc tggtggaagt tcaaaatcat acaacaaatt aaaaaatcag   91140
tctgatgctt tcttataaag ttcgataaat atgcatctat cctacaaacc tgtaattcta   91200
ttcttgaata tttacccccc aaaatgaaaa cataagtcca caaaaatcta tataaatatt   91260
catagcagct ttatgtttta taaactcaaa ataaaaacta tttcaatgtt ttcatcaaaa   91320
gaaaatgaaa actatttaaa tggtttcatc aaaagaaaat gaaaaagaa tttccagtat    91380 atttatacaa aggaatacta ttcatcaaca aggaacaagt tactgatagt ctcagaagca   91440
tgaacaaacc tcaaaaatat attaaggaaa gaagccagac gtcaaagtgt atagtctgta   91500
tgagtccatt catgtgagtt tatagaaaac acaatttatg gtgaaagaaa ccaatagcat   91560
ttgacactgg ccgtgggaag agggtagcag agattgattg agcagccaca caagggagtt   91620
tctggggtgg tgaaaatgtt ctgcattgtg agggcagtgt gggctacaca agtatatgta   91680
tttatcaaat ctcatccagc tacatttaag atctgtgcat ctcactctat gtgaaaatat   91740
actcaactga aaaacagagc aggtatctgt ttcaggtgct acatcacttg atacgtccag   91800
ttgtgttaaa aaccactgcc taacatcctc aaatggggga tctgggcttg agactaggtc   91860
acatgtgtag agtctctaca gagaccgtgt tggattccca tgctccataa tacgttccaa   91920
gttttctcag acagccacag gtcatgaatg tgaggattct gagaggttgg agcaacgttc   91980
ttgggaggca taatggggaa ggcattctcc aagattcctc cagcctgggg tcttcacctg   92040
ctgtgcctct tactgcattg ttttctgact catccatagc cacttgaccc cttcagatcc   92100
catagtctac ctagccgtct ccctttatgc cttgggtccc gctgttcttt caactcatca   92160
cccattcctt cagtcccaga gtggctgcag ccagcagagg atggactgag agcaggagag   92220
gaggtcgtgc ccatgaaccc atcctagaga agcagcatcc tgcctgggag ctagtttttcc  92280 agggaagctt ttataagtcc tgtagaccca aacccacttg ctctaccaga tacagtatttt  92340 atagtaatac tattttcatg attatttttat attgcaaatg tagagcattt atgctacact   92400
atgagtaaat agagtaaggg ggctggcatg ggaattatat aatcttggat gccacttctt   92460
```

```
ccttgggaa atgtatttga gttccaactt acatattact atatagtctt atagagagag    92520
agacaaagag ctagacagac agagatatct ttgtatgtgc attaaaaaat ctaagataca    92580
tatttcaaaa tctgtgtcat ttattctgga ggaaagtatt tggcagaagg tgaaaggaag    92640
atattctgat cctttcttgt acagacatgt attatctcag ttttcataga gagcatatac    92700 tactttgat gttttaaaac aaaaattata atctgtgatg tgtccacagt tgtttaaaag     92760
ttgaagctga agaccatttg tgcttgtggc aatattattg tggtataatg ggaatatttc    92820
aaaggcactt gttaacactt tgttacagca aaatgtagag ggcgctaagt gcccttgaat    92880
attctcccat ctctggtgac ctgtgttgtt ttgaaatttg cagtggcctg accaggaact    92940
actgcaggaa tccagatgct gagattcgcc cttggtgtta ccatggat cccagtgtca     93000 ggtgggagta ctgcaacctg acacgatgtc cagtgacaga atcgagtgtc ctcacaactc    93060
ccacagtggc cccggttcca agcacagagg ctccttctga acaaggtaag aaatttgtgg    93120
ttagacatct atatactggg atgaaaaacc atgaaaaatc ttactgatgc agaagccttc    93180
agtggtacac tggagggttg gttgagggtc tgcaatgtgg aggaaagcct cagcgccctc    93240 tctggggat ccagaactgt gattttggc acgctgtgag gaggcagtgt ctttaggaag      93300
ggcacggtgt ctttaggaag ggcacagacc cgccagggca ctggacttac cactcccctg    93360
gttattaaat gggtcatttc agtgtcctag ccaaaatgga tattctaaca gcctgccaaa    93420
tatgtgaaga tttccaagcc aataagcctt tccagtgatt taaagtagac tttttcatt    93480 gcaatctaca gtttgcagtt tcttaagaac atggcctttg agtatgatat cctagagaaa    93540
cctaaggaga ctgcattatt tttctattgt cctggggctg catagcagga ggtaaccaac   93600
gaatgctgtc tctccctggc ctatctcagt cttcacagg ctctgttcac ctcagctttg     93660
aagttagaaa tttctaggtg ttcttgcctc ttccttctcat gaaacctgca ttggcagtga   93720
gtctacagaa gaagaggaag agaattctgc tttgttacaa ttcaggactc tgggcactag   93780
aagattccct atctctcctc caagggaata agttgtttgt ctctaaccct ccttgagaaa   93840
caatgagtct ttgcctgcac tcctaaatgt aggatgattt cctgcccaaa ttttcaaaag   93900
attaagcctt ttgccttggt atgagcaatg gtctagggaa atgcgcaagg gtcttgtgtc   93960
ggcccctgac tgaccaccag tcacctccta cagcctgcac caaggaatgc attgcattct   94020
ggtcttctgc cctgtggttc tcatgaaaac cagcagagat tcatatgatg gagctgcaca   94080
tgaatgtaat ttccaatgtc cagcattctc ctctgttctt tatctttaga tttaaaaata   94140
atgtttctat gaacttatta aaattctaga atactatgaa tctactgggt cttttcacat    94200
ccttttgcta ctagtagaaa aaagaatagt aataattttc agaggctact gtccagtatg   94260
tgacataaat tgtctcccat gtttctctgc tcatgcaatt actgagtatg atttattta    94320 ttttaatttc agcaccacct gagaaaagcc ctgtggtcca ggattgctac catggtgatg    94380
gacggagtta tcgaggcata tcctccacca ctgtcacagg aaggacctgt caatcttggt   94440
catctatgat accacactgg catcagagga ccccagaaaa ctacccaaat gcgtatgtat   94500
ttgattaaaa ccataagagg agcaacagcc aactcaaata ttggttagaa gacccatgct   94560
ttaagctcac ttcctaggga caaatttctc ttagactcac attttggcaa aatgtctcag   94620
gacctttgct tttgagcaaa gagtctaaga gaagagaaat tttaggcctg ctattttcc   94680 taatagttt atggaaggag tagaatatac ggaagtggcg aagtcatatt aatgtaaagc     94740
tcagaagata aatgaccaaa gcttaaacac agcaccattc cacaatgccc actaaaaatc    94800
aatgtcatct ttcactcgtg caattctgtc attctaaatt tcaattcccg aaggtttgtt    94860
```

```
tgccattttt gtcatgggta ataagtaaaa aaaaaaaaat taagatgtgt atatatatat    94920
atatatatat atatatacac acacacacac acacacaaac atctgaatat ttatatatat    94980
gtctgaatat ttatatactt gtgtataaaa cttatattta aattttttgca taaatttata    95040 tattttttaat atttcattaa aaattatatt gtttcactat gtatgtctga gtattttttat  95100 atattttaat ataacatttt aaatatttat ataaaatat tcaggtatgt aactgaatat     95160
tcatttacac acacaaatat atgtgtgcat gtgtgtatat atatatatac ccatatatat    95220
atatatatat atatatacat atatatatat atatatatat gtatatatat atatatatat    95280
atatatacac acacacacac acacacatac atacaggtat aaacacactg ggcctgaagc    95340
accagtggtc tgaaaggaca tgtgttgcca ggacttgaag agcaaaagca ggaaggcgga    95400
tgagagtcag gaggtacaca aacgctgaaa agtaaaatgg acaagtacat ggacaaaaag    95460
caggtataag cataacagcc ttttggaagt aaatgactat aaaatatatg aaaatactgt    95520
tttcacaagt tgcacaacag atagtagtgt attgagataa tttagaacag aaaacaaatg    95580
tgatcaaccc cataagtgtg ctgtatttca tcatggattg aaggaaaaag agatggagcc    95640
caagaagacc acagcagtct tgatgaactg agagacacca gagtttggga ttacaaaggc    95700
agctgggatt ttctacactt ggtaataatg agaaagaatt tgtggagata aagagctaca    95760
gtcatgtacc tagaagtcac ctcagtgtaa tataaatctg catatgcaca gggagtgatt    95820
ccacaatgaa agtaggacaa agaacagcta ctggggaaag aataactaca agggaacaat    95880
gagttcaatg gagatggcag agctcacaaa gcactggggg atatttgagt tcttaccagc    95940
tagaaaagag acctcattgc aaatcttggg cattcagtag agaccccaga aaagccactc    96000
tttggaaaca gagttgatgt attttaagag caaaatctac tccacaaaaa tcctagcaaa    96060
attgaaaagc aagtcagaaa gaccaaaatc ctctcaacat aaattagttg cccatcagaa    96120
gaaagcttaa cctcttcata ggtaaacaat aaaatcaaat tgctcagtta tctggcatcc    96180
acaatatgtg acataaattt aaaaatttac tagacataca agaagcattt agtgtgatcc    96240
ataaccagga gaaaaatcat tcaatacaaa tagacccaga aatgacagaa atgatagaat    96300
tagcaaaaac atttaaaata tacatatgat catttgatct tgtgatcaga tatcacaaga    96360
gaagaaagag atacttgaac agaaaaaatg cctgaagcaa tgatggctga aaactttcca    96420
aatatgaaga aaaaaaagct cacagattca agaaaactaa tcaatcagaa atatgatttt    96480
gaaaagtaaa aatgtatgat ttactttggc aaatcttctt ggttaaattg tctaaaatca    96540
aagaaagcta ggaaaatttt ataagccaga ggaaaaaaga ttgtttatat aaaggaacag    96600
ttacacaaat gactgatgcc ttctcatcag aaacaatgaa agtcagaaac aataaagtaa    96660
catctttaaa gtaatagaag aaaaacccaa gaggtgaggg atcgtggcag acaggaggca    96720
ggactagatt gcagctctgg acagagcagc atgcagaggc tcatattgtg aattttagcc    96780
ccatattgac tgcaagaaca gaccagcaat cctgagagga cccacagacc gtgtgaagga    96840
agcagactgc tcctgcagga taagggagac accccaaata ctgtgagttc cccaactgca    96900
gaagtggaaa agggaggcct tactccctca aacacacccc acaactggag aagctgaaag    96960
tctgtttgca ggagaagttc ccaacttttac ctgggcctca gtaaatttag agagctgagc    97020
caagcaaaat atagggggtag aggaagcagc agagaagacc tcagagcttg ctggatcccc    97080
aagcagctca ttcctgcctg gcaccacaga gatccatcag aagtgtggcc aaaggaacag    97140
agggtaaaac tccacatgga ggactgctct acctgaactt tctaacaatt tgaacagggg    97200
```

| | |
|---|---|
| gagaagcctc ctggccagaa cttgggggag ggcatgaatc tggtttgcag acttcacagg | 97260 |
| tgggggaagg actaaagccc ttttctttca cagctgggag gtggaaagcc tcaggcaagt | 97320 |
| tttcaagcct gactttcccc ccacctggaa acagacttgg agctgttgcg gggttggggg | 97380 |
| catggtggga gtaagaccag cccttcagtt tgcatgggtg ctgggtgagg cctgtgactg | 97440 |
| acagcttccc tccacttccc cgacaactca gatgactcag cagaggcagc cataatcctc | 97500 |
| ctaggtacac aactccagtg acctgggaac ttcaccccca caccatacag aagcttcagt | 97560 |
| aagacgtgcc caaggaaagt ctgagctcag acacgcctag tcccaccccc aactgatggt | 97620 |
| ccttccctac ccaccctggt agcagaagac aaagagcata taatctttgg agttctaggg | 97680 |
| cccacccacc tctagtccct ctccacacta gtatagctga tgcaggaggc caaccagcac | 97740 |
| aaaaatagag cattaaacca ccaaagctag gaacccctat ggagtccatt gcaccctcct | 97800 |
| ccacctccac cagaacaggc actggtatcc acagctgaga gacccataga tggttcacat | 97860 |
| cacaggactc tgtacagaca gtccccagta ccagcccaga gctgggtaga cttgctaggt | 97920 |
| ggcaagaccc agaagacagg caataatcac tgcagttcag ctcacaggaa gccacatcca | 97980 |
| taggaaaaga gggagagtac tacatcaagg gaacacccca tgggataaaa acatctgaac | 98040 |
| aacagccttc agccctacct tccctctgac acagtctacc caaatgagaa ggaaccagaa | 98100 |
| aaccaaccct ggtaatatga caaaacaagg ctcatcacac tcccagttca ccagcaatgg | 98160 |
| atccaaacca agaagaaatc cctgatttac ctgaaagaga attcaggagg ttagttatta | 98220 |
| agctaatcag ggagggacca gagaaaggca agcccaatg caaggaaatc caaaaaaaaa | 98280 |
| aaggtataag aagtaaaagg tgaaatattc aacaaaatag atagcttaat aaaaaaacaa | 98340 |
| taaaaaattc agtagacttt ggacacacct ttggaaatgt gacatgctct ggaaagtctc | 98400 |
| agcaatagaa ctgaacaagt agaaaaaata aattcagagc tcaaagacaa ggacttcaaa | 98460 |
| ttaacccaat ccaacaaaga caaagaataa aggataagaa aatatgaaca aagccttcaa | 98520 |
| gatgtctggg attatgttaa atgaccaaat ataagaataa tcgtggctcc tgaggaaaaa | 98580 |
| gacaatacta aaagcttgga aaacatattt gggggaataa ctggggaaaa cttacctggc | 98640 |
| cttgctggac acctagacat gcaaatacaa gaaacacaaa gaacatgtaa atacaagcag | 98700 |
| cacaaagaac acctgggaaa ttcatcacaa aaagatctta gcctaggcac attctcatca | 98760 |
| ggttatgcaa agttaagacg aaggcaagaa tcttaagagc tgtgagacag aagcaccagg | 98820 |
| taatgtataa aggaaaccct atcagattaa cagccagttt ttcagcagga actgtacaag | 98880 |
| ctataaagga ttggagccct atcatagcct cctcaaacaa aacaattatc agtcaagaat | 98940 |
| tttgtatcca gcgaaagtaa gcatcatata tgaaggaaag atacagtcgt ttttggacaa | 99000 |
| acaaatgcta agagaattca ccattaccaa gtcaccacta gaagaactgc taaaaggagc | 99060 |
| tctaaatctt gaaacaaatc ctagaaacac atgaaaacag aatctcttta aagcataaat | 99120 |
| cacacaggac ctataaaaca aaagtacaag ttaaaaaaca aaaacaaaaa acaaaaccaa | 99180 |
| agtacggagg caataaagaa tatgatgaat gcagtggcac ctcacatttc aatgctaaaa | 99240 |
| ttgaatctaa atggcctaaa tgctccactt aaaggataca aaagagttg gtggctggca | 99300 |
| agatggctga ataggaacag ctccagtctg ccgctcccg tgagatcaac acatagggtg | 99360 |
| ggtcattctc tgcatttccaa ccaaggtacc cggctcatct cattgggact ggttagacag | 99420 |
| tgggtgcagc ccacagaggg tgacctgaag cagggtgggg tgtcacctca cctgggaagt | 99480 |
| ggaagggtc agggaactcc ctcccctagc caaaggaagc cgtgagggac tgtgccgtga | 99540 |
| agaccagtgc attctggcac aaatactatg cttttcccac ggtctttgca acctgaagac | 99600 |

```
caggagattc ccttgggtgc ctacaccacc agggccctgg atttcaagcc caaaactggg   99660
ctggcatttg ggcagacact aagctagctg caggagtttt ttttcatacc ccagtggtcc   99720
ctggaatgcc agcaagacag aaccattcac ccccgtgaag aaagggctga agccagggag   99780
ctaagtggtc tttctcagtg gatcccaccc ccatggagcc cagcaagcta agctccactg   99840
gcttgaaatt cttgctgcca gcacagcagt ctgaagttga cctgggacgc tcaagcttgg   99900
tgggaggagg ggtatccaca aatactgggg cttgagtagg aggttttccc ctcacagtgt   99960
aagcaaaacc gctaggaagt ttgaactggg cagggtgcac tgcagcttgg caaagccatt  100020
gtagcaagag tgcctctcta gattcctcct ctctgggcag ggcatctctg aaagaaaggc  100080
agcagcccca gtcagaagct tatagataaa actcccatct ccctgggaca gagcaactgg  100140
aggaaggggt ggctgtgagt gcagctccag cagacttagt ttcctgcctg ccagctctga  100200
aaagagcacc agatccccca acacagcact agagctctga taagggacag actgcctcct  100260
caagtgggtc ctggtttcag aagataataa gaaactcctc tgagctaaag gagcatgttc  100320
taacacaatg caaggaagct aagaaccttg aaaaaggtca gaggaattgc taactacagt  100380
aagcagttta gagaagaaca taaatgacct tagggagctg aaaaacacag cacgagaact  100440
tcatgacaca tacacaagta tcaatagcaa aatcgatcaa gtggaagaaa ggatatcaga  100500
gattgaaaat caacttaatg aagtaaagcg tgaaaacaag attaaggaat aaagaatgaa  100560
aaggaatgaa caaatcctcc aagtatggga ctatgtgaaa agattgaacc tacgtttgat  100620
tggtgtacct gaaagtgatg ggagaatgga accaagttgg aaaacactct tcaggatatt  100680
atccaggaga acttccccaa cctagcaaga caggccaaca ttcaaattaa ggaaatacag  100740
agaataccac attcaaattc aggaaataca gagaacacca caaagatact cctcaagaag  100800
agcaacctga agacacataa tcgtcagatt caccaaggtt gaaatgaagg aaaaaaatgt  100860
tgagggcagc cagagagaaa gtttgggtta cccacaaagg gaacccatc agactaacag  100920 tggatcttcc tgcagaaact ctacaagcca gaagagagtg ggaggccaat attcaacatt  100980 ctttttttact attattatac tttaagttct agggtacatg tgcacaaggt gcaggtttgt  101040
tacatatgta tacatgtgcc atgttggtgt gctgcaccca ttaactcttc atttacatta  101100
ggtatatctc ctaatactat ccctccccac tcccccatc ccatgacagg ccccggtgtg  101160
tgatgttccc cactctgtgt ccatgtactc tcattgttca attcccacct atgagtgaga  101220
acattcggtg tttggatttc tgtccttgtg atagtttgct gagaatgatg gtttccagct  101280
tcatccacat ccctacaaag gacatgaagt catccttctt tatggctgca tagtattcca  101340
tggtgtatat gtgccacatt ttcttaatcc agtctaccat tgatggacgt ttgtgttggt  101400
tccaagtctt tgctattgtg aatagtgccg caataaacat atgtgtgcat gtgtctttat  101460
agcagcatga tttataatcc tttagatata tatccagtaa ttgtatggct gtgtcaaatg  101520
gtatttctag ttctaaatcc ttgaggaatc accgcactgt cttccacaat ggttgaacta  101580
gtttacagtc ccaccaccag tgtaaaaatg ttcctatttc tccacatcct ctctagcatc  101640 tgttgttttcc tgactttta atgatcacca ttctaactgg tatgagatgg tatctcattg  101700
tggttttgat ttgcatttct ctgatggcca gtgatggtga gcactttttc atgtgtctct  101760
tgactgcata aaagttttct tttgagaatt gtctgttaat atcctttgcc aacttttga  101820 tggggttgtt tgattttttt tcttgtaaat ttgtttatgt tctttgtaga ttctggatat  101880
tagccctttg tcagatgggt agattgtaaa aattttctcc cattctgtag cttgcctgtt  101940
```

```
cattctgagg gtagtttctt ttgctgtgca gaagctcttt agtttaatta gatcccattg   102000
gtcaattttg gcttttgttg ctattgcttt tggtgattta gtcatgaagt ccttgcccat   102060
gcctatgtcc tgaatggtat tgcttaggtt ttcttctagg gtttatatgg ttttaggtct   102120
aacatttaag tctttaatcc atcttgaatt aatttttata taaggtgtaa ggaagggatc   102180
cagtttcagc tttctacata tggctaggca gttttcccag caccatgtat taaataggga   102240
aacctttccc tatttcttgt ttttgtcagg tttgtcatag atcagatggt tgtagatgtg   102300
tggtattatt tctgagggct ctgttctgtt ccattggtct atatctctgt tttggtacca   102360
gtaccatgct gttttggtta ctgtagcctt gtaatgtagt ttgaagtcag gcagagtgat   102420
gcctccagct ttgctttttt ggcttaggat tgtcttggca atgcatgctc ttttttgttc   102480
catatgaact ttaaagtagt tttttccaat tctgtgaaga aagtcattgg tagcttgatg   102540
gggatggcat tgaatctata aattaccttc ggcagtatgg ccattttcac aatattgatt   102600
cttcctatcc atgagcatgg aatgttcttc catttgtttg tgtcctcttt tatttcatta   102660
agcagtggtt tgtagttctc cttgaagagg tccttcccat cccttgtaag ttggattcct   102720
aggtatttta ttctctttga agcaattgtg aatgggagtt catccatgtc cctacaaagg   102780
acatgaagtc atgtatggga atgcttgtga tttttgcaca ttgattttgt atcttgagac   102840
tttgctgaag ttgcttatca gcttaaggag attttggtct gagaagatgg ggttttctaa   102900
atatacaatc atgtcatctg caaacaggga caatttaact tcctcttttc ctaactgaat   102960
accctttatt tccttctcct gcctaattgc cctggccaga acttccaaca ctatgttgaa   103020
taggagtggt gagagagggc atccctgtct tgtgccagtt ttcaaaggga atgcttccag   103080
tttttgccca ttcagtatga tattggctat gggtttgtca taaatagctc ttattatttt   103140
gagatatgtc ccatcaatac atagtttatt gagagttcag catggagagc tgttgaattt   103200
tgtcaaaggc cttttctgca tctattgaga taatcatgtg gtttttgtct ttggttctgt   103260
ttatatgatg gattacattt attgatttgc atatgttgaa ccagccttgc atcccaggga   103320
taaagccaac ttgatcatgg tggataagct ttttgatgtg ctgctggatt cggtttgcca   103380
gtattttatt gaggattttt gcatcaatgt tcatcatgga tgttggtcta aaattctcat   103440
ttttgttgtg tctctgccag gatttggtat caggatgatg ctggcctcat aaaatgagtt   103500
agggaggatt ccctcttttt ctatgattgg aatagtttca gaagaattgg taccagctcc   103560
tctttgtatc tgtggtagaa ttcggctatg aatctctcct ggactttttt tggttggtag   103620
gctcttaatt attgcctcaa tttcagagcc tgttattggt ctattcaagg attcaatttc   103680
tttctggttt agtcttggta gggtgtatgt gtccaggaat ttttccattt cttctagatt   103740
ttctagttta tttgcacaga ggtgtttata atattctctg atggtagttt gtatttctgt   103800
gggattggta gtgatatccc ctttatcatt ttttattgca tctatttgat tcttctctct   103860
tttcttcttt attagtcttg ctagtggtct atcaattttg ttgatctttt caaaaaacca   103920
gctcctggat tcattgatgt tttgaaggtt ttttgtgtc tctatctcct tcagttctgc   103980
tctggtctta gttatttctt gccttctgct agcttttta tgtgtttgct cttgcttctc   104040
tagttctttt aatggtgatg ttagggtgtc aattttagat cttcctgct ttctcttgtg   104100 ggcatttagt gctgtaaatc tcccctaca cactgcttta aatgtgtccc agagattctg   104160
gtatgttgtg tctttgttgt cattggtttc aaagaatatc tttatttctg ccttcatttc   104220
gttacatacc cagtagtcac tcaggtgcag gttgttcagt ttccatatag ttgagcagtt   104280
tttaatgagt ttcttaatcc tgagtcctag tttgattgca ctgtggtctg agacacagtt   104340
```

```
tgttataatt tctgttcttt tacatttgct gaggaatgcc tcacttccaa ctatctggtc   104400
aatttcagaa taagtgcgat gtggtgctga gaagaatgta tattctgttg atttggggtg   104460
gagagttctg tagatgtcta ttaggtctgc ttggtgcaga gctgagttca attcctggat   104520
atccatgtta actttctgtc tcattgatct gtctaatgtt gacagtgggg tgttaaagtc   104580
tcccattatt attgtgtggg agtctaagtc tctttgtagg tctctaagga cttgctttat   104640
gaatctaggt gctcctgtat tgggtgcata tatatttagg atagttagct cttcttgtta   104700
aattggtccc tttaccatta tgtaatggcc ttctttgtct cttttgatct ttgttagttt   104760
aaagtctgtt ttatcagaga ctaggattgc aaccoctgct tttttgttg ttttccattt   104820 gcttggtaga tcttcctcca tccctttatt ttgagcctat gtgtgtctct gcacgtgaga   104880
tgtgtcttca gaatacagca cactgatgga tcttgactct ttatccaatt ttccagtctg   104940
tgtcttttaa ttggagcatt tagcccattt acatttaagg ttaatatttt tatgtgtgaa   105000
tttgatcctg tcatcatgat gttcgctggt tattttgctc attagttgat gcagtttctt   105060
cctagcatcg atggttttta caatttggca tgtttgtgca gtggctgata ccgattgttt   105120 cttttccatgt ttagtgcttc cttcaggagc tcttgtaagg caggcctggt ggtgacaaaa   105180
tctctcagca tttgcttgtc tgtaaaggat tttatttctc cttcacttat gaagcttagt   105240
ttggctggat atgatattct cagttgaaaa ttcttttctt taagaatgtt gaatattggc   105300
tgccactctc ttctggcttg tagagtttct gctgagagat ctgctgttag tctgatgggc   105360 ttcccttttgt gggtaacccg acctttctgg tgaatctgac aattatgtgt cttggagtta   105420
ctcttctcga ggagtatttt tgtggcattc tctgtatttc ctgaatttga atgttggcct   105480
gcctttgtag gttggggaag ttctcctgga taatatcctg aagagtgttt tccaacttgg   105540
ttccattctc ctcgtcactt tcaggtacac caagcagatg tagatttggt cttttcacat   105600
agtcccatat ttattggagg ctttgttcat ttcttttac tccttttttt ctctaaactt   105660
ctcttctcgc ttcatttcat tcatttgatc tttaatcact gatacccttt cttccacttg   105720
attgaatcaa ctactgaaac ttgttcatgt gtcacgtagt tctcgtgcca tggttttcag   105780
ctccattaga tcatttaagg tcttctctat gctgtttatt ttagtctgcc attcatctaa   105840 acttttcaa ggttttagc ttcttttgcaa tgggttcgaa catccttctt tagctcggag   105900
aaatttgtta ttacagatcg tctgaagcct tcttctctca actcatcaaa gtcattctct   105960
gtccagcttt gttctgttgc tcgtgaggag ctgcgttcct tcggaggaga agaggcaccc   106020 tgattttag aattttcagc tgttctgctc tggtttctcc ccatctttgt ggtttatcta   106080
cctttggttc ttgatgatgg tgatgtacag atgggttttt ggtgtggatg tcttttctgt   106140
ttgttagttt tccttctaac agtcaggacc ctcagctgca ggtctgttgg agtttgctgg   106200
aggtccactc cagtccctgt ttgcctgggt attaccagtg gaggctgcag aacagcaaat   106260
attacagaac agcaaatgtt gctgcctgat tcttcctctg gaagcttcat ctcagagggg   106320
cacccagctg tatgaggtgt cagttggccc ctactgggag gtgtccccca gttaggctac   106380 tcggggtca cggacccact tgaggaggca gtctgtccat tctcagatct caaactctct   106440
gctgggagaa ccactactct cttcaaagct gtcagacagg gatgtttaag tctgcagaag   106500
tttctgctgc cttttgttca gctatgccct gcccccagag gtggagtcta cagaggcagg   106560
caggtctcct tgagctgtgg tgggctccac ccagtttgag cttcctggtc gctttgttta   106620
cctactcaag tctcagcaat ggcagacgcc cctcccccag ctttgctgcc gccttgcagt   106680
```

```
tcggtctcag actactgtgc tagcagttca atctcagact gctgtactag cagtgagcaa    106740
ggctctgtgg gcatgggacc ctctgagcca tgtgcaggat ataatctcct ggtgtgccgt    106800
ttgctaagac cattggaaaa gtgcaatatt agggtgggag tgtcccgatt ttccgggtac    106860
atctgtcatg gcttcccttg gctaggaaag ggaattccct gaccccttac acttcccggg    106920
tgaggcaata tcccgccttg cttcggctca ctctccgtgg gctgcaccca ctgtctgaca    106980
agccccggtg agatgaaccc agtacctcag ctggaaatgc agaaaccacc catcttctgc    107040
tttgctcatg ctgggaactg tggactggag ctgttcctat tcggccatct tgaaacctcc    107100
cctctctcac gatcacaagg tcccacaata ggccgtctgc aggctgagga gcaagaaaag    107160
ccagtctgaa ttccaaaact gaagaaattg gagtctgatg ttcaagggca ggaaacatcc    107220
agtgccaaag aaagatgtag aatattcaac attcttaaag aaaataattt tcaacctaga    107280
atttcatatc cagccaaact aagctttata acaaaggaga agtaaaatcc tttacaaaca    107340
agcaaatgct gaggaatttt gtcaacacca ggcctgcctt acaagaggtc ctgaagaaaa    107400
cactaaatat ggaaaggaaa aaccagtaac agctactgca aaaacatacc aaattgtaaa    107460
caccatcaac actataaaga aactgcatca actaatgggc aaaatagcca gctagcatca    107520
taatgacagg atcaaattca cacataacaa tattaaccct aaatgtaaat gggctaaatg    107580
ccccaattaa aagacacaga ctgggaaatt gaataaagag tcaagaccca ttggtttgct    107640
gtgttcagaa gacccatctc agggtgaaaa gacatacatg ggctcaaaat aaagaaatga    107700
aggaatattt accaagcaaa tggaaagaaa aaaaagcag cggttgcaat cttagtcttt     107760
gatgaaacag actttaaacc atcaaagatc aaaagagaca aaggagggca ttacctaatg    107820
gtaaaagtat caatgcaaca agaagatctg actgtcctac ttatatatgc acccaataca    107880
ggagcaccca gattaataaa gcaagttctt agagacctac aaagagactt agacttccac    107940
acaaaaatag tgggagactt taacaccccca cagccaatat tagatcgacg tgacagaaaa    108000
ttaacaagga tattcaggac gtgaattcag ctctggacca agctgaccta atagacatct    108060
acagaactcg acaccacaaa tcaacagaat atacattctt ctcagcacca cattgcactt    108120
attctaaaat tgaccacata attggaagta aaacacttct cagcaaatgc cgtagaatgg    108180
aaatcataac aaaacagtctc tcagaccaaa gtgcaatcaa actagaactc aggattaata    108240
aactcactca aaaccacaca actatatgga aactgaacaa cctgctcctg aattactact    108300
gggtaaataa caaaattaag gcagaagtag ataagttctt agaaaccaaa gagaacaaag    108360
acacaatgtg ccagaatctc tggtacacag ctaaagccat gtttagaggg aaatttatag    108420
cactaaatgc ccacaggaga aagcgggaaa gatctaaaat caacacccta acatcacaat    108480
tcaaagaacc agagaagcaa gagcaaacaa atacaaaagc tagcagaaga caagaaataa    108540
ctaagatcag agcagaactg aagggggataa agacacgaaa accctttaaa aaattaataa    108600
atccaagagc tggttttttg aaaagattaa caaaatacat agaagcctag ccagactaat    108660
aaagaagaaa atagagaaga atcaaataga cacaataaag aataataaag gggatatcac    108720
caatgatgcc acagaaatac aaactaccat cagagaatac tttaaacacc tctatgcaaa    108780
taaaatagaa aatctaaaag aaatggataa attcctggac acatcacccc tcccaagact    108840
aaaccaggaa gaagtcaaat ccctgaatag accaataaca gttctgaaa tcgaggcagt     108900
aattaatagc ttaccaacca aaaaagccc agaccagagg gattaacagt caaatcctaa    108960
cagagggtaca aagaagagct agtactattc cttctgaaac tattccacac aatagaaaaa    109020
gagggactcc tgcctaactc atttttatgag gccagcatca ttctgatacc aaaacctggc    109080
```

```
agagacacaa caagaaaaga aaatttcagg ccaacatccc tgatgaacat caatgtgaaa  109140
atcctcaata aaatactggc aaactgaatc cagcagcaca tcaaaaagct tatccaccat  109200
gatcaagttg gcttcatccc tgggatgcaa ggctggttca acatattcaa atcaataaac  109260
ataatccatc acataaacag aaccaatgac aaaaaccgta tgattatcgc aatagacgca  109320
gaaaaggcct ttgataaaat tcaataccca atcatgctaa aaactcttaa taaactaggt  109380
attgatggag catgtctcaa aataataaga gctacttatg acaaatgcat agccaatatc  109440
atactgaatg agcagaagct ggaagcattc cctttgaaaa ccagcacaag acaaggatgc  109500
cctctctcac cactcctatt caacatagta ttggaaattc tgtccagggc aatcaggcaa  109560
gagaaagaaa taaggtatt caagtgggaa gagagggagt caaattattt ctctttgcag  109620
atgacatgat tgtatattta gaaaactcta tcatctcagc ccaaaatctc cttaagctga  109680
taagcaactt cagcaaagtc tcaggataca aaatcaatgt gcaaaaatca caagcattcc  109740
tatacaccaa taagagacac agagccaaat cctgagtgaa ttcccattca caattgctac  109800
aaagagaata aaatatacct aggaatccaa cttacaaggg atgtgaagga cctcttcaag  109860
gagaactaca aaccactgct caaggaaata agataggaca caaacaaatg gaaaacatt  109920 ccatgctaat ggattggaag aatcaatatt gtgaaaattg ccatactgcc caaagtgatt  109980
tatagattca atgttatccc catcaagcta ccattgattt cttcacataa ttagaaaaaa  110040
ctactttcaa tttcatatgg aatagaaaaa gggcctgtat atccaagaca acctaagcaa  110100
aaagaacaaa gctggaggca tcatgctatc tgacttcaaa atatactaca aggctacagt  110160
aacaaaaaca gcatggtatg gtactggtac caaaacagat atatagacca atagaacaga  110220
acagaggcct cagaaataac accacacatc tacaactatt ggatctttga caaactggac  110280
aaaaataagc aatggggaaa ggattcccta tttaataaat ggtgttggga aaactggcta  110340
gccatatgca gaaaactgaa actggatccc ttccttacac cttatacaca aattaactca  110400
agatagatta agaattaaa tgtaagacct aaaaccataa aaaccctaga agacactttg  110460
ggaggccgag gtggatggat cacgaggtca ggagatcgag accatcttgg ctaacacagt  110520
gaaagcccat ctctactaaa aatacaaaaa attagctggg tgtggtcgtg ggcacctgta  110580
gtcccagcta cttgggaggc tgaggcagga gaatggcatg agctgaggag gttgagcttg  110640
cagcaagcca agattgtgcc actgcactcc agcctgggca acagagtgag actccatcaa  110700
aaaaacaaaa acaaaaacaa aaaatcaaac cctagaagaa aacataggca ataccattca  110760
ggacataggc atgggagaag acttcatgac taaaacagca aaaccaatgg caacaaaagc  110820
caaaatttac aaatcagatc taattaaaat aaagagcttc tgcacagcaa aaaactctca  110880
tcagagtgaa aaagcaacct atggagaaaa attctgtggt ctagccatct gacaaagggc  110940
taatgtttag aatgtacaag caacttaaac aaatgtacaa gaaaaaaaaa acaacccat  111000 caaaaagtgg gcaaaggata tgaacagaca cttctgacag gaagacccttt atgtggctga  111060 caaacatgaa aaaagctcat catcactgtt aattagagaa atgcaaatcg aaaccacaat  111120
gagataccat ctcatgcccg ttagaatggc gatcattaaa aagtcaggaa acaacagatg  111180
ctgaagagga tgtgtggaga aagaggaaca catttacact gttggtggga gtgtaaatta  111240
gttcaaccat tgtggaagac agtgcggtga ttcctcaagg atctagaacc agaagtacca  111300
tttgacccag caatcccatt actgggtata tacccaaagg attataaatc attctacaat  111360
aaagacacat gcacacgtat gtttattgta gcactattca caatagcaaa gacttggaac  111420
```

```
caactgaaat gcccatcaat gatagactgg ataaagaaaa tgtggcacat atacactgtg   111480
gaatactatg cagccataaa acaggatgag ttcatgtctt ttgcagggac atggatgaag   111540
ctggaaacca tcattctcag caaactaaca caagaacaga aaaccaaaca ccatatgttc   111600
tcactcataa gtgtgagttg aacaatgaga acacatggac acaggaaggg gaacatcaca   111660
cacaggggcc tgttggggag ttgaggctag gggagggatt ggattaggag aaatacctaa   111720
tgtagatgat gggttgctgg gtgcagcaaa ccaccatgac acgtgtatac ctatgtaaca   111780
aacccacaca ttctacacat gtatctcaga acttaaagta taataataat aagatacaga   111840
actgcagaat gaataagaac tcaccaacca tctgctgcct tcaggagact catttaagac   111900
ataaggactc acataaactt aaagtaaatg ggtggaaata ataataagtg gtgtcactga   111960
tgtggaggta gattataaaa ctcttatcat atgctggtgg aagatcaaaa tgataaaacg   112020
aattaaaaaa tcagtcagat ggtttcttaa aaagttccat caatatgcct ctatcttaca   112080
aacctgcaat tctattcctg aatctttatc ccaaggaaat gaaaaagtaa gtccacaaag   112140
agttctatat gaatatttat aggagcttta tttattataa ttcaaactgt aaaaataatt   112200
tcaatgttca tcaataacaa aatgaaaaaa taatttgcaa cctactggta cacttgaata   112260
ctattcagca ctgagtatct taaatagcat ggatggagct caaaaatata ctcaggaaag   112320
aagccatgta tattctgtat gagttcattt acatgagatc atttacattt cctccaaaag   112380
aggaaaaact aatttctgtt gaaagaaacc aatgtatttg cctctggcag tggtaagggg   112440
gtagcacaga ttaattgggt agggactcaa gagagtttct ggggtcacag aaatgttccg   112500
tgtggtgatg ggagtttggg ctccacaggt ataggtgttg atccaaaatc atcaaaaaaa   112560
caacattgca gatctgtgca tctcactctg tgggaaagta tatctcaact gtaaaagggg   112620
cagaaattgc ttttaaacgc tcagccttt agcacatcca gttgcttgga gaaccagctt   112680
actcaaatgg gggtctaggc tggagactag gtcacaggca tagagtctct aaactttccc   112740
atggcacata atacgtttca ggttttctca gagagctgca ggttagtaat ctgaggattc   112800
tgacaagttg ggtcaacgtt cctaggaggc atgaatggga gtgcattctc taagatccct   112860 ccacccagg gtccttgctt tctgtgcctc ttactccatt gttttctgac tcctctgtag   112920
ccactcgacc tcttcagatc ccattgtcta cccagccatc gccctttatg acttgggtcc   112980
cactgttctt tcatctcatc ctccattccc tcagtttcgg agtggctgcc gctagcagag   113040
gatggactga gagcaggaga ggtggtcctg cccaggaacc catcctagag aaatggcatc   113100
ctgtctggga gctagttttt tagggcaggt tttataagtc ttgtaaagcc agacacactt   113160
gatctacctg gtatgttatt tacagtaata ctattttcat aattgctttt cactctaaaa   113220
gtagagcctt ttagctacac tgtgagtaaa taaaggggct ggcctgggaa tggtatcatg   113280
ttggatgttg tttcttccct gaagtaatat atatcagtta caatttacat gttactgcag   113340
agtcctagag agagacacag agaatgagac agataccaat acatttttat gtgcattaaa   113400
aaaatctaag gccaggcgca gtggctcaca cctgtaatcc cagcactttg ggaggccgag   113460
gtgggtggat cacgaggtca ggagattgag accatcctgg ctaacacggt gaaaccctgt   113520
ctctactaaa aatacaaaaa attagccagg cgtggtggcg ggcgcctgta gtcccagcta   113580
ctcaggagac tgaggcagga aatggcttg aacccaggag gcagaccttg cagtgagccg   113640
agattgcgcc actgcactcc agtctgggcg acagagcgag actccgtcac aaaaaaaaaa   113700
aaaaatctaa aatgcactct tcaaaatcta tgtcatttat tctggaggaa tgcagttggc   113760
agaaggagga agatattccg aattttttctt gtatacatt atgtatgatc tcagttttt   113820
```

```
tatggatcat agaccaattt tgatatttta aaataaaaat tataatctat cttggaaatt  113880
tacatggttc tttagaactt gaggaccgtt tttgcttttc ggaatattat tgtacctaaa  113940
atgggaatat tacaacgtca cttttttaaca ctttgttata acaaagttta gacagcgctg  114000
ggtgcccctg aattttttcc cgcctcttgt gacctgtgtt gttttggaat ttgcagtggc  114060
ctgaccgaga actactgcag gaatccagat tctgggaaac aaccctggtg ttacacaacc  114120
gatccgtgtg tgaggtggga gtactgcaat ctgacacaat gctcagaaac agaatcaggt  114180
gtcctagaga ctcccactgt tgttccagtt ccaagcatgg aggctcattc tgaagcaggt  114240
aagaagtctg tggccagata tctacacatt tgaacattgg gatgaaaaga gatggaaaat  114300
ctgactgatg cagaagcctt ccatgctaca cagaaacttg agggtatggc aggtggaaag  114360
aagcctcagc actctctctg gtggagcaat ttttggcgca acgtgcgtgg gcggtgactt  114420
caggaatggt gcaaacccac ctgggcactt gacttaccac tcactttgtt atgaaagggg  114480
ttatctcggt gttccagaca aaattccaat tctaacatca ggccaaattt gtgccaaatt  114540
tcacactagt gagtgtttcc aggcatttat taaaatggac agtgttcatt gcaatcttca  114600
gcattgcagt tgctgaggta tgtggccgct gagtttgtca tcctggggaa acctaatatg  114660
atgatattta ttccatctaa tcctggggct atttggcagt aaataccaca gaatacacta  114720
tttctctggc ttatttcagt cttaggtagg ctctgcacac ctatgcttgg aaggcaggaa  114780
tttcttggtg ttccttgtgcc ttcttctcat ggaacgtgca tctttggtgt gtgttgagag  114840
gaagggtagt agacttctgc tttgttgcaa tgcaggatgc tggaacaaga ggattccctg  114900
tctctactgt aagggaataa gattttagcc tccatccttc tctaagaagc aatgtgtctt  114960
tgcctccaag tactagatgc aggaccatga actgccccgt ccaccagaag cttaaggctt  115020
tggcttttca ggagcaatca tctagggaac tgtgcagggt tttcatgtct gtcccctact  115080
gacagccaat caccatacag cctgcataac ctaatccatc atcgtctggt ttcctgcctc  115140
attgttttca tgaacaacca gtagagagcc atacgaaaga gcttgcacat gagtctttgt  115200
tccaattgta agagcactga taggtccttt tcccaccagg ttttgaatat aaaatttcta  115260
agaacttatt aaaatattag aatgttatta atctattgtt tttgcttcag catgtccttc  115320
tgcttgtgag tatactaaag agaacagtca taattctgaa actactgtcc tgtttgtgtc  115380
ataaattgct tcacatgttt ctgcatacta gtagttactc agcttgattt tgtctatttt  115440
cagcaccaac tgagcaaacc cctgtggtcc ggcagtgcta ccatggtaat ggccagagtt  115500
atcgaggcac attctccacc actgtcacag gaaggacatg tcaatcttgg tcatccatga  115560
caccacaccg gcatcagagg accccagaaa actacccaaa tgagtatgtc tttgatgtta  115620
cttgtaagag gagcaacagc caacttaagt tcctcctaga agagccttgc ttcaagctaa  115680
cttgttagga caaatttccc ttagacccag aaggtgtgtc aaaatgtcca gacaactttg  115740
cttttgatca aagagtctga gagaataggt attttaggct tgctatcttt tctaatagtc  115800
tgatggaagc agaaggctac atggagctga tgaggtcttt ttaatataaa gctcaagaga  115860
tcaaatgatc aaatacttag agtgccattc tacaaggctc ataaaagatc aatgcactct  115920
ttcacccatg caattctatc attctaacct cccttctctg aaatgaaggc ttttgccat  115980 ttttgtcatg ggtcacaagt aaataattca catgtatatg agtatatata taaccaggtg  116040
tgtttattca gactagtatg tatatatata catatatatg ttcatataag ttagtattca  116100
tatatatgtt catatatata tgttcataca gactagtatt catatatata tacatatata  116160
```

```
tatacacaca catatatata tatatatata tgttctaggg aaacatgcaa ggtttttatg   116220
tctgtccctg actgatgacc aaatacccta tagcctgcac agctgcaagc tgtatagcca   116280
tacaatttgc aggacacaca cacatacaca cacacacaca cacacacaca cactaacata   116340
taatataata taatataata taatataata taatataata taatataatt aatatatata   116400
aacctgtgtg aacacactgg gttctaagct ccagttttct gaagggatat gggttgccag   116460
gagaggaaga gcaaaagcaa gaatgtagat gagaattagg aagtaaacag atatggagat   116520
taaaatgggc aggtacatgg acaaaaaacc aggtctgaca aaaactggct ttctgccata   116580
aatgactata aaagatatta aaaaacactt tccacatgtt ggacaagaga cagtacagga   116640
ctgagataat ttagaaaagg aaatgaatga gcgcaactcc gtaactatta tgactttctt   116700
cctggagaac cttcctggac tgaagggcaa ggaattggag ccaaagccaa ccacagcagt   116760
cttgctgaac tgaggaaaga gactggagtt tgggatagct aagaaaatgt gtattttcta   116820
tgctaggtaa taatgagaaa gaatttgtgg tgaaaaggag ctgaaggaat atgcatggaa   116880
gtctaatata aactgcatat gcacaggagg aaattctaca aagtgggaca gagaaccact   116940
actggggaaa ggacaaattc agggaaacag tgagctcaat ggtgacgcca gagctcacgt   117000
agcactgggg gataccgggg ttctgatcag cccgaggaga gacacctcat tgaacatctc   117060
gggcattcag tagagacccc agaaaagtca tactttagga gtaggattta tgccttctta   117120
gaataaagac taccccagaa acaccctagt aaagcttaaa aaccaagtct aaaaggaccc   117180
aaatgatctc caagtaaatt aactgcctga cagaagaaaa ctcaaccatc actggaggta   117240
aataacatga ttacagtgct ctgtaatgtt gcattcacaa ggagtgacat catttaaaaa   117300
tttatgaggc aggaaaaagc aattagtgtg atccataact aggagaaaaa ccagtcaata   117360
caaatagacc aagaaatagt agaaacgatg gaattgacaa agaaattaaa actgtatata   117420
tgataattgt gttcaaagat ttaaagaaaa catgaacatg agggaaacaa atgcagaata   117480
taaaaaaaag caaatgcgta aaacaaccaa atggaaatta aagaactaca aaaaagtata   117540
accttaataa aatactcact ggatggcctt aatattagtt tatacattac agaagaaaaa   117600
gtgaaccaga agataactca atgaaagcca tacaatctgt aagacacaca cacacgcaca   117660
cgcgcgcgcg cgcacacaca cacacacaca gagagagaga gagagagaaa gagagagaga   117720
gaaaggctga aaaaaataaa tagaacctta aggatatcag tgaaaatagc aaaagattta   117780
atatatgggt aaagcaagtc acagaaggac gggaaggaga tattgggaca gaaaaaaata   117840
ctcaaagcaa tgatggctga agactttaca cgtatgaaga aaatgataaa ctcacagtca   117900
agaagctcaa tgaatcagaa atagtatttt taaaagcaaa actctatgat ttacttgggt   117960
acattataga taaatcgtcc aacatcaaag ataacaagga taatcttata agccagagga   118020
aaacaatatc atttacatag agggacagta atgaaagtga ccgatgcctt ctccttggaa   118080
acaatggcat aacatcttta aagtgataaa gagaaataaa aacagatcaa cctaggacga   118140
catgtccagc caaacaaac aaataaacaa aaaacccctt taaataaac gtgatgtaaa   118200 tacgtattct gccacctcca gaggaaacaa gcaaaaaaac aaaagaatgt tccaaggca   118260 ggcttctgta ttaaaagatt ttaaggaaag ttattcaggt agaagaaaaa taataccaga   118320
tgggaacttt aatccatact aagtaatgaa gagccctgga aatggcaaat ggcaatgtca   118380
atataaaata ctcttatta tctaattttt aaatgtattt aaaggacaat ttgtgatatt   118440
aattaaaata ataggaatat attgttgttt caacgtatgt agtagtaaaa ttcataaaaa   118500
cagtagcaca aataatgcag atgataactg gaagtatact gttaatgagt ttttgcatt   118560
```

```
atccatgaag ttatataata ttaatagatg gttgaatgtg atagtttaag gtgggatatt   118620
ataaatccta ggacaaccaa aaaaatttaa actgagagga atggatagta agaggaatag   118680
tccttttatg caaaagaagg aagaaaaaga ggaataaaga atataaaaga tatggtgtaa   118740
acagaaaata catagcatta ttgtagacac aaactgaact accttatgag tatattaaat   118800
ataaaaggat taagcattac aaataaaagg cagagattgt aaattgaata aaaaccacag   118860
ctaagtgtgt tcttttttaga ataaatactc tttaagtgta aagatctact ttaaacacca   118920
aaatatgaaa aaggatatat accatgaaaa cctgaatcat aaataagctg gagtggtgat   118980
taatggatgc aggcactcct aaagactaat aagtgaatgt ggtcaaattg aagaaacaaa   119040
agtatatacg tgctcaatgt gcaaaaactt tttctgtata catgctatga tcctttggaa   119100
aattaaagtt ttaaagcaat atcactgaca atagtatcaa aaccaaaaaa tatttagtga   119160
taaatttcac acactatgct caaggactat acaccttgca ctagaaaaca atgttgagga   119220
aagaattaaa agatctaaat atacaccatg cttatagatt aaaagactcc atatcagttc   119280
tcgtgaaatt gatctttgga tgaaacccac acccaagcac tattgcaaca gtcctttttt   119340
ggaaaaaaaa attggaggac ttatatacct taatataaag acttataaaa gtacaggaat   119400
caagacatgt ggtattggcc tggcccctttg gctcatgcct gttaccccaa catttttggga   119460 ggctgagtct ggaggatggc ttgagcccag atgttcaaga ccagccttag caacagagtg   119520
agaccctctc tctacaaaaa ataaacaatt agatcgatgt gatgacttgc acatgtagtt   119580
tcagctactc ggaatgctga ggtgagagga ttgcttgact caggaggtct agccatgagt   119640
gagcattgat catgcctctg cattccagcc tggatgatgg aatgagacac tgtctcaaaa   119700
aaaaaaaaaa aaaaggatat gtgttattgg ccaaaaaagt atgcaaacct aaaaagggat   119760
ggcccaccac cagacccaca tacatatatg gtaaatggat tttccgtata gatggcaaag   119820
caattcaatg gagacaaaaa tgttttacaa aatcattctg aaccatttgg atatccatga   119880
tacaaaacaa aagcagaact tgacttttgc ttttcatctc aaattatttt gatatctctt   119940
ccacctaagt gtcagagcta aaactgaacc tgaaatatga agttccatg aaaaaatata   120000 aaatcttcac aaccttggag aaggcaaact tttttgaggc aggagtctgt aaacactcac   120060
tataaaataa aacaaattat aatgtgggct ttcatgaaaa ctcatgctta ccaaaagtca   120120
ttgttaagaa aataaatagg caagtaacac atgagaagaa aaatgctctc tgtccatata   120180
tctgacaaat ggcttgtgtc cagaatatag gaacatttct cccactcact aaacagagga   120240
caaacaacta atgggcaaca gattgaatag gcatttcttg gggatagata gatgtacaca   120300
tagccaataa gcacctgaaa aaatgtccag tatctcagcc atgaaaaata aagagttata   120360
atcatcatga gatgtcacca aacacccaat ggacatggat attattaaga agacaccaca   120420
gtaactgatg tcactgatgt agagcaagga tgtgaaactc tctcatatgc tggtgaaagt   120480
gcaaaatgat acaaccactt ttgaaatcag tctgatagtt tctccaaaag ttcaataaat   120540
gcacttttac cctacaaacc tgcaatcctg tttgtgaata tttaccccac agaaatggaa   120600
acataagtcc acgaagacat ctccaagaat attcatagca gctttatttt ttataacccc   120660
aaactgtaga caatttcaat gtcaatcaat aagaaaatga ataaataatt tgtgaactag   120720
tcatacaatg gcatactgtt cagcaataaa agggagcatg ttttgatac tctcaaatag   120780 tatggaagat gctcaaaaat attacattaa agaaagatgc cagataacaa aaatgaacat   120840
tatgtatgag tctattgatg taaggttcca gaaaggtaaa actaatttct ggtgaaagaa   120900
```

```
accaatatca tttgcctctg gccatgggaa gagagtagca gagattgatt gagcagtaaa   120960
acgaagtttt tttctggggt gatgtaaatg tcctgtattg tgattgaagt gtgagttaca   121020
caagtgtaca tgttcatcag aagtcatcaa actacatcta agatctgtgc atttgactat   121080
acatgaaaat atacctcagt tgaaaataga tcaataacct ccctcatata ctatacttgc   121140
taacacagcc agctgcttgg agaaccagct tgctggaatg gagaatctgg gcttgagact   121200
gggtcacatg tatagagtct ctacagagac aatgttgcat tcccacggta cataatacat   121260
ttcaaggttt ctcagacagc cacatgtcat gaatgtgagg attctgagag gttggagcaa   121320
cattcctggg aggaacgaag gggagcacat tctccaagat cccccaccac cggggtcctc   121380
accggctgtg cttttttttt ttttttcctt gacagagtct cgctctgtcg ccaggcagga   121440
gtgtaatggc ccaatctcgg ctgattgcag cctccaactc cagggttcaa gagattctcc   121500
tgcctcagct tcatgagtag ctgggactac agatgtgcgc cactgcgccc agctaatttt   121560
tgtattttta gtagacacgg gttttgcca tgttggccaa gatggtctcg ctctgttgac   121620
ctcgtgatcc acccgccttg gcttcccaaa gtgctgggat tacaggcgtg agccaaagca   121680
cccagcctgt gcctctcact tactcaattg ttttctgaa ccctccatag ctggtggacc   121740
ttttcagatc ccatagtcta gccagccctc tcactttatg ccttgggtcc cactgttcct   121800
tcatctcatc ccccttctgt cagtcccgca gtggctgtgg ccagtagagg atggactgag   121860
agtaggagag gaggttctgc ccaggaaccc atcctagaga aacagcatcc tgcctgggac   121920
ctagtcttcc aggtcagctt ttataagtct tttagactca aactcacttg acccacctga   121980
agtggtattg acaataatgc tattttcatg gttgttttc actgtaaatg cagagccttt   122040
tagctacacg actagtacag agagtaaggg aggctggcct gggaatgata tcatcttgga   122100
tggcatttcc tccttggaga aatatatgtt agttccaact cacatgttac tatacagtcc   122160
tgtagaaaga gatacagaga gttagacagg tatagacgca tttgtatatg cataacaatc   122220
tataagacac acatcaaaat ccgtataccg gttcctctag gggtatgtgc ttggcagaag   122280
gtagaaggag ggtattctgg ttcctttctt ttgcacattt atgtatgatc tcagttttta   122340
tatggagcat tgatagggtt tggctatgtc cccacccaaa atctcatctt gacttgtaat   122400
ctctataatc ctgataatcc ccatgtgtca agggcaggac caggtggagg taactggatc   122460
atgggggcag tttctcccag gctgttctca tgacagtgag agagtctcct gagatctgat   122520
ggttttgtaa gtgtctggca tttcccctac ttgcacttac tctgtcctgc cgcctgtgaa   122580
gaaggtgcct gtttctccct tgccttctgc catgactgta aatttccaga ggcctcccca   122640
gcaatgtgga actgtgagtc aattaaaact cttttctttg taacttaccc agtctgtctc   122700
gggtatttcc tcatagcaat gtgagaacgg gctaatacaa gcatatacta cttttgatat   122760
tttaaaataa aaattatcat ctatctttga aaggcatgca caaatgggaa gttgaggaac   122820
atttgtgttg tggcaattgt atgatacctt taatgggaat atttcaaaga cacttgttaa   122880
gactttgtta gaacaaaatg tagagggtgc tggatgtccc tgaatattct tccgcctcct   122940
gtaacttgta ttgctttgga atttccagtg gcctgacaat gaactactgc aggaatccag   123000
atgccgatac aggcccttgg tgttttacca tggaccccag catcaggtgg gagtactgca   123060
acctgacgcg atgctcagac acagaaggga ctgtggtcgc tcctccgact gtcatccagg   123120
ttccaagcct agggcctcct tctgaacaag gtaagaagtc tgtgtcttac cttgtctagc   123180
acatacctct ctatgtgctt ggacaacggg atgaaaagac atgaaaaacc acactgatgc   123240
agaagccttt agtgctacac gggagctcga gtgttggttg aggttctgcc atgaccaagg   123300
```

```
aagtctcagt gccgtccctg ggaaagccag agctgtgatt tttggcacaa cttgtgggag   123360
tagtgacttt aggactggcg caaaacctcc agggtgctca acttaaccac tcaccttatt   123420
ctaaaatggg ttatttcagt gtcccagtca aattcctatt ctaacatgct gtcaactgtg   123480
tgattatttc caagccaata agcatttcca gtaatttctt aaaatagtgt tcattgcagt   123540
cttcagcgtt gtggctcctg agggatgtgg cccctgattc tgtcgtccta gagaagcctg   123600
acatgactgc attgattctg tatcgtcctg ggtctatgtg gctgcctggc tgtctgtaat   123660
catctgtttt attttattt ttttctacag actgtatgtt tgggaatggg aaaggatacc   123720
ggggcaagaa ggcaaccact gttactggga cgccatgcca ggaatgggct gcccaggagc   123780
cccatagaca cagcacgttc attccaggga caaataaatg ggcaggtctg gaaaaaaatg   123840
taagccactt tgatttggac tcttttttccc tttgctgaca aatcttttca aacagaagag   123900
gggcagagga aaatactgga aagacttcag gaggctaagc gtaattagcc ttagcatgga   123960
aagtgcaagc agcacaggcc agcaaagccc cacgcgtgtg ggggttctca ggcctcttct   124020
cttttgacat ttctttactg tttccattgt tgggtgctgt ttctcgtttc tagtgcttgt   124080
cctctaagcc aggggtcccc actccagtac tggtactggt actggtactg gaactggtaa   124140
ttatctgtgg cctgttagga actgggctgc acagcaggag gtgagcttcg ggggagcaaa   124200
caaagcttca tctgtatttt ctgctgcttc ccatcactct catagctgcc tgagctctgc   124260
cagctgtcag atcagaggca gcattagatt atcatagcac aaaccctatt gtgaactgca   124320
catgtgagga atctagattg catgctcctt atgagaatct aatgcctgat gatctgtcat   124380
gcttccatca cccccagatg ggaccaccta cttgcaggaa aattagctca gggctcccac   124440
tgattttacc ttatggtgag atgcacattt atttcattat atattacaat gtaataataa   124500
ttgaaataaa gtgcacgata aatggaaggt acttgagtca tcctttaacc atcgccccct   124560 cacccccaggt gcacagaaaa attgccttt atgaaactgg tctctggtgc caaaaaagtt   124620
ggggaaccac actgctctgg gttctagtag tcagagatgc cctctatgag gcttaagtca   124680
gatttttcta gaaagagttt ggatgggcca tcaggtcacc atgagacttc ccttagcctc   124740
atgcattctc tgtgatggtt tactttgggg cctatgaata gggaagactg agatatagga   124800
aaaaccaaag tgtctgtgtt ccccccactct cacacccatg taacataaca cttctcacac   124860
cagatatggg gggatttctc ctcacacccc aagcgagtct ccagcagata ccagctgggt   124920
gtcctacaat gtaactcggt cctgacactc tatctggaga cagtgtcaga tcccacaagt   124980
taaggctcag tcctacaaga ctgccccact gcagatgcca atcccaagtt gcaggctgtg   125040
acctgtactt ctgcccagct ggataaagat ctgttttttct atatgaccct ccatgggttt   125100
gattactttg ctagagtggc tcacagaact cagggaaaca cgttactttt atttacccat   125160
ttattataaa agatattaaa aaggatcctg gtgaacagcc aggtggaaga gatgcacagg   125220
gcaaggcacg tgggaagggg ctcagagcct ctatgccctc tccagtgcac cagtcccag   125280 taccctaagt gttcagcaac ccagaagctc tccaagtgca gtcttgttgg gtttttatgg   125340
aggcttcatt acagaggcac agttgattac atcattggcc atcggtgatc ggctcacctt   125400
cggcccctct tccctccctg gaggttggag ggtgggctg aacagttcca accctcaagt   125460
cacatggttg gttcccttgg caaccagccc ctggggctat ccaggaaccc accaagagtt   125520
gcttcattgc agctcccttc acccaggaaa ctccaaggga tttaggagct ctgtgttaag   125580
aactgggggg cagagaccca atatacattt cttattctat cacaatatca caggaagcta   125640
```

-continued

```
aggatgatac tgcctttgtg tgtcttggct gtggatggtg cataatgcat ggaagtaagc    125700
atttctgaat caacagcaaa caggctttat caggtagaag accccctcagc gccccaggga   125760 caaagctcat caatgatgtc ccactgtcct ctgaggctct agctctaaga cctccagtgg    125820
gtcaagctcc tggagaagtg gcacattctc caaagaccct tcagggtcac cacaccctgg    125880
ttaagggtgt ggcctcataa ctccttttga ctatgactga tggcttacag catagaaaga    125940
aataactttg tcaaaaaata taataatgat agaaaggaag aaggaacgct cccttttgtc     126000
ttctaagaat agatgtgaaa tgtgtgtgcc ttagaatatc ttctccctct cctgctccac     126060
gtgagctgga gcttacatgc ctgcttgttt tcagtactgc cgtaaccctg atggtgacat    126120
caatggtccc tggtgctaca caatgaatcc aagaaaactt tttgactact gtgatatccc     126180
tctctgtggt aagttgcctt ctgttttggt aaggaaactg cttccttaat atggatttgg     126240
aaaaaaaaaa gcaaaaaaaa cagaaaatgg cttttgagct gagtgcttct ggggaggaga     126300
tggctgccct ctccaccaga gcctgctttt catcatggcc accttgaacc tgccctacta    126360
ttggccccat ttgttaggaa acacccgcc cctcccacca cacacacata aataaaataa     126420
atgtcaaatt cccaaagggc aaacttagag gtgatctaat cagcccggga tagtcccacc     126480
gaacccttct ttgtctagcg tgggatgcat gaaaaacaaa tttagagtca ttatgatgaa    126540
aaactgtcct cttctgcagc tgagaagaaa aaaaaaatac gagcagcagg aaacagctaa    126600
gcatgtaatg cacattgtaa acctcagatg gccatcctag gaaatcaatg aagggtagtg    126660
cagctcttta gccccagatg gcctttctcg taagattact actcatgagt cccattagcg    126720
acattgctta gagactgctt gttaggttcc ttcctcattg ctctgagact cttattggga    126780
gtatgaggct tggatcaggg gaagggggaat tgacattaga tcttaaatga ttggggtaac   126840
aaatccatgg gggaaaaaaa gccacttgta cttgttccct atttttcttcc tgctgaccaa   126900 tcaacttgtc tgtccgagtt acagaacacc accctggact tttcttttgt gtaatttggt    126960
tgcttgtggt tgggtctgcc atgtgaaggg accttgagct gggggaagaa ggttggcctc    127020
caagtccact gaagaccagc atcctgagat tgcctgggga ggtggtacag ggcagtgatg    127080
aagatcatgg gagccacact gcccatcgtc acatttgggc cactcctggg gagagcaaga    127140
gggaagaagg agaggttagg gtgataggaa agattctact tggccaatat tattataatg     127200
tggcattgtg gtctctggat ttagtgtgag ttgatagctg acttttttct cgagtggggtg    127260 cttttgttct attttgtcgg tgctattgca gaagcatctt ggtggttcct ctacctcaaa    127320
gtctcttgat ggggtcagtt ccagttctcc gcttctggcc ccatctagta cacgccactg    127380
cctctcactg cctgggctct ctatccttga caggctgcct tgaatttaag cccagtctga    127440
cttacctgcc tcaaacaccc acagtagtgc ctgggactca tgcacctttg actcccatgg    127500
aagggaagtg cagtagcttc ccaggtgcaa ttctgctgtc ctcacccaca ttgaggatgt    127560
atgagaatca ggttcttaga gattggagaa agaaggaaga atgggaacaa gatttcttcc    127620
aatggactgt gaggttcccc accttacttt gatgtaagac aagtgaggtt aaccccaagc    127680
ctggtgagga gggttcccat cagacacttg gaaatcctga ggactgtttc ctgcagaagg    127740
atgtggttgg tgggatattc aggtttgact catgattgag aaagttagag cctctggttg   127800
gagaaagagt ttaataacta tttcatttcc accaacacat tcagtacgaa taataaataa    127860
gtaaaaataa atagaaacat tcagtttat tttgaatagt aggagtaggg tataatttct     127920
gtagttactc ttttagtaca atgatgcatg tttactgtat gtaaggcata ctagcagaaa    127980
ttgagctcag cactagaaaa gatgattgca ttccatgcca tgcttctttt ttacaaaaga   128040
```

```
cttctataga tagattctca aaacaaccca cagcaaatga aaagttattt ggaaaactca   128100
ggttccagat tcactggagt gtagaatctc tggttggttg gggaggaatt tcctcttgca   128160
gttgttatta ataattatat gaataattat taactatatt aatatttata gttttgaaga   128220
ccttgaaggg ctggagacaa cagagaagca tttttgaaca ccctctgtag cccctgcact   128280
gttgtaggca ttgatgggtg gtaccaaaga tgggacactt tccctacctc cagagacctt   128340
gtgggcttgc tgcagagaga aggcaggag gaggaaaaga agaatagagg cacatgtgtg   128400
taaattaccc ccacagcagt cagttagtca tgggaggctc cccagaagaa ctgtcctgaa   128460
gctggctgag agaaggcaac atttcaacat aggacagtta tccttgctac ataaaatcac   128520
atacacacat gcacatatgt ccacacacag agactcacat gcaaaagaat cctttgtgcc   128580
tttcagtaaa ctttcatgg tttagaaaga acttatattt ccttgaaagg agagtgtcct   128640
ttgttgttta ctaccacttt ttaaacttag aaagaaaaat ctaaagagtg tttatgattt   128700
taccatttaa tttcacctt gagatgtgaa aaactagtgc ttggaattcg tcctgaatta   128760
aacgacacaa ttgctaactt ggactcaaat gcgacttctt ttcccacctt gtgccacagc   128820
atcctcttca tttgattgtg ggaagcctca agtggagccg aagaaatgtc ctggaagcat   128880
tgtagggggg tgtgtggccc acccacattc ctggccctgg caagtcagtc tcagaacaag   128940
gtaagaacag gcccagaaac catctatact gtccttccat gtaagcccca caaacccctt   129000
ctacatttac acagaaccca cacagctgat gcatcaatac ctgcctctct gttttctgaa   129060
ggaggaaaaa atatagaaaa attaaaaaaa gttatattat tataggttct ctacttgaa    129120 aatagccaaa atacaaatct ttttcttgat ctgggcagtt ccatcaaaat ctgtaggcac   129180
agtgatttgc accaagttcc aatacttttg gaaaatattg aagatgctct gagggtttct   129240
atggatatcc attgtctcac tgtcagatga aagaaaggg aagttttag aaatgtgaca     129300 ctttgcagtg agggaggaca agagcaaact tacctacagt ctatcacagg cacagatttt   129360
tttttacact tttgtgaatc attgaattca atgccgaggc tattcatcta ttcacaaaca   129420
catgaacaaa ttatggggttg tgatccccat aaatgaagag taatcagtcc gaacccacag   129480
aacctggaca ttttgggtat cgtttcagtg gaacatgcaa ttcgtaagtt cagtttgctt   129540
gggtgtctct taggaagaac acataggaca cagacccatc tgcctgcatg ttttgcttcc   129600
tcatctcctt tctacaccag ggcacctgtg ctcaattgct gttctcctct aaagagactt   129660
ccttctgtaa gtttgtgaaa tgccatcgac aaacctgatc gcatcgcatt tcactctgct   129720
gttgagttga ttttcttta ctttatcgtt tgtaacttct tgctctacag agctttcacc    129780
ttccacatat ttcagattca ttcttcccta aactgtgtgg tggtctatgt cctcactgac   129840
tatcaacata ctgccatcat gcacttccta tctctattcc tcttcgttgc aatctggctc   129900
caagtggctc acaccattat tctgatctat caactgccta cacagtccta gaaagtaagt   129960
gagtcaagaa acatccccca aaagtaaaact tttcaggtaa gatcagaaga ccctcatgag   130020
tcactgctgc tcaggatcgt atctggctcc ttgaagagtg accttgcata gatcttgtca   130080
taaaaaatga aagagacctt gggaaggtct tgggctggtc acttttgtca gagtccaggg   130140
ctgtggggtg aaagccacag ctatagagct tcattctgga gtcacttagc tttgctctcc   130200
tggggacagg ctgtgcctat tcttgcctca ggcatcaaaa aaagtggcac agatgggccc   130260
ttctgaaaaa tctcactact ggagcacagc tcgaagtttc tactatcctg acgttgggcg   130320
gtagtccttt gctttgggaa tatgaacatg atcaaaactg agtgaacttg tcttcctggc   130380
```

```
tttctgtaca atgaagtaga acaaaccatc caatttgacc aaagccttgg catgttttct    130440
ttctaggttt ggaaagcact tctgtggagg caccttaata tccccagagt gggtgctgac    130500
tgctgctcac tgcttgaaga agtacgttta agggaaaact gacatggggt cttatcttca    130560
agactttttt cctccctctc ttcctccatc ccttctttct tcccaccctc cccttccttc    130620
ctccccacct ctcttccttt tctggaagga acactaggaa ccagggaatg catgcagaat    130680
cctgaggcag aatttccagg gcaattggat gagagaggag ggaagtgttt ctagaggaa     130740
tctgcagagg gaagacccag tgcaagtgat tttttggacc tgtataaacc gcaggacaga    130800
gctgttcact accagaggca tcaatctgta ttgcattgct ctagagcaat atctgaggct    130860
gaataattta taaagaaaag agtttaattg gcacatgttt ctgcaggctt tacaggaagc    130920
aggatgctgt catctcctct gcttctgtgt gggcctaagg aagattacaa tcatggtgga    130980
gggcaaagtg ggagcaggca tgtcacatgg ccagagcagg agcaagagac agagagagat    131040
gggggtgggg tgctgcacaa taccaaatga ccagactttg caagaactaa gagtgagagc    131100
tcactgatca ccatgaagat gtggcccaag ccattcaaga gggatgcacc tctatgatcc    131160
aaacccccttt cacaggccat agctccatca ctggggacta cagttgaaca cgagatttag    131220
gtggggacaa atatcaaac tatatcacag tctctgatga aacagattga gaacagacct      131280
taactgtcag tttccagcaa attgtgaatt ttgtttcttg ccactcataa gtcactgatt    131340
ctgggtggcc gagggtgtca gagggacagc gccaagttca tggcacagag gatacctgaa    131400
ggggctggac catattttc tcttgacatc ctcatctttt ctaggtcctc aaggccttca     131460
tcctacaagg tcatcctggg tgcacaccaa gaagtgaacc tcgaatctca tgttcaggaa    131520
atagaagtgt ctaggctgtt cttggagccc acacaagcag atattgcctt gctaaagcta    131580
agcaggtact cgctcacctg tggtcttcac cccacgctgg tgaagatatt tgctttatgt    131640
ctgggtttta tgggccatgg ccactgcatg gcagtgggga ggaactgtct atcacatgaa    131700
aggctcaagg gctttgggga cagcatcaat cttcaacccc agccctgcca catgttagtt    131760
gtgctctta aaaggcaga aggattcgtt tcctcacgtg gaaaagaga taccctgtta        131820
cccgtaaaac ttacttaatg ttcaccagtt catccacatt catgatcagg gaaaggttgt    131880
tattccaggc taactattct cctttcataa taatatgctg gagagaatca aatgagattg    131940
catttcaaag cgcttgaaaa accaccatat cgagccatgc ttagtgtggg cgcctctaat    132000
cactgctatt caggaggctg acgaggaaga attgcttgag cccaggactt caaggctgta    132060
ggcagctatg attgtgccac tgcactccag gctgggtgac agatcaagac cctgtctcaa    132120
caaaagaaaa gaaaacaaaa caaatgaaca gaaatattcc acaatgtcaa aaaaaaaaa     132180
aacccacaca acatacaatt tacaaatgca aataataata ttattgttgt cttctttgat    132240
tttctctttc ctggtgaaat tttgttttat taagcctgac aaagtgatac ctttgcttac    132300
atcacttaaa gttagtctat ttggacctag gtgacagtac aatcagctaa gaaacagtat    132360
ttgtaggaga ggcaggtttg ggacaggtga caaggcatgt ggggtgctcg ctgtgctggt    132420
ggctctggaa ggcagggtgt caatgcagac agggatgagc atggcctggt tgggaaggca    132480
tggggcaggc aggagcctga gctgctctcc tgggcctggt cacaagccca tggcagcttc    132540
tctgggtctg tgaactgagg ggtgatgtcc tggaatcctc tgacactcta ggaaggagag    132600
aagggccttt ctggctcagc ctttataaac agtagctgat ctccctcttg ctccccaggg    132660
tcctccccac catcccagca aatgtgcaaa tacaagatct ctgctcctca tggtcctcag    132720
agagctgggg tgttctgatg gcttgaacaa gtcacttagg aaatgtgggg ttttggaggc    132780
```

```
attctctgat aggctgatac gttttgagtt tagagttccc accgcacatc cccacacccc 132840
tagagtctag ggcatttagt gctccatgag ggaacctgta gagtgaggac atctgcatca 132900
caggctgggc cttctagtgt ccagaagcag aaagtgtgtc tgcttcaaag ttggtgctaa 132960
tgatgatttt tggtcagaat acggcatttc tcatttccat tcctttatcc ccttgaactt 133020
actaaagtag aatcaggtct aaaaaccaga gttctaatct ttaagagtcc ctgggattct 133080
aaggtatatg aatgtccttg gaaaacaata ccatttagtt catgcaaggt gcttatttcc 133140
catcctcttt catttgatgt ctagcatttt actgcattct taccaccacg gtttagtaac 133200
attcacgagg aggaagtgga ggatccagat ggagcaactt gctctgggca cacaaggcat 133260
ttgcaatttt ataccctctt gatgatgtct cagccagaca ttctgcccag tcatcaatgc 133320
cctcttcaat taatatgaaa ggacacactt ggcatgagat tccaatcgtg cacagaatat 133380
acatgagaag tgtgcctttg tcatccctac tttcaaaggc taaggccacc ctcagtttct 133440
tgcatgcaac tgatgccttt caaatgaaac cttacatctg tgtagtccat aggcaaccac 133500
aggcaaatgt gagggtgaaa cgctgtgttc tacattgttc tgtgtcagtg aagcaaggca 133560
gtgccagctc agagggctct ggggcttcaa ggcaggatg cctggttgta ggtactgcca 133620
cttccagctg ggcagtgaaa cataactgct aatactttcc ttacaggcct gccgtcatca 133680
ctgacaaagt aatgccagct tgtctgccat ccccagacta catggtcacc gccaggactg 133740
aatgttacat cactggctgg ggagaaaccc aaggtgagat caattccatt gcccacgtaa 133800
caaattgttt ttgaccttca gtgcatgtta caaaatgagc attttggaga tagttgtaca 133860
aattcctacc catgaatgtg gtctacccac tcctgacttt gcctggacac ctgtctatgt 133920
ctccataatc agtcttcaag ggacttgggc aaggggagcg gtgccatttc cttgagtctc 133980
tctctttttt gttttcagaa tcttttaatt ttttttgtaa tgattgtatg tttcccttac 134040
aacaaaaaca aacaccagta gaggtctttg agtctcttaa tcataatttc agcattcata 134100
ttgcttcccc aggtaagtgg ggttttgacc cagccctcaa gttaagggtg ttagattatt 134160
tttcatgtga aattagacag actgcgtttc taaacatggt gcaaacagt aacgacaaaa 134220 gttgtaatta aactattctt cttcccaaat acccacatgt ctaatgtgtg tgtgagggtg 134280
ttaggcaggg gacctgaagc tgggggagag gcagacagtt cccatggccc caagtctagg 134340
atggcatttg gtattggttg atgggtgaga gcaagagagg gaatatttt gtgcatgatg 134400 tggtatcagc acctgtacta catttatgg attccttctt ctctttgcgg tatgccctga 134460
caataattat atccgtcagc cttacccccct tggcagtagg aaaactgaaa ctgtcttaaa 134520
gtctcagctc tactttctca gaggtgcagg caagggcact gggagtctgg ggccctggaa 134580
aactgttctg actctgccac ttgccagata gacctgaact agacacgtta cctctttgta 134640
ccacttggct ctaatccctt atctgtaaaa ccagcatttt caaatggtgc tttgcacatc 134700
agccttttgc ataagctttg atttgataaa atgttttttg tgtttttaaa aagattaaaa 134760
accacaggtt tagataattt caaagtaggc ttcccttttt ctgtcatttt cctattattt 134820
ttaaaacctc acctccttga ctccttgttc cctttttctg cactgctgag tctgggagca 134880
ctgaggccag gtaaaaggaa acttggcaaa tgagggggcac ctatgggtgt gggaggctgc 134940
tcctggtgtt tgcatatttt aaaatttaaa tgctacaaac cactgtgagt taggtattat 135000
tgttcctatt ttaccattga ggaagctggg gctcagagaa ggtggagggt ggtacagaca 135060
aacctgaatt ggaaccctgg ctcctgccta tgggctgtca ggacttagaa aagtcgtgag 135120
```

```
ctctcgctga ttgtttcctc agctgatgtg ggctgcaggg ctgttatggg ggaaataata  135180
agaaagtgca tcaagtgctg agcacatcct aagcactcca tcatggcagc tcctactact  135240
aataaagaat agaattatat ctaacatgat tctttcttgc aagtgacaga aaatccaact  135300
caaattggat taagcaaaac aagggaaatt cttagtgagc tgcaaagttt tcaggctcac  135360
atgatggccc caaatcccag gtcctcccaa tcatggagta ggcactattt gggggcacaa  135420
aggtgacatt cccatggctg cagatgctgt ggtgctgtgg ctgtaccggg aaagaataag  135480
aaaggccact ctcccaatta tgtgaacaat agtctgccca ctctgagaag tcaaacttgg  135540
gtcacagtcc tgcccctgaa cccatcactg actggctctg acctgcacca attgttccat  135600
gttggaggtg aaggcaagac cccactaata cccataaggg gcaaaagtta gatagatcct  135660
tcaagaggat tatgggaggt agggcaaaaa gctgctgggc agccagaaag caaacagagc  135720
ctctatgata cctcaactga tgaaagcatg aagctaaaat cataaggatc tgggtgtgag  135780
ttctggctct cccatcttcc atgtgacatt gggcagttat ttaatctctt ttagcctccg  135840 cttttctcatc ttacatatga gataattgtg aggattaaga ttacacataa tcatcatcat  135900
caccgtccac cactaccacc atcatcccca tcaacatcat cgccaccact atcatcattc  135960
ttactggcac taccatcacc atcaccacca ttccaccacc atcaccaata tcatcactgt  136020
caacatcatt accaccatca ccatcaccac caccatcatc attactacca ctaccactac  136080
taccaccatc accatcacca ccattccacc accatcacca atatcatcac tctcaacatc  136140
atcaccatca ccatcaccac caccatcatc atcattacta ccactaccac tactaccacc  136200
atcaccatca ccactgtccc actactatca gcatgacatc accatcacca ccaccatcat  136260
cattaccacc gctactacca acatcaccat caccacaatt ctactgccat caccattaac  136320
attaccacca ccatcatcac tatcaccatc accaccatca tcaccactgc cattatcact  136380
gccaccatca tcactatcct ctatatttcc tcatctgtat tatcattact accaccatca  136440
ctatcaccac catcgtcacc atcataatca ccatcaacac catctccaat accaccatca  136500
ctgtaaccat catcaccacc accatgatca ctatcaccat catcacaatg atcactgtaa  136560
ccatcattac tacccaccac catcaccact actccaccac catcaccatt atcattacca  136620
tcaccattat caccaccatc atcatcacca gcaccaccat catcaccagc accaccatca  136680
ccatcaccat cattaacacc atcactatca ccattggttt aatcatcacc accatcatca  136740
taaataaaca tcacataacc agggtgtagc tgggtgttga ccccagagcc cactcactgt  136800
ttcctctctc ccacccccat ccacacattt ctaaccacca tcctgcactg ggctcccagt  136860
ctcctctggt ctcacccaca tgtccactga gaaaaggatt ttcagaacac caactagacc  136920
aggaggagcc acatacataa ctcaggcctg cttatcaact ttctacatgt taataatgac  136980
atcagatcaa tgggtgttct cagcttctca gaaggaggtc aaaattctcc ccctctcccc  137040
ttcatgtgtc cagaccttcc cggatttgga tgtaccaagt gcagagtggt gttgaggcca  137100
aggggctcat ccatgtaagt ctcatctgca atcactgggc tgatcccgtg gccctgtctc  137160
cagggcgcca tcagagaggg cttcaatcct caggttacct gtggcccacc ctgccctcag  137220
aggtgccatc tctacattgg ccacgagatg gcagcacata tcatagact gcattaattt  137280 cccagcaact cctggtgggt tttccctctt atcaggatgt ttgccttgct cagagagcaa  137340
atctgagagc agtgacacct aacttaactt tcagcaaaat attttgagaa gggtgcccct  137400
ttacacatct gtgcagtcca ggtgatgcat ccccatgccca atgctcggta gtcaggagga  137460
gcttcctcca tgcagctctg cggaagagac tcttccacgc tgctcatgta aactccagat  137520
```

```
tcggtgtcag ttttctgaca ccgaagacaa tgatctaagt gcagtcaagg gctttgggga   137580
aagcaggaga gagtgcctca gttctagcct gtgccatgct tgcaaagttt tgcaaaattc   137640
taatgagagc tgggcttgca acattggaaa cttggattat ttgtgagagc actgagaaat   137700
ccctgggcat gtccatctgg aaaaacagca tttcctctgg cactttagca gaggttctgt   137760
ttcaatttgg cgaaggaaat taagcagttt ttcacaaaag aagaactaca acgaggagaa   137820
ttgtccctag tatttcttct ccctaattgt caaggaagtg taaattagaa aatgaatcag   137880
gacaatttcc acctactatg ttagctaata ttttaaaaat tgaatatcac aagggtgagg   137940
caaagtaatt gttttccagt gacattttcc actgtcacac cctttttagag aataatttgg   138000 caatgttact gtgagataga aatatgtcta tataattatg ggaactgaga cttcagaaag   138060
taataaggaa taagaatgaa atttatgaac aaacatgtgg aaggttggaa gcaagagtgg   138120
ggccaacacg catggggagg aagcatttgg gcagcgactc cgcagaccca gactcaagct   138180
gagctataca acctccttac gcctcagttt cctcaactga agaacaggaa tgacaagtgc   138240
ctgtttcata ggaccgttgt gaggattaag tgagatatac cacattatga gcttgtgcct   138300
ggaaaggttg attcttagta aatgatgact attcttttt attgcaataa aatttataca   138360
acatagagtt actattttaa ccattttgc aggtaccact gagtggcatt cagtacattc   138420
acaatggtgt gcaaccgtca ccatatttcc aggacatttt tctcatcccc aaaggaaacc   138480
tcatgcccat taagcagtca ctcctcatta aaatattagt tatgaagact gtagcatttt   138540
tttaaaaact catgatataa cattgattga aaaaatcagt ataggaaatt gtgcattatg   138600
atgtaatagt aaagaagca tataaaaatc tgaaaaaagt atataaaaag aatagcaatt   138660
gtatttctca gactctcttt acattgtaaa aatcattttg atagcttcaa aagaaaagca   138720
aaaagtacac aaacaacaac caaccccaaa gcagcatgac aaagcccaga ttgttgaatc   138780
caggtcttgg gaacataaaa tcttatatga catttgcact ttaatgggtc agagagtcca   138840
gtggcattgg gagctgcctt tgttctgca gcctcacgga cagacaggag gtccagctcc   138900
actgctctgt tcttctggaa tttcctcgtg aacaagcttt ggcctcagta accatttctt   138960
tcatcttttt aaacacaggt accttttggga ctggccttct caaggaagcc cagctccttg   139020
ttattgagaa tgaagtgtgc aatcactata agtatatttg tgctgagcat ttggccagag   139080
gcactgacag ttgccaggta agaaaagatc aatagatcaa agtcttgtgc tctcccgtct   139140
cagtctcagt cccttagacg tcagtcccaa agtggcaaat tcaggaaggt tttgtcagtg   139200
gaagacccca gtctaagtgt tgctcagaaa ctcccccagat ctgtccctga atgcatattc   139260
agatcatcta aggagacgtc ttggggcttg agttccagat ccatagcaag ggagccgtaa   139320
gtgccataac tacctcaggc cactcacctt cctggtgtgt gctggtcacc agtgactgaa   139380
gtggtggctt ttccagtaga gaggaaggta gagggtacag gaccgagaca aattacacac   139440
acttaacaat gatgtccagg ctagcccagt ctaaaggaaa caccaagtta ggaagcaatg   139500
catgcaggat tcacaaggga ttatttttt tcccaggaaa aaactaagtg atgtggtttt   139560
gttgaataga ctttgctaag tacttaagca ctgcagatgc ttgagtaata tgctcataag   139620
ttcctttctg atttgaatta ctgggaaaat gtacatatgg ataagagaag gatggcatcc   139680
catattaaaa ggttggcagc ttaaagctca catgaatttt cccctacctc tgtttagggt   139740
gacagtggag ggcctctggt ttgcttcgag aaggacaaat acattttaca aggagtcact   139800
tcttggggtc ttggctgtgc acgccccaat aagcctggtg tctatgctcg tgtttcaagg   139860
```

```
tttgttactt ggattgaggg aatgatgaga aataattaat tggacgggag acagagtgaa    139920
gcatcaacct acttagaagc tgaaacgtgg gtaaggattt agcatgctgg aaataataga    139980
cagcaatcaa acgaagacac tgttcccagc taccagctat gccaaacctt ggcatttttg    140040
gtattttgt gtataagctt ttaaggtctg actgacaaat tctgtattaa ggtgtcatag     140100
ctatgacatt tgttaaaaat aaactctgca cttatttga tttgaattaa ttttggtttt     140160
ggtcttcaaa attttcatgc tcttttcatc ccatctattt ttattttat ttttagact      140220
ttacgtcctg gggtacatgt gcagaatgtg caggtttgtt acatagatgt acacgtgcca    140280
tggtagtttg ctgcacccat caacctgtca tctaattcgg tatttctttt agttctatcc    140340
ctcccctagc cctccacccc ttgacaggcc caggtgtgtg atgttgccct ccctgtgtcc    140400
atgtgttctc attgttcaac tcacacttat gagtgagaac atgccgtgtt tgttttctg    140460
ttcttgtgtt agtttgctga gaatgatagt ttccagcttc atccatgtcc ctgcaaagga    140520
catgaactca tcctttttta tggctgcata gaattccatg gtgtatatgt gccacatttt    140580
atccaatcta acattgatgg gcaattgggt tggttccaac tctttgctat tgtgaatagt    140640
gccacaataa acatacgtgt gcatgtgttt tcatagcaga atgatttata atcctctggg    140700
tatataccca gtaatgggat tgcagggtca aatggtgttt ctggtgctag atctttgagg    140760
aatcaccaca ctgtcttcca caatggttga actaatttat gctcccacca acaatatcaa    140820
ggcattccta tttctccaca tcctctccag catctgttgt ttcctgactt tttaatgatc    140880
gccattctaa ctggcatgag atggtatctc attgtggttt tgatttgcat ttctctaatg    140940
atcagtgatg atgagctttt ctcatatgtt tgttggctgc ataaatgcct tttttggaga    141000
agcatctgtt catatccttt gcccactttt tgatggtgtt gttttttct ggtaaatttg     141060
tttaagttct ttgtagattc tggatattag ccttttgtca gatggataga tggcaaaaat    141120
tttatcctat tatgtaggtt gcctgttcac tccgatgata gtttcttttg ctgtgcagaa    141180
gctctttggt ttaattagat ctcatttgtc tattttggct tttgttacca ttgctttag    141240
tgttttagtc atgaagtctt ctcccatgct atgtcctgaa tggtattgcc taagttttct    141300
tccagggttt ttatggtttt aggttttgca tttaagtctt taatccatct tgagttaatt    141360
tttgtataag taatgcccct cttgtctct tttgatcttt gttggcttaa agtatatttt     141420
atcagagact agaattgcaa tccctgcttt tttttttctt tttgctttcc ttttgcttgg    141480
taaatattct tccatccctt tattttgagc ctatgtatgt ctgcacatga gataggtttc    141540
ctgaatacag cacaccaatg ggtcttgact ctttattcaa tttgccagtc tgtgtctttt    141600
aattggggc atttagtcca tttacattta aggttaatat tgttatgtgt gaatttgatc    141660
ctgtcattat gatgctagcg ggttatttg cccattagtt gatgcagttt cttcatagtg     141720
tggatggcct ttacaatttg gtagttttg cagtggctgg taccaattgt tccttccat     141780
gtttagtgct tcgttcagga gctcttgtga ggcaggcctt gtggtgacaa aatcttcag    141840
catttgcttg tctgtaaagg attttatttc tcctttgctt atgaagctta gtttcgctgg    141900
gtatgaaatt ctgggttgaa aattattttc tttagaatg ttgaatattg gcccccactc     141960
tcttcgggct tgtgggttt ctgcagagag atccactgtt agtctgattg gcttcccttt     142020
ccgggtaacc caacctttct ctctggctgc ccttagaaat ttttccttca tttcaacctt    142080
ggtgaatctg acgattatgt cttgaggtgg ctcttctcga ggagtatctt tgtggtgttc    142140
tctgtatttc ctgaatttga atgttggtct gtcttgctag gttggggaag ctctccttga    142200
taatatcctg aagagtgttt tccaacttgg ttctattctc cccatcactt tcaggtacat    142260
```

```
caatcaaatg tagatttggt cttttcacat agtcccatat ttcttggagc ctttgtttat 142320
tcctttcat  tctttatcct ctattcttgt cttcttgctt tatttcatta agttgatctt 142380
caatctctga tatcctttct tttgcttgat cgatttggct attgatactt gtatatgctt 142440
cacaaagttc ttatgctgtg ttttcagtc  agatcaggtc atttatgttc ttctctaaac 142500
tggttattct acttagcaat tcatgtaacc tttttcaag  gttcttagct tctttgcatt 142560
gggttagaac atgctgcttt agctcggagg attttgttat tatacacctt atataatagc 142620
ctgatataac tataagatt  ttttgtaagc accatcgtaa ccacaaagca aaaacctaaa 142680
gtagatatac aaaagataaa aaggaatcaa agcataccac tagagaaaat cacttaatca 142740
caaataaaga tacgaagagt ggaataaagg aacgaagggt ctacaaaaca accagaaagc 142800
aattaacaaa atggtgatag cagatcttac ctataaataa ttatcttgaa tggaaatgga 142860
ttaaatttc  caataaaaag acatacagtg gccaaataga ttaaaaaata agatccaact 142920
atatgatgcc tataacacac tcacttcacc tgtaaggact caaacagact gaaagtaaag 142980
ggatggaaaa aatattctat gcaaatggaa acaagaagat agaggggtag ttatacagat 143040
tgagtatcac taatccaaac atctgaaatc tgaaatactc caaaattaaa aatgtttaag 143100
tgccaacatg atgttcaaag gaaatgttct tcggagcatt ttggatttt  gtgtttaggg 143160
atgcaaaaac agtaaatata taatttgtat tagtccattc tcacactgct ataaagaata 143220
ctacaaagag actgagtaat tataaggaa  agatgtttaa ttaactcaga gttccacagg 143280
cttaacagga agcatggcta aggaggccac aggaaactta taatcatggc ggaagatgaa 143340
ggagaagcag gcaccttctt cacaaggtgg caggacggag tgtgagtgtg tgaaggagga 143400
actgtcaaac acttataaaa ccatcagatc ttgtgggaac tcactcactc tcacaagaac 143460
agcataggga aaaccgcccc catgatccaa tcccctccca ctgggctcct cccttgacac 143520
atggggatca tgagggttac aattcacgat gagatttggg tgggacacag ccaaaccata 143580
tcataatgca aacattgcaa aaacaattca aaattcaaaa catttctggt ttcaggcatt 143640
ttggataagg gaaactcaac tcaacatgag gtaaagcaga cttaagtca  aaaactgtaa 143700
aaagagacga agaagaatgt aataataagg agatcagttc attacaaata tatagcaatt 143760
ataaatatat attaatatat atacccaaaa ttgtagtacc tacatatagt aactaaaaca 143820
aacattaata gatctcacag gagagctaca ctgtaatata tcatagtag  cacacttgaa 143880
tagctccact ttcactaatg gacagatcat ccagacagag aatcaatatg gaaacacgag 143940
acttaaacta cactttagcc aagtagacct aacagaaata tatagaacat tccatccaac 144000
agcagtagaa tacacattat tctcaagtgc acagggaata ttctccagaa tagatcatat 144060
gttaggtcac aaaactagtc aaaaaatgta agaagattga aatcatatca ggttttttt  144120
ttagatcata atcgtatgaa actagaaatc aataatgggg gaatattgga aaatccacaa 144180
atagatagaa attaatcaat atgctcctga acaatcaatg agtcgaagaa gatattaaaa 144240
gaggaaattt taaaaaatca agacatgagt tcatgtcctt tgcagggaca tgaatgaagc 144300
tggaaaccat cattctcagc aaactatcat aaggacagaa atccaaacac cgcatgttct 144360
cactcatagg taggaattga acaatgagaa cacttggcca cagggcgggg aacatcacac 144420
accagggctt gtcagggggt gggaagctgg tgaagggata gcattaggag aaatatctaa 144480
tgtaaatgac gagttgatgg gtgcagcaaa ccaacacggc acatgtatac ctatgtaaca 144540
aacctgcacg ttgtgcacat gtaccccaga acttaaagta taataataaa aaagaaata  144600
```

```
tttgtttttg atttatatgc caatcagaca aaatgtgaaa agccctactg aaattaagta    144660
tcaccatgaa agataaattc tggataattt tttcaagttt taacaatgta gctttaattg    144720
gagaaagcta tcatttggaa tgagttaatc tatcctatac taaaataagt cacttgcttt    144780
aaaacataat aaatatgatt ttgaattgaa aacaaaaaca actcaagaca aaggaaaatg    144840
gacacactaa cataccaata atttatagta tgcagcaaaa gtggttttaa gagggaagct    144900
tttaccaata aacacttcca ttaaaaaaga agatctcaaa taagcaacct aagattacac    144960
ctcaacaaac tagacaaaga actaactaac ccaaagttta gtagaaggaa agaaataata    145020
aagatcacat cagaaatagt aaagactaaa aaactgatac caaaagaaa taaaactact    145080
agttggtttt caataaaata acaaaattga ccaactttta gctagattaa gaaaaacaga    145140
gaatactcaa ataaaaccag aaagaggaga cattacaata gatactacag aagtacaaac    145200
gatcataaga gactactatg aataattaca tgccaacaaa ttggataact tagaagaaat    145260
ggatgaattc ctagagcaaa aacctacaa agactgactc agaagaaat agaaaatctg    145320
aacagaccaa taatgtgtac atgattgtat cagtaataac aagtctccca tcaatgaaaa    145380
ggccaggacc taatggcttc actgctgaag cataccaaac attacaaaga ctaatatcaa    145440
ccctcctcaa actcttctta aaaactaaaa agaaggaatg ctttcacatt cattttatga    145500
ggatagcatt acactgatac taaacacaga aaaataatac gctaataaaa gaacattaca    145560
ggcaatatcc ctgataaaca tatgtgcaaa atccgcaac aaaatactag aaaactgaat    145620
ccagtagcac tttaaaaaga tcattcacca tgatcaagtg cgatttgttt cacgaatgca    145680
agaatagttc aacttacaca aataaataaa tgaaaggatg gatgataaaa atgtgtatct    145740
atatatatat gttttataca cacacacaca cacacacaca cacacacaca cagaggaata    145800
ttattcagcc ttaatgaaga agaaaatcct gcctttgcat caacctggag gacattataa    145860
taagtgaaat aagccagaca cagaaaggca aatactgtgt gatctcgctt acatatggaa    145920
tctaagaaag tcaaattcct agaaatagag agtagcttag tgattgccag agccgtggaa    145980
gggggaaatg gagagatgtt gatcaaagga tacaactgta tagctttgca agataaatag    146040
gttctggaga tctaatgtgc agaatggtga ctagagttaa taatactgta ttgcatactt    146100
gaaatttgct aaaagagttg atcttaagtg tcctcaccat atacacaaaa gtattatgtg    146160
aggtggtgaa tattttaatt agcttatgat aataatttca cagtgtacat ctatattaag    146220
gcattacatt gtacatctta aatatatata attttattt gtgaagtgta cctcaataaa    146280
actggaaaaa ataattgaaa agtaatgaaa aaaattaaaa gctattatgt gtcaaatgac    146340
attatcaaga aagtgaaaag caacctactg atgaagcaaa cctattgaca aaggcctggt    146400
gtccagaata tattaagatc tctaggctgg gagcagtggc tcacacctgt aatcccagca    146460
cttggggagg ccaaggtggg aggatcactt gagcctggga gttcgacact gcagtgagct    146520
atgattgggc cactgccctc caggctgcgt gacagagtga gactgccatc tcttaaccca    146580
cttcttattt agaaaaagaa aatatgtagc ttgctgcctg catagtattc ttggggcaaa    146640
tgggaaatga gttaaaaaaa aaaaaagaa ctcttacaac tcaacaataa aagaaaaac    146700
aagaacgtga atagacattt tttccaaaaa agatatacaa ataggcaata agtacatgaa    146760
atgatggtca acatcattag tcattaagaa aatgccaata aaatcacaat gaaataagac    146820
ttcatatcca ttaaaatgtc tataatttaa aaaatggaaa ataacaagca tttgtgagga    146880
tgtggagaaa ttagaatcct gtatattgct ggtgggaatg tacagggaaa atggtttggc    146940
cactgtggaa aacaatttga cagttcctta aaatgctaaa catagaatta ccatgtgatc    147000
```

```
taacaatttt actcttaggt gtatatatac aagaattgaa aacaagtgcc caaacagata  147060
ccttgcatga gaatgttcat agcagcactg ttacaacagc cacacccaaa tgtcaatcaa  147120
tagatgaggg gataaacaaa ttgtggttta tacagctaca aaaaggaatg aagtactggt  147180
atccgctaca tggctgaaac ttgaaagcaa gggctgggat ggggtcatgg aaagtaccag  147240
cttattgggt actgcattgt gctttggggt catgaaaatg ttttggaact ggatggaggt  147300
ggtggttgcc aatgtgaaca tactaaatac aacgcattgt tcactataag actgctactt  147360
ttcttatgag aatttcactt caattaaaaa ataccttcca tgtatccttt ctaaggatga  147420
tactagaata tttgctttgg caaaatgagg aagtaacttt ttttaaaaag gaagatgtgg  147480
gatccatgaa acgggatcaa atatcagaga ggaaaggggg tcttctggat gacagtccat  147540
ggagatccca caactgcaca gcaggccggc tgtgcaccca ggccacacca gagcagagcc  147600
ggtggttccc gaggagctct ctggaagaaa aacgctagat ggcctgattg gtttgggggc  147660
atattgaaaa ggtatataac tgagaatttg gagtggaatt aggaaacaga cataaaagct  147720
tacagaaaag aaaataatga attctaggga gaaatataaa aggatactac aggcctcagt  147780
tacataaaca ctgaatattt acttaaccaa aattacaata taattacata attattttag  147840
gtacatatgg caaaaggatg tgtgggtgta tgtagtatgt acggtgtgtg aagtgtatgt  147900
gtgtggtatg tggacggtat gtgtatgctg tgtatgccaa taaatcaca atgaaataag  147960 acttcatatc cattaaaatg tctataattt aaatgtctat aattttaaaa atggaaaaca  148020
cttctcatat ggcaggagca ggagcaaggg tgggggaggt accacacaca cttaaacaac  148080
cagatctcct gagaactcac tatcaggaga acagcacctg gagaaggtgc taaaccattc  148140
atgagttact gccctatgag ccaatcacct cccatcagac cccgcctcca cactaaggat  148200
tacaatttga cttgaaattt gggcatgaac acagatcgaa accatatcaa taggtaatga  148260
ctaaaactga aaaagaagt accacagtca gaaagttatt tagagagctg aaggtaaatg  148320
ccaataggat cagttgaaag aattggaggt ggccgggtgc ggtggctcag gcctgtaatc  148380
ccagcacttt gggaggcgga ggtgggtgga tcgccctgag gtcaggagtt tgagaccagc  148440
ctggccaaca tggtgaaacc cagtctctac taaaaataca aaaattagcc aggcctggtg  148500
gtggacgccg tagtcccagc tactcaagag gctgaggcag gagaatcgct tgaaccaggg  148560
aggtgaaggt tgcagtgaac cgagatcgtg ccactgcact ccagcctggg tgacagagca  148620
aaactccatc tcaaaaataa atgaaataaa gaattggaag tgtttgcctc tggagagaag  148680
gaaacgcagt aattctgtaa aaacagaact ttttactttt tttcttttt ttttttttt  148740 tgagacagag tctccttctg tcacccaggc tggagtgcag tggtgcagtc ttggctcacc  148800
gcaacctctg cctcttgggt tcaagcaatt cccgtgcctc agcctcccaa gtagctagga  148860
ttacagatat gggctgctat atccagctaa tttttttta tttttattag agatgaagtt  148920
tcaccatgtt ggccaatctg gtctcaagct cctggactca tgatcctcct gcctcggcct  148980
tccaaattgc tatgattaca ggtgtgagcc accatgcctg gacagaactt tttgactctt  149040
taaactatgt gcatatataa agctgattta aaaaaaacca agtaaaataa ttttaaaatg  149100
ttccaaaaca gattggatgg gtacacactt catcatgagt ggttgaggga gactgggtta  149160
gagatgagga aattccaggg actggggaaa agttaaaatg acaaactgtt cacaattgtt  149220
aactgcaggt tgtgggaaag ttggtaagtt gctacagtgt ttgttccctc tgtaggtttg  149280 catatatttta acatttctta aattagcata ataatgaact gtgtaatcag ctgtagagtt  149340
```

```
gagggtgtgg agctggcaca ggacagctga gctactggtt taaaataaat gacatttaaa    149400
aaaatggcta tttgtagaat taacagatat aagacaccct gatcaaggga tgataagaaa    149460
ggactccagg gctctgtctc agctgtcttg gcaacacctg gaagacatgg gcctctgcaa    149520
ggtctcatac tttcaggagg tgttgatgaa ggatatggac agatctgaag ctctgggcac    149580
tgcatggtct gagaagagaa gctccggaaa cgcgggagct gagtgcagat gcagaagggc    149640
tgtcatccag cagagggta ggtgacaact ggcctagcga gtgacccta tcatggctac     149700 atttgttgat cactttcttt gtatgaggca ctgctgtgat tgcattaaat ttccacttac    149760
ctaaatccaa cgttgtgcac ttgtgaattt ctactcttac aaaaaacaca acggcaacaa    149820
cctcaaacca gtaatctagt caaaaaagca attcccaagg catgacattc agattcatca    149880
gcactcacag agactacagt gattgctgat aacgccaact taatacctgg ccaacagcat    149940
ggatcctgac ctccactttt cttgtgtgtt tacagaacca caaaaggtg cagtgttttc     150000 a                                                                   150001
```

<210> SEQ ID NO 3
<211> LENGTH: 138001
<212> TYPE: DNA
<213> ORGANISM: Homo sapiens

<400> SEQUENCE: 3

```
ctctcccaaa ttgtcaaaga agtataaatt agaaaatgaa tcaggacaat ttcaacctgt       60
tagattagct aatatttaaa aattgaacac tcatacaagt gtggtgaagt gattgttttc     120
tagtgacatt ttacactgtc ataaccttct agaaaataaa ttggcagtgt tattgggaga    180
cagaaatatg tctatataat ttatgggaac ttaggctcag aaaatattaa ggaataagaa    240
tgaactttat gaacaaagat gtggagggt ggaagcaaga ggggggccaa cgcgcacggg     300
gaggaagcat ttgggcagtg actccgcaga cccaggctca ggttgaacta gacaacctcc    360
ttacacctca gttccttaa ctgtagagca ggagtgatgg aactgcctgt tcatgggac      420 tgttgtgagg atgaagtgag atacaccaca ttataagctt gtgcctggaa aggataatgc    480
ttagtaaatg atgactattc ttttttattg caataaaatg tacacagcgt aagagttact    540 atttttaacca tttttgcagg gtaccaccaa gtggcattta gtacattcac agtggtgtgc   600
aaccatcatc atatttccag aatattttcc tcatccccaa aggaaacctc atgctcatta    660
atcagtagct ctcctttaaa atattagtta tgaagatcat agcactatac aaaactcatt    720
atgtaatgtt gagtgaaaaa atcagggtgt gaaattttgt gatatgatgt aattagtgaa    780
agaagcatac aaaagtctg aaaatataaa acaatagca attgcatttc tcagactcta     840
catttaaaca ttattcttta tggttttaaa agcaaagaaa aaggtaaaga aacaacaacc    900
aaccgcaaag caccatgaca aagctcagat tgttaaatcc aggttttgg aacatagact     960 cttatatgac gtttacactc tccagggttc agagagtctg gcagcattgg gagctgcctt   1020
gtgttctaca gcctcacgga cagacaggag gtccatcacc actgctctgt tcttctggag   1080
tttccttgtg aacatgttgt ggacgtagtt accatttctt tcatcttttt aaacacaggt   1140
acctttgggg ctggctttct caaggaagcc cagctccctg tgattgagaa tgaagtgtgc   1200
aatcgctatg agtttctgaa tggaagagtc aaatccactg agctctgtgc tgggcatttg   1260
gctggaggca ttgacagttg caaggtaaga aagatcaag agaccaaagt tagtcttgtg    1320
ctctcctgtc tcagtctcag tcccttagac ttgagtccca aagtagcgaa ttcaagtagg   1380
atttaatcaa tggaagaccc cagtctaagt gttgctcaga aactccctag atctgtccca   1440
```

```
aatgtatatt cagatcatcc aaggggactt cttggggctt gagttccaga tcagcagcaa      1500
gggagccata agtgccataa ctacctcaga ccactcaccc tcctggggtg tcccggtggc      1560
cagggactaa agtggtgatt tttctggtag ggaaggaggt agagggtaca ggacagagac      1620
taactgcaca caatatctga gactggagct cagatattgc tgatgatcag agttggcgtg      1680
tctccccaat tgatttacaa ctggggcttg gatactgttt taaacgggag gagcctccta      1740
accatcttga cacaaccact gacgtgacta cactagagat agactctttc cacttaattc      1800
taccactctt gctttacttc atgagaacga aaatgtaaga ttgcaccatg aattcatttg      1860
cggaaagatt gatactatgc ttttatttta ttttatttta ttttatttta ttttatttta      1920
ttttattgag actctcaccc cggttgaagt gcactgacgt gattttggct cactgcaact      1980
tccacctcct gggttcaagt gaatactcca gcctccctag tagctgggat tacaggtgcc      2040
caccaccacg cctggctaat ttttgtattt ttagtagaga tggggtttca ccacattggc      2100
ctggctggtc tcaaactcct gaccttgtga tccacctgtc ttggcctccc aaagtgctgg      2160
gattacagag ttgagccacc gcactcgacc ctatgtttta tttttaaaaa tatttattta      2220
tttatttaag ccacaactac tagaatagga aggattgata ttttattaat tttatttggt      2280
atttattatt ttttttttctt tcctgagaca ttcttgctct gtcacccagg ctggagtgca      2340
gtggcacatt cttggctcac tgcaacctcc atctcctgtg ttcaagcaat tctagtgcct      2400
cagcctactt agtagctggg atgactggca tgtgcctcca cacccagcta atttttgtat      2460
tttttgtaga cacagggttt tggcatgttg cccaggcttg tctcaaactc ctggcctcag      2520
gtgatccatc tgccgtggcc tcccaaaatg ctgggattat aggcatgagc caccaccccc      2580
tcctggaagg attgatatct tataacataa tttataatta cagaaaacat gtgagttcac      2640
taggaataaa taaattttga agataataaa agattttcac ttatgttgtc atttcggcac      2700
agtttggtat aggatgtgga gatgttaaca tttataccta gcttgctcgt aaactaagac      2760
ctgaaagggt tgtgtctatc agctgcaccc ctgggtagcg acacaacctc gggaaggcct      2820 cagcccccctc ctcgtacagc actgcctgtt ggaaagcttg agggaggcta tggatgtgca      2880
gcacttggca gagggtctgg tcatggaagt taccagcaaa tatgagctac ttttatgatt      2940
ttattttatc caaaagaaag agaatgaaag aagaggggag gaaacaagac taatcaggaa      3000
agatgaaggt ctaggggtga gggaaggagt aaggagacat aaaggcaatg tggagcagct      3060
gaggggggaa atggctttca ccacttccca gcatctattg acattgcact ctcaaatatt      3120
ttataagact ctatattcaa ggtaatgttt gaaccctgct gagccagtgg catgggtctc      3180
tgagagaatc attaacttaa tttgactatc tggtttgtgg gtgcgtttac tctcatgtaa      3240
gtcaacaatg tcctgggatt gggacacact ttctgggcac tgctggccag tcccaaaatg      3300
gaacataagg aagtggttct tctacttctt ttatttctga aatcaggtaa gacatagttt      3360
ttttaaatta taagaattat tttttctccc acaatgtagt aaaaatacat atgccatggc      3420
tttatgtgca attcatttaa tttttgattc atgaaattcc cagttcaaaa tcttgtatat      3480
gattgaaaaa ttcttaaaaa aataagttta atttccccgt gaagactgtc acggtgctgg      3540
aatgaatggg cagaaaaaat aatggttgat ttttctaatc taaaagagtg tgcctacatg      3600
atggccagtc tggctgaaaa ataaatagcc attgtagcta actatgcaaa ggatggctaa      3660
gctcttcgct tggttctcag tttcattaat ttatatcatc tctgttcagg tgccatgctc      3720
ccctcactag caagttgaaa caatgaaata actctttgaa tatgtttggt tccttgacct      3780
```

```
gttcatggag tgggactcag catttctctc tttgttatgg cctgagtaag gctttccatc    3840
ggtatacatt tgcttcttat ccctggagaa attatacaca tccatttgcc agatgatata    3900
cgcatataat gattcaacaa atactcaggg tatttgttga gtgggttagg tccccacatt    3960
tttatacata catacacaca tacacaccgt gtgtgattgt gaatgtaagt gtgtgtcctt    4020
tacaaatact agcttattta gctcatggta taggtagggt agcatagtca tccccatttt    4080
ataaacaaag aaatctagac ttaggaaaat catgttattt gtctcgtgac caaattccca    4140
aatcaaggaa ataaagaaac ctggatttaa gccagatttc caagaaaaaa tctagggctc    4200
ttctcacttt ttcatctttg ttccaacatt tgaaaaaata aatctaaaca cattccaatg    4260
taactgaaga gcaggttaat tgtttgccac ttgcagaatc caattaagaa gagagaagtc    4320
tggtataaag aaagtgattt gcttccaaag ctagcttagg ggaagaaatg cagcagtcct    4380
gccgtactac ttcactttag gagcagaaag tggcactttt aaaaggcaac agaggaggcg    4440
agcaaggatt caggggtcca tgctagcttg ggcaccttat ccaccaggta gttgagcagt    4500
tgcctgctgg tgcctttgtg agcagggtgt tgtcccttga ggcaaatctc tggagggtga    4560
gagttttgta gtgggcatgc tttggtttat aaatcacctg tgaactcagg agttccatct    4620
tgaagcacat acatagttag atgaacttgc cctgcaggga gagtctgatg aaagggaggt    4680
agatgcttgc aatttaatct ataaattacc agataaaatt ttacaagttg actttaaagt    4740
caaacacatt tgaatttagt ggaagccatt caagaaaata tcaaagaaaa tacagagcag    4800
gagaagatta agcaaagagt tttttgggga aattggtgtc tatgtctgtg tgtgtaggga    4860
gtgcagggga tatgaatatt ctatttcagc ccatggaaac taggatgtag atcactgtga    4920
acttattcag caggctacac ccaaaggcta gaacaaactt ctctgccaca ggattaacat    4980 atgtttttaat cgacctgggg ggcacattct ctgataagct cttttggaaa gccaggcttt    5040
ctgtggacgt gttatctttc caatgtgtgc tggaatgccc ggggagagga aaaagtttct    5100
tttacagcca tgctcagtga gaagcggaga acatcttct attcacaaat tgctaagtct    5160
tttacacatg caaatatgca tacacattca cacaccacag tgaggaagaa attctcacac    5220
cattaataaa atacatttac ttcagtagca atatacatct acattttgcc tataatataa    5280
aagtattttt cctattaaaa gatttgttta atgtttcttc accaacaaat aaaccctatt    5340
aaatccccat tgccatatga gccctggagg tgaatcagag aaacaaaagg attgtggaaa    5400
aatcatcagg ttaaaaaaag aaaaattgat tctgttttgg gatatttcct agcaacatga    5460
gctggggagg ggatctcagc agtgatgctc tatgaagcat aataaaatga cacagttaca    5520
ggtaacttag ttaaagggg aaataaatgg aagtttcctc ttttttgaata tcaattgtag    5580 cctgctctgc tacatttcaa aaacactctt caaaatgttt aactgaactc actgtaggaa    5640
gcaccttatt aatttattgt gtgttttgaa gtcacactgt gagctataga atttacccaa    5700
gcacaactct tcctggaaaa gagagttcaa atgagaaaca gtgcggggtg aagacatgga    5760
tatgggccta aaatatctat ttctcaatga tattttgata tatctatcaa gtgcttttta    5820
gtggattagg ttcagaatgc atcagccaat gcctgttcaa taatccagtt ttccagcata    5880
gagcatatta aattgaggaa ggacaaagtc acagaggtgg ggagcaggtg gactgtggcc    5940
aaggactttg catgaaacag tgagcgtgca tcctcctcct tgccctgccc tcatggtctg    6000
tgtactctca ggaggtcagg acaggccttt ctgagaatga gaatctgttc atctgccttt    6060
ctactggata cttgtcatcg gcatacaaac acatgttctc tgcagtgtgt catctttcag    6120
aacctcccct gaccctgtat tccctagaag tctcgctgct ttcagagcca ggcttctctc    6180
```

```
ctgctgccac ccccactgct cttctagtca ctctttaacc cactccatct gcatgtggcc    6240
cccaccacac ccctcaaagt ggtcaaggtt gtcctgttgc ttaattccat ggaagcttgg    6300
ctatcttcat tttattagcc tcttttggcc tctcaccctg tgaaaatcac tacattttgt    6360
gccagagatg gagctggcat ctccaggctt ggaagagggc tgctgaagct cagccaggtg    6420
tcctaaggag cctcaggaca ggggatgctc agtagccttg caatgggaac acagctgagc    6480
cccacttggc caccctttgc cacaaccagg cagaaagcag cttttgaaca gatttgttgc    6540
ctcagatttg atctcaaaga aaaatcgtgg gcagtattgg tcccaggttc tgctttttta    6600
caatttcctc tgaaatctgg atgcctatca acaccttgga aaaactgaat tctccccaac    6660
taatagtggt gtgtcactgt agtaagccta gtacaaaaat ggccttcttt gtggaggagc    6720
ttcatatcct ccattttttt tttgcttaat ttttgcccaa gatgagaaca taatttagtt    6780 cacttttat ttattcccaa catcatccat gcaccaacat ttttgtaact aaaggaggga    6840
ccattcagaa gatgcttatc aactgtcaaa gtgacagtgt tacaaccaat gcacatattg    6900
taagaaatca acaatggcc tccaaggttc atttctacac agggattagc agatcaacat    6960
caatcttggc aacacagttg ccactgatgg tgtcttattt tttttatcat gacatggcaa    7020
tcaagagcaa acatgattta ttcttattta agattttatg gttagactag gcagatagct    7080
agatatgagc aggaggtgga agcccctgag agaatggagg tctggagaat ctgaaacccc    7140
agagattacc caagtcctgc atgctagaca tgagtggagg aggggaata cctaggtaga    7200 aaagaatgcc ccttaagatg cccagcagtc gctcactgtg cagttaactt ttcagaatgc    7260
tgctagatac atgctgatag ggagggaaga gggcaaagga gaaattccta agagatacac    7320
ggttgcagtt agtatacatc tgagtgctat acaaccttct ttgggtggtg gcaagaagca    7380
atgcagccat tacgtagaat tcatatcaaa cacctgtatc acaggtgtta aagaaacaag    7440
aaacattgta cttcttgtat tcttaataat gatttgcaat attgtcttta gtatcactgc    7500
aaacctctat aaatatgatt tttaaaaagt atttctttag gttggaatta cttctacgca    7560
ttgacttatc ttcctgggtt tcattagccg tacccgttgt actttcttcc ttaccactgt    7620
ttatctcaaa ctcttgagat taaagtatgg gctcaggagg gagcgaggag cttcaggact    7680
ctcacggacc tccagcacag tgtagctgcc ttatggaaaa gtggccacac tgttttctgc    7740
actggtccct gccctacta ttcctcactg ggcagagcac agccaccctg gccctgcctg    7800
aacattttag tcagtgttgg ctctgtgctt ctctggggag gaaatccaag agacaaccca    7860
cagcccctct gccatttcag ctgcagcagt accaccgtta atgcccttgg gcttgagaaa    7920
gaagggacct ggccacttcc ctgacacctc cagcacacag cagggaaaga attccagttt    7980
ctctttcttg tgagctttca cctgctactc ttcaccaggc aaggctcctg gcttgggccc    8040
acagtgcagg cacctcgaac tcagttgaac atttccactg gctgcactct gtgttttgt    8100 ggggtgaagc tccagaggt gactgaaagt ccttctgcca ctaacactgc agtcatactg    8160
cccttgctgt acttggacta gggaaggaaa aaagatcctg agtgctttac tcacacccca    8220
gtgtgcccca gccaccctat ggaaaagagg ccagtgtgtc atccctgcaa gcaccctgag    8280
gcccctgccc ctgctgcccc caagctgtag agccagaata taaagctggc agaaaaatgt    8340
aaaaaggcta gactggctta gcctcccagc ctacatcttt ctcctgtgct ggatccttcc    8400
tgctcttgaa catcggactc caagttcttc agctgtggga cttggactgt cttccttgct    8460
cctcagattg caggtggcct attatgggac cttgtaatct tgtgagttaa taccacttaa    8520
```

```
taagctcccc tttgtgtgag tatatctata tctatagata gatataggta tactcactat    8580
atatacacat atatacatat actctctctc tctctctctc atatatatat atatataatc    8640
tcctattagt tctgtccctc tagagaaccc cgactaatac agattttcat accagaagtg    8700
gttcttgagg aacagaatat taaggatgga attctttcat tggttttggg acttctggtg    8760
ttggctgatt aatatgatta gaccaaaaaa tgctaaggac tctacttcta atagtatgga    8820
gaacactgat agtacttggc ctgaattgtt tagagagtta tgcaaaataa atgcatttga    8880
cactactgat tcatcactta tgagaggcaa ggagtttagt gactctatac ataatacctt    8940
tgactatatg tggagaacca aggaacataa tgaagttggt tgattgctcc taagttctct    9000
ggagaaagag atgaaagaaa atgatgatct caggggatct gtctcccacc ttcagaagca    9060
gatactgagc cacaaatctg ctaagattgc cctgaatgag agttttaact cctgtagaga    9120
aagagttgaa attgtgaaaa aacagagaca agctgttatc atgcgagtag ctgatctgca    9180
acaagaggtg catgcacagc cttgccaggt gtttactgtt aaagtgaggg cattgactgg    9240
aaaaaaatgg gaccctggaa cttggagtgg ggatgtgtgg gagaaccctg atgaagctga    9300
ggacactgag tttgtgaact ctgatgaaac tttttttgcca gaagaaacag tttccccatc    9360
cccagtagtg gtaacatccc ctccctgacc cgtgctgcca ttagcctttc cacctttgtc    9420
tgaggatgta aaccctgcac tgcttgaggc aacagtgatg gccttccctg aggcagctgc    9480
caggcaagat aatgttgatt ctcctcaaga ggcaccccta atgcccctga atgcttctag    9540
acctataact aggctaaatt ccttgcgggc cccagaggtg aggttcagag tgtgacccat    9600
gaggaggtgc attatactct aaaagaactg cttaagcttt ctaatttata ttggcagaaa    9660
tctggagaac aggcatggga atggatatta agggtaaggg ataatggtgg aagggacata    9720
gagttggatc aagctgaatt tattggtttg gccctactaa gtagggattc tgcatttaat    9780
gttgcagctc ggggacttag aaaaggttct gatagggccg ggagcagtgg ctcacgcctg    9840
taatcccagc accttgggag gcgggggcgg gcagatcacg agatcaggag attgagacaa    9900
ttctggctaa aatggtgaaa ccccatctct gctaaaaata caaaaattag ctgggcatgg    9960
tgatgcgtaa ctgtaatctc atctacttgg gaggctgagg caagagaact gcttgaacct   10020
gtgaggcaga gattgcagtg agccaagatc gccccactgc attccagcct ggtaacagag   10080
caagactcca tttccaaaaa aaaaaaaaaa aaagttataa tagtttattt gcttggttag   10140
ctgaaatatg gattaaaaga tggtccaatg ttagtgagct ggaaatgcct tggtttaatg   10200
tagaggaagt gatccaaagg cttagggaga ttaggatggt ggagtggatt agtcacttta   10260
gacctactca tcccagctgg gagggtccag aagatacacc cttggccgaa gctttgtgaa   10320
atagatttgt gagagcagca cctgtatttt tgaagagccc gtaattgctc ttctctgtat   10380
gtcagatcta acagtaggaa ccacagtcac tcaactacaa aatttaaata caatgggaat   10440
aattggatcc tgaggtggca ggggccaagt gttggcactg aaccatcaaa ggcaaggtgg   10500
gcataactac cataatagac agcagaggca aagcagccat cagaatagtc tgactcatgt   10560
agagctctgg cattggctaa ttaatcatgg tgttcctaga agtgaaattg atgggaaacc   10620
tactgtattc ctacttgatt tatataaaca aaaaactgcc aggtagaatg gactaaagac   10680
taatctgaat tataaaaaca gagaatcatg ggccctcaat caatttccag actcgaacct   10740
gttacagttc cagaacccac tgaatgaagg ggaggctgga tcccttgag gaaggacacc   10800
actaggctac tgcaaactta tgctgttact ctttctccca tccttcccta aggagacctc   10860
tggcctttta ccagggtaac tgtgtgtact ggagaaaggg aagtaatgag acatttcaga   10920
```

```
aagtactgga cactggctct gagctgacgt tgattccagg gtacccaaaa cgttattgtg    10980
gttccccagt taaagtaggg gcttatggag gttaggtaat taatggagtt ttagctcatt    11040
tctgacttac agtggttcca gtgggtccct ggacttatcc tctggtcatt ttcccagtgc    11100
caaaatgcat aatttgtata gacatactta ttagctggca gaaatgccac attggctccc    11160
tgactggtag gatgagggct attatggtgg gaaaggccaa acagaagcca ttagagctgt    11220
ctctacctag aaaaataaaa aaatcaaaaa caatatccca tccctggagg gactgaagtg    11280
attagtgtca ccatcaagga cttgaaagac gcaggggtgg tgattcccac cacatccctg    11340
ttcaactctc ccatttgacc tgtgcagagg acagatggat cttggaaaat gatggtggat    11400
tattttaagc ttaaccaagt ggtgactcca attgcagctg ctctaccagt tgtggttttg    11460
ttgcttgagc aaattaacac atctcctggt gcctggtatg cagccattgg cttggcaagt    11520
ggcttttttct ccattcctgt ccataagacc caccagaagc aatttgcctt cagctgacaa    11580
ggccagcatt atcctttac caccctacct caggggtgta tcaactctcc agctttgtgt    11640
cataatctta tttggagaga ccttgctcgc ttttcacttc cacgagatat aacactggtc    11700
cattacattc atgacattat gatgattgga tacagtgagc aagaagtagc aaacacactg    11760
aacttattgg tgagacattt gtatgccaga ggatgggaaa taaatccagc taaaatttag    11820
ggactttcta cctcggtaaa atttctaggg ttccagtggc atgagaccta tggagatatt    11880
ccttctaagg tgaagcataa cttgctgcgt ttggcccctc ttacaaccaa gaaagaggca    11940
caatgcctgg tgggcctatt tggattttgg aggcaacaca ttcctcgttt gggtgtgtta    12000
ctctggccca tttatcgagt gacctgaaag gctgccagat ttaagtgcag tctagaacaa    12060
aagaaggctc tgaaacaggt ccaggctgct gtgaaagctg ctctgccatt tgggccacat    12120
gaccccgcag atccaatggt gcttgaggtg tcagtggcag atagggatgc tgtttggagc    12180
ctttggcagg ccccccatagg tgaatcacag tggagacctc taggattttg gagcaaggcc    12240
ctgccacttc tgcagataac tactctcctt ttgagagaca gctattggtc tgttattggg    12300
cttttggtggt aactgaacgt ttgactgtgg gtcataaagt caccatgcta cctgaacctg    12360
cctatcatga actggttgct ttctgaccca tctagccatg aagtgggtca gcacagcggc    12420
atttcatcat caaattgaag tggtgtgtat gtgatcgggc ttgagcaggt cctgaaggca    12480
caagtaagtt acataaggaa gtggctcaaa tgcccatgtt ctccactcat gccaccctgc    12540
cttccctccc ccagcctgca ccaatggcct catggggagt tccctatgat cagttgacag    12600
aggaagggaa gactaaggac tggttcatag atggttctgc acgatatgca ggcaccaccc    12660
gaaagtggac agctgcagca ctatatccac tttctaaatg catgtgtaca cttgtgctaa    12720
gaaaatatct ttattttatt tcctttattt ttcctttatc atgtgacctt agatttatgg    12780
acttcacatc agcatttaag catttaagtg ttgttcatat cagcatttaa atattgttaa    12840
ccttatgtaa taacttttgg tttggggatt ggtgcgtttc tggttgtatg aggatagttg    12900
tattatatta ggcataatta tgaccttatt attgtcttta tttgaagatt atgtatgatt    12960
tcaggatgtg tgtatgggtt caagttgaca aggagttgga cttgtgatgg ttaatactgt    13020
caacttgatt ggattgaaag atgcaaagta ttaatctcgg ttatgtctgt gagggtgtgg    13080
caaaaggaga ttaacatttg agtcagtggg ctgggaaggc agacccaccc ttaatctggg    13140
tacacaccat ctaatcaagt tccagtgtgg ccagattgta aagcagggag aaaaatgtga    13200
aaagactaga ctgaattagc ttcccagcct acatctttct cctgtgccaa atgcttcctg    13260
```

```
ctcttgaaca tcggactcca agttcttcag cgttgggagt tggactggct ttccttgctcc   13320
tcagcttgca gagggcctgt tgtggaacct tgtgatccgc tgagttaata ctacttaata   13380
agatcccctt tatatacata taatatatta tattatatat aatatatata atatatatta   13440
tatataatat atataatata ttatatatta tatataatat atattatata ttatatataa   13500
tatatattat atataatata tattatatat tatatattat atataatata tattatatat   13560
aatatatata aaatatatat atatcctatt agttctgtcc ctctagagaa ccctgactaa   13620
tacaatttat gtcattaatc tcatttattg atttgtatac attgaaccaa ccttatatcc   13680
caggaataaa acctacttga ttgtggtgga ttagcttttt gatgtactct tggattcaat   13740
tgctggtatt ttattgagaa tttttgcatc tgtgttcatc aaggatattg gcttgaagtt   13800
ttcttttttt gttgttccat atcagaatga tgacgacctc atagaatgag ttagtctgtc   13860
ctcttttatc ttttggaatt gtttcaggag gcttgatatc agctcttctt tatatgactg   13920
gtatactttg gctaggaatc tctctggtcc aggggttttt ctggtgtagg tttttaatta   13980
ctgattcaac ttcagaactc attactcatt attgagttct aaaactcact ttcatgtact   14040
cttcaaaaga ctgtcttctt ctgttgttga gcggggtgtt ctctcaaggt cgtttaggtg   14100
aaggtggttg ctggtgttct tctgtatcct tactgcttgt cttctctttt ttttattgac   14160
tactgaggat taatggtgat gtgtccaact ttaactctag attagtctat ttctcttta   14220
gattgtaact ctgttttata tattttgaag ctctgttgtt aggcatgtgt atttggattg   14280
ttaggtcttc ttgatgatga cctttatcat tatgtaatgt ttcttcttat ctctggaagt   14340
attcgttgtt ctgaagtcta tttgtgctga tatgaataca gccttacag ctctatttc   14400
actagtattt gtatatcttt ttctcagctt ttaaattgag atgttcagac catttgcatt   14460
aaagtagttg ttaataggat taaatttaaa tctaccatta agttggttat ttctctttgt   14520
cccatttaaa ctttgttcct tttttcatat ttttctgcct tcatttatat tgagtttatc   14580
tccacgactt acttattaaa ttaatttta atggttttag tattttccac aatgtttata   14640
atatatactt tgattttttc acattccacc ttcaaatgac agaattatac tggatatata   14700
gaaatcttac atcattgcac ttctccttcc tccctctcaa aatgttgtgc tattgctctt   14760
tgtaatagag gcttacttct attatgttat agctctcata atacattgac actatttta   14820
ccctgaataa tcagttgttt tttaaagtga ttatgactac aaatattttg aataatttct   14880
ttatttacc atttctggtg ctccttatct tttacagtag atcccaattt ccatctggag   14940
tcacattctt tctgtgaaaa acaacccttta gcatttctta tagcacggga ctgctgttgc   15000
tgttgtcttt cagcttttct ttgtctgaag aagtcttat tttgccttca gtttttaaaa   15060
gtgattttgc tgagtataga tactgggttg agagtttcat tccttgtatc atttaacaa   15120
tgatgttcca ttatattccg ttttgaatag tttctgacta gaaatctgat ctttgtttct   15180
ttgtattcaa tagttccttt ttctctgact gcctttaaga tattctcatc tttgtttttc   15240
aacagtttga ctataatttg tttattatta acttttgta tttattctgc ttgaggtttc   15300
ctgagctcct tggatttgca gattgttgat tttttattgtt tttgtaaaat tcatagccat   15360
tatctattct actgttttgt ttttttttc acttctctct ctctgtattc ttcttttgg   15420
actgtaagta ttcaaatgtt agatcattca tattgcttca taaaccttat atgcttcttc   15480
tgctttttt tttttgtcag gaactctttt tttgtatctg tgttggtttg gataagttct   15540
agtagactat gttcaagtt tatggattatt ttgttagttg tgtctaattg actcctcagt   15600
gcattcagag aattcttcat ctctgatatt ataaatctct tcctagcatt ttcatgttac   15660
```

```
tcttttctat agtttccatc tctttgctga aattctcccc ctatccatgg atattgtcca    15720
cctttaccac aagattcttt aacatattaa cataggtatc atacaaaccc aaactgatag    15780
tttccagatg gtgtcttttc tgagtctgtc tgtcttgatt gctttattat ttaacagtga    15840
cttatcttcc ctcttcagct tttggtgtgt cttgtaattg tttaatcaaa cactgggtat    15900
cataaatgga ggaacagtag agattgcagt aaatattatt tatgctttga aatgggcacc    15960
catcttctgt tgaaaatatg ttttgtggtc aattgagtca acctagtaac tggttgaact    16020
gaatttggca tttgtgcttg ttgcttttat cttaaatgca ccacaggttt aaattcctcc    16080
agtgatgggt gctgctatc ttttgcttag agtggggcct ggggtgtgga agaattttct    16140
cagtgttcct atctattatt agattttagc agtcactgca tgcctgcact acagagggga    16200
tatcttcata cacataatct aaccccattg aaactgctgt ttcttcttaa tgaatgctca    16260
atctttggtg gaaataaaca aatgctgtat ctcctggagc cacttcagtc ttagtcaggt    16320
tctgcagggc tttgaaggga atgcattctc agtattcttg tgccttattt ggatggaact    16380
tgaacctgtg gtgggtttgg agagaaagag tagcagacgt ctgctatgtt gcaatgcagg    16440
atgctgggca caagaaaatt tccagtctct cctccaagga aataagattt gatcatctac    16500
ctatccctga gaagtgaagg gctttgcctg cggtgctaga tgcaaaacca ttttttctccc    16560 cccattgccc agaaacttaa ggcttttggct tttctgagca gtggtctagg gaattgtgca    16620
aggttttcat atttgacccct gacagcccat caccacctac agcttgcagt gccaaatgta    16680
tctccctctg atctctcctg tcctgtggtc ctcatgaaca ttaagaagag atttctaaaa    16740
aagagcttgc acatgagcat agtttctggt gagaagaatt ctgatatgtt aacttcctct    16800
aaacttttaa ataaaatatt tctaagaatt aaataaagtt ctagaatgat atgaatctat    16860
tcctttggtt ttttgcacgt ctgtctgcct gctaatcaag agaagagaat ggtcgtaatt    16920
ctcagagact ttttcctgtt tgtgtcataa atgacttcac attttttct gttctaagaa    16980 ctattcagct tgatttcttc tgttttaatt ttagcagcac ctgagcaaag ccatgtggtc    17040
caggattgct accatggtga tggacagagt tatcgaggca cgtactccac cactgtcaca    17100
ggaaggacct gccaagcttg gtcatctatg acaccacatc aacataatag gaccacagaa    17160
aactacccaa atgcgtatgt cattaatctt acagtaagca aaacaaggtc caagtaaaat    17220
ttgtcttaga aaaggtgtgc gtcaagctaa cttcttatga ttaaattttt ctcacacata    17280
gaatgcatgg caaaatgtct gagaaacatt actttgagca aagagtatga tagaagagaa    17340
atgttaagct ggctctcttt cctgagagtt tgataaaatc aggagaatat ctggcggtgg    17400
tgaggccaca ataatggaaa atcagaatgt ttagacagag tcagcttcaa caacactcac    17460
taaaggtcaa tgtgatcttt accccttgaa attctataat tctaatctcc aattcctgaa    17520
gtgaaggttg tgttggcctt ttctgtcttg gctcacaagt aaatgatatg tgcatatcta    17580
tggaaaggcg aatctatctt tttctatatc tatgtctatt ccaacgggta gaaacaccct    17640
gggtcctgag caccagtggt ctgaaggaat acgggttgcc aggaagagag aagcaaaggc    17700
aggaaggcag atgaaagtaa gaaatgagac agatgctaaa caataaaaag tgcgggaaga    17760
tagacagaag ctggggtctg accacaccat ggccagtctt tcacacataa gtgactacca    17820
aagacaagaa aaaatgattt ccgcttgttg gacaatagat ggtagaggac caagggaatt    17880
gcgagagaga gaacaatgag atcaactcaa cagatgcact ggttttcttc ctggagaccc    17940
ttcctgcact gaagggcagg agatggagcc caaaaaaac tgtagccatc ttgctgaaca    18000
```

-continued

```
gaggagggac attggagttt gggattattc aggtggctag gattttctag gcctgctaac    18060
aatgagaaca gatttgtgga ggaaaggagt tctagaaata tgcatagaaa tctcctcgag    18120
tcattggcta acatgaagc tgcatgtaca cagaaaatag atccacaaga aagtagggca     18180
aagaacatct acggaagagc agcaactaca atggaacagt gagctcaata acatgacag    18240
agctcaaata gcactaaggg atattggagt ttggaccaca cagaggagag agacttcact    18300
gaacatcttg ggcattcagt agagacccag gaaaagccat actttaggag tagaattagt    18360
atattcttag aataaaggca gctccacaca aacaatagca aaactgaaaa ggaagtctcc    18420
aagcatcaga atgatgtcca agtcaatgaa ctgcctctga gaggaaaact caaccatctt    18480
tagaggtaaa catcaaagtc aagtggctca gctatgcagt atccacagtg tgaggcctaa    18540
atataaaact tgactacaca tagaaaacctt ttagtgtgac ccacaagcag gaggaaaatc    18600
agccaataca aacagaccca gaagagacag aaatgattag aatggcataa aaatttgaca    18660
tatcactata taataattga gttctaggat ttaagaaaac atgaatatag aatgcaacag    18720
acaccttatc cagagacagt aagagtataa agagccaaat cgaagaacta ctaagagata    18780
tgtcttaaat gaaaaaatta ctagatggcc tccccatcta gttagacatt tcagaagaaa    18840
ataccaaatg aaaaataatt gcatagaacc tacagaacca gatacacaca tacaaaaacac    18900
acgcatgcat acacacacac tcaaacatgt ataagcttac aaacacacac acacatccac    18960
aaatgctgaa aaatgaaatc aaccgagcca cacagacata aaggaaaaca taaaaagatt    19020
tcctacatgt gggaagcaag tcacagaaag ggggaaggag attggaacag aaatatatac    19080
tgaaagcaag gatggctgaa aattttccaa atataaagaa gattaaaaaa tcacggactc    19140
aagaagctca atggatcaga aaaataattt ctaaaatgac aattataggg tgccactggg    19200
tacatagcag ttcaactgtc agagggcaaa gacataatac acagaaaaat ctcgtaagga    19260
acgggaaaaa caaaaagctg tgtcttgcta gaggaacagt gatacaagtg actaatgtgt    19320
tcccatcaga aacactgcaa cctggacaca aagaataac attaaagtaa taaacgtaag    19380
aaagaagagc tcaactgaga aggctacatc cagcaataaa atgccttgaa gttcatccat    19440
gttggaggaa tgcacattgt gcactcccct aaacaaagaa accggaaact gtaagacttt    19500
ggaatcagca ggcttatgta acaaaagagg tgaccctaag gaattaagga gaagaagaat    19560
agaacaagaa gggaactttc tgcagcctat ataatgaaga acctagcaat tggcaaatgt    19620
agatgaaaat gctacatgtt ttcttgatca aacgtttata tcttttttaaa tgagagttga    19680
cgagttgaag caaaatgata ccaatatatt taactttacc atatgtagaa gtaaaaattt    19740
gaacatgtag cataaatcat gtagggatta attggaagtg taccactgta agtttcttac    19800
ctcatgcacg atagtatgta atactaataa aaggttaatg tgtgggttca aagggatatt    19860
gcaaatccta gagcaatcac aaagttttta actctgaggt ttgttgtata ataacaatat    19920
tttatgtatt caaagagggg aagccaagga agaaaaaaaa gtctttaaag agctctggct    19980
cttagtacat ccagttgctc attgaatgag cttcctggaa tggagggtct gggactgaga    20040
ctaggccaca tgtgtagagc cactagagac acaatgttgg atccccatgg cccataatac    20100
atttcccatt ttctcaggca gccacaggtc atgaatgtga ggatactgag aggttggagc    20160
aacgttcttg ggaggcataa ggaagagcga atgcttcaag atccccgcag cccaaactcc    20220
tcagctgctt tgcctcctaa ttcattgttt tttgctcctc catagctgtc cgacctcttc    20280
agatctctta gtcttcctgc catcttcctt tatgccatgg gacccactgt tctttcaact    20340
catcccccag ttctggagtg gctgtggaca gcagaggata gactgagagc aggagagaag    20400
```

```
gtcctgccca ggaacccatt ctagagatac tgcattctgc ctgggagcaa gttttccagg    20460
gcagctttga gaagtcttgc agaaacaaac ctacttgacc gacatgatat gggaatgaca    20520
gacagtaata ctatttgcac aatgcttttc catgggaaag gtagagcctt ttcactaggt    20580
tttgagtaca tggagtgtga gagttgacct ggaaaggtta tcctccttga tgccatgttt    20640
tctctgaaga actacatgtt cgttgcaact cccacattag aatatgaagt cctaccgaga    20700
gagatacgga gactagacag atacagatgc atttgcatgt gaatacacaa tcccacaata    20760
cagacgtcaa aacccatacc agttattcca gagagatgga ttgggcagaa ggcagaagga    20820
gaatactctg atcgttttc ggccacgtgt gtgtgttatc tcagtgtttc taagaagcgt    20880
ttgctacttt agattttta tttaaaaaaa atagtaataa tctattaagt atgagagatg    20940
tgcagagagg attagtgatc gagagccatt tttgctggtg gcaatcatat ggtacttta    21000 atgggaatat tagaaaggca ccggtaatga ccttgttgca gcacaaagga gagagtgtgg    21060
ggtgcccctg catgttgtcc cacctcttgt gacgtgtatc gttttggaat ttccagtggc    21120
ttgatcatga actactgcag gaatccagat gctgtggcag ctccttattg ttatacgagg    21180
gatcccggtg tcaggtggga gtactgcaac ctgacgcaat gctcagacgc agaagggact    21240
gccgtcgcgc ctccgactgt tacccccggtt ccaagcctag aggctccttc cgaacaaggt    21300
aaggagtctg tggccagaca tctacacgct tcgatgctgg gatgaaaagc catggaaatt    21360
cccactgatg cagccgcctt caatggtaaa cggatgctcg agtgttgcct gagttctacc    21420
atgtaggagg aagcctccgt gcactctctg ggggagccag cggagtgatt tctggtgcaa    21480
cgtggttggg ctttgtcttt aggatgggca caaaccctcc aggggggatcg acttcaaaat    21540 tcaccttgtt gtaaaacggg ctacctcagt gtcccagcca aaattttat tgtaacatgc    21600 tgtcaggtgt gtcactcttt ccaagccagt aagcttttcc ggggatttct tcaagtagcc    21660
agcattcaga gcaatcttca gcattgcaga ttctgagaaa tgtggctctg gagcctgtca    21720
ccctcgagaa acctaagagg gctgcattga ttccatgtgg ccctgggtct atggagcagt    21780
acatgagctc ccagtgctct aaggctcttc agccctaggc tttgaaggga gtgatttctc    21840
agtattctta aacctctttc tgatgacact tgtacctgtg aggggtctag agagaaagag    21900
tagtagactc ctactttact acaattcagg atgcagggca tgagaggatt ccctctctcc    21960
tccaagggaa gaagcttttg gcgtgcacac atccctgaga agcaaagtgt ctttgtcttc    22020
agtcagatac ataggaccgt tttctgcccc atggcccgga agccaaaggc cttggctttc    22080
atgatcaacg gtctagggaa acatgcaaaa tttccatgtc tgtcccaaac tctgcccccg    22140
acagccaatt accacctgca gcccgcattg ccaaatgcgg tgccgtttgc atgaagattc    22200
agtagagttt cctagaaagg tgctacctcg tgagctcact ttccaatgag gaatctgatc    22260
tgttgtgttt ctctaaggtg tcaggtgaaa tatttccaag aacttactac agttctagaa    22320
tgggaggaat ctgttgcttt ggtgtttgtt tgttggtcgg ttttctcaca tccatctgcc    22380
tatggataag gaaaagagaa cggtcgtaat tctcatagac tccttctctgg ttgtgtcaca    22440 aatggcttca catgtttctc tatgctcaga gatactcagc ttgatttccc gtgttttcat    22500
ttcagcaccg actgagcaaa ggcctggggt gcaggagtgc taccatggta atggacagag    22560
ttatcgaggc acatactcca ccactgtcac aggaagaacc tgccaagctt ggtcatctat    22620
gacaccacac tcgcatagtc ggaccccaga atactaccca aatgcgtatg tctttgttct    22680
ttaccataag agaagaaagg gccaagtgaa gtttctgtta caagagatgt gtctcaagct    22740
```

```
gagttctccg aactcaactt gtgacagatg cagatggcgt agcaaaatgt ctcaggatga   22800
ttgccttgga gctaagggtc tgagagaagg gaaatgttaa gctccctctc cttcctccta   22860
gttctattga gcagaaggga aatctggagg tgaggagatc acattatgaa gaaagtcaga   22920
atgacaaagg accagacact tagattaccc ttccacaaca ccaactaaac gtcaatggag   22980
actttccagt tggaattccg ttattctggc ttccacttcc tgaagggaag gttgcgtttg   23040 cctttctct ctgggttcaa gaggaaagaa taggtgctta tttatggaca ggtgaattga   23100
tctgtttcta tatctacgta tattccgatt gtcagaaaaa cactcgttcc taagtaccag   23160
tggcctgaag ggatacaggt tcccagcaag agaagatcca aggaaggaag gcagatgaga   23220
gtcagcacag agagggatgc tgaaaagtaa aagggatggg tggatggaga gaagcccggg   23280
tctgaccacc caatggccaa tattttggcc acaagcgact accagagaca tggaaaaatg   23340
gtttctacat gtgggacaac agatggtaga ggacctagag aattgagaga ggggcaatga   23400
tgggctccac tccgcagatg ccttggcttt cttcctggat acccttcctg cactgaatag   23460
caaggagatg gagcccaagc agactgtagc catcttgctg aatggaggag agggattgga   23520
gtttgggatg actgtggtag ctgaaatttt tctaggtctg ctagaaataa gaactggttt   23580
gtgtggagga aaagagctct acaaatacgc atagaagtct cctccagtcg ttggcctgac   23640
atgacgctgc ctgtgcacag gaaatggttc cacgagaaag tgtggcaaag aacatttact   23700
gagaaacagc aagtacaaga gcacaggaag ctcaataaag aagagagaga tcacatagca   23760
ctctgggata ctggagttct tcccagctag accagagagt cctcacggag cacattgcca   23820
attcagtgga gaccccagaa cagccgtaat ttaaaggtac acttagtata ttactagaat   23880
aaagtcagct gcagacaacc ccttgcacag ctggaaagca agtgtccaag catcaaatcg   23940
gtttccaatc aatgaagtgc ctgtgagagg aaatctcaac tctctttaga agtaaacaac   24000
aaagtcgatt gcctcagcta tgcggtatcc gcagagtgag tcctaaattt aaaatctgac   24060
tacatgtaga aaagcgtttc gtgtgaccca tgaccaggaa ataaatcggg taatacaaac   24120
aggctcagga atgagagaaa tgattagaat tgcgtgaaaa tttgacatat cagtatgata   24180
actgatttca aatatttaaa aaaacaacat gcaagaaagc agatatcata tcaagagaaa   24240
ttaacagtac agaatagcca aattaaatta agaggtagt ataaaaaaag tatgtcttaa   24300
ttgaaaaaaa ttactgtatg gccggctgat caatttagac gtttcagagg aaaacattac   24360
ccaacacaca attctagaga acctacagaa tgagctacac acacacacac acacacacac   24420
acacacactg aaaacacacc catactcaca cacacgcaga aactcacaag ttctaacaca   24480
cacagacacg cgcaccctg aagaaacagt gaaatataaa attaagcgag cctcacagac   24540
atgtaggaaa atatgaaaag atttcctgca tgtgggaagc aagtcacagt aaagagcaag   24600
ggagtttata atagaaacaa ataccagaat caaggatggc tgataacttt tcaattacga   24660
agaacattaa aaaaaatcac agaatcgtga aactcaaggg atcatatagg gaatttcgga   24720 aaaaaaccc aacctgtatg atgtactttt gtacatcaca gttcgaaggt aacaaggcaa   24780
agatgtaata agaagaaacc tgtcacgaga aactggagga aaaagagctg tgtcttccta   24840
caagtacact gatacaaatt gccaatgtgt tcacctcaga aacactggaa gccagatacc   24900
agggaatatt gttaaaatga taatcaggaa caaaagaga tcaaccggga atgctgaatc   24960
cagcaataaa atgccttgaa ggtcatccat gtcggataaa tgcatattgt gcactgcccc   25020
aaagaaagaa accggaaact gtaagaattg gaaatcagca ggcttatgta acaagagagg   25080
tgacccgaag gaattaggta gaagaagaat tgaacaagaa aggaactttc tgcagcccac   25140
```

```
gtaatgaaga atccagcaat tggcaaatgt agatagatgt aaatgcaaaa tattttcttg    25200
atcaaatttc tatatctttg taaatgagag ttgactactt gaaacaaaat gatagcaaga    25260
tatttaactt cagcatatgt agaggtaaga atttgaaatg gtagcataaa tcacgaaggg    25320
attaattcga agtgtaccgt tgtaagtttc tttacctcat gcacgatggt gtgtcatatt    25380
aataaaaggg tactgtgcgg gttcgaaggg atattgcaaa tcctagagca atcacaaagg    25440
tttgaactct gaggtttttg gtataataag aatagtccat gcattcaaaa gagggaagcc    25500
aaggaagaac tagaagtctt tcaagagctc aggctcttat acatccagtt gctcattgaa    25560
ccagcttcct ggaatggagg gtctgggggtt gagactaggc cacaagtcta gagtctctag    25620
agagacagtg ttggaacccc atggcccata atacatttcc cattttctca ggcagccaga    25680
ggtcatgaat gtgaggatac tgggaggttg gagcaacgtt cttgggaggc ataaggaaga    25740
gcgaatgctt caagatcccc gcagcccaaa ctactcgcct gctttgcccc ctaatgcatt    25800
tttctctgct gctccgtagc tgtccgacct cttcagatct cttagtccac cctgccgtct    25860
tcctttatgc catgggtccc actgttcttt caactcatcc cccttccct cagtcccgga    25920 gtagctgcgg ccagcagagg gtagactgag agcaggagag aaggacctgc ctaggaaccc    25980
cttctagaga tactgcatcc tgcctgggag caagttttcc agggcagctt tgagaagtct    26040
tggagaaaca aacctactaa acctgacaga cagtaatact attttgcacaa tgcttttctg    26100 tgggaaaggt agagcctttt cactacgtat tgagtacata gagtgtgagg gttgacctgg    26160
aacggctatc ctcctggatg acgtgtgttt tctgaagaac tacatgttcg ttgcaactcc    26220
cacattagaa tatgaagtcc taccgagaga gatacggaga ctagacagat acagatgcat    26280
ttgcatgtga atacacaatc ccacaataca gacgtcaaaa cccataccag ttattccaga    26340
gagatggatt gggcagaagg cagaaggaga atactctgat cgttttcgg ccacgtgtgt    26400 gtgttatctc agtgtttcta agaagcgttt gctactttag attttttatt taaaaaaata    26460
gtaataatct attaagtatg agagatgtgc agagaggatt agtgatcgag agccattttt    26520
gctggtggca atcatatggt acttttaatg ggaatattag aaaggcaccg gtaatgacct    26580
tgttgcagca caaaggagag agtgtggggt gcccctgcat gttgtccac ctcttgtgac    26640 gtgtatcgtt ttggaatttc cagtggcttg atcatgaact actgcaggaa tccagatgct    26700
gtggcagctc cttattgtta tacgagggat cccggtgtca ggtgggagta ctgcaacctg    26760
acgcaatgct cagacgcaga agggactgcc gtcgcgcctc cgactgttac cccggttcca    26820
agcctagagg ctccttccga acaaggtaag gagtctgtgg ccagacatct acacgcttcg    26880
atgctgggat gaaaagccat ggaaattccc actgatgcag ccgccttcaa tggtaaacgg    26940
atgctcgagt gttgcctgag ttctaccatg taggaggaag cctccgtgca ctctctgggg    27000
gagccagcgg agtgatttct ggtgcaacgt ggttgggctt tgtctttagg atgggcacaa    27060
accctccagg gggatcgact tcaaaattca ccttgttgta aaacgggcta cctcagtgtc    27120
ccagccaaaa tttttattgt aacatgctgt caggtgtgtc actctttcca agccagtaag    27180
cttttccggg gatttcttca agtagccagc attcagagca atcttcagca ttgcagattc    27240
tgagaaatgt ggctctggag cctgtcaccc tcgagaaacc taagagggct gcattgattc    27300
catgtggccc tgggtctatg gagcagtaca tgagctccca gtgctctaag gctcttcagc    27360
cctaggcttt gaagggagtg atttctcagt attcttaaac ctctttctga tgacacttgt    27420
acctgtgagg ggtctagaga gaaagagtag tagactccta ctttactaca attcaggatg    27480
```

```
cagggcatga gaggattccc tctctcctcc aagggaagaa gcttttggcg tgcacacatc   27540
cctgagaagc aaagtgtctt tgtcttcagt cagatacata ggaccgtttt ctgccccatg   27600
gcccggaagc caaaggcctt ggctttcatg atcaacggtc tagggaaaca tgcaaaattt   27660
ccatgtctgt cccaaactct gcccccgaca gccaattacc acctgcagcc cgcattgcca   27720
aatgcggtgc cgtttgcatg aagattcagt agagtttcct agaaaggtgc tacctcgtga   27780
gctcactttc caatgaggaa tctgatctgt tgtgtttctc taaggtgtca ggtgaaatat   27840
ttccaagaac ttactacagt tctagaatgg gaggaatctg ttgctttggt gtttgtttgt   27900
tggtcggttt tctcacatcc atctgcctat ggataaggaa aagagaacgg tcgtaattct   27960
catagactcc tttctggttg tgtcacaaat ggcttcacat gtttctctat gctcagagat   28020
actcagcttg atttcccgtg ttttcatttc agcaccgact gagcaaaggc ctggggtgca   28080
ggagtgctac catggtaatg gacagagtta tcgaggcaca tactccacca ctgtcacagg   28140
aagaacctgc caagcttggt catctatgac accacactcg catagtcgga ccccagaata   28200
ctacccaaat gcgtatgtct tgttctttta ccataagaga agaaagggcc aagtgaagtt   28260
tctgttacaa gagatgtgtc tcaagctgag ttctccgaac tcaacttgtg acagatgcag   28320
atggcgtagc aaaatgtctc aggatgattg ccttggagct aagggtctga gagaagggaa   28380
atgttaagct ccctctcctt cctcctagtt ctattgagca aagggaaat ctggaggtga   28440
ggagatcaca ttatgaagaa agtcagaatg acaaaggacc agacacttag attacccttc   28500
cacaacacca actaaacgtc aatggagact ttccagttgg aattccgtta ttctggcttc   28560
cacttcctga agggaaggtt gcgtttgcct tttctctctg ggttcaagag gaagaaatag   28620
gtgcttattt atggacaggt gaattgatct gtttctatat ctacgtatat tccgattgtc   28680
agaaaaacac tcgttcctaa gtaccagtgg cctgaaggga tacaggttcc cagcaagaga   28740
agatccaagg aaggaaggca gatgagagtc agcacagaga gggatgctga aaagtaaaag   28800
ggatgggtgg atggagagaa gcccgggtct gaccacccaa tggccaatat tttggccaca   28860
agcgactacc agagacatgg aaaaatggtt tctacatgtg ggacaacaga tggtagagga   28920
cctagagaat tgagagaggg gcaatgatgg gctccactcc gcagatgcct tggctttctt   28980
cctggatacc cttcctgcac tgaatagcaa ggagatggag cccaagcaga ctgtagccat   29040
cttgctgaat ggaggagagg gattggagtt tgggatgact gtggtagctg aaattttttct  29100
aggtctgcta gaaataagaa ctggtttgtg gaggaaaaga gctctacaaa tacgcataga   29160
agtctcctcc agtcgttggc ctgacatgac gctgcctgtg cacaggaaat ggttccacga   29220
gaaagtgtgg caaagaacat ttactgagaa acagcaagta caagagcaca ggaagctcaa   29280
taaagaagag agagatcaca tagcactctg ggatactgga gttcttccca gctagaccag   29340
agagtcctca cggagcacat tgccaattca gtggagaccc cagaacagcc gtaatttaaa   29400
ggtacactta gtatattact agaataaagt cagctgcaga caaccccttg cacagctgga   29460
aagcaagtgt ccaagcatca aatcggtttc caatcaatga agtgcctgtg agaggaaatc   29520
tcaactctct ttagaagtaa acaacaaagt cgattgcctc agctatgcgg tatccgcaga   29580
gtgagtccta aatttaaaat ctgactacat gtagaaaagc gtttcgtgtg acccatgacc   29640
aggaaataaa tcgggtaata caaacaggct caggaatgag agaaatgatt agaattgcgt   29700
gaaaatttga catatcagta tgataactga tttcaaatat ttaaaaaaac aacatgcaag   29760
aaagcagata tcatatcaag agaaattaac agtacagaat agccaaatta aattaaagag   29820
ctagtataaa aaaagtatgt cttaattgaa aaaaattact gtatggccgg ctgatcaatt   29880
```

```
tagacgtttc agaggaaaac attacccaac acacaattct agagaaccta cagaatgagc    29940
tacacacaca cacacacaca cacacacaaa ctgaaaacac acccatactc acacacacg    30000
agaaactcac aagttctaac acacacagac acgcgcaccc ctgaagaaac agtgaaatat    30060
aaaattaagc gagcctcaca gacatgtagg aaaatatgaa aagatttcct gcatgtggga    30120
agcaagtcac agtaaagagc aagggagttt ggaatagaaa caaataccgg aatcaaggat    30180
ggctgataac ttttcaatta cgaagaacat taaaaaaaat cacagaatcg tgaaactcaa    30240
gggatcacat agggaatttc ggaaaaaaaa cccaacctgt atgatgtact tttgtacatc    30300
acagttcgaa ggtaacaagg caaagatata ataagaagaa acctgtcacg agaaactgga    30360
ggaaaaagag ctgtgtcttc ctacaagtac actgatacaa attgccaatg tgttcacctc    30420
agaaacactg gaagccagat accagggaat attgttaaaa tgataatcag gaacaaaaag    30480
agatcaaccg ggaatgctga atccagcaat aaaatgcctt gaagatcatc catgtcggat    30540
aaatgcatat tgtgcactgc cccaaagaaa gaaaccggaa actgtaagaa ttggaaatca    30600
gcaggcttat gtaacaagag aggtgacccg aaggaattag gtagaagaag aattgaacaa    30660
gaaaggaact ttctgcagcc cacgtaatga agaatccagc aattggcaaa tgtagataga    30720
tgtaaatgca aaatattttc ttgatcaaat ttctatatct ttgtaaatga gagttgacta    30780
cttgaaacaa aatgatagca agatatttaa cttcagcata tgtagaggta agaatttgaa    30840
atggtagcat aaatcacgaa gggattaatt cgaagtgtac cgttgtaagt ttctttacct    30900
catgcacgat ggtgtgtcat attaataaaa gggtactgtg cgggttcgaa gggatattgc    30960
aaatcctaga gcaatcacaa aggtttgaac tctgaggttt ttggtataat aagaatagtc    31020
catgcattca aaagagggaa gccaaggaag aactagaagt ctttcaagag ctcaggctct    31080
tatacatcca gttgctcatt gaaccagctt cctggaatgg agggtctggg gttgagacta    31140
ggccacaagt ctagagtctc tagagagaca gtgttggaac cccatggccc ataatacatt    31200
tcccattttc tcaggcagcc agaggtcatg aatgtgagga tactgggagg ttggagcaac    31260
gttcttggga ggcataagga agagcgaatg cttcaagatc cccgcagccc aaactactcg    31320
cctgctttgc cccctaatgc attttttctct gctgctccgt agctgtccga cctcttcaga    31380
tctcttagtc caccctgccg tcttccttta tgccatgggt cccactgttc tttcaactca    31440
tccccctttc cctcagtccc ggagtagctg cggccagcag agggtagact gagagcagga    31500
gagaaggacc tgcctaggaa cccccttctag agatactgca tcctgcctgg gagcaagttt    31560
tccagggcag ctttgagaag tcttggagaa acaaacctac taaacctgac agacagtaat    31620
actatttgca caatgctttt ctgtgggaaa ggtagagcct tttcactacg tattgagtac    31680
atagagtgtg agggttgacc tggaacggct atcctcctgg atgacgtgtg ttttctgaag    31740
aactacatgt tcgttgcaac tcccacatta gaatatgaag tcctaccgag agagatacgg    31800
agactagaca gatacagatg catttgcatg tgaatacaca atcccacaat acagacgtca    31860
aaacccatac cagttattcc agagagatgg attgggtagg aggcagaagg agaatactct    31920
gatcgttttt cggccacgtg tgtgtgttat ctcagtgttt ctaagaagcg tttgctactt    31980
tagattttt atttaaaaaa aatagtaata atctattaag tatgagagat gtgcagagag    32040
gattagtgat cgagagccat ttttgctggt ggcaatcata tggtactttt aatgggaata    32100
ttagaaaggc accggtaatg accttgttgc agcacaaagg agagagtgtg gggtgccccct   32160
gcatgttgtc ccacctcttg tgacgtgtat cgttttggaa tttccagtgg cttgatcatg    32220
```

```
aactactgca ggaatccaga tgctgtggca gctccttatt gttatacgag ggatcccggt   32280
gtcaggtggg agtactgcaa cctgacgcaa tgctcagacg cagaagggac tgccgtcgcg   32340
cctccgactg ttaccccggt tccaagccta gaggctcctt ccgaacaagg taaggagtct   32400
gtggccagac atctcacgcg ttcgatgctg ggatgaaaag ccatggaaat tcccactgat   32460
gcagccgcct tcaatggtaa acggatgctc gagtgttgcc ggagttctgc catgttgggg   32520
gaagcctccg tgtactctct gggggagcca gcggagtgat ttctggtgca acttgggtgg   32580
gctttgtctt tagaatgggc acaaaccttc cagggtgatg ggcttcacaa ctcacctcct   32640
tctaaaatgg gctatctcag tgtcttagcc aaaattttta ttgtaacgtg ctgtcaggtg   32700
tgtgattctt tctgtcgcag taagcttttc tggggatttc ttcaagtagc cagcagtcag   32760
tgcaatcttc agcattgcag atttcaaaaa atgtggctct ggagcctgtc atcctcgaga   32820
aacctaacag ggctgcatta attccatatg gtcctgggtc tatggagcag tatatgagct   32880
cccaatgctc taaggctctt cagtcctagg ctttgaaggg agtgatttct cagtgttctt   32940
aaacctcttt ctgatggcac ttgtacctgt gaggggtcta gagagaaagg ttagtagact   33000
tctcctttac tgcaattcag gatgcagggc atgagaagat tccctccctc ctccaaggga   33060
agaaggtttt ggcgtgcaca catccttgag aagcaaagtg tctttgcctt cagtcagata   33120
tataggatcg ttttctgccc catggcctgg aagccagagg ccttggcttt catgatcaac   33180
gatctaggga aacatgcaaa atttccatgt ctttccccctc ctctgccctc gacagccaat   33240
taccacctgc atcctgcatt gccaaatgca gtgccctttg tatgaacatt cagtagagtt   33300
tcatagaaag gtgctacttc gtgagcgcac tttgcagtga aaggagtct gttctgttct   33360 gtttttctaa ggatttcagg tgaaatattt cctagaactt actacagttc tagattggta   33420
ggaatctgta ggtttgctgt atgttttttg gttggttttc tcccatccat ctgcctacag   33480
gtaagggaaa gataacgttc gtaattctca tagactcctt tctggttgtg tcataaatgg   33540
cttcacatat ttcgttattc tcagagatac tcagtttatt tcttgtgttt tcatttcagc   33600
accgactgag cagaggcctg gggtgcagga gtgctaccac ggtaatggac agagttatcg   33660
aggcacatac tccaccactg tcactggaag aacctgccaa gcttggtcat ctatgacacc   33720
acactcgcat agtcggaccc cagaatacta cccaaatgcg tatgtctttg ttctttacca   33780
taagagaaga aagggccaag tgaagtttct gttacaagag atgtgtctca agctgagttc   33840
tccgaactca acttgtgaca gatgcagatg gcgtagcaaa atgtctcagg atgattgcct   33900
tggagctaag ggtctgagag aagggaaatg ttaagctccc tctccttcct cctagttcta   33960
ttgagcagaa gggaaatctg gaggtgagga gatcacatta tgaagaaagt cagaatgaca   34020
aaggaccaga cacttagatt acccttccac aacaccaact aaacgtcaat ggagactttc   34080
cagttggaat tccgttattc tggcttccac ttcctgaagg gaaggttgcg tttgcctttt   34140
ctctctgggt tcaagaggaa agaataggtg cttatttatg gacaggtgaa ttgatctgtt   34200
tctatatcta cgtatattcc gattgtcaga aaaacactcg ttcctaagta ccagtggcct   34260
gaagggatac aggttcccag caagagaaga tccaaggaag gaaggcagat gagagccagc   34320
acagagaggg atgctgaaaa gtaaaaggga tgggtggatg gagagaagcc cgggtctgac   34380
cacccaatgg ccaatatttt ggccacaagc gactaccaga gacatggaaa aatggtttct   34440
acatgtggga caacagatgg tagaggacct agagaattga gagaggggca atgatgggct   34500
ccactccgca gatgccttgg ctttcttcct ggataccctt cctgcactga atagcaagga   34560
gatggagccc aagcagactg tagccatctt gctgaatgga ggagagggat tggagtttgg   34620
```

```
gatgactgtg gtagctgaaa tttttctagg tctgctagaa ataagaactg gtttgtggag    34680
gaaaagagct ctacaaatac gcatagaagt ctcctccagt cgttggcctg acatgacgct    34740
gcctgtgcac aggaaatggt tccacgagaa agtgtggcaa agaacattta ctgagaaaca    34800
gcaagtacaa gagcacagga agctcaataa agaagagaga gatcacatag cactctggga    34860
tactggagtt cttcccagct agaccagaga gtcctcacgg agcacattgc caattcagtg    34920
gagaccccag aacagccgta atttaaaggt acacttagta tattactaga ataaagtcag    34980
ctgcagacaa ccccttgcac agctggaaag caagtgtcca agcatcaaat cggtttccaa    35040
tcaatgaagt gcctgtggga ggaaatctca actctcttta gaagtaaaca acaaagtcga    35100
ttgcctcagc tatgcggtat ccgcagagtg agtcctaaat ttaaaatctg actacatgta    35160
gaaaagcgtt tcgtgtgacc catgaccagg aaataaatcg ggtaatacaa acaggctcag    35220
gaatgagaga aatgattaga attgcgtgaa aatttgacat atcagtatga taactgattt    35280
caaatattta aaaaacaac atgcaagaaa gcagatatca tatcaagaga aattaacagt    35340
acagaatagc caaattaaat taaagagcta gtataaaaaa agtatgtctt aattgaaaaa    35400
aattactgta tggccggctg atcaaattag acgtttcaga ggaaaacatt acccaacaca    35460
caattctaga gaacctacag aatgagctac acacacacac acacacacac acacacacac    35520
tgaaaacaca cccatactca cacacacgca gaaactcaca agttctaaca cacacagaca    35580
cgcgcacccc tgaagaaaca gtgaaatata aaattaagcg agcctcacag acatgtagga    35640
aaatatgaaa agatttcctg catgtgggaa gcaagtcaca gtaaagagca agggagtttg    35700
gaatagaaac aaataccgga atcaaggatg gctgataact tttcaattac gaagaacatt    35760
aaaaaaaatc acagaatcgt gaaactcaag ggatcatata gggaatttcg gaaaaaaaac    35820
ccaacctgta tgatgtactt tgtacatca cagttcgaag gtaacaaggc aaagatataa    35880
taagaagaaa cctgtcacga gaaactggag gaaaaagagc tgtgtcttcc tacaagtaca    35940
ctgatacaaa ttgccaatgt gttcacctca gaaacactgg aagccagata ccagggaata    36000
ttgttaaaat gataatcagg aacaaaaaga gatcaaccgg gaatgctgaa tccagcaata    36060
aaatgccttg aagatcatcc atgtcggata aatgcatatt gtgcactgcc ccaaagaaag    36120
aaaccggaaa ctgtcagaat tggaaatcag caggcttatg taacaagaga ggtgacccga    36180
aggaattagg tagaagaaga attgaacaag aaaggaactt tctgcagccc acgtaatgaa    36240
gaatccagca attggcaaat gtagatagat gtaaatgcaa aatattttct tgatcaaatt    36300
tctatatctt tgtaaatgag agttgactac ttgaaacaaa atgatagcaa gatatttaac    36360
ttcagcatat gtagaggtaa gaatttgaaa tggtagcata aatcacgaag ggattaattc    36420
gaagtgtacc gttgtaagtt tctttacctc atgcacgatg gtgtgtcata ttaataaaag    36480
ggtactgtgc gggttcgaag ggatattgca aatcctagag caatcacaaa ggtttgaact    36540
ctgaggtttt tggtataata agaatagtcc atgcattcaa aagagggaag ccaaggaaga    36600
actagaagtc tttcaagagc tcaggctctt atacatccag ttgctcattg aaccagcttc    36660
ctggaatgga gggtctgggg ttgagactag gccacaagtc tagagtctct agagagacag    36720
tgttggaacc ccatggccca taatacattt cccattttct caggcagcca gaggtcatga    36780
atgtgaggat actgggaggt tggagcaacg ttcttgggag gcataaggaa gagcgaatgc    36840
ttcaagatcc ccgcagccca aactactcgc ctgctttgcc ccctaatgca tttttctctg    36900
ctgctccgta gctgtccgac ctcttcagat ctcttagtcc accctgccgt cttcctttat    36960
```

```
gccatgggtc ccattgttct ttcaactcat cccccttttcc ctcagtcccg gagtagctgc   37020
ggccagcaga gggtagactg agagcaggag agaaggacct gcctaggaac cccttctaga   37080
gatactgcat cctgcctggg agcaagtttt ccagggcagc tttgagaagt cttggagaaa   37140
caaacctact aaacctgaca gacagtaata ctatttgcac aatgcttttc tgtgggaaag   37200
gtagagcctt ttcactacgt attgagtaca tagagtgtga gggttgacct ggaacggcta   37260
tcctcctgga tgacgtgcgt tttctgaaga actacatgtt cgttgcaact cccacattag   37320
aatatgaagt cctaccgaga gagatacgga gactagacag atacagatgc atttgcatgt   37380
gaatacacaa tcccacaata cagacgtcaa aacccatacc agttattcca gagagatgga   37440
ttgggcagaa ggcagaagga gaatactctg atcgttttc ggccacgtgt gtgtgttatc   37500
tcagtgtttc taagaagcgt ttgctacttt agattttta tttaaaaaaa atagtaataa   37560
tctattaagt atgagagatg tgcagagagg attagtgatc gagagccatt tttgctggtg   37620
gcaatcatat ggtacttta atgggaatat tagaaaggca ccggtaatga ccttgttgca   37680
gcacaaagga gagagtgtgg ggtgcccctg catgttgtcc cacctcttgt gacgtgtatc   37740
gttttggaat ttccagtggc ttgatcatga actactgcag gaatccagat gctgtggcag   37800
ctccttattg ttatacgagg gatcccggtg tcaggtggga gtactgcaac ctgacgcaat   37860
gctcagacgc agaagggact gccgtcgcgc ctccgactgt taccccggtt ccaagcctag   37920
aggctccttc cgaacaaggt aaggagtctg tggccagaca tctacacgct tcgatgctgg   37980
gatgaaaagc catggaaatt cccactgatg cagccgcctt caatggtaaa cggatgctcg   38040
agtgttgcct gagttctacc atgtaggagg aagcctccgt gcactctctg ggggagccag   38100
cggagtgatt tctggtgcaa cgtggttggg cttttgtcttt aggatgggca caaaccctcc   38160
agggggatcg acttcaaaat tcaccttgtt gtaaaacggg ctacctcagt gtcccagcca   38220
aaatttttat tgtaacatgc tgtcaggtgt gtcactcttt ccaagccagt aagcttttcc   38280
ggggatttct tcaagtagcc agcattcaga gcaatcttca gcattgcaga ttctgagaaa   38340
tgtggctctg gagcctgtca ccctcgagaa acctaagagg gctgcattga ttccatgtgg   38400
ccctgggtct atggagcagt acatgagctc ccagtgctct aaggctcttc agccctaggc   38460
tttgaaggga gtgatttctc agtattctta aacctctttc tgatgacact tgtacctgtg   38520
aggggtctag agagaaagag tagtagactc ctactttact acaattcagg atgcagggca   38580
tgagaggatt ccctctctcc tccaagggaa gaagcttttg gcgtgcacac atccctgaga   38640
agcaaagtgt ctttgtcttc agtcagatac ataggaccgt tttctgcccc atggcccgga   38700
agccaaaggc cttggctttc atgatcaacg gtctagggaa acatgcaaaa tttccatgtc   38760
tgtcccaaac tctgccccg acagccaatt accacctgca gcccgcattg ccaaatgcgg   38820
tgccgtttgc atgaagattc agtagagttt cctagaaagg tgctacctcg tgagctcact   38880
ttccaatgag gaatctgatc tgttgtgttt ctctaaggtg tcaggtgaaa tatttccaag   38940
aacttactac agttctagaa tgggaggaat ctgttgcttt ggtgtttgtt tgttggtcgg   39000 tttttctcaca tccatctgcc tatggataag gaaaagagaa cggtcgtaat tctcatagac   39060 tccttctctgg ttgtgtcaca aatggcttca catgttctc tatgctcaga gatactcagc   39120
ttgatttccc gtgttttcat ttcagcaccg actgagcaaa ggcctggggt gcaggagtgc   39180
taccatggta atggacagag ttatcgaggc acatactcca ccactgtcac aggaagaacc   39240
tgccaagctt ggtcatctat gacaccacac tcgcatagtc ggaccccaga atactaccca   39300
aatgcgtatg tctttgttct ttaccataag agaagaaagg gccaagtgaa gtttctgtta   39360
```

```
caagagatgt gtctcaagct gagttctccg aactcaactt gtgacagatg cagatggcgt    39420
agcaaaatgt ctcaggatga ttgccttgga gctaagggtc tgagagaagg gaaatgttaa    39480
gctccctctc cttcctccta gttctattga gcagaaggga atctggagg tgaggagatc     39540 acattatgaa gaaagtcaga atgacaaagg accagacact tagattaccc ttccacaaca    39600
ccaactaaac gtcaatggag actttccagt tggaattccg ttattctggc ttccacttcc    39660
tgaagggaag gttgcgtttg cctttctct ctggggttcaa gaggaaagaa taggtgctta    39720
tttatggaca ggtgaattga tctgtttcta tatctacgta tattccgatt gtcagaaaaa    39780
cactcgttcc taagtaccag tggcctgaag ggatacaggt tcccagcaag agaagatcca    39840
aggaaggaag gcagatgaga gtcagcacag agagggatgc tgaaaagtaa aagggatggg    39900
tggatggaga gaagcccggg tctgaccacc caatggccaa tattttggcc acaagcgact    39960
accagagaca tggaaaaatg gtttctacat gtgggacaac agatggtaga ggacctagag    40020
aattgagaga ggggcaatga tgggctccac tccgcagatg ccttggcttt cttcctggat    40080
acccttcctg cactgaatag caaggagatg gagcccaagc agactgtagc catcttgctg    40140
aatggaggag agggattgga gtttgggatg actgtggtag ctgaaatttt tctaggtctg    40200
ctagaaataa gaactggttt gtggaggaaa agagctctac aaatacgcat agaagtctcc    40260
tccagtcgtt ggcctgacat gacgctgcct gtgcacagga aatggttcca cgagaaagtg    40320
tggcaaagaa catttactga gaaacagcaa gtacaagagc acaggaagct caataaagaa    40380
gagagagatc acatagcact ctgggatact ggagttcttc ccagctagac cagagagtcc    40440
tcacggagca cattgccaat tcagtggaga ccccagaaca gccgtaattt aaaggtacac    40500
ttagtatatt actagaataa agtcagctgc agacaacccc ttgcacagct ggaaagcaag    40560
tgtccaagca tcaaatcggt ttccaatcaa tgaagtgcct gtgagaggaa atctcaactc    40620
tctttagaag taaacaacaa agtcgattgc ctcagctatg cggtatccgc agagtgagtc    40680
ctaaatttaa aatctgacta catgtagaaa agcgtttcgt gtgacccatg accaggaaat    40740
aaatcgggta atacaaacag gctcaggaat gagagaaatg attagaattg cgtgaaaatt    40800
tgaaatatca gtatgataac tgatttcaaa tatttaaaaa acaacatgc aagaaagcag     40860 atatcatatc aagagaaatt aacagtacag aatagccaaa ttaaattaaa gagctagtat    40920
aaaaaaagta tgtcttaatt gaaaaaaatt actgtatggc cggctgatca atttagacgt    40980
ttcagaggaa acattaccc aacacacaat tctagagaac ctacagaatg agctacacac      41040
acacacacac acacacacac aaactgaaaa cacacccata ctcacacaca cgcagaaact    41100
cacaagttct aacacacaca gacacgcgca cccctgaaga aacagtgaaa tataaaatta    41160
agcgagcctc acagacatgt aggaaaatat gaaaagattt cctgcatgtg ggaagcaagt    41220
cacagtaaag agcaagggag tttggaatag aaacaaatac cagaatcaag gatggctgat    41280
aacttttcaa ttcgaagaa cattaaaaaa atcacagaa tcgtgaaact caagggatca      41340
catagggaat ttcggaaaaa aaacccaacc tgtatgatgt actttgtac atcacagttc     41400 gaaggtaaca aggcaaagat ataataagaa gaaacctgtc acgagaaact ggaggaaaaa    41460
gagctgtgtc ttcctacaag tacactgata caaattgcca atgtgttcac ctcagaaaca    41520
ctggaagcca gataccaggg aatattgtta aaatgataat caggaacaaa aagagatcaa    41580 ccggaatgc tgaatccagc aataaaatgc cttgaagatc atccatgtcg gataaatgca     41640
tattgtgcac tgccccaaag aaagaaaccg gaaactgtaa gaattggaaa tcagcaggct    41700
```

```
tatgtaacaa gagaggtgac ccgaaggaat taggtagaag aagaattgaa caagaaagga   41760
actttctgca gcccacgtaa tgaagaatcc agcaattggc aaatgtagat agatgtaaat   41820
gcaaaatatt ttcttgatca aatttctata tctttgtaaa tgagagttga ctacttgaaa   41880
caaaatgata gcaagatatt taacttcagc atatgtagag gtaagaattt gaatggtag    41940 cataaatcac gaagggatta attcgaagtg taccgttgta agtttctta cctcatgcac    42000 gatggtgtgt catattaata aagggtact gtgcgggttc gaaggatat tgcaaatcct     42060 agagcaatca caaaggtttg aactctgagg ttttggtat aataagaata gtccatgcat    42120
tcaaaagagg gaagccaagg aagaactaga agtctttcaa gagctcaggc tcttatacat   42180
ccagttgctc attgaaccag cttcctggaa tggagggtct ggggttgaga ctaggccaca   42240
agtctagagt ctctagagag acagtgttgg aaccccatgg cccataatac atttcccatt   42300
ttctcaggca gccagaggtc atgaatgtga ggatactggg aggttggagc aacgttcttg   42360
ggaggcataa ggaagagcga atgcttcaag atccccgcag cccaaactac tcgcctgctt   42420 tgcccctaa tgcattttc tctgctgctc cgtagctgtc cgacctcttc agatctctta     42480
gtccaccctg ccgtcttcct ttatgccatg ggtcccactg ttctttcaac tcatcccct    42540 ttccctcagt cccggagtag ctgcggccag cagagggtag actgagagca ggagagaagg   42600
acctgcctag gaacccttc tagagatact gcatcctgcc tgggagcaag ttttccaggg    42660
cagctttgag aagtcttgga gaaacaaacc tactaaacct gacagacagt aatactattt   42720
gcacaatgct tttctgtggg aaaggtagag ccttttcact acgtattgag tacatagagt   42780
gtgagggttg acctggaacg gctatcctcc tggatgacgt gtgttttctg aagaactaca   42840
tgttcgttgc aactcccaca ttagaatatg aagtcctacc gagagagata cggagactag   42900
acagatacag atgcatttgc atgtgaatac acaatcccac aatacagacg tcaaaaccca   42960
taccagttat tccagagaga tggattgggc agaaggcaga aggagaatac tctgatcgtt   43020
tttcggccac gtgtgtgtgt tatctcagtg ttttctaagaa gcgtttgcta ctttagattt   43080
tttatttaaa aaaatagta ataatctatt aagtatgaga gatgtgcaga gaggattagt    43140
gatcgagagc cattttgct ggtggcaatc atatggtact tttaatggga atattagaaa    43200
ggcaccggta atgaccttgt tgcagcacaa aggagagagt gtggggtgcc cctgcatgtt   43260
gtcccacctc ttgtgacgtg tatcgttttg gaatttccag tggcttgatc atgaactact   43320
gcaggaatcc agatgctgtg gcagctcctt attgttatac gagggatccc ggtgtcaggt   43380
gggagtactg caacctgacg caatgctcag acgcagaagg gactgccgtc gcgcctccga   43440
ctgttacccc ggttccaagc ctagaggctc cttccgaaca aggtaaggag tctgtggcca   43500
gacatctaca cgcttcgatg ctgggatgaa aagccatgga aattcccact gatgcagccg   43560
ccttcaatgg taaacggatg ctcgagtgtt gcctgagttc taccatgtag gaggaagcct   43620
ccgtgcactc tctgggggag ccagcggagt gatttctggt gcaacgtggt tgggctttgt   43680
ctttaggatg ggcacaaacc ctccagggg atcgacttca aaattcacct tgttgtaaaa    43740
cgggctacct cagtgtccca gccaaaattt ttattgtaac atgctgtcag gtgtgtcact   43800 cttttccaagc cagtaagctt ttccggggat tccttcaagt agccagcatt cagagcaatc   43860
ttcagcattg cagattctga gaaatgtggc tctggagcct gtcaccctcg agaaacctaa   43920
gagggctgca ttgattccat gtggccctgg gtctatggag cagtacatga gctcccagtg   43980
ctctaaggct cttcagccct aggctttgaa gggagtgatt tctcagtatt cttaaacctc   44040
tttctgatga cacttgtacc tgtgaggggt ctagagagaa agagtagtag actcctactt   44100
```

```
tactacaatt caggatgcag ggcatgagag gattccctct ctcctccaag ggaagaagct   44160
tttggcgtgc acacatccct gagaagcaaa gtgtctttgt cttcagtcag atacatagga   44220
ccgttttctg ccccatggcc cggaagccaa aggccttggc tttcatgatc aacggtctag   44280
ggaaacatgc aaaatttcca tgtctgtccc aaactcttcc cccgacagcc aattaccacc   44340
tgcagcccgc attgccaaat gcggtgccgt ttgcatgaag attcagtaga gtttcctaga   44400
aaggtgctac ctcgtgagct cactttccaa tgaggaatct gatctgttgt gtttctctaa   44460
ggtgtcaggt gaaatatttc caagaactta ctacagttct agaatgggag gaatctgttg   44520
ctttggtgtt tgtttgttgg tcggttttct cacatccatc tgcctatgga taaggaaaag   44580
agaacggtcg taattctcat agactccttt ctggttgtgt cacaaatggc ttcacatgtt   44640
tctctatgct cagagatact cagcttgatt cccgtgttt tcatttcagc accgactgag    44700
caaaggcctg gggtgcagga gtgctaccat ggtaatggac agagttatcg aggcacatac   44760
tccaccactg tcacaggaag aacctgccaa gcttggtcat ctatgacacc acactcgcat   44820
agtcggaccc cagaatacta cccaaatgcg tatgtctttg ttctttacca taagagaaga   44880
aagggccaag tgaagtttct gttacaagag atgtgtctca agctgagttc tccgaactca   44940
acttgtgaca gatgcagatg gcgtagcaaa atgtctcagg atgattgcct tggagctaag   45000
ggtctgagag aagggaaatg ttaagctccc tctccttcct cctagttcta ttgagcagaa   45060
gggaaatctg gaggtgagaa gatcacatta tgaagaaagt cagaatgaca aaggaccaga   45120
cacttagatt acccttccac aacaccaact aaacgtcaat ggagactttc cagttggaat   45180
tccgttattc tggcttccac ttcctgaagg gaaggttgcg tttgccttt ctctctgggt     45240 tcaagaggaa agaataggtg cttatttatg gacaggtgaa ttgatctgtt tctatatcta   45300
cgtatattcc gattgtcaga aaaacactcg ttcctaagta ccagtggcct gaagggatac   45360
aggttcccag caagaagaa tccaaggaag gaaggcagat gagagtcagc acagagaggg    45420
atgctgaaaa gtaaagggga tgggtggatg gagagaagcc cgggtctgac cacccaatgg   45480
ccaatatttt ggccacaagc gactaccaga gacatgaaaa aatggtttct acatgtggga   45540
caacagatgg tagaggacct agagaattga gagagggca atgatgggct ccactccgca    45600
gatgccttgg cttcttcct ggatacccctt cctgcactga atagcaagga gatggagccc    45660
aagcagactg tagccatctt gctgaatgga ggagagggat tggagtttgg gatgactgtg   45720
gtagctgaaa ttttctagg tctgctagaa ataagaactg gtttgtgtgg aggaaaagag    45780
ctctacaaat acgcatagaa gtctcctcca gtcgttggcc tgacatgacg ctgcctgtgc   45840
acaggaaatg gttccacgag aaagtgtggc aaagaacatt tactgagaaa cagcaagtac   45900
aagagcacac gaagctcaat aaagaagaga gagatcacat agcactctgg gatactggag   45960
ttcttcccag ctagaccaga gagtcctcac ggagcacatt gccaattcag tggagacccc   46020
agaacagccg taatttaaag gtacacttag tatattacta gaataaagtc agctgcagac   46080
aaccccttgc acagctggaa agcaagtgtc caagcatcaa atcggtttcc aatcaatgaa   46140
gtgcctgtga gaggaaatct caactctctt tagaagtaaa caacaaagtc gattgcctca   46200
gctatgcggt atccgcagag tgagtcctaa atttaaaatc tgactacatg tagaaaagcg   46260
tttcgtgtga cccatgacca ggaaataaat cgggtaatac aaacaggctc aggaatgaga   46320
gaaatgatta gaattgcgtg aaaatttgac atatcagtat gataactgat ttcaaatatt   46380
taaaaaaaca acatgcaaga aagcagatat catatcaaga gaaattaaca gtacagaata   46440
```

| | |
|---|---|
| gccaaattaa attaaagagg tagtataaaa aaagtatgtc ttaattgaaa aaaattactg | 46500 |
| tatggccggc tgatcaattt agacgtttca gaggaaaaca ttacccaaca cacaattcta | 46560 |
| gagaacctac agaatgagct acacacacac acacacacac acacacaaac tgaaaacaca | 46620 |
| cccatactca cacacacgca gaaactcaca agttctaaca cacacagaca cgcgcacccc | 46680 |
| tgaagaaaca gtgaaatata aaattaagcg agcctcacag acatgtagga aaatatgaaa | 46740 |
| agatttcctg catgtgggaa gcaagtcaca gtaaagagca agggagtttg aatagaaac | 46800 |
| aaataccgga atcaaggatg gctgataact tttcaattac gaagaacatt aaaaaaaatc | 46860 |
| acagaatcgt gaaactcaag ggatcacata gggaatttcg gaaaaaaaac ccaacctgta | 46920 |
| tgatgtactt ttgtacatca cagttcgaag gtaacaaggc aaagatataa taagaagaaa | 46980 |
| cctgtcacga gaaactggag gaaaagagc tgtgtcttcc tacaagtaca ctgatacaaa | 47040 |
| ttgccaatgt gttcacctca gaaacactgg aagccagata ccagggaata ttgttaaaat | 47100 |
| gataatcagg aacaaaaaga gatcaaccgg gaatgctgaa tccagcaata aaatgccttg | 47160 |
| aaggtcatcc atgtcggata aatgcatatt gtgcactgcc ccaaagaaag aaaccggaaa | 47220 |
| ctgtaagaat tggaaatcag caggcttatg taacaagaga ggtgacccga aggaattagg | 47280 |
| tagaagaaga attgaacaag aaaggaactt tctgcagccc acgtaatgaa gaatccagca | 47340 |
| attggcaaat gtagatagat gtaaatgcaa atatttctct tgatcaaatt tctatatctt | 47400 |
| tgtaaatgag agttgactac ttgaaacaaa atgatagcaa gatatttaac ttcagcatat | 47460 |
| gtagaggtaa gaatttgaaa tggtagcata aatcacgaag ggattaattc gaagtgtacc | 47520 |
| gttgtaagtt tctttacctc atgcacgatg gtgtgtcata ttaataaaag ggtactgtgc | 47580 |
| gggttcgaag ggatattgca aatcctagag caatcacaaa ggtttgaact ctgaggtttt | 47640 |
| tggtataata agaatagtcc atgcattcaa aagagggaag ccaaggaaga actagaagtc | 47700 |
| tttcaagagc tcaggctctt atacatccag ttgctcattg aaccagcttc ctggaatgga | 47760 |
| gggtctgggg ttgagactag gccacaagtc tagagtctct agagagacag tgttggaacc | 47820 |
| ccatggccca taatacattt cccattttct caggcagcca gaggtcatga atgtgaggat | 47880 |
| actgggaggt tggagcaacg ttcttgggag gcataaggaa gagcgaatgc ttcaagatcc | 47940 |
| ccgcagccca aactactcgc ctgctttgcc ccctaatgca ttttttctctg ctgctccgta | 48000 |
| gctgtccgac ctcttcagat ctcttagtcc accctgccgt cttcctttat gccatgggtc | 48060 |
| ccactgttct ttcaactcat cccccttttcc ctcagtcccg gagtagctgc ggccagcaga | 48120 |
| gggtagactg agagcaggag agaaggacct gcctaggaac cccttctaga gatactgcat | 48180 |
| cctgcctggg agcaagtttt ccagggcagc tttgagaagt cttggagaaa caaacctact | 48240 |
| aaacctgaca gacagtaata ctatttgcac aatgctttc tgtgggaaag gtagagcctt | 48300 |
| ttcactacgt attgagtaca tagagtgtga gggttgacct ggaacggcta tcctcctgga | 48360 |
| tgacgtgcgt tttctgaaga actacatgtt cgttgcaact cccacattag aatatgaagt | 48420 |
| cctaccgaga gagatacgga gactagacag atacagatgc atttgcatgt gaatacacaa | 48480 |
| tcccacaata cagacgtcaa aacccatacc agttattcca gagagatgga ttgggcagaa | 48540 |
| ggcagaagga gaatactctg atcgtttttc ggccacgtgt gtgtgttatc tcagtgtttc | 48600 |
| taagaagcgt ttgctacttt agattttta tttaaaaaaa atagtaataa tctattaagt | 48660 |
| atgagagatg tgcagagagg attagtgatc gagagccatt tttgctggtg gcaatcatat | 48720 |
| ggtacttttta atgggaatat tagaaaggca ccggtaatga ccttgttgca gcacaaagga | 48780 |
| gagagtgtgg ggtgccccctg catgttgtcc cacctcttgt gacgtgtatc gttttggaat | 48840 |

```
ttccagtggc ttgatcatga actactgcag gaatccagat gctgtggcag ctccttattg   48900
ttatacgagg gatcccggtg tcaggtggga gtactgcaac ctgacgcaat gctcagacgc   48960
agaagggact gccgtcgcgc ctccgactgt taccccggtt ccaagcctag aggctccttc   49020
cgaacaaggt aaggagtctg tggccagaca tctacacgct tcgatgctgg gatgaaaagc   49080
catggaaatt cccactgatg cagccgcctt caatggtaaa cggatgctcg agtgttgcct   49140
gagttctacc atgtaggagg aagcctccgt gcactctctg ggggagccag cggagtgatt   49200
tctggtgcaa cgtggttggg ctttgtcttt aggatgggca caaaccctcc aggggatcg    49260 acttcaaaat tcaccttgtt gtaaaacggg ctacctcagt gtcccagcca aaattttat    49320 tgtaacatgc tgtcaggtgt gtcactcttt ccaagccagt aagcttttcc ggggatttct   49380
tcaagtagcc agcattcaga gcaatcttca gcattgcaga ttctgagaaa tgtggctctg   49440
gagcctgtca ccctcgagaa acctaagagg gctgcattga ttccatgtgg ccctgggtct   49500
atggagcagt acatgagctc ccagtgctct aaggctcttc agccctaggc tttgaaggga   49560
gtgatttctc agtattctta aacctctttc tgatgacact tgtacctgtg aggggtctag   49620
agagaaagag tagtagactc ctactttact acaattcagg atgcagggca tgagaggatt   49680
ccctctctcc tccaagggaa gaagcttttg gcgtgcacac atccctgaga agcaaagtgt   49740 cttttgtcttc agtcagatac ataggaccgt tttctgcccc atggcccgga agccaaaggc   49800
cttggctttc atgatcaacg gtctagggaa acatgcaaaa tttccatgtc tgtcccaaac   49860
tctgcccccg acagccaatt accacctgca gcccgcattg ccaaatgcgg tgccgtttgc   49920
atgaagattc agtagagttt cctagaaagg tgctacctcg tgagctcact ttccaatgag   49980
gaatctgatc tgttgtgttt ctctaaggtg tcaggtgaaa tatttccaag aacttactac   50040
agttctagaa tgggaggaat ctgttgcttt ggtgtttgtt tgttggtcgg ttttctcaca   50100
tccatctgcc tatggataag gaaaagagaa cggtcgtaat tctcatagac tccttctgg    50160 ttgtgtcaca aatggcttca catgtttctc tatgctcaga gatactcagc ttgatttccc   50220
gtgttttcat ttcagcaccg actgagcaaa ggcctggggt gcaggagtgc taccatggta   50280
atggacagag ttatcgaggc acatactcca ccactgtcac aggaagaacc tgccaagctt   50340
ggtcatctat gacaccacac tcgcatagtc ggaccccaga atactaccca aatgcgtatg   50400 tcttttgttct ttaccataag agaagaaagg gccaagtgaa gttctgttta caagagatgt   50460
gtctcaagct gagttctccg aactcaactt gtgacagatg cagatggcgt agcaaaatgt   50520
ctcaggatga ttgccttgga gctaagggtc tgagagaagg gaaatgttaa gctccctctc   50580
cttcctccta gttctattga gcagaaggga aatctggagg tgaggagatc acattatgaa   50640
gaaagtcaga atgacaaagg accagacact tagattaccc ttccacaaca ccaactaaac   50700
gtcaatggag actttccagt tggaattccg ttattctggc ttccacttcc tgaagggaag   50760
gttgcgtttg ccttttctct ctgggttcaa gaggaaagaa taggtgctta tttatggaca   50820
ggtgaattga tctgtttcta tatctacgta tattccgatt gtcagaaaaa cactcgttcc   50880
taagtaccag tggcctgaag ggatacaggt tcccagcaag agaagatcca aggaaggaag   50940
gcagatgaga gtcagcacag agagggatgc tgaaaagtaa aagggatggg tggatggaga   51000
gaagcccggg tctgaccacc caatggccaa tatttggcc acaagcgact accagagaca    51060
tggaaaaatg gttctacat gtgggacaac agatggtaga ggacctagag aattgagaga    51120
ggggcaatga tgggctccac tccgcagatg ccttggcttt cttcctggat acccttcctg   51180
```

-continued

```
cactgaatag caaggagatg gagcccaagc agactgtagc catcttgctg aatggaggag    51240
agggattgga gtttgggatg actgtggtag ctgaaatttt tctaggtctg ctagaaataa    51300
gaactggttt gtgtggagga aaagagctct acaaatacgc atagaagtct cctccagtcg    51360
ttggcctgac atgacgctgc ctgtgcacag gaaatggttc cacgagaaag tgtggcaaag    51420
aacatttact gagaaacagc aagtacaaga gcacaggaag ctcaataaag aagagagaga    51480
tcacatagca ctctgggata ctggagttct tcccagctag accagagagt cctcacggag    51540
cacattgcca attcagtgga gaccccagaa cagccgtaat ttaaaggtac acttagaata    51600
ttactagaat aaagtcagct gcagacaacc ccttgcacag ctggaaagca agtgtccaag    51660
catcaaatcg gtttccaatc aatgaagtgc ctgtgagagg aaatctcaac tctctttaga    51720
agtaaacaac aaagtcgatt gcctcagcta tgcggtatcc gcagagtgag tcctaaattt    51780
aaaatctgac tacatgtaga aaagcgtttc gtgtgaccca tgaccaggaa ataaatcggg    51840
taatacaaac aggctcagga atgagagaaa tgattagaat tgcgtgaaaa tttgacatat    51900
cagtatgata actgatttca aatatttaaa aaaacaacat gcaagaaagc agatatcata    51960
tcaagagaaa ttaacagtac agaatagcca aattaaatta aagagctagt ataaaaaaag    52020
tatgtcttaa ttgaaaaaaa ttactgtatg gccggctgat caaattagac gtttcagagg    52080
aaaacattac ccaacacaca attttagaga acctacagaa tgagctacac acacacacac    52140
acacacacac acacacacaa actgaaaaca cacccatact cacacacacg cagaaactca    52200
caagttctaa cacacacaga cacgcgcacc cctgaagaaa cagtgaaata taaaattaag    52260
cgagcctcac agacatgtag gaaaatatga aaagatttcc tgcatgtggg aagcaagtca    52320
cagtaaagag caagggagtt tataatagaa acaaatacca gaatcaagga tggctgataa    52380
cttttcaatt acgaagaaca ttaaaaaaaa tcacagaatc gtgaaactca agggatcata    52440
tagggaattt cggaaaaaaa acccaacctg tatgatgtac ttttgtacat cacagttcga    52500
aggtaacaag gcaaagatgt aataagaaga aacctgtcac gagaaactgg aggaaaaaga    52560
gctgtgtctt cctacaagta cactgataca aattgccaat gtgttcacct cagaaacact    52620
ggaagccaga taccagggaa tattgttaaa atgataatca ggaacaaaaa gagatcaacc    52680
gggaatgctg aatccagcaa taaaatgcct tgaaggtcat ccatgtcgga taaatgcata    52740
ttgtgcactg ccccaaagaa agaaaccgga aactgtaaga attggaaatc agcaggctta    52800
tgtaacaaga gaggtgaccc gaaggaatta ggtagaagaa gaattgaaca agaaaggaac    52860
tttctgcagc ccacgtaatg aagaatccag caattggcaa atgtagatag atgtaaatgc    52920
aaaatatttt cttgatcaaa tttctatatc tttgtaaatg agagttgact acttgaaaca    52980
aaatgatagc aagatattta acttcagcat atgtagaggt aagaatttga aatggtagca    53040
taaatcacga agggattaat tcgaagtgta ccgttgtaag tttctttacc tcatgcacga    53100
tggtgtgtca tattaataaa agggtactgt gcgggttcga agggatattg caaatcctag    53160
agcaatcaca aaggtttgaa ctctgaggtt tttggtataa taagaatagt ccatgcattc    53220
aaaagaggga agccaaggaa gaactagaag tctttcaaga gctcaggctc ttatacatcc    53280
agttgctcat tgaaccagct tcctggaatg gagggtctgg ggttgagact aggccacaag    53340
tctagagtct ctagagagac agtgttggaa ccccatggcc cataatacat ttcccatttt    53400
ctcaggcagc cagaggtcat gaatgtgagg atactgggag gttggagcaa cgttcttggg    53460
aggcataagg aagagcgaat gcttcaagat ccccgcagcc caaactactc gcctgctttg    53520 cccctaatg cattttctc tgctgctccg tagctgtccg acctcttcag atctcttagt    53580
```

```
ccaccctgcc gtcttccttt atgccatggg tcccactgtt ctttcaactc atccccettt   53640
ccctcagtcc cggagtagct gcggccagca gagggtagac tgagagcagg agagaaggac   53700
ctgcctagga acccettcta gagatactgc atcctgcctg ggagcaagtt ttccagggca   53760
gctttgagaa gtcttggaga aacaaaccta ctaaacctga cagacagtaa tactatttgc   53820
acaatgcttt tctgtgggaa aggtagagcc ttttcactac gtattgagta catagagtgt   53880
gagggttgac ctggaacggc tatcctcctg gatgacgtgc gttttctgaa gaactacatg   53940
ttcgttgcaa ctcccacatt agaatatgaa gtcctaccga gagagatacg gagactagac   54000
agatacagat gcatttgcat gtgaatacac aatcccacaa tacagacgtc aaaacccata   54060
ccagttattc cagagagatg gattgggcag aaggcagaag gagaatactc tgatcgtttt   54120
tcggccacgt gtgtgtgtta tctcagtgtt tctaagaagc gtttgctact ttagattttt   54180
tatttaaaaa aaatagtaat aatctattaa gtatgagaga tgtgcagaga cgattagtga   54240
tcgagagcca ttttttgctgg tggcaatcat atggtacttt taatgggaat attagaaagg   54300
caccggtaat gaccttgttg cagcacaaag gagagagtgt ggggtgcccc tgcatgttgt   54360
cccacctctt gtgacgtgta tcgttttgga atttccagtg gcttgatcat gaactactgc   54420
aggaatccag atgctgtggc agctccttat tgttatacga gggatcccgg tgtcaggtgg   54480
gagtactgca acctgacgca atgctcagac gcagaaggga ctgccgtcgc gcctccgact   54540
gttaccccgg ttccaagcct agaggctcct tccgaacaag gtaaggagtc tgtggccaga   54600
catctacacg cttcgatgct gggatgaaaa gccatgaaaa ttcccactga tgcagccgcc   54660
ttcaatggta aacggatgct cgagtgttgc ctgagttcta ccatgtagga ggaagcctcc   54720
gtgcactctc tgggggagcc agcggagtga tttctggtgc aacgtggttg ggctttgtct   54780
ttaggatggg cacaaaccct ccaggggat cgacttcaaa attcaccttg ttgtaaaacg   54840
ggctacctca gtgtcccagc caaaattttt attgtaacat gctgtcaggt gtgtcactct   54900
ttccaagcca gtaagctttt ccggggattt cttcaagtag ccagcattca gagcaatctt   54960
cagcattgca gattctgaga aatgtggctc tggagcctgt catcctcgag aaacctaaca   55020
gggctgcatt aattccatat ggtcctgggt ctatggagca gtatatgagc tcccaatgct   55080
ctaaggctct tcagtcctag gctttgaagg gagtgatttc tcagtgttct taaacctctt   55140
tctgatggca cttgtacctg tgaggggtct agagagaaag gttagtagac ttctccttta   55200
ctgcaattca ggatgcaggg catgagaaga ttccctccct cctccaaggg aagaaggttt   55260
tggcgtgcac acatccttga gaagcaaagt gtctttgcct tcagtcagat atataggatc   55320
gttttctgcc ccatggcctg gaagccagag gccttggctt tcatgatcaa cgatctaggg   55380
aaacatgcaa aatttccatg tctttcccct cctctgccct cgacagccaa ttaccacctg   55440
catcctgcat tgccaaatgc agtgcccttt gtatgaacat tcagtagagt ttcatagaaa   55500
ggtgctactt cgtgagcgca ctttgcagtg agaaggagtc tgttctgttc tgttttttcta  55560
aggatttcag gtgaaatatt tcctagaact tactacagtt ctagattggt aggaatctgt   55620
aggtttgctg tatgtttttt ggttggtttt ctcccatcca tctgcctaca ggtaagggaa   55680
agataacgtt cataattctc atagactcct ttctggttgt gtcataaatg gcttcacata   55740
tttcgttatt ctcagagata ctcagtttat ttcttgtgtt ttcatttcag caccgactga   55800
gcagaggcct ggggtgcagg agtgctacca cggtaatgga cagagttatc gaggcacata   55860
ctccaccact gtcactggaa gaacctgcca agcttggtca tctatgacac cacactcgca   55920
```

```
tagtcggacc ccagaatact acccaaatgc gtatgtcttt gttctttacc ataagagaat    55980
aaagggccaa ctgaagtttc tgtgacaaga gacatgcttc aagctgagtt ctccgaactc    56040
aacttgtgtc agattcagat ggtgtagcaa aatgtctcag gatgatttcc ttggagctaa    56100
gggtctgaga aagagaaat gttaagctgc ctcaccttcc tcctagtttt gtggagcaga     56160
agggaaatga ggaggcgagg agatcacctt atgaagaaag tcagaatgac gaaccaccaa    56220
acacttagat taccccttgcc caacacccac taagcgtcaa tgaagacttt ccagttggaa   56280
ttccgttatt ctgacttcca attcctgaag ggaagattgt gtttgccttt tctgtctggg    56340
ctcatgagga aagtttatgt gcttacttat ggacaggtga attgatctgt ttctatttct    56400
acctgtattc caatagggag aaaatctctt ggtcctaagt accagtggcc tgaaaggata    56460
gaggttccca gcaagagaag atccaaggaa ggaaggcaga tgagagtcag cacagagagg    56520
gatgctgaaa agtaaaaggg atgggtagat ggatagaagc cctggtctga ccaccccatg    56580
gccaatcatt tggccataat caacaaccaa agacatggaa aaatggtttc tacatgtggg    56640
acaacagatg gtagaggacc tagagaattg agagagggcc aatgatgagc tcaactccat    56700
agatgccttg gctttcttcc tggatacccct tcctgcactg aatagcaagg agatggagct    56760
caagcagcct gtagccatct agctgagcag aggagaggga ttggagtttg ggatgactct    56820 ggtatttct aggtccgcta caaataagaa ctggtttgtg gaggaaagga gctctacaaa    56880
tacgcataga agtctcctcc agtagttggc ctcacatgac actgcatgtg cacagaaaat    56940
ggttctacag aaagtgtggc aaagaacatt tactgagaaa cagcaactac aagagaacag    57000
caagctcaat taagaagata gagatcacat agcactctgt gttattggag ttcttaccag    57060
ctagatgaga gagtgctcac ggaacacatt gccaattcag tggagacccc agaacagcca    57120
taatttcaaa gtacaattag tatattacta gaataaaggc agctgcagac aaccccttgc    57180
acagctgaaa agcaagtgtc caagcatcaa atgggtttcc aatcaatgaa gtgcctgtga    57240
gaggaaatct caactctctt cagaagtaaa caacaaagtc aattgcctca gctatgcggt    57300
atccccagag tgagtcctaa attaaaaatt tgactacgtg tagaaaagaa tttcgtgtga    57360
tccatgacca gaaaataaat caggcaatac aaacaggctc agaaatgaca tcgataatta    57420
gaattgcatg aaaatttgac atatcagtat gataactgat ttcagatatt taaaaaagt    57480 gcaacaaagc aggtatcata tcaagacaaa ttaatagtat agaatagcca atcaaatta    57540 aagaactatt atacaaaaag tatgtcttaa atgaagaaat tactgtatgt ccgcctgaaa    57600 aattagatg tttcagaaga aaaaattaac caaaaacaat tctgcagaac ctacagaatg    57660
agccacacac acacacattc aaaacacacc catacacaca cacatgcaaa aactcacaag    57720
ttctaacaca cacacaaaca cacacacaca tgcacatccc taaagaaata gggaaatata    57780
aaattaaccg accctcagag acatgcagga aaatataaga gatttcctg catgtgggaa    57840 gcaagtcaca gtaaagagca agggagtttg gagtagatac aaataccgga atcacgatg    57900 gctgataact tttcaattat gaagaacgtt agaaaaatca cagattcatg aaactaaagg    57960
gatcaaatag gaaatttcga gaaaaaaac tacatgatgc acttctctac atcacagttc    58020
aaaggtaaca aggcaaggat ataagaagaa gaaacatctc acgagaaact ggagaaaaaa    58080
gagctgtgtc ttcctagagt acagtgatac aaattgctaa tgcgttcacc tcagaaacac    58140
tggaagccag ataccaggga atattattaa aatgataatg aggaacaaga agagatcaac    58200
cgagaatgct gaatccagca ataaaatgcc ttgaagatca tccatgttgg ataaatgcat    58260
attgtgcact gcccaaaaca aagaaactgg aaagtgtaag actttggaat cagcaggctt    58320
```

```
atgtagcaac agaggtgacc cgaaagaatt aggtataaga agaatagaag aattgcatga   58380
aaatttgaca tatgactaag ataactattt caaatattta aaaaagatg aatatgtaat   58440 aaaacagata aaatatcaaa agaaagtaac agtattgact agccaaatca aattaaagac   58500
ttagtgtaaa aagctatgtc ttaaaagaaa aaattactgg atggctgcct gatcaattta   58560
gacatttctg aataggaaac taaccaaaaa tcaattctac agaaccaact acacacatat   58620
atacacatac aacacaccca tacacaccca cgcaaaaact cacaagttca cacacacaca   58680
cacacacaca caaccctcaa gaaatagtga aatagaaaac caaccgaacc tcacagacat   58740
gttgcaaaat aggaaaagat ttcctgcata tgggaagcaa gtcacagaaa agagaacggg   58800
agattggaaa cagaaacaaa taccggaatc aaggatggcc gaaaactttt cattgatcaa   58860
gaatattaac aaaatcgcaa aaacacgaaa ttcaatgcat caaataggcg tttcgaaaaa   58920
aagaaaaaat ctggtatgat gcacttttgt acttcacatt ttcacggtaa aagacaaag   58980 atataataac aagaaacttc ttatgagaaa ctggggaaaa acaagctgtt tcttgctaga   59040
agaacagtga tacaaattgc taatgcattc tcgtcaaaaa cactggaagc cagataccgg   59100
gaatgttatt aatgtggtaa acaggaacaa gaagagatca accaagaatg ctaaatccag   59160
caataaaatg ccttgaagat catccatgct gcataaatgt atgttgtgca ctgccccaaa   59220
caaagaaacc ggaaactgta agaatttgga atcagcaggc tgatgtaaca agagaggtga   59280
cccaaaggaa ttaggtagaa gaagaatagt acaagaaggg aactttctgc agcccatgta   59340
atgaagaacc cagcaattgg caaatgtaga tgtaaatgca aaatattttc ttgaccaaat   59400
ttctatatat ttttaaatga gcgttgacta ctggaaacaa aatgatagca atatatttaa   59460
ttttagcata tgtagaggta agaatttgaa caagtagcgt aaatcatgta gggaataatt   59520
agaagtgtac cattgtaagt ttcttacctc atgcacaatg gtatgtaata ttaataaaat   59580
gttactgtgt gggttcaagg agatattgca aatcctagag caatcacaaa gttttgaact   59640
ctgaggtata ttgtataata agaatattcc atgtattcaa aagagagaag ccaaggaaga   59700
aagaaatttg tcacgagttt gggctcttag tacatcctgt agctcattga accagcttcc   59760
tggaatggag ggtctgggat tgacactagg ccacatgtat agagtctcta gagagacagt   59820
gtttcatccc catggcccgt aatacatttc ccattttctc aggcagccac aggtcatgaa   59880
tgtgaggata gagagaggtt ggagcaacgt tcttgggagg cataaggaag agcaaatgct   59940
tcaagatccc cgcagcccaa actcctacct gctttgcccc taatgcagt gttcctccgt   60000 agctgtccga cctcttcaga tctcttagtc taccctgcca tcttccttta tgccatgggt   60060
cccactgttc tttcaactca tcccccttte cctcagtgca gagtagctgc ggccagcaga   60120
gggtagactg agagcaggag agaaggtcct gcccaggaac ccattctaga gatgctgcat   60180
tctgcctggg agcaagttt ccagggcagc tttgagaagt cttgcagaaa caaacctatt   60240
tgacccacat gatatgggaa tgacagaaag taatacaatt tgcacagtgc ttttccatgg   60300
gaaaagtaga gccttttcgc gaggttttga gtacatagag agtgaaggtt gacctggaaa   60360
ggttatcctc ctggatccca tgttttttct gaagaactac ctgttagttg caacttgcac   60420
attagaatat gaagtcctac cgagagagat acgagaact agataaatac agatacttt    60480 gtatgtgaat aaacgattcc acaatacaca catcaaaatc cataccagtt attccagaga   60540
gatggattgg gcagaaggca gaaggagaat actctgatcg ttttttgccc acgtgtatgt   60600
attatctcag tgtttctaag aagcgtttgc tactttagat ttttttttat aataataatc   60660
```

```
ttttaagtat gagaaatgtg cagacaggat tagtgattga gagccatttg tgcttgtggc    60720
aatcatatgg tacttttatg ggaatattag aaaggcactg gtaatgacct tgttgcagca    60780
caaaggagag ggtgtggggt gcccctgcat attgtcccac ctcttgtgac gtgtatcgtt    60840
ttggaatttc cagtggcttg atcatgaact actgcaggaa tccagatcct gtggcagccc    60900
cttattgtta tacgagggat cccagtgtca ggtgggagta ctgcaacctg acacaatgct    60960
cagacgcaga agggactgcc gtcgcgcctc caactattac cccgattcca agcctagagg    61020
ctccttctga acaaggtaag gagcctgtgg ccagaaacct acacgtttcg atgctgggat    61080
gaaaagccat ggaaattccc actgatgcag cagcctccaa tggtaaacgg atgctcgagt    61140
gttgactgag ttctgtcatg taggaggaag cctccgtgca ctctctgggg gagccagcgg    61200
attgatttct ggtacaacgt tgggtgggct gtgtctttag aattggcaca aaccctccag    61260
ggtgatcgac ttcacaactc acctcgttga aaaatgggct atctcagtgt cttagccaaa    61320 attttttattg taacatgctg tcagatgtgt gactctttcc aagccagtaa gcttttcctg    61380
ggacttcttc aattagccag cattcagtgc aatcttcagc attgcagatt cagagaaatg    61440
tggctctgga gcctgtcacc cttgagaaac agggctaaca gggttgcatt aattccaaat    61500
caccctggtt ctatggagca gtacatgaac tcccaatgat ctatgtttca ggacttcctc    61560
agtcataggt gggctctgca gccctaggtt tttaagtgag tgactgcccc gtgttctggt    61620
ggcagttgta cctgtgagcg gtctggatag aaagagtcgg agacttctgt attattgcaa    61680
ctcaggatgt gggtcatgag aggatttcat ctctcctgca ggggagtaag ctgttcgcct    61740
ccacccatcc ctgataactg aagtgtcttt gtctgcagtc ctagacgaag gactgttgtc    61800
tctcccatgg cccagaagct gaagaccttg ccttttgtta tgaaacgttc attgttttca    61860
tgtctgtccg tttctctgcc cctaacaccc aatcaccatg tatggcctgt acccccaaat    61920
gcatcgtgct ttgctgtttg ctgccccata gtcctcatga acattcagta gaaattccca    61980
taaatgtgct tgcacgtgag cacagtttcc attgagaagc cctctcattt gtccttttt    62040 tctaagcttt tatgtgaaat atttctaaga acttactaca gttctaaagt gttaggaatt    62100
tgtttctttg gtgttttgt ttgttggttg gttgttgctt ttctcaagtc catctgccta    62160
caaataaaga aacaagaatg ttacttgtca tattctcctg aggtcataat tctcagagac    62220 tttttctgg tttgtgccat aagtggcttc acatgtttgt ctcttcttgg aaacactcag    62280
tttgatttct tttcttttca tttcagcacc aactgagcaa aggcctgggg tgcaggagtg    62340
ctaccacgga aatggacaga gttatcaagg cacatacttc attactgtca caggaagaac    62400
ctgccaagct tggtcatcta tgacaccaca ctcgcatagt cggaccccag catactaccc    62460
aaatgcgtat gtctattttc tttaccataa gtgaaggaag ggtcagtgga aatttctgtt    62520
agtagagtca tgcttcaagc tgagtgttca ggactcaagt tgtctcagat gaacagtgca    62580
tagcaaaatg tctcaggaac attgtctttg agcaaagagt ctaagagaag acaaatgtta    62640
atctggctct ccttcctcct agtttaatgg agcagaaagg tatctggagg caaggatatc    62700
acattaagaa acaagtcaag atgacaaatg atgaaactct tagagtaccc ttccacaaca    62760
cccactaagg ttcaatgcag ccttttctcc ttggaattct attaaactaa actccaattc    62820
ctgaagtgaa ggttctgttg gggttttctg ttttggctta caaggaaagt atatatgtat    62880
atctatggag aggcaaatct atctcttttct atatctacgt ctattccaat atgtagaaac    62940
acagtcggtt ctgaccacca gtggtctgaa gggatactgg ttgttagaga ataaaaatgg    63000
caggaaggca gatgagagtc agcaaagaga gagatcctgt aaagtaaaag ggtggataga    63060
```

```
tggacagaag cccaggtctg accagcccat ggccaggctt taggccataa gtgacaccaa   63120
agacatggaa aaatggtttc tacatgttgg acaacagaca gtagtggacc aaaagaatag   63180
tgacaggggg aacaatgaga tcaactccat agataccttg gctttcttcc tggaggccct   63240
tcttgcactg aagagcaagg tgatggagcc cagatggact gtagccatct tcctgaatgc   63300
aggagagaga ttggaatttg ggactactgt ggtagctagg attttatagg cctgctgaga   63360
atgagaatgg atttgtggat gaaaggagct ccaggggcac gcatagtagt ctcctcgaat   63420
ctttggctaa acatgacgtt gcatgtgccc agaaaaaggt tccacaagaa agtagagaaa   63480
agaatatatc ctgaggaata gcaactgcga ttgaacagtg agctcaataa agaggacaga   63540
gccctcatag cattctggga tactggagtt ctgaccagct ggaggagaga cctcactgaa   63600
cctcttggga atacagtaga gactccagaa aagtcatact ttaggagtag aattagtaaa   63660
tttctagaaa aaaaggcagc tctagacaaa ccctggcaaa actgaaaagc aagtctccaa   63720
gcattaaaat catttccaag tcaattaact gcctgggaga ggaaaaccct ctttagaggt   63780
aaacaacaaa gtcaagtggc tcagctatgt ggtgttcaca gtgtgagttc taaatttaaa   63840
acttgactac acatagagaa gcttttagta tgaaccatga ccaggtgaaa aatcagtcaa   63900
tacaaataga cctagaaatg acagaaatga ttagaatggc aaaaaatttg acatatcaat   63960
atgtcaactg agttttaggt tttaagaaaa catgaatacg gaatgaagca gataccatat   64020
caagagacag taacagtata gaagagccaa attaaattaa agaactagta taagaaggta   64080
tgtcttaaat gaaaaaatta ctggatgtat tcccaatgga gtgagatgtt tcagaagtaa   64140
aaactaactg aaaaacaatt ttataccacc tacagaacca gctacacata cacaaatgac   64200
acacacatat acacacatac tcacacatgc acaggcttag aaacatgcac gcacacacac   64260
acacacacac acacacacct ccacaaatac taaaaaatga aatccactga tcctcacaga   64320
caggcgggaa aatataaaaa gatttcctgc atgtgggtag gaagtcacag aaggagagga   64380
aggagagatt gctacaggaa caaatactgg aagcaaggat agctaaaaac ttttcaaata   64440
agaagaatat taaaaaccac agattcaaga agctgaatga atcagacagg gaatttccaa   64500
aaaaaaaaaa aaaaaaactg tatgattcac ttttgtacat caccgttcaa cagtcagaag   64560
gcaaagatat aataacaaga aacatctcat gagaaactgg aggaaaaaga gctgtgtctt   64620
gctagaagaa cagtgataca aattgctaat gcattctcat cagaaacact ggaacccagt   64680
taacagggga tatcattaaa atgataaact agaaaaaaaa gagatcaaat gagaatgcta   64740
catccagcaa taaaatgcct tgaagatcat ccatgttgga taaatgcata ttgtgcactg   64800
ccccaaataa ataaaccaaa aactaataat ttggaatcag caggcttgtg taacaagaga   64860
tgttgcccaa agaaaattag ctagaagaag aatagttcaa gaggagaact ttctgcagcc   64920
cacgtaatga agaacccagc aaatggcaaa tgtagatgta aatgcaaaat attttcttga   64980
tcaaatttct atatcttttt aaatgagagt tgactacttg aagcaaaatg atagcaatat   65040
atttaacttt agcatatgta gaggtaaaaa tttgaacata tagactaaat catgtgggga   65100
ataattggaa gtgtaccatt gtaagtttct taccttatcc acgatggtat gtaatattaa   65160
tgaaaggttg aatttgtggg tccaaaggga tattgtaaat cctaaagcaa tcataaaatt   65220
ttgaattctg agggatatta tataataaga attttccatg tatccaaaag agggaagcca   65280
aggaagaaaa agaagtcttt caagtactca agctctgagc acatccagtt gctcattgaa   65340
ccagcttcct ggaatggagg gtctgggctt gagactaggt cacatgtgta gagtctctag   65400
```

```
agagacagtg ttggatcccc atggcccata atacatttcc cgttttccca ggcagccaca   65460
ggtcacgaat gggaggattc tgagaggttg gagcaatgtt cttaggaggc ataaggagga   65520
gtgaatgctc tgagatttcc ccagcctgag gtcctccata gctgcccgac ctcttcagac   65580
ctcatagtct gcccagctgt ctcccttttat gccatgagtg ccactgttct ttcaactcat   65640
cccccattcc ctcagtcccg gaattgctgt ggccagcaga ggatggactg agagcaggag   65700
aggaagtcct gaccaggaac ccatcctaga gatactgcat cctgcctgaa agctaggttt   65760
ccagggcagc tttgagaagt cttgcagaaa gaaacccact tgacccacct gatacggtat   65820
cgacagacag gaatacttt tgtgcaatgg ttttacatgc tgaacataga gccttttggc   65880
tacattttga gtacattgaa tgagactgct ggcctgggaa ggatatcatg ctggatgcca   65940
tttttttctc tggagaacta tgtgttagtt ccaactcgca cattactata tgaagtccta   66000
cacagagaga tacggagagc tagacagata gagatacttt tgtatgtgca taaccaattc   66060
cacaatacac acgtcaaaat ccataccagt tattccagag agatggattg ggcagaaggc   66120
agaaggagga tattctgatc cctttttggc cacatgtatg tataatctca gtgtttctag   66180
gaagtgtgtg ctgcattaga tttttttttct ttaaaaaaag tgataatata ttaagtatga   66240
gaaatgtgca gagaggatta gagattgaga gccatttgtc attgtggcaa ttgtatggta   66300
tctcttttgg gaatatttca aaggcaccag taatgacctt gttgtagcaa aatatacagt   66360
gttcctgcat atgtacccat tttttgtgat gtgtattctt ttggaatttc cagtggcttg   66420
atcaagaact actgccgaaa tccagatcct gtggcagccc cttggtgtta caacagat     66480 cccagtgtca ggtgggagta ctgcaacctg acacgatgct cagatgcaga atggactgcc   66540
ttcgtccctc cgaatgttat tctggctcca agcctagagg ctttttttga acaaggtaag   66600
aagttgtgcc agacatttac ctgcttggat gctgggatga aaagccatgg ataccccac   66660 tgacgcacaa cccttcagtg ctacactggt tctcgtgtgt tggttctggg tctgccatgt   66720
gggaggaagc cttagcgcac tctctggggg agccagaggt gtgattttg gtgcaacctg   66780 tgcgagctgt gtctttagga tgggcggaaa ccattctggg tgctcgactt caccactccc   66840
ctcattgtaa aagggctat ctcattgtcc tagacaaaat tcttattgta atatgctgtc   66900
agatgtgtgt gtctttccaa gccagtaaac ttttccaggg atttcttcaa gtagacagca   66960
ttcagtgcaa tcttcagcat tgcagattcc gagaaatgtg gctctagatc ctgttatcct   67020
tgagaaacct aactgggttg cattaattcc atatctccct gggtctgtgg agtagtacat   67080
gagctcccga agctctatct ctcaggtctt tttcagtccg aggcaggttg tgcagttctt   67140
agctttgaag ggagtgattt tttcgtgtgc ttttgcctct ttctgatgga acttgtacct   67200 gcgggggggtc tggagaaaaa gagtagtaga cttttgctttt attgcaatgc attatgctgg   67260
gcacgagagg attccctatc ttattgtagg tgataagctt ttggcctcca ctcatccctg   67320
agaagtgaag tgttgttgcc tacagttta gctgcaggac tgttgtctgc cccatcacca   67380
ggagtttaat gctttctttt ttgagcaatc atctagggac acatgcaagg tttttatatg   67440
tccttgcctc ctccccaaaa aaccatttta atgcttggag acttgctttt cagctttgcc   67500
aaatgcatca ccctttcttc tatgctgttc catgtcgtca tgaacactct gtagagattc   67560
ctagaaatga gcttccatgt tagtggagtt tccgatgaga agcaatctga tatttctttt   67620
ccactaagtt ttacatgaaa tatttctaag aacttactac agttctagaa tggtaggcat   67680
ctcttacttt cgtgtttgtt tgtgtgtttt ctcatgtcca tttgcctatt aataaagaat   67740
agagaatggt tgtaaatctc agtgactctt ttttggttta tgtcataaat ggcttcctgt   67800
```

```
atttttctgt tctaggaaat aataagcttg atgtcttctg ttttaatttc agcactgact   67860
gaggaaaccc ccggggtaca ggactgctac taccattatg gacagagtta ccgaggcaca   67920
tactccacca ctgtcacagg aagaacttgc caagcttggt catctatgac accacaccag   67980
catagtcgga ccccagaaaa ctacccaaat gcgtacgtct ttgttcttta ccataagcga   68040
aggaagggcc aatggaagtt tctgttagaa gagtcatgct tcaaggtgac tgctcaggac   68100
tcaacttggc tcagatgcag aggaacattt cctgtgagca aaagttctta gagaagactt   68160 tgttttttg agacagagtc ttgctttgtt gcccaggctg gagtgcagtg gcatgatctc    68220
ggctcactgc aagctccgcc tcccgggttc acaccattct cctgcttcag cctctctagc   68280
agctgggact acaggcaccc accaccacac ccggctaatt ttttgtattt ttagtagaga   68340
cagggtttca ctgttctagc caggatggtc ttggtctcct gacctcgtga tccgcctgcc   68400
tcagcctccc aaagtgctgg gattacaggc gtgagccacc gtgcctggct gagaagacat   68460
tttttaagct ggctctcctt cctcctagtt ttatggaagc agaaggatat atggagttga   68520
gaagatctta ttaataaaac agccgggatg acaaatgacc aaagagttag agtatccttc   68580
tacaacatcg gctgagggtt aatacaacct tttcaccttg gaattctatc attctaagct   68640
ctagtccctg aagtgaatgt tgtgttggcc ttttgcatct tgggtcacag ggaattgata   68700
cttgcacatc tatggagagg caaatctttt tctatctact tcttttcaa tgggtacaaa    68760 cacacttggt cctgagcacc agtggtctga agagatacgg tctgcccaga ggagaagaac   68820
aaaggcagga aagcagatga gagtcagcaa aggggcgatg ctgaaaagta aaaggggcgg   68880
gtagatggac agaagccatg atctggccat tctatggcca gtctttcggc cataagtgac   68940
taccaaagac acggcaaaac ggtttccaca tgttgaacaa cagatgctag aggaccaaga   69000
gtattgcaag agggagaaaa tgagatcaac ccatcaatgc cttggctttc ttcaaggaga   69060
cccttcctgc actgaagagc aaggagatgg agcccaagct gactgtagcc atgttgctga   69120
acagaggaga gtgattggac tttgggatta ctcaggtagt taggattttc tagccatgct   69180
aagagtaaga atggacttgt ggaggatagg agctccaggc atagaagtct cctcaagtgt   69240
tagtctaaac ataaagcagc acttgcatag aagattttcc acaagaaaat atggcaaaaa   69300
aacaccatat attgaggaac aacaactaca agggaacagt gagcttaata aaggtgacag   69360
agctcacata gtgctctgga atattggagt tttgaccagc tagagagaag agacctcatt   69420
gaaaatcttg ggcattcagt agagacctca gaaaagtcag actttatgag tagactttgt   69480
atattcctag aataaaggca gctccagaaa aaacctagca aagctgaaaa gcaaatctcc   69540
aagcattaaa atggtgtcct agtcaattaa ctgccttcta aagaaaact caacactctt    69600 tacaggtgaa caacaaagtt aagttgctga gctatgcaat atccacagtg tgagtcctaa   69660
atttataact ttactacaca taaaaaagca tttagtgtga accataacca ggaaaataat   69720
cagtcaataa aaatagaacc aggaatgata gaaatgattt aaatggcatg agaatttgac   69780
atattagtat cataactgca ttgctggatt taagaaaaca taaacatgga acgtaacaga   69840
tatcatatca agggaaagta aaaggataaa agagtcaaat caaattaaag gactattaaa   69900
aggtatatct taaatgaaaa attcactgga tggtctccca atcaggttag ttgtttccag   69960
ggaaaaaatt aactgaaaaa taattcaata gaatctacag aaatagctgc acatatatac   70020
acacaatggc acacgtgcac acacccacac ccacacaggt gtgaatccta gagccacacg   70080
agcattgaaa catagagaag taaaaattgt tcattgagga atatgtagca atgctcaatg   70140
```

```
tgttttaccc taataagagc ttttgtgatg tatgattgaa aaactgacac aactgaagag   70200
agaaatagat aagcccacac tctgagttag agatttcctt gattctctca ctatggttat   70260
aaatctttcc caaacacaac aggctagaac aaatatgcag aaaattagac atagtatctt   70320
tgttctcaat aaaaacgtcg acctatttaa cattataccg aactaccgag tacacattaa   70380
agtgtgcatg gagcattcac tgaggtgtac tctacacatg accttccagc aagtctccat   70440
agatttaaaa gaattaaagt catacagagt gtgtcacttt attctcccag aataaagtga   70500
gatatgaata atgagaagtt tgccagcttc tcaaatattt gggagtcata cggtgcattt   70560
caaaatactc tttgggacaa agaaaacatc actaaggaat ttagaaaagt tttgaactga   70620
gtaagaatat aacacaattt atccaaactt aggagatgca gtgaatgtct ttaggctttt   70680
acataatttt agatgctctt agggaaaaac agaagcatgt aataatcaag atttcaaact   70740
gcaattctca aagtgtagtc tagagaaacc tgaggacctt tgagtacctt cagagacagt   70800
ccatgaggtt aaaggacttt gctacgtgaa aagtaagatg ctattggccc tttttacttt   70860
cattttccaa caagagaaga ggggagtttt ccagcagtta cataatatgt aatggcatca   70920
tgtctctgat ggctaagaaa atgggcaatt gttgactttg tgtgttaaaa aaattctcag   70980
tgttggtttc ttatactata aatattcatc ttgtgttttg aaaagaaaaa gctctttgga   71040
atcccctatg aacaaagact ttgcagttg ttgatctaag accacagctt aaatatctac   71100
acaagaaaaa aaaaaaagc aataagagc caaggaaagc agatggaagg aagtagtcca   71160
aaccagtgac attcagtgaa caagaaaaga gaccaacaag ggagtaaact cttgaaacag   71220
aaagttgatt ctttgaaaag atccatatga ttgaacacag tctggctaaa caaatgacag   71280
accaatgagg gtgcacaacc atcaccatct ggagtaacag aggagaggtg ccattactat   71340
agcatcttcc agttctgaaa gctgaaaaga agattttgag aacaattgta tgtgaataaa   71400
ttcaggaatg ttaatcatgt gggccaattc ctgaggaaga caacaaatca gcaaaccaga   71460
tgctgaatag ttagtgtagt cctgtagaga gacatacaga gaggctgaca gagaaatatt   71520
tgtatgtgca taaaacaatc tacaagacac acttcaaaat caatctcagt taatctggag   71580
gaacatattt cacagaaggt ggaaggaggg tattctgatc ctcttgtaca ttgtacaaca   71640
ttgtacaatg tacagagtat aattgtacaa gtacaattga agttgtacaa gtacaagtgc   71700
aacttgcaca atgtacagag taaacattga tgtttactct caattttctt atggagcaca   71760
gatgactttg gatgtgttac aatatgaatg ataatttgtc tttgagatgt tcgcagttgt   71820
ttagaagttg aggaccattt gtgcatatta tgggaccttt agtgaaaata tttcaaagtc   71880 tcttttttaca ctttgttaca gcaaaatgta gagggcgcta agtgcccttg aatcttctcc   71940
catctctggt gacctgtgtt gttttgaaat ttgcagtggc ctgaccagga actactgcag   72000
gaatccagat gctgagattc gcccttggtg ttacaccatg atcccagtg tcaggtggga   72060 gtactgcaac ctgacacaat gcctggtgac agaatcaagt gtccttgcaa ctctcacggt   72120
ggtcccagat ccaagcacag aggcttcttc tgaagaaggt aggaagtcta tggccagaca   72180
accacaccct aggacgttgg gatgaaaaga gttgcaaaat cttagtgata tagaagcctt   72240
ccatgctcac acaattccaa gtagaatgtg gactcagggt cagccactgg gaaggaacac   72300
tcagcgcctt ctctgggaga accagagctg tgatgtttgg taccctgtga aagggtggta   72360
tctataggaa gggtgcagac cctctagggc actggactta ccactcccct ggttattcaa   72420
aggatcattt tagtgtctta gccagaagaa tattctaaca ttttgccaaa tttgtgaaga   72480
tttaccaagc tcatgataag ccttttcatgg tatttcttca agtagtcagt gttcattgca   72540
```

```
tctttggctt tgcggtttcg gaggaatgcg gttttttgagt ctgtcatcct tgagaaacct   72600
aatatgactt ttcttagttc catatacttc tgggtccagg tagcagtaca tagccaacaa   72660
atgctccatc gttctggcct atctccatct taagccagtc ctgcacaact aggctttgat   72720
gggagggatc tctcagtgtt cttgcccctc cttctcatgg aacatatatc tgtgttggtc   72780
tctgagaaga agagtagtgg atatctactt tgttgcaatg cagaatcctg ggccaaagat   72840
accagccatc cctccaaggg aataaaattt tggccagtag ccctctctga gagacaattt   72900
gtctttgcct acgagtccta gatgcaggac cgcttcctgc cccatcttca agaagctgaa   72960
ggctttggct ttggaggatc agcagtctag ggaaatgtgt gacggtttca tgtctgtccc   73020
cactgacagt caatcaccac ctacaacctg cacagcctga tgcatagcag tctagttttcc  73080 tgccttattc tcaggaacac ccagaagatg tctatattaa agagcatgca catgagtgca   73140
attttgactg ataggcactc tgatctttcc tttggtgcct gtgttttaaa ggaaatcttt   73200
ctaagaactc gttaaagttc tagaatgcta tgaatctttg ggttttatta ttggtatgtc   73260
catctgcctg ctagtacaga acagagcatg gtagtctttc tcagagacaa tgatcctgtt   73320
tcagtcacag atttcttctg atgcttctgt gttctagaaa ttactcagct tgatttctcc   73380
tctttgaatt tcagcaccaa cggagcaaag ccccggggtc caggattgct accatggtga   73440
tggacagagt tatcgaggct cattctctac cactgtcaca ggaaggacat gtcagtcttg   73500
gtcctctatg acaccacact ggcatcagag acaacagaa tattatccaa atgggtacaa    73560
ccttgagttt tcttcaaaga cagacagcag ccccccttaca tttctcttgg aagggccatg  73620
cttccaacta acttcttatg acaaatttat ctcagatctg gaatgttggg tagaatgtct   73680
caggcttctt tcttcaggca cagtgtctga aaggagagaa atgtcaggcc agctctcttt   73740
tctcatagtt gacagaagca ggaggatatt tgaaggtggt gagttctcat gaatagaaag   73800
ctcaggacac atggccacgt gcttagaaat agcaccattc cacaatgccc actaaagacc   73860
aatgcaatag ttcaaccagg gatttctgtc attctaatct ccaagtcctg aagtgaaggt   73920
tgtattagcc atgttcatct tgggcaacaa ataaaggata tctatgttga catccagatc   73980
ttccaatcac tttctcctct aacctgtacc tgggttctga gaacaaggta tctgaagagc   74040
tatgtgttgc cagcacatga ggggcaaaag taggaaggca gctgagagtc aggaagtata   74100
aagattctga agagttacac atgcaggaag atggacagaa acccagttca gaccacgtca   74160
gcgtttctgc catgaaggac tatcaaatac ataggaaaag tgttttcata ggttggacaa   74220
cagacatgac aggcctgaga aaattcagaa agggaatcaa aggagatcaa ccttatcatg   74280
tccctggcat ccttccttga gacccttgaa gggcaagcag atggagccca gctgaccaca   74340
gcagtcttgc ttaactgagg agagagactg gagtttgtga tgcctcaggc atctgacgta   74400
ttctaggctg gctaagaatg agaggggatt tgtggaggaa aggagctcca agaatacaca   74460
ccgaagtctt ctcaaggctt tggctaaata caaagctgcg tatgcacaag gagagttttc   74520
acaaagaaag aacaataaag aaaagctact ggggaaagaa caactgcaag ggaacagtga   74580
gctcaatgga gatgctagag ctcacatagc actgggggat atttgagttc tgaccactca   74640
gaggagagac acctcactga acatcttggg cattcagtag aggtcaaaga aagccataat   74700
ttgggagtag gatcttcgga ttcctagaaa taaggtgact ccagaaacac tccagcaacc   74760
cttcttccaa gccagtctaa aaggatccaa atgatttcca agtaaattaa ctgccttcca   74820
gaaaaaagta aactcaaccc tccttagagg taaggaacga atacaagttt ctcagttata   74880
```

```
tgacatcccc agagtgcaac ttgcatttaa aaatttacta gacacaaaag aagttttcac   74940
tgtgatccat aactgggaga aaaatcactc aacacaaata ggcccagaaa taatagaaat   75000
tatggcattg gcaagaacat ttaaaatgca cctctgagaa ctgtgtttca ggaaaatgtc   75060
agcaaaagct gaccatgaga gaaatgaatg cataatatca gaaagaaaaa gaattgaaga   75120
gccaaatgga aatttaaaaa ctgagaaaag ttatatctgt aatgaggaat tcactggatg   75180
gccttataac cagtttagat attatggtag gaaaaggtga acgagaaaat gattcaatta   75240
aagctagaca aaccacaaga cagacagaca gacacaaata cacatacaca caatgactga   75300
accaattaat caacagagcc tcaaggacat ctaggaaaac atccacacat ttaatatatg   75360
tgttaggcaa gtcacagaaa gagaggaaaa agataatgtg acagaagtta tacttgaagc   75420
catgacggct gacaaatttc caaacataca gaaaatgaga aattcatagt catgaagctc   75480
aatgactcag gtatagattt ttaaagagca aaactctgat ttactggggt acatcatagt   75540
taaattgtct gatttcaaag ctaagaagaa aaaaggggg ttcctatgaa caaacatttt   75600
gacagttgat ctaagaccac agcttaaata tctaggcaag aaaagcaaa taagacacaa   75660 ggaaagggga tggatggaaa tagtccaaac caatgacatt cagtgaacaa gaaaatagac   75720
caacaaagga gtaaatccat gaaacagaaa gttggttctt tgaaaagatt catgtgattg   75780
accacagtct ggctgaacag atgacagacc aaggagggag tacaaccatc accatttgaa   75840
gtaacagggg agaggagcca ttgctatacc atactccagg tctgaaagct gacaagaaga   75900
tatcaagaaa aactgtatgt gaataaattc atgaatgtag atcatgtgga tcaattcctt   75960
aggtaaacaa caaatcagca aaccagatac tgaatagatt gggtactcct atagaaagac   76020
atacagatag ccagacagag aaacatttgt acgtgcataa aacaatctac aagactcact   76080
tcaaaatctc tcagttaatc caaagtaaca tatttggcag aaggtggaag gagggtattc   76140
tgatcctttc ttgtacacat tgatgttttc tctcggtttt cttatggagt atagacgagt   76200
ttggatgtgt tacaataaga atgataatct gtctttgaaa tgttcacagt tgtttagaag   76260
ttgaggacga tttgtgattg ttacaggacc tttagtgaga atatttcaaa gtcacttttt   76320
accactttgt tacaacaaaa tgtagaggat gtctggtgcc cttgtatctt ctcccatctc   76380
tggtgaactg tattgttttg taatttgcag tggcctgacc aggaactact gcaggaatcc   76440
agatgctgag attagtcctt ggtgttatac catggatccc aatgtcagat gggagtactg   76500
caacctgaca caatgtccag tgacagaatc aagtgtcctt gcgacgtcca cggctgtttc   76560
tgaacaaggt aagaagtctc tggccagaca accacaccct tggacgttgg gataaaagaa   76620
gttgcaaaat cttagtgata cagaagcctt ccatgctgca cgggaatctg aatgtggact   76680
cagggtcagc caatgggaag gaagcctcag cgccttctct gggggaacca gggctgagat   76740 tttggcacc ccgtgacagg gtggtgtctt taggaagcgt gcagaccttc tagggcactg   76800
gatttaccac tccctggtt attcaataga ttatttcagt gtcctagtga aaatggatat   76860
tctaacatcc tgccaaattt gtgatgattt accaagctca tcatgagcct ttcctggtat   76920
ttcttcaagt agacagtact cattgcaaac ttcagcttta cagtttcaga ggaatgtggt   76980
ttttgagtct gtcatccttg agaaacctga tatgactttta cttagttcca tatcctcctg   77040
ggtctaggta acagtacata gccagcaaat gctctatctc cctgtctacc ttaatcttag   77100
gcaggtgctg cacacctagg ctttgatgga agggatttct tagtgttctt gcccctcctt   77160
ctcatggaac acgtatctgt gttgctgttt gtgaagaaga gtagtggatg tctactttgt   77220
tgcaatgcag gatcctgggc ccaagatttc ccgccgtccc tccaagggaa taaaattttg   77280
```

```
gccagtaccc ctctctgaga gacaatgtgt ctttgcctgg aagtcctaga tggaggacca   77340
cttcctgccc catcttccag aaacttaagg cttttggcttt ggaggatcag tgctctggag   77400
aaatgtgtga cggtttcatg tctgccccca ctgacaacca ccacctacag cctgcaccgc   77460
ctgatgcatg gcactctggt ctcctgcctt gttctcagga cacccaaaa gagatctttg    77520 ccaaagaaca ggcacatgag tgcaattttg actgataggc actctgatct gtcctttggt   77580
gcccaggttt taaagaaaat ctttctaaaa actcattgaa gttccagaat gctatgaatc   77640
tttgagcttt gttattggca tgtccatctg cctactaatg tagaacagag catggtcgtc   77700
attttcagag atgatgtcct gtttctatca tggatttttt ttctcatgct tctgtgttct   77760
ggaaattact cagtttgttt tctcctcttt gaatttcagc accaacggag caaagcccca   77820
cagtccagga ctgctaccat ggtgatggac agagttatcg aggctcattc tccaccactg   77880
ttacaggaag acatgtcag tcttggtcct ctatgacacc acactggcat cagagaacca    77940
cagaatacta cccaaatggg tatgtctttg agttttctcc caagagaaac agccaccac    78000 ttaaatttct cctggaagag ccatgcttcc agctaacttc ttatgaccca atttctctca   78060
gacccagaat gttggacaga atgtctcagg cttcttgctt tgggcacagg gtctgagagg   78120
agagaaatgt caggccagct ctcttttctc atagttgata gaagtaggag gatacttgga   78180
ggtggtgagg tctcatgaat agaaagctca gaagaacata tgaccatgtg cttagaaata   78240
gcaccattcc acaatgccca ctaaagacca gtgaaatagt tcaaccaggg aattctgtca   78300
ttctaatctc caagccctgg agtgaaggtt gtgtttgcca tgtttgtctt gggtaacaag   78360
tgaaggatat ctatattgac ttcgagatct tccgatcact ttctcctcta acctgtataa   78420
acacattggg ttctgagaac aaggtgtctg aaaagctatg tgttgccagc ccatgagggg   78480
caaaaggagg aaggcagctg agagtcagga agtatagaga tgctgaagag ttacacattc   78540
aggaagatgg acagaaaccc atgtctggct atgccagcct ttctgccatg aaggactatc   78600
aaatacatga gaaaacagtt ttcacaggtt ggacaacaga tatggtaggc ttgagagaac   78660
tgagaaaggg aatcaaagga gatcaacttc atcattaacc tgtcttcctt cctggacaca   78720
gtgttggatt gaaggacaag cagatggagc ccagctgacc acagcagtct tgcttaactg   78780
aggagagaga ctggagtctg cgatgcctca ggcagctgat gtgttctagg ctggctaaga   78840
atgagaaggg atttgtggaa gaaaggagct ccaggaatac acacagaagt ctcctcaagg   78900
ctttggctaa atacaaagct gcgtatgcac agggagagtt ttcataaaga aagaacaaca   78960
aagaaaagct acttgggaaa gaacaactgc aggggaacag taagctcaat ggagatgcca   79020
gagctcacat agcactgggg gatatttgaa ttctgaccac tcagaggaga aacacctcac   79080
tacattttgg gcattcagta gagaccaaag aaagctgtat tttgggattg ggatcatctt   79140
attcctagaa tcaaggtgac tccagaaaaa ctccaacaac ccttcttcca agccagtcta   79200
aaaggatcca aatgatctcc aagtaaatta actgcattcc acaagaaaaa aaaaactcaa   79260
ccccccttag aggcaaggga caaatacaag ttgctcagtt atatggcatt cctattgcgt   79320
tacttctatt taaaaattta atagagacac aagaagcttt cactgtgata cataactggg   79380
agaaaaaatc actcaacaca aacaggccca gaaattatag aattgatgac attggtgaga   79440
acatttaaaa tgcacctctg agaactgtgt ttcaggaaaa tgtcagcaaa agctgaccat   79500
gagagaaaca aaagcagaat agcaagagaa aagaaaagaa ccggagagcc aaatgaaaat   79560
taaagaactg agaaaaggta catctctaat gaagaactca ctggatggcc ttatcatcac   79620
```

```
tttagacatt acggtaggaa aggtgaccta gaaataatt caataggagc tacacaaatc   79680
acaggacaga cagacagacc aacagacaga aacacacaca cacacacaca cacacacaca   79740
cacacacaca cacacacaca aagactgaac ctattaatca acagagcctc aagggcatct   79800
aggaaaaatc cacacattta atatatgtgt taggcaagtc acagaaggag aagaaaagaa   79860
tatcatgaca gacattatac ttgaagcgat gatggctcgc aacacgccaa atatacagaa   79920
aacaagaaac tcatagtcaa gaagctaaat gactcaggta tagaatttta aagagcaaaa   79980
ctctatgatt tactgggata tatcatagtt aagttgcctc aattcaaagc taaaagaaa   80040 aaaagggggt tcctatgaac aacagctttg acagctgttg atctaagacc acagcttaaa   80100
tatctaggca aggaaaagca aataaggcac aaggaaagag gatggaagga aatagtccaa   80160
accaatgaca ttcagtggaa aagaaaatag accaacaaag gagtaaatcc atgaaacaga   80220
aagttaggtt ctttgaaaag tctatatgat tggccaaagt ctggctaaac agatgacaga   80280
ccaaggaggg agcatatcca tcaccatcat gagtaacagg agagagatgc cattgctata   80340
gcatcctcca ggtgtgaaag ctgagaagta gatattgaga tcaactgtat gtaaataaat   80400
tcatgaatgt agatcatgtg gatggattgc ttaggtaaat aacaaatcag caaatcaaac   80460
actgaataga tcatgcagtt ttatagagac ttacagacag cctgacagat aaacatttgt   80520
atgtacgtga acaatctcc aagacacact tcaaatcccc tctcggttaa tccaaaggaa   80580
tgtatttggc agaaggtaga aggagggtat tctgatcctt tctggtacac attgatgttt   80640
tctctcagtt ttcttataaa gcatagatta ctttgaatgt gttacaataa gaatcataag   80700
ctgtctttga aatgttgaca gttgtttaga agttgaggac catttgtgag tgttatggga   80760
ctttagtgag aatatttcaa atttgcttgt ttacacttttg ttacaagaaa acatagaggg   80820
tgccaggtgg tgctgtatct tctccaatct ctggtgacct gtattgtttt ggaatttgca   80880
gtggcctgac caggaactac tgcaggaatc cagatgctga gattcgccct tggtgttata   80940
ccatggatcc cagtgtcaga tgggagtact gcaacctgac gcaatgtcca gtgatggaat   81000
caactctcct cacaactccc acggtggtcc cagttccaag cacagagctt ccttctgaag   81060
aaggtaagaa gcctgcagtc agacaaccat accctcggac attgggataa aaagatttgc   81120
aaaatctttg tgatgcagaa aacttccatg ctgcacagga agtcgaaggt gaagtcatgg   81180
acagccaatg ggaaggaagc ttcagtgcct tctctggggg gaccagagct gggatgttga   81240
gtgccttgtg agggatggtg tctttaaaag gggcacagac cctctaggac actggattta   81300
tcacttccct gttatcaaac gaatcatatt agtgtcctag ccaagatgga tattctaaca   81360
tcctgccaaa cttgtgaaga tataccaagc tcctaagcct gtccagccct ttcttcaagt   81420
aggcagtgtt tattgcagtc ttcagcttta ccatttgaa ggaatgccat ttttgaggct   81480
gttgttcttg agaaacctaa catgtcttca ttagatccgt attgtcctga gactttgaag   81540
cagtacatag ccaccaaatt gtttatctcc ccagcctacc ttcatcttgg gcatgccttc   81600
cacacctagg atttgaggga agggatttct cagtgttctc atccctgctt tcatggaac   81660 atttatctcc gttgtttttt gagaagaaga gtagtggatg tcagctttct tgtaatgagg   81720
gatcctgggc ccaagattcc ctgtctcccc tcctaggcta taaattttg gcctgtactc   81780 cttctccctg agaggcaatg tgtctttacc tacaagtcct agatgcaaga tcctttctg   81840 ccccacaccc cagaatctga aggcttttgc tttggaggag cagtggtcta gtgtgcaagg   81900
gtttcatgta taccccccac taacagccaa tcaccaccta tagcctgaac agcttgatgc   81960
atggcaccct ggtctcctgc cttgttctca tgaacaccca gaagaggtgt aagcaaaaga   82020
```

```
ccattcacat gagtgtaatt ttgaagtata ggcactctga tctgtttttt gtttgtttct   82080
ttgtttgttt gttttccagg gttgaattaa aatatttatg actacttatt aaatttctag   82140
aatcctataa gtctatttgt attttttattc tacatttcaa tttgcatgct aatatagaag   82200
agtgtaaatt gttaatcctc agattattcc actttgtgtg tcataatttt tttcacattt   82260 ccctttttcta ggcaatactg agcttgattt tctcttttaa tttcagcacc aactgaaaac   82320
agcactgggg tccaggactg ctaccgaggt gatggacaga gttatcgagg cacactctcc   82380
accactatca caggaagaac atgtcagtct tggtcgtcta tgacaccaca ttggcatcgg   82440
aggatcccat tatactatcc aaatgcgtat gtctatcatg ttagccataa aaggaacaat   82500
agtcaactaa aatttctctt agctggccca tgctacaagc tcacttccta ggtccaaatt   82560
tctcatagac tcagagtttg tagcaaaatg tctcaggaaa cttacttttg agcaaaaggt   82620
ctgaatgaag agaagtttta ggattgctat cttttcataac aatttgatgg aagcagcagg   82680
atatatggag gtggtgaagt ctcattaatg taaagctaag gagatcaaat gaccaaatgc   82740
tgagacaaag tatcattcca caatgcccac taaaggtcca tgcagtcttt caaccatgca   82800
attctatcat tctatcctcc attccctgaa gtgaaatttg tgtttgccat ttttgacacg   82860
aatcagaagt aacaaattca ggctgggtgc agtggctcag gcctgtgatc ccaacacttt   82920
gggaggacaa gacgggcaga tcaccagagg tcaggagttc aagaccagcc tggctaacat   82980
ggcaaaaccc catctctacg aaaaattaaa aaattagccg gtcatggtgg tgggtacctg   83040
taattccaac tacttgggag gctgaggcag gagaaacact tgagcctggg attcagagtt   83100
tgctgtgagc cgagaacatg ccactgcact ccagcctggg tgacagagca agactcaatc   83160
tcaaaaaaaa aaaaaaagaa gaagaagaag aaagaagaa gaggaagaag aagaagagga   83220
agaagaagaa gaagaagaag aggaagagga agaggaggag gaggaggagg aggaagaaga   83280
agaagaagaa gaagaagaag aagaagaaga agaagaagaa gaagaagaag aagaagaaga   83340
aaatagaaat gagtgcatat atttatatat gagtactagc ctgtatgaac acactgggtt   83400
ctaagcacca gttttctgaa gggatatggg ttgtcaggca gagtaaaagc aggaatgcag   83460
atgagagtca ggaagtaaac agatgtggtg attaaaatgg gcaggtacat ggacaaaaaa   83520
atgcatgtct gacaaaaact ggcctcttgc cataagtgag tatgaataat atggaaaaac   83580
tgtttgcaca tgttgaacag cagacagtac aacctgagat agtttagaaa gggaaacaaa   83640
taagatcaac cccataatta cccttcctag acttaagggc aaagagtttt aaccaaagca   83700
ttccacagca gtcttgctaa actggggaga gagactggag ttttgtttac taataaaacc   83760
gagattttct aggttaggta ataatgagaa agtatttgtg gagaaaagga gctccaggaa   83820
tacacacaga agtctcttca agtctctggc tgaacagaaa gctgtgtatg cacagaaaga   83880
gtttccagag agaaaggaga acaaagaaca gctactgggg aaagaacaac tgctggggaa   83940
cagtgagctc aatgaagatg ccagagctca catagcactg ggaggtattt gagctctgac   84000
cagcctgagg agagacactt cattgaacat cttgggcatt cagcaaagac cccaaaaaac   84060
catacttcag gagtagaatt aatgcattcc tagaataaag tctactccag aaacacccta   84120
gaaaagctta gaaaccaagt ctaaaaagat ccaaatgatc tccaagtaaa ttaattgcct   84180
gtcagaagaa aacaacctct tcagaggtaa acaacaaaat taaattgctc aattatatag   84240
tatgcacaat gtgtggcata catttaaaaa tttgctaaac atacaaaaag catttagtgt   84300
gacccataac caggagaaaa atcagtcaat acaaatagac ccaaaaatga taaaaataac   84360
```

```
agaattggca aggagattta aaatgtatgt atcataattg tgttcaagga tttaaagaaa    84420
gcgtggacaa gaaataaata aatggataat atcaacagaa agaaaaattg taaaaggacc    84480
aaatggagag tcaagaactg aaaaaaaaga catctcttta atgagaaaat cactacatgg    84540
ccttataatc atattagata gtacagatga taaagctaac tagaaaatat tagggtggtg    84600
caaaccatag cacgcttata caaagcctga gaagataaac agagcctcaa ggacatctat    84660
gaaaatatca aaatatttaa tatttgttta aagcaagtca cagaggaagg gaaagagata    84720
ttggaacaga aaaaatactt gaagcagtga tggctgatga ctttctaaat atggaaaaaa    84780
tgataaactc acatagtcaa gaagctcaat ggatcagata taggatttta aaaagtaaag    84840
ctgtatgatt tatttggaca catcataatt aaattgtcca taatcaaaga tagaaagtaa    84900
aatcttattt gaagcccaag ggaaaaaaca tacctttaca tagagtaaca gtgacacaaa    84960
tgactgatgc cttctcatca gaaacaacac aaatcagaaa caatagaata acacctttag    85020
agtggtaaga agaaaaaaag atcaaatcag aaacaacaaa ataacacgtt tagagtggta    85080
aggaggaaaa caagatcaaa tcagaaacaa tggaataaca cctttagagt gtaagaaaga    85140
aaaaaagatc aaatcaggaa caacagaata acgccttcag agtggtaaga aggaaaacaa    85200
gataaaatca gaaacaatga aataacaccct ttagagtagt aagaagaaga aaagatcagg    85260
tcagaaaaaa tggaataata tgctaagaag aaaaaaaaag atcaagtcag aaacaatgga    85320
ataacacctt tagagtgaaa agaaggaaaa aaacccagca agcttaaacg ctatgcacag    85380
caaacaattc cactgaaaat gaatgttacg taagtacata ttctgtcctc ctaaaaacaa    85440
agaacaaata aaagaatgtt tcatcagcag gattatgtaa taaagatgt gaagaatgc    85500 tatgtaagta aagaaaaat aataccatat gggaattggc atcaaaacca caaatacta    85560 tcaaacaaa aaaactttat tgataaattt aacacaatat gcaaaagaac tataccatgt    85620
atactacata acattggtga gaagaaaatt agaagatcta aataaagaca catcatgctt    85680
atagattaaa aaatccaatg tcacttttca caaaactgat ctttagtttc aacccacacc    85740
caagcagaat tcctgcagtc ttttcttgaa aacctaacag aatgtatatg ctagaatcac    85800
caagacaatc tttaaaaaga ataaaaaact tggaataaaa tcacaagttt gtgggataga    85860
tgcatatggt aatatggaaa ttctcataaa gacacagtaa tcaagacatg tggtattggc    85920
tgggacgctt ggctgtaatc ctaacacttt ggaggccaa gatgagagga ttgcctgaga    85980
tgaggagttg cagacaagcc tgggcaacat agcaagaccc tcatctctac aaatatttaa    86040
aaaaattagc caggtttggt gccatgtgcc tgtagtccca gctattcagg aagctgaggt    86100
gggaggatca ctggagccca tgaggtggag gctgaaatga gccatgattg tgctactgaa    86160
ctttagcctg ggagacagat taaaaccttc cctctctctc tcaaacaaac aaacaaaaaa    86220
tacatagtat tgggcaaaac atatgcaaac aaaaacagaa aagggtcagc ataaatttac    86280
atatatggtc aattttatttt caatacaggt agcaaagcaa tttaatgagg aaatttttt    86340 ccaaaattgg tctgaaacaa ctggatagcc atagaaaaaa actataacaa atgtgacgct    86400
tgaatcctac tgtatgactc aaattaaatt aatttgagat agctcttaga cctcaatgta    86460
acagctaatt ctgaggctga aatataagac tgctatgaaa agtatagta tcttataacc    86520 ttggagaagg aaaaatttt tgagggaaga accagaaaac actaactgta aagaaaaca    86580 aatgataatg tggacattca ttgaataaaa acttatgctc accaaatatg actgttaaga    86640
aaataaataa gtaagtaaca cactggaaga aaaacactct catccatata tctgacaaat    86700
ggcctgtatc cagagtatag aaacatttct cccactcact aatcagagga caaacaacct    86760
```

```
aatcaaaatg ggcaacaggc ttgaatagtc atttcttagg agaagatgca cacagagcca    86820
acaatcacct gaaaaagtgc acaacatctt agccatcaaa aatcaagagt tataaccctc    86880
ataagatgac actgaacatc cagtgtacat ggatatcatt aagaagacac aataataagt    86940
ggtgtcaccg atttggagct agaatgtgcc actctctcat atgctggtgg aagttcaaaa    87000
tcatacaaca aattaaaaaa tcagtctgat gctttcttat aaagttcgat aaatatgcat    87060
ctatcctaca aacctgtaat tctattcttg aatatttacc ccccaaaatg aaaacataag    87120
tccacaaaaa tctatataaa tattcatagc agctttatgt tttataaact caaaataaaa    87180
actatttcaa tgttttcatc aaaagaaaat gaaaactatt taaatggttt catcaaaaga    87240
aaatgaaaaa agaatttcca gtatatttat acaaggaat actattcatc aacaaggaac    87300
aagttactga tagtctcaga agcatgaaca aacctcaaaa atatattaag gaagaagcc     87360 agacgtcaaa gtgtatagtc tgtatgagtc cattcatgtg agtttataga aaacacaatt    87420
tatggtgaaa gaaaccaata gcatttgaca ctggccgtgg gaagagggta gcagagattg    87480
attgagcagc cacacaaggg agtttctggg gtggtgaaaa tgttctgcat tgtgagggca    87540
gtgtgggcta cacaagtata tgtatttatc aaatctcatc cagctacatt taagatctgt    87600
gcatctcact ctatgtgaaa atatactcaa ctgaaaaaca gagcaggtat ctgtttcagg    87660
tgctacatca cttgatacgt ccagttgtgt taaaaaccac tgcctaacat cctcaaatgg    87720
gggatctggg cttgagacta ggtcacatgt gtagagtctc tacagagacc gtgttggatt    87780
cccatgctcc ataatacgtt ccaagttttc tcagacagcc acaggtcatg aatgtgagga    87840
ttctgagagg ttggagcaac gttcttggga ggcataatgg ggaaggcatt ctccaagatt    87900
cctccagcct ggggtcttca cctgctgtgc ctcttactgc attgttttct gactcatcca    87960
tagccacttg accccttcag atcccatagt ctacctagcc gtctcccttt atgccttggg    88020
tcccgctgtt ctttcaactc atcacccatt ccttcagtcc cagagtggct gcagccagca    88080
gaggatggac tgagagcagg agaggaggtc gtgcccatga acccatccta gagaagcagc    88140
atcctgcctg ggagctagtt ttccagggaa gcttttataa gtcctgtaga cccaaaccca    88200
cttgctctac cagatacagt atttatagta atactatttt catgattatt ttatattgca    88260
aatgtagagc atttatgcta cactatgagt aaatagagta aggggctgg catgggaatt    88320 atataatctt ggatgccact tcttccttgg ggaaatgtat ttgagttcca acttacatat    88380
tactatatag tcttatagag agagagacaa agagctagac agacagagat atctttgtat    88440
gtgcattaaa aaatctaaga tacatatttc aaaatctgtg tcatttattc tggaggaaag    88500
tatttggcag aaggtgaaag gaagatattc tgatcctttc ttgtacagac atgtattatc    88560
tcagttttca tagagagcat atactacttt tgatgtttta aaacaaaaat tataatctgt    88620
gatgtgtcca cagttgttta aaagttgaag ctgaagacca tttgtgcttg tggcaatatt    88680
attgtggtat aatgggaata tttcaaaggc acttgttaac actttgttac agcaaaatgt    88740
agagggcgct aagtgcccct tgaatattctc ccatctctgg tgacctgtgt tgttttgaaa    88800
tttgcagtgg cctgaccagg aactactgca ggaatccaga tgctgagatt cgcccttggt    88860
gttacaccat ggatcccagt gtcagtgggg agtactgcaa cctgacacga tgtccagtga    88920
cagaatcgag tgtcctcaca actcccacag tggccccggt tccaagcaca gaggctcctt    88980
ctgaacaagg taagaaattt gtggttagac atctatatac tgggatgaaa aaccatggaa    89040
aatcttactg atgcagaagc cttcagtggt acactggagg gttggttgag ggtctgcaat    89100
```

```
gtggaggaaa gcctcagcgc cctctctggg ggatccagaa ctgtgatttt tggcacgctg    89160
tgaggaggca gtgtctttag gaagggcacg gtgtctttag gaagggcaca gacccgccag    89220
ggcactggac ttaccactcc cctggttatt aaatgggtca tttcagtgtc ctagccaaaa    89280
tggatattct aacagcctgc caaatatgtg aagatttcca agccaataag cctttccagt    89340
gatttaaagt agactttttt cattgcaatc tacagtttgc agtttcttaa gaacatggcc    89400
tttgagtatg atatcctaga gaacctaagg gagactgcat tatttttcta ttgtcctggg    89460
gctgcatagc aggaggtaac caacgaatgc tgtctctccc tggcctatct cagtctttca    89520
caggctctgt tcacctcagc tttgaagtta gaaatttcta ggtgttcttg cctcttcttc    89580
tcatgaaacc tgcattggca gtgagtctac agaagaagag gaagagaatt ctgctttgtt    89640
acaattcagg actctgggca ctagaagatt ccctatctct cctccaaggg aataagttgt    89700
ttgtctctaa ccctccttga gaaacaatga gtctttgcct gcactcctaa atgtaggatg    89760
atttcctgcc caaattttca aaagattaag ccttttgcct tggtatgagc aatggtctag    89820
ggaaatgcgc aagggtcttg tgtcggcccc tgactgacca ccagtcaccct cctacagcct    89880 gcaccaagga atgcattgca ttctggtctt ctgccctgtg gttctcatga aaaccagcag    89940
agattcatat gatggagctg cacatgaatg taatttccaa tgtccagcat tctcctctgt    90000
tctttatctt tagatttaaa aataatgttt ctatgaactt attaaaattc tagaatacta    90060
tgaatctact gggtctttc acatcctttt gctactagta gaaaaagaa tagtaataat    90120 tttcagaggc tactgtccag tatgtgacat aaattgtctc ccatgtttct ctgctcatgc    90180
aattactgag tatgatttat tttattttaa tttcagcacc acctgagaaa agccctgtgg    90240
tccaggattg ctaccatggt gatggacgga gttatcgagg catatcctcc accactgtca    90300
caggaaggac ctgtcaatct tggtcatcta tgataccaca ctggcatcag aggaccccag    90360
aaaactaccc aaatgcgtat gtatttgatt aaaaccataa gaggagcaac agccaactca    90420
aatattggtt agaagaccca tgctttaagc tcacttccta gggacaaatt tctcttagac    90480
tcacattttg gcaaaatgtc tcaggacctt tgcttttgag caaagagtct aagagaagag    90540
aaattttagg cctgctattt ttcctaatag ttttatggaa ggagtagaat atacggaagt    90600
ggcgaagtca tattaatgta aagctcagaa gataaatgac caaagcttaa acacagcacc    90660
attccacaat gcccactaaa aatcaatgtc atctttcact cgtgcaattc tgtcattcta    90720
aatttcaatt cccgaaggtt tgtttgccat ttttgtcatg ggtaataagt aaaaaaaaaa    90780
aaattaagat gtgtatatat atatatatat atatatatat acacacacac acacacacac    90840
aaacatctga atatttatat atatgtctga atatttatat acttgtgtat aaaacttata    90900
tttaaatttt tgcataaatt tatatatttt taatatttca ttaaaaatta tattgtttca    90960
ctatgtatgt ctgagtattt ttatatattt taatataaca ttttaaatat ttatatataa    91020
atattcaggt atgtaactga atattcattt acacacacaa atatatgtgt gcatgtgtgt    91080
atatatatat atacccatat atatatatat atatatatat acatatatat atatatatat    91140
atatgtatat atatatatat atatatatat acacacacac acacacacac atacatacag    91200
gtataaacac actgggcctg aagcaccagt ggtctgaaag gacatgtgtt gccaggactt    91260
gaagagcaaa agcaggaagg cggatgagag tcaggaggta cacaaacgct gaaaagtaaa    91320
atggacaagt acatggacaa aaagcaggta taagcataac agccttttgg aagtaaatga    91380
ctataaaata tatgaaaata ctgttttcac aagttgcaca acagatagta gtgtattgag    91440
ataatttaga acagaaaaca aatgtgatca accccataag tgtgctgtat ttcatcatgg    91500
```

```
attgaaggaa aaagagatgg agcccaagaa gaccacagca gtcttgatga actgagagac   91560
accagagttt gggattacaa aggcagctgg gattttctac acttggtaat aatgagaaag   91620
aatttgtgga gataaagagc tacagtcatg tacctagaag tcacctcagt gtaatataaa   91680
tctgcatatg cacagggagt gattccacaa tgaaagtagg acaaagaaca gctactgggg   91740
aaagaataac tacaagggaa caatgagttc aatggagatg gcagagctca caaagcactg   91800
ggggatattt gagttcttac cagctagaaa agagacctca ttgcaaatct tgggcattca   91860
gtagagaccc cagaaaagcc actctttgga aacagagttg atgtatttta agagcaaaat   91920
ctactccaca aaaatcctag caaaattgaa agcaagtca gaaagaccaa aatcctctca   91980
acataaatta gttgcccatc agaagaaagc ttaacctctt cataggtaaa caataaaatc   92040
aaattgctca gttatctggc atccacaata tgtgacataa atttaaaaat ttactagaca   92100
tacaagaagc atttagtgtg atccataacc aggagaaaaa tcattcaata caaatagacc   92160
cagaaatgac agaaatgata gaattagcaa aaacatttaa aatatacata tgatcatttg   92220
atcttgtgat cagatatcac aagagaagaa agagatactt gaacagaaaa aatgcctgaa   92280
gcaatgatgg ctgaaaactt tccaaatatg aagaaaaaa agctcacaga ttcaagaaaa   92340
ctaatcaatc agaaatatga ttttgaaaag taaaaatgta tgatttactt tggcaaatct   92400
tcttggttaa attgtctaaa atcaaagaaa gctaggaaaa ttttataagc cagaggaaaa   92460
aagattgttt atataaagga acagttacac aaatgactga tgccttctca tcagaaacaa   92520
tgaaagtcag aaacaataaa gtaacatctt taaagtaata gagaaaaac ccaagaggtg   92580 agggatcgtg gcagacagga ggcaggacta gattgcagct ctggacagag cagcatgcag   92640
aggctcatat tgtgaatttt agccccatat tgactgcaag aacagaccag caatcctgag   92700
aggacccaca gaccgtgtga aggaagcaga ctgctcctgc aggataaggg agacacccca   92760
aatactgtga gttccccaac tgcagaagtg gaaagggag gccttactcc ctcaaacaca   92820
ccccacaact ggagaagctg aaagtctgtt tgcaggagaa gttcccaact ttacctgggc   92880
ctcagtaaat ttagagagct gagccaagca aaatataggg gtagaggaag cagcagagaa   92940
gacctcagag cttgctggat ccccaagcag ctcattcctg cctggcacca cagagatcca   93000
tcagaagtgt ggccaaagga acagagggta aaactccaca tggaggactg ctctacctga   93060
actttctaac aatttgaaca gggggagaag cctcctggcc agaacttggg ggagggcatg   93120
aatctggttt gcagacttca caggtggggg aaggactaaa gccctttct ttcacagctg   93180 ggaggtggaa agcctcaggc aagttttcaa gcctgacttt cccccccacct ggaaacagac   93240 ttggagctgt tgcggggttg ggggcatggt gggagtaaga ccagcccttc agtttgcatg   93300
ggtgctgggt gaggcctgtg actgacagct tccctccact tccccgacaa ctcagatgac   93360
tcagcagagg cagccataat cctcctaggt acacaactcc agtgacctgg gaacttcacc   93420
cccacaccat acagaagctt cagtaagacg tgcccaagga aagtctgagc tcagacacgc   93480
ctagtcccac ccccaactga tggtccttcc ctacccaccc tggtagcaga agacaaagag   93540
catataatct ttggagttct agggcccacc cacctctagt ccctctccac actagtatag   93600
ctgatgcagg aggccaacca gcacaaaaat agagcattaa accaccaaag ctaggaaccc   93660
ctatggagtc cattgcaccc tcctccacct ccaccagaac aggcactggt atccacagct   93720
gagagaccca tagatggttc acatcacagg actctgtaca gacagtcccc agtaccagcc   93780
cagagctggg tagacttgct aggtggcaag acccagaaga caggcaataa tcactgcagt   93840
```

```
tcagctcaca ggaagccaca tccataggaa aagagggaga gtactacatc aagggaacac    93900
cccatgggat aaaaacatct gaacaacagc cttcagccct accttccctc tgacacagtc    93960
tacccaaatg agaaggaacc agaaaaccaa ccctggtaat atgacaaaac aaggctcatc    94020
acactcccag ttcaccagca atggatccaa accaagaaga aatccctgat ttacctgaaa    94080
gagaattcag gaggttagtt attaagctaa tcagggaggg accagagaaa ggcaaagccc    94140
aatgcaagga aatccaaaaa aaaaaaggta taagaagtaa aaggtgaaat attcaacaaa    94200
atagatagct taataaaaaa acaataaaaa attcagtaga ctttggacac acctttggaa    94260
atgtgacatg ctctggaaag tctcagcaat agaactgaac aagtagaaaa aataaattca    94320
gagctcaaag acaaggactt caaattaacc caatccaaca aagacaaaga ataaggata    94380 agaaaatatg aacaaagcct tcaagatgtc tgggattatg ttaaatgacc aaatataaga    94440
ataatcgtgg ctcctgagga aaaagacaat actaaaagct tggaaaacat atttggggga    94500
ataactgggg aaaacttacc tggccttgct ggacacctag acatgcaaat acaagaaaca    94560
caaagaacat gtaaatacaa gcagcacaaa gaacacctgg gaaattcatc acaaaaagat    94620
cttagcctag gcacattctc atcaggttat gcaaagttaa gacgaaggca agaatcttaa    94680
gagctgtgag acagaagcac caggtaatgt ataaggaaa ccctatcaga ttaacagcca    94740 gttttttcagc aggaactgta caagctataa aggattggag ccctatcata gcctcctcaa    94800 acaaacaat tatcagtcaa gaattttgta tccagcgaaa gtaagcatca tatatgaagg    94860
aaagatacag tcgttttttgg acaaacaaat gctaagagaa ttcaccatta ccaagtcacc    94920
actagaagaa ctgctaaaag gagctctaaa tcttgaaaca aatcctagaa acacatgaaa    94980
acagaatctc tttaaagcat aaatcacaca ggacctataa acaaaagta caagttaaaa    95040 aacaaaaaca aaaacaaaa ccaaagtacg gaggcaataa agaatatgat gaatgcagtg    95100
gcacctcaca tttcaatgct aaaattgaat ctaaatggcc taaatgctcc acttaaagga    95160 tacaaaaga gttggtggct ggcaagatgg ctgaatagga acagctccag tctgccgctc    95220
cccgtgagat caacacatag ggtgggtcat ttctgcattt ccaaccaagg tacccggctc    95280
atctcattgg gactggttag acagtggggtg cagcccacag agggtgacct gaagcagggt    95340
ggggtgtcac ctcacctggg aagtggaagg ggtcagggaa ctccctcccc tagccaaagg    95400
aagccgtgag ggactgtgcc gtgaagacca gtgcattctg gcacaaatac tatgcttttc    95460
ccacggtctt tgcaacctga agaccaggag attcccttgg gtgcctacac caccagggcc    95520 ctggattca agcccaaaac tgggctggca tttgggcaga cactaagcta gctgcaggag    95580
ttttttttca taccccagtg gtccctggaa tgccagcaag acagaaccat tcaccccgt    95640 gaagaaaggg ctgaagccag ggagctaagt ggtctttctc agtggatccc accccatgg    95700 agcccagcaa gctaagctcc actggcttga aattcttgct gccagcacag cagtctgaag    95760
ttgacctggg acgctcaagc ttggtgggag gaggggtatc cacaaatact ggggcttgag    95820
taggaggttt tcccctcaca gtgtaagcaa aaccgctagg aagtttgaac tgggcagggt    95880
gcactgcagc ttggcaaagc cattgtagca agagtgcctc tctagattcc tcctctctgg    95940
gcagggcatc tctgaaagaa aggcagcagc cccagtcaga agcttataga taaaactccc    96000
atctccctgg gacagagcaa ctggaggaag gggtggctgt gagtgcagct ccagcagact    96060
tagtttcctg cctgccagct ctgaaaagag caccagatcc cccaacacag cactagagct    96120
ctgataaggg acagactgcc tcctcaagtg ggtcctggtt tcagaagata ataagaaact    96180
cctctgagct aaaggagcat gttctaacac aatgcaagga agctaagaac cttgaaaaag    96240
```

```
gtcagaggaa ttgctaacta cagtaagcag tttagagaag aacataaatg accttaggga    96300
gctgaaaaac acagcacgag aacttcatga cacatacaca agtatcaata gcaaaatcga    96360
tcaagtggaa gaaaggatat cagagattga aaatcaactt aatgaagtaa agcgtgaaaa    96420
caagattaag gaataaagaa tgaaaaggaa tgaacaaatc ctccaagtat gggactatgt    96480
gaaaagattg aacctacgtt tgattggtgt acctgaaagt gatgggagaa tggaaccaag    96540
ttggaaaaca ctcttcagga tattatccag gagaacttcc ccaacctagc aagacaggcc    96600
aacattcaaa ttaaggaaat acagagaata ccacattcaa attcaggaaa tacagagaac    96660
accacaaaga tactcctcaa gaagagcaac ctgaagacac ataatcgtca gattcaccaa    96720
ggttgaaatg aaggaaaaaa atgttgaggg cagccagaga gaaagtttgg gttacccaca    96780
aagggaaccc catcagacta acagtggatc ttcctgcaga aactctacaa gccagaagag    96840
agtgggaggc caatattcaa cattctttt tactattatt atactttaag ttctagggta    96900
catgtgcaca aggtgcaggt ttgttacata tgtatacatg tgccatgttg gtgtgctgca    96960
cccattaact cttcatttac attaggtata tctcctaata ctatccctcc ccactccccc    97020
catcccatga caggccccgg tgtgtgatgt tccccactct gtgtccatgt actctcattg    97080
ttcaattccc acctatgagt gagaacattc ggtgtttgga tttctgtcct tgtgatagtt    97140
tgctgagaat gatggtttcc agcttcatcc acatccctac aaaggacatg aagtcatcct    97200
tctttatggc tgcatagtat tccatggtgt atatgtgcca cattttctta atccagtcta    97260
ccattgatgg acgtttgtgt tggttccaag tctttgctat tgtgaatagt gccgcaataa    97320
acatatgtgt gcatgtgtct ttatagcagc atgatttata atcctttaga tatatatcca    97380
gtaattgtat ggctgtgtca aatggtattt ctagttctaa atccttgagg aatcaccgca    97440
ctgtcttcca caatggttga actagtttac agtcccacca ccagtgtaaa aatgttccta    97500
tttctccaca tcctctctag catctgttgt ttcctgactt tttaatgatc accattctaa    97560
ctggtatgag atggtatctc attgtggttt tgatttgcat ttctctgatg gccagtgatg    97620
gtgagcactt tttcatgtgt ctcttgactg cataaaagtt ttcttttgag aattgtctgt    97680
taatatcctt tgccaacttt ttgatggggt tgtttgattt tttttcttgt aaatttgttt    97740
atgttctttg tagattctgg atattagccc tttgtcagat gggtagattg taaaaatttt    97800
ctcccattct gtagcttgcc tgttcattct gagggtagtt tcttttgctg tgcagaagct    97860
ctttagttta attagatccc attggtcaat tttggctttt gttgctattg cttttggtga    97920
tttagtcatg aagtccttgc ccatgcctat gtcctgaatg gtattgctta ggttttcttc    97980
tagggtttat atggttttag gtctaacatt taagtcttta atccatcttg aattaatttt    98040
tatataaggt gtaaggaagg gatccagttt cagctttcta catatggcta ggcagttttc    98100
ccagcaccat gtattaaata gggaaacctt tccctatttc ttgtttttgt caggtttgtc    98160
atagatcaga tggttgtaga tgtgtggtat tatttctgag ggctctgttc tgttccattg    98220
gtctatatct ctgtttggt accagtacca tgctgttttg gttactgtag ccttgtaatg    98280
tagtttgaag tcaggcagag tgatgcctcc agctttgctt ttttggctta ggattgtctt    98340
ggcaatgcat gctctttttt gttccatatg aactttaaag tagttttttc caattctgtg    98400
aagaaagtca ttggtagctt gatggggatg gcattgaatc tataaattac cttaggcagt    98460
atggccattt tcacaatatt gattcttcct atccatgagc atggaatgtt cttccatttg    98520
tttgtgtcct ctttatttc attaagcagt ggtttgtagt tctccttgaa gaggtccttc    98580
```

```
ccatcccttg taagttggat tcctaggtat tttattctct ttgaagcaat tgtgaatggg    98640
agttcatcca tgtccctaca aaggacatga agtcatgtat gggaatgctt gtgattttg     98700 cacattgatt ttgtatcttg agactttgct gaagttgctt atcagcttaa ggagattttg    98760
gtctgagaag atggggtttt ctaaatatac aatcatgtca tctgcaaaca gggacaattt    98820
aacttcctct tttcctaact gaatacccct tatttccttc tcctgcctaa ttgccctggc    98880
cagaacttcc aacactatgt tgaataggag tggtgagaga gggcatccct gtcttgtgcc    98940
agttttcaaa gggaatgctt ccagtttttg cccattcagt atgatattgg ctatgggttt    99000
gtcataaata gctcttatta ttttgagata tgtcccatca atacatagtt tattgagagt    99060
tcagcatgga gagctgttga attttgtcaa aggccttttc tgcatctatt gagataatca    99120
tgtggttttt gtctttggtt ctgtttatat gatggattac atttattgat ttgcatatgt    99180
tgaaccagcc ttgcatccca gggataaagc caacttgatc atggtggata agcttttga    99240 tgtgctgctg gattcggttt gccagtattt tattgaggat ttttgcatca atgttcatca    99300
tggatgttgg tctaaaattc tcattttgt tgtgtctctg ccaggattg gtatcaggat      99360 gatgctggcc tcataaaatg agttagggag gattccctct ttttctatga ttggaatagt    99420
ttcagaagaa ttggtaccag ctcctctttg tatctgtggt agaattcggc tatgaatctc    99480
tcctggactt ttttggttg gtaggctctt aattattgcc tcaatttcag agcctgttat     99540
tggtctattc aaggattcaa tttctttctg gtttagtctt ggtagggtgt atgtgtccag    99600 gaattttcc atttcttcta gattttctag tttatttgca cagaggtgtt tataatattc     99660
tctgatggta gtttgtatt ctgtgggatt ggtagtgata tcccctttat cattttat       99720 tgcatctatt tgattcttct ctctttcct ctttattagt cttgctagtg gtctatcaat     99780
tttgttgatc ttttcaaaaa accagctcct ggattcattg atgttttgaa ggttttttg     99840 tgtctctatc tccttcagtt ctgctctggt cttagttatt tcttgccttc tgctagcttt    99900
ttaatgtgtt tgctcttgct tctctagttc ttttaatggt gatgttaggg tgtcaatttt    99960
agatctttcc tgctttctct tgtgggcatt tagtgctgta aatctccccc tacacactgc   100020
tttaaatgtg tcccagagat tctggtatgt tgtgtctttg ttgtcattgg tttcaaagaa   100080
tatctttatt tctgccttca tttcgttaca tacccagtag tcactcaggt gcaggttgtt   100140
cagtttccat atagttgagc agttttaat gagtttctta atcctgagtc ctagtttgat    100200
tgcactgtgg tctgagagac agtttgttat aatttctgtt cttttacatt tgctgaggaa   100260
tgcctcactt ccaactatct ggtcaatttc agaataagtg cgatgtggtg ctgagaagaa   100320
tgtatattct gttgatttgg ggtggagagt tctgtagatg tctattaggt ctgcttggtg   100380
cagagctgag ttcaattcct ggatatccat gttaactttc tgtctcattg atctgtctaa   100440
tgttgacagt ggggtgttaa agtctcccat tattattgtg tgggagtcta agtctctttg   100500
taggtctcta aggacttgct ttatgaatct aggtgctcct gtattgggtg catatatatt   100560
taggatagtt agctcttctt gttaaattgg tccctttacc attatgtaat ggccttcttt   100620
gtctcttttg atctttgtta gtttaaagtc tgttttatca gagactagga ttgcaacccc   100680 tgctttttt gttgttttcc atttgcttgg tagatcttcc tccatccctt tattttgagc    100740
ctatgtgtgt ctctgcacgt gagatgtgtc ttcagaatac agcacactga tggatcttga   100800
ctctttatcc aatttccag tctgtgtctt ttaattggag catttagccc atttacattt     100860
aaggttaata tttttatgtg tgaatttgat cctgtcatca tgatgttcgc tggttatttt   100920
gctcattagt tgatgcagtt tcttcctagc atcgatggtt tttacaattt ggcatgtttg   100980
```

```
tgcagtggct gataccgatt gtttctttcc atgtttagtg cttccttcag gagctcttgt    101040
aaggcaggcc tggtggtgac aaaatctctc agcatttgct tgtctgtaaa ggattttatt    101100
tctccttcac ttatgaagct tagtttggct ggatatgata ttctcagttg aaaattcttt    101160
tctttaagaa tgttgaatat tggctgccac tctcttctgg cttgtagagt ttctgctgag    101220
agatctgctg ttagtctgat gggcttccct ttgtgggtaa cccgacctttc tggtgaatc     101280 tgacaattat gtgtcttgga gttactcttc tcgaggagta ttttttgtggc attctctgta   101340 tttcctgaat ttgaatgttg gcctgccttt gtaggttggg gaagttctcc tggataatat    101400
cctgaagagt gttttccaac ttggttccat tctcctcgtc actttcaggt acaccaagca    101460
gatgtagatt tggtcttttc acatagtccc atatttattg gaggctttgt tcatttcttt    101520
ttactccttt ttttctctaa acttctcttc tcgcttcatt tcattcattt gatctttaat    101580
cactgatacc ctttcttcca cttgattgaa tcaactactg aaacttgttc atgtgtcacg    101640
tagttctcgt gccatggttt tcagctccat tagatcattt aaggtcttct ctatgctgtt    101700
tattttagtc tgccattcat ctaaactttt tcaaggtttt tagcttcttt gcaatgggtt    101760
cgaacatcct tctttagctc ggagaaattt gttattacag atcgtctgaa gccttcttct    101820
ctcaactcat caaagtcatt ctctgtccag ctttgttctg ttgctcgtga ggagctgcgt    101880
tccttcggag gagaagaggc accctgattt ttagaatttt cagctgttct gctctggttt    101940
ctccccatct ttgtggttta tctaccttta gttcttgatg atggtgatgt acagatgggg    102000
ttttggtgtg gatgtctttt ctgtttgtta gttttccttc taacagtcag gaccctcagc    102060
tgcaggtctg ttggagtttg ctggaggtcc actccagtcc ctgtttgcct gggtattacc    102120
agtggaggct gcagaacagc aaatattaca gaacagcaaa tgttgctgcc tgattcttcc    102180
tctggaagct tcatctcaga ggggcaccca gctgtatgag gtgtcagttg gcccctactg    102240
ggaggtgtcc cccagttagg ctactcgggg gtcacggacc cacttgagga ggcagtctgt    102300
ccattctcag atctcaaact ctctgctggg agaaccacta ctctcttcaa agctgtcaga    102360
cagggatgtt taagtctgca gaagtttctg ctgccttttg ttcagctatg ccctgccccc    102420
agaggtggag tctacagagg caggcaggtc tccttgagct gtggtgggct ccacccagtt    102480
tgagcttcct ggtcgctttg tttacctact caagtctcag caatggcaga cgcccctccc    102540
ccagctttgc tgccgccttg cagttcggtc tcagactact gtgctagcag ttcaatctca    102600
gactgctgta ctagcagtga gcaaggctct gtgggcatgg gaccctctga gccatgtgca    102660
ggatataatc tcctggtgtg ccgtttgcta agaccattgg aaaagtgcaa tattagggtg    102720
ggagtgtccc gattttccgg gtacatctgt catggcttcc cttggctagg aaagggaatt    102780
ccctgacccc ttacacttcc cgggtgaggc aatatcccgc cttgcttcgg ctcactctcc    102840
gtgggctgca cccactgtct gacaagcccc ggtgagatga acccagtacc tcagctggaa    102900
atgcagaaac cacccatctt ctgctttgct catgctggga actgtggact ggagctgttc    102960
ctattcggcc atcttgaaac ctcccctctc tcacgatcac aaggtccaca aataggccgt    103020
ctgcaggctg aggagcaaga aaagccagtc tgaattccaa aactgaagaa attggagtct    103080
gatgttcaag ggcaggaaac atccagtgcc aaagaaagat gtagaatatt caacattctt    103140
aaagaaaata attttcaacc tagaatttca tatccagcca aactaagctt tataacaaag    103200
gagaagtaaa atccttttaca aacaagcaaa tgctgaggaa ttttgtcaac accaggcctg    103260
ccttacaaga ggtcctgaag aaaacactaa atatggaaag gaaaaaccag taacagctac    103320
```

```
tgcaaaaaca taccaaattg taaacaccat caacactata aagaaactgc atcaactaat  103380
gggcaaaata gccagctagc atcataatga caggatcaaa ttcacacata acaatattaa  103440
ccttaaatgt aaatgggcta aatgcoccaa ttaaaagaca cagactggga aattgaataa  103500
agagtcaaga cccattggtt tgctgtgttc agaagaccca tctcagggtg aaagacata   103560 catgggctca aataaagaa atgaaggaat atttaccaag caatggaaa gaaaaaaaaa    103620 gcagcggttg caatcttagt cttttgatgaa acagacttta aaccatcaaa gatcaaaaga  103680
gacaaaggag ggcattacct aatggtaaaa gtatcaatgc aacaagaaga tctgactgtc  103740
ctacttatat atgcacccaa tacaggagca cccagattaa taaagcaagt tcttagagac  103800
ctacaaagag acttagactt ccacacaaaa atagtgggag actttaacac cccacagcca  103860
atattagatc gacgtgacag aaaattaaca aggatattca ggacgtgaat tcagctctgg  103920
accaagctga cctaatagac atctacagaa ctcgacacca caaatcaaca gaatatacat  103980
tcttctcagc accacattgc acttattcta aaattgacca cataattgga agtaaaacac  104040
ttctcagcaa atgccgtaga atggaaatca taacaaacag tctctcagac caaagtgcaa  104100
tcaaactaga actcaggatt aataaactca ctcaaaacca cacaactata tggaaactga  104160
acaacctgct cctgaattac tactgggtaa ataacaaaat taaggcagaa gtagataagt  104220
tcttagaaac caaagagaac aaagacacaa tgtgccagaa tctctggtac acagctaaag  104280
ccatgtttag agggaaattt atagcactaa atgcccacga gagaaagcgg gaaagatcta  104340
aaatcaacac cctaacatca caattcaaag aaccagagaa gcaagagcaa acaaatacaa  104400
aagctagcag aagacaagaa ataactaaga tcagagcaga actgaagggg ataaagacac  104460 gaaaacccctt taaaaaatta ataaatccaa gagctggtt tttgaaaaga ttaacaaaat  104520
acatagaagc ctagccagac taataaagaa gaaaatagag aagaatcaaa tagacacaat  104580
aaagaataat aaagggggata tcaccaatga tgccacagaa atacaaacta ccatcagaga  104640
atactttaaa cacctctatg caaataaaat agaaaatcta aaagaaatgg ataaattcct  104700
ggacacatac acactcccaa gactaaacca ggaagaagtc aaatcccccga atagaccaat  104760 aacaagttct gaaatcgagg cagtaattaa tagcttacca accaaaaaaa gcccagacca  104820
gagggattaa cagtcaaatc ctaacagagg tacaaagaag agctagtact attccttctg  104880
aaactattcc acacaataga aaagaggga ctcctgccta actcatttta tgaggccagc   104940
atcattctga taccaaaacc tggcagagac acaacaagaa aagaaaattt caggccaaca  105000
tccctgatga acatcaatgt gaaaatcctc aataaaatac tggcaaactg aatccagcag  105060
cacatcaaaa agcttatcca ccatgatcaa gttggcttca tccctgggat gcaaggctgg  105120
ttcaacatat tcaaatcaat aaacataatc catcacataa acagaaccaa tgacaaaaac  105180
cgtatgatta tcgcaataga cgcagaaaag gcctttgata aaattcaata cccaatcatg  105240
ctaaaaactc ttaataaact aggtattgat ggagcatgtc tcaaaataat aagagctact  105300
tatgacaaat gcatagccaa tatcatactg aatgagcaga agctggaagc attccctttg  105360
aaaaccagca aagacaagg atgccctctc tcaccactcc tattcaacat agtattggaa   105420
attctgtcca gggcaatcag gcaagagaaa gaaataaagg tattcaagtg ggaagagagg  105480
gagtcaaatt atttctcttt gcagatgaca tgattgtata tttagaaaac tctatcatct  105540
cagcccaaaa tctccttaag ctgataagca acttcagcaa agtctcagga tacaaaatca  105600
atgtgcaaaa atcacaagca ttcctataca ccaataagag acacagagcc aaatcctgag  105660
tgaattccca ttcacaattg ctacaaagag aataaaatat acctaggaat ccaacttaca  105720
```

```
agggatgtga aggacctctt caaggagaac tacaaaccac tgctcaagga aataagatag  105780
gacacaaaca aatggaaaaa cattccatgc taatggattg gaagaatcaa tattgtgaaa  105840
attgccatac tgcccaaagt gatttataga ttcaatgtta tccccatcaa gctaccattg  105900
atttcttcac ataattagaa aaaactactt tcaatttcat atggaataga aaagggcct   105960 gtatatccaa gacaacctaa gcaaaagaa  caaagctgga ggcatcatgc tatctgactt  106020
caaaatatac tacaaggcta cagtaacaaa acagcatgg  tatggtactg gtaccaaaac  106080
agatatatag accaatagaa cagaacagag gcctcagaaa taacaccaca catctacaac  106140
tattggatct ttgacaaact ggacaaaaat aagcaatggg gaaaggattc cctatttaat  106200
aaatggtgtt gggaaaactg gctagccata tgcagaaaac tgaaactgga tcccttcctt  106260 acacttata  cacaaattaa ctcaagatag attaaagaat taaatgtaag acctaaaacc  106320 ataaaaccc  tagaagacac tttgggaggc cgaggtggat ggatcacgag gtcaggagat  106380
cgagaccatc ttggctaaca cagtgaaagc ccatctctac taaaaataca aaaaattagc  106440
tgggtgtggt cgtgggcacc tgtagtccca gctacttggg aggctgaggc aggagaatgg  106500
catgagctga ggaggttgag cttgcagcaa gccaagattg tgccactgca ctccagcctg  106560
ggcaacagag tgagactcca tcaaaaaaac aaaaacaaaa acaaaaaatc aaaccctaga  106620
agaaaacata ggcaatacca ttcaggacat aggcatggga gaagacttca tgactaaaac  106680
agcaaaacca atggcaacaa agccaaaat  ttacaaatca gatctaatta aaataaagag  106740
cttctgcaca gcaaaaaact ctcatcagag tgaaaaagca acctatggag aaaaattctg  106800
tggtctagcc atctgacaaa gggctaatgt ttagaatgta caagcaactt aaacaaatgt  106860
acaagaaaaa aaaacaacc  ccatcaaaaa gtgggcaaag gatatgaaca gacacttctg  106920
acaggaagac ctttatgtgg ctgacaaaca tgaaaaaagc tcatcatcac tgttaattag  106980
agaaatgcaa atcgaaacca caatgagata ccatctcatg cccgttagaa tggcgatcat  107040
taaaaagtca ggaaacaaca gatgctgaag aggatgtgtg gagaaagagg aacacattta  107100
cactgttggt gggagtgtaa attagttcaa ccattgtgga agacagtgcg gtgattcctc  107160
aaggatctag aaccagaagt accatttgac ccagcaatcc cattactggg tatataccca  107220
aaggattata aatcattcta caataaagac acatgcacac gtatgtttat tgtagcacta  107280
ttcacaatag caaagacttg gaaccaactg aaatgcccat caatgataga ctggataaag  107340
aaaatgtggc acatatacac tgtggaatac tatgcagcca taaaacagga tgagttcatg  107400
tcttttgcag ggacatggat gaagctgaa  accatcattc tcagcaaact aacacaagaa  107460
cagaaaacca acaccatat  gttctcactc ataagtgtga gttgaacaat gagaacacat  107520
ggacacagga aggggaacat cacacacagg ggcctgttgg ggagttgagg ctaggggagg  107580
gattggatta ggagaaatac ctaatgtaga tgatgggttg ctgggtgcag caaaccacca  107640
tgacacgtgt ataccatgt  aacaaaccca cacattctac acatgtatct cagaacttaa  107700
agtataataa taataagata cagaactgca gaatgaataa gaactcacca accatctgct  107760
gccttcagga gactcattta agacataagg actcacataa acttaaagta aatgggtgga  107820
aataataata agtggtgtca ctgatgtgga ggtagattat aaaactctta tcatatgctg  107880
gtggaagatc aaaatgataa aacgaattaa aaaatcagtc agatggtttc ttaaaaagtt  107940
ccatcaatat gcctctatct tacaaacctg caattctatt cctgaatctt tatcccaagg  108000
aaatgaaaaa gtaagtccac aaagagttct atatgaatat ttataggagc tttattttatt 108060
```

-continued

```
ataattcaaa ctgtaaaaat aatttcaatg ttcatcaata acaaaatgaa aaataatttt   108120
gcaacctact ggtacacttg aatactattc agcactgagt atcttaaata gcatggatgg   108180
agctcaaaaa tatactcagg aaagaagcca tgtatattct gtatgagttc atttacatga   108240
gatcatttac atttcctcca aaagaggaaa aactaatttc tgttgaaaga aaccaatgta   108300
tttgcctctg gcagtggtaa gggggtagca cagattaatt gggtagggac tcaagagagt   108360
ttctggggtc acagaaatgt tccgtgtggt gatgggagtt tgggctccac aggtataggt   108420
gttgatccaa aatcatcaaa aaacaacat tgcagatctg tgcatctcac tctgtgggaa   108480
agtatatctc aactgtaaaa agggcagaaa ttgcttttaa acgctcagcc ttttagcaca   108540
tccagttgct tggagaacca gcttactcaa atggggtct aggctggaga ctaggtcaca   108600
ggcatagagt ctctaaactt tcccatggca cataatacgt ttcaggtttt ctcagagagc   108660
tgcaggttag taatctgagg attctgacaa gttgggtcaa cgttcctagg aggcatgaat   108720
gggagtgcat tctctaagat ccctccaccc cagggtcctt gctttctgtg cctcttactc   108780
cattgttttc tgactcctct gtagccactc gacctcttca gatcccattg tctacccagc   108840
catcgccctt tatgacttgg gtcccactgt tctttcatct catcctccat tccctcagtt   108900
tcggagtggc tgccgctagc agaggatgga ctgagagcag gagaggtggt cctgcccagg   108960
aacccatcct agagaaatgg catcctgtct gggagctagt ttttagggc aggttttata   109020 agtcttgtaa agccagacac acttgatcta cctggtatgt tatttacagt aatactattt   109080
tcataattgc ttttcactct aaaagtagag cctttagct acactgtgag taaataaagg   109140
ggctggcctg ggaatggtat catgttggat gttgtttctt ccctgaagta atatatatca   109200
gttacaattt acatgttact gcagagtcct agagagagac acagagaatg agacagatac   109260
caatacattt ttatgtgcat taaaaaaatc taaggccagg cgcagtggct cacacctgta   109320
atcccagcac tttgggaggc cgaggtgggt ggatcacgag gtcaggagat tgagaccatc   109380
ctggctaaca cggtgaaacc ctgtctctac taaaaataca aaaaattagc caggcgtggt   109440
ggcgggcgcc tgtagtccca gctactcagg agactgaggc aggagaatgg cttgaaccca   109500
ggaggcagac cttgcagtga gccgagattg cgccactgca ctccagtctg ggcgacagag   109560
cgagactccg tcacaaaaaa aaaaaaaat ctaaatgca ctcttcaaaa tctatgtcat   109620
ttattctgga ggaatgcagt tggcagaagg aggaagatat tccgaatttt tcttgtatac   109680
atttatgtat gatctcagtt ttttttatgga tcatagacca attttgatat tttaaaataa   109740
aaattataat ctatcttgga aatttacatg gttctttaga acttgaggac cgttttgct   109800 tttcggaata ttattgtacc taaaatggga atattacaac gtcactttt aacactttgt   109860 tataacaaag tttagacagc gctgggtgcc cctgaatttt ttcccgcctc ttgtgacctg   109920
tgttgttttg gaatttgcag tggcctgacc gagaactact gcaggaatcc agattctggg   109980
aaacaaccct ggtgttacac aaccgatccg tgtgtgaggt gggagtactg caatctgaca   110040
caatgctcag aaacagaatc aggtgtccta gagactccca ctgttgttcc agttccaagc   110100
atggaggctc attctgaagc aggtaagaag tctgtggcca gatatctaca catttgaaca   110160
ttgggatgaa aagagatgga aaatctgact gatgcagaag ccttccatgc tacacagaaa   110220
cttgagggta tggcaggtgg aaagaagcct cagcactctc tctggtggag caattttgg   110280 cgcaacgtgc gtgggcggtg acttcaggaa tggtgcaaac ccacctgggc acttgactta   110340
ccactcactt tgttatgaaa gggggttatct cggtgttcca gacaaaattc caattctaac   110400
atcaggccaa atttgtgcca aatttcacac tagtgagtgt ttccaggcat ttattaaaat   110460
```

```
ggacagtgtt cattgcaatc ttcagcattg cagttgctga ggtatgtggc cgctgagttt 110520
gtcatcctgg ggaaacctaa tatgatgata tttattccat ctaatcctgg ggctatttgg 110580
cagtaaatac cacagaatac actatttctc tggcttattt cagtcttagg taggctctgc 110640
acacctatgc ttggaaggca ggaatttctt ggtgttcttg tgccttcttc tcatggaacg 110700
tgcatctttg gtgtgtgttg agaggaaggg tagtagactt ctgctttgtt gcaatgcagg 110760
atgctggaac aagaggattc cctgtctcta ctgtaaggga ataagatttt agcctccatc 110820
cttctctaag aagcaatgtg tctttgcctc caagtactag atgcaggacc atgaactgcc 110880
ccgtccacca gaagcttaag gctttggctt ttcaggagca atcatctagg gaactgtgca 110940
gggttttcat gtctgtcccc tactgacagc caatcaccat acagcctgca taacctaatc 111000
catcatcgtc tggtttcctg cctcattgtt ttcatgaaca accagtagag agccatacga 111060
aagagcttgc acatgagtct ttgttccaat tgtaagagca ctgataggtc cttttcccac 111120
caggttttga atataaaatt tctaagaact tattaaaata ttagaatgtt attaatctat 111180
tgtttttgct tcagcatgtc cttctgcttg tgagtatact aaagagaaca gtcataattc 111240
tgaaactact gtcctgtttg tgtcataaat tgcttcacat gtttctgcat actagtagtt 111300
actcagcttg attttgtcta ttttcagcac caactgagca aacccctgtg gtccggcagt 111360
gctaccatgg taatgccag agttatcgag gcacattctc caccactgtc acaggaagga 111420
catgtcaatc ttggtcatcc atgacaccac accggcatca gaggacccca gaaaactacc 111480
caaatgagta tgtctttgat gttacttgta agaggagcaa cagccaactt aagttcctcc 111540
tagaagagcc ttgcttcaag ctaacttgtt aggacaaatt tcccttagac ccagaaggtg 111600
tgtcaaaatg tccagacaac tttgcttttg atcaaagagt ctgagagaat aggtattta 111660 ggcttgctat cttttctaat agtctgatgg aagcagaagg ctacatggag ctgatgaggt 111720
ctttttaata taaagctcaa gagatcaaat gatcaaatac ttagagtgcc attctacaag 111780
gctcataaaa gatcaatgca ctctttcacc catgcaattc tatcattcta acctcccttc 111840
tctgaaatga aggcttttg ccattttgt catgggtcac aagtaaataa ttcacatgta 111900
tatgagtata tatataacca ggtgtgttta ttcagactag tatgtatata tacatata 111960 tatgttcata taagttagta ttcatatata tgttcatata tatatgttca tacagactag 112020
tattcatata tatatacata tatatataca cacacatata tatatatata tatatgttct 112080
agggaaacat gcaaggtttt tatgtctgtc cctgactgat gaccaaatac cctatagcct 112140
gcacagctgc aagctgtata gccatacaat ttgcaggaca cacacacata cacacacaca 112200
cacacacaca cacacactaa catataatat aatataatat aatataatat aatataatat 112260
aatataatat aattaatata tataaacctg tgtgaacaca ctgggttcta agctccagtt 112320
ttctgaaggg atatggggttg ccaggagagg aagagcaaaa gcaagaatgt agatgagaat 112380
taggaagtaa acagatatgg agattaaaat gggcaggtac atggacaaaa aaccaggtct 112440
gacaaaaact ggctttctgc cataaatgac tataaaagat attaaaaaac actttccaca 112500
tgttggacaa gagacagtac aggactgaga taatttagaa aaggaaatga atgagcgcaa 112560
ctccgtaact attatgactt tcttcctgga gaaccttcct ggactgaagg gcaaggaatt 112620
ggagccaaag ccaaccacag cagtcttgct gaactgagga aagagactgg agtttgggat 112680
agctaagaaa atgtgtattt tctatgctag gtaataatga gaaagaattt gtggtgaaaa 112740
ggagctgaag gaatatgcat ggaagtctaa tataaactgc atatgcacag ggagaaattc 112800
```

```
tacaaagtgg gacagagaac cactactggg gaaaggacaa attcagggaa acagtgagct 112860
caatggtgac gccagagctc acgtagcact gggggatacc gggggttctga tcagcccgag 112920
gagagacacc tcattgaaca tctcgggcat tcagtagaga ccccagaaaa gtcatacttt 112980
aggagtagga tttatgcctt cttagaataa agactacccc agaaacaccc tagtaaagct 113040
taaaaaccaa gtctaaaagg acccaaatga tctccaagta aattaactgc ctgacagaag 113100
aaaactcaac catcactgga ggtaaataac atgattacag tgctctgtaa tgttgcattc 113160
acaaggagtg acatcattta aaaatttatg aggcaggaaa aagcaattag tgtgatccat 113220
aactaggaga aaaaccagtc aatacaaata gaccaagaaa tagtagaaac gatggaattg 113280
acaaagaaat taaaactgta tatatgataa ttgtgttcaa agatttaaag aaaacatgaa 113340
catgagggaa acaaatgcag aatataaaaa aaagcaaatg cgtaaaacaa ccaaatggaa 113400
attaaagaac tacaaaaaag tataaccctta ataaaatact cactggatgg ccttaatatt 113460
agtttataca ttacagaaga aaagtgaac cagaagataa ctcaatgaaa gccatacaat 113520
ctgtaagaca cacacacacg cacacgcgcg cgcgcgcaca cacacacaca cacagagaga 113580
gagagagaga gaaagagaga gagagaaagg ctgaaaaaaa taaatagaac cttaaggata 113640
tcagtgaaaa tagcaaaaga tttaatatat gggtaaagca agtcacagaa ggacgggaag 113700
gagatattgg gacagaaaaa aatactcaaa gcaatgatgg ctgaagactt tacacgtatg 113760
aagaaaatga taaactcaca gtcaagaagc tcaatgaatc agaaatagta ttttttaaaag 113820
caaaactcta tgatttactt gggtacatta tagataaatc gtccaacatc aaagataaca 113880
aggataatct tataagccag aggaaaacaa tatcatttac atagagggac agtaatgaaa 113940
gtgaccgatg ccttctcctt ggaaacaatg gcataacatc tttaaagtga taaagagaaa 114000
taaaaacaga tcaacctagg acgacatgtc cagccaaaac aaacaaataa acaaaaaaac 114060
cctttaaaat aaacgtgatg taaatacgta ttctgccacc tccagaggaa acaagcaaaa 114120
aaacaaaaga atgttttccaa ggcaggcttc tgtattaaaa gattttaagg aaagttattc 114180
aggtagaaga aaaataatac cagatgggaa ctttaatcca tactaagtaa tgaagagccc 114240
tggaaatggc aaatggcaat gtcaatataa aatactctta tttatctaat ttttaaatgt 114300
atttaaagga caatttgtga tattaattaa aataatagga atatattgtt gtttcaacgt 114360
atgtagtagt aaaattcata aaaacagtag cacaaataat gcagatgata actgaagta 114420
tactgttaat gagttttttg cattatccat gaagttatat aatattaata gatggttgaa 114480
tgtgatagtt taaggtggga tattataaat cctaggacaa ccaaaaaat ttaaactgag 114540
aggaatggat agtaagagga atagtccttt tatgcaaaag aaggaagaaa aagaggaata 114600
aagaatataa aagatatggt gtaaacagaa aatacatagc attattgtag acacaaactg 114660
aactaccta tgagtatatt aaatataaaa ggattaagca ttacaaataa aaggcagaga 114720
ttgtaaattg aataaaaacc acagctaagt gtgttctttt tagaataaat actctttaag 114780
tgtaaagatc tactttaaac accaaaatat gaaaaggat atataccatg aaaacctgaa 114840
tcataaataa gctggagtgg tgattaatgg atgcaggcac tcctaaagac taataagtga 114900
atgtggtcaa attgaagaaa caaaagtata tacgtgctca atgtgcaaaa acttttttctg 114960
tatacatgct atgatccttt ggaaaattaa agttttaaag caatatcact gacaatagta 115020
tcaaaaccaa aaaatattta gtgataaatt tcacacacta tgctcaagga ctatacacct 115080
tgcactagaa aacaatgttg aggaaagaat taaaagatct aaatatacac catgcttata 115140
gattaaaaga ctccatatca gttctcgtga aattgatctt tggatgaaac ccacacccaa 115200
```

```
gcactattgc aacagtcctt ttttggaaaa aaaaattgga ggacttatat accttaatat 115260
aaagacttat aaaagtacag gaatcaagac atgtggtatt ggcctggccc cttggctcat 115320
gcctgttacc ccaacatttt gggaggctga gtctggagga tggcttgagc ccagatgttc 115380
aagaccagcc ttagcaacag agtgagaccc tctctctaca aaaataaac aattagatcg 115440 atgtgatgac ttgcacatgt agtttcagct actcggaatg ctgaggtgag aggattgctt 115500
gactcaggag gtctagccat gagtgagcat tgatcatgcc tctgcattcc agcctggatg 115560
atggaatgag acactgtctc aaaaaaaaaa aaaaaaagg atatgtgtta ttggccaaaa 115620
aagtatgcaa acctaaaaag ggatggccca ccaccagacc cacatacata tatggtaaat 115680
ggattttccg tatagatggc aaagcaattc aatggagaca aaaatgtttt acaaaatcat 115740
tctgaaccat ttggatatcc atgatacaaa acaaaagcag aacttgactt ttgcttttca 115800
tctcaaatta ttttgatatc tcttccacct aagtgtcaga gctaaaactg aacctgaaat 115860
atgaaagttc catgaaaaaa tataaaatct tcacaaccttt ggagaaggca aactttttttg 115920 aggcaggagt ctgtaaacac tcactataaa ataaaacaaa ttataatgtg ggctttcatg 115980
aaaactcatg cttaccaaaa gtcattgtta agaaaataaa taggcaagta acacatgaga 116040
agaaaaatgc tctctgtcca tatatctgac aaatggcttg tgtccagaat ataggaacat 116100 ttctccccact cactaaacag aggacaaaca actaatgggc aacagattga ataggcattt 116160
cttggggata gatagatgta cacatagcca ataagcacct gaaaaaatgt ccagtatctc 116220
agccatgaaa aataaagagt tataatcatc atgagatgtc accaacacc caatggacat 116280 ggatattatt aagaagacac cacagtaact gatgtcactg atgtagagca aggatgtgaa 116340
actctctcat atgctggtga aagtgcaaaa tgatacaacc acttttgaaa tcagtctgat 116400
agtttctcca aaagttcaat aaatgcactt ttaccctaca aacctgcaat cctgttttgtg 116460 aatatttacc ccacagaaat ggaaacataa gtccacgaag acatctccaa gaatattcat 116520
agcagcttta tttttttataa ccccaaactg tagacaattt caatgtcaat caataagaaa 116580
atgaataaat aatttgtgaa ctagtcatac aatggcatac tgttcagcaa taaagggag 116640 catgttttttg atactctcaa atagtatgga agatgctcaa aaatattaca ttaaagaaag 116700
atgccagata acaaaaatga acattatgta tgagtctatt gatgtaaggt tccagaaagg 116760
taaaactaat ttctggtgaa agaaaccaat atcatttgcc tctggccatg ggaagagagt 116820
agcagagatt gattgagcag taaaacgaag ttttttttctg gggtgatgta aatgtcctgt 116880
attgtgattg aagtgtgagt tacacaagtg tacatgttca tcagaagtca tcaaactaca 116940
tctaagatct gtgcatttga ctatacatga aaatatacct cagttgaaaa tagatcaata 117000
acctccctca tatactatac ttgctaacac agccagctgc ttgagaacc agcttgctgg 117060 aatggagaat ctgggcttga gactgggtca catgtataga gtctctacag agacaatgtt 117120
gcattcccac ggtacataat acatttcaag gtttctcaga cagccacatg tcatgaatgt 117180
gaggattctg agaggttgga gcaacattcc tgggaggaac gaagggagc acattctcca 117240 agatccccca ccaccggggt cctcaccggc tgtgcttttt ttttttttttt tcttgacaga 117300 gtctcgctct gtcgccaggc aggagtgtaa tggcccaatc tcggctgatt gcagcctcca 117360
actccagggt tcaagagatt ctcctgcctc agcttcatga gtagctggga ctacagatgt 117420
gcgccactgc gcccagctaa ttttgtatt tttagtagag acggggtttt gccatgttgg 117480
ccaagatggt ctcgctctgt tgacctcgtg atccacccgc cttggcttcc caaagtgctg 117540
```

```
ggattacagg cgtgagccaa agcacccagc ctgtgcctct cacttactca attgtttttc 117600
tgaaccctcc atagctggtg gaccttttca gatcccatag tctagccagc cctctcactt 117660
tatgccttgg gtcccactgt tccttcatct catcccsctt ctgtcagtcc cgcagtggct 117720
gtggccagta gaggatggac tgagagtagg agaggaggtt ctgcccagga acccatccta 117780
gagaaacagc atcctgcctg ggacctagtc ttccaggtca gcttttataa gtcttttaga 117840
ctcaaactca cttgacccac ctgaagtggt attgacaata atgctatttt catggttgtt 117900
tttcactgta aatgcagagc cttttagcta cacgactagt acagagagta agggaggctg 117960
gcctgggaat gatatcatct tggatggcat ttcctccttg gagaaatata tgttagttcc 118020
aactcacatg ttactataca gtcctgtaga aagagataca gagagttaga caggtataga 118080
cgcatttgta tatgcataac aatctataag acacacatca aaatccgtat accggttcct 118140
ctaggggtat gtgcttggca aaggtagaa ggagggtatt ctggttcctt tcttttgcac 118200
atttatgtat gatctcagtt tttatatgga gcattgatag ggtttggcta tgtccccacc 118260
caaaatctca tcttgacttg taatctctat aatcctgata atccccatgt gtcaaggca 118320
ggaccaggtg gaggtaactg gatcatgggg gcagtttctc ccaggctgtt ctcatgacag 118380
tgagagagtc tcctgagatc tgatggtttt gtaagtgtct ggcatttccc ctacttgcac 118440
ttactctgtc ctgccgcctg tgaagaaggt gcctgtttct cccttgcctt ctgccatgac 118500
tgtaaatttc cagaggcctc cccagcaatg tggaactgtg agtcaattaa aactctttc 118560
tttgtaactt acccagtctg tctcgggtat ttcctcatag caatgtgaga acgggctaat 118620
acaagcatat actactttg atattttaaa ataaaaatta tcatctatct ttgaaaggca 118680
tgcacaaatg ggaagttgag gaacatttgt gttgtggcaa ttgtatgata cctttaatgg 118740
gaatatttca aagacacttg ttaagactt gttagaacaa aatgtagagg gtgctggatg 118800
tccctgaata ttcttccgcc tcctgtaact tgtattgctt tggaatttcc agtggcctga 118860
caatgaacta ctgcaggaat ccagatgccg atacaggccc ttggtgtttt accatggacc 118920
ccagcatcag gtgggagtac tgcaacctga cgcgatgctc agacacagaa gggactgtgg 118980
tcgctcctcc gactgtcatc caggttccaa gcctagggcc tccttctgaa caaggtaaga 119040
agtctgtgtc ttaccttgtc tagcacatac ctctctatgt gcttggacaa cgggatgaaa 119100
agacatgaaa aaccacactg atgcagaagc ctttagtgct acacgggagc tcgagtgttg 119160
gttgaggttc tgccatgacc aaggaagtct cagtgccgtc cctgggaaag ccagagctgt 119220
gattttggc acaacttgtg ggagtagtga ctttaggact ggcgcaaaac ctccaggggtg 119280
ctcaacttaa ccactcacct tattctaaaa tgggttattt cagtgtccca gtcaaattcc 119340
tattctaaca tgctgtcaac tgtgtgatta tttccaagcc aataagcatt tccagtaatt 119400
tcttaaaata gtgttcattg cagtcttcag cgttgtggct cctgagggat gtggccctg 119460
attctgtcgt cctagagaag cctgacatga ctgcattgat tctgtatcgt cctgggtcta 119520
tgtggctgcc tggctgtctg taatcatctg ttttatttt atttttttct acagactgta 119580
tgtttgggaa tgggaaagga taccggggca agaaggcaac cactgttact gggacgccat 119640
gccaggaatg ggctgcccag gagccccata gacacagcac gttcattcca gggacaaata 119700
aatgggcagg tctggaaaaa aatgtaagcc actttgattt ggactctttt tccctttgct 119760
gacaaatctt ttcaaacaga agaggggcag aggaaaatac tggaaagact tcaggaggct 119820
aagcgtaatt agccttagca tggaaagtgc aagcagcaca ggccagcaaa gccccacgcg 119880
tgtgggggtt ctcaggcctc ttctcttttg acatttcttt actgtttcca ttgttgggtg 119940
```

```
ctgtttctcg tttctagtgc ttgtcctcta agccaggggt ccccactcca gtactggtac 120000
tggtactggt actggaactg gtaattatct gtggcctgtt aggaactggg ctgcacagca 120060
ggaggtgagc ttcggggag caaacaaagc ttcatctgta ttttctgctg cttcccatca 120120
ctctcatagc tgcctgagct ctgccagctg tcagatcaga ggcagcatta gattatcata 120180
gcacaaaccc tattgtgaac tgcacatgtg aggaatctag attgcatgct ccttatgaga 120240
atctaatgcc tgatgatctg tcatgcttcc atcaccccca gatgggacca cctacttgca 120300
ggaaaattag ctcagggctc ccactgattt taccttatgg tgagatgcac atttatttca 120360
ttatatatta caatgtaata ataattgaaa taaagtgcac gataaatgga aggtacttga 120420
gtcatccttt aaccatcgcc ccctcacccc aggtgcacag aaaaattgcc ttttatgaaa 120480
ctggtctctg gtgccaaaaa agttggggaa ccacactgct ctgggttcta gtagtcagag 120540
atgccctcta tgaggcttaa gtcagatttt tctagaaaag atttggatgg ccatcaggt 120600 caccatgaga cttcccttag cctcatgcat tctctgtgat ggtttacttt ggggcctatg 120660
aatagggaag actgagatat aggaaaaacc aaagtgtctg tgttccccca ctctcacacc 120720
catgtaacat aacacttctc acaccagata tggggggatt tctcctcaca ccccaagcga 120780
gtctccagca gataccagct gggtgtccta caatgtaact cggtcctgac actctatctg 120840
gagacagtgt cagatcccac aagttaaggc tcagtcctac aagactgccc cactgcagat 120900
gccaatccca agttgcaggc tgtgacctgt acttctgccc agctggataa agatctgttt 120960
ttctatatga ccctccatgg gtttgattac tttgctagag tggctcacag aactcaggga 121020
aacacgttac tttttatttac ccattttatta taaaagatat taaaaaggat cctggtgaac 121080
agccaggtgg aagagatgca cagggcaagg cacgtgggaa ggggctcaga gcctctatgc 121140
cctctccagt gcaccagtcc ccagtaccct aagtgttcag caacccagaa gctctccaag 121200
tgcagtcttg ttgggttttt atggaggctt cattacagag gcacagttga ttacatcatt 121260
ggccatcggt gatcggctca ccttcggccc ctcttccctc cctggaggtt ggagggtggg 121320
gctgaacagt tccaaccctc aagtcacatg gttggttccc ttggcaacca gcccctgggg 121380
ctatccagga acccaccaag agttgcttca ttgcagctcc cttcacccag gaaactccaa 121440
gggatttagg agctctgtgt taagaactgg ggggcagaga cccaatatac atttcttatt 121500
ctatcacaat atcacaggaa gctaaggatg atactgcctt tgtgtgtctt ggctgtggat 121560
ggtgcataat gcatggaagt aagcatttct gaatcaacag caaacaggct ttatcaggta 121620
gaagacccct cagcgcccca gggacaaagc tcatcaatga tgtcccactg tcctctgagg 121680
ctctagctct aagacctcca gtgggtcaag ctcctggaga agtggcacat tctccaaaga 121740
cccttcaggg tcaccacacc ctggttaagg gtgtggcctc ataactcctt ttgactatga 121800
ctgatggctt acagcataga aagaaataac tttgtcaaaa aatataataa tgatagaaag 121860
gaagaaggaa cgctcccttt tgtcttctaa gaatagatgt gaaatgtgtg tgccttagaa 121920
tatcttctcc ctctcctgct ccacgtgagc tggagcttac atgcctgctt gttttcagta 121980
ctgccgtaac cctgatggtg acatcaatgg tccctggtgc tacacaatga atccaagaaa 122040 acttttttgac tactgtgata tccctctctg tggtaagttg ccttctgttt tggtaaggaa 122100
actgcttcct taatatggat ttggaaaaaa aaagcaaaa aaaacagaaa atggcttttg 122160
agctgagtgc ttctggggag gagatggctg ccctctccac cagagcctgc ttttcatcat 122220
ggccaccttg aacctgccct actattggcc ccatttgtta ggaaaacacc cgcccctccc 122280
```

```
accacacaca cataaataaa ataaatgtca aattcccaaa gggcaaactt agaggtgatc   122340
taatcagccc gggatagtcc caccgaaccc ttctttgtct agcgtgggat gcatgaaaaa   122400
caaatttaga gtcattatga tgaaaaactg tcctcttctg cagctgagaa gaaaaaaaaa   122460
atacgagcag caggaaacag ctaagcatgt aatgcacatt gtaaacctca gatggccatc   122520
ctaggaaatc aatgaagggt agtgcagctc tttagcccca gatggccttt ctcgtaagat   122580
tactactcat gagtcccatt agcgacattg cttagagact gcttgttagg ttccttcctc   122640
attgctctga gactcttatt gggagtatga ggcttggatc aggggaaggg gaattgacat   122700
tagatcttaa atgattgggg taacaaatcc atgggggaaa aaaagccact tgtacttgtt   122760
ccctattttc ttcctgctga ccaatcaact tgtctgtccg agttacagaa caccaccctg   122820
gacttttctt ttgtgtaatt tggttgcttg tggttgggtc tgccatgtga agggaccttg   122880
agctggggga agaaggttgg cctccaagtc cactgaagac cagcatcctg agattgcctg   122940
gggaggtggt acagggcagt gatgaagatc atgggagcca cactgcccat cgtcacattt   123000
gggccactcc tggggagagc aagagggaag aaggagaggt tagggtgata ggaaagattc   123060
tacttggcca atattattat aatgtggcat tgtggtctct ggatttagtg tgagttgata   123120
gctgactttt ttctcgagtg ggtgcttttg ttctattttg tcggtgctat tgcagaagca   123180
tcttggtggt tcctctacct caaagtctct tgatggggtc agttccagtt ctccgcttct   123240
ggccccatct agtacacgcc actgcctctc actgcctggg ctctctatcc ttgacaggct   123300
gccttgaatt taagcccagt ctgacttacc tgcctcaaac acccacagta gtgcctggga   123360
ctcatgcacc tttgactccc atggaaggga agtgcagtag cttcccaggt gcaattctgc   123420
tgtcctcacc cacattgagg atgtatgaga atcaggttct tagagattgg agaaagaagg   123480
aagaatggga acaagatttc ttccaatgga ctgtgaggtt ccccaccttc ctttgatgta   123540
agacaagtga ggttaacccc aagcctggtg aggagggttc ccatcagaca cttggaaatc   123600
ctgaggactg tttcctgcag aaggatgtgg ttggtgggat attcaggttt gactcatgat   123660
tgagaaagtt agagcctctg gttggagaaa gagtttaata actatttcat ttccaccaac   123720
acattcagta cgaataataa ataagtaaaa ataaatagaa acattcagtt ttattttgaa   123780
tagtaggagt agggtataat ttctgtagtt actcttttag tacaatgatg catgtttact   123840
gtatgtaagg catactagca gaaattgagc tcagcactag aaaagatgat tgcattccat   123900
gccatgcttc ttttttacaa aagacttcta tagatagatt ctcaaaacaa cccacagcaa   123960
atgaaaagtt atttggaaaa ctcaggttcc agattcactg gagtgtagaa tctctggttg   124020
gttgggagg aatttcctct tgcagttgtt attaataatt atatgaataa ttattaacta   124080
tattaatatt tatagttttg aagaccttga agggctggag acaacagaga agcattttg   124140
aacaccctct gtagcccctg cactgttgta ggcattgatg ggtggtacca aagatgggac   124200
actttcccta cctccagaga ccttgtgggc ttgctgcaga gagaaggcag ggaggaggaa   124260
aagaagaata gaggcacatg tgtgtaaatt accccacag cagtcagtta gtcatgggag   124320
gctccccaga agaactgtcc tgaagctggc tgagagaagg caacatttca acataggaca   124380
gttatccttg ctacataaaa tcacatacac acatgcacat atgtccacac acagagactc   124440
acatgcaaaa gaatcctttg tgcctttcag taaactttac atggtttaga aagaacttat   124500
atttccttga aaggagagtg tccttgttg tttactacca cttttaaac ttagaaagaa   124560
aaatctaaag agtgtttatg attttaccat ttaatttcac ctttgagatg tgaaaaacta   124620
gtgcttggaa ttcgtcctga attaaacgac acaattgcta acttggactc aaatgcgact   124680
```

```
tcttttccca ccttgtgcca cagcatcctc ttcatttgat tgtgggaagc ctcaagtgga 124740
gccgaagaaa tgtcctggaa gcattgtagg ggggtgtgtg gcccacccac attcctggcc 124800
ctggcaagtc agtctcagaa caaggtaaga acaggcccag aaaccatcta tactgtcctt 124860
ccatgtaagc cccacaaaac ccttctacat ttacacagaa cccacacagc tgatgcatca 124920
atacctgcct ctctgttttc tgaaggagga aaaatatag aaaaattaaa aaaagttata 124980
ttattatagg ttctctactt ggaaaatagc caaaatacaa atcttttttct tgatctgggc 125040 agttccatca aaatctgtag gcacagtgat ttgcaccaag ttccaatact tttggaaaat 125100
attgaagatg ctctgagggt ttctatggat atccattgtc tcactgtcag atgaaaagaa 125160
agggaagttt ttagaaatgt gacactttgc agtgagggag acaagagca aacttaccta 125220 cagtctatca caggcacaga ttttttttta cacttttgtg aatcattgaa ttcaatgccg 125280
aggctattca tctattcaca aacacatgaa caaattatgg gttgtgatcc ccataaatga 125340
agagtaatca gtccgaaccc acagaacctg gacattttgg gtatcgtttc agtggaacat 125400
gcaattcgta agttcagttt gcttgggtgt ctcttaggaa gaacacatag gacacagacc 125460
catctgcctg catgttttgc ttcctcatct cctttctaca ccagggcacc tgtgctcaat 125520
tgctgttctc ctctaaagag acttccttct gtaagtttgt gaaatgccat cgacaaacct 125580
gatcgcatcg catttcactc tgctgttgag ttgatttttc tttactttat cgtttgtaac 125640
ttcttgctct acagagcttt caccttccac atatttcaga ttcattcttt cctaaactgt 125700
gtggtggtct atgtcctcac tgactatcaa catactgcca tcatgcactt cctatctcta 125760
ttcctcttcg ttgcaatctg gctccaagtg gctcacacca ttattctgat ctatcaactg 125820
cctacacagt cctagaaagt aagtgagtca agaaacatcc cccaaaagta aacttttcag 125880
gtaagatcag aagaccctca tgagtcactg ctgctcagga tcgtatctgg ctccttgaag 125940
agtgaccttg catagatctt gtcataaaaa atgaaagaga ccttgggaag gtcttgggct 126000 ggtcacttt tgtcagagtcc agggctgtgg ggtgaaagcc acagctatag agcttcattc 126060
tggagtcact tagctttgct ctcctgggga caggctgtgc ctattcttgc ctcaggcatc 126120 aaaaaagtg gcacagatgg gcccttctga aaaatctcac tactggagca cagctcgaag 126180
tttctactat cctgacgttg ggcggtagtc ctttgctttg ggaatatgaa catgatcaaa 126240
actgagtgaa cttgtcttcc tggctttctg tacaatgaag tagaacaaac catccaattt 126300
gaccaaagcc ttggcatgtt ttcttctag gtttggaaag cacttctgtg gaggcacctt 126360
aatatcccca gagtgggtgc tgactgctgc tcactgcttg aagaagtacg tttaagggaa 126420
aactgacatg gggtcttatc ttcaagactt ttttcctccc tctcttcctc catcccttct 126480
ttcttcccac cctcccсcttc cttcctcccc acctctcttc cttttctgga aggaacacta 126540
ggaaccaggg aatgcatgca gaatcctgag gcagaatttc cagggcaatt ggatgagaga 126600
ggagggaagt gtttctagag ggaatctgca gagggaagac ccagtgcaag tgatttttg 126660 gacctgtata aaccgcagga cagagctgtt cactaccaga ggcatcaatc tgtattgcat 126720
tgctctagag caatatctga ggctgaataa tttataaaga aaagagttta attggcacat 126780
gtttctgcag gctttacagg aagcaggatg ctgtcatctc ctctgcttct gtgtgggcct 126840
aaggaagatt acaatcatgg tggagggcaa agtgggagca ggcatgtcac atggccagag 126900
caggagcaag agacagagag agatggggtg ggggtgctgc acaataccaa atgaccagac 126960
tttgcaagaa ctaagagtga gagctcactg atcaccatga agatgtggcc caagccattc 127020
```

-continued

```
aagagggatg cacctctatg atccaaaccc ctttcacagg ccatagctcc atcactgggg 127080
actacagttg aacacgagat ttaggtgggg acaaatatac aaactatatc acagtctctg 127140
atgaaacaga ttgagaacag accttaactg tcagtttcca gcaaattgtg aattttgttt 127200
cttgccactc ataagtcact gattctgggt ggccgagggt gtcagaggga cagcgccaag 127260
ttcatggcac agaggatacc tgaaggggct ggaccatatt tttctcttga catcctcatc 127320
ttttctaggt cctcaaggcc ttcatcctac aaggtcatcc tgggtgcaca ccaagaagtg 127380
aacctcgaat ctcatgttca ggaaatagaa gtgtctaggc tgttcttgga gcccacacaa 127440
gcagatattg ccttgctaaa gctaagcagg tactcgctca cctgtggtct tcacccacg 127500 ctggtgaaga tatttgcttt atgtctgggt tttatgggcc atggccactg catggcagtg 127560
gggaggaact gtctatcaca tgaaaggctc aagggctttg gggacagcat caatcttcaa 127620
ccccagccct gccacatgtt agttgtgctc tttaaaaagg cagaaggatt cgtttcctca 127680
cgtggaaaaa gagatacct gttacccgta aaacttactt aatgttcacc agttcatcca 127740
cattcatgat cagggaaagg ttgttattcc aggctaacta ttctcctttc ataataatat 127800
gctggagaga atcaaatgag attgcatttc aaagcgcttg aaaaaccacc atatcgagcc 127860
atgcttagtg tgggcgcctc taatcactgc tattcaggag gctgacgagg aagaattgct 127920
tgagcccagg acttcaaggc tgtaggcagc tatgattgtg ccactgcact ccaggctggg 127980
tgacagatca agaccctgtc tcaacaaaag aaaagaaaac aaaacaaatg aacagaaata 128040
ttccacaatg tcaaaaaaaa aaaaaaccca cacaacatac aatttacaaa tgcaaataat 128100
aatattattg ttgtcttctt tgattttctc tttcctggtg aaattttgtt ttattaagcc 128160
tgacaaagtg ataccttgc ttacatcact taaagttagt ctatttggac ctaggtgaca 128220
gtacaatcag ctaagaaaca gtatttgtag gagaggcagg tttgggacag gtgacaaggc 128280
atgtggggtg ctcgctgtgc tggtggctct ggaaggcagg gtgtcaatgc agacagggat 128340
gagcatggcc tggttgggaa ggcatggggc aggcaggagc tgagctgct ctcctggcc 128400 tggtcacaag cccatggcag cttctctggg tctgtgaact gaggggtgat gtcctggaat 128460
cctctgacac tctaggaagg agagaagggc ctttctggct cagcctttat aaacagtagc 128520
tgatctccct cttgctcccc agggtcctcc ccaccatccc agcaaatgtg caaatacaag 128580
atctctgctc ctcatggtcc tcagagagct ggggtgttct gatggcttga acaagtcact 128640
taggaaatgt ggggttttgg aggcattctc tgataggctg atacgttttg agtttagagt 128700
tcccaccgca catccccaca cccctagagt ctagggcatt tagtgctcca tgagggaacc 128760
tgtagagtga ggacatctgc atcacaggct gggccttcta gtgtccagaa gcagaaagtg 128820
tgtctgcttc aaagttggtg ctaatgatga ttttggtca gaatacggca tttctcattt 128880
ccattccttt atccccttga acttactaaa gtagaatcag gtctaaaaac cagagttcta 128940
atctttaaga gtccctggga ttctaaggta tatgaatgtc cttggaaaac aataccattt 129000
agttcatgca aggtgcttat ttcccatcct ctttcatttg atgtctagca ttttactgca 129060
ttcttaccac cacggtttag taacattcac gaggaggaag tggaggatcc agatggagca 129120
acttgctctg ggcacacaag gcatttgcaa ttttataccc tcttgatgat gtctcagcca 129180
gacattctgc ccagtcatca atgccctctt caattaatat gaaaggacac acttggcatg 129240
agattccaat cgtgcacaga atatacatga gaagtgtgcc tttgtcatcc ctactttcaa 129300
aggctaaggc caccctcagt ttcttgcatg caactgatgc ctttcaaatg aaaccttaca 129360
tctgtgtagt ccataggcaa ccacaggcaa atgtgagggt gaaacgctgt gttctacatt 129420
```

```
gttctgtgtc agtgaagcaa ggcagtgcca gctcagaggg ctctggggct tcaaggcagg 129480
gatgcctggt tgtaggtact gccacttcca gctgggcagt gaaacataac tgctaatact 129540
ttccttacag gcctgccgtc atcactgaca aagtaatgcc agcttgtctg ccatcccag 129600 actacatggt caccgccagg actgaatgtt acatcactgg ctgggagaa acccaaggtg 129660 agatcaattc cattgcccac gtaacaaatt gttttttgacc ttcagtgcat gttacaaaat 129720
gagcattttg gagatagttg tacaaattcc tacccatgaa tgtggtctac ccactcctga 129780
ctttgcctgg acacctgtct atgtctccat aatcagtctt caagggactt gggcaagggg 129840
agcggtgcca tttccttgag tctctctctt ttttgttttc agaatctttt aatttttttt 129900
gtaatgattg tatgtttccc ttacaacaaa acaaacacc agtagaggtc tttgagtctc 129960
ttaatcataa tttcagcatt catattgctt ccccaggtaa gtggggtttt gacccagccc 130020
tcaagttaag ggtgttagat tatttttcat gtgaaattag acagactgcg tttctaaaca 130080
tggtgcaaaa cagtaacgac aaaagttgta attaaactat tcttcttccc aaatacccac 130140
atgtctaatg tgtgtgtgag ggtgttaggc aggggacctg aagctggggg agaggcagac 130200
agttcccatg gccccaagtc taggatggca tttggtattg gttgatgggt gagagcaaga 130260
gagggaatat ttttgtgcat gatgtggtat cagcacctgt actacatttt atggattcct 130320
tcttctcttt gcggtatgcc ctgacaataa ttatatccgt cagccttacc cccttggcag 130380
taggaaaact gaaactgtct taaagtctca gctctacttt ctcagaggtg caggcaaggg 130440
cactgggagt ctggggccct ggaaaactgt tctgactctg ccacttgcca gatagacctg 130500
aactagacac gttacctctt tgtaccactt ggctctaatc ccttatctgt aaaaccagca 130560
ttttcaaatg gtgctttgca catcagcctt ttgcataagc tttgatttga taaaatgttt 130620
tttgtgtttt taaaagagtt aaaaaccaca ggtttagata atttcaaagt aggcttccct 130680
ttttctgtca ttttcctatt attttttaaaa cctcacctcc ttgactcctt gttcccttt 130740 tctgcactgc tgagtctggg agcactgagg ccaggtaaaa ggaaacttgg caaatgaggg 130800
gcacctatgg gtgtgggagg ctgctcctgg tgtttgcata ttttaaaatt taaatgctac 130860
aaaccactgt gagttaggta ttattgttcc tattttacca ttgaggaagc tggggctcag 130920
agaaggtgga gggtggtaca gacaaacctg aattggaacc ctggctcctg cctatgggct 130980
gtcaggactt agaaagtcg tgagctctcg ctgattgttt cctcagctga tgtgggctgc 131040
agggctgtta tgggggaaat aataagaaag tgcatcaagt gctgagcaca tcctaagcac 131100
tccatcatgg cagctcctac tactaataaa gaatagaatt atatctaaca tgattctttc 131160
ttgcaagtga cagaaaatcc aactcaaatt ggattaagca aaacaaggga aattcttagt 131220
gagctgcaaa gttttcaggc tcacatgatg gccccaaatc ccaggtcctc ccaatcatgg 131280
agtaggcact atttggggggc acaaaggtga cattcccatg gctgcagatg ctgtggtgct 131340
gtggctgtac cgggaaagaa taagaaaggc cactctccca attatgtgaa caatagtctg 131400
cccactctga gaagtcaaac ttgggtcaca gtcctgcccc tgaacccatc actgactggc 131460
tctgacctgc accaattgtt ccatgttgga ggtgaaggca agaccccact aatacccata 131520
aggggcaaaa gttagataga tccttcaaga ggattatggg aggtagggca aaaagctgct 131580 ggcagccag aaagcaaaca gagcctctat gatacctcaa ctgatgaaag catgaagcta 131640
aaatcataag gatctgggtg tgagttctgg ctctcccatc ttccatgtga cattgggcag 131700
ttatttaatc tcttttagcc tccgctttct catcttacat atgagataat tgtgaggatt 131760
```

```
aagattacac ataatcatca tcatcaccgt ccaccactac caccatcatc cccatcaaca   131820
tcatcgccac cactatcatc attcttactg gcactaccat caccatcacc accattccac   131880
caccatcacc aatatcatca ctgtcaacat cattaccacc atcaccatca ccaccaccat   131940
catcattact accactacca ctactaccac catcaccatc accaccattc caccaccatc   132000
accaatatca tcactctcaa catcatcacc atcaccatca ccaccaccat catcatcatt   132060
actaccacta ccactactac caccatcacc atcaccactg tcccactact atcagcatga   132120
catcaccatc accaccacca tcatcattac caccgctact accaacatca ccatcaccac   132180
aattctactg ccatcaccat taacattacc accaccatca tcactatcac catcaccacc   132240
atcatcacca ctgccattat cactgccacc atcatcacta tcctctatat ttcctcatct   132300
gtattatcat tactaccacc atcactatca ccaccatcgt caccatcata atcaccatca   132360
acaccatctc caataccacc atcactgtaa ccatcatcac caccaccatg atcactatca   132420
ccatcatcac aatgatcact gtaaccatca ttactaccca ccaccatcac cactactcca   132480
ccaccatcac cattatcatt accatcacca ttataccacc catcatcatc accagcacca   132540
ccatcatcac cagcaccacc atcaccatca ccatcattaa caccatcact atcaccattg   132600
gtttaatcat caccaccatc atcataaata aacatcacat aaccagggtg tagctgggtg   132660
ttgaccccag agcccactca ctgtttcctc tctcccaccc ccatccacac atttctaacc   132720
accatcctgc actgggctcc cagtctcctc tggtctcacc cacatgtcca ctgagaaaag   132780
gattttcaga acaccaacta gaccaggagg agccacatac ataactcagg cctgcttatc   132840
aactttctac atgttaataa tgacatcaga tcaatgggtg ttctcagctt ctcagaagga   132900
ggtcaaaatt ctcccctct ccccttcatg tgtccagacc ttcccggatt tggatgtacc   132960
aagtgcagag tggtgttgag gccaaggggc tcatccatgt aagtctcatc tgcaatcact   133020
gggctgatcc cgtggccctg tctccagggc gccatcagag agggcttcaa tcctcaggtt   133080
acctgtggcc caccctgccc tcagaggtgc catctctaca ttggccacga gatggcagca   133140
catactcata gactgcatta atttcccagc aactcctggt gggttttccc tcttatcagg   133200
atgtttgcct tgctcagaga gcaaatctga gagcagtgac acctaactta actttcagca   133260
aaatattttg agaagggtgc ccctttacac atctgtgcag tccaggtgat gcatcccatg   133320
cccaatgctc ggtagtcagg aggagcttcc tccatgcagc tctgcggaag agactcttcc   133380
acgctgctca tgtaaactcc agattcggtg tcagttttct gacaccgaag acaatgatct   133440
aagtgcagtc aagggctttg gggaaagcag gagagagtgc ctcagttcta gcctgtgcca   133500
tgcttgcaaa gttttgcaaa attctaatga gagctgggct tgcaacattg gaaacttgga   133560
ttatttgtga gagcactgag aaatccctgg gcatgtccat ctggaaaaac agcatttcct   133620
ctggcacttt agcagaggtt ctgtttcaat ttggcgaagg aaattaagca gtttttcaca   133680
aaagaagaac tacaacgagg agaattgtcc ctagtatttc ttctccctaa ttgtcaagga   133740
agtgtaaatt agaaaatgaa tcaggacaat ttccacctac tatgttagct aatatttaa   133800 aaattgaata tcacaagggt gaggcaaagt aattgttttc cagtgacatt ttccactgtc   133860 acacccttt agagaataat ttggcaatgt tactgtgaga tagaaatatg tctatataat   133920
tatgggaact gagacttcag aaagtaataa ggaataagaa tgaaatttat gaacaaacat   133980
gtggaaggtt ggaagcaaga gtggggccaa cacgcatggg gaggaagcat ttgggcagcg   134040
actccgcaga cccagactca agctgagcta tacaacctcc ttacgcctca gtttcctcaa   134100
ctgaagaaca ggaatgacaa gtgcctgttt cataggaccg ttgtgaggat taagtgagat   134160
```

```
ataccacatt atgagcttgt gcctggaaag gttgattctt agtaaatgat gactattctt 134220
ttttattgca ataaaattta tacaacatag agttactatt ttaaccattt ttgcaggtac 134280
cactgagtgg cattcagtac attcacaatg gtgtgcaacc gtcaccatat ttccaggaca 134340
tttttctcat ccccaaagga aacctcatgc ccattaagca gtcactcctc attaaaatat 134400
tagttatgaa gactgtagca ttttttttaaa aactcatgat ataacattga ttgaaaaaat 134460
cagtatagga aattgtgcat tatgatgtaa tagtaaaaga agcatataaa aatctgaaaa 134520
aagtatataa aaagaatagc aattgtattt ctcagactct ctttacattg taaaaatcat 134580
tttgatagct tcaaaagaaa agcaaaaagt acacaaacaa caaccaaccc caaagcagca 134640
tgacaaagcc cagattgttg aatccaggtc ttgggaacat aaaatcttat atgacatttg 134700
cactttaatg ggtcagagag tccagtggca ttgggagctg ccttgtgttc tgcagcctca 134760
cggacagaca ggaggtccag ctccactgct ctgttcttct ggaatttcct cgtgaacaag 134820
ctttggcctc agtaaccatt tctttcatct tttttaaacac aggtaccttt gggactggcc 134880
ttctcaagga agcccagctc cttgttattg agaatgaagt gtgcaatcac tataagtata 134940
tttgtgctga gcatttggcc agaggcactg acagttgcca ggtaagaaaa gatcaataga 135000
tcaaagtctt gtgctctccc gtctcagtct cagtcccttaa gacgtcagtc ccaaagtggc 135060
aaattcagga aggttttgtc agtggaagac cccagtctaa gtgttgctca gaaactcccc 135120
agatctgtcc ctgaatgcat attcagatca tctaaggaga cgtcttgggg cttgagttcc 135180
agatccatag caagggagcc gtaagtgcca taactacctc aggccactca ccttcctggt 135240
gtgtgctggt caccagtgac tgaagtggtg gcttttccag tagagaggaa ggtagagggt 135300
acaggaccga gacaaattac acacacttaa caatgatgtc caggctagcc cagtctaaag 135360
gaaacaccaa gttaggaagc aatgcatgca ggattcacaa gggattattt ttttttcccag 135420 gaaaaaacta agtgatgtgg ttttgttgaa tagactttgc taagtactta agcactgcag 135480
atgcttgagt aatatgctca taagttcctt tctgatttga attactggga aaatgtacat 135540
atggataaga gaaggatggc atcccatatt aaaaggttgg cagcttaaag ctcacatgaa 135600
ttttccccta cctctgttta gggtgacagt ggagggcctc tggtttgctt cgagaaggac 135660
aaatacattt tacaaggagt cacttcttgg ggtcttggct gtgcacgccc caataagcct 135720
ggtgtctatg ctcgtgtttc aaggtttgtt acttggattg agggaatgat gagaaataat 135780
taattggacg ggagacagag tgaagcatca acctacttag aagctgaaac gtgggtaagg 135840
atttagcatg ctggaaataa tagacagcaa tcaaacgaag acactgttcc cagctaccag 135900
ctatgccaaa ccttggcatt tttggtattt ttgtgtataa gcttttaagg tctgactgac 135960
aaattctgta ttaaggtgtc atagctatga catttgttaa aaataaactc tgcacttatt 136020
ttgatttgaa ttaatttttgg ttttggtctt caaaattttc atgctctttt catcccatct 136080
atttttattt ttattttttta gactttacgt cctggggtac atgtgcagaa tgtgcaggtt 136140
tgttacatag atgtacacgt gccatggtag tttgctgcac ccatcaacct gtcatctaat 136200
tcggtatttc ttttagttct atccctcccc tagccctcca ccccttgaca ggcccaggtg 136260
tgtgatgttg ccctccctgt gtccatgtgt tctcattgtt caactcacac ttatgagtga 136320
gaacatgccg tgtttgtttt tctgttcttg tgttagtttg ctgagaatga tagtttccag 136380
cttcatccat gtccctgcaa aggacatgaa ctcatccttt tttatggctg catagaattc 136440
catggtgtat atgtgccaca ttttatccaa tctaacattg atgggcaatt gggttggttc 136500
```

```
caactctttg ctattgtgaa tagtgccaca ataaacatac gtgtgcatgt gttttcatag    136560
cagaatgatt tataatcctc tgggtatata cccagtaatg ggattgcagg gtcaaatggt    136620
gtttctggtg ctagatcttt gaggaatcac cacactgtct tccacaatgg ttgaactaat    136680
ttatgctccc accaacaata tcaaggcatt cctatttctc cacatcctct ccagcatctg    136740
ttgtttcctg acttttaat gatcgccatt ctaactggca tgagatggta tctcattgtg    136800
gttttgattt gcatttctct aatgatcagt gatgatgagc ttttctcata tgttgttgg    136860 ctgcataaat gccttttttg gagaagcatc tgttcatatc ctttgcccac ttttgatgg    136920 tgttgttttt ttctggtaaa tttgtttaag ttctttgtag attctggata ttagcctttt    136980
gtcagatgga tagatggcaa aaattttatc ctattatgta ggttgcctgt tcactccgat    137040
gatagtttct tttgctgtgc agaagctctt tggtttaatt agatctcatt tgtctatttt    137100
ggcttttgtt accattgctt ttagtgtttt agtcatgaag tcttctccca tgctatgtcc    137160
tgaatggtat tgcctaagtt ttcttccagg gtttttatgg ttttaggttt tgcatttaag    137220
tctttaatcc atcttgagtt aatttttgta taagtaatgc ccttctttgt ctcttttgat    137280
ctttgttggc ttaaagtata ttttatcaga gactagaatt gcaatccctg ctttttttt    137340 tcttttgct ttcctttgc ttggtaaata ttcttccatc cctttatttt gagcctatgt    137400
atgtctgcac atgagatagg tttcctgaat acagcacacc aatgggtctt gactctttat    137460
tcaatttgcc agtctgtgtc ttttaattgg gggcatttag tccatttaca tttaaggtta    137520
atattgttat gtgtgaattt gatcctgtca ttatgatgct agcgggttat tttgcccatt    137580
agttgatgca gtttcttcat agtgtggatg gcctttacaa tttggtagtt tttgcagtgg    137640
ctggtaccaa ttgttccttt ccatgtttag tgcttcgttc aggagctctt gtgaggcagg    137700
ccttgtggtg acaaaatctt tcagcatttg cttgtctgta aaggatttta tttctccttt    137760
gcttatgaag cttagtttcg ctgggtatga aattctgggt tgaaaattat tttcttttag    137820
aatgttgaat attggcccc actctcttcg ggcttgttgg gtttctgcag agagatccac    137880
tgttagtctg attggcttcc ctttccgggt aacccaacct ttctctctgg ctgcccttag    137940 aaattttttcc ttcatttcaa ccttggtgaa tctgacgatt atgtcttgag gtggctcttc    138000
t                                                                   138001
```

<210> SEQ ID NO 4
<211> LENGTH: 13938
<212> TYPE: DNA
<213> ORGANISM: Homo sapiens

<400> SEQUENCE: 4

```
ctgggattgg gacacacttt ctggacactg ctggccagtc ccaaaatgga acataaggaa      60
gtggttcttc tacttctttt atttctgaaa tcagcagcac ctgagcaaag ccatgtggtc     120
caggattgct accatggtga tggacagagt tatcgaggca cgtactccac cactgtcaca     180
ggaaggacct gccaagcttg gtcatctatg acaccacatc aacataatag gaccacagaa     240
aactacccaa atgctggctt gatcatgaac tactgcagga tccagatgc tgtggcagct     300 ccttattgtt atacgaggga tcccggtgtc aggtgggagt actgcaacct gacgcaatgc     360
tcagacgcag aagggactgc cgtcgcgcct ccgactgtta ccccggttcc aagcctagag     420
gctccttccg aacaagcacc gactgagcaa aggcctgggg tgcaggagtg ctaccatggt     480
aatggacaga gttatcgagg cacatactcc accactgtca caggaagaac ctgccaagct     540
tggtcatcta tgacaccaca ctcgcatagt cggaccccag aatactaccc aaatgctggc     600
```

```
ttgatcatga actactgcag gaatccagat gctgtggcag ctccttattg ttatacgagg    660
gatcccggtg tcaggtggga gtactgcaac ctgacgcaat gctcagacgc agaagggact    720
gccgtcgcgc ctccgactgt taccccggtt ccaagcctag aggctccttc cgaacaagca    780
ccgactgagc aaaggcctgg ggtgcaggag tgctaccatg gtaatggaca gagttatcga    840
ggcacatact ccaccactgt cacaggaaga acctgccaag cttggtcatc tatgacacca    900
cactcgcata gtcggacccc agaatactac ccaaatgctg gcttgatcat gaactactgc    960
aggaatccag atgctgtggc agctccttat tgttatacga gggatcccgg tgtcaggtgg   1020
gagtactgca acctgacgca atgctcagac gcagaaggga ctgccgtcgc gcctccgact   1080
gttaccccgg ttccaagcct agaggctcct tccgaacaag caccgactga gcaaaggcct   1140
ggggtgcagg agtgctacca tggtaatgga cagagttatc gaggcacata ctccaccact   1200
gtcacaggaa gaacctgcca agcttggtca tctatgacac cacactcgca tagtcggacc   1260
ccagaatact acccaaatgc tggcttgatc atgaactact gcaggaatcc agatgctgtg   1320
gcagctcctt attgttatac gagggatccc ggtgtcaggt gggagtactg caacctgacg   1380
caatgctcag acgcagaagg gactgccgtc gcgcctccga ctgttacccc ggttccaagc   1440
ctagaggctc cttccgaaca agcaccgact gagcaaaggc ctggggtgca ggagtgctac   1500
catggtaatg gacagagtta tcgaggcaca tactccacca ctgtcacagg aagaacctgc   1560
caagcttggt catctatgac accacactcg catagtcgga ccccagaata tacccaaat   1620 gctggcttga tcatgaacta ctgcaggaat ccagatgctg tggcagctcc ttattgttat   1680
acgagggatc ccggtgtcag gtgggagtac tgcaacctga cgcaatgctc agacgcagaa   1740
gggactgccg tcgcgcctcc gactgttacc ccggttccaa gcctagaggc tccttccgaa   1800
caagcaccga ctgagcaaag gcctggggtg caggagtgct accatggtaa tggacagagt   1860
tatcgaggca catactccac cactgtcaca ggaagaacct gccaagcttg gtcatctatg   1920
acaccacact cgcatagtcg accccagaa tactacccaa atgctggctt gatcatgaac   1980
tactgcagga atccagatgc tgtggcagct ccttattgtt atacgaggga tcccggtgtc   2040
aggtgggagt actgcaacct gacgcaatgc tcagacgcag aagggactgc cgtcgcgcct   2100
ccgactgtta ccccggttcc aagcctagag gctccttccg aacaagcacc gactgagcaa   2160
aggcctgggg tgcaggagtg ctaccatggt aatggacaga gttatcgagg cacatactcc   2220
accactgtca caggaagaac ctgccaagct tggtcatcta tgacaccaca ctcgcatagt   2280
cggaccccag aatactaccc aaatgctggc ttgatcatga actactgcag gaatccagat   2340
gctgtggcag ctccttattg ttatacgagg gatcccggtg tcaggtggga gtactgcaac   2400
ctgacgcaat gctcagacgc agaagggact gccgtcgcgc ctccgactgt taccccggtt   2460
ccaagcctag aggctccttc cgaacaagca ccgactgagc aaaggcctgg ggtgcaggag   2520
tgctaccatg gtaatggaca gagttatcga ggcacatact ccaccactgt cacaggaaga   2580
acctgccaag cttggtcatc tatgacacca cactcgcata gtcggacccc agaatactac   2640
ccaaatgctg gcttgatcat gaactactgc aggaatccag atgctgtggc agctccttat   2700
tgttatacga gggatcccgg tgtcaggtgg gagtactgca acctgacgca atgctcagac   2760
gcagaaggga ctgccgtcgc gcctccgact gttaccccgg ttccaagcct agaggctcct   2820
tccgaacaag caccgactga gcaaaggcct ggggtgcagg agtgctacca tggtaatgga   2880
cagagttatc gaggcacata ctccaccact gtcacaggaa gaacctgcca agcttggtca   2940
```

```
tctatgacac cacactcgca tagtcggacc ccagaatact acccaaatgc tggcttgatc    3000
atgaactact gcaggaatcc agatgctgtg gcagctcctt attgttatac gagggatccc    3060
ggtgtcaggt gggagtactg caacctgacg caatgctcag acgcagaagg gactgccgtc    3120
gcgcctccga ctgttacccc ggttccaagc ctagaggctc cttccgaaca agcaccgact    3180
gagcaaaggc ctggggtgca ggagtgctac catggtaatg gacagagtta tcgaggcaca    3240
tactccacca ctgtcacagg aagaacctgc caagcttggt catctatgac accacactcg    3300
catagtcgga ccccagaata ctacccaaat gctggcttga tcatgaacta ctgcaggaat    3360
ccagatgctg tggcagctcc ttattgttat acgagggatc ccggtgtcag gtgggagtac    3420
tgcaacctga cgcaatgctc agacgcagaa gggactgccg tcgcgcctcc gactgttacc    3480
ccggttccaa gcctagaggc tccttccgaa caagcaccga ctgagcaaag gcctggggtg    3540
caggagtgct accatggtaa tggacagagt tatcgaggca catactccac cactgtcaca    3600
ggaagaacct gccaagcttg gtcatctatg acaccacact cgcatagtcg accccagaa    3660 tactacccaa atgctggctt gatcatgaac tactgcagga atccagatgc tgtggcagct    3720
ccttattgtt atacgaggga tcccggtgtc aggtgggagt actgcaacct gacgcaatgc    3780
tcagacgcag aagggactgc cgtcgcgcct ccgactgtta ccccggttcc aagcctagag    3840
gctccttccg aacaagcacc gactgagcaa aggcctgggg tgcaggagtg ctaccatggt    3900
aatggacaga gttatcgagg cacatactcc accactgtca caggaagaac ctgccaagct    3960
tggtcatcta tgacaccaca ctcgcatagt cggaccccag aatactaccc aaatgctggc    4020
ttgatcatga actactgcag gaatccagat gctgtggcag ctccttattg ttatacgagg    4080
gatcccggtg tcaggtggga gtactgcaac ctgacgcaat gctcagacgc agaagggact    4140
gccgtcgcgc tccgactgt taccccggtt ccaagcctag aggctccttc cgaacaagca    4200
ccgactgagc aaaggcctgg ggtgcaggag tgctaccatg gtaatggaca gagttatcga    4260
ggcacatact ccaccactgt cacaggaaga acctgccaag cttggtcatc tatgacacca    4320
cactcgcata gtcggacccc agaatactac ccaaatgctg gcttgatcat gaactactgc    4380
aggaatccag atgctgtggc agctccttat tgttatacga gggatcccgg tgtcaggtgg    4440
gagtactgca acctgacgca atgctcagac gcagaaggga ctgccgtcgc gcctccgact    4500 gttacccgg ttccaagcct agaggctcct tccgaacaag caccgactga gcaaaggcct    4560
ggggtgcagg agtgctacca tggtaatgga cagagttatc gaggcacata ctccaccact    4620
gtcacaggaa gaacctgcca agcttggtca tctatgacac cacactcgca tagtcggacc    4680
ccagaatact acccaaatgc tggcttgatc atgaactact gcaggaatcc agatgctgtg    4740
gcagctcctt attgttatac gagggatccc ggtgtcaggt gggagtactg caacctgacg    4800
caatgctcag acgcagaagg gactgccgtc gcgcctccga ctgttacccc ggttccaagc    4860
ctagaggctc cttccgaaca agcaccgact gagcaaaggc ctggggtgca ggagtgctac    4920
catggtaatg gacagagtta tcgaggcaca tactccacca ctgtcacagg aagaacctgc    4980
caagcttggt catctatgac accacactcg catagtcgga ccccagaata ctacccaaat    5040
gctggcttga tcatgaacta ctgcaggaat ccagatgctg tggcagctcc ttattgttat    5100
acgagggatc ccggtgtcag gtgggagtac tgcaacctga cgcaatgctc agacgcagaa    5160
gggactgccg tcgcgcctcc gactgttacc ccggttccaa gcctagaggc tccttccgaa    5220
caagcaccga ctgagcaaag gcctggggtg caggagtgct accatggtaa tggacagagt    5280
tatcgaggca catactccac cactgtcaca ggaagaacct gccaagcttg gtcatctatg    5340
```

```
acaccacact cgcatagtcg gaccccagaa tactacccaa atgctggctt gatcatgaac    5400
tactgcagga atccagatgc tgtggcagct ccttattgtt atacgaggga tcccggtgtc    5460
aggtgggagt actgcaacct gacgcaatgc tcagacgcag aagggactgc cgtcgcgcct    5520
ccgactgtta ccccggttcc aagcctagag gctccttccg aacaagcacc gactgagcaa    5580
aggcctgggg tgcaggagtg ctaccatggt aatggacaga gttatcgagg cacatactcc    5640
accactgtca caggaagaac ctgccaagct tggtcatcta tgacaccaca ctcgcatagt    5700
cggaccccag aatactaccc aaatgctggc ttgatcatga actactgcag gaatccagat    5760
gctgtggcag ctccttattg ttatacgagg atcccggtg tcaggtggga gtactgcaac     5820
ctgacgcaat gctcagacgc agaagggact gccgtcgcgc ctccgactgt taccccggtt    5880
ccaagcctag aggctccttc cgaacaagca ccgactgagc aaaggcctgg ggtgcaggag    5940
tgctaccatg gtaatggaca gagttatcga ggcacatact ccaccactgt cacaggaaga    6000
acctgccaag cttggtcatc tatgacacca cactcgcata gtcggacccc agaatactac    6060
ccaaatgctg gcttgatcat gaactactgc aggaatccag atgctgtggc agctccttat    6120
tgttatacga gggatcccgg tgtcaggtgg gagtactgca acctgacgca atgctcagac    6180
gcagaaggga ctgccgtcgc gcctccgact gttaccccgg ttccaagcct agaggctcct    6240
tccgaacaag caccgactga gcaaaggcct ggggtgcagg agtgctacca tggtaatgga    6300
cagagttatc gaggcacata ctccaccact gtcacaggaa gaacctgcca agcttggtca    6360
tctatgacac cacactcgca tagtcggacc ccagaatact acccaaatgc tggcttgatc    6420
atgaactact gcaggaatcc agatgctgtg gcagctcctt attgttatac gagggatccc    6480
ggtgtcaggt gggagtactg caacctgacg caatgctcag acgcagaagg gactgccgtc    6540
gcgcctccga ctgttacccc ggttccaagc ctagaggctc cttccgaaca agcaccgact    6600
gagcaaaggc ctggggtgca ggagtgctac catggtaatg acagagtta tcgaggcaca    6660 tactccacca ctgtcacagg aagaacctgc caagcttggt catctatgac accacactcg    6720
catagtcgga ccccagaata ctacccaaat gctggcttga tcatgaacta ctgcaggaat    6780
ccagatgctg tggcagctcc ttattgttat acgagggatc ccggtgtcag gtgggagtac    6840
tgcaacctga cgcaatgctc agacgcagaa gggactgccg tcgcgcctcc gactgttacc    6900
ccggttccaa gctagaggc tccttccgaa caagcaccga ctgagcaaag gcctggggtg    6960
caggagtgct accatggtaa tggacagagt tatcgaggca catactccac cactgtcaca    7020
ggaagaacct gccaagcttg gtcatctatg acaccacact cgcatagtcg gaccccagaa    7080
tactacccaa atgctggctt gatcatgaac tactgcagga atccagatgc tgtggcagct    7140
ccttattgtt atacgaggga tcccggtgtc aggtgggagt actgcaacct gacgcaatgc    7200
tcagacgcag aagggactgc cgtcgcgcct ccgactgtta ccccggttcc aagcctagag    7260
gctccttccg aacaagcacc gactgagcaa aggcctgggg tgcaggagtg ctaccatggt    7320
aatggacaga gttatcgagg cacatactcc accactgtca caggaagaac ctgccaagct    7380
tggtcatcta tgacaccaca ctcgcatagt cggaccccag aatactaccc aaatgctggc    7440
ttgatcatga actactgcag gaatccagat gctgtggcag ctccttattg ttatacgagg    7500
gatcccggtg tcaggtggga gtactgcaac ctgacgcaat gctcagacgc agaagggact    7560
gccgtcgcgc ctccgactgt taccccggtt ccaagcctag aggctccttc cgaacaagca    7620
ccgactgagc aaaggcctgg ggtgcaggag tgctaccatg gtaatggaca gagttatcga    7680
```

```
ggcacatact ccaccactgt cacaggaaga acctgccaag cttggtcatc tatgacacca    7740
cactcgcata gtcggacccc agaatactac ccaaatgctg gcttgatcat gaactactgc    7800
aggaatccag atgctgtggc agctccttat tgttatacga gggatcccgg tgtcaggtgg    7860
gagtactgca acctgacgca atgctcagac gcagaaggga ctgccgtcgc gcctccgact    7920
gttaccccgg ttccaagcct agaggctcct tccgaacaag caccgactga gcagaggcct    7980
ggggtgcagg agtgctacca cggtaatgga cagagttatc gaggcacata ctccaccact    8040
gtcactggaa gaacctgcca agcttggtca tctatgacac cacactcgca tagtcggacc    8100
ccagaatact acccaaatgc tggcttgatc atgaactact gcaggaatcc agatgctgtg    8160
gcagctcctt attgttatac gagggatccc ggtgtcaggt gggagtactg caacctgacg    8220
caatgctcag acgcagaagg gactgccgtc gcgcctccga ctgttacccc ggttccaagc    8280
ctagaggctc cttccgaaca agcaccgact gagcaaaggc ctggggtgca ggagtgctac    8340
catggtaatg gacagagtta tcgaggcaca tactccacca ctgtcacagg aagaacctgc    8400
caagcttggt catctatgac accacactcg catagtcgga ccccagaata ctacccaaat    8460
gctggcttga tcatgaacta ctgcaggaat ccagatgctg tggcagctcc ttattgttat    8520
acgagggatc ccggtgtcag gtgggagtac tgcaacctga cgcaatgctc agacgcagaa    8580
gggactgccg tcgcgcctcc gactgttacc ccggttccaa gcctagaggc tccttccgaa    8640
caagcaccga ctgagcaaag gcctggggtg caggagtgct accatggtaa tggacagagt    8700
tatcgaggca catactccac cactgtcaca ggaagaacct gccaagcttg gtcatctatg    8760
acaccacact cgcatagtcg daccccagaa tactacccaa atgctggctt gatcatgaac    8820
tactgcagga atccagatgc tgtggcagct ccttattgtt atacgaggga tcccggtgtc    8880
aggtgggagt actgcaacct gacgcaatgc tcagacgcag aagggactgc cgtcgcgcct    8940
ccgactgtta ccccggttcc aagcctagag gctccttccg aacaagcacc gactgagcag    9000
aggcctgggg tgcaggagtg ctaccacggt aatggacaga gttatcgagg cacatactcc    9060
accactgtca ctggaagaac ctgccaagct tggtcatcta tgacaccaca ctcgcatagt    9120
cggaccccag aatactaccc aaatgctggc ttgatcatga actactgcag gaatccagat    9180
gctgtggcag ctccttattg ttatacgagg gatcccggtg tcaggtggga gtactgcaac    9240
ctgacgcaat gctcagacgc agaagggact gccgtcgcgc tccgactgt taccccggtt    9300
ccaagcctag aggctccttc cgaacaagca ccgactgagc agaggcctgg ggtgcaggag    9360
tgctaccacg gtaatggaca gagttatcga ggcacatact ccaccactgt cactggaaga    9420
acctgccaag cttggtcatc tatgacacca cactcgcata gtcggacccc agaatactac    9480
ccaaatgctg gcttgatcat gaactactgc aggaatccag atgctgtggc agctccttat    9540
tgttatacga gggatcccgg tgtcaggtgg gagtactgca acctgacgca atgctcagac    9600
gcagaaggga ctgccgtcgc gcctccgact gttaccccgg ttccaagcct agaggctcct    9660
tccgaacaag caccgactga gcagaggcct ggggtgcagg agtgctacca cggtaatgga    9720
cagagttatc gaggcacata ctccaccact gtcactggaa gaacctgcca agcttggtca    9780
tctatgacac cacactcgca tagtcggacc ccagaatact acccaaatgc tggcttgatc    9840
atgaactact gcaggaatcc agatgctgtg gcagctcctt attgttatac gagggatccc    9900
ggtgtcaggt gggagtactg caacctgacg caatgctcag acgcagaagg gactgccgtc    9960
gcgcctccga ctgttacccc ggttccaagc ctagaggctc cttccgaaca agcaccgact   10020
gagcagaggc ctggggtgca ggagtgctac cacggtaatg gacagagtta tcgaggcaca   10080
```

```
tactccacca ctgtcactgg aagaacctgc caagcttggt catctatgac accacactcg   10140
catagtcgga ccccagaata ctacccaaat gctggcttga tcatgaacta ctgcaggaat   10200
ccagatcctg tggcagcccc ttattgttat acgagggatc ccagtgtcag gtgggagtac   10260
tgcaacctga cacaatgctc agacgcagaa gggactgccg tcgcgcctcc aactattacc   10320
ccgattccaa gcctagaggc tccttctgaa caagcaccaa ctgagcaaag gcctggggtg   10380
caggagtgct accacggaaa tggacagagt tatcaaggca catacttcat tactgtcaca   10440
ggaagaacct gccaagcttg gtcatctatg acaccacact cgcatagtcg gaccccagca   10500
tactacccaa atgctggctt gatcaagaac tactgccgaa atccagatcc tgtggcagcc   10560
ccttggtgtt atacaacaga tcccagtgtc aggtgggagt actgcaacct gacacgatgc   10620
tcagatgcag aatggactgc cttcgtccct ccgaatgtta ttctggctcc aagcctagag   10680
gcttttttg aacaagcact gactgaggaa accccggggg tacaggactg ctactaccat   10740
tatggacaga gttaccgagg cacatactcc accactgtca caggaagaac ttgccaagct   10800
tggtcatcta tgacaccaca ccagcatagt cggaccccag aaaactaccc aaatgctggc   10860
ctgaccagga actactgcag gaatccagat gctgagattc gcccttggtg ttacaccatg   10920
gatcccagtg tcaggtggga gtactgcaac ctgacacaat gcctggtgac agaatcaagt   10980
gtccttgcaa ctctcacggt ggtcccagat ccaagcacag aggcttcttc tgaagaagca   11040
ccaacggagc aaagccccgg ggtccaggat tgctaccatg gtgatggaca gagttatcga   11100
ggctcattct ctaccactgt cacaggaagg acatgtcagt cttggtcctc tatgacacca   11160
cactggcatc agaggacaac agaatattat ccaaatggtg gcctgaccag gaactactgc   11220
aggaatccag atgctgagat tagtccttgg tgttatacca tggatcccaa tgtcagatgg   11280
gagtactgca acctgacaca atgtccagtg acagaatcaa gtgtccttgc gacgtccacg   11340
gctgtttctg aacaagcacc aacggagcaa agccccacag tccaggactg ctaccatggt   11400
gatggacaga gttatcgagg ctcattctcc accactgtta caggaaggac atgtcagtct   11460
tggtcctcta tgacaccaca ctggcatcag agaaccacag aatactaccc aaatggtggc   11520
ctgaccagga actactgcag gaatccagat gctgagattc gcccttggtg ttataccatg   11580
gatcccagtg tcagatggga gtactgcaac ctgacgcaat gtccagtgat ggaatcaact   11640
ctcctcacaa ctcccacggt ggtcccagtt ccaagcacag agcttccttc tgaagaagca   11700
ccaactgaaa acagcactgg ggtccaggac tgctaccgag gtgatggaca gagttatcga   11760
ggcacactct ccaccactat cacaggaaga acatgtcagt cttggtcgtc tatgacacca   11820
cattggcatc ggaggatccc attatactat ccaaatgctg gcctgaccag gaactactgc   11880
aggaatccag atgctgagat tcgcccttgg tgttacacca tggatcccag tgtcaggtgg   11940
gagtactgca acctgacacg atgtccagtg acagaatcga gtgtcctcac aactcccaca   12000
gtggccccgg ttccaagcac agaggctcct tctgaacaag caccacctga aaaagccct    12060
gtggtccagg attgctacca tggtgatgga cggagttatc gaggcatatc ctccaccact   12120
gtcacaggaa ggacctgtca atcttggtca tctatgatac cacactgcat cagaggacc    12180
ccagaaaact acccaaatgc tggcctgacc gagaactact gcaggaatcc agattctggg   12240
aaacaaccct ggtgttacac aaccgatccg tgtgtgaggt gggagtactg caatctgaca   12300
caatgctcag aaacagaatc aggtgtccta gagactccca ctgttgttcc agttccaagc   12360
atggaggctc attctgaagc agcaccaact gagcaaaccc ctgtggtccg gcagtgctac   12420
```

-continued

```
catggtaatg gccagagtta tcgaggcaca ttctccacca ctgtcacagg aaggacatgt    12480
caatcttggt catccatgac accacaccgg catcagagga ccccagaaaa ctacccaaat    12540
gatggcctga caatgaacta ctgcaggaat ccagatgccg atacaggccc ttggtgtttt    12600
accatggacc ccagcatcag gtgggagtac tgcaacctga cgcgatgctc agacacagaa    12660
gggactgtgg tcgctcctcc gactgtcatc caggttccaa gcctagggcc tccttctgaa    12720
caagactgta tgtttgggaa tgggaaagga taccggggca agaaggcaac cactgttact    12780
gggacgccat gccaggaatg ggctgcccag gagccccata gacacagcac gttcattcca    12840
gggacaaata aatgggcagg tctggaaaaa aattactgcc gtaaccctga tggtgacatc    12900
aatggtccct ggtgctacac aatgaatcca agaaaacttt ttgactactg tgatatccct    12960
ctctgtgcat cctcttcatt tgattgtggg aagcctcaag tggagccgaa gaaatgtcct    13020
ggaagcattg tagggggggtg tgtggcccac ccacattcct ggccctggca agtcagtctc    13080
agaacaaggt ttggaaagca cttctgtgga ggcaccttaa tatccccaga gtgggtgctg    13140
actgctgctc actgcttgaa gaagtcctca aggccttcat cctacaaggt catcctgggt    13200
gcacaccaag aagtgaacct cgaatctcat gttcaggaaa tagaagtgtc taggctgttc    13260
ttggagccca cacaagcaga tattgccttg ctaaagctaa gcaggcctgc cgtcatcact    13320
gacaaagtaa tgccagcttg tctgccatcc ccagactaca tggtcaccgc caggactgaa    13380
tgttacatca ctggctgggg agaaacccaa ggtacctttg ggactggcct tctcaaggaa    13440
gcccagctcc ttgttattga gaatgaagtg tgcaatcact ataagtatat ttgtgctgag    13500
catttggcca gaggcactga cagttgccag ggtgacagtg gagggcctct ggtttgcttc    13560
gagaaggaca aatacatttt acaaggagtc acttcttggg gtcttggctg tgcacgcccc    13620
aataagcctg gtgtctatgc tcgtgtttca aggtttgtta cttggattga gggaatgatg    13680
agaaataatt aattggacgg gagacagagt gaagcatcaa cctacttaga agctgaaacg    13740
tgggtaagga tttagcatgc tggaaataat agacagcaat caaacgaaga cactgttccc    13800
agctaccagc tatgccaaac cttggcattt ttggtatttt tgtgtataag cttttaaggt    13860
ctgactgaca aattctgtat taaggtgtca tagctatgac atttgttaaa aataaactct    13920
gcacttattt tgatttga                                                 13938
```

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
acagcaatca aacgaagaca ctg                                              23

<210> SEQ ID NO 6
<211> LENGTH: 28
<212> TYPE: DNA
<213> ORGANISM: Artificial Sequence
<220> FEATURE:
<223> OTHER INFORMATION: Primer

<400> SEQUENCE: 6
agcttataca caaaaatacc aaaaatgc                                         28

<210> SEQ ID NO 7
<211> LENGTH: 27

```
<212> TYPE: DNA
<213> ORGANISM: Artificial Sequence
<220> FEATURE:
<223> OTHER INFORMATION: Probe

<400> SEQUENCE: 7
tcccagctac cagctatgcc aaacctt                                        27

<210> SEQ ID NO 8
<211> LENGTH: 16
<212> TYPE: DNA
<213> ORGANISM: Artificial Sequence
<220> FEATURE:
<223> OTHER INFORMATION: Primer

<400> SEQUENCE: 8
ccacagtggc cccggt                                                    16

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
acagggcttt tctcaggtgg t                                              21

<210> SEQ ID NO 10
<211> LENGTH: 28
<212> TYPE: DNA
<213> ORGANISM: Artificial Sequence
<220> FEATURE:
<223> OTHER INFORMATION: Probe

<400> SEQUENCE: 10
ccaagcacag aggctccttc tgaacaag                                       28

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
ggcaggtcct tcctgtgaca                                                20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
cctgtgacag tggtggagta                                                20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
```

-continued

```
tcctgtgaca gtggtggagt                                           20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
cttcctgtga cagtggtgga                                           20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
ccttcctgtg acagtggtgg                                           20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
tccttcctgt gacagtggtg                                           20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
gtccttcctg tgacagtggt                                           20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
ggtccttcct gtgacagtgg                                           20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
aggtccttcc tgtgacagtg                                           20

<210> SEQ ID NO 20
<211> LENGTH: 20
<212> TYPE: DNA
<213> ORGANISM: Artificial Sequence
```

<220> FEATURE:
<223> OTHER INFORMATION: Synthetic oligonucleotide

<400> SEQUENCE: 20
caggtccttc ctgtgacagt                                                    20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
gcaggtcctt cctgtgacag                                                    20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
tggcaggtcc ttcctgtgac                                                    20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
ttggcaggtc cttcctgtga                                                    20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
cttggcaggt ccttcctgtg                                                    20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
gcttggcagg tccttcctgt                                                    20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
tcttcctgtg acagtggtgg                                                    20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
ttcttcctgt gacagtggtg						20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
gttcttcctg tgacagtggt						20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
ggttcttcct gtgacagtgg						20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
aggttcttcc tgtgacagtg						20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
caggttcttc ctgtgacagt						20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
tggcaggttc ttcctgtgac						20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
ttggcaggtt cttcctgtga                                               20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
cttggcaggt tcttcctgtg                                               20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
agcttggcag gttcttcctg                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
actatgcgag tgtggtgtca                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
gactatgcga gtgtggtgtc                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
cgactatgcg agtgtggtgt                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
ccgactatgc gagtgtggtg                                               20

<210> SEQ ID NO 40

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
tccgactatg cgagtgtggt                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
gtccgactat gcgagtgtgg                                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
ggtccgacta tgcgagtgtg                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
gggtccgact atgcgagtgt                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
ctgctcagtc ggtgcttgtt                                               20

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
cctctgctca gtcggtgctt                                               20

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
```
gcctctgctc agtcggtgct 20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
cttccagtga cagtggtgga 20

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
ttcttccagt gacagtggtg 20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
gttcttccag tgacagtggt 20

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
ggttcttcca gtgacagtgg 20

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
gaccttaaaa gcttatacac 20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
gtcagacctt aaaagcttat 20

<210> SEQ ID NO 53
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 53
tgtcagtcag accttaaaag                                              20

<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 54
gaatttgtca gtcagacctt                                              20

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 55
agaatttgtc agtcagacct                                              20

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 56
ccttaataca gaatttgtca                                              20

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 57
gctccgttgg tgcttgttca                                              20

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
tgctccgttg gtgcttgttc                                              20

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 59
ttgctccgtt ggtgcttgtt                                              20
```

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 60
tttgctccgt tggtgcttgt                                               20

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 61
ctttgctccg ttggtgcttg                                               20

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 62
tcctgtaaca gtggtggaga                                               20

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 63
ttcctgtaac agtggtggag                                               20

<210> SEQ ID NO 64
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 64
cttcctgtaa cagtggtgga                                               20

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 65
ccttcctgta acagtggtgg                                               20

<210> SEQ ID NO 66
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 66
tccttcctgt aacagtggtg                                                   20

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 67
gtccttcctg taacagtggt                                                   20

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 68
tgtccttcct gtaacagtgg                                                   20

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 69
tggagccaga ataacattcg                                                   20

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 70
cctctaggct tggagccaga                                                   20

<210> SEQ ID NO 71
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 71
agttcttcct gtgacagtgg                                                   20

<210> SEQ ID NO 72
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 72
gtccgactat gctggtgtgg                                                   20

```
<210> SEQ ID NO 73
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 73
ggtccgacta tgctggtgtg                                           20

<210> SEQ ID NO 74
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 74
gggtccgact atgctggtgt                                           20

<210> SEQ ID NO 75
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 75
cctctaggct tggaatcggg                                           20

<210> SEQ ID NO 76
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 76
gttcagaagg agcctctagg                                           20

<210> SEQ ID NO 77
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 77
tgttcagaag gagcctctag                                           20

<210> SEQ ID NO 78
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 78
gcttgttcag aaggagcctc                                           20

<210> SEQ ID NO 79
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 79
tgcttgttca gaaggagcct                                               20

<210> SEQ ID NO 80
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 80
gtgcttgttc agaaggagcc                                               20

<210> SEQ ID NO 81
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 81
ggtgcttgtt cagaaggagc                                               20

<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 82
tggtgcttgt tcagaaggag                                               20

<210> SEQ ID NO 83
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 83
gctcagttgg tgcttgttca                                               20

<210> SEQ ID NO 84
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 84
tgctcagttg gtgcttgttc                                               20

<210> SEQ ID NO 85
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 85
gcttggatct gggaccaccg                                               20

<210> SEQ ID NO 86
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 86
gcctccatgc ttggaactgg                                             20

<210> SEQ ID NO 87
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 87
gctcagttgg tgctgcttca                                             20

<210> SEQ ID NO 88
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 88
cctcgataac tctggccatt                                             20

<210> SEQ ID NO 89
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 89
tcctgtgaca gtggtggaga                                             20

<210> SEQ ID NO 90
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 90
gtaggttgat gcttcactct                                             20

<210> SEQ ID NO 91
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 91
cgtttgattg ctgtctatta                                             20

<210> SEQ ID NO 92
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 92
```

```
ctctgtgctt ggatctggga                                              20

<210> SEQ ID NO 93
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 93
cctctgtgct tggatctggg                                              20

<210> SEQ ID NO 94
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 94
gcctctgtgc ttggatctgg                                              20

<210> SEQ ID NO 95
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 95
agaagcctct gtgcttggat                                              20

<210> SEQ ID NO 96
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 96
ttcagaagaa gcctctgtgc                                              20

<210> SEQ ID NO 97
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 97
gctccgttgg tgcttcttca                                              20

<210> SEQ ID NO 98
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 98
tttgctccgt tggtgcttct                                              20

<210> SEQ ID NO 99
<211> LENGTH: 20
<212> TYPE: DNA
<213> ORGANISM: Artificial Sequence
```

```
<220> FEATURE:
<223> OTHER INFORMATION: Synthetic oligonucleotide

<400> SEQUENCE: 99
gctttgctcc gttggtgctt                                              20

<210> SEQ ID NO 100
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 100
ggctttgctc cgttggtgct                                              20

<210> SEQ ID NO 101
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 101
gggctttgct ccgttggtgc                                              20

<210> SEQ ID NO 102
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 102
ccttcctgtg acagtggtag                                              20

<210> SEQ ID NO 103
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 103
tccttcctgt gacagtggta                                              20

<210> SEQ ID NO 104
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 104
tgtccttcct gtgacagtgg                                              20

<210> SEQ ID NO 105
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 105
cctctaggct tggaaccggg                                              20
```

```
<210> SEQ ID NO 106
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 106
tgcttgttcg gaaggagcct                                                   20

<210> SEQ ID NO 107
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 107
gtgcttgttc ggaaggagcc                                                   20

<210> SEQ ID NO 108
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 108
gcttggaact gggaccaccg                                                   20

<210> SEQ ID NO 109
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 109
ctgtgcttgg aactgggacc                                                   20

<210> SEQ ID NO 110
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 110
ctctgtgctt ggaactggga                                                   20

<210> SEQ ID NO 111
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 111
cctgtgacag tggtgga                                                      17

<210> SEQ ID NO 112
<211> LENGTH: 17
<212> TYPE: DNA
<213> ORGANISM: Artificial Sequence
<220> FEATURE:
<223> OTHER INFORMATION: Synthetic oligonucleotide
```

```
<400> SEQUENCE: 112
tcctgtgaca gtggtgg                                              17

<210> SEQ ID NO 113
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 113
ttcctgtgac agtggtg                                              17

<210> SEQ ID NO 114
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 114
cttcctgtga cagtggt                                              17

<210> SEQ ID NO 115
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 115
ccttcctgtg acagtgg                                              17

<210> SEQ ID NO 116
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 116
tccttcctgt gacagtg                                              17

<210> SEQ ID NO 117
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 117
gtccttcctg tgacagt                                              17

<210> SEQ ID NO 118
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 118
ggtccttcct gtgacag                                              17

<210> SEQ ID NO 119
```

```
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 119
ccgactatgc gagtgtg                                                    17

<210> SEQ ID NO 120
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 120
gtccgactat gcgagtg                                                    17

<210> SEQ ID NO 121
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 121
ggtccgacta tgcgagt                                                    17

<210> SEQ ID NO 122
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 122
gtcagacctt aaaagct                                                    17

<210> SEQ ID NO 123
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 123
aagcctctgt gcttgga                                                    17

<210> SEQ ID NO 124
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 124
agcctctgtg cttggat                                                    17

<210> SEQ ID NO 125
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 125
```

```
gcctctgtgc ttggatc                                          17
```

<210> SEQ ID NO 126
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 126

```
gctccgttgg tgcttct                                          17
```

<210> SEQ ID NO 127
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 127

```
ctctgtgctt ggaactg                                          17
```

<210> SEQ ID NO 128
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 128

```
tgcctcgata actctgt                                          17
```

<210> SEQ ID NO 129
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 129

```
tgtgcctcga taactct                                          17
```

<210> SEQ ID NO 130
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 130

```
gctcagttgg tgctgct                                          17
```

<210> SEQ ID NO 131
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 131

```
gcgtttgctc ttcttcttgc gtttttt                               27
```

<210> SEQ ID NO 132
<211> LENGTH: 3987
<212> TYPE: DNA

<213> ORGANISM: Macaca mulatta

<400> SEQUENCE: 132

```
atgtatcgtt ttggaatttc cagtggcttg atcaggaact actgcaggaa tccagatcct      60
gtggcagccc cttattgtta tacgatggat cccaatgtca ggtgggagta ctgcaacctg     120
acacaatgct cagatgcaga agggactgcc gtcgcacctc cgaatgtcac cctggttcca     180
agcctagagg ctccttccga caatcaccg actgagcaaa ggcctggggt gcaggagtgc      240
taccacggta atggacagag ttatcgaggc acatacttca ccactgtgac aggaagaacc     300
tgccaagctt ggtcatctat gacaccgcac tctcatagtc ggaccccgga aaactaccca     360
aatggtggct tgatcaggaa ctactgcagg aatccagatc ctgtggcagc cccttattgt     420
tataccatgg atcccaatgt caggtgggag tactgcaacc taacacaatg ctcagacgca     480
gaagggattg ccgtcacacc tctgactgtt accccggttc aagcctaga ggctccttcc      540
aagcaagcac caactgagca aaggcctggt gtccaggagt gctaccatgg taatggacag     600
agttatcgag gcacatactt caccactgtg acaggaagaa cctgccaagc ttggtcatct     660
atgacaccac attctcatag tcgtacccca gaaaactacc caaatggcag tccgacctct     720
tcagatctct tagtctaccc tgccgtcttc cttgatgcca tgggtccac tgttctttca     780
actcatccgc tttcctcag tcccggagtg gctgcgacca gcagaggata tattgagagc     840
aagagagaag caccgactga gcaaaggcct ggggtgcagg agtgctacca cggtaatgga    900
cagagttatc gaggcacata cttcaccact gtgacaggaa gaacctgcca agcttggtca    960
tctatgacac cgcactctca tagtcggacc ccggaaaact acccaaatgg tggcttgatc   1020
aggaactact gcaggaatcc agatcctgtg gcagccccctt attgttatac catggatccc   1080
agtgtcaggt gggagtactg caacctgaca caatgctcag acgcagaagg gactgccgtc   1140
gcacctccga atgtcacccc ggttccaagc ctagaggctc cttctgagca agcaccaact   1200
gagcaaaggc ttggggtgca ggagtgctac acagtaatg acagagtta tcgaggcaca    1260
tacttcacca ctgtgacagg aagaacctgc caagcttggt catctatgac accacactct   1320
catagtcgga cccagaaaaa ctacccaaat gctggcttgg tcaagaacta ctgccgaaat   1380
ccagatcctg tggcagcccc ttggtgttat acaacggatc ccagtgtcag gtgggagtac   1440
tgcaacctga cacgatgctc agatgcagaa gggactgctg tcgtgcctcc aaatattatt   1500
ccggttccaa gcctagaggc ttttcttgaa caagaaccga ctgaggaaac ccccggggta   1560
caggagtgct actaccatta tggacagagt tatagaggca catccccac cactgttaca    1620
ggaagaactt gccaagcttg gtcatctatg acaccacacc agcatagtcg accccaaaa    1680
aactatccaa atgctggcct gaccaggaac tactgcagga atccagatgc tgagattcgc   1740
ccttggtgtt ataccatgga tcccagtgtc aggtgggagt actgcaacct gacacaatgt   1800
ctggtgacag aatcaagtgt ccttgaaact ctcacagtgg tcccagatcc aagcacacag   1860
gcttcttctg aagaagcacc aacggagcaa agtcccgagg tccaggactg ctaccatggt   1920
gatggacaga gttatcgagg ctcattctcc accactgtca caggaaggac atgtcagtct   1980
tggtcctcta tgacaccaca ctggcatcag aggacaacag aatattatcc agatggtggc   2040
ctgaccagga actactgcag gaatccagat gctgagattc gcccttggtg ttataccatg   2100
gatcccagtg tcaggtggga gtactgcaac ctgacacaat gtccagtgac agaatcaagt   2160
gtcctcgcaa cgtccatggc tgtttctgaa caagcaccaa tggagcaaag ccccggggtc   2220
caggactgct accatggtga tggacagagt tatcgaggtt cattctccac cactgtcaca   2280
```

-continued

```
ggaaggacat gtcagtcttg gtcctctatg acaccacact ggcatcagag gaccatagaa    2340
tactacccaa atggtggcct gaccaagaac tactgcagga atccagatgc tgagattcgc    2400
ccttggtgtt ataccatgga tcccagagtc agatgggagt actgcaacct gacacaatgt    2460
gtggtgatgg aatcaagtgt ccttgcaact cccatggtgg tcccagttcc aagcagagag    2520
gttccttctg aagaagcacc aactgaaaac agccctgggg tccaggactg ctaccaaggt    2580
gatggacaga gttatcgagg cacattctcc accactatca caggaagaac atgtcagtct    2640
tggttgtcta tgacaccaca tcggcatcgg aggatcccat tacgctatcc aaatgctggc    2700
ctgaccagga actattgcag aaatccagat gctgagattc gcccttggtg ttacaccatg    2760
gatcccagtg tcaggtggga gtactgcaac ctgacacaat gtccagtgac agaatcaagt    2820
gtcctcacaa ctcccacggt ggtcccggtt ccaagcacag aggctccttc tgaacaagca    2880
ccacctgaga aagccctgt ggtccaggat tgctaccatg gtgatggaca gagttatcga    2940
ggcacatcct ccaccactgt cacaggaagg aactgtcagt cttggtcatc tatgatacca    3000
cactggcatc agaggacccc agaaaactac ccaaatgctg gcctgaccag gaactactgc    3060
aggaatccag attctgggaa caacccctgg tgttacacga ctgatccatg tgtgaggtgg    3120
gagtactgca acctgacaca atgctcagaa acagaatcag gtgtcctaga actcccact    3180 gttgttccgg ttccaagcat ggaagctcat tctgaagcag caccaactga gcaaacccct    3240
gtggtccagc agtgctacca tggtaatgga cagagttatc gaggcacatt ctccaccact    3300
gtcacaggaa ggacatgtca atcttggtca tccatgacac cacaccagca taagaggacc    3360
ccggaaaacc acccaaatga tggcttgaca atgaactact gcaggaatcc agatgctgac    3420
acaggccctt ggtgttttac catggacccc agcgtcaggc gggagtactg caacctgacg    3480
cgatgctcag acacagaagg gactgtggtc acacctccga ctgttatccc ggttccaagc    3540
ctagaggctc cttctgaaca agtgcttgga attcatcctg aattaaacga cacaattgct    3600
aacttggact caaaggtgaa ttcttttccca ccttgtgcca cagcatcctc ttcatttgat    3660
tgtgggaagc ctcaagtgga gccaaagaaa tgtcctggaa gcattgtagg tgggtgtgtg    3720
gcccacccac attcctggcc ctggcaagtc agtcttagaa caaggtttgg aaagcacttc    3780
tgtggaggca ccttaatatc cccagagtgg gtgctgactg ctgcttgctg cttggagacg    3840
ttctcaaggc cttccttcta caaggtcatc ctgggtgcac accaagaagt gaatctcgaa    3900
tctcatgttc aagaaataga agtgtctagg ttgttcttgg agcccatagg agcagatatt    3960
gccttgctaa agctaagcag gtactaa                                       3987
```

<210> SEQ ID NO 133
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 133
ggttcttcca gtgacagtgg                                              20

<210> SEQ ID NO 134
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 134
atgcctcgat aactccgtcc                                                                              20

METHODS AND COMPOSITIONS FOR MODULATING APOLIPOPROTEIN (A) EXPRESSION

CROSS REFERENCED TO RELATED APPLICATIONS

This application is a continuation of International Serial No. PCT/US2013/042532 filed May 23, 2013, which claims benefit of priority to U.S. Provisional Application 61/651,539 filed May 24, 2012, each of which is incorporated herein by reference in its entirety. This application is also a continuation of U.S. patent application Ser. No. 14/401,761 filed Nov. 17, 2014, which claims priority under 35 U.S.C. §371 to International Serial No. PCT/US2013/041701 filed May 17, 2013, which claims benefit of priority to U.S. Provisional Application 61/648,556 filed May 17, 2012, each of which is incorporated herein by reference in its entirety.

SEQUENCE LISTING

The present application is being filed along with a Sequence Listing in electronic format. The Sequence Listing is provided as a file entitled BIOL0177USSEQ_ST25.txt created Nov. 24, 2014, which is 424 Kb in size. The information in the electronic format of the sequence listing is incorporated herein by reference in its entirety.

FIELD

Embodiments described herein provide methods, compounds, and compositions for reducing expression of apolipoprotein (a) mRNA and protein in an animal. Such methods, compounds, and compositions are useful to treat, prevent, or ameliorate cardiovascular and/or metabolic diseases, disorders or conditions.

BACKGROUND

Lipoproteins are globular, micelle-like particles that consist of a non-polar core of acylglycerols and cholesteryl esters surrounded by an amphiphilic coating of protein, phospholipid and cholesterol. Lipoproteins have been classified into five broad categories on the basis of their functional and physical properties: chylomicrons, very low density lipoproteins (VLDL), intermediate density lipoproteins (IDL), low density lipoproteins (LDL), and high density lipoproteins (HDL). Chylomicrons transport dietary lipids from intestine to tissues. VLDLs, IDLs and LDLs all transport triacylglycerols and cholesterol from the liver to tissues. HDLs transport endogenous cholesterol from tissues to the liver Lipoprotein particles undergo continuous metabolic processing and have variable properties and compositions. Lipoprotein densities increase without increasing particle diameter because the density of their outer coatings is less than that of the inner core. The protein components of lipoproteins are known as apolipoproteins. At least nine apolipoproteins are distributed in significant amounts among the various human lipoproteins.

The lipoprotein(a) [Lp(a)] particle was identified nearly 50 years ago and is comprised of a highly unique LDL particle in which one apolipoprotein B (apoB) protein is linked via a disulfide bond to a single apolipoprotein(a) [apo(a)] protein. The apo(a) protein shares a high degree of homology with plasminogen particularly within the kringle IV type 2 repetitive domain. Levels of circulating Lp(a) are inversely proportional to the number of kringle IV type 2 variable repeats present in the molecule and, as both alleles are co-expressed within individuals, can display heterozygous plasma isoform profiles (Kraft et al., Eur J Hum Genet, 1996; 4(2): 74-87). It is thought that this kringle repeat domain in apo(a) may be responsible for its pro-thrombotic and anti-fibrinolytic properties, potentially enhancing atherosclerotic progression.

Apo(a) is transcriptionally regulated by IL-6 and in studies in rheumatoid arthritis patients treated with an IL-6 inhibitor (tocilizumab), plasma levels were reduced by 30% after 3 month treatment (Schultz et al., PLoS One 2010; 5:e14328).

Apo(a) has been shown to preferentially bind oxidized phospholipids and potentiate vascular inflammation (Bergmark et al., J Lipid Res 2008; 49:2230-2239; Tsimikas et al., Circulation. 2009; 119(13):1711-1719).

Further, studies suggest that the Lp(a) particle may also stimulate endothelial permeability, induce plasminogen activator inhibitor type-1 expression and activate macrophage interleukin-8 secretion (Koschinsky and Marcovina, Curr Opin Lipidol 2004; 15:167-174). Importantly, recent genetic association studies revealed that Lp(a) was an independent risk factor for myocardial infarction, stroke, peripheral vascular disease and abdominal aortic aneurysm (Rifai et al., Clin Chem 2004; 50:1364-71; Erqou et al., JAMA 2009; 302:412-23; Kamstrup et al., Circulation 2008; 117:176-84). Further, in the recent Precocious Coronary Artery Disease (PROCARDIS) study, Clarke et al. (Clarke et al., NEJM (2009)361; 2518-2528) described robust and independent associations between coronary heart disease and plasma Lp(a) concentrations. Additionally, Solfrizzi et al., suggested that increased serum Lp(a) may be linked to an increased risk for Alzheimer's Disease (AD) (Solfrizzi et al., J Neurol Neurosurg Psychiatry 2002, 72:732-736. Currently, in the clinic setting, examples of indirect apo(a) inhibitors for treating cardiovascular disease include aspirin, Niaspan, Mipomersen, Anacetrapib, Epirotirome and Lomitapide which reduce plasma Lp(a) levels by 18%, 39%, 32%, 36%, 43% and 17%, respectively. Additionally, Lp(a) apheresis has been used in the clinic to reduce apo(a) containing Lp(a) particles.

To date, therapeutic strategies to treat cardiovascular disease by directly targeting apo(a) levels have been limited. Ribozyme oligonucleotides (U.S. Pat. No. 5,877,022) and antisense oligonucleotides (WO 2005/000201; WO 2003/014397; U.S. Pat. No. 8,138,328; Merki et al., J Am Coll Cardiol 2011; 57:1611-1621) have been developed, but none of the compounds directly targeting apo(a) are currently used in the clinic.

Thus, there remains a clear unmet medical need for novel agents which can potently and selectively reduce apo(a) levels in patients at enhanced risk for cardiovascular events due to chronically elevated plasma Lp(a) levels.

SUMMARY

Provided herein are compositions and methods for modulating expression of apo(a) mRNA and protein. In certain embodiments, the apo(a) specific inhibitor decreases expression of apo(a) mRNA and protein.

In certain embodiments, the composition is an apo(a) specific inhibitor. In certain embodiments, the apo(a) specific inhibitor is a nucleic acid, protein, or small molecule. In certain embodiments, the apo(a) specific inhibitor is an antisense oligonucleotide targeting apo(a). In certain embodiments, the apo(a) specific inhibitor is a modified oligonucleotide consisting of 12 to 30 linked nucleosides and comprising a nucleobase sequence comprising a portion of at least 8 contiguous nucleobases complementary to an equal length portion of nucleobases 3901 to 3920 of SEQ ID NO: 1, wherein the nucleobase sequence of the modified oligonucleotide is at least 80% complementary to SEQ ID NO: 1. In certain embodiments, the apo(a) specific inhibitor is a modified oligonucleotide consisting of 12 to 30 linked nucleosides and having a nucleobase sequence comprising at least 8, least 9, least 10, least 11, at least 12, least 13, at least 14, at least 15, at least 16, at least 17, least 18, least 19, or 20 contiguous nucleobases of the nucleobase sequence of SEQ ID NO: 1-130, 133, 134. In certain embodiments, the apo(a) specific inhibitor is a modified oligonucleotide consisting of 20 linked nucleosides and having a nucleobase sequence comprising at least 8 contiguous nucleobases of any of SEQ ID NO: 58, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

Certain embodiments provide a composition comprising a compound described herein, or a salt thereof, and a pharmaceutically acceptable carrier or diluent.

In certain embodiments, the modulation of apo(a) expression occurs in a cell or tissue. In certain embodiments, the modulations occur in a cell or tissue in an animal. In certain embodiments, the animal is a human. In certain embodiments, the modulation is a reduction in apo(a) mRNA level. In certain embodiments, the modulation is a reduction in apo(a) protein level. In certain embodiments, both apo(a) mRNA and protein levels are reduced. Such reduction may occur in a time-dependent or in a dose-dependent manner.

Certain embodiments provide compositions and methods for use in therapy. Certain embodiments provide compositions and methods for preventing, treating, delaying, slowing the progression and/or ameliorating apo(a) related diseases, disorders, and conditions. Certain embodiments provide compositions and methods for preventing, treating, delaying, slowing the progression and/or ameliorating Lp(a) related diseases, disorders, and conditions. In certain embodiments, such diseases, disorders, and conditions are inflammatory, cardiovascular and/or metabolic diseases, disorders, and conditions. In certain embodiments, the compositions and methods for therapy include administering an apo(a) specific inhibitor to an individual in need thereof. In certain embodiments, the apo(a) specific inhibitor is a nucleic acid. In certain embodiments, the nucleic acid is an antisense compound. In certain embodiments, the antisense compound is a modified oligonucleotide.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or", unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure are hereby expressly incorporated by reference for the portions of the document discussed herein, as well as in their entirety.

DEFINITIONS

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE, MOE, 2'-O(CH$_2$)$_2$—OCH$_3$ and 2'-O-(2-methoxyethyl)) refers to an O-methoxyethyl modification of the 2' position of a furanosyl ring. A 2'-O-methoxyethyl modified sugar is a modified sugar.

"2'-deoxyribonucleoside" means a nucleoside comprising 2'-H furanosyl sugar moiety, as found in naturally occurring deoxyribonucleosides (DNA).

"2'-MOE nucleoside" (also 2'-O-methoxyethyl nucleoside) means a nucleoside comprising a 2'-MOE modified sugar moiety. "2'-O-methoxyethyl nucleotide" means a nucleotide comprising a 2'-O-methoxyethyl modified sugar moiety.

"3'-fluoro-HNA" (also "F-HNA" or "3'-F-HNA") means the sugar moiety of a nucleoside having the following structure:

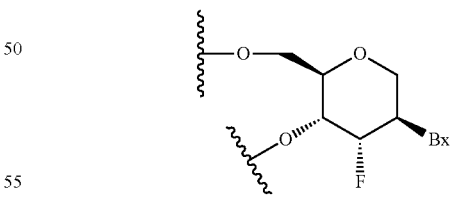

wherein Bx is a nucleobase.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5' position. A 5-methylcytosine is a modified nucleobase.

"About" means within ±10% of a value. For example, if it is stated, "a marker may be increased by about 50%", it is implied that the marker may be increased between 45%-55%.

"Active pharmaceutical agent" means the substance or substances in a pharmaceutical composition that provide a therapeutic benefit when administered to an individual. For example, in certain embodiments an antisense oligonucleotide targeted to apo(a) is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" or "administration" means providing a pharmaceutical agent to an individual, and includes, but is not limited to, administering by a medical professional and self-administering. Administration of a pharmaceutical agent to an individual can be continuous, chronic, short or intermittent. Administration can parenteral or non-parenteral.

"Agent" means an active substance that can provide a therapeutic benefit when administered to an animal. "First Agent" means a therapeutic compound of the invention. For example, a first agent can be an antisense oligonucleotide targeting apo(a). "Second agent" means a second therapeutic compound of the invention (e.g. a second antisense oligonucleotide targeting apo(a)) and/or a non-apo(a) therapeutic compound.

"Amelioration" or "ameliorate" or "ameliorating" refers to a lessening of at least one indicator, sign, or symptom of an associated disease, disorder, or condition. The severity of indicators can be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody can refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, snoRNAs, miRNAs, and satellite repeats.

As used herein, the term "antisense compound" encompasses pharmaceutically acceptable derivatives of the compounds described herein.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid. As used herein, the term "antisense oligonucleotide" encompasses pharmaceutically acceptable derivatives of the compounds described herein.

"Apo(a)" means any nucleic acid or protein sequence encoding apo(a). For example, in certain embodiments, apo(a) includes a DNA sequence encoding apo(a), a RNA sequence transcribed from DNA encoding apo(a) (including genomic DNA comprising introns and exons), a mRNA sequence encoding apo(a), or a peptide sequence encoding apo(a).

"Apo(a) nucleic acid" means any nucleic acid encoding apo(a). For example, in certain embodiments, an apo(a) nucleic acid includes a DNA sequence encoding apo(a), a RNA sequence transcribed from DNA encoding apo(a) (including genomic DNA comprising introns and exons), and a mRNA sequence encoding apo(a).

"Apo(a) mRNA" means a mRNA encoding an apo(a) protein.

"Apo(a) protein" means any protein sequence encoding Apo(a).

"Apo(a) specific inhibitor" refers to any agent capable of specifically inhibiting the expression of an apo(a) nucleic acid and/or apo(a) protein. For example, apo(a) specific inhibitors include nucleic acids (including antisense compounds), peptides, antibodies, small molecules, and other agents capable of inhibiting the expression of apo(a) nucleic acid and/or apo(a) protein. In certain embodiments, by specifically modulating apo(a) nucleic acid expression and/or apo(a) protein expression, apo(a) specific inhibitors can affect other components of the lipid transport system including downstream components. Similarly, in certain embodiments, apo(a) specific inhibitors can affect other molecular processes in an animal.

"Atherosclerosis" means a hardening of the arteries affecting large and medium-sized arteries and is characterized by the presence of fatty deposits. The fatty deposits are called "atheromas" or "plaques," which consist mainly of cholesterol and other fats, calcium and scar tissue, and damage the lining of arteries.

"Bicyclic sugar" means a furanosyl ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"Cardiovascular disease" or "cardiovascular disorder" refers to a group of conditions related to the heart, blood vessels, or the circulation. Examples of cardiovascular diseases include, but are not limited to, aneurysm, angina, arrhythmia, atherosclerosis, cerebrovascular disease (stroke), coronary heart disease, hypertension, dyslipidemia, hyperlipidemia, hypertriglyceridemia and hypercholesterolemia.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Cholesterol" is a sterol molecule found in the cell membranes of all animal tissues. Cholesterol must be transported in an animal's blood plasma by lipoproteins including very low density lipoprotein (VLDL), intermediate density lipoprotein (IDL), low density lipoprotein (LDL), and high density lipoprotein (HDL). "Plasma cholesterol" refers to the sum of all lipoproteins (VDL, IDL, LDL, HDL) esterified and/or non-esterified cholesterol present in the plasma or serum.

"Cholesterol absorption inhibitor" means an agent that inhibits the absorption of exogenous cholesterol obtained from diet.

"Co-administration" means administration of two or more agents to an individual. The two or more agents can be in a single pharmaceutical composition, or can be in separate pharmaceutical compositions. Each of the two or more agents can be administered through the same or different routes of administration. Co-administration encompasses parallel or sequential administration.

"Complementarity" means the capacity for pairing between nucleobases of a first nucleic acid and a second nucleic acid. In certain embodiments, complementarity between the first and second nucleic acid can be between two DNA strands, between two RNA strands, or between a DNA and an RNA strand. In certain embodiments, some of the nucleobases on one strand are matched to a complementary hydrogen bonding base on the other strand. In certain embodiments, all of the nucleobases on one strand are matched to a complementary hydrogen bonding base on the other strand. In certain embodiments, a first nucleic acid is an antisense compound and a second nucleic acid is a target nucleic acid. In certain such embodiments, an antisense oligonucleotide is a first nucleic acid and a target nucleic acid is a second nucleic acid.

"Constrained ethyl" or "cEt" refers to a bicyclic nucleoside having a furanosyl sugar that comprises a methyl (methyleneoxy) (4'-CH(CH$_3$)—O-2') bridge between the 4' and the 2' carbon atoms.

"Constrained ethyl nucleoside" (also cEt nucleoside) means a nucleoside comprising a bicyclic sugar moiety comprising a 4'-CH(CH$_3$)—O-2' bridge.

"Contiguous nucleobases" means nucleobases immediately adjacent to each other.

"Cross-reactive" means an oligomeric compound targeting one nucleic acid sequence can hybridize to a different nucleic acid sequence. For example, in some instances an antisense oligonucleotide targeting human apo(a) can cross-react with an apo(a) from another species. Whether an oligomeric compound cross-reacts with a nucleic acid sequence other than its designated target depends on the degree of complementarity the compound has with the non-target nucleic acid sequence. The higher the complementarity between the oligomeric compound and the non-target nucleic acid, the more likely the oligomeric compound will cross-react with the nucleic acid.

"Cure" means a method that restores health or a prescribed treatment for an illness.

"Coronary heart disease (CHD)" means a narrowing of the small blood vessels that supply blood and oxygen to the heart, which is often a result of atherosclerosis.

"Deoxyribonucleotide" means a nucleotide having a hydrogen at the 2' position of the sugar portion of the nucleotide. Deoxyribonucleotides can be modified with any of a variety of substituents.

"Diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

"Diabetic dyslipidemia" or "type 2 diabetes with dyslipidemia" means a condition characterized by Type 2 diabetes, reduced HDL-C, elevated triglycerides (TG), and elevated small, dense LDL particles.

"Diluent" means an ingredient in a composition that lacks pharmacological activity, but is pharmaceutically necessary or desirable. For example, the diluent in an injected composition can be a liquid, e.g. saline solution.

"Dyslipidemia" refers to a disorder of lipid and/or lipoprotein metabolism, including lipid and/or lipoprotein overproduction or deficiency. Dyslipidemias can be manifested by elevation of lipids such as chylomicron, cholesterol and triglycerides as well as lipoproteins such as low-density lipoprotein (LDL) cholesterol.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month. Doses can also be stated as mg/kg or g/kg.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a second nucleic acid is a target nucleic acid.

"Furanosyl" means a structure comprising a 5-membered ring comprising four carbon atoms and one oxygen atom.

"Gapmer" means a chimeric antisense compound in which an internal region having a plurality of nucleosides that support RNaseH cleavage is positioned between external regions having one or more nucleosides, wherein the nucleosides comprising the internal region are chemically distinct from the nucleoside or nucleosides comprising external regions. The internal region may be referred to as a "gap" and the external regions may be referred to as the "wings."

"Gap-widened" means a chimeric antisense compound having a gap segment of 12 or more contiguous 2'-deoxyribonucleosides positioned between and immediately adjacent to 5' and 3' wing segments having from one to six nucleosides.

"Glucose" is a monosaccharide used by cells as a source of energy and inflammatory intermediate. "Plasma glucose" refers to glucose present in the plasma.

"High density lipoprotein-C" or "HDL-C" means cholesterol associated with high density lipoprotein particles. Concentration of HDL-C in serum (or plasma) is typically quantified in mg/dL or nmol/L. "Serum HDL-C" and "plasma HDL-C" mean HDL-C in serum and plasma, respectively.

"HMG-CoA reductase inhibitor" means an agent that acts through the inhibition of the enzyme HMG-CoA reductase, such as atorvastatin, rosuvastatin, fluvastatin, lovastatin, pravastatin, and simvastatin.

"Hybridization" means the annealing of complementary nucleic acid molecules. In certain embodiments, complementary nucleic acid molecules include an antisense compound and a target nucleic acid.

"Hypercholesterolemia" means a condition characterized by elevated cholesterol or circulating (plasma) cholesterol, LDL-cholesterol and VLDL-cholesterol, as per the guidelines of the Expert Panel Report of the National Cholesterol Educational Program (NCEP) of Detection, Evaluation of Treatment of high cholesterol in adults (see, Arch. Int. Med. (1988) 148, 36-39).

"Hyperlipidemia" or "hyperlipemia" is a condition characterized by elevated serum lipids or circulating (plasma) lipids. This condition manifests an abnormally high concentration of fats. The lipid fractions in the circulating blood are cholesterol, low density lipoproteins, very low density lipoproteins, chylomicrons and triglycerides. The Fredrickson classification of hyperlipidemias is based on the pattern of TG and cholesterol-rich lipoprotein particles, as measured by electrophoresis or ultracentrifugation and is commonly used to characterize primary causes of hyperlipidemias such as hypertriglyceridemia (Fredrickson and Lee, Circulation, 1965, 31:321-327; Fredrickson et al., New Eng J Med, 1967, 276 (1): 34-42).

"Hypertriglyceridemia" means a condition characterized by elevated triglyceride levels. Its etiology includes primary (i.e. genetic causes) and secondary (other underlying causes such as diabetes, metabolic syndrome/insulin resistance, obesity, physical inactivity, cigarette smoking, excess alcohol and a diet very high in carbohydrates) factors or, most often, a combination of both (Yuan et al. *CMAJ*, 2007, 176:1113-1120).

"Identifying" or "selecting an animal with metabolic or cardiovascular disease" means identifying or selecting a subject prone to or having been diagnosed with a metabolic disease, a cardiovascular disease, or a metabolic syndrome; or, identifying or selecting a subject having any symptom of a metabolic disease, cardiovascular disease, or metabolic syndrome including, but not limited to, hypercholesterolemia, hyperglycemia, hyperlipidemia, hypertriglyceridemia, hypertension increased insulin resistance, decreased insulin sensitivity, above normal body weight, and/or above normal body fat content or any combination thereof. Such identification can be accomplished by any method, including but not limited to, standard clinical tests or assessments, such as measuring serum or circulating (plasma) cholesterol, measuring serum or circulating (plasma) blood-glucose, measuring serum or circulating (plasma) triglycerides, measuring blood-pressure, measuring body fat content, measuring body weight, and the like.

"Improved cardiovascular outcome" means a reduction in the occurrence of adverse cardiovascular events, or the risk thereof. Examples of adverse cardiovascular events include, without limitation, death, reinfarction, stroke, cardiogenic shock, pulmonary edema, cardiac arrest, and atrial dysrhythmia.

"Immediately adjacent" means there are no intervening elements between the immediately adjacent elements, for example, between regions, segments, nucleotides and/or nucleosides.

"Increasing HDL" or "raising HDL" means increasing the level of HDL in an animal after administration of at least one compound of the invention, compared to the HDL level in an animal not administered any compound.

"Individual" or "subject" or "animal" means a human or non-human animal selected for treatment or therapy.

"Individual in need thereof" refers to a human or non-human animal selected for treatment or therapy that is in need of such treatment or therapy.

"Induce", "inhibit", "potentiate", "elevate", "increase", "decrease", "reduce" or the like denote quantitative differences between two states. For example, "an amount effective to inhibit the activity or expression of apo(a)" means that the level of activity or expression of apo(a) in a treated sample will differ from the level of apo(a) activity or expression in an untreated sample. Such terms are applied to, for example, levels of expression, and levels of activity.

"Inflammatory condition" refers to a disease, disease state, syndrome, or other condition resulting in inflammation. For example, rheumatoid arthritis and liver fibrosis are inflammatory conditions. Other examples of inflammatory conditions include sepsis, myocardial ischemia/reperfusion injury, adult respiratory distress syndrome, nephritis, graft rejection, inflammatory bowel disease, multiple sclerosis, arteriosclerosis, atherosclerosis and vasculitis.

"Inhibiting the expression or activity" refers to a reduction or blockade of the expression or activity of a RNA or protein and does not necessarily indicate a total elimination of expression or activity.

"Insulin resistance" is defined as the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

"Insulin sensitivity" is a measure of how effectively an individual processes glucose. An individual having high insulin sensitivity effectively processes glucose whereas an individual with low insulin sensitivity does not effectively process glucose.

"Internucleoside linkage" refers to the chemical bond between nucleosides.

"Intravenous administration" means administration into a vein.

"Linked nucleosides" means adjacent nucleosides which are bonded together.

"Lipid-lowering" means a reduction in one or more lipids (e.g., LDL, VLDL) in a subject. "Lipid-raising" means an increase in a lipid (e.g., HDL) in a subject. Lipid-lowering or lipid-raising can occur with one or more doses over time.

"Lipid-lowering therapy" or "lipid lowering agent" means a therapeutic regimen provided to a subject to reduce one or more lipids in a subject. In certain embodiments, a lipid-lowering therapy is provided to reduce one or more of apo(a), CETP, apoB, total cholesterol, LDL-C, VLDL-C, IDL-C, non-HDL-C, triglycerides, small dense LDL particles, and Lp(a) in a subject. Examples of lipid-lowering therapy include, but are not limited to, apoB inhibitors, statins, fibrates and MTP inhibitors.

"Lipoprotein", such as VLDL, LDL and HDL, refers to a group of proteins found in the serum, plasma and lymph and are important for lipid transport. The chemical composition of each lipoprotein differs, for example, in that the HDL has a higher proportion of protein versus lipid, whereas the VLDL has a lower proportion of protein versus lipid.

"Lp(a)" comprises apo(a) and a LDL like particle containing apoB. The apo(a) is linked to the apoB by a disulfide bond.

"Low density lipoprotein-cholesterol (LDL-C)" means cholesterol carried in low density lipoprotein particles. Concentration of LDL-C in serum (or plasma) is typically quantified in mg/dL or nmol/L. "Serum LDL-C" and "plasma LDL-C" mean LDL-C in the serum and plasma, respectively.

"Major risk factors" refers to factors that contribute to a high risk for a particular disease or condition. In certain embodiments, major risk factors for coronary heart disease include, without limitation, cigarette smoking, hypertension, high LDL, low HDL-C, family history of coronary heart disease, age, and other factors disclosed herein.

"Metabolic disorder" or "metabolic disease" refers to a condition characterized by an alteration or disturbance in metabolic function. "Metabolic" and "metabolism" are terms well known in the art and generally include the whole range of biochemical processes that occur within a living organism. Metabolic disorders include, but are not limited to, hyperglycemia, prediabetes, diabetes (type 1 and type 2), obesity, insulin resistance, metabolic syndrome and dyslipidemia due to type 2 diabetes.

"Metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Mismatch" or "non-complementary nucleobase" refers to the case when a nucleobase of a first nucleic acid is not capable of pairing with the corresponding nucleobase of a second or target nucleic acid.

"Mixed dyslipidemia" means a condition characterized by elevated cholesterol and elevated triglycerides.

"Modified internucleoside linkage" refers to a substitution or any change from a naturally occurring internucleoside bond (i.e. a phosphodiester internucleoside bond). For example, a phosphorothioate linkage is a modified internucleoside linkage.

"Modified nucleobase" refers to any nucleobase other than adenine, cytosine, guanine, thymidine, or uracil. For example, 5-methylcytosine is a modified nucleobase. An "unmodified nucleobase" means the purine bases adenine (A) and guanine (G), and the pyrimidine bases thymine (T), cytosine (C), and uracil (U).

"Modified nucleoside" means a nucleoside having at least one modified sugar moiety, and/or modified nucleobase.

"Modified nucleotide" means a nucleotide having at least one modified sugar moiety, modified internucleoside linkage and/or modified nucleobase.

"Modified oligonucleotide" means an oligonucleotide comprising at least one modified nucleotide.

"Modified sugar" refers to a substitution or change from a natural sugar. For example, a 2'-O-methoxyethyl modified sugar is a modified sugar.

"MOE nucleoside" means a nucleoside comprising a 2'-substituted sugar moiety comprising MOE at the 2'-position.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids (ssDNA), double-stranded nucleic acids (dsDNA), small interfering ribonucleic acids (siRNA), and microRNAs (miRNA). A nucleic acid may also comprise any combination of these elements in a single molecule.

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the oligonucleotide and the target nucleic acid are considered to be complementary at that nucleobase pair.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base, and not necessarily the linkage at one or more positions of an oligomeric compound; for example nucleoside mimetics having morpholino, cyclohexenyl, cyclohexyl, tetrahydropyranyl, bicyclo or tricyclo sugar mimetics such as non-furanose sugar units.

"Nucleotide" means a nucleoside having a phosphate group covalently linked to the sugar portion of the nucleoside.

"Nucleotide mimetic" includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

"Oligomeric compound" or "oligomer" means a polymer of linked monomeric subunits which is capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, chronic, short or intermittent.

"Peptide" means a molecule formed by linking at least two amino acids by amide bonds. Peptide refers to polypeptides and proteins.

"Pharmaceutical agent" means a substance that provides a therapeutic benefit when administered to an individual. For example, in certain embodiments, an antisense oligonucleotide targeted to apo(a) is a pharmaceutical agent.

"Pharmaceutical composition" or "composition" means a mixture of substances suitable for administering to an individual. For example, a pharmaceutical composition can comprise one or more active agents and a pharmaceutical carrier e.g., a sterile aqueous solution.

"Pharmaceutically acceptable carrier" means a medium or diluent that does not interfere with the structure of the compound. Certain of such carriers enable pharmaceutical compositions to be formulated as, for example, tablets, pills, dragees, capsules, liquids, gels, syrups, slurries, suspension and lozenges for the oral ingestion by a subject. Certain of such carriers enable pharmaceutical compositions to be formulated for injection, infusion or topical administration. For example, a pharmaceutically acceptable carrier can be a sterile aqueous solution.

"Pharmaceutically acceptable derivative" encompasses derivatives of the compounds described herein such as solvates, hydrates, esters, prodrugs, polymorphs, isomers, isotopically labelled variants, pharmaceutically acceptable salts and other derivatives known in the art.

"Pharmaceutically acceptable salts" means physiologically and pharmaceutically acceptable salts of antisense compounds, i.e., salts that retain the desired biological activity of the parent compound and do not impart undesired toxicological effects thereto. The term "pharmaceutically acceptable salt" or "salt" includes a salt prepared from pharmaceutically acceptable non-toxic acids or bases, including inorganic or organic acids and bases. "Pharmaceutically acceptable salts" of the compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the compounds described herein are in the form of a sodium salt.

"Phosphorothioate linkage" means a linkage between nucleosides where the phosphodiester bond is modified by replacing one of the non-bridging oxygen atoms with a sulfur atom. A phosphorothioate linkage (P=S) is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form (i.e., a drug) within the body or cells thereof by the action of endogenous enzymes or other chemicals or conditions.

"Raise" means to increase in amount. For example, to raise plasma HDL levels means to increase the amount of HDL in the plasma.

"Reduce" means to bring down to a smaller extent, size, amount, or number. For example, to reduce plasma triglyceride levels means to bring down the amount of triglyceride in the plasma.

"Region" or "target region" is defined as a portion of the target nucleic acid having at least one identifiable structure, function, or characteristic. For example, a target region may encompass a 3' UTR, a 5' UTR, an exon, an intron, an exon/intron junction, a coding region, a translation initiation region, translation termination region, or other defined nucleic acid region. The structurally defined regions for apo(a) can be obtained by accession number from sequence databases such as NCBI and such information is incorporated herein by reference. In certain embodiments, a target region may encompass the sequence from a 5' target site of one target segment within the target region to a 3' target site of another target segment within the target region.

"Ribonucleotide" means a nucleotide having a hydroxy at the 2' position of the sugar portion of the nucleotide. Ribonucleotides can be modified with any of a variety of substituents.

"Second agent" or "second therapeutic agent" means an agent that can be used in combination with a "first agent". A second therapeutic agent can include, but is not limited to, antisense oligonucleotides targeting apo(a) or apoB. A second agent can also include anti-apo(a) antibodies, apo(a) peptide inhibitors, cholesterol lowering agents, lipid lowering agents, glucose lowering agents and anti-inflammatory agents.

"Segments" are defined as smaller, sub-portions of regions within a nucleic acid. For example, a "target segment" means the sequence of nucleotides of a target nucleic acid to which one or more antisense compounds is targeted. "5' target site" refers to the 5'-most nucleotide of a target segment. "3' target site" refers to the 3'-most nucleotide of a target segment. Alternatively, a "start site" can refer to the 5'-most nucleotide of a target segment and a "stop site" refers to the 3'-most nucleotide of a target segment. A target segment can also begin at the "start site" of one sequence and end at the "stop site" of another sequence.

"Shortened" or "truncated" versions of antisense oligonucleotides or target nucleic acids taught herein have one, two or more nucleosides deleted.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity to a target nucleic acid to induce a desired effect while exhibiting minimal or no effects on non-target nucleic acids under conditions in which specific binding is desired, i.e. under physiological conditions in the case of in vivo assays and therapeutic treatments.

"Statin" means an agent that inhibits the activity of HMG-CoA reductase.

"Subcutaneous administration" means administration just below the skin.

"Subject" means a human or non-human animal selected for treatment or therapy.

"Sugar moiety" means a naturally occurring sugar moiety or a modified sugar moiety of a nucleoside.

"Symptom of cardiovascular disease or disorder" means a phenomenon that arises from and accompanies the cardiovascular disease or disorder and serves as an indication of it. For example, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever are symptoms of cardiovascular disease or disorder.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Therapeutically effective amount" means an amount of a pharmaceutical agent that provides a therapeutic benefit to an individual.

"Therapeutic lifestyle change" means dietary and lifestyle changes intended to lower fat/adipose tissue mass and/or cholesterol. Such change can reduce the risk of developing heart disease, and may includes recommendations for dietary intake of total daily calories, total fat, saturated fat, polyunsaturated fat, monounsaturated fat, carbohydrate, protein, cholesterol, insoluble fiber, as well as recommendations for physical activity.

"Treat" or "treating" refers to administering a compound described herein to effect an alteration or improvement of a disease, disorder, or condition.

"Triglyceride" or "TG" means a lipid or neutral fat consisting of glycerol combined with three fatty acid molecules.

"Type 2 diabetes," (also known as "type 2 diabetes mellitus", "diabetes mellitus, type 2", "non-insulin-dependent diabetes", "NIDDM", "obesity related diabetes", or "adult-onset diabetes") is a metabolic disorder that is primarily characterized by insulin resistance, relative insulin deficiency, and hyperglycemia.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Wing segment" means one or a plurality of nucleosides modified to impart to an oligonucleotide properties such as enhanced inhibitory activity, increased binding affinity for a target nucleic acid, or resistance to degradation by in vivo nucleases.

Certain Embodiments

Certain embodiments provide a compounds and methods for decreasing apo(a) mRNA and protein expression. In certain embodiments, the compound is an apo(a) specific inhibitor for treating, preventing, or ameliorating an apo(a) associated disease. In certain embodiments, the compound is an antisense oligonucleotide targeting apo(a).

Certain embodiments provide a compounds and methods for decreasing Lp(a) levels. In certain embodiments, the compound is an apo(a) specific inhibitor for treating, preventing, or ameliorating an Lp(a) associated disease. In certain embodiments, the compound is an antisense oligonucleotide targeting apo(a).

Certain embodiments provide a compound comprising a modified oligonucleotide targeting apo(a) consisting of 12 to 30 linked nucleosides. In certain embodiments, the modified oligonucleotide consists of 15 to 30, 18 to 24, 19 to 22, 13 to 25, 14 to 25, 15 to 25 linked nucleosides. In certain embodiments, the modified oligonucleotide comprises at least 12, at least 13, at least 14, at least 15, at least 16, at least 17, at least 18, at least 19, at least 20, at least 21, at least 22, at least 23, at least 24, at least 25, at least 26, at least 27, at least 28, at least 29 or 30 linked nucleosides. In certain embodiments, the modified oligonucleotide consists of 20 linked nucleosides.

Certain embodiments provide a compound comprising a modified oligonucleotide targeting apo(a) comprising at least 8, at least 9, at least 10, at least 11, at least 12, at least 13, at least 14, at least 15, at least 16, at least 17, at least 18, at least 19, or 20 contiguous nucleobases complementary to an equal length portion of any of SEQ ID NOs: 1-4. Certain embodiments provide a compound comprising a modified oligonucleotide targeting an apo(a) segment comprising at least 8, at least 9, at least 10, at least 11, at least 12, at least 13, at least 14, at least 15, at least 16, at least 17, at least 18, at least 19, or 20 contiguous nucleobases complementary to an equal length portion of any of the target segments shown in Tables 3-13 and 28-30. In the tables, the "Start Site" refers to the 5'-most nucleotide of a target segment and "Stop Site" refers to the 3'-most nucleotide of a target segment. A target segment can range from the start site to the stop site of each sequence listed in the tables. Alternatively, the target segment can range from the start site of one sequence and end at the stop site of another sequence. For example, as shown in Table 5, a target segment can range from 3901-3920, the start site to the stop site of SEQ ID NO: 58. In another example, as shown in Table 5, a target segment can range from 3900-3923, the start site of SEQ ID NO: 57 to the stop site of SEQ ID NO: 61.

Certain embodiments provide a compound comprising a modified oligonucleotide targeting apo(a), wherein the nucleobase sequence of the modified oligonucleotide is at least 80%, at least 85%, at least 90%, at least 95%, or 100% complementary to any of SEQ ID NOs: 1-4. Certain embodiments provide a compound comprising a modified oligonucleotide targeting apo(a), wherein the nucleobase sequence of the modified oligonucleotide is at least 80%, at least 85%, at least 90%, at least 95%, or 100% complementary to any of the target segments shown in Tables 3-13 and 28-30.

Certain embodiments provide a compound comprising a modified oligonucleotide targeting apo(a) consisting of 12 to 30 linked nucleosides and comprising a nucleobase sequence comprising a portion of at least 8, at least 9, at least 10, at least 11, at least 12, at least 13, at least 14, at least 15, at least 16, at least 17, at least 18, at least 19, or 20 contiguous nucleobases complementary to an equal length portion of nucleobases 3901 to 3920 of SEQ ID NO: 1, wherein the nucleobase sequence of the modified oligonucleotide is at least 80% complementary to SEQ ID NO: 1.

Certain embodiments provide a compound comprising a modified oligonucleotide targeting apo(a) consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29 or 30 contiguous nucleobases complementary to an equal length portion of nucleobases 3900 to 3923 of SEQ ID NO: 1, wherein the nucleobase sequence of the modified oligonucleotide is at least 80% complementary to SEQ ID NO: 1.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 12-130, 133, 134. In certain embodiments, the modified oligonucleotide has a nucleobase sequence comprising at least 8 contiguous nucleobases of any one of the nucleobase sequences of SEQ ID NOs: 12-130, 133, 134.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 12-20, 22-33, 35-44, 47-50, 51, 53, 57-62, 65-66, 68, 70-79, 81, 85-86, 89-90, 92-94, 97, 105-110, 103-104, 133-134.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 12-19, 26-30, 32, 35, 38-44, 46-47, 50, 57-58, 61, 64-66, 68, 72-74, 76-77, 92-94, 103-110.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 111, 114-121, 123-129.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 14, 17, 18, 26-28, 39, 71, 106-107.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 14, 26-29, 39-40, 82.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 14, 16-18.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 26-27, 107.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 28-29, 39-40, 47.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of any of the nucleobase sequences of SEQ ID NOs: 28, 93, 104, 134.

Certain embodiments provide a compound comprising a modified oligonucleotide targeting apo(a) consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of the nucleobase sequence of SEQ ID NO: 58.

In certain embodiments, the modified oligonucleotide has a nucleobase sequence comprising at least 8 contiguous nucleobases of the nucleobase sequence of SEQ ID NO: 58.

Certain embodiments provide a compound comprising a modified oligonucleotide targeting apo(a), wherein the modified oligonucleotide is single-stranded.

Certain embodiments provide a compound comprising a modified oligonucleotide targeting apo(a), wherein at least one internucleoside linkage is a modified internucleoside linkage. In certain embodiments, each internucleoside linkage is a phosphorothioate internucleoside linkage.

Certain embodiments provide a compound comprising a modified oligonucleotide targeting apo(a), wherein at least one nucleoside comprises a modified nucleobase. In certain embodiments, the modified nucleobase is a 5-methylcytosine.

Certain embodiments provide a compound comprising a modified oligonucleotide targeting apo(a), wherein the modified oligonucleotide comprises at least one modified sugar. In certain embodiments, the modified sugar is a bicyclic sugar. In certain embodiments, the modified sugar comprises a 2'-O-methoxyethyl, a constrained ethyl, a 3'-fluoro-HNA or a 4'-(CH$_2$)$_n$—O-2' bridge, wherein n is 1 or 2.

Certain embodiments provide a compound comprising a modified oligonucleotide targeting apo(a), wherein the modified oligonucleotide consists of 12 to 30 linked nucleosides and comprises: (a) a gap segment consisting of linked deoxynucleosides; (b) a 5' wing segment consisting of linked nucleosides; (c) a 3' wing segment consisting of linked nucleosides; and wherein the gap segment is positioned between the 5' wing segment and the 3' wing segment and wherein each nucleoside of each wing segment comprises a modified sugar.

Certain embodiments provide a compound comprising a modified oligonucleotide targeting apo(a), wherein the modified oligonucleotide consists of 20 linked nucleosides and comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

Certain embodiments provide a compound comprising a modified oligonucleotide targeting apo(a), wherein the modified oligonucleotide consists of 20 linked nucleosides and has a nucleobase sequence comprising at least 8 contiguous nucleobases of any of SEQ ID NOs: 12-130, 133, 134, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

Certain embodiments provide a compound comprising a modified oligonucleotide targeting apo(a), wherein the modified oligonucleotide consists of 20 linked nucleosides and has a nucleobase sequence comprising at least 8 contiguous nucleobases of SEQ ID NO: 58, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

Certain embodiments provide a modified oligonucleotide targeting apo(a), wherein the modified oligonucleotide consists of 20 linked nucleosides with the nucleobase sequence of SEQ ID NO: 58, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

In certain embodiments, the compound is in a salt form. In further embodiments, the compound further comprises of a pharmaceutically acceptable carrier or diluent. In certain embodiments, the compound comprising a modified oligonucleotide targeting apo(a), or a salt thereof, and a pharmaceutically acceptable carrier or diluent.

Certain embodiments provide a composition comprising a compound as described herein, wherein the viscosity level of the compound is less than 40 centipoise (cP). In certain embodiments, the antisense compounds as described herein are efficacious by virtue of having a viscosity of less than 40 cP, less than 35 cP, less than 30 cP, less than 25 cP, less than 20 cP or less than 15 cP when measured by the parameters as described in Example 13.

Certain embodiments provide compositions and methods for use in therapy to treat an apo(a) related disease, disorder or condition. Certain embodiments provide compositions and methods for use in therapy to treat an Lp(a) related disease, disorder or condition. In certain embodiments, the composition is a compound comprising an apo(a) specific inhibitor. In certain embodiments, the apo(a) specific inhibitor is a nucleic acid. In certain embodiments, the nucleic acid is an antisense compound. In certain embodiments, the antisense compound is a modified oligonucleotide targeting apo(a). In certain embodiments, the modified oligonucleotide targeting apo(a), is used in treating, preventing, slowing progression, ameliorating a cardiovascular and/or metabolic disease, disorder or condition. In certain embodiments, the compositions and methods for therapy include administering an apo(a) specific inhibitor to an individual in need thereof.

Certain embodiments provide compositions and methods for reducing apo(a) levels. Certain embodiments provide compositions and methods for reducing Lp(a) levels. In certain embodiments, reducing apo(a) levels in a tissue, organ or subject improves the ratio of LDL to HDL or the ratio of TG to HDL.

Certain embodiments provide compositions and methods for preventing, treating, delaying, slowing the progression and/or ameliorating apo(a) related diseases, disorders, and conditions in a subject in need thereof. Certain embodiments provide compositions and methods for preventing, treating, delaying, slowing the progression and/or ameliorating Lp(a) related diseases, disorders, and conditions in a subject in need thereof. In certain embodiments, such diseases, disorders, and conditions include cardiovascular and/or metabolic diseases, disorders, and conditions. Certain such cardiovascular diseases, disorders or conditions include, but are not limited to, aneurysm (e.g., abdominal aortic aneurysm), angina, arrhythmia, atherosclerosis, cerebrovascular disease, coronary artery disease, coronary heart disease, dyslipidemia, hypercholesterolemia, hyperlipidemia, hypertension, hypertriglyceridemia, myocardial infarction, peripheral vascular disease (e.g., peripheral artery disease, peripheral artery occlusive disease), retinal vascular occlusion, or stroke. Certain such metabolic diseases, disorders or conditions include, but are not limited to, hyperglycemia, prediabetes, diabetes (type I and type II), obesity, insulin resistance, metabolic syndrome and diabetic dyslipidemia. Certain such inflammatory diseases, disorders or conditions include, but are not limited to, coronary artery disease (CAD), Alzheimer's Disease and thromboembolic diseases, disorder or conditions Certain thromboembolic diseases, disorders or conditions include, but are not limited to, stroke, thrombosis (e.g., venous thromboembolism), myocardial infarction and peripheral vascular disease.

Certain embodiments provide a method of reducing at least one symptom of a cardiovascular disease, disorder or condition. In certain embodiments, the symptoms include, but are not limited to, angina, chest pain, shortness of breath, palpitations, weakness, dizziness, nausea, sweating, tachycardia, bradycardia, arrhythmia, atrial fibrillation, swelling in the lower extremities, cyanosis, fatigue, fainting, numbness of the face, numbness of the limbs, claudication or cramping of muscles, bloating of the abdomen, and fever.

In certain embodiments, the modulation of apo(a) or Lp(a) expression occurs in a cell, tissue or organ. In certain embodiments, the modulations occur in a cell, tissue or organ in an animal. In certain embodiments, the modulation is a reduction in apo(a) mRNA level. In certain embodiments, the modulation is a reduction in apo(a) protein level. In certain embodiments, both apo(a) mRNA and protein levels are reduced. In certain embodiments, the modulation is a reduction in Lp(a) level. Such reduction may occur in a time-dependent or in a dose-dependent manner.

In certain embodiments, the subject or animal is human.

In certain embodiments, the compound is parenterally administered. In further embodiments, the parenteral administration is subcutaneous.

In certain embodiments, the compound is co-administered with a second agent or therapy. In certain embodiments, the second agent is a glucose-lowering agent. In certain embodiments, the second agent is a LDL, TG or cholesterol lowering agent. In certain embodiments, the second agent is an anti-inflammatory agent. In certain embodiments, the second agent is an Alzheimer Disease drug. In certain embodiments, the second agent can be, but is not limited to, a non-steroidal anti-inflammatory drug (NSAID e.g., aspirin), niacin (e.g., Niaspan), nicotinic acid, an apoB inhibitor (e.g., Mipomersen), a CETP inhibitor (e.g., Anacetrapib), an apo(a) inhibitor, a thyroid hormone analog (e.g., Eprotirome), a HMG-CoA reductase inhibitor (e.g., a statin), a fibrate (e.g., Gemfibrozil) and an microsomal triglyceride transfer protein inhibitor (e.g., Lomitapide). The therapy can be, but is not limited to, Lp(a) apheresis. Agents or therapies can be co-administered or administered concomitantly. Agents or therapies can be sequentially or subsequently administered.

Certain embodiments provide use of a compound targeted to apo(a) for decreasing apo(a) levels in an animal. Certain embodiments provide use of a compound targeted to apo(a) for decreasing Lp(a) levels in an animal. Certain embodiments provide use of a compounds targeted to apo(a) for the treatment, prevention, or amelioration of a disease, disorder, or condition associated with apo(a). Certain embodiments provide use of a compounds targeted to apo(a) for the treatment, prevention, or amelioration of a disease, disorder, or condition associated with Lp(a).

Certain embodiments provide use of a compound targeted to apo(a) in the preparation of a medicament for decreasing apo(a) levels in an animal. Certain embodiments provide use of a compound targeted to apo(a) in the preparation of a medicament for decreasing Lp(a) levels in an animal. Certain embodiments provide use of a compound for the preparation of a medicament for the treatment, prevention, or amelioration of a disease, disorder, or condition associated with apo(a). Certain embodiments provide use of a compound for the preparation of a medicament for the treatment, prevention, or amelioration of a disease, disorder, or condition associated with Lp(a).

Certain embodiments provide a kit for treating, preventing, or ameliorating a disease, disorder or condition as described herein wherein the kit comprises: (i) an apo(a) specific inhibitor as described herein; and optionally (ii) a second agent or therapy as described herein.

A kit of the present invention can further include instructions for using the kit to treat, prevent, or ameliorate a disease, disorder or condition as described herein by combination therapy as described herein.

Antisense Compounds

Oligomeric compounds include, but are not limited to, oligonucleotides, oligonucleosides, oligonucleotide analogs, oligonucleotide mimetics, antisense compounds, antisense oligonucleotides, ribozymes, microRNAs and siRNAs. An oligomeric compound may be "antisense" to a target nucleic acid, meaning that it is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to an apo(a) nucleic acid is 12 to 30 subunits in length. In other words, such antisense compounds are from 12 to 30 linked subunits. In other embodiments, the antisense compound is 8 to 80, 10 to 80, 12 to 50, 15 to 30, 18 to 24, 19 to 22, 13 to 25, 14 to 25 or 15 to 25 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In certain such embodiments, the antisense compounds are 8 linked subunits in length. In some embodiments the antisense compound is an antisense oligonucleotide. In some embodiments, the linked subunits are nucleosides.

In certain embodiments, the antisense compound comprises a shortened or truncated modified oligonucleotide. The shortened or truncated modified oligonucleotide can have one or more nucleosides deleted from the 5' end (5' truncation), one or more nucleosides deleted from the 3' end (3' truncation) or one or more nucleosides deleted from the central portion. Alternatively, the deleted nucleosides can be dispersed throughout the modified oligonucleotide, for example, in an antisense compound having one nucleoside deleted from the 5' end and one nucleoside deleted from the 3' end.

When a single additional nucleoside is present in a lengthened oligonucleotide, the additional nucleoside can be located at the central portion, 5' or 3' end of the oligonucleotide. When two or more additional nucleosides are present, the added nucleosides can be adjacent to each other, for example, in an oligonucleotide having two nucleosides added to the central portion, to the 5' end (5' addition), or alternatively to the 3' end (3' addition), of the oligonucleotide. Alternatively, the added nucleosides can be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to an apo(a) nucleic acid have chemically modified subunits arranged in patterns, or motifs, to confer to the antisense compounds properties, such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of a RNA:DNA duplex.

Antisense compounds having a gapmer motif are considered chimeric antisense compounds. In a gapmer an internal region having a plurality of nucleotides that supports RNase H cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH2) n-O-2' bridge, where n=1 or n=2). Preferably, each distinct region comprises uniform sugar moieties. The wing-gap-wing motif is frequently described as "X—Y—Z", where "X" represents the length of the 5' wing region, "Y" represents the length of the gap region, and "Z" represents the length of the 3' wing region. As used herein, a gapmer described as "X—Y—Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same; in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more nucleotides. Thus, gapmers include, but are not limited to, for example 5-10-5, 4-8-4, 4-12-3, 4-12-4, 3-14-3, 2-13-5, 2-12-2, 2-16-2, 1-18-1, 3-10-3, 2-10-2, 1-10-1, 2-8-2, 6-8-6, 5-8-5, 1-8-1, 2-6-2, 2-13-2, 1-8-2, 2-8-3, 3-10-2, 1-18-2 or 2-18-2.

In certain embodiments, the antisense compound as a "wingmer" motif, having a wing-gap or gap-wing configuration, i.e. an X—Y or Y—Z configuration as described above for the gapmer configuration. Thus, wingmer configurations include, but are not limited to, for example 5-10, 8-4, 4-12, 12-4, 3-14, 16-2, 18-1, 10-3, 2-10, 1-10, 8-2, 2-13 or 5-13.

In certain embodiments, antisense compounds targeted to an apo(a) nucleic acid possess a 5-10-5 gapmer motif.

In certain embodiments, an antisense compound targeted to an apo(a) nucleic acid has a gap-widened motif.

Target Nucleic Acids, Target Regions and Nucleotide Sequences

Nucleotide sequences that encode the apo(a) target sequence include, without limitation, the following: GENBANK Accession No. NM_005577.2, incorporated herein as SEQ ID NO: 1; GENBANK Accession No. NT_007422.12 truncated from nucleotides 3230000 to 3380000, incorporated herein as SEQ ID NO: 2; GENBANK Accession No. NT_025741.15 truncated from nucleotides 65120000 to 65258000, designated herein as SEQ ID NO: 3; and GENBANK Accession No. NM_005577.1, incorporated herein as SEQ ID NO: 4.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage or a nucleobase. Antisense compounds described by Isis Number (Isis No.) indicate a combination of nucleobase sequence and motif.

In certain embodiments, a "target region" is a structurally defined region of the target nucleic acid. For example, a target region can encompass a 3' UTR, a 5' UTR, an exon, an intron, an exon/intron junction, a coding region, a translation initiation region, a translation termination region, or other defined nucleic acid region. The structurally defined regions for apo(a) can be obtained by accession number from sequence databases such as NCBI and such information is incorporated herein by reference. In certain embodiments, a target region can encompass the sequence from a 5' target site of one target segment within the target region to a 3' target site of another target segment within the same target region.

In certain embodiments, a "target segment" is a smaller, sub-portion of a target region within a nucleic acid. For example, a target segment can be the sequence of nucleotides of a target nucleic acid to which one or more antisense compounds are targeted. "5' target site" refers to the 5'-most nucleotide of a target segment. "3' target site" refers to the 3'-most nucleotide of a target segment.

A target region can contain one or more target segments. Multiple target segments within a target region can be overlapping. Alternatively, they can be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed, herein.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

Suitable target segments can be found within a 5' UTR, a coding region, a 3' UTR, an intron, an exon, or an exon/intron junction. Target segments containing a start codon or a stop codon are also suitable target segments. A suitable target segment can specifically exclude a certain structurally defined region, such as the start codon or stop codon.

The determination of suitable target segments can include a comparison of the sequence of a target nucleic acid to other sequences throughout the genome. For example, the BLAST algorithm can be used to identify regions of similarity amongst different nucleic acids. This comparison can prevent the selection of antisense compound sequences that can hybridize in a non-specific manner to sequences other than a selected target nucleic acid (i.e., non-target or off-target sequences).

There can be variation in activity (e.g., as defined by percent reduction of target nucleic acid levels) of the antisense compounds within an active target region. In certain embodiments, reductions in apo(a) mRNA levels can be indicative of inhibition of apo(a) expression. Reductions in levels of an apo(a) protein can be indicative of inhibition of target mRNA expression. Further, phenotypic changes can be indicative of inhibition of apo(a) expression. For example, an increase in HDL levels, decrease in LDL levels, decrease in cholesterol levels or decrease in triglyceride levels, are among phenotypic changes that can be assessed for inhibition of apo(a) expression. Other phenotypic indications, e.g., symptoms associated with a cardiovascular disease, may also be assessed; for example, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever.

Hybridization

In some embodiments, hybridization occurs between an antisense compound disclosed herein and an apo(a) nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art (Sambrooke and Russell, Molecular Cloning: A Laboratory Manual, 3$^{rd}$ Ed., 2001). In certain embodiments, the antisense compounds provided herein are specifically hybridizable with an apo(a) nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an apo(a) nucleic acid).

Noncomplementary nucleobases between an antisense compound and an apo(a) nucleic acid can be tolerated provided that the antisense compound remains able to specifically hybridize to a target nucleic acid. Moreover, an antisense compound can hybridize over one or more segments of an apo(a) nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 75%, 80%, 85%, 86%, 87%, 88%, 89%, 90%, 91%, 92%, 93%, 94%, 95%, 96%, 97%, 98%, 99%, or 100% complementary to an apo(a) nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases can be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound may be fully complementary to an apo(a) nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase(s) can be at the 5' end or 3' end of the antisense compound. Alternatively, the non-complementary nucleobase(s) can be at an internal position of the antisense compound. When two or more non-complementary nucleobases are present, they can be contiguous (i.e. linked) or non-contiguous. In one embodiment, a non-complementary nucleobase is located in the wing segment of a gapmer antisense oligonucleotide.

In certain embodiments, antisense compounds that are, or are up to, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an apo(a) nucleic acid, or specified portion thereof.

In certain embodiments, antisense compounds that are, or are up to, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an apo(a) nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein can also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases can be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, 25, 26, 27, 28, 29 or 30 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, 25, 26, 27, 28, 29 or 30 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides can also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an apo(a) nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(=O)—$N(R_m)(R_n)$, and O—$CH_2$—C(=O)—$N(R_1)$—$(CH_2)_2$—$N(R_m)(R_n)$, where each $R_l$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-$(CH_2)$—O-2' (LNA); 4'-$(CH_2)$—S-2; 4'-$(CH_2)_2$—O-2' (ENA); 4'-CH($CH_3$)—O-2' and 4'-CH($CH_2OCH_3$)—O-2' (and analogs thereof see U.S. Pat. No. 7,399,845, issued on Jul. 15, 2008); 4'-C($CH_3$)($CH_3$)—O-2' (and analogs thereof see published International Application WO/2009/006478, published Jan. 8, 2009); 4'-$CH_2$—N($OCH_3$)-2' (and analogs thereof see published International Application WO/2008/150729, published Dec. 11, 2008); 4'-$CH_2$—O—N($CH_3$)-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—C(H)($CH_3$)-2' (see Chattopadhyaya et al., *J. Org. Chem.*, 2009, 74, 118-134); and 4'-$CH_2$—C(=$CH_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example β-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C($R_a$)($R_b$)]$_n$—, —C($R_a$)=C($R_b$)—, —C($R_a$)=N—, —C(=O)—, —C(=$NR_a$)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —[C($R_a$)($R_b$)]$_n$—, —[C($R_a$)($R_b$)]$_n$—O—, —C($R_aR_b$)—N(R)—O— or —C($R_aR_b$)—O—N(R)—. In certain embodiments, the bridge is 4'-$CH_2$-2', 4'-$(CH_2)_2$-2', 4'-$(CH_2)_3$-2', 4'-$CH_2$—O-2', 4'-$(CH_2)_2$—O-2', 4'-$CH_2$—O—

N(R)-2' and 4'-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-2'-methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

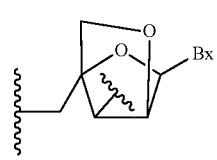
(A)

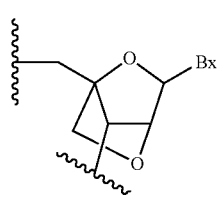
(B)

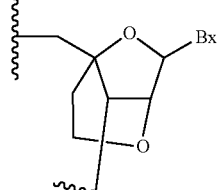
(C)

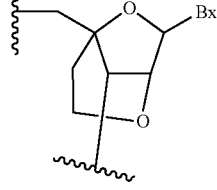
(D)

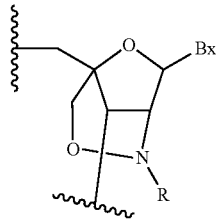
(E)

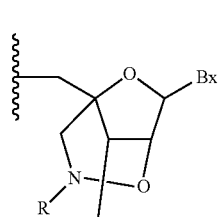

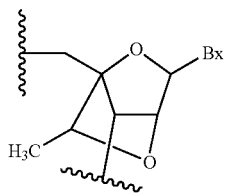
(F)

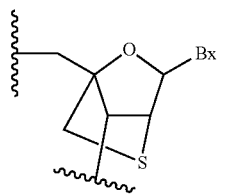
(G)

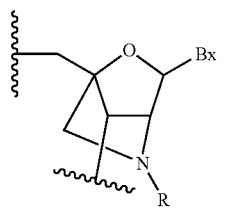
(H)

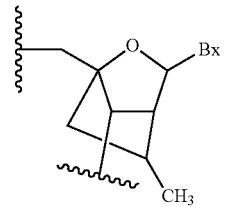
(I)

(J)

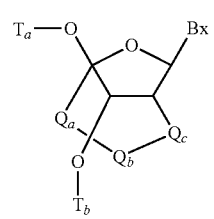

wherein Bx is the base moiety and R is independently H, a protecting group or C$_1$-C$_{12}$ alkyl.

In certain embodiments, bicyclic nucleosides are provided having Formula I:

$$\text{I}$$

wherein:
Bx is a heterocyclic base moiety;
-Q$_a$-Q$_b$-Q$_c$- is —CH$_2$—N(R$_c$)—CH$_2$—, —C(=O)—N(R$_c$)—CH$_2$—, —CH$_2$—O—N(R$_c$)—, —CH$_2$—N(R$_c$)—O— or —N(R$_c$)—O—CH$_2$;
R$_c$ is C$_1$-C$_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

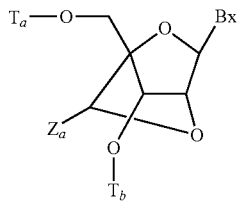

II wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

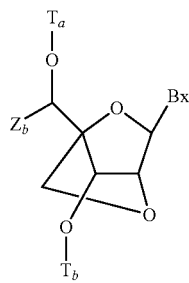

III wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

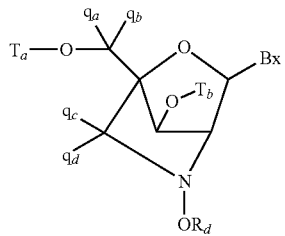

IV wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

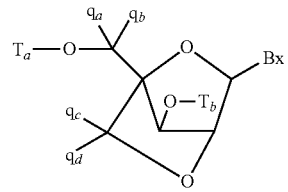

V wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, alkoxy, substituted $C_1$-$C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, O—C(=O)—$NJ_jJ_k$, $N(H)C(=NH)NJ_jJ_k$, $N(H)C(=O)NJ_jJ_k$ or $N(H)C(=S)NJ_jJ_k$;

or $q_e$ and $q_f$ together are $=C(q_g)(q_h)$;

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

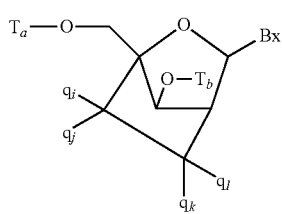

VI wherein:

Bx is a heterocyclic base moiety;

$T_a$ and $T_b$ are each, independently, H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH$_2$)$_3$-2' bridge and the alkenyl analog bridge 4'-CH=CH—CH$_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocyclic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[(CH$_2$)$_n$O]$_m$CH$_3$, O(CH$_2$)$_n$NH$_2$, O(CH$_2$)$_n$CH$_3$, O(CH$_2$)$_n$F, O(CH$_2$)$_n$ONH$_2$, OCH$_2$C(=O)N(H)CH$_3$, and O(CH$_2$)$_n$ON[(CH$_2$)$_n$CH$_3$]$_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, SCH$_3$, OCN, Cl, Br, CN, F, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854), fluoro HNA (F-HNA) or those compounds having Formula VII:

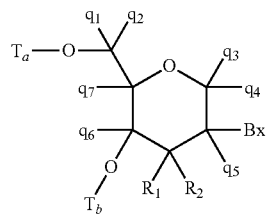

VII wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, OC(=X)$J_1$, OC(=X)$NJ_1J_2$, $NJ_3$C(=X) $NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is methoxyethoxy and $R_2$ is H. In certain embodiments, $R_1$ is H and $R_2$ is fluoro; $R_1$ is H and $R_2$ is methoxy, and $R_1$ is H and $R_2$ is methoxyethoxy.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—$N(R_m)(R_n)$, or O—$CH_2$—C($=$O)—$N(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH($CH_3$)—O-2') bridging group. In certain embodiments, the (4'-CH($CH_3$)—O-2') modified nucleosides are arranged throughout the wings of a gapmer motif. In certain embodiments, the modified sugar moiety is a cEt. In certain embodiments, the cEt modified nucleotides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and 0-6 substituted purines, including 2 aminopropyladenine, 5-propynyluracil and 5-propynylcytosine.

In certain embodiments, antisense compounds targeted to an apo(a) nucleic acid comprise one or more modified nucleobases. In certain embodiments, gap-widened antisense oligonucleotides targeted to an apo(a) nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to an apo(a) nucleic acid can be utilized in pharmaceutical compositions by combining the antisense compound with a suitable pharmaceutically acceptable diluent or carrier.

In certain embodiments, the "pharmaceutical carrier" or "excipient" is a pharmaceutically acceptable solvent, suspending agent or any other pharmacologically inert vehicle for delivering one or more nucleic acids to an animal. The excipient can be liquid or solid and can be selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipients, which do not deleteriously react with nucleic acids, suitable for parenteral or non-parenteral administration can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to an apo(a) nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or an oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds can be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602, published on Jan. 16, 2003.

Cell Culture and Antisense Compounds Treatment

The effects of antisense compounds on the level, activity or expression of apo(a) nucleic acids can be tested in vitro in a variety of cell types. Cell types used for such analyses are available from commercial vendors (e.g. American Type Culture Collection, Manassas, Va.; Zen-Bio, Inc., Research Triangle Park, N.C.; Clonetics Corporation, Walkersville, Md.) and are cultured according to the vendor's instructions using commercially available reagents (e.g., Invitrogen Life Technologies, Carlsbad, Calif.). Illustrative cell types include, but are not limited to, HepG2 cells, Hep3B cells, Huh7 (hepatocellular carcinoma) cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 μg/mL per 100 nM antisense oligonucleotide.

Another reagent used to introduce antisense oligonucleotides into cultured cells includes Oligofectamine™ (Invitrogen Life Technologies, Carlsbad, Calif.). Antisense oligonucleotide is mixed with Oligofectamine™ in Opti-MEM™-1 reduced serum medium (Invitrogen Life Technologies, Carlsbad, Calif.) to achieve the desired concentration of oligonucleotide with an Oligofectamine™ to oligonucleotide ratio of approximately 0.2 to 0.8 μL per 100 nM.

Another reagent used to introduce antisense oligonucleotides into cultured cells includes FuGENE 6 (Roche Diagnostics Corp., Indianapolis, Ind.). Antisense oligomeric compound was mixed with FuGENE 6 in 1 mL of serum-free RPMI to achieve the desired concentration of oligonucleotide with a FuGENE 6 to oligomeric compound ratio of 1 to 4 μL of FuGENE 6 per 100 nM.

Another technique used to introduce antisense oligonucleotides into cultured cells includes electroporation (Sambrooke and Russell in *Molecular Cloning. A Laboratory Manual*. Third Edition. Cold Spring Harbor Laboratory Press, Cold Spring Harbor, N.Y. 2001).

Cells are treated with antisense oligonucleotides by routine methods. Cells are typically harvested 16-24 hours after antisense oligonucleotide treatment, at which time RNA or protein levels of target nucleic acids are measured by methods known in the art and described herein (Sambrooke and Russell in *Molecular Cloning. A Laboratory Manual*. Third Edition. Cold Spring Harbor Laboratory Press, Cold Spring Harbor, N.Y. 2001). In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art (Sambrooke and Russell in *Molecular Cloning. A Laboratory Manual*. Third Edition. Cold Spring Harbor Laboratory Press, Cold Spring Harbor, N.Y. 2001). Antisense oligonucleotides are typically used at concentrations ranging from 1 nM to 300 nM when transfected with LIPOFECTAMINE2000® (Invitrogen, Carlsbad, Calif.), Lipofectin® (Invitrogen, Carlsbad, Calif.) or Cytofectin™ (Genlantis, San Diego, Calif.). Antisense oligonucleotides are used at higher concentrations ranging from 625 to 20,000 nM when transfected using electroporation.

RNA Isolation

RNA analysis can be performed on total cellular RNA or poly(A)+mRNA. Methods of RNA isolation are well known in the art (Sambrooke and Russell in *Molecular Cloning. A Laboratory Manual*. Third Edition. Cold Spring Harbor Laboratory Press, Cold Spring Harbor, N.Y. 2001). For example, RNA can be prepared using TRIZOL® (Invitrogen, Carlsbad, Calif.) according to the manufacturer's recommended protocols.

Analysis of Inhibition of Target Levels or Expression

Inhibition of levels or expression of an apo(a) nucleic acid can be assayed in a variety of ways known in the art (Sambrooke and Russell in *Molecular Cloning. A Laboratory Manual*. Third Edition. Cold Spring Harbor Laboratory Press, Cold Spring Harbor, N.Y., 2001). For example, target nucleic acid levels can be quantitated by, e.g., Northern blot analysis, competitive polymerase chain reaction (PCR), or quantitative real-time PCR. RNA analysis can be performed on total cellular RNA or poly(A)+mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems (Foster City, Calif.) and used according to manufacturer's instructions.

Quantitative Real-Time PCR Analysis of Target RNA Levels

Quantitation of target RNA levels can be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT and real-time-PCR reactions are carried out by methods well known to those skilled in the art.

Gene (or RNA) target quantities obtained by real time PCR can be normalized using either the expression level of a gene whose expression is constant, such as cyclophilin A or GAPDH, or by quantifying total RNA using RIBOGREEN® (Invitrogen, Inc. Carlsbad, Calif.). Cyclophilin A or GAPDH expression can be quantified by real time PCR, by being run simultaneously with the target, multiplexing, or separately. Total RNA is quantified using RIBOGREEN® RNA quantification reagent (Invitrogen, Inc. Carlsbad, Calif.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems, Foster City, Calif.) is used to measure RIBOGREEN® fluorescence.

Probes and primers can be designed to hybridize to an apo(a) nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of apo(a) nucleic acids can be assessed by measuring apo(a) protein levels. Protein levels of apo(a) can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS) (Sambrooke and Russell in *Molecular Cloning. A Laboratory Manual*. Third Edition. Cold Spring Harbor Laboratory Press, Cold Spring Harbor, N.Y. 2001). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of apo(a) are commercially available.

In Vivo Testing of Antisense Compounds

Antisense compounds, for example, antisense oligonucleotides, are tested in animals to assess their ability to inhibit expression of apo(a) and produce phenotypic changes. Testing can be performed in normal animals, or in experimental disease models. For administration to animals, antisense oligonucleotides are formulated in a pharmaceutically acceptable diluent, such as saline or phosphate-buffered saline. Administration includes parenteral routes of administration. Calculation of antisense oligonucleotide dosage and dosing frequency depends upon factors such as route of administration and animal body weight. Following a period of treatment with antisense oligonucleotides, RNA is isolated from tissue and changes in apo(a) nucleic acid expression are measured. Changes in apo(a) protein levels are also measured.

Certain Indications

In certain embodiments, provided herein are methods of treating an individual comprising administering one or more pharmaceutical compositions as described herein. In certain embodiments, the individual has an apo(a) related disease. In certain embodiments, the individual has an Lp(a) related disease. In certain embodiments, the individual has an inflammatory, cardiovascular and/or a metabolic disease, disorder or condition.

In certain embodiments, the cardiovascular diseases, disorders or conditions include, but are not limited to, aneurysm (e.g., abdominal aortic aneurysm), angina, arrhythmia, atherosclerosis, cerebrovascular disease, coronary artery disease, coronary heart disease, dyslipidemia, hypercholesterolemia, hyperlipidemia, hypertension, hypertriglyceridemia, myocardial infarction, peripheral vascular disease (e.g., peripheral artery disease), stroke and the like.

In certain embodiments, the compounds targeted to apo(a) described herein modulate physiological markers or phenotypes of the cardiovascular disease, disorder or condition. For example, administration of the compounds to animals can decrease LDL and cholesterol levels in those animals compared to untreated animals. In certain embodiments, the modulation of the physiological markers or phenotypes can be associated with inhibition of apo(a) by the compounds.

In certain embodiments, the physiological markers of the cardiovascular disease, disorder or condition can be quantifiable. For example, LDL or cholesterol levels can be measured and quantified by, for example, standard lipid tests. For such markers, in certain embodiments, the marker can be decreased by about 5, 10, 15, 20, 25, 30, 35, 40, 45, 50, 55, 60, 65, 70, 75, 80, 85, 90, 95 or 99%, or a range defined by any two of these values.

Also, provided herein are methods for preventing, treating or ameliorating a symptom associated with the cardiovascular disease, disorder or condition in a subject in need thereof. In certain embodiments, provided is a method for reducing the rate of onset of a symptom associated with the cardiovascular disease, disorder or condition. In certain embodiments, provided is a method for reducing the severity of a symptom associated with the cardiovascular disease, disorder or condition. In such embodiments, the methods comprise administering a therapeutically effective amount of a compound targeted to an apo(a) nucleic acid to an individual in need thereof.

The cardiovascular disease, disorder or condition can be characterized by numerous physical symptoms. Any symptom known to one of skill in the art to be associated with the cardiovascular disease, disorder or condition can be prevented, treated, ameliorated or otherwise modulated with the compounds and methods described herein. In certain embodiments, the symptom can be any of, but not limited to, angina, chest pain, shortness of breath, palpitations, weakness, dizziness, nausea, sweating, tachycardia, bradycardia, arrhythmia, atrial fibrillation, swelling in the lower extremities, cyanosis, fatigue, fainting, numbness of the face, numbness of the limbs, claudication or cramping of muscles, bloating of the abdomen or fever.

In certain embodiments, the metabolic diseases, disorders or conditions include, but are not limited to, hyperglycemia, prediabetes, diabetes (type I and type II), obesity, insulin resistance, metabolic syndrome and diabetic dyslipidemia.

In certain embodiments, compounds targeted to apo(a) as described herein modulate physiological markers or phenotypes of the metabolic disease, disorder or condition. For example, administration of the compounds to animals can decrease glucose and insulin resistance levels in those animals compared to untreated animals. In certain embodiments, the modulation of the physiological markers or phenotypes can be associated with inhibition of apo(a) by the compounds.

In certain embodiments, physiological markers of the metabolic disease, disorder or condition can be quantifiable. For example, glucose levels or insulin resistance can be measured and quantified by standard tests known in the art. For such markers, in certain embodiments, the marker can be decreased by about 5, 10, 15, 20, 25, 30, 35, 40, 45, 50, 55, 60, 65, 70, 75, 80, 85, 90, 95 or 99%, or a range defined by any two of these values. In another example, insulin sensitivity can be measured and quantified by standard tests known in the art. For such markers, in certain embodiments, the marker can be increase by about 5, 10, 15, 20, 25, 30, 35, 40, 45, 50, 55, 60, 65, 70, 75, 80, 85, 90, 95 or 99%, or a range defined by any two of these values.

Also, provided herein are methods for preventing, treating or ameliorating a symptom associated with the metabolic disease, disorder or condition in a subject in need thereof. In certain embodiments, provided is a method for reducing the rate of onset of a symptom associated with the metabolic disease, disorder or condition. In certain embodiments, provided is a method for reducing the severity of a symptom associated with the metabolic disease, disorder or condition. In such embodiments, the methods comprise administering a therapeutically effective amount of a compound targeted to an apo(a) nucleic acid to an individual in need thereof.

The metabolic disease, disorder or condition can be characterized by numerous physical symptoms. Any symptom known to one of skill in the art to be associated with the metabolic disease, disorder or condition can be prevented, treated, ameliorated or otherwise modulated with the compounds and methods described herein. In certain embodiments, the symptom can be any of, but not limited to, excessive urine production (polyuria), excessive thirst and increased fluid intake (polydipsia), blurred vision, unexplained weight loss and lethargy.

In certain embodiments, the inflammatory diseases, disorders or conditions include, but are not limited to, coronary artery disease (CAD), Alzheimer's Disease and thromboembolic diseases, disorder or conditions. Certain thromboembolic diseases, disorders or conditions include, but are not limited to, stroke, thrombosis, myocardial infarction and peripheral vascular disease.

In certain embodiments, the compounds targeted to apo(a) described herein modulate physiological markers or phenotypes of the inflammatory disease, disorder or condition. For example, administration of the compounds to animals can decrease inflammatory cytokine or other inflammatory markers levels in those animals compared to untreated animals. In certain embodiments, the modulation of the physiological markers or phenotypes can be associated with inhibition of apo(a) by the compounds.

In certain embodiments, the physiological markers of the inflammatory disease, disorder or condition can be quantifiable. For example, cytokine levels can be measured and quantified by standard tests known in the art. For such markers, in certain embodiments, the marker can be decreased by about 5, 10, 15, 20, 25, 30, 35, 40, 45, 50, 55, 60, 65, 70, 75, 80, 85, 90, 95 or 99%, or a range defined by any two of these values.

Also, provided herein are methods for preventing, treating or ameliorating a symptom associated with the inflammatory disease, disorder or condition in a subject in need thereof. In certain embodiments, provided is a method for reducing the rate of onset of a symptom associated with the inflammatory disease, disorder or condition. In certain embodiments, provided is a method for reducing the severity of a symptom associated with the inflammatory disease, disorder or condition. In such embodiments, the methods comprise administering a therapeutically effective amount of a compound targeted to an apo(a) nucleic acid to an individual in need thereof.

In certain embodiments, provided are methods of treating an individual with an apo(a) related disease, disorder or condition comprising administering a therapeutically effective amount of one or more pharmaceutical compositions as described herein. In certain embodiments, the individual has elevated apo(a) levels. In certain embodiments, provided are methods of treating an individual with an Lp(a) related disease, disorder or condition comprising administering a therapeutically effective amount of one or more pharmaceutical compositions as described herein. In certain embodiments, the individual has elevated Lp(a) levels. In certain embodiments, the individual has an inflammatory, cardiovascular and/or metabolic disease, disorder or condition. In certain embodiments, administration of a therapeutically effective amount of an antisense compound targeted to an apo(a) nucleic acid is accompanied by monitoring of apo(a) or Lp(a) levels. In certain embodiments, administration of a therapeutically effective amount of an antisense compound targeted to an apo(a) nucleic acid is accompanied by monitoring of markers of inflammatory, cardiovascular and/or metabolic disease, or other disease process associated with the expression of apo(a), to determine an individual's response to the antisense compound. An individual's response to administration of the antisense compound targeting apo(a) can be used by a physician to determine the amount and duration of therapeutic intervention with the compound.

In certain embodiments, administration of an antisense compound targeted to an apo(a) nucleic acid results in reduction of apo(a) expression by at least about 15, 20, 25, 30, 35, 40, 45, 50, 55, 60, 65, 70, 75, 80, 85, 90, 95 or 99%, or a range defined by any two of these values. In certain embodiments, apo(a) expression is reduced to ≤100 mg/dL, ≤90 mg/dL, ≤80 mg/dL, ≤70 mg/dL, ≤60 mg/dL, ≤50 mg/dL, ≤40 mg/dL, ≤30 mg/dL, ≤20 mg/dL or ≤10 mg/dL.

In certain embodiments, administration of an antisense compound targeted to an apo(a) nucleic acid results in reduction of Lp(a) expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to apo(a) are used for the preparation of a medicament for treating a patient suffering or susceptible to an inflammatory, cardiovascular and/or a metabolic disease, disorder or condition.

Dosing

In certain embodiments, pharmaceutical compositions are administered according to a dosing regimen (e.g., dose, dose frequency, and duration) wherein the dosing regimen can be selected to achieve a desired effect. The desired effect can be, for example, reduction of apo(a) or the prevention, reduction, amelioration or slowing the progression of a disease or condition associated with apo(a).

In certain embodiments, the variables of the dosing regimen are adjusted to result in a desired concentration of pharmaceutical composition in a subject. "Concentration of pharmaceutical composition" as used with regard to dose regimen can refer to the compound, oligonucleotide, or active ingredient of the pharmaceutical composition. For example, in certain embodiments, dose and dose frequency are adjusted to provide a tissue concentration or plasma concentration of a pharmaceutical composition at an amount sufficient to achieve a desired effect.

Dosing is dependent on severity and responsiveness of the disease state to be treated, with the course of treatment lasting from several days to several months, or until a cure is effected or a diminution of the disease state is achieved. Dosing is also dependent on drug potency and metabolism. In certain embodiments, dosage is from 0.01 µg to 100 mg per kg of body weight, or within a range of 0.001 mg-1000 mg dosing, and may be given once or more daily, weekly, monthly or yearly, or even once every 2 to 20 years. Following successful treatment, it can be desirable to have the patient undergo maintenance therapy to prevent the recurrence of the disease state, wherein the oligonucleotide is administered in maintenance doses, ranging from 0.01 µg to 100 mg per kg of body weight or ranging from 0.001 mg to 1000 mg dosing, once or more daily, weekly, monthly, yearly to once every 2 to 20 years.

Certain Combination Therapies

In certain embodiments, a first agent comprising the compound described herein is co-administered with one or more secondary agents or therapy. In certain embodiments, such second agents are designed to treat the same disease, disorder, or condition as the first agent described herein. In certain embodiments, such second agents are designed to treat a different disease, disorder, or condition as the first agent described herein. In certain embodiments, a first agent is designed to treat an undesired side effect of a second agent. In certain embodiments, second agents are co-administered with the first agent to treat an undesired effect of the first agent. In certain embodiments, such second agents are designed to treat an undesired side effect of one or more pharmaceutical compositions as described herein. In certain embodiments, second agents are co-administered with the first agent to produce a combinational effect. In certain embodiments, second agents are co-administered with the first agent to produce a synergistic effect. In certain embodiments, the co-administration of the first and second agents permits use of lower dosages than would be required to achieve a therapeutic or prophylactic effect if the agents were administered as independent therapy.

In certain embodiments, one or more compositions described herein and one or more other pharmaceutical agents are administered at the same time. In certain embodiments, one or more compositions of the invention and one or more other pharmaceutical agents are administered at different times. In certain embodiments, one or more compositions described herein and one or more other pharmaceutical agents are prepared together in a single formulation. In certain embodiments, one or more compositions described herein and one or more other pharmaceutical agents are prepared separately.

In certain embodiments, second agents include, but are not limited to, an apo(a) lowering agent, a Lp(a) lowering agent, an agent for treating Alzheimer's Disease, an agent to reduce thromboembolism formation, a cholesterol lowering agent, a non-HDL lipid lowering (e.g., LDL) agent, a HDL raising agent, fish oil, niacin, nicotinic acid, a fibrate, a statin, DCCR (salt of diazoxide), a glucose-lowering agent, an anti-inflammatory agent and/or an anti-diabetic agent. In certain embodiments, the first agent is administered in combination with the maximally tolerated dose of the second agent. In certain embodiments, the first agent is administered to a subject that fails to respond to a maximally tolerated dose of the second agent.

Examples of apo(a) lowering agents include an apo(a) antisense oligonucleotide different from the first agent, niacin, nicotinic acid, or an apoB antisense oligonucleotide (i.e. Mipomersen). An example of an apo(a) lowering therapy is Lp(a) apheresis.

Examples of glucose-lowering and/or anti-diabetic agents include, but are not limited to, a therapeutic lifestyle change, PPAR agonist, a dipeptidyl peptidase (IV) inhibitor, a GLP-1 analog, insulin or an insulin analog, an insulin secretagogue, a SGLT2 inhibitor, a human amylin analog, a biguanide, an alpha-glucosidase inhibitor, metformin, sulfonylurea, rosiglitazone, meglitinide, thiazolidinedione, alpha-glucosidase inhibitor and the like. The sulfonylurea can be acetohexamide, chlorpropamide, tolbutamide, tolazamide, glimepiride, a glipizide, a glyburide, or a gliclazide. The meglitinide can be nateglinide or repaglinide. The thiazolidinedione can be pioglitazone or rosiglitazone. The alpha-glucosidase can be acarbose or miglitol.

Examples of cholesterol or lipid lowering therapy include, but are not limited to, a therapeutic lifestyle change, statins, bile acids sequestrants, niacin, nicotinic acid, CETP inhibitors and peroxisome proliferation activated receptor agonists such as fibrates. The statins can be atorvastatin, fluvastatin, lovastatin, pravastatin, rosuvastatin and simvastatin and the like. The bile acid sequestrants can be colesevelam, cholestyramine, colestipol and the like. The fibrates can be gemfibrozil, fenofibrate, clofibrate and the like. The CETP inhibitor can be a CETP antisense oligonucleotide or Torcetrapib.

Certain Treatment Populations

Certain subjects with high Lp(a) levels are at a significant risk of various diseases (Lippi et al., Clinica Chimica Acta, 2011, 412:797-801; Solfrizz et al.). In many subjects with high Lp(a) levels, current treatments cannot reduce their Lp(a) levels to safe levels. Apo(a) plays an important role in the formation of Lp(a), hence reducing apo(a) can reduce Lp(a) and prevent, treat or ameliorate a disease associated with Lp(a).

In certain embodiments, treatment with the compounds and methods disclosed herein is indicated for a human animal with elevated apo(a) levels and/or Lp(a) levels. In certain embodiments, the human has elevated apo(a) levels ≥30 mg/dL, ≥40 mg/dL, ≥50 mg/dL, ≥60 mg/dL, ≥70 mg/dL, ≥80 mg/dL, ≥90 mg/dL or ≥100 mg/dL.

Certain Compounds

Selected gapmer antisense oligonucleotides from PCT application WO2005/000201 (incorporated by reference in its entirety herein) were assessed (Example 1) and the most potent compound, ISIS 144367, was used as a benchmark comparison for the newly designed antisense oligonucleotides described herein.

About 90 of the newly designed antisense oligonucleotides were found to be more potent than the benchmark, ISIS 144367, as assessed by single dose in vitro studies (Examples 2-3, 5). Of the about 90 antisense oligonucleotides, about 83 were selected for in vitro multi-dose response studies and 64 antisense oligonucleotides were found to be more potent than the benchmark (Examples 4, 6).

About 32 antisense oligonucleotides were further selected for in vivo studies in human apo(a) transgenic mice (Example 7). Multiple antisense oligonucleotides were identified that were more potent than the benchmark in vivo.

About 24 antisense oligonucleotides were further selected for viscosity testing in vitro (Example 13). Antisense oligonucleotides that were viscous were not carried forward in further studies.

About 14 antisense oligonucleotides were further selected for in vivo studies in rodent tolerability and pharmacokinetics (Examples 8-10). The studies indicated that ISIS 494372 was the best tolerated antisense oligonucleotide.

ISIS 494283, 494284, 494286, 494301, 494302 and 494372 were tested in cynomolgus monkeys (Examples 11-12). The studies indicated that ISIS 494372 was well tolerated and potent in monkeys.

EXAMPLES

Non-Limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1

Dose-Dependent Antisense Inhibition of Human Apolipoprotein (a) (Apo(a)) in Human Primary Hepatocytes Selected gapmer antisense oligonucleotides from a previous publication (WO2005/000201, the content of which is incorporated by reference in its entirety herein) were tested in a single dose assay in human primary hepatocytes. Cells were obtained from Tissue Transformation Technologies (BD Biosciences, Franklin Lakes, N.J.) and treated with 150 nM of antisense oligonucleotide. After a treatment period of approximately 16 hours, RNA was isolated from the cells and apo(a) mRNA levels were measured by quantitative real-time PCR. Human apo(a) primer probe set hAPO(a)3' (forward sequence ACAGCAATCAAACGAAGACACTG, designated herein as SEQ ID NO: 5; reverse sequence AGCTTATACACAAAAATACCAAAAATGC, designated herein as SEQ ID NO: 6; probe sequence TCCCAGCTAC-CAGCTATGCCAAACCTT, designated herein as SEQ ID NO: 7) was used to measure mRNA levels. Additionally, mRNA levels were also measured using human apo(a) primer probe set hAPO(a)12kB (forward sequence CCACA-GTGGCCCCGGT, designated herein as SEQ ID NO: 8; reverse sequence ACAGGGCTTTTCTCAGGTGGT, designated herein as SEQ ID NO: 9; probe sequence CCAAGCACAGAGGCTCCTTCTGAACAAG, designated herein as SEQ ID NO: 10). Apo(a) mRNA levels were normalized to GAPDH mRNA expression. Results are presented in Table 1 as percent inhibition of apo(a), relative to untreated control cells.

TABLE 1

Antisense inhibition of human apo(a) in human primary hepatocytes

| ISIS No | % inhibition (hAPO(a)3' PPset) | % inhibition (hAPO(a)12kB PPset) |
|---|---|---|
| 144367 | 68 | 77 |
| 144368 | 42 | 59 |
| 144369 | 43 | 69 |
| 144370 | 80 | 75 |
| 144371 | 42 | 57 |
| 144372 | 87 | 54 |
| 144373 | 63 | 49 |
| 144374 | 45 | 80 |
| 144375 | 33 | 11 |
| 144376 | 62 | 82 |
| 144377 | 42 | 72 |
| 144378 | 0 | 72 |
| 144379 | 73 | 46 |
| 144380 | 75 | 78 |
| 144381 | 63 | 64 |
| 144382 | 0 | 58 |

TABLE 1-continued

Antisense inhibition of human apo(a) in human primary hepatocytes

| ISIS No | % inhibition (hAPO(a)3′ PPset) | % inhibition (hAPO(a)12kB PPset) |
|---|---|---|
| 144383 | 63 | 79 |
| 144384 | 38 | 0 |
| 144385 | 40 | 94 |
| 144386 | 47 | 61 |
| 144387 | 38 | 60 |
| 144388 | 0 | 57 |
| 144389 | 52 | 39 |
| 144390 | 12 | 0 |
| 144391 | 73 | 57 |
| 144392 | 43 | 50 |
| 144393 | 83 | 82 |
| 144394 | 40 | 76 |
| 144395 | 80 | 84 |
| 144396 | 53 | 72 |
| 144397 | 23 | 64 |
| 144398 | 7 | 33 |
| 144399 | 43 | 44 |
| 144400 | 70 | 75 |
| 144401 | 87 | 72 |

Several antisense oligonucleotides were selected for further testing in a dose response assay.

The selected antisense oligonucleotides were tested in human primary hepatocytes with 25 nM, 50 nM, 150 nM, or 300 nM concentrations of antisense oligonucleotide, as specified in Table 2 below. After a treatment period of approximately 16 hours, RNA was isolated from the cells and apo(a) mRNA levels were measured by quantitative real-time PCR. Human apo(a) primer probe set hAPO(a)3′ was used to measure mRNA levels. Apo(a) mRNA levels were normalized to GAPDH mRNA expression. Results are presented as percent inhibition of apo(a), relative to untreated control cells.

TABLE 2

Dose-dependent antisense inhibition of human apo(a) in human primary hepatocytes, as measured with hAPO(a)3′

| ISIS No | 25 nM | 50 nM | 150 nM | 300 nM |
|---|---|---|---|---|
| 144367 | 52 | 78 | 76 | 74 |
| 144370 | 64 | 74 | 68 | 66 |
| 144385 | 0 | 15 | 43 | 5 |
| 144393 | 0 | 9 | 39 | 25 |
| 144395 | 17 | 9 | 8 | 32 |

ISIS 144367 demonstrated better efficacy and dose-dependency than the other antisense oligonucleotides. Hence, ISIS 144367 was considered the benchmark antisense oligonucleotide to compare the potency of newly designed antisense oligonucleotides disclosed herein.

Example 2

Antisense Inhibition of Human Apo(a) in Transgenic Mouse Primary Hepatocytes

Antisense oligonucleotides were newly designed targeting an apo(a) nucleic acid and were tested for their effects on apo(a) mRNA in vitro. The antisense oligonucleotides were tested for potency in a series of parallel experiments that had similar culture conditions. Primary hepatocytes from human apo(a) transgenic mice (Frazer, K. A. et al., Nat. Genet. 1995. 9: 424-431) were used in this study. Hepatocytes at a density of 35,000 cells per well were transfected using electroporation with 1,000 nM antisense oligonucleotide. After a treatment period of approximately 24 hours, RNA was isolated from the cells and apo(a) mRNA levels were measured by quantitative real-time PCR. Human primer probe set hAPO(a)12kB was used to measure mRNA levels. Apo(a) mRNA levels were adjusted according to total RNA content, as measured by RIBOGREEN®. The results for each experiment are presented in separate tables shown below. ISIS 144367 from was used as a benchmark for the new antisense oligonucleotides and also included in the studies. Results are presented as percent inhibition of apo(a), relative to untreated control cells. A total of 1,511 gapmers were tested under these culture conditions. Only those antisense oligonucleotides that were selected for further study are presented in the table below with each table representing a separate experiment.

The newly designed chimeric antisense oligonucleotides were designed as 5-10-5 MOE gapmers. The gapmers are 20 nucleosides in length, wherein the central gap segment comprises of ten 2′-deoxynucleosides and is flanked by wing segments on the 5′ direction and the 3′ direction comprising five nucleosides each. Each nucleoside in the 5′ wing segment and each nucleoside in the 3′ wing segment has a 2′-MOE modification. The internucleoside linkages throughout each gapmer are phosphorothioate (P=S) linkages. All cytosine residues throughout each gapmer are 5-methylcytosines.

The apo(a) target sequence contains multiple Kringle repeat sequences, therefore, an antisense oligonucleotide may target one or more regions of apo(a) depending whether on the oligonucleotide targets a Kringle sequence or not. "Start site" indicates the 5′-most nucleoside to which the gapmer is targeted in the human sequence. "Stop site" indicates the 3′-most nucleoside to which the gapmer is targeted human sequence. An apo(a) antisense oligonucleotide may have more than one "Start site" or "Stop site" depending on whether or not it targets a Kringle repeat.

Most gapmers listed in the Tables are targeted with 100% complementarity to one or more regions of either the human apo(a) mRNA, designated herein as SEQ ID NO: 1 (GENBANK Accession No. NM_005577.2) or the human apo(a) genomic sequence, designated herein as SEQ ID NO: 2 (GENBANK Accession No. NT_007422.12 truncated from nucleotides 3230000 to 3380000), or both. 'n/a' indicates that the antisense oligonucleotide does not target that particular sequence with 100% complementarity.

TABLE 3

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 90 | 21210 | 21229 | 11 |
| 494157 | 238 | 257 | CCTGTGACAGTGGTGGAGTA | 95 | 21199 | 21218 | 12 |

TABLE 3-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
|  | 580 | 599 |  |  | 26690 | 26709 |  |
|  | 922 | 941 |  |  | 32237 | 32256 |  |
|  | 1606 | 1625 |  |  | 43330 | 43349 |  |
|  | 1948 | 1967 |  |  | 48874 | 48893 |  |
|  | 2290 | 2309 |  |  | 54420 | 54439 |  |
|  | 3316 | 3335 |  |  | 72037 | 72056 |  |
| 494158 | 239 | 258 | TCCTGTGACAGTGGTGGAGT | 95 | 21200 | 21219 | 13 |
|  | 581 | 600 |  |  | 26691 | 26710 |  |
|  | 923 | 942 |  |  | 32238 | 32257 |  |
|  | 1607 | 1626 |  |  | 43331 | 43350 |  |
|  | 1949 | 1968 |  |  | 48875 | 48894 |  |
|  | 2291 | 2310 |  |  | 54421 | 54440 |  |
|  | 3317 | 3336 |  |  | 72038 | 72057 |  |
| 494159 | 241 | 260 | CTTCCTGTGACAGTGGTGGA | 97 | 21202 | 21221 | 14 |
|  | 583 | 602 |  |  | 26693 | 26712 |  |
|  | 925 | 944 |  |  | 32240 | 32259 |  |
|  | 1609 | 1628 |  |  | 43333 | 43352 |  |
|  | 1951 | 1970 |  |  | 48877 | 48896 |  |
|  | 2293 | 2312 |  |  | 54423 | 54442 |  |
|  | 3319 | 3338 |  |  | 72040 | 72059 |  |
|  | 4663 | 4682 |  |  | 94404 | 94423 |  |
|  | 5005 | 5024 |  |  | 115515 | 115534 |  |
| 494160 | 242 | 261 | CCTTCCTGTGACAGTGGTGG | 97 | 21203 | 21222 | 15 |
|  | 4664 | 4683 |  |  | 94405 | 94424 |  |
|  | 5006 | 5025 |  |  | 115516 | 115535 |  |
| 494161 | 243 | 262 | TCCTTCCTGTGACAGTGGTG | 96 | 21204 | 21223 | 16 |
|  | 4665 | 4684 |  |  | 94406 | 94425 |  |
|  | 5007 | 5026 |  |  | 115517 | 115536 |  |
| 494162 | 244 | 263 | GTCCTTCCTGTGACAGTGGT | 95 | 21205 | 21224 | 17 |
|  | 3664 | 3683 |  |  | 77585 | 77604 |  |
|  | 4666 | 4685 |  |  | 94407 | 94426 |  |
|  | 5008 | 5027 |  |  | 115518 | 115537 |  |
| 494163 | 245 | 264 | GGTCCTTCCTGTGACAGTGG | 96 | 21206 | 21225 | 18 |
|  | 4667 | 4686 |  |  | 94408 | 94427 |  |
| 494164 | 246 | 265 | AGGTCCTTCCTGTGACAGTG | 93 | 21207 | 21226 | 19 |
|  | 4668 | 4687 |  |  | 94409 | 94428 |  |
| 494165 | 247 | 266 | CAGGTCCTTCCTGTGACAGT | 91 | 21208 | 21227 | 20 |
|  | 4669 | 4688 |  |  | 94410 | 94429 |  |
| 494166 | 248 | 267 | GCAGGTCCTTCCTGTGACAG | 89 | 21209 | 21228 | 21 |
| 494167 | 250 | 269 | TGGCAGGTCCTTCCTGTGAC | 92 | 21211 | 21230 | 22 |
| 494168 | 251 | 270 | TTGGCAGGTCCTTCCTGTGA | 89 | 21212 | 21231 | 23 |
| 494169 | 252 | 271 | CTTGGCAGGTCCTTCCTGTG | 92 | 21213 | 21232 | 24 |
| 494170 | 253 | 272 | GCTTGGCAGGTCCTTCCTGT | 88 | 21214 | 21233 | 25 |

TABLE 4

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 91 84 | 21210 | 21229 | 11 |
| 494283 | 584 | 603 | TCTTCCTGTGACAGTGGTGG | 93 | 26694 | 26713 | 26 |
|  | 926 | 945 |  |  | 32241 | 32260 |  |
|  | 1610 | 1629 |  |  | 43334 | 43353 |  |

TABLE 4-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| | 1952 | 1971 | | | 48878 | 48897 | |
| | 2294 | 2313 | | | 54424 | 54443 | |
| | 3320 | 3339 | | | 72041 | 72060 | |
| 494284 | 585 | 604 | TTCTTCCTGTGACAGTGGTG | 95 | 26695 | 26714 | 27 |
| | 927 | 946 | | | 32242 | 32261 | |
| | 1611 | 1630 | | | 43335 | 43354 | |
| | 1953 | 1972 | | | 48879 | 48898 | |
| | 2295 | 2314 | | | 54425 | 54444 | |
| | 3321 | 3340 | | | 72042 | 72061 | |
| 494285 | 586 | 605 | GTTCTTCCTGTGACAGTGGT | 95 | 26696 | 26715 | 28 |
| | 928 | 947 | | | 32243 | 32262 | |
| | 1612 | 1631 | | | 43336 | 43355 | |
| | 1954 | 1973 | | | 48880 | 48899 | |
| | 2296 | 2315 | | | 54426 | 54445 | |
| | 3322 | 3341 | | | 72043 | 72062 | |
| 494286 | 587 | 606 | GGTTCTTCCTGTGACAGTGG | 95 | 26697 | 26716 | 29 |
| | 929 | 948 | | | 32244 | 32263 | |
| | 1613 | 1632 | | | 43337 | 43356 | |
| | 1955 | 1974 | | | 48881 | 48900 | |
| | 2297 | 2316 | | | 54427 | 54446 | |
| 494287 | 588 | 607 | AGGTTCTTCCTGTGACAGTG | 95 | 26698 | 26717 | 30 |
| | 930 | 949 | | | 32245 | 32264 | |
| | 1614 | 1633 | | | 43338 | 43357 | |
| | 1956 | 1975 | | | 48882 | 48901 | |
| | 2298 | 2317 | | | 54428 | 54447 | |
| 494288 | 589 | 608 | CAGGTTCTTCCTGTGACAGT | 91 | 26699 | 26718 | 31 |
| | 931 | 950 | | | 32246 | 32265 | |
| | 1615 | 1634 | | | 43339 | 43358 | |
| | 1957 | 1976 | | | 48883 | 48902 | |
| | 2299 | 2318 | | | 54429 | 54448 | |
| | 2983 | 3002 | | | 66500 | 66519 | |
| 494290 | 592 | 611 | TGGCAGGTTCTTCCTGTGAC | 90 | 26702 | 26721 | 32 |
| | 934 | 953 | | | 32249 | 32268 | |
| | 1618 | 1637 | | | 43342 | 43361 | |
| | 1960 | 1979 | | | 48886 | 48905 | |
| | 2302 | 2321 | | | 54432 | 54451 | |
| | 2986 | 3005 | | | 66503 | 66522 | |
| 494291 | 593 | 612 | TTGGCAGGTTCTTCCTGTGA | 89 | 26703 | 26722 | 33 |
| | 935 | 954 | | | 32250 | 32269 | |
| | 1619 | 1638 | | | 43343 | 43362 | |
| | 1961 | 1980 | | | 48887 | 48906 | |
| | 2303 | 2322 | | | 54433 | 54452 | |
| | 2987 | 3006 | | | 66504 | 66523 | |
| 494292 | 594 | 613 | CTTGGCAGGTTCTTCCTGTG | 94 | 26704 | 26723 | 35 |
| | 936 | 955 | | | 32251 | 32270 | |
| | 1620 | 1639 | | | 43344 | 43363 | |
| | 1962 | 1981 | | | 48888 | 48907 | |
| | 2304 | 2323 | | | 54434 | 54453 | |
| | 2988 | 3007 | | | 66505 | 66524 | |
| 494294 | 596 | 615 | AGCTTGGCAGGTTCTTCCTG | 90 | 26706 | 26725 | 36 |
| | 938 | 957 | | | 32253 | 32272 | |
| | 1622 | 1641 | | | 43346 | 43365 | |
| | 1964 | 1983 | | | 48890 | 48909 | |
| | 2306 | 2325 | | | 54436 | 54455 | |
| | 2990 | 3009 | | | 66507 | 66526 | |
| 494299 | 626 | 645 | ACTATGCGAGTGTGGTGTCA | 91 | 26736 | 26755 | 37 |
| | 968 | 987 | | | 32283 | 32302 | |
| | 1310 | 1329 | | | 37830 | 37849 | |
| | 1652 | 1671 | | | 43376 | 43395 | |
| | 1994 | 2013 | | | 48920 | 48939 | |
| | 2336 | 2355 | | | 54466 | 54485 | |
| | 2678 | 2697 | | | 60021 | 60040 | |
| | 3020 | 3039 | | | 66537 | 66556 | |

TABLE 4-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 494300 | 627 | 646 | GACTATGCGAGTGTGGTGTC | 93 | 26737 | 26756 | 38 |
|  | 969 | 988 |  |  | 32284 | 32303 |  |
|  | 1311 | 1330 |  |  | 37831 | 37850 |  |
|  | 1653 | 1672 |  |  | 43377 | 43396 |  |
|  | 1995 | 2014 |  |  | 48921 | 48940 |  |
|  | 2337 | 2356 |  |  | 54467 | 54486 |  |
|  | 2679 | 2698 |  |  | 60022 | 60041 |  |
|  | 3021 | 3040 |  |  | 66538 | 66557 |  |
| 494301 | 628 | 647 | CGACTATGCGAGTGTGGTGT | 93 | 26738 | 26757 | 39 |
|  | 970 | 989 |  |  | 32285 | 32304 |  |
|  | 1312 | 1331 |  |  | 37832 | 37851 |  |
|  | 1654 | 1673 |  |  | 43378 | 43397 |  |
|  | 1996 | 2015 |  |  | 48922 | 48941 |  |
|  | 2338 | 2357 |  |  | 54468 | 54487 |  |
|  | 2680 | 2699 |  |  | 60023 | 60042 |  |
|  | 3022 | 3041 |  |  | 66539 | 66558 |  |
| 494302 | 629 | 648 | CCGACTATGCGAGTGTGGTG | 94 | 26739 | 26758 | 40 |
|  | 971 | 990 |  |  | 32286 | 32305 |  |
|  | 1313 | 1332 |  |  | 37833 | 37852 |  |
|  | 1655 | 1674 |  |  | 43379 | 43398 |  |
|  | 1997 | 2016 |  |  | 48923 | 48942 |  |
|  | 2339 | 2358 |  |  | 54469 | 54488 |  |
|  | 2681 | 2700 |  |  | 60024 | 60043 |  |
|  | 3023 | 3042 |  |  | 66540 | 66559 |  |
| 494303 | 630 | 649 | TCCGACTATGCGAGTGTGGT | 93 | 26740 | 26759 | 41 |
|  | 972 | 991 |  |  | 32287 | 32306 |  |
|  | 1314 | 1333 |  |  | 37834 | 37853 |  |
|  | 1656 | 1675 |  |  | 43380 | 43399 |  |
|  | 1998 | 2017 |  |  | 48924 | 48943 |  |
|  | 2340 | 2359 |  |  | 54470 | 54489 |  |
|  | 2682 | 2701 |  |  | 60025 | 60044 |  |
|  | 3024 | 3043 |  |  | 66541 | 66560 |  |
| 494304 | 631 | 650 | GTCCGACTATGCGAGTGTGG | 94 | 26741 | 26760 | 42 |
|  | 973 | 992 |  |  | 32288 | 32307 |  |
|  | 1315 | 1334 |  |  | 37835 | 37854 |  |
|  | 1657 | 1676 |  |  | 43381 | 43400 |  |
|  | 1999 | 2018 |  |  | 48925 | 48944 |  |
|  | 2341 | 2360 |  |  | 54471 | 54490 |  |
|  | 2683 | 2702 |  |  | 60026 | 60045 |  |
|  | 3025 | 3044 |  |  | 66542 | 66561 |  |
| 494305 | 632 | 651 | GGTCCGACTATGCGAGTGTG | 93 | 26742 | 26761 | 43 |
|  | 974 | 993 |  |  | 32289 | 32308 |  |
|  | 1316 | 1335 |  |  | 37836 | 37855 |  |
|  | 1658 | 1677 |  |  | 43382 | 43401 |  |
|  | 2000 | 2019 |  |  | 48926 | 48945 |  |
|  | 2342 | 2361 |  |  | 54472 | 54491 |  |
|  | 2684 | 2703 |  |  | 60027 | 60046 |  |
|  | 3026 | 3045 |  |  | 66543 | 66562 |  |
| 494306 | 633 | 652 | GGGTCCGACTATGCGAGTGT | 92 | 26743 | 26762 | 44 |
|  | 975 | 994 |  |  | 32290 | 32309 |  |
|  | 1317 | 1336 |  |  | 37837 | 37856 |  |
|  | 1659 | 1678 |  |  | 43383 | 43402 |  |
|  | 2001 | 2020 |  |  | 48927 | 48946 |  |
|  | 2343 | 2362 |  |  | 54473 | 54492 |  |
|  | 2685 | 2704 |  |  | 60028 | 60047 |  |
|  | 3027 | 3046 |  |  | 66544 | 66563 |  |
| 494307 | 1190 | 1209 | CTGCTCAGTCGGTGCTTGTT | 91 | n/a | n/a | 45 |
|  | 2558 | 2577 |  |  |  |  |  |
| 494310 | 1193 | 1212 | CCTCTGCTCAGTCGGTGCTT | 90 | n/a | n/a | 46 |
|  | 2561 | 2580 |  |  |  |  |  |
| 494311 | 1194 | 1213 | GCCTCTGCTCAGTCGGTGCT | 88 | 37714 | 37733 | 47 |
|  | 2562 | 2581 |  |  | 59905 | 59924 |  |

TABLE 4-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 494334 | 1267 2635 | 1286 2654 | CTTCCAGTGACAGTGGTGGA | 90 | 37787 59978 | 37806 59997 | 48 |
| 494336 | 1269 2637 | 1288 2656 | TTCTTCCAGTGACAGTGGTG | 90 | 37789 59980 | 37808 59999 | 49 |
| 494337 | 1270 2638 | 1289 2657 | GTTCTTCCAGTGACAGTGGT | 95 | 37790 59981 | 37809 60000 | 50 |
| 494338 | 1271 2639 | 1290 2658 | GGTTCTTCCAGTGACAGTGG | 91 | 37791 59982 | 37810 60001 | 133 |
| 494521 | 6393 | 6412 | GACCTTAAAAGCTTATACAC | 82 | 140049 | 140068 | 51 |
| 494525 | 6397 | 6416 | GTCAGACCTTAAAAGCTTAT | 84 | 140053 | 140072 | 52 |
| 494530 | 6402 | 6421 | TGTCAGTCAGACCTTAAAAG | 82 | 140058 | 140077 | 53 |
| 494535 | 6407 | 6426 | GAATTTGTCAGTCAGACCTT | 85 | 140063 | 140082 | 54 |
| 494536 | 6408 | 6427 | AGAATTTGTCAGTCAGACCT | 83 | 140064 | 140083 | 55 |
| 494544 | 6417 | 6436 | CCTTAATACAGAATTTGTCA | 82 | 140073 | 140092 | 56 |

TABLE 5

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 84 | 21210 | 21229 | 11 |
| 494371 | 3900 | 3919 | GCTCCGTTGGTGCTTGTTCA | 93 | n/a | n/a | 57 |
| 494372 | 3901 | 3920 | TGCTCCGTTGGTGCTTGTTC | 93 | n/a | n/a | 58 |
| 494373 | 3902 | 3921 | TTGCTCCGTTGGTGCTTGTT | 83 | n/a | n/a | 59 |
| 494374 | 3903 | 3922 | TTTGCTCCGTTGGTGCTTGT | 89 | n/a | n/a | 60 |
| 494375 | 3904 | 3923 | CTTTGCTCCGTTGGTGCTTG | 85 | n/a | n/a | 61 |
| 494386 | 3977 | 3996 | TCCTGTAACAGTGGTGGAGA | 86 | 81985 | 82004 | 62 |
| 494387 | 3978 | 3997 | TTCCTGTAACAGTGGTGGAG | 82 | 81986 | 82005 | 63 |
| 494388 | 3979 | 3998 | CTTCCTGTAACAGTGGTGGA | 86 | 81987 | 82006 | 64 |
| 494389 | 3980 | 3999 | CCTTCCTGTAACAGTGGTGG | 92 | 81988 | 82007 | 65 |
| 494390 | 3981 | 4000 | TCCTTCCTGTAACAGTGGTG | 92 | 81989 | 82008 | 66 |
| 494391 | 3982 | 4001 | GTCCTTCCTGTAACAGTGGT | 84 | 81990 | 82009 | 67 |
| 494392 | 3983 | 4002 | TGTCCTTCCTGTAACAGTGG | 81 | 81991 | 82010 | 68 |

TABLE 6

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 86 | 21210 | 21229 | 11 |
| 498369 | 3203 | 3222 | TGGAGCCAGAATAACATTCG | 91 | 70667 | 70686 | 69 |

TABLE 6-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 498379 | 3213 | 3232 | CCTCTAGGCTTGGAGCCAGA | 85 | 70677 | 70696 | 70 |
| 498408 | 3323 | 3342 | AGTTCTTCCTGTGACAGTGG | 86 | 72044 | 72063 | 71 |
| 498433 | 3367 | 3386 | GTCCGACTATGCTGGTGTGG | 87 | 72088 | 72107 | 72 |
| 498434 | 3368 | 3387 | GGTCCGACTATGCTGGTGTG | 86 | 72089 | 72108 | 73 |
| 498435 | 3369 | 3388 | GGGTCCGACTATGCTGGTGT | 83 | 72090 | 72109 | 74 |

TABLE 7

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 90 | 21210 | 21229 | 11 |
| 498229 | 2871 | 2890 | CCTCTAGGCTTGGAATCGGG | 90 | 65117 | 65136 | 75 |
| 498238 | 2883 | 2902 | GTTCAGAAGGAGCCTCTAGG | 93 | 65129 | 65148 | 76 |
| 498239 | 2884 | 2903 | TGTTCAGAAGGAGCCTCTAG | 94 | 65130 | 65149 | 77 |
| 498240 | 2887 / 4573 | 2906 / 4592 | GCTTGTTCAGAAGGAGCCTC | 98 | n/a | n/a | 78 |
| 498241 | 2888 / 4574 | 2907 / 4593 | TGCTTGTTCAGAAGGAGCCT | 94 | n/a | n/a | 79 |
| 498242 | 2889 / 4575 | 2908 / 4594 | GTGCTTGTTCAGAAGGAGCC | 96 | n/a | n/a | 80 |
| 498243 | 2890 / 4576 | 2909 / 4595 | GGTGCTTGTTCAGAAGGAGC | 97 | n/a | n/a | 81 |
| 498244 | 2891 / 4577 | 2910 / 4596 | TGGTGCTTGTTCAGAAGGAG | 92 | n/a | n/a | 82 |
| 498251 | 2898 | 2917 | GCTCAGTTGGTGCTTGTTCA | 90 | n/a | n/a | 83 |
| 498252 | 2899 | 2918 | TGCTCAGTTGGTGCTTGTTC | 90 | n/a | n/a | 84 |

TABLE 8

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 91 | 21210 | 21229 | 11 |
| 498517 | 3548 | 3567 | GCTTGGATCTGGGACCACCG | 89 | 76233 | 76252 | 85 |

TABLE 9

| ISIS NO | SEQ ID NO: 1 Start | SEQ ID NO: 1 Stop | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 94 | 21210 | 21229 | 11 |
| 498833 | 4900 | 4919 | GCCTCCATGCTTGGAACTGG | 94 | 114205 | 114224 | 86 |
| 498859 | 4926 | 4945 | GCTCAGTTGGTGCTGCTTCA | 92 | n/a | n/a | 87 |

TABLE 9-continued

| ISIS NO | SEQ ID NO: 1 Start | SEQ ID NO: 1 Stop | Sequence | % inhibition | SEQ ID NO: 2 Start Site | SEQ ID NO: 2 Stop Site | SEQ ID NO |
|---|---|---|---|---|---|---|---|
| 498868 | 4978 | 4997 | CCTCGATAACTCTGGCCATT | 94 | 115488 | 115507 | 88 |
| 498875 | 5003 | 5022 | TCCTGTGACAGTGGTGGAGA | 94 | 115513 | 115532 | 89 |

TABLE 10

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 92 | 21210 | 21229 | 11 |
| 499020 | 6257 | 6276 | GTAGGTTGATGCTTCACTCT | 91 | 139913 | 139932 | 90 |
| 499041 | 6318 | 6337 | CGTTTGATTGCTGTCTATTA | 90 | 139974 | 139993 | 91 |

TABLE 11

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 91 | 21210 | 21229 | 11 |
| 498523 | 3554 | 3573 | CTCTGTGCTTGGATCTGGGA | 94 | 76239 | 76258 | 92 |
| 498524 | 3555 | 3574 | CCTCTGTGCTTGGATCTGGG | 96 | 76240 | 76259 | 93 |
| 498525 | 3556 | 3575 | GCCTCTGTGCTTGGATCTGG | 94 | 76241 | 76260 | 94 |
| 498529 | 3560 | 3579 | AGAAGCCTCTGTGCTTGGAT | 89 | 76245 | 76264 | 95 |
| 498535 | 3566 | 3585 | TTCAGAAGAAGCCTCTGTGC | 89 | 76251 | 76270 | 96 |
| 498550 | 3582 | 3601 | GCTCCGTTGGTGCTTCTTCA | 90 | n/a | n/a | 97 |
| 498553 | 3585 | 3604 | TTTGCTCCGTTGGTGCTTCT | 87 | n/a | n/a | 98 |
| 498555 | 3587 3905 | 3606 3924 | GCTTTGCTCCGTTGGTGCTT | 90 | n/a | n/a | 99 |
| 498556 | 3588 3906 | 3607 3925 | GGCTTTGCTCCGTTGGTGCT | 89 | 77509 81914 | 77528 81933 | 100 |
| 498557 | 3589 3907 | 3608 3926 | GGGCTTTGCTCCGTTGGTGC | 89 | 77510 81915 | 77529 81934 | 101 |
| 498579 | 3662 | 3681 | CCTTCCTGTGACAGTGGTAG | 87 | 77583 | 77602 | 102 |
| 498580 | 3663 | 3682 | TCCTTCCTGTGACAGTGGTA | 92 | 77584 | 77603 | 103 |
| 498581 | 3665 5009 | 3684 5028 | TGTCCTTCCTGTGACAGTGG | 94 | 77586 115519 | 77605 115538 | 104 |

TABLE 12

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 100 | 21210 | 21229 | 11 |
| 494230 | 477 819 1161 | 496 838 1180 | CCTCTAGGCTTGGAACCGGG | 95 | 25380 30927 36471 | 25399 30946 36490 | 105 |

TABLE 12-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| | 1503 | 1522 | | | 42020 | 42039 | |
| | 1845 | 1864 | | | 47564 | 47583 | |
| | 2187 | 2206 | | | 53110 | 53129 | |
| | 2529 | 2548 | | | 58662 | 58681 | |
| 494243 | 494 | 513 | TGCTTGTTCGGAAGGAGCCT | 93 | n/a | n/a | 106 |
| | 836 | 855 | | | | | |
| | 1178 | 1197 | | | | | |
| | 1520 | 1539 | | | | | |
| | 1862 | 1881 | | | | | |
| | 2204 | 2223 | | | | | |
| | 2546 | 2565 | | | | | |
| 494244 | 495 | 514 | GTGCTTGTTCGGAAGGAGCC | 95 | n/a | n/a | 107 |
| | 837 | 856 | | | | | |
| | 1179 | 1198 | | | | | |
| | 1521 | 1540 | | | | | |
| | 1863 | 1882 | | | | | |
| | 2205 | 2224 | | | | | |
| | 2547 | 2566 | | | | | |

TABLE 13

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 96 | 21210 | 21229 | 11 |
| 494466 | 4208 | 4227 | GCTTGGAACTGGGACCACCG | 95 | 85138 | 85157 | 108 |
| 494470 | 4212 | 4231 | CTGTGCTTGGAACTGGGACC | 94 | 85142 | 85161 | 109 |
| 494472 | 4214 | 4233 | CTCTGTGCTTGGAACTGGGA | 92 | 85144 | 85163 | 110 |

Example 3

Dose-Dependent Antisense Inhibition of Apo(a) in Transgenic Mouse Primary Hepatocytes Gapmers from the studies described above exhibiting significant in vitro inhibition of apo(a) mRNA were selected and tested at various doses in transgenic mouse primary hepatocytes in a series of parallel studies with similar culture conditions. Cells were plated at a density of 35,000 per well and transfected using electroporation with 0.0625 µM, 0.125 µM, 0.25 µM, 0.500 µM, or 1.000 µM concentrations of antisense oligonucleotide. After a treatment period of approximately 16 hours, RNA was isolated from the cells and apo(a) mRNA levels were measured by quantitative real-time PCR. Apo(a) primer probe set hAPO(a)12kB was used to measured mRNA levels. Apo(a) mRNA levels were adjusted according to total RNA content, as measured by RIBOGREEN®. Results are presented as percent inhibition of apo(a), relative to untreated control cells.

The results of each of the studies are depicted in the Tables presented below with each table representing a separate experiment. The half maximal inhibitory concentration ($IC_{50}$) of each oligonucleotide is also presented in the Tables. Apo(a) mRNA levels were significantly reduced in a dose-dependent manner in antisense oligonucleotide treated cells. The potency of the newly designed oligos was compared with the benchmark oligonucleotide ISIS 144367.

TABLE 14

| ISIS No | 0.0625 µM | 0.125 µM | 0.250 µM | 0.500 µM | 1.000 µM | $IC_{50}$ (µM) |
|---|---|---|---|---|---|---|
| 144367 | 11 | 27 | 46 | 62 | 80 | 0.31 |
| 494157 | 11 | 47 | 53 | 76 | 87 | 0.23 |
| 494158 | 19 | 57 | 75 | 84 | 88 | 0.13 |
| 494159 | 41 | 65 | 77 | 84 | 92 | 0.07 |
| 494160 | 44 | 69 | 76 | 85 | 91 | 0.06 |
| 494161 | 40 | 64 | 74 | 85 | 91 | 0.08 |
| 494162 | 36 | 63 | 76 | 87 | 88 | 0.09 |
| 494163 | 20 | 59 | 75 | 85 | 92 | 0.13 |
| 494164 | 3 | 45 | 62 | 74 | 90 | 0.21 |
| 494165 | 25 | 39 | 57 | 71 | 75 | 0.19 |
| 494166 | 17 | 30 | 47 | 59 | 76 | 0.31 |
| 494167 | 30 | 43 | 55 | 72 | 80 | 0.18 |
| 494168 | 25 | 36 | 44 | 59 | 75 | 0.28 |
| 494169 | 19 | 39 | 51 | 61 | 81 | 0.25 |

TABLE 15

| ISIS No | 0.0625 µM | 0.125 µM | 0.250 µM | 0.500 µM | 1.000 µM | $IC_{50}$ (µM) |
|---|---|---|---|---|---|---|
| 144367 | 23 | 40 | 58 | 76 | 88 | 0.19 |
| 494170 | 38 | 34 | 60 | 76 | 84 | 0.13 |
| 494230 | 55 | 71 | 89 | 95 | 97 | 0.03 |
| 494243 | 47 | 73 | 87 | 92 | 97 | 0.05 |
| 494244 | 58 | 73 | 86 | 92 | 96 | 0.03 |
| 494283 | 54 | 70 | 84 | 93 | 94 | 0.05 |
| 494284 | 45 | 62 | 83 | 92 | 95 | 0.07 |

TABLE 15-continued

| ISIS No | 0.0625 µM | 0.125 µM | 0.250 µM | 0.500 µM | 1.000 µM | IC₅₀ (µM) |
|---|---|---|---|---|---|---|
| 494285 | 56 | 70 | 84 | 92 | 95 | 0.04 |
| 494286 | 51 | 70 | 87 | 93 | 95 | 0.05 |
| 494287 | 32 | 60 | 67 | 87 | 91 | 0.11 |
| 494288 | 26 | 41 | 61 | 79 | 88 | 0.17 |
| 494290 | 30 | 43 | 64 | 81 | 87 | 0.15 |
| 494291 | 29 | 40 | 56 | 75 | 85 | 0.18 |

TABLE 16

| ISIS No | 0.0625 µM | 0.125 µM | 0.250 µM | 0.500 µM | 1.000 µM | IC₅₀ (µM) |
|---|---|---|---|---|---|---|
| 144367 | 10 | 38 | 62 | 68 | 84 | 0.23 |
| 494292 | 17 | 36 | 74 | 85 | 90 | 0.17 |
| 494294 | 10 | 34 | 53 | 80 | 91 | 0.22 |
| 494299 | 32 | 29 | 56 | 77 | 88 | 0.16 |
| 494300 | 34 | 46 | 76 | 86 | 90 | 0.12 |
| 494301 | 44 | 56 | 72 | 86 | 89 | 0.09 |
| 494302 | 42 | 59 | 78 | 88 | 89 | 0.08 |
| 494303 | 37 | 58 | 70 | 86 | 89 | 0.10 |
| 494304 | 46 | 71 | 78 | 89 | 90 | 0.05 |
| 494305 | 39 | 58 | 62 | 85 | 87 | 0.10 |
| 494306 | 31 | 52 | 65 | 79 | 88 | 0.13 |
| 494307 | 23 | 23 | 39 | 65 | 78 | 0.34 |
| 494310 | 14 | 29 | 62 | 70 | 88 | 0.25 |

TABLE 17

| ISIS No | 0.0625 µM | 0.125 µM | 0.250 µM | 0.500 µM | 1.000 µM | IC₅₀ (µM) |
|---|---|---|---|---|---|---|
| 144367 | 0 | 29 | 45 | 73 | 92 | 0.27 |
| 494311 | 28 | 53 | 65 | 85 | 95 | 0.13 |
| 494334 | 20 | 44 | 66 | 86 | 96 | 0.16 |
| 494336 | 15 | 38 | 54 | 84 | 97 | 0.20 |
| 494337 | 28 | 50 | 77 | 90 | 98 | 0.12 |
| 494338 | 21 | 40 | 68 | 91 | 98 | 0.15 |
| 494371 | 19 | 0 | 71 | 89 | 97 | 0.15 |
| 494372 | 33 | 44 | 77 | 91 | 97 | 0.12 |
| 494373 | 15 | 36 | 65 | 83 | 95 | 0.19 |
| 494374 | 3 | 17 | 51 | 83 | 90 | 0.24 |
| 494375 | 1 | 34 | 56 | 80 | 93 | 0.23 |
| 494386 | 13 | 26 | 46 | 73 | 91 | 0.25 |
| 494387 | 17 | 27 | 45 | 67 | 88 | 0.28 |

TABLE 18

| ISIS No | 0.0625 µM | 0.125 µM | 0.250 µM | 0.500 µM | 1.000 µM | IC₅₀ (µM) |
|---|---|---|---|---|---|---|
| 144367 | 35 | 42 | 62 | 70 | 91 | 0.15 |
| 494537 | 19 | 34 | 54 | 79 | 90 | 0.21 |
| 494544 | 10 | 38 | 73 | 86 | 94 | 0.17 |
| 498229 | 36 | 58 | 80 | 92 | 97 | 0.10 |
| 498238 | 41 | 57 | 75 | 91 | 97 | 0.09 |
| 498239 | 56 | 71 | 79 | 90 | 94 | 0.03 |
| 498240 | 91 | 94 | 98 | 99 | 100 | <0.06 |
| 498241 | 75 | 84 | 91 | 96 | 98 | <0.06 |
| 498242 | 11 | 27 | 42 | 47 | 63 | 0.49 |
| 498243 | 91 | 93 | 96 | 98 | 99 | <0.06 |
| 498244 | 4 | 0 | 0 | 13 | 43 | >1.00 |
| 498251 | 30 | 30 | 42 | 73 | 89 | 0.26 |
| 498252 | 37 | 33 | 58 | 80 | 92 | 0.20 |
| 498369 | 22 | 22 | 10 | 22 | 34 | >1.00 |

TABLE 19

| ISIS No | 0.0625 µM | 0.125 µM | 0.250 µM | 0.500 µM | 1.000 µM | IC₅₀ (µM) |
|---|---|---|---|---|---|---|
| 144367 | 15 | 32 | 54 | 75 | 90 | 0.22 |
| 498379 | 29 | 48 | 71 | 80 | 95 | 0.13 |
| 498408 | 38 | 57 | 77 | 88 | 96 | 0.09 |
| 498433 | 29 | 36 | 70 | 88 | 96 | 0.15 |
| 498434 | 49 | 43 | 50 | 78 | 90 | 0.19 |
| 498435 | 27 | 39 | 57 | 78 | 93 | 0.18 |
| 498517 | 64 | 72 | 82 | 93 | 98 | <0.06 |
| 498721 | 77 | 84 | 88 | 96 | 97 | <0.06 |
| 498833 | 73 | 78 | 91 | 95 | 99 | <0.06 |
| 498859 | 7 | 24 | 37 | 62 | 75 | 0.36 |
| 498868 | 7 | 14 | 39 | 63 | 81 | 0.36 |
| 498875 | 16 | 21 | 33 | 55 | 81 | 0.39 |
| 499020 | 7 | 24 | 23 | 55 | 78 | 0.36 |
| 499041 | 6 | 16 | 33 | 64 | 83 | 0.35 |

TABLE 20

| ISIS No | 0.0625 µM | 0.125 µM | 0.250 µM | 0.500 µM | 1.000 µM | IC₅₀ (µM) |
|---|---|---|---|---|---|---|
| 144367 | 14 | 47 | 64 | 79 | 91 | 0.14 |
| 498523 | 36 | 50 | 80 | 87 | 95 | 0.11 |
| 498524 | 43 | 79 | 87 | 93 | 97 | 0.01 |
| 498525 | 32 | 49 | 75 | 86 | 96 | 0.12 |
| 498529 | 21 | 49 | 57 | 78 | 90 | 0.17 |
| 498535 | 20 | 34 | 55 | 76 | 86 | 0.21 |
| 498550 | 12 | 50 | 69 | 84 | 96 | 0.11 |
| 498553 | 8 | 43 | 55 | 77 | 91 | 0.21 |
| 498555 | 13 | 35 | 68 | 86 | 94 | 0.19 |
| 498556 | 27 | 37 | 71 | 85 | 91 | 0.15 |
| 498557 | 18 | 42 | 75 | 89 | 95 | 0.16 |
| 498579 | 16 | 38 | 67 | 89 | 95 | 0.16 |
| 498580 | 36 | 57 | 81 | 91 | 96 | 0.10 |
| 498581 | 34 | 64 | 75 | 93 | 97 | 0.05 |

TABLE 21

| ISIS No | 0.0625 µM | 0.125 µM | 0.250 µM | 0.500 µM | 1.000 µM | IC₅₀ (µM) |
|---|---|---|---|---|---|---|
| 144367 | 0 | 9 | 26 | 49 | 77 | 0.47 |
| 494388 | 0 | 0 | 21 | 33 | 55 | 0.89 |
| 494389 | 0 | 15 | 22 | 50 | 79 | 0.46 |
| 494390 | 5 | 20 | 37 | 68 | 81 | 0.33 |
| 494391 | 7 | 20 | 32 | 54 | 68 | 0.46 |
| 494392 | 18 | 24 | 40 | 57 | 76 | 0.35 |
| 494466 | 33 | 45 | 58 | 69 | 82 | 0.16 |
| 494470 | 45 | 58 | 68 | 79 | 87 | 0.08 |
| 494472 | 37 | 50 | 60 | 69 | 83 | 0.13 |
| 494521 | 0 | 0 | 0 | 15 | 54 | 0.17 |
| 494525 | 0 | 0 | 2 | 28 | 65 | 0.85 |
| 494530 | 0 | 6 | 27 | 51 | 80 | 0.46 |
| 494535 | 0 | 7 | 24 | 53 | 74 | 0.49 |
| 494536 | 0 | 2 | 15 | 42 | 67 | 0.63 |

TABLE 22

| ISIS No | 0.0625 µM | 0.125 µM | 0.250 µM | 0.500 µM | 1.000 µM | IC₅₀ (µM) |
|---|---|---|---|---|---|---|
| 144367 | 0 | 4 | 16 | 26 | 77 | 0.65 |
| 498379 | 12 | 18 | 27 | 32 | 63 | 0.81 |
| 498408 | 0 | 11 | 46 | 50 | 77 | 0.41 |
| 498433 | 22 | 30 | 46 | 60 | 83 | 0.27 |
| 498434 | 39 | 29 | 25 | 47 | 78 | 0.40 |
| 498435 | 21 | 28 | 26 | 43 | 73 | 0.50 |
| 498517 | 44 | 48 | 63 | 70 | 84 | 0.11 |
| 498721 | 54 | 54 | 66 | 75 | 89 | <0.06 |
| 498833 | 44 | 51 | 58 | 67 | 83 | 0.11 |
| 498859 | 0 | 29 | 14 | 35 | 66 | 0.69 |

TABLE 22-continued

| ISIS No | 0.0625 µM | 0.125 µM | 0.250 µM | 0.500 µM | 1.000 µM | IC$_{50}$ (µM) |
|---|---|---|---|---|---|---|
| 498868 | 0 | 12 | 9 | 26 | 60 | 1.07 |
| 498875 | 0 | 30 | 31 | 53 | 78 | 0.40 |
| 499020 | 0 | 27 | 19 | 45 | 74 | 0.51 |
| 499041 | 0 | 12 | 10 | 37 | 65 | 0.77 |

As presented in the Tables above, ISIS 494157 (SEQ ID NO: 12), ISIS 494158 (SEQ ID NO:13), ISIS 494159 (SEQ ID NO:14), ISIS 494160 (SEQ ID NO: 15), ISIS 494161 (SEQ ID NO:16), ISIS 494162 (SEQ ID NO: 17), ISIS 494163 (SEQ ID NO: 18), ISIS 494164 (SEQ ID NO: 19), ISIS 494165 (SEQ ID NO: 20), ISIS 494167 (SEQ ID NO: 22), ISIS 494168 (SEQ ID NO: 23), ISIS 494169 (SEQ ID NO: 24), ISIS 494170 (SEQ ID NO: 25), ISIS 494230 (SEQ ID NO: 105), ISIS 494243 (SEQ ID NO: 106), ISIS 494244 (SEQ ID NO: 107), ISIS 494283 (SEQ ID NO: 26), ISIS 494284 (SEQ ID NO: 27), ISIS 494285 (SEQ ID NO: 28), ISIS 494286 (SEQ ID NO: 29), ISIS 494287 (SEQ ID NO: 30), ISIS 494288 (SEQ ID NO: 31), ISIS 494290 (SEQ ID NO: 32), ISIS 494291 (SEQ ID NO: 33), ISIS 494292 (SEQ ID NO: 35), ISIS 494294 (SEQ ID NO: 36), ISIS 494299 (SEQ ID NO: 37), ISIS 494300 (SEQ ID NO: 38), ISIS 494301 (SEQ ID NO: 39), ISIS 494302 (SEQ ID NO: 40), ISIS 494303 (SEQ ID NO: 41), ISIS 494304 (SEQ ID NO: 42), ISIS 494305 (SEQ ID NO:43), ISIS 494306 (SEQ ID NO: 44), ISIS 494311 (SEQ ID NO: 47), ISIS 494334 (SEQ ID NO: 48), ISIS 494336 (SEQ ID NO: 49), ISIS 494337 (SEQ ID NO: 50), ISIS 494338 (SEQ ID NO: 133), ISIS 494371 (SEQ ID NO: 57), ISIS 494372 (SEQ ID NO: 58), ISIS 494373 (SEQ ID NO: 59), ISIS 494374 (SEQ ID NO: 60), ISIS 494375 (SEQ ID NO: 61), ISIS 494386 (SEQ ID NO: 62), ISIS 494389 (SEQ ID NO: 65), ISIS 494390 (SEQ ID NO: 66), ISIS 494392 (SEQ ID NO: 68), ISIS 494466 (SEQ ID NO: 108), ISIS 494470 (SEQ ID NO: 109), ISIS 494472 (SEQ ID NO: 110), ISIS 494521 (SEQ ID NO: 51), ISIS 494530 (SEQ ID NO: 53), ISIS 498229 (SEQ ID NO: 75), ISIS 498238 (SEQ ID NO: 76), ISIS 498239 (SEQ ID NO: 77), ISIS 498240 (SEQ ID NO: 78), ISIS 498241 (SEQ ID NO: 79), ISIS 498243 (SEQ ID NO: 81), ISIS 498379 (SEQ ID NO: 70), ISIS 498408 (SEQ ID NO: 71), ISIS 498433 (SEQ ID NO: 72), ISIS 498434 (SEQ ID NO: 73), ISIS 498435 (SEQ ID NO: 74), ISIS 498517 (SEQ ID NO: 85), ISIS 498523 (SEQ ID NO: 92), ISIS 498524 (SEQ ID NO: 93), ISIS 498525 (SEQ ID NO: 94), ISIS 498550 (SEQ ID NO: 97), ISIS 498580 (SEQ ID NO: 103), ISIS 498581 (SEQ ID NO: 104), ISIS 498721 (ATGCCTCGATAACTC-CGTCC; SEQ ID NO: 134), ISIS 498833 (SEQ ID NO: 86), ISIS 498875 (SEQ ID NO: 89), and ISIS 499020 (SEQ ID NO: 90) were more potent than ISIS 144367 (SEQ ID NO: 11).

Example 4

Dose-Dependent Antisense Inhibition of Apo(a) in Transgenic Mouse Primary Hepatocytes Potent gapmers from the studies described above were further selected and tested at various doses in transgenic mouse primary hepatocytes in a series of studies with similar culture conditions. Cells were plated at a density of 35,000 per well and transfected using electroporation with 0.049 µM, 0.148 µM, 0.444 µM, 1.333 µM, or 4.000 µM concentrations of antisense oligonucleotide, as specified in Tables below. After a treatment period of approximately 16 hours, RNA was isolated from the cells and apo(a) mRNA levels were measured by quantitative real-time PCR. Apo(a) primer probe set hAPO(a)12kB was used to measured mRNA levels. Apo(a) mRNA levels were adjusted according to total RNA content, as measured by RIBOGREEN®. Results are presented as percent inhibition of apo(a), relative to untreated control cells.

The results of each of the studies are depicted in the Tables presented below with each table representing a separate experiment. The half maximal inhibitory concentration (IC$_{50}$) of each oligonucleotide is also presented in the Tables. Apo(a) mRNA levels were significantly reduced in a dose-dependent manner in antisense oligonucleotide treated cells. The potency of the newly designed oligos was compared with the benchmark oligonucleotide, ISIS 144367. As presented in the Tables below, ISIS 494157 (SEQ ID NO: 12), ISIS 494158 (SEQ ID NO:13), ISIS 494159 (SEQ ID NO:14), ISIS 494160 (SEQ ID NO: 15), ISIS 494161 (SEQ ID NO:16), ISIS 494162 (SEQ ID NO: 17), ISIS 494163 (SEQ ID NO: 18), ISIS 494164 (SEQ ID NO: 19), ISIS 494230 (SEQ ID NO: 105), ISIS 494243 (SEQ ID NO: 106), ISIS 494244 (SEQ ID NO: 107), ISIS 494283 (SEQ ID NO: 26), ISIS 494284 (SEQ ID NO: 27), ISIS 494285 (SEQ ID NO: 28), ISIS 494286 (SEQ ID NO: 29), ISIS 494287 (SEQ ID NO: 30), ISIS 494290 (SEQ ID NO: 32), ISIS 494292 (SEQ ID NO: 35), ISIS 494300 (SEQ ID NO: 38), ISIS 494301 (SEQ ID NO: 39), ISIS 494302 (SEQ ID NO: 40), ISIS 494303 (SEQ ID NO: 41), ISIS 494304 (SEQ ID NO: 42), ISIS 494305 (SEQ ID NO: 43), ISIS 494306 (SEQ ID NO: 44), ISIS 494310 (SEQ ID NO: 46), ISIS 494311 (SEQ ID NO: 47), ISIS 494337 (SEQ ID NO: 50), ISIS 494371 (SEQ ID NO: 57), ISIS 494372 (SEQ ID NO: 58), ISIS 494375 (SEQ ID NO: 61), ISIS 494388 (SEQ ID NO: 64), ISIS 494389 (SEQ ID NO: 65), ISIS 494390 (SEQ ID NO: 66), ISIS 494392 (SEQ ID NO: 68), ISIS 494466 (SEQ ID NO: 108), ISIS 494470 (SEQ ID NO: 109), ISIS 494472 (SEQ ID NO: 110), ISIS 498238 (SEQ ID NO: 76), ISIS 498239 (SEQ ID NO: 77), ISIS 498433 (SEQ ID NO: 72), ISIS 498434 (SEQ ID NO: 73), ISIS 498435 (SEQ ID NO: 74), ISIS 498523 (SEQ ID NO: 92), ISIS 498524 (SEQ ID NO: 93), ISIS 498525 (SEQ ID NO: 94), ISIS 498580 (SEQ ID NO: 103), and ISIS 498581 (SEQ ID NO: 104) were more potent than ISIS 144367 (SEQ ID NO: 11).

TABLE 23

| ISIS No | 0.049 µM | 0.148 µM | 0.444 µM | 1.333 µM | 4.000 µM | IC$_{50}$ (µM) |
|---|---|---|---|---|---|---|
| 144367 | 0 | 26 | 67 | 89 | 92 | 0.32 |
| 494157 | 23 | 50 | 83 | 96 | 96 | 0.15 |
| 494158 | 26 | 62 | 85 | 96 | 96 | 0.11 |
| 494159 | 42 | 65 | 87 | 95 | 94 | 0.07 |
| 494160 | 51 | 70 | 88 | 94 | 94 | <0.05 |
| 494161 | 36 | 67 | 87 | 95 | 96 | 0.08 |
| 494162 | 40 | 69 | 89 | 94 | 95 | 0.07 |
| 494163 | 41 | 57 | 87 | 95 | 94 | 0.08 |
| 494164 | 15 | 43 | 75 | 93 | 96 | 0.20 |
| 494230 | 39 | 77 | 94 | 99 | 99 | 0.05 |
| 494243 | 39 | 76 | 92 | 98 | 99 | 0.06 |
| 494244 | 58 | 79 | 91 | 97 | 99 | 0.02 |
| 494283 | 18 | 45 | 80 | 93 | 91 | 0.18 |
| 494284 | 9 | 53 | 80 | 95 | 94 | 0.18 |

TABLE 24

| ISIS No | 0.049 µM | 0.148 µM | 0.444 µM | 1.333 µM | 4.000 µM | IC$_{50}$ (µM) |
|---|---|---|---|---|---|---|
| 144367 | 21 | 40 | 79 | 94 | 93 | 0.18 |
| 494285 | 53 | 68 | 90 | 97 | 97 | <0.05 |
| 494286 | 46 | 69 | 89 | 96 | 97 | 0.05 |

TABLE 24-continued

| ISIS No | 0.049 µM | 0.148 µM | 0.444 µM | 1.333 µM | 4.000 µM | IC$_{50}$ (µM) |
|---|---|---|---|---|---|---|
| 494287 | 31 | 38 | 79 | 94 | 95 | 0.15 |
| 494290 | 22 | 53 | 74 | 93 | 94 | 0.16 |
| 494292 | 37 | 51 | 81 | 93 | 95 | 0.11 |
| 494294 | 22 | 40 | 72 | 91 | 94 | 0.19 |
| 494299 | 15 | 43 | 75 | 93 | 95 | 0.20 |
| 494300 | 25 | 38 | 79 | 95 | 95 | 0.17 |
| 494301 | 23 | 48 | 82 | 92 | 95 | 0.15 |
| 494302 | 26 | 59 | 86 | 93 | 94 | 0.12 |
| 494303 | 10 | 58 | 84 | 92 | 91 | 0.16 |
| 494304 | 25 | 62 | 83 | 93 | 93 | 0.12 |

TABLE 25

| ISIS No | 0.049 µM | 0.148 µM | 0.444 µM | 1.333 µM | 4.000 µM | IC$_{50}$ (µM) |
|---|---|---|---|---|---|---|
| 144367 | 23 | 40 | 70 | 90 | 94 | 0.19 |
| 494305 | 20 | 48 | 82 | 93 | 95 | 0.16 |
| 494306 | 26 | 53 | 78 | 91 | 92 | 0.14 |
| 494310 | 36 | 50 | 79 | 88 | 92 | 0.12 |
| 494311 | 38 | 50 | 74 | 93 | 95 | 0.12 |
| 494334 | 20 | 42 | 73 | 90 | 94 | 0.19 |
| 494336 | 5 | 39 | 74 | 92 | 95 | 0.23 |
| 494337 | 23 | 51 | 87 | 96 | 96 | 0.14 |
| 494338 | 12 | 42 | 82 | 93 | 95 | 0.19 |
| 494371 | 28 | 49 | 82 | 94 | 94 | 0.14 |
| 494372 | 28 | 54 | 81 | 93 | 88 | 0.13 |
| 494373 | 21 | 28 | 67 | 86 | 92 | 0.25 |
| 494375 | 26 | 40 | 77 | 85 | 92 | 0.18 |

TABLE 26

| ISIS No | 0.049 µM | 0.148 µM | 0.444 µM | 1.333 µM | 4.000 µM | IC$_{50}$ (µM) |
|---|---|---|---|---|---|---|
| 144367 | 5 | 33 | 65 | 78 | 81 | 0.32 |
| 494388 | 30 | 32 | 60 | 82 | 86 | 0.25 |
| 494389 | 30 | 45 | 69 | 84 | 84 | 0.17 |
| 494390 | 32 | 47 | 67 | 83 | 87 | 0.16 |
| 494392 | 23 | 38 | 54 | 79 | 82 | 0.31 |
| 494466 | 48 | 67 | 86 | 91 | 95 | 0.04 |
| 494470 | 74 | 87 | 92 | 96 | 98 | <0.05 |
| 494472 | 69 | 84 | 92 | 96 | 97 | <0.05 |
| 494544 | 5 | 18 | 49 | 74 | 79 | 0.48 |
| 498238 | 25 | 51 | 76 | 92 | 96 | 0.15 |
| 498239 | 25 | 62 | 83 | 93 | 97 | 0.12 |
| 498379 | 5 | 21 | 53 | 71 | 81 | 0.55 |
| 498408 | 1 | 38 | 63 | 79 | 80 | 0.32 |
| 498433 | 23 | 43 | 70 | 77 | 79 | 0.21 |

TABLE 27

| ISIS No | 0.049 µM | 0.148 µM | 0.444 µM | 1.333 µM | 4.000 µM | IC$_{50}$ (µM) |
|---|---|---|---|---|---|---|
| 144367 | 0 | 40 | 76 | 90 | 93 | 0.26 |
| 498434 | 32 | 44 | 64 | 78 | 84 | 0.20 |
| 498435 | 24 | 42 | 64 | 77 | 79 | 0.23 |
| 498517 | 28 | 23 | 53 | 81 | 85 | 0.45 |
| 498523 | 50 | 64 | 81 | 90 | 93 | <0.05 |
| 498524 | 53 | 70 | 84 | 93 | 96 | <0.05 |
| 498525 | 38 | 55 | 80 | 92 | 96 | 0.09 |
| 498550 | 12 | 18 | 62 | 81 | 83 | 0.33 |
| 498557 | 13 | 33 | 67 | 79 | 83 | 0.33 |
| 498579 | 6 | 42 | 69 | 80 | 85 | 0.31 |
| 498580 | 6 | 46 | 76 | 82 | 83 | 0.23 |
| 498581 | 5 | 40 | 78 | 81 | 84 | 0.25 |
| 498721 | 40 | 31 | 58 | 78 | 83 | 0.35 |
| 498833 | 21 | 20 | 58 | 80 | 90 | 0.44 |

Example 5

Antisense Inhibition of Human Apo(a) in Transgenic Mouse Primary Hepatocytes

Additional antisense oligonucleotides were newly designed targeting an apo(a) nucleic acid and were tested for their effects on apo(a) mRNA in vitro. The antisense oligonucleotides were tested in a series of experiments that had similar culture conditions. Primary hepatocytes from human apo(a) transgenic mice were used in this study. Hepatocytes at a density of 35,000 cells per well were transfected using electroporation with 1,000 nM antisense oligonucleotide. After a treatment period of approximately 24 hours, RNA was isolated from the cells and apo(a) mRNA levels were measured by quantitative real-time PCR. Human primer probe set hAPO(a)12kB was used to measure mRNA levels. Apo(a) mRNA levels were adjusted according to total RNA content, as measured by RIBOGREEN®. The results for each experiment are presented in separate tables shown below. ISIS 144367 was also included in the studies for comparison. Results are presented as percent inhibition of apo(a), relative to untreated control cells. A total of 231 antisense oligonucleotides were tested under these culture conditions. Only those antisense oligonucleotides that were selected for further studies are presented below.

The newly designed chimeric antisense oligonucleotides were designed as 3-10-4 MOE gapmers. The gapmers are 17 nucleosides in length, wherein the central gap segment comprises of ten 2'-deoxynucleosides and is flanked by wing segments on the 5' direction and the 3' direction comprising three nucleosides and four nucleosides respectively. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines.

The apo(a) target sequence contains multiple Kringle repeat sequences, therefore, an antisense oligonucleotide may target one or more regions of apo(a) depending whether on the oligonucleotide targets a Kringle sequence or not. "Start site" indicates the 5'-most nucleoside to which the gapmer is targeted in the human sequence. "Stop site" indicates the 3'-most nucleoside to which the gapmer is targeted human sequence. An apo(a) antisense oligonucleotide may have more than one "Start site" or "Stop site" depending on whether or not it targets a Kringle repeat.

Most gapmers listed in the Tables are targeted with 100% complementarity to multiple regions of either the human apo(a) mRNA, designated herein as SEQ ID NO: 1 (GENBANK Accession No. NM_005577.2) or the human apo(a) genomic sequence, designated herein as SEQ ID NO: 2 (GENBANK Accession No. NT_007422.12 truncated from nucleotides 3230000 to 3380000), or both. 'n/a' indicates that the antisense oligonucleotide does not target that particular sequence with 100% complementarity.

TABLE 28

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 64 | 21210 | 21229 | 11 |
| 510542 | 241 | 257 | CCTGTGACAGTGGTGGA | 79 | 21202 | 21218 | 111 |
| | 583 | 599 | CCTGTGACAGTGGTGGA | | 26693 | 26709 | |
| | 925 | 941 | CCTGTGACAGTGGTGGA | | 32240 | 32256 | |
| | 1609 | 1625 | CCTGTGACAGTGGTGGA | | 43333 | 43349 | |
| | 1951 | 1967 | CCTGTGACAGTGGTGGA | | 48877 | 48893 | |
| | 2293 | 2309 | CCTGTGACAGTGGTGGA | | 54423 | 54439 | |
| | 3319 | 3335 | CCTGTGACAGTGGTGGA | | 72040 | 72056 | |
| | 4663 | 4679 | CCTGTGACAGTGGTGGA | | 94404 | 94420 | |
| | 5005 | 5021 | CCTGTGACAGTGGTGGA | | 115515 | 115531 | |
| 510543 | 242 | 258 | TCCTGTGACAGTGGTGG | 75 | 21203 | 21219 | 112 |
| | 584 | 600 | TCCTGTGACAGTGGTGG | | 26694 | 26710 | |
| | 926 | 942 | TCCTGTGACAGTGGTGG | | 32241 | 32257 | |
| | 1610 | 1626 | TCCTGTGACAGTGGTGG | | 43334 | 43350 | |
| | 1952 | 1968 | TCCTGTGACAGTGGTGG | | 48878 | 48894 | |
| | 2294 | 2310 | TCCTGTGACAGTGGTGG | | 54424 | 54440 | |
| | 3320 | 3336 | TCCTGTGACAGTGGTGG | | 72041 | 72057 | |
| | 4664 | 4680 | TCCTGTGACAGTGGTGG | | 94405 | 94421 | |
| | 5006 | 5022 | TCCTGTGACAGTGGTGG | | 115516 | 115532 | |
| 510544 | 243 | 259 | TTCCTGTGACAGTGGTG | 73 | 21204 | 21220 | 113 |
| | 585 | 601 | TTCCTGTGACAGTGGTG | | 26695 | 26711 | |
| | 927 | 943 | TTCCTGTGACAGTGGTG | | 32242 | 32258 | |
| | 1611 | 1627 | TTCCTGTGACAGTGGTG | | 43335 | 43351 | |
| | 1953 | 1969 | TTCCTGTGACAGTGGTG | | 48879 | 48895 | |
| | 2295 | 2311 | TTCCTGTGACAGTGGTG | | 54425 | 54441 | |
| | 3321 | 3337 | TTCCTGTGACAGTGGTG | | 72042 | 72058 | |
| | 4665 | 4681 | TTCCTGTGACAGTGGTG | | 94406 | 94422 | |
| | 5007 | 5023 | TTCCTGTGACAGTGGTG | | 115517 | 115533 | |
| 510545 | 244 | 260 | CTTCCTGTGACAGTGGT | 65 | 21205 | 21221 | 114 |
| | 586 | 602 | CTTCCTGTGACAGTGGT | | 26696 | 26712 | |
| | 928 | 944 | CTTCCTGTGACAGTGGT | | 32243 | 32259 | |
| | 1612 | 1628 | CTTCCTGTGACAGTGGT | | 43336 | 43352 | |
| | 1954 | 1970 | CTTCCTGTGACAGTGGT | | 48880 | 48896 | |
| | 2296 | 2312 | CTTCCTGTGACAGTGGT | | 54426 | 54442 | |
| | 3322 | 3338 | CTTCCTGTGACAGTGGT | | 72043 | 72059 | |
| | 3664 | 3680 | CTTCCTGTGACAGTGGT | | 77585 | 77601 | |
| | 4666 | 4682 | CTTCCTGTGACAGTGGT | | 94407 | 94423 | |
| | 5008 | 5024 | CTTCCTGTGACAGTGGT | | 115518 | 115534 | |
| 510546 | 245 | 261 | CCTTCCTGTGACAGTGG | 74 | 21206 | 21222 | 115 |
| | 3665 | 3681 | CCTTCCTGTGACAGTGG | | 77586 | 77602 | |
| | 4667 | 4683 | CCTTCCTGTGACAGTGG | | 94408 | 94424 | |
| | 5009 | 5025 | CCTTCCTGTGACAGTGG | | 115519 | 115535 | |
| 510547 | 246 | 262 | TCCTTCCTGTGACAGTG | 77 | 21207 | 21223 | 116 |
| | 3666 | 3682 | TCCTTCCTGTGACAGTG | | 77587 | 77603 | |
| | 4668 | 4684 | TCCTTCCTGTGACAGTG | | 94409 | 94425 | |
| | 5010 | 5026 | TCCTTCCTGTGACAGTG | | 115520 | 115536 | |
| 510548 | 247 | 263 | GTCCTTCCTGTGACAGT | 73 | 21208 | 21224 | 117 |
| | 3667 | 3683 | GTCCTTCCTGTGACAGT | | 77588 | 77604 | |
| | 4669 | 4685 | GTCCTTCCTGTGACAGT | | 94410 | 94426 | |
| | 5011 | 5027 | GTCCTTCCTGTGACAGT | | 115521 | 115537 | |
| 510549 | 248 | 264 | GGTCCTTCCTGTGACAG | 67 | 21209 | 21225 | 118 |
| | 4670 | 4686 | GGTCCTTCCTGTGACAG | | 94411 | 94427 | |
| 510595 | 632 | 648 | CCGACTATGCGAGTGTG | 76 | 26742 | 26758 | 119 |
| | 974 | 990 | CCGACTATGCGAGTGTG | | 32289 | 32305 | |
| | 1316 | 1332 | CCGACTATGCGAGTGTG | | 37836 | 37852 | |
| | 1658 | 1674 | CCGACTATGCGAGTGTG | | 43382 | 43398 | |
| | 2000 | 2016 | CCGACTATGCGAGTGTG | | 48926 | 48942 | |
| | 2342 | 2358 | CCGACTATGCGAGTGTG | | 54472 | 54488 | |
| | 2684 | 2700 | CCGACTATGCGAGTGTG | | 60027 | 60043 | |
| | 3026 | 3042 | CCGACTATGCGAGTGTG | | 66543 | 66559 | |
| 510597 | 634 | 650 | GTCCGACTATGCGAGTG | 70 | 26744 | 26760 | 120 |
| | 976 | 992 | GTCCGACTATGCGAGTG | | 32291 | 32307 | |
| | 1318 | 1334 | GTCCGACTATGCGAGTG | | 37838 | 37854 | |
| | 1660 | 1676 | GTCCGACTATGCGAGTG | | 43384 | 43400 | |
| | 2002 | 2018 | GTCCGACTATGCGAGTG | | 48928 | 48944 | |
| | 2344 | 2360 | GTCCGACTATGCGAGTG | | 54474 | 54490 | |

TABLE 28-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
|  | 2686 | 2702 | GTCCGACTATGCGAGTG |  | 60029 | 60045 |  |
|  | 3028 | 3044 | GTCCGACTATGCGAGTG |  | 66545 | 66561 |  |
| 510598 | 635 | 651 | GGTCCGACTATGCGAGT | 70 | 26745 | 26761 | 121 |
|  | 977 | 993 | GGTCCGACTATGCGAGT |  | 32292 | 32308 |  |
|  | 1319 | 1335 | GGTCCGACTATGCGAGT |  | 37839 | 37855 |  |
|  | 1661 | 1677 | GGTCCGACTATGCGAGT |  | 43385 | 43401 |  |
|  | 2003 | 2019 | GGTCCGACTATGCGAGT |  | 48929 | 48945 |  |
|  | 2345 | 2361 | GGTCCGACTATGCGAGT |  | 54475 | 54491 |  |
|  | 2687 | 2703 | GGTCCGACTATGCGAGT |  | 60030 | 60046 |  |
|  | 3029 | 3045 | GGTCCGACTATGCGAGT |  | 66546 | 66562 |  |

TABLE 29

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 83 | 21210 | 21229 | 11 |
| 510783 | 6400 | 6416 | GTCAGACCTTAAAAGCT | 75 | 140056 | 140072 | 122 |
| 512944 | 3561 | 3577 | AAGCCTCTGTGCTTGGA | 81 | 76246 | 76262 | 123 |
| 512947 | 3560 | 3576 | AGCCTCTGTGCTTGGAT | 85 | 76245 | 76261 | 124 |
| 512958 | 3559 | 3575 | GCCTCTGTGCTTGGATC | 82 | 76244 | 76260 | 125 |
| 512959 | 3585 | 3601 | GCTCCGTTGGTGCTTCT | 77 | n/a | n/a | 126 |

TABLE 30

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 144367 | 249 | 268 | GGCAGGTCCTTCCTGTGACA | 76 | 21210 | 21229 | 11 |
| 510701 | 4217 | 4233 | CTCTGTGCTTGGAACTG | 78 | 85147 | 85163 | 127 |
| 510702 | 219 | 235 | TGCCTCGATAACTCTGT | 79 | 21180 | 21196 | 128 |
|  | 561 | 577 |  |  | 26671 | 26687 |  |
|  | 903 | 919 |  |  | 32218 | 32234 |  |
|  | 1245 | 1261 |  |  | 37765 | 37781 |  |
|  | 1587 | 1603 |  |  | 43311 | 43327 |  |
|  | 1929 | 1945 |  |  | 48855 | 48871 |  |
|  | 2271 | 2287 |  |  | 54401 | 54417 |  |
|  | 2613 | 2629 |  |  | 59956 | 59972 |  |
|  | 4299 | 4315 |  |  | 86472 | 86488 |  |
| 510704 | 563 | 579 | TGTGCCTCGATAACTCT | 80 | 26673 | 26689 | 129 |
|  | 905 | 921 |  |  | 32220 | 32236 |  |
|  | 1247 | 1263 |  |  | 37767 | 37783 |  |
|  | 1589 | 1605 |  |  | 43313 | 43329 |  |
|  | 1931 | 1947 |  |  | 48857 | 48873 |  |
|  | 2273 | 2289 |  |  | 54403 | 54419 |  |
|  | 2615 | 2631 |  |  | 59958 | 59974 |  |
|  | 4301 | 4317 |  |  | 86474 | 86490 |  |
|  | 4985 | 5001 |  |  | 115495 | 115511 |  |
| 510757 | 4929 | 4945 | GCTCAGTTGGTGCTGCT | 74 | n/a | n/a | 130 |

Example 6

Dose-Dependent Antisense Inhibition of Apo(a) in Transgenic Mouse Primary Hepatocytes Potent gapmers from the studies described above were further selected and tested at various doses in transgenic mouse primary hepatocytes in a series of studies with similar culture conditions. Cells were plated at a density of 35,000 per well and transfected using electroporation with 0.156 μM, 0.313 μM, 0.625 μM, 1.250 μM, 2.500 μM, or 5.000 μM concentrations of antisense oligonucleotide, as specified in the Tables below. After a treatment period of approximately 16 hours, RNA was isolated from the cells and apo(a) mRNA levels were measured by quantitative real-time PCR. Apo(a) primer probe set hAPO(a)12kB was used to measured mRNA levels. Apo(a) mRNA levels were adjusted according to total RNA content, as measured by RIBOGREEN®. Results are presented as percent inhibition of apo(a), relative to untreated control cells.

The results of each of the studies are depicted in the Tables presented below with each study represented in a separate table. The half maximal inhibitory concentration ($IC_{50}$) of each oligonucleotide is also presented in the Tables.

TABLE 31

| ISIS No | 0.156 μM | 0.312 μM | 0.625 μM | 1.250 μM | 2.500 μM | 5.000 μM | $IC_{50}$ (μM) |
|---|---|---|---|---|---|---|---|
| 144367 | 28 | 55 | 70 | 83 | 90 | 92 | 0.31 |
| 510542 | 33 | 58 | 75 | 87 | 89 | 90 | 0.27 |
| 510543 | 33 | 45 | 68 | 78 | 89 | 89 | 0.34 |
| 510544 | 33 | 50 | 65 | 78 | 88 | 90 | 0.33 |
| 510545 | 33 | 58 | 76 | 87 | 91 | 90 | 0.26 |
| 510546 | 39 | 62 | 76 | 87 | 89 | 91 | 0.22 |
| 510547 | 36 | 66 | 82 | 84 | 86 | 91 | 0.22 |
| 510548 | 50 | 70 | 82 | 91 | 88 | 90 | 0.13 |
| 510549 | 32 | 59 | 73 | 85 | 86 | 90 | 0.27 |
| 510595 | 26 | 57 | 78 | 88 | 90 | 90 | 0.29 |
| 510597 | 30 | 53 | 76 | 85 | 89 | 89 | 0.30 |

TABLE 32

| ISIS No | 0.156 μM | 0.312 μM | 0.625 μM | 1.250 μM | 2.500 μM | 5.000 μM | $IC_{50}$ (μM) |
|---|---|---|---|---|---|---|---|
| 144367 | 36 | 52 | 78 | 87 | 93 | 94 | 0.26 |
| 510598 | 48 | 58 | 81 | 88 | 93 | 92 | 0.18 |
| 510701 | 45 | 59 | 78 | 87 | 95 | 95 | 0.18 |
| 510702 | 49 | 63 | 75 | 90 | 94 | 95 | 0.15 |
| 510704 | 55 | 67 | 80 | 93 | 94 | 95 | <0.16 |
| 510757 | 34 | 48 | 68 | 79 | 90 | 93 | 0.33 |
| 510783 | 21 | 32 | 51 | 58 | 78 | 84 | 0.69 |
| 512944 | 57 | 72 | 81 | 91 | 96 | 97 | <0.16 |
| 512947 | 64 | 74 | 86 | 92 | 96 | 97 | <0.16 |
| 512958 | 48 | 69 | 83 | 91 | 96 | 97 | 0.13 |
| 512959 | 39 | 59 | 76 | 84 | 93 | 93 | 0.22 |

TABLE 33

| ISIS No | 0.156 μM | 0.312 μM | 0.625 μM | 1.250 μM | 2.500 μM | 5.000 μM | $IC_{50}$ (μM) |
|---|---|---|---|---|---|---|---|
| 144367 | 41 | 58 | 75 | 81 | 88 | 87 | 0.22 |
| 510542 | 38 | 54 | 69 | 74 | 85 | 83 | 0.27 |
| 510545 | 21 | 43 | 73 | 77 | 80 | 78 | 0.39 |
| 510546 | 37 | 58 | 73 | 81 | 83 | 81 | 0.24 |
| 510547 | 38 | 58 | 72 | 79 | 84 | 86 | 0.24 |
| 510548 | 40 | 63 | 77 | 79 | 81 | 84 | 0.21 |
| 510549 | 37 | 47 | 67 | 77 | 81 | 83 | 0.31 |
| 510595 | 34 | 66 | 73 | 81 | 80 | 75 | 0.23 |
| 510597 | 39 | 59 | 74 | 83 | 76 | 77 | 0.23 |

TABLE 34

| ISIS No | 0.156 μM | 0.312 μM | 0.625 μM | 1.250 μM | 2.500 μM | 5.000 μM | $IC_{50}$ (μM) |
|---|---|---|---|---|---|---|---|
| 144367 | 33 | 60 | 72 | 83 | 81 | 81 | 0.26 |
| 510598 | 47 | 62 | 75 | 75 | 76 | 76 | 0.18 |
| 510701 | 41 | 67 | 80 | 87 | 92 | 91 | 0.19 |
| 510702 | 51 | 64 | 77 | 80 | 80 | 83 | 0.13 |

TABLE 34-continued

| ISIS No | 0.156 µM | 0.312 µM | 0.625 µM | 1.250 µM | 2.500 µM | 5.000 µM | IC$_{50}$ (µM) |
|---|---|---|---|---|---|---|---|
| 510704 | 54 | 61 | 77 | 84 | 89 | 80 | 0.12 |
| 512944 | 71 | 74 | 81 | 88 | 92 | 94 | 0.02 |
| 512947 | 65 | 77 | 86 | 90 | 93 | 95 | 0.03 |
| 512958 | 63 | 73 | 84 | 92 | 93 | 96 | 0.06 |
| 512959 | 39 | 62 | 80 | 82 | 86 | 82 | 0.22 |

Apo(a) mRNA levels were significantly reduced in a dose-dependent manner in antisense oligonucleotide-treated cells. The potency of the newly designed oligonucleotides was compared with the benchmark oligonucleotide, ISIS 144367. As presented in the Tables above, ISIS 510542 (SEQ ID NO: 111), ISIS 510545 (SEQ ID NO: 114), ISIS 510546 (SEQ ID NO: 115), ISIS 510547 (SEQ ID NO: 116), ISIS 510548 (SEQ ID NO: 117), ISIS 510549 (SEQ ID NO: 118), ISIS 510595 (SEQ ID NO: 119), ISIS 510597 (SEQ ID NO: 120), ISIS 510598 (SEQ ID NO: 121), ISIS 510701 (SEQ ID NO: 127), ISIS 510702 (SEQ ID NO: 128), ISIS 510704 (SEQ ID NO: 129), ISIS 512944 (SEQ ID NO: 123), ISIS 512947 (SEQ ID NO: 124), ISIS 512958 (SEQ ID NO: 125), and ISIS 512959 (SEQ ID NO: 126) were more potent than ISIS 144367 (SEQ ID NO: 11).

Example 7

Effect of In Vivo Antisense Inhibition of Human Apo(a) in Human Apo(a) Transgenic Mice Transgenic mice with the human apo(a) gene (Frazer, K. A. et al., Nat. Genet. 1995. 9: 424-431) were utilized in the studies described below. ISIS antisense oligonucleotides that demonstrated statistically significant inhibition of apo(a) mRNA in vitro as described above were evaluated further in this model.

Study 1

Female human apo(a) transgenic mice were maintained on a 12-hour light/dark cycle and fed ad libitum normal lab chow. The mice were divided into treatment groups consisting of 4 mice each. The groups received intraperitoneal injections of ISIS 494159, ISIS 494160, ISIS 494161, ISIS 494162, ISIS 494163, ISIS 494230, ISIS 494243, ISIS 494244, ISIS 494283, ISIS 494284, ISIS 494285, ISIS 494286, ISIS 494301, ISIS 494302, ISIS 494304, ISIS 494466, ISIS 494470, ISIS 494472, ISIS 498239, ISIS 498408, ISIS 498517, ISIS 494158, ISIS 494311, ISIS 494337, ISIS 494372, ISIS 498238, ISIS 498523, ISIS 498525, ISIS 510548, ISIS 512944, ISIS 512947, or ISIS 512958 at a dose of 25 mg/kg twice a week for 2 weeks. One group of mice received intraperitoneal injections of PBS twice a week for 2 weeks. The PBS group served as the control group. Two days following the final dose, the mice were euthanized, organs harvested and analyses done.

Inhibition of Human Apo(a) mRNA

Total RNA was extracted from the livers of some of the treatment groups, and human apo(a) mRNA was quantitated by RT-PCR. The results are presented in Table 35, expressed as percent inhibition of apo(a) mRNA compared to the PBS control.

TABLE 35

Percent inhibition of human apo(a) mRNA in transgenic mice

| ISIS No | % inhibition |
|---|---|
| 144367 | 98 |
| 494159 | 100 |
| 494160 | 95 |
| 494161 | 98 |
| 494162 | 100 |
| 494163 | 100 |
| 494230 | 96 |
| 494243 | 99 |
| 494244 | 99 |
| 494283 | 100 |
| 494284 | 100 |
| 494285 | 100 |
| 494286 | 98 |
| 494301 | 99 |
| 494302 | 96 |
| 494304 | 94 |
| 494466 | 97 |
| 494470 | 93 |
| 494472 | 98 |
| 498239 | 72 |
| 498408 | 100 |
| 498517 | 98 |

The data demonstrates significant inhibition of apo(a) mRNA by several ISIS oligonucleotides. ISIS 494159 (SEQ ID NO: 14), ISIS 494162 (SEQ ID NO: 17), ISIS 494163 (SEQ ID NO: 18), ISIS 494243 (SEQ ID NO: 106), ISIS 494244 (SEQ ID NO: 107), ISIS 494283 (SEQ ID NO: 26), ISIS 494284 (SEQ ID NO: 27), ISIS 494285 (SEQ ID NO: 28), ISIS 494301 (SEQ ID NO: 39), and ISIS 498408 (SEQ ID NO: 71) were more potent than the benchmark ISIS 144367 (SEQ ID NO: 11).

Inhibition of Human Apo(a) Protein

Plasma human apo(a) protein was measured from all treatment groups using an Apo(a) ELISA kit (Mercodia 10-1106-01, Uppsala, Sweden). The results are presented in Table 36, expressed as percent inhibition of apo(a) mRNA compared to the PBS control.

TABLE 36

Percent inhibition of human apo(a) protein in transgenic mice

| ISIS No | % inhibition |
|---|---|
| 144367 | 86 |
| 494159 | 86 |
| 494160 | 0 |
| 494161 | 82 |
| 494162 | 84 |
| 494163 | 82 |
| 494230 | 60 |
| 494243 | 84 |
| 494244 | 87 |
| 494283 | 98 |

TABLE 36-continued

Percent inhibition of human apo(a) protein in transgenic mice

| ISIS No | % inhibition |
|---|---|
| 494284 | 98 |
| 494285 | 89 |
| 494286 | 89 |
| 494301 | 93 |
| 494302 | 88 |
| 494304 | 83 |
| 494466 | 76 |
| 494470 | 73 |
| 494472 | 72 |
| 498239 | 54 |
| 498408 | 84 |
| 498517 | 56 |
| 494158 | 71 |
| 494311 | 83 |
| 494337 | 80 |
| 494372 | 78 |
| 498238 | 58 |
| 498523 | 47 |
| 498525 | 58 |
| 510548 | 74 |
| 512944 | 18 |
| 512947 | 65 |
| 512958 | 72 |

The data demonstrates significant inhibition of apo(a) mRNA by several ISIS oligonucleotides. ISIS 494159 (SEQ ID NO: 14), ISIS 494244 (SEQ ID NO: 82), ISIS 494283 (SEQ ID NO: 26), ISIS 494284 (SEQ ID NO: 27), ISIS 494285 (SEQ ID NO: 28), ISIS 494286 (SEQ ID NO: 29), ISIS 494301 (SEQ ID NO: 39), and ISIS 494302 (SEQ ID NO: 40) were as potent as or more potent than the benchmark ISIS 144367 (SEQ ID NO: 11).

Study 2

ISIS 494159, ISIS 494161, ISIS 494162, ISIS 494163, and ISIS 494243 were further evaluated in this transgenic model. ISIS 144367 was included for comparison.

Treatment

Female human apo(a) transgenic mice were divided into treatment groups consisting of 4 mice each. The groups received intraperitoneal injections of ISIS 144367, ISIS 494159, ISIS 494161, ISIS 494162, ISIS 494163, or ISIS 494243 at doses of 1.5 mg/kg, 5 mg/kg, 15 mg/kg, or 50 mg/kg twice a week for 2 weeks. One group of mice received intraperitoneal injections of PBS twice a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in Table 37, expressed as percent inhibition of apo(a) mRNA compared to the PBS control.

TABLE 37

Dose-dependent inhibition of human apo(a) mRNA in transgenic mice

| ISIS No | Dose (mg/kg/wk) | % inhibition | $ED_{50}$ |
|---|---|---|---|
| 144367 | 100 | 71 | 31 |
| | 30 | 42 | |
| | 10 | 0 | |
| | 3 | 5 | |
| 494159 | 100 | 91 | 5 |
| | 30 | 67 | |
| | 10 | 48 | |
| | 3 | 39 | |
| 494161 | 100 | 82 | 6 |
| | 30 | 49 | |
| | 10 | 61 | |
| | 3 | 30 | |
| 494162 | 100 | 90 | 5 |
| | 30 | 67 | |
| | 10 | 58 | |
| | 3 | 25 | |
| 494163 | 100 | 83 | 5 |
| | 30 | 66 | |
| | 10 | 58 | |
| | 3 | 21 | |
| 494243 | 100 | 80 | 32 |
| | 30 | 26 | |
| | 10 | 0 | |
| | 3 | 6 | |

The data demonstrates significant inhibition of apo(a) mRNA by several ISIS oligonucleotides. ISIS 494159 (SEQ ID NO: 14), ISIS 494161 (SEQ ID NO: 16), 494162 (SEQ ID NO:17), and ISIS 94163 (SEQ ID NO: 18) were more efficacious than the benchmark ISIS 144367 (SEQ ID NO: 11).

Reduction of Human Apo(a) Protein Levels

Blood was collected from the treatment groups, and human apo(a) protein levels were quantitated by an Apo(a) ELISA kit (Mercodia 10-1106-01, Uppsala, Sweden). The results are presented in Table 38, expressed as percent reduction of apo(a) protein levels compared to the PBS control.

TABLE 38

Dose-dependent inhibition of human apo(a) protein in transgenic mice

| ISIS No | Dose (mg/kg/wk) | % inhibition | $ED_{50}$ |
|---|---|---|---|
| 144367 | 100 | 73 | 71 |
| | 30 | 0 | |
| | 10 | 6 | |
| | 3 | 69 | |
| 494159 | 100 | 88 | 2 |
| | 30 | 88 | |
| | 10 | 85 | |
| | 3 | 36 | |
| 494161 | 100 | 90 | 2 |
| | 30 | 85 | |
| | 10 | 73 | |
| | 3 | 44 | |
| 494162 | 100 | 89 | 3 |
| | 30 | 78 | |
| | 10 | 76 | |
| | 3 | 24 | |
| 494163 | 100 | 90 | 3 |
| | 30 | 86 | |
| | 10 | 60 | |
| | 3 | 37 | |
| 494243 | 100 | 61 | 174 |
| | 30 | 0 | |
| | 10 | 0 | |
| | 3 | 0 | |

The data demonstrates significant reduction of apo(a) plasma protein levels by several ISIS oligonucleotides. ISIS 494159 (SEQ ID NO: 14), ISIS 494161 (SEQ ID NO: 16), ISIS 494162 (SEQ ID NO: 17), and ISIS 494163 (SEQ ID NO: 18) were more efficacious than the benchmark ISIS 144367 (SEQ ID NO: 11).

Study 3

ISIS 494244, ISIS 494283, and ISIS 494284 were further evaluated in this model. ISIS 144367 was included for comparison.

Treatment

Female human apo(a) transgenic mice were divided into treatment groups consisting of 4 mice each. The groups received intraperitoneal injections of ISIS 144367, ISIS 494244, ISIS 494283, or ISIS 494284 at doses of 0.75 mg/kg, 2.5 mg/kg, 7.5 mg/kg, or 25 mg/kg twice a week for 2 weeks. One group of mice received intraperitoneal injections of PBS twice a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in Table 39, expressed as percent inhibition of apo(a) mRNA compared to the PBS control.

TABLE 39

Dose-dependent inhibition of human apo(a) mRNA in transgenic mice

| ISIS No | Dose (mg/kg/wk) | % inhibition | $ED_{50}$ |
|---|---|---|---|
| 144367 | 50 | 75 | 22 |
|  | 15 | 60 |  |
|  | 5 | 0 |  |
|  | 1.5 | 0 |  |
| 494244 | 50 | 73 | 18 |
|  | 15 | 41 |  |
|  | 5 | 34 |  |
|  | 1.5 | 0 |  |
| 494283 | 50 | 74 | 16 |
|  | 15 | 52 |  |
|  | 5 | 24 |  |
|  | 1.5 | 0 |  |
| 494284 | 50 | 73 | 16 |
|  | 15 | 58 |  |
|  | 5 | 17 |  |
|  | 1.5 | 2 |  |

The data demonstrates significant inhibition of apo(a) mRNA by several ISIS oligonucleotides. ISIS 494244 (SEQ ID NO: 107), ISIS 494283 (SEQ ID NO: 26), and ISIS 494284 (SEQ ID NO: 27) were more efficacious than the benchmark, ISIS 144367 (SEQ ID NO: 11).

Reduction of Human Apo(a) Protein Levels

Blood was collected from the treatment groups, and human apo(a) protein levels were quantitated by an Apo(a) ELISA kit (Mercodia 10-1106-01, Uppsala, Sweden). The results are presented in Table 40, expressed as percent reduction of apo(a) protein levels compared to the PBS control.

TABLE 40

Dose-dependent inhibition of human apo(a) plasma protein in transgenic mice

| ISIS No | Dose (mg/kg/wk) | % inhibition | $ED_{50}$ |
|---|---|---|---|
| 144367 | 50 | 64 | 16 |
|  | 15 | 14 |  |
|  | 5 | 0 |  |
|  | 1.5 | 0 |  |
| 494244 | 50 | 67 | 2 |
|  | 15 | 60 |  |
|  | 5 | 58 |  |
|  | 1.5 | 0 |  |
| 494283 | 50 | 64 | 4 |
|  | 15 | 65 |  |
|  | 5 | 64 |  |
|  | 1.5 | 69 |  |
| 494284 | 50 | 66 | 4 |
|  | 15 | 63 |  |
|  | 5 | 51 |  |
|  | 1.5 | 54 |  |

The data demonstrates significant reduction of apo(a) plasma protein levels by several ISIS oligonucleotides. ISIS 494244 (SEQ ID NO: 107), ISIS 494283 (SEQ ID NO: 26), and ISIS 494284 (SEQ ID NO: 27) were more efficacious than the benchmark, ISIS 144367 (SEQ ID NO: 11).

Study 4

ISIS 494285, ISIS 494286, ISIS 494301, ISIS 494302, and ISIS 494311 were further evaluated in this model.

Treatment

Male human apo(a) transgenic mice were divided into treatment groups consisting of 4 mice each. Each such group received intraperitoneal injections of ISIS 494285, ISIS 494286, ISIS 494301, ISIS 494302, or ISIS 494311 at doses of 5 mg/kg, 15 mg/kg, or 50 mg/kg once a week for 2 weeks. One group of 3 mice received intraperitoneal injections of PBS once a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in Table 41, expressed as percent inhibition of apo(a) mRNA compared to the PBS control. The data demonstrates significant inhibition of apo(a) mRNA by ISIS 494285 (SEQ ID NO: 28), ISIS 494286 (SEQ ID NO: 29), ISIS 494301 (SEQ ID NO: 39), ISIS 494302 (SEQ ID NO: 40) and ISIS 494311 (SEQ ID NO: 47).

TABLE 41

Dose-dependent inhibition of human Apo(a) mRNA in transgenic mice

| ISIS No | Dose (mg/kg/wk) | % inhibition | $ED_{50}$ |
|---|---|---|---|
| 494285 | 50 | 98 | 1 |
|  | 15 | 97 |  |
|  | 5 | 79 |  |
| 494286 | 50 | 97 | 1 |
|  | 15 | 91 |  |
|  | 5 | 80 |  |
| 494301 | 50 | 98 | 3 |
|  | 15 | 96 |  |
|  | 5 | 59 |  |
| 494302 | 50 | 98 | 2 |
|  | 15 | 88 |  |
|  | 5 | 72 |  |

TABLE 41-continued

Dose-dependent inhibition of human Apo(a) mRNA in transgenic mice

| ISIS No | Dose (mg/kg/wk) | % inhibition | $ED_{50}$ |
|---|---|---|---|
| 494311 | 50 | 99 | 1 |
|  | 15 | 96 |  |
|  | 5 | 87 |  |

Reduction of Human Apo(a) Protein Levels

Blood was collected from the treatment groups, and human apo(a) protein levels were quantitated by an Apo(a) ELISA kit (Mercodia 10-1106-01, Uppsala, Sweden). The results are presented in Table 42, expressed as percent reduction of apo(a) protein levels compared to the PBS control. The data demonstrates significant reduction of apo (a) plasma protein levels by ISIS 494285, ISIS 494286, ISIS 494301, ISIS 494302 and ISIS 494311.

TABLE 42

Dose-dependent inhibition of human apo(a) protein in transgenic mice

| ISIS No | Dose (mg/kg/wk) | % inhibition | $ED_{50}$ |
|---|---|---|---|
| 494285 | 50 | 88 | 2 |
|  | 15 | 88 |  |
|  | 5 | 72 |  |
| 494286 | 50 | 90 | 2 |
|  | 15 | 85 |  |
|  | 5 | 75 |  |
| 494301 | 50 | 89 | 5 |
|  | 15 | 86 |  |
|  | 5 | 38 |  |
| 494302 | 50 | 90 | 3 |
|  | 15 | 82 |  |
|  | 5 | 61 |  |
| 494311 | 50 | 90 | 3 |
|  | 15 | 82 |  |
|  | 5 | 69 |  |

Study 5

ISIS 494372, ISIS 498524, ISIS 498581, ISIS 498721, and ISIS 498833 were further evaluated in this model.

Treatment

Female human apo(a) transgenic mice were divided into treatment groups consisting of 4 mice each. The groups received intraperitoneal injections of ISIS 494372, ISIS 498524, ISIS 498581, ISIS 498721, or ISIS 498833 at doses of 5 mg/kg, 15 mg/kg, or 50 mg/kg once a week for 2 weeks. One group of 3 mice received intraperitoneal injections of PBS once a week for 2 weeks. The PBS group served as the control group. Two days following the final dose, the mice were euthanized, organs harvested and analyses done.

Inhibition of Human Apo(a) mRNA

Total RNA was extracted from the livers of the treatment groups, and human apo(a) mRNA was quantitated by RT-PCR. The results are presented in Table 43, expressed as percent inhibition of apo(a) mRNA compared to the PBS control. The data demonstrates significant inhibition of apo(a) mRNA by ISIS 494372 (SEQ ID NO: 28), ISIS 498524 (SEQ ID NO: 93), ISIS 498581 (SEQ ID NO: 104), and ISIS 498721 (ATGCCTCGATAACTCCGTCC; SEQ ID NO: 134).

TABLE 43

Dose-dependent inhibition of human Apo(a) mRNA in transgenic mice

| ISIS No | Dose (mg/kg/wk) | % inhibition | $ED_{50}$ |
|---|---|---|---|
| 494372 | 50 | 88 | 18 |
|  | 15 | 49 |  |
|  | 5 | 0 |  |
| 498524 | 50 | 83 | 8 |
|  | 15 | 74 |  |
|  | 5 | 34 |  |
| 498581 | 50 | 98 | 7 |
|  | 15 | 58 |  |
|  | 5 | 48 |  |
| 498721 | 50 | 97 | 14 |
|  | 15 | 68 |  |
|  | 5 | 0 |  |
| 498833 | 50 | 61 | 155 |
|  | 15 | 0 |  |
|  | 5 | 17 |  |

Reduction of Human Apo(a) Protein Levels

Blood was collected from the treatment groups, and human apo(a) protein levels were quantitated by an Apo(a) ELISA kit (Mercodia 10-1106-01, Uppsala, Sweden). The results are presented in Table 44, expressed as percent reduction of apo(a) protein levels compared to the PBS control. The data demonstrates significant reduction of apo (a) plasma protein levels by ISIS 494372 (SEQ ID NO: 28), ISIS 498581 (SEQ ID NO: 104), and ISIS 498721 (ATGCCTCGATAACTCCGTCC; SEQ ID NO: 134).

TABLE 44

Dose-dependent inhibition of human apo(a) protein in transgenic mice

| ISIS No | Dose (mg/kg/wk) | % inhibition | $ED_{50}$ |
|---|---|---|---|
| 494372 | 50 | 68 | 32 |
|  | 15 | 25 |  |
|  | 5 | 12 |  |
| 498524 | 50 | 38 | 118 |
|  | 15 | 0 |  |
|  | 5 | 0 |  |
| 498581 | 50 | 79 | 9 |
|  | 15 | 52 |  |
|  | 5 | 49 |  |
| 498721 | 50 | 81 | 10 |
|  | 15 | 63 |  |
|  | 5 | 29 |  |
| 498833 | 50 | 15 | 738 |
|  | 15 | 0 |  |
|  | 5 | 67 |  |

Example 8

Tolerability of Antisense Oligonucleotides Targeting Human Apo(a) in Rodent Models Gapmer antisense oligonucleotides targeting human apo (a) were selected from the studies described above for tolerability studies in CD1 mice and in Sprague Dawley rats. Rodents do not express endogenous apo(a), hence these studies tested the tolerability of each human antisense oligonucleotide in an animal rather than any phenotypic changes that may be caused by inhibiting apo(a) in the animal.

Tolerability in CD1 Mice: Study 1

CD1® mice (Charles River, Mass.) are a multipurpose mice model, frequently utilized for safety and efficacy testing. The mice were treated with ISIS antisense oligonucleotides selected from studies described above and evaluated for changes in the levels of various plasma chemistry markers.

Treatment

Groups of male CD1 mice were injected subcutaneously twice a week for 6 weeks with 50 mg/kg of ISIS 494159, ISIS 494161, ISIS 494162, ISIS 494244, ISIS 494283, ISIS 494284, ISIS 494285, ISIS 494286, ISIS 494301, ISIS 494302, ISIS 494311, ISIS 494337, ISIS 494372, and ISIS 510548. One group of six-week old male CD1 mice was injected subcutaneously twice a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, creatinine, and BUN were measured using an automated clinical chemistry analyzer (Hitachi Olympus AU400e, Melville, N.Y.). The results are presented in Table 45. ISIS oligonucleotides that caused changes in the levels of any of the liver or kidney function markers outside the expected range for antisense oligonucleotides were excluded in further studies.

TABLE 45

Plasma chemistry markers of CD1 mice

|  | ALT (IU/L) | AST (IU/L) | Albumin (g/dL) | BUN (mg/dL) | Creatinine (mg/dL) | Bilirubin (mg/dL) |
|---|---|---|---|---|---|---|
| PBS | 38 | 71 | 2.9 | 25.2 | 0.16 | 0.15 |
| ISIS 494159 | 615 | 525 | 2.7 | 23.9 | 0.11 | 0.20 |
| ISIS 494161 | 961 | 670 | 2.6 | 23.7 | 0.15 | 0.14 |
| ISIS 494162 | 1373 | 1213 | 2.7 | 23.7 | 0.14 | 0.18 |
| ISIS 494283 | 237 | 242 | 2.5 | 26.2 | 0.14 | 0.13 |
| ISIS 494284 | 192 | 307 | 2.3 | 27.1 | 0.14 | 0.10 |
| ISIS 494285 | 582 | 436 | 2.3 | 25.4 | 0.16 | 0.11 |
| ISIS 494286 | 191 | 227 | 2.5 | 21.1 | 0.12 | 0.15 |
| ISIS 494301 | 119 | 130 | 2.7 | 26.4 | 0.15 | 0.12 |
| ISIS 494302 | 74 | 96 | 2.8 | 24.8 | 0.14 | 0.15 |
| ISIS 494311 | 817 | 799 | 2.7 | 28.7 | 0.12 | 0.17 |
| ISIS 494337 | 722 | 397 | 2.5 | 20.0 | 0.13 | 0.11 |
| ISIS 494372 | 73 | 164 | 2.6 | 28.5 | 0.16 | 0.11 |
| ISIS 510548 | 2819 | 2245 | 3.1 | 26.0 | 0.15 | 0.15 |

Organ Weights

Liver, spleen and kidney weights were measured at the end of the study, and are presented in Table 46. ISIS oligonucleotides that caused any changes in organ weights outside the expected range for antisense oligonucleotides were excluded from further studies.

TABLE 46

Organ weights of CD1 mice (g)

|  | Kidney | Liver | Spleen |
|---|---|---|---|
| PBS | 0.68 | 2.0 | 0.13 |
| ISIS 494159 | 0.68 | 3.0 | 0.21 |
| ISIS 494161 | 0.62 | 3.5 | 0.20 |
| ISIS 494162 | 0.60 | 3.3 | 0.20 |
| ISIS 494283 | 0.65 | 2.8 | 0.24 |
| ISIS 494284 | 0.69 | 2.7 | 0.29 |
| ISIS 494285 | 0.59 | 3.2 | 0.21 |
| ISIS 494286 | 0.64 | 2.8 | 0.25 |
| ISIS 494301 | 0.72 | 3.0 | 0.43 |
| ISIS 494302 | 0.63 | 2.3 | 0.23 |
| ISIS 494311 | 0.61 | 3.2 | 0.19 |
| ISIS 494337 | 0.56 | 2.3 | 0.17 |

TABLE 46-continued

Organ weights of CD1 mice (g)

|  | Kidney | Liver | Spleen |
|---|---|---|---|
| ISIS 494372 | 0.60 | 2.5 | 0.27 |
| ISIS 510548 | 0.55 | 3.7 | 0.20 |

Tolerability in Sprague Dawley Rats

Sprague-Dawley rats are a multipurpose model used for safety and efficacy evaluations. The rats were treated with ISIS antisense oligonucleotides selected from studies described above and evaluated for changes in the levels of various plasma chemistry markers.

Treatment

Groups of male Sprague Dawley rats were injected subcutaneously twice a week for 8 weeks with 30 mg/kg of ISIS 494159, ISIS 494161, ISIS 494162, ISIS 494244, ISIS 494283, ISIS 494284, ISIS 494285, ISIS 494286, ISIS 494301, ISIS 494302, ISIS 494311, ISIS 494337, ISIS 494372, and ISIS 510548. One group of six male Sprague Dawley rats was injected subcutaneously twice a week for 8 weeks with PBS. Rats were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, creatinine, and BUN were measured using an automated clinical chemistry analyzer (Hitachi Olympus AU400e, Melville, N.Y.). The results are presented in Table 47. ISIS oligonucleotides that caused changes in the levels of any of the liver or kidney function markers outside the expected range for antisense oligonucleotides were excluded in further studies.

TABLE 47

Plasma chemistry markers of Sprague Dawley rats

|  | ALT (IU/L) | AST (IU/L) | Bilirubin (mg/dL) | Albumin (mg/dL) | BUN (mg/dL) | Creatinine (mg/dL) |
|---|---|---|---|---|---|---|
| PBS | 30 | 82 | 0.09 | 3.2 | 19 | 0.28 |
| ISIS 494159 | 182 | 208 | 0.14 | 3.4 | 22 | 0.35 |
| ISIS 494161 | 36 | 86 | 0.13 | 3.4 | 23 | 0.35 |
| ISIS 494162 | 102 | 158 | 0.17 | 2.6 | 28 | 0.32 |
| ISIS 494283 | 53 | 156 | 0.13 | 2.9 | 24 | 0.32 |
| ISIS 494284 | 34 | 113 | 0.08 | 2.0 | 28 | 0.32 |
| ISIS 494285 | 110 | 294 | 0.10 | 1.4 | 110 | 0.52 |
| ISIS 494286 | 40 | 83 | 0.07 | 1.6 | 48 | 0.44 |
| ISIS 494301 | 38 | 132 | 0.08 | 3.0 | 18 | 0.33 |
| ISIS 494302 | 47 | 105 | 0.09 | 3.2 | 19 | 0.34 |
| ISIS 494311 | 93 | 185 | 0.51 | 2.7 | 23 | 0.30 |
| ISIS 494372 | 54 | 119 | 0.12 | 3.0 | 19 | 0.33 |
| ISIS 510548 | 116 | 181 | 0.11 | 1.7 | 65 | 0.66 |

Kidney Function

To evaluate the effect of ISIS oligonucleotides on kidney function, urine levels of total protein and creatinine were measured using an automated clinical chemistry analyzer (Hitachi Olympus AU400e, Melville, N.Y.). Results are presented in Table 48, expressed in mg/dL.

TABLE 48

Kidney function markers (mg/dL) in Sprague-Dawley rats

|  | Creatinine | Total protein |
|---|---|---|
| PBS | 103 | 118 |
| ISIS 494159 | 70 | 279 |
| ISIS 494161 | 105 | 315 |
| ISIS 494162 | 58 | 925 |
| ISIS 494283 | 114 | 1091 |
| ISIS 494284 | 97 | 2519 |
| ISIS 494285 | 38 | 2170 |
| ISIS 494286 | 51 | 625 |
| ISIS 494301 | 62 | 280 |
| ISIS 494302 | 101 | 428 |
| ISIS 494311 | 48 | 1160 |
| ISIS 494372 | 46 | 154 |
| ISIS 510548 | 55 | 2119 |

Organ Weights

Liver, spleen and kidney weights were measured at the end of the study, and are presented in Table 49. ISIS oligonucleotides that caused any changes in organ weights outside the expected range for antisense oligonucleotides were excluded from further studies.

TABLE 49

Organ weights of Sprague Dawley rats (g)

|  | Kidney | liver | Spleen |
|---|---|---|---|
| PBS | 3.5 | 13.1 | 0.9 |
| ISIS 494159 | 3.1 | 11.7 | 1.6 |
| ISIS 494161 | 2.8 | 12.5 | 2 |
| ISIS 494162 | 3.1 | 14.2 | 1.6 |
| ISIS 494283 | 3.3 | 12.9 | 2.3 |
| ISIS 494284 | 4.1 | 15.8 | 2.7 |
| ISIS 494285 | 3.8 | 13.4 | 0.8 |
| ISIS 494286 | 4.2 | 16.7 | 2.5 |
| ISIS 494301 | 3.2 | 12.1 | 2.3 |
| ISIS 494302 | 3.4 | 13.3 | 2.4 |
| ISIS 494311 | 3.5 | 17.4 | 3.2 |
| ISIS 494372 | 3.6 | 12.9 | 3.2 |
| ISIS 510548 | 6.4 | 21.2 | 1.5 |

The finding from the rodent tolerability studies showed that in general, taking into consideration all the tolerability markers screened, ISIS 494372 was the best tolerated antisense compound in both the CD1 mouse model and the Sprague Dawley rat model.

Example 9

Pharmacokinetics of Antisense Oligonucleotide in CD1 Mice

CD1 mice were treated with ISIS oligonucleotides and the oligonucleotide concentrations in the liver and kidney were evaluated.
Treatment Groups of four CD1 mice each were injected subcutaneously twice per week for 6 weeks with 50 mg/kg of ISIS 494283, ISIS 494284, ISIS 494286, ISIS 494301, ISIS 494302, or ISIS 494372. The mice were sacrificed 2 days following the final dose. Livers were harvested for analysis.
Measurement of Oligonucleotide Concentration The concentration of the total oligonucleotide concentration was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTT-GCTCTTCTTCTTGCGTTTTTT, designated herein as SEQ ID NO: 131) was added prior to extraction. Tissue sample concentrations were calculated using calibration curves, with a lower limit of quantitation (LLOQ) of approximately 1.14 µg/g. Half-lives were then calculated using WinNonlin software (PHARSIGHT).

The results are presented in Table 50, expressed as µg/g liver or kidney tissue. The data indicates that ISIS 494372 was at an acceptable concentration in the liver and kidneys.

TABLE 50

Oligonucleotide concentration (µg/g tissue) of ISIS oligonucleotides in CD1 mice

| ISIS No | Liver | Kidney |
|---|---|---|
| 494283 | 581 | 549 |
| 494284 | 511 | 678 |
| 494286 | 368 | 445 |
| 494301 | 812 | 347 |
| 494302 | 617 | 263 |
| 494372 | 875 | 516 |

Example 10

Pharmacokinetics of Antisense Oligonucleotide in Sprague Dawley Rats

Male Sprague Dawley rats were treated with ISIS oligonucleotides and the oligonucleotide concentrations in the liver and kidney were evaluated.
Treatment Groups of four rats each were injected subcutaneously twice per week for 3 weeks with 10 mg/kg of ISIS 494283, ISIS 494284, ISIS 494286, ISIS 494301, ISIS 494302, or ISIS 494372. The rats were sacrificed 2 days following the final dose. Livers were harvested for analysis.
Measurement of Oligonucleotide Concentration The concentration of the total oligonucleotide concentration was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTT-GCTCTTCTTCTTGCGTTTTTT, designated herein as SEQ ID NO: 131) was added prior to extraction. Tissue sample concentrations were calculated using calibration curves, with a lower limit of quantitation (LLOQ) of approximately 1.14 µg/g. Half-lives were then calculated using WinNonlin software (PHARSIGHT).

The results are presented in Table 51, expressed as µg/g liver or kidney tissue. The data indicates that ISIS 494372 was at an acceptable concentration in the liver and kidneys.

TABLE 51

Oligonucleotide concentration (µg/g tissue) of ISIS oligonucleotides in Sprague Dawley rats

| ISIS No | Liver | Kidney |
|---|---|---|
| 494283 | 220 | 434 |
| 494284 | 178 | 573 |

TABLE 51-continued

Oligonucleotide concentration (μg/g tissue)
of ISIS oligonucleotides in Sprague Dawley rats

| ISIS No | Liver | Kidney |
|---|---|---|
| 494286 | 234 | 448 |
| 494301 | 279 | 540 |
| 494302 | 205 | 387 |
| 494372 | 288 | 663 |

Example 11

Effect of ISIS Antisense Oligonucleotides Targeting Human Apo(a) in Cynomolgus Monkeys Cynomolgus monkeys were treated with ISIS antisense oligonucleotides selected from studies described above. At the time this study was undertaken, the cynomolgus monkey genomic sequence was not available in the National Center for Biotechnology Information (NCBI) database; therefore, cross-reactivity with the cynomolgus monkey gene sequence could not be confirmed. Instead, the sequences of the ISIS antisense oligonucleotides used in the cynomolgus monkeys was compared to a rhesus monkey sequence for homology. It is expected that ISIS oligonucleotides with homology to the rhesus monkey sequence are fully cross-reactive with the cynomolgus monkey sequence as well.

The human antisense oligonucleotides tested are also cross-reactive with the rhesus mRNA sequence (XM_001098061.1; designated herein as SEQ ID NO: 132). The greater the complementarity between the human oligonucleotide and the rhesus monkey sequence, the more likely the human oligonucleotide can cross-react with the rhesus monkey sequence. The start and stop sites of each oligonucleotide to SEQ ID NO: 132 is presented in Table 52. Each antisense oligonucleotide targets more than one region in SEQ ID NO:132 and has multiple start sites. "Start site" indicates the 5'-most nucleotide to which the gapmer is targeted in the rhesus monkey sequence. 'Mismatches' indicates the number of nucleotides mismatched between the human oligonucleotide sequence and the rhesus sequence.

Antisense oligonucleotide tolerability, as well as their pharmacokinetic profile in the liver and kidney, was evaluated.

TABLE 52

Antisense oligonucleotides complementary to SEQ ID NO: 132

| ISIS No | Start Site | Mismatches |
|---|---|---|
| 494283 | 278 | 2 |
|  | 620 | 2 |
|  | 923 | 2 |
|  | 1265 | 2 |
|  | 1607 | 1 |
|  | 1949 | 1 |
|  | 2267 | 1 |
|  | 2609 | 1 |
|  | 2951 | 1 |
|  | 3293 | 1 |
| 494284 | 279 | 1 |
|  | 621 | 1 |
|  | 924 | 1 |
|  | 1266 | 1 |
|  | 1608 | 1 |
|  | 1950 | 1 |
|  | 2268 | 1 |
|  | 2610 | 1 |
|  | 2952 | 1 |
|  | 3294 | 1 |
| 494286 | 281 | 1 |
|  | 623 | 1 |
|  | 926 | 1 |
|  | 1268 | 1 |
|  | 1610 | 2 |
|  | 1952 | 2 |
|  | 2270 | 2 |
|  | 2612 | 2 |
|  | 2954 | 2 |
|  | 3296 | 2 |
| 494301 | 322 | 2 |
|  | 664 | 2 |
|  | 967 | 2 |
|  | 1309 | 1 |
|  | 1651 | 2 |
| 494302 | 323 | 2 |
|  | 968 | 2 |
|  | 1310 | 1 |
|  | 1652 | 2 |
| 494372 | 1186 | 2 |
|  | 1870 | 1 |
|  | 2188 | 1 |

Treatment

Prior to the study, the monkeys were kept in quarantine for at least a 30-day period, during which the animals were observed daily for general health. The monkeys were 2-4 years old and weighed between 2 and 4 kg. Seven groups of four randomly assigned male cynomolgus monkeys each were injected subcutaneously with ISIS oligonucleotide or PBS using a stainless steel dosing needle and syringe of appropriate size into the one of four sites on the back of the monkeys. The injections were given in clock-wise rotation; one site per dosing. The monkeys were dosed four times a week for the first week (days 1, 3, 5, and 7) as loading doses, and subsequently once a week for weeks 2-12, with 40 mg/kg of ISIS 494283, ISIS 494284, ISIS 494286, ISIS 494301, ISIS 494302, or ISIS 494372. A control group of 8 cynomolgus monkeys was injected with PBS subcutaneously thrice four times a week for the first week (days 1, 3, 5, and 7), and subsequently once a week for weeks 2-12.

During the study period, the monkeys were observed at least once daily for signs of illness or distress. Any animal experiencing more than momentary or slight pain or distress due to the treatment, injury or illness was treated by the veterinary staff with approved analgesics or agents to relieve the pain after consultation with the Study Director. Any animal in poor health or in a possible moribund condition was identified for further monitoring and possible euthanasia. For instance, one animal in the treatment group of ISIS 494302 was found moribund on day 56 and was euthanized. Scheduled euthanasia of the animals was conducted on days 86 and 87 by exsanguination under deep anesthesia. The protocols described in the Example were approved by the Institutional Animal Care and Use Committee (IACUC).

Target Reduction

RNA Analysis

On day 86, RNA was extracted from liver tissue for real-time PCR analysis of apo(a) using human primer probe set ABI Hs00916691_m1 (Applied Biosystems, Carlsbad Calif.). Results are presented as percent inhibition of apo(a) mRNA, relative to PBS control. As shown in Table 53, treatment with ISIS antisense oligonucleotides resulted in significant reduction of apo(a) mRNA in comparison to the PBS control.

The mRNA levels of plasminogen, another kringle-containing protein, were also measured. Treatment with ISIS 494372 did not alter the mRNA levels of plasminogen.

TABLE 53

Percent Inhibition of apo(a) mRNA in the cynomolgus monkey liver relative to the PBS control

| ISIS No | % inhibition |
|---|---|
| 494283 | 91 |
| 494284 | 99 |
| 494286 | 96 |
| 494301 | 88 |
| 494302 | 89 |
| 494372 | 93 |

Protein Analysis

On different days, one mL of blood was collected from the cephalic, saphenous, or femoral vein of all study monkeys. The blood samples were put into tubes containing K2-EDTA for plasma separation. The tubes were centrifuged at 3,000 rpm for 10 min at room temperature to obtain plasma. Apo(a) protein levels were analyzed by an Apo(a) ELISA kit (Mercodia 10-1106-01, Uppsala, Sweden). Results are presented as percentage change of levels from the baseline. As shown in Table 54, treatment with several ISIS antisense oligonucleotides resulted in significant reduction of apo(a) protein levels in comparison to the PBS control. Specifically, treatment with ISIS 494372 reduced cynomolgous plasma protein levels of apo(a).

The protein levels of apoB were also measured in the study groups. Antisense inhibition of apo(a) had no effect on apoB levels.

TABLE 54

Apo(a) plasma protein levels (% inhibition over baseline values) in the cynomolgus monkey

| | Day 16 | Day 30 | Day 44 | Day 56 | Day 72 | Day 86 |
|---|---|---|---|---|---|---|
| PBS | 0 | 0 | 10 | 0 | 0 | 0 |
| ISIS 494283 | 78 | 79 | 81 | 66 | 66 | 70 |
| ISIS 494284 | 92 | 95 | 95 | 93 | 93 | 94 |
| ISIS 494286 | 92 | 95 | 96 | 94 | 94 | 94 |
| ISIS 494301 | 41 | 45 | 52 | 20 | 17 | 29 |
| ISIS 494302 | 17 | 0 | 2 | 0 | 0 | 20 |
| ISIS 494372 | 67 | 80 | 83 | 79 | 78 | 81 |

Tolerability Studies
Body and Organ Weight Measurements

To evaluate the effect of ISIS oligonucleotides on the overall health of the animals, body and organ weights were measured at day 86. Body weights were measured and are presented in Table 55. Organ weights were measured and the data is presented in Table 56. The results indicate that treatment with ISIS 494372 was well tolerated in terms of the body and organ weights of the monkeys.

TABLE 55

Body weights (g) in the cynomolgus monkey

| | Day 14 | Day 35 | Day 49 | Day 56 | Day 70 | Day 84 |
|---|---|---|---|---|---|---|
| PBS | 2637 | 2691 | 2748 | 2733 | 2739 | 2779 |
| ISIS 494283 | 2591 | 2670 | 2698 | 2656 | 2704 | 2701 |
| ISIS 494284 | 2559 | 2661 | 2676 | 2675 | 2662 | 2646 |
| ISIS 494286 | 2693 | 2770 | 2838 | 2800 | 2796 | 2816 |
| ISIS 494301 | 2587 | 2604 | 2627 | 2591 | 2596 | 2604 |
| ISIS 494302 | 2759 | 2760 | 2839 | 2825 | 3113 | 3122 |
| ISIS 494372 | 2719 | 2877 | 2985 | 2997 | 3037 | 3036 |

TABLE 56

Organ weights (% body weight) in the cynomolgus monkey

| | Spleen | Kidneys | Liver | Heart | Lungs |
|---|---|---|---|---|---|
| PBS | 0.14 | 0.38 | 2.2 | 0.33 | 0.51 |
| ISIS 494283 | 0.24 | 0.95 | 2.8 | 0.33 | 0.49 |
| ISIS 494284 | 0.19 | 0.60 | 2.6 | 0.36 | 0.55 |
| ISIS 494286 | 0.22 | 0.63 | 2.7 | 0.38 | 0.55 |
| ISIS 494301 | 0.38 | 0.81 | 3.0 | 0.36 | 0.61 |
| ISIS 494302 | 0.17 | 0.95 | 2.5 | 0.39 | 0.57 |
| ISIS 494372 | 0.18 | 1.16 | 2.6 | 0.36 | 0.56 |

Liver Function

To evaluate the effect of ISIS oligonucleotides on hepatic function, monkeys were fasted overnight prior to blood collection. Approximately 1.5 mL of blood was collected from each animal and put into tubes without anticoagulant for serum separation. The tubes were kept at room temperature for a minimum of 90 min and then centrifuged at 3,000 rpm for 10 min at room temperature to obtain serum. Levels of various liver function markers were measured using a Toshiba 200FR NEO chemistry analyzer (Toshiba Co., Japan). Plasma levels of ALT and AST were measured and the results are presented in Table 57, expressed in IU/L. Bilirubin, a liver function marker, was similarly measured and is presented in Table 57, expressed in mg/dL. The results indicate that treatment with ISIS 494372 was well tolerated in terms of the liver function in monkeys.

TABLE 57

Liver function markers in cynomolgus monkey plasma

| | ALT (IU/L) | AST (IU/L) | Bilirubin (mg/dL) |
|---|---|---|---|
| PBS | 33 | 43 | 0.20 |
| ISIS 494283 | 75 | 73 | 0.12 |
| ISIS 494284 | 115 | 79 | 0.17 |
| ISIS 494286 | 67 | 73 | 0.13 |
| ISIS 494301 | 129 | 90 | 0.15 |
| ISIS 494302 | 141 | 75 | 0.15 |
| ISIS 494372 | 46 | 75 | 0.17 |

C-Reactive Protein Level Analysis

To evaluate any inflammatory effect of ISIS oligonucleotides in cynomolgus monkeys, blood samples were taken for analysis. The monkeys were fasted overnight prior to blood collection. Approximately 1.5 mL of blood was collected from each animal and put into tubes without anticoagulant for serum separation. The tubes were kept at room temperature for a minimum of 90 min and then centrifuged at 3,000 rpm for 10 min at room temperature to obtain serum. C-reactive protein (CRP), which is synthesized in the liver and which serves as a marker of inflammation, was measured using a Toshiba 200FR NEO chemistry analyzer (Toshiba Co., Japan). The results indicate that treatment with ISIS 494372 did not cause any inflammation in monkeys.

TABLE 58

C-reactive protein levels (mg/L) in cynomolgus monkey plasma

|  | CRP |
| --- | --- |
| PBS | 1.4 |
| ISIS 494283 | 14.7 |
| ISIS 494284 | 7.7 |
| ISIS 494286 | 4.4 |
| ISIS 494301 | 3.5 |
| ISIS 494302 | 2.4 |
| ISIS 494372 | 10.2 |

Complement C3 Analysis

To evaluate any effect of ISIS oligonucleotides on the complement pathway in cynomolgus monkeys, blood samples were taken for analysis on day 84 (pre-dose) and day 85 (24 hours post-dose). Approximately 0.5 mL of blood was collected from each animal and put into tubes without anticoagulant for serum separation. The tubes were kept at room temperature for a minimum of 90 min and then centrifuged at 3,000 rpm for 10 min at room temperature to obtain serum. C3 was measured using a Toshiba 200FR NEO chemistry analyzer (Toshiba Co., Japan). The results indicate that treatment with ISIS 494372 did not cause any effect on the complement pathway in monkeys.

TABLE 59

Complement C3 levels (mg/dL) in cynomolgus monkey plasma

|  | Pre-dose | Post-dose |
| --- | --- | --- |
| PBS | 140 | 139 |
| ISIS 494283 | 127 | 101 |
| ISIS 494284 | 105 | 75 |
| ISIS 494286 | 84 | 38 |
| ISIS 494301 | 118 | 76 |
| ISIS 494302 | 98 | 58 |
| ISIS 494372 | 123 | 109 |

Hematology

To evaluate any effect of ISIS oligonucleotides in cynomolgus monkeys on hematologic parameters, blood samples of approximately 0.5 mL of blood was collected on day 87 from each of the available study animals in tubes containing $K_2$-EDTA. Samples were analyzed for red blood cell (RBC) count, white blood cells (WBC) count, as well as for platelet count, using an ADVIA120 hematology analyzer (Bayer, USA). The data is presented in Table 60.

The data indicate that treatment with ISIS 494372 was well tolerated in terms of the hematologic parameters of the monkeys.

TABLE 60

Blood cell counts in cynomolgus monkeys

|  | WBC (×10³/μL) | RBC (×10⁶/μL) | Platelet (×10³/μL) |
| --- | --- | --- | --- |
| PBS | 15 | 6.3 | 329 |
| ISIS 494283 | 16 | 5.3 | 456 |
| ISIS 494284 | 13 | 6.3 | 330 |
| ISIS 494286 | 14 | 5.5 | 304 |
| ISIS 494301 | 15 | 6.0 | 392 |
| ISIS 494302 | 12 | 6.3 | 305 |
| ISIS 494372 | 11 | 6.1 | 447 |

Example 12

Characterization of the Pharmacological Activity of ISIS 494372 in Cynomolgus Monkeys The pharmacological activity of ISIS 494372 was characterized by measuring liver apo(a) mRNA and plasma apo(a) levels in monkeys administered the compound over 13 weeks and allowed to recover for another 13 weeks.

Treatment

Five groups of 14 randomly assigned male and female cynomolgus monkeys each were injected subcutaneously with ISIS oligonucleotide or PBS using a stainless steel dosing needle and syringe of appropriate size into the one of four sites on the back (scapular region) of the monkeys. The monkeys were dosed four times a week for the first week (days 1, 3, 5, and 7) as loading doses, and subsequently once a week for weeks 2-13 as maintenance doses, as shown in the table below. The loading dose during the first week is expressed as mg/kg/dose, while the maintenance doses on weeks 2-13 are expressed as mg/kg/week.

TABLE 61

Dosing groups in cynomolgus monkeys

|  |  |  | Number of animals for necropsy | | |
| --- | --- | --- | --- | --- | --- |
| Group | Test Article | Dose | Interim | Terminal | Recovery |
| 1 | PBS | — | 4 | 6 | 4 |
| 2 | ISIS | 4 | — | 6 | — |
| 3 | 494372 | 8 | — | 6 | — |
| 4 |  | 12 | 4 | 6 | 4 |
| 5 |  | 40 | 4 | 6 | 4 |

Liver samples from animals were taken at the interim, terminal and recovery phases of the study for the analyses of apo(a) mRNA. In addition, plasma samples were collected on different days to measure apo(a) protein levels. This non-clinical study was conducted in accordance with the United States Food and Drug Administration (FDA) Good Laboratory Practice (GLP) Regulations, 21 CFR Part 58.

RNA Analysis

Liver samples were collected from monkeys on days 30, 93, and 182, and frozen. Briefly, a piece (0.2 g) of frozen liver was homogenized in 2 mL of RLT solution (Qiagen). The resulting lysate was applied to Qiagen RNeasy mini columns After purification and quantification, the tissues were subjected to RT-PCR analysis. The Perkin-Elmer ABI Prism 7700 Sequence Detection System, which uses real-time fluorescent RT-PCR detection, was used to quantify apo(a) mRNA. The assay is based on a target-specific probe labeled with fluorescent reporter and quencher dyes at opposite ends. The probe was hydrolyzed through the 5'-exonuclease activity of Taq DNA polymerase, leading to an increasing fluorescence emission of the reporter dye that can be detected during the reaction. A probe set (ABI Rhesus LPA probe set ID Rh02789275_m1, Applied Biosystems, Carlsbad Calif.) targeting position 1512 of the rhesus monkey apo(a) mRNA transcript GENBANK Accession No XM_001098061.2 (SEQ ID NO: XXX) sequence was used to measure cynomolgus monkey liver apo(a) mRNA expression levels. Apo(a) expression was normalized using RIBOGREEN®. Results are presented as percent inhibition of apo(a) mRNA, relative to PBS control.

As shown in Table 62, treatment with ISIS 494372 resulted in a dose-dependent reduction of apo(a) mRNA in comparison to the PBS control. At day 30, hepatic apo(a)

mRNA expression was reduced in a dose-dependent manner by 74% and 99% in the 12 mg/kg/week and 40 mg/kg/week dosing cohorts, respectively. These reductions are statistically significant by one-way ANOVA (Dunnett's multiple comparison test, P<0.05).

Apo(a) mRNA levels were also measured during the recovery phase. Liver expression levels at day 88 after the last dose were still reduced 49% and 69% in the 12 mg/kg/week and 40 mg/kg/week dosing cohorts, respectively.

TABLE 62

Percent inhibition levels of liver apo(a) mRNA in the dosing phase in cynomolgus monkeys treated with ISIS 494372

| Day | Dose (mg/kg/wk) | % inhibition |
|---|---|---|
| 30 | 12 | 73 |
|  | 40 | 99 |
| 93 | 4 | 44 |
|  | 8 | 43 |
|  | 12 | 53 |
|  | 40 | 93 |

Protein Analysis

Approximately 20 μl of plasma was analyzed using a commercially available apo(a) ELISA kit (Mercodia 10-1106-01, Uppsala, Sweden). The assay protocol was performed as described by the manufacturer. The results are presented in Tables 63 and 64 as percentage change from Day 1 pre-dose apo(a) plasma protein concentrations. Statistically significant differences from Day 1 baseline plasma apo(a) using the Dunnett's multicomparison test are marked with an asterisk.

Maximal reduction in plasma apo(a) protein was observed in all dosing cohorts by Day 93. In the recovery phase, apo(a) plasma protein levels in the 40 mg/kg/week dosing cohort were at 22% and 93% of the baseline after 4 and 13 weeks (Days 121 and 182) of recovery, respectively. The rate of recovery in the 12 mg/kg/week cohort was similar to that seen in the 40 mg/kg/week cohort.

TABLE 63

Apo(a) plasma protein levels as a percent of Day 1 levels in the dosing phase in cynomolgus monkeys treated with ISIS 494372

| Day | Dose (mg/kg/wk) | % |
|---|---|---|
| 30 | 4 | 93 |
|  | 8 | 70 |
|  | 12 | 49 |
|  | 40 | 15* |
| 93 | 4 | 73 |
|  | 8 | 56 |
|  | 12 | 32* |
|  | 40 | 11* |

TABLE 64

Apo(a) plasma protein levels as a percent of Day 1 levels in the recovery phase in cynomolgus monkeys treated with ISIS 494372

| Day | Dose (mg/kg/wk) | % |
|---|---|---|
| 121 | 12 | 38* |
|  | 40 | 22* |
| 182 | 12 | 84 |
|  | 40 | 93 |

Example 13

Measurement of Viscosity of ISIS Antisense Oligonucleotides Targeting Human Apo(a)

The viscosity of select antisense oligonucleotides from the studies described above was measured with the aim of screening out antisense oligonucleotides which have a viscosity more than 40 cP. Oligonucleotides having a viscosity greater than 40 cP would have less than optimal viscosity.

ISIS oligonucleotides (32-35 mg) were weighed into a glass vial, 120 μL of water was added and the antisense oligonucleotide was dissolved into solution by heating the vial at 50° C. Part (75 μL) of the pre-heated sample was pipetted to a micro-viscometer (Cambridge). The temperature of the micro-viscometer was set to 25° C. and the viscosity of the sample was measured. Another part (20 μL) of the pre-heated sample was pipetted into 10 mL of water for UV reading at 260 nM at 85° C. (Cary UV instrument). The results are presented in Table 65 and indicate that most of the antisense oligonucleotides solutions are optimal in their viscosity under the criterion stated above. Those that were not optimal are marked as 'viscous'. Specifically, ISIS 494372 was optimal in its viscosity under the criterion stated above.

TABLE 65

Viscosity and concentration of ISIS antisense oligonucleotides targeting human Apo(a)

| ISIS No | Motif | Viscosity (cP) | Concentration (mg/mL) |
|---|---|---|---|
| 494158 | 5-10-5 MOE | 9.0 | 350 |
| 494159 | 5-10-5 MOE | 11.7 | 325 |
| 494161 | 5-10-5 MOE | 12.0 | 350 |
| 494162 | 5-10-5 MOE | 25.8 | 350 |
| 494163 | 5-10-5 MOE | Viscous | 275 |
| 494243 | 5-10-5 MOE | 28.4 | 325 |
| 494244 | 5-10-5 MOE | 19.2 | 300 |
| 494283 | 3-10-4 MOE | 13.4 | 300 |
| 494284 | 5-10-5 MOE | 13.4 | 350 |
| 494285 | 5-10-5 MOE | 23.1 | 350 |
| 494286 | 5-10-5 MOE | 16.5 | 275 |
| 494301 | 5-10-5 MOE | 17.1 | 325 |
| 494302 | 5-10-5 MOE | 24.3 | 350 |
| 494304 | 5-10-5 MOE | 49.3 | 275 |
| 494311 | 5-10-5 MOE | 10.8 | 325 |
| 494337 | 5-10-5 MOE | 29.5 | 325 |
| 494372 | 5-10-5 MOE | 12.5 | 350 |
| 494466 | 5-10-5 MOE | Viscous | 275 |
| 494470 | 5-10-5 MOE | 16.7 | 350 |
| 494472 | 5-10-5 MOE | 23.6 | 350 |
| 498408 | 5-10-5 MOE | 31.5 | 300 |
| 510548 | 5-10-5 MOE | 9.0 | 350 |
| 512947 | 3-10-4 MOE | 6.8 | 350 |
| 512958 | 5-10-5 MOE | 26.0 | 350 |

The invention claimed is:

1. A method of lowering apo(a) and/or Lp(a) levels in a subject, comprising:
administering to said subject a compound comprising a modified oligonucleotide, wherein:
the modified oligonucleotide consists of 14 to 25 linked nucleosides and comprises a nucleobase sequence comprising a portion of at least 14 contiguous nucleobases complementary to an equal length portion of nucleobases 3900 to 3923 of SEQ ID NO: 1, wherein the nucleobase sequence of the modified oligonucleotide is at least 95% complementary to SEQ ID NO: 1, or a salt thereof, whereby apo(a) and/or Lp(a) levels are reduced in the animal subject.

2. The method of claim 1, wherein the subject has elevated apo(a) and/or Lp(a) levels or a condition associated with elevated apo(a) and/or Lp(a) levels.

3. The method of claim 1, wherein apo(a) mRNA and/or protein levels are lowered.

4. The method of claim 1, wherein the modified oligonucleotide consists of 18 to 24, 19 to 22, 15 to 25, 16 or 20 linked nucleosides.

5. The method of claim 1, wherein the modified oligonucleotide comprises a nucleobase sequence comprising a portion of at least 16, at least 18, at least 19, or at least 20 contiguous nucleobases complementary to an equal length portion of SEQ ID NO: 1.

6. The method of claim 1, wherein the nucleobase sequence of the modified oligonucleotide is at least 96%, 97%, 98% or 99% complementary to SEQ ID NO: 1, or is 100% complementary to SEQ ID NO: 1.

7. The method of claim 1, wherein the modified oligonucleotide consists of 14 to 25 linked nucleosides and comprises a nucleobase sequence comprising at least 14, at least 15, at least 16, at least 17, at least 18, at least 19, or 20 contiguous nucleobases of the nucleobase sequence of SEQ ID NO: 58.

8. The method of claim 1, wherein the modified oligonucleotide is single-stranded.

9. The method of claim 1, wherein at least one internucleoside linkage is a modified internucleoside linkage.

10. The method of claim 9, wherein the at least one internucleoside linkage is a phosphorothioate internucleoside linkage.

11. The method of claim 1, wherein the modified oligonucleotide comprises at least one modified sugar.

12. The method of claim 11, wherein at least one modified sugar is a bicyclic sugar.

13. The method of claim 11, wherein at least one modified sugar comprises a 2'-O-methoxyethyl, a constrained ethyl, a 3'-fluoro-HNA or a 4'-(CH$_2$)$_n$—O-2' bridge, wherein n is 1 or 2.

14. The method of claim 1, wherein at least one nucleoside comprises a modified nucleobase.

15. The method of claim 14, wherein the modified nucleobase is a 5-methylcytosine.

16. The method of claim 1, wherein the modified oligonucleotide consists of 14 to 25 linked nucleosides and comprises:
a gap segment consisting of linked deoxynucleosides;
a 5' wing segment consisting of linked nucleosides;
a 3' wing segment consisting of linked nucleosides;
wherein the gap segment is positioned between the 5' wing segment and the 3' wing segment and wherein each nucleoside of each wing segment comprises a modified sugar.

17. The method of claim 16, wherein the modified oligonucleotide consists of 20 linked nucleosides and comprises:
a gap segment consisting of ten linked deoxynucleosides;
a 5' wing segment consisting of five linked nucleosides;
a 3' wing segment consisting of five linked nucleosides;
wherein the gap segment is positioned between the 5' wing segment and the 3' wing segment, wherein each nucleoside of each wing segment comprises a 2'-O-methoxyethyl sugar, wherein at least one internucleoside linkage is a modified internucleoside linkage and wherein each cytosine residue is a 5-methylcytosine.

18. The method of claim 16, wherein the modified oligonucleotide consists of 20 linked nucleosides.

19. The method of claim 1, wherein the modified oligonucleotide consists of 20 contiguous linked nucleosides of SEQ ID NO: 58 and the modified oligonucleotide further comprises:
a gap segment consisting of ten linked deoxynucleosides;
a 5' wing segment consisting of five linked nucleosides;
a 3' wing segment consisting of five linked nucleosides;
wherein the gap segment is positioned between the 5' wing segment and the 3' wing segment, wherein each nucleoside of each wing segment comprises a 2'-O-methoxyethyl sugar, wherein at least one internucleoside linkage is a modified internucleoside linkage and wherein each cytosine residue is a 5-methylcytosine.

20. The method of claim 1, wherein a therapeutically effective dose of the modified oligonucleotide is administered, whereby a disease associated with elevated apo(a) and/or elevated Lp(a) levels in the subject is treated, its onset delayed, the progression slowed or a symptom ameliorated.

21. The method of claim 20, wherein the disease is an inflammatory, cardiovascular or metabolic disorder or condition.

22. The method of claim 1, wherein the subject is a human subject.

23. The method of claim 1, wherein the compound is a first agent and is co-administered with one or more secondary agents or therapy.

24. The method of claim 1, wherein the modified oligonucleotide has a viscosity of less than 40 cP.

25. The method of claim 23, wherein the one or more secondary agents or therapy is/are selected from among an apo(a) lowering agent, a Lp(a) lowering agent, an agent to reduce thromboembolism formation, a glucose-lowering agent, a LDL lowering agent, a triglyceride lowering agent, a cholesterol lowering agent, a HDL raising agent, an anti-inflammatory agent, an Alzheimer Disease drug, a non-steroidal anti-inflammatory drug (NSAID), fish oil, niacin, nicotinic acid, an apoB inhibitor, a CETP inhibitor, a thyroid hormone analog, a HMG-CoA reductase inhibitor, a fibrate, a microsomal triglyceride transfer protein inhibitor and Lp(a) apheresis.

* * * * *